(12) United States Patent
Hartung et al.

(10) Patent No.: US 12,156,890 B2
(45) Date of Patent: *Dec. 3, 2024

(54) COMPOSITIONS AND METHODS FOR NEURALGENESIS

(71) Applicant: The Johns Hopkins University, Baltimore, MD (US)

(72) Inventors: Thomas Hartung, Baltimore, MD (US); David Pamies, Baltimore, MD (US); Helena T. Hogberg, Nottingham, MD (US)

(73) Assignee: The Johns Hopkins University, Baltimore, MD (US)

( * ) Notice: Subject to any disclaimer, the term of this patent is extended or adjusted under 35 U.S.C. 154(b) by 1070 days.

This patent is subject to a terminal disclaimer.

(21) Appl. No.: 16/077,411

(22) PCT Filed: Feb. 10, 2017

(86) PCT No.: PCT/US2017/017464
§ 371 (c)(1),
(2) Date: Aug. 10, 2018

(87) PCT Pub. No.: WO2017/139638
PCT Pub. Date: Aug. 17, 2017

(65) Prior Publication Data
US 2019/0046583 A1    Feb. 14, 2019

Related U.S. Application Data

(60) Provisional application No. 62/294,112, filed on Feb. 11, 2016.

(51) Int. Cl.
| | | |
|---|---|---|
| A61K 35/00 | (2006.01) | |
| A61K 35/30 | (2015.01) | |
| A61K 38/41 | (2006.01) | |
| C12N 5/00 | (2006.01) | |
| C12N 5/074 | (2010.01) | |
| G01N 33/50 | (2006.01) | |
| G01N 33/58 | (2006.01) | |
| G01N 33/68 | (2006.01) | |

(52) U.S. Cl.
CPC .............. *A61K 35/30* (2013.01); *A61K 38/41* (2013.01); *C12N 5/0062* (2013.01); *C12N 5/0696* (2013.01); *G01N 33/50* (2013.01); *G01N 33/58* (2013.01); *G01N 33/6893* (2013.01); *C12N 2501/11* (2013.01); *C12N 2501/115* (2013.01); *C12N 2501/13* (2013.01); *C12N 2501/22* (2013.01)

(58) Field of Classification Search
CPC ...... A61K 35/30; A61K 38/41; C12N 5/0062; C12N 5/0696; C12N 2501/11; C12N 2501/115; C12N 2501/13; C12N 2501/22; G01N 33/50; G01N 33/05; G01N 33/6893
See application file for complete search history.

(56) References Cited

U.S. PATENT DOCUMENTS

| | | | |
|---|---|---|---|
| 2006/0270032 A1 | 11/2006 | Bhatia et al. | |
| 2007/0015210 A1* | 1/2007 | Ezekiel ................ | C12N 5/0603 435/7.1 |
| 2012/0052568 A1* | 3/2012 | Subramanian ....... | C12N 5/0607 435/325 |
| 2015/0267164 A1 | 9/2015 | Laukkanen et al. | |

OTHER PUBLICATIONS

Dingle et al ("Three-Dimensional Neural Spheroid Culture: An In Vitro Model for Cortical Studies," Tissue Engineering: Part C, vol. 21, No. 12, 2015).*
Choi et al ("Size-controllable networked neurospheres as a 3D neuronal tissue model for Alzheimer's disease studies," Biomaterials 34 (2013 2938-2946) (Year: 2013).*
Wang et al ("Capillary electrophoresis of induced pluripotent stem cells during differentiation toward neurons;" Journal of the Taiwan Institute of Chemical Engineers 45 (2014) 2096-2105). (Year: 2014).*
Dingle et al., "Three-Dimensional Neural Spheroid Culture: An In Vitro Model for Cortical Studies", Tissue Eng Part C Methods, 21(12):1274-83 (2015).
Nunes, Marta C., et al. "Identification and isolation of multipotential neural progenitor cells from the subcortical white matter of the adult human brain." Nature medicine 9.4 (2003): 439-447 (9 pages).
Uroukov, Ivan S., et al. "Electrophysiological measurements in three-dimensional in vivo-mimetic organotypic cell ultures: Preliminary studies with hen embryo brain spheroids." Neuroscience letters 404.1-2 (2006): 33-38 (6 pages).
Douvaras, Panagiotis, et al. "Efficient generation of myelinating oligodendrocytes from primary progressive multiple sclerosis patients by induced pluripotent stem cells." Stem cell reports 3.2 (2014): 250-259 (10 pages).
Hayase, Makoto, et al. "Committed neural progenitor cells derived from genetically modified bone marrow stromal cells meliorate deficits in a rat model of stroke." Journal of Cerebral Blood Flow & Metabolism 29.8 (2009): 1409-1420 (12 pages).

(Continued)

*Primary Examiner* — Anoop K Singh
*Assistant Examiner* — David A Montanari
(74) *Attorney, Agent, or Firm* — Fox Rothschild LLP

(57) ABSTRACT

The present invention relates to novel compositions and methods to produce 3D organ equivalents of the brain (i.e. "mini-brains"). The invention also relates to methods of using human induced pluripotent stem cells, a combination of growth and other soluble factors and gyratory shaking. Cells from healthy or diseased donors or animals can be used to allow testing different genetic backgrounds. The model can be further enhanced by using genetically modified cells, adding micro-glia or their precursors or indicator cells (e.g. with reporter genes or tracers) as well as adding endothelial cells to form a blood-brain-barrier.

28 Claims, 32 Drawing Sheets
Specification includes a Sequence Listing.

(56) References Cited

OTHER PUBLICATIONS

Hopkins, Amy M., et al. "3D in vitro modeling of the central nervous system." Progress in neurobiology 125 (2015): 1-25.
Pamies, David, et al. "A human brain microphysiological system derived from induced pluripotent stem cells to study eurological diseases and toxicity." Allex 34.3 (2017): 362 (27 pages).
European Search Report of counterpart EP Application No. 17 75 0868, dated Dec. 19, 2020 (11 pages).
Written Opinion of International Application No. PCT/US2017/017464, dated Jul. 10, 2017.

\* cited by examiner

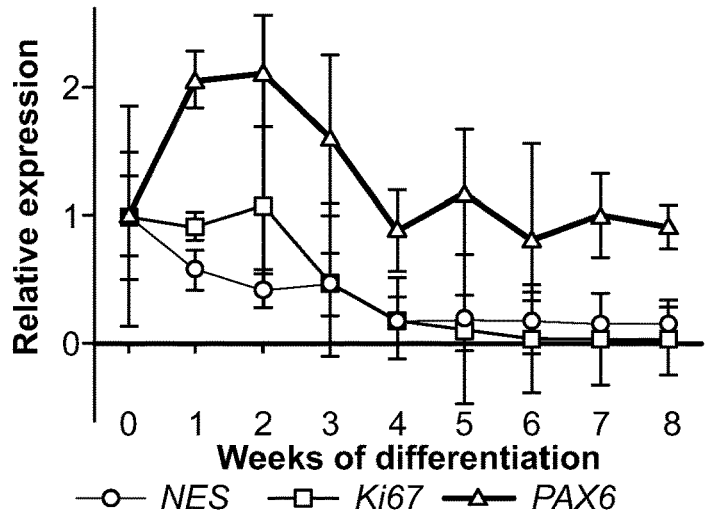
FIG. 1C1
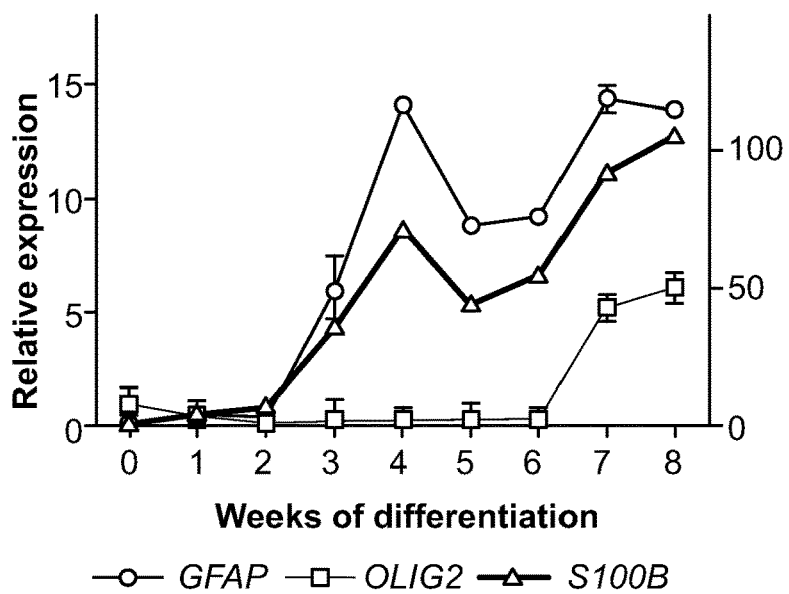
FIG. 1C2

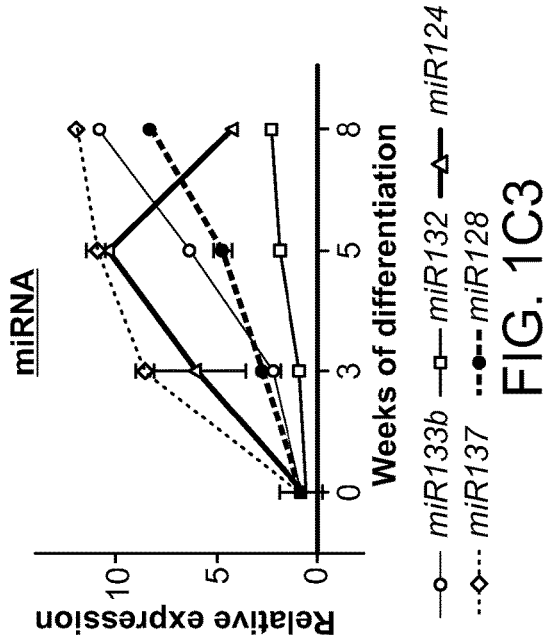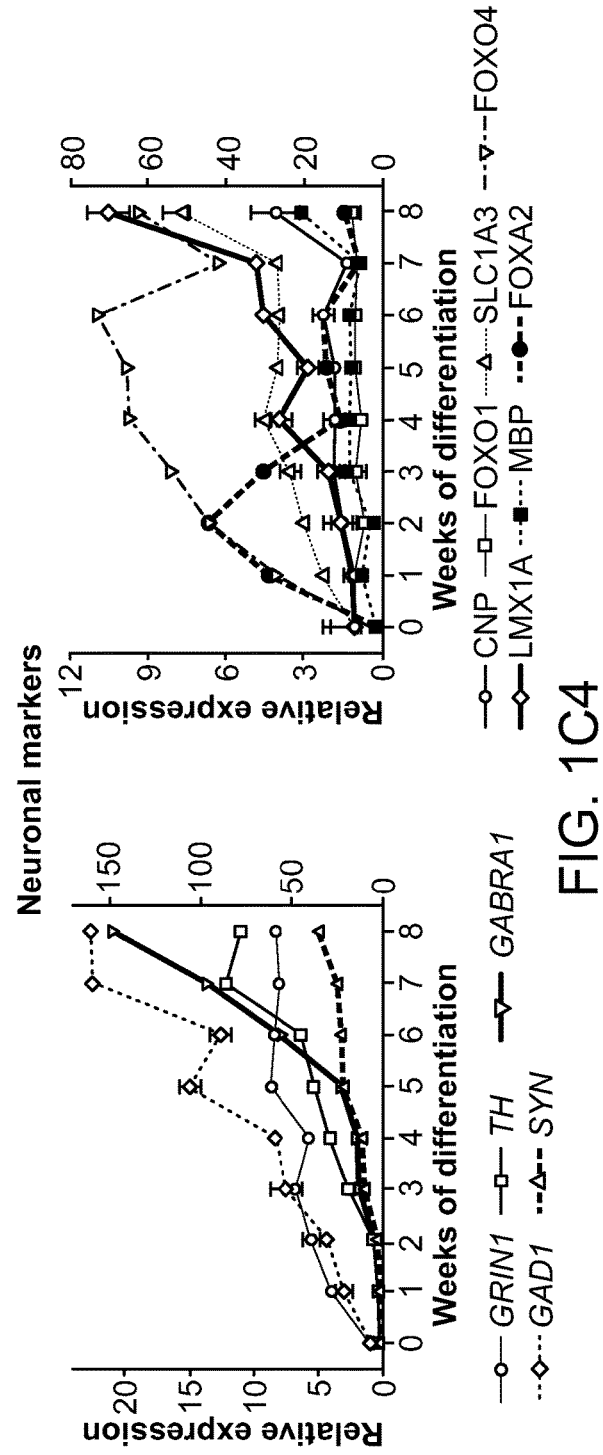

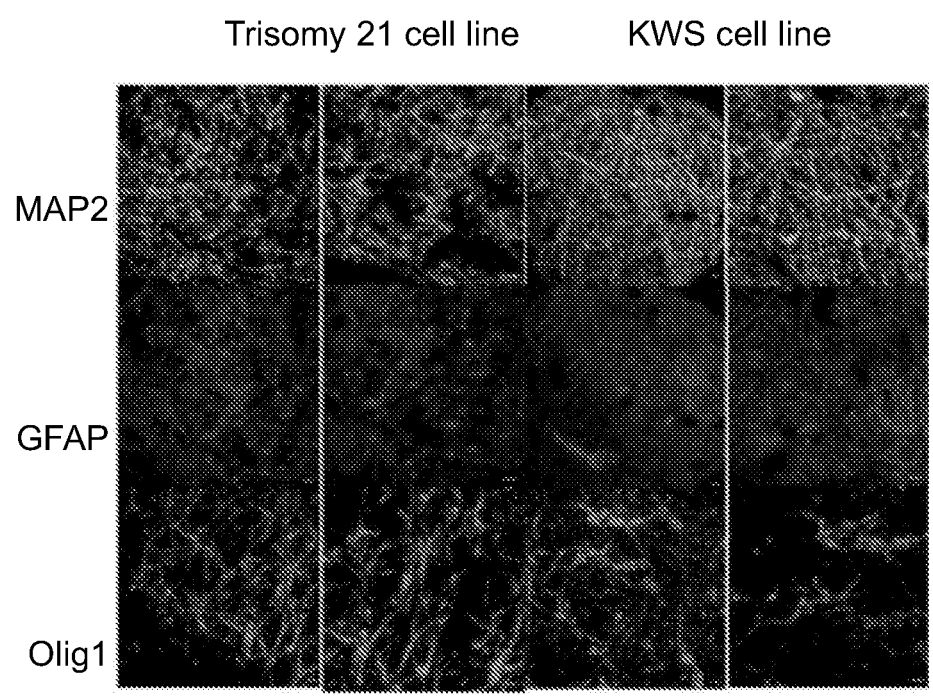
FIG. 1C5

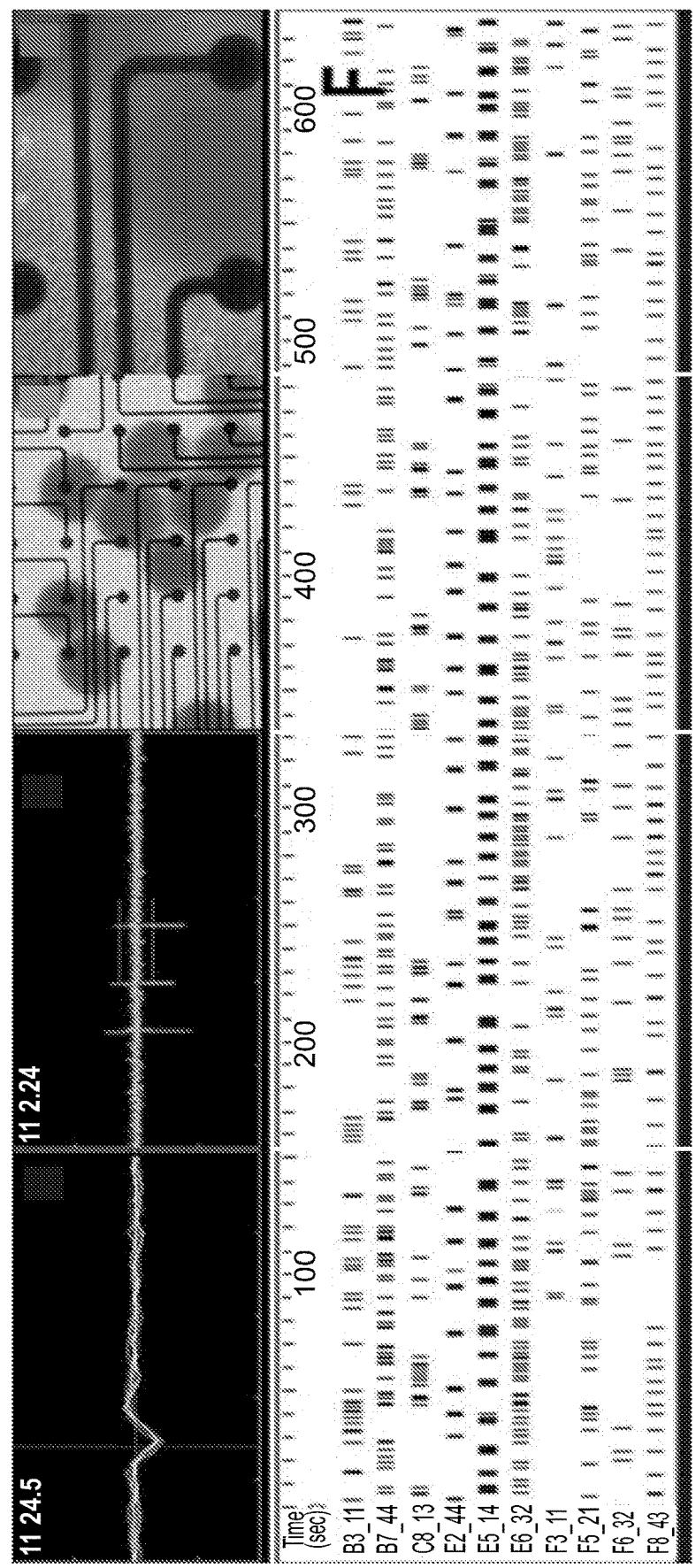

Amp/Deletion Table

| Chr | Amp/Del | Start-Stop (bp) | Size (kb) | Chr Band | # Probes | Log2 Ratio | Genes[α] | Overlap Normal CNVs?[β] |
|---|---|---|---|---|---|---|---|---|
| 2 | GAIN | 44,479,791-49,652,038 | 5,172 | p21-p16.3 | 219 | 0.328063 | SLC3A1, SIX3, SIX2, PRKCE, *EPAS1, PIGF, SOCS5, MCFD2, TTC7A, CALM2, MSH2, KCNK12, MSH6, FBXO11, LHCGR, FSHR*, PREPL, CAMKMT, UNQ6975, SRBD1, LOC388946, ATP6V1E2, RHOQ, CRIPT, LOC388948, LOC100134259, C2orf61, EPCAM, MIR559, FOXN2, KLRAQ1, STON1- | No |
| 10 | GAIN | 124,347,870-124,351,275 | 3 | q26.13 | 6 | 0.782955 | *DMBT1* | Yes |
| 11 | GAIN | 54,872,150-55,032,155 | 160 | q11 | 5 | 0.619389 | TRIM48 | Yes |
| 14 | GAIN | 19,265,142-20,421,677 | 1,157 | q11.2 | 22 | 0.490838 | OR11H12, POTEG, POTEM, OR11H2, OR4Q3, OR4M1, OR4N2, OR4K2, OR4K5, OR4K1 | Yes |
| 14 | GAIN | 67,306,385-67,514,841 | 208 | q23.3 | 28 | 0.555366 | GRHN | Yes |
| 18 | LOSS | 132,387-14,158,122 | 14,026 | p11.32-p11.21 | 541 | -0.89217 | Too Numerous | No |
| 18 | DEL | 7,694,140-7,821,430 | 127 | p11.23 | 6 | -4.90876 | *PTPRM* | Yes |
| 18 | LOSS | 14,556,513-15,047,825 | 491 | p11.21 | 14 | -0.5347 | ANKRD30B, MIR3156-2 | Yes |
| X | GAIN | 58,141,950-58,428,287 | 286 | p11.1 | 9 | 0.478356 | | Yes |

FIG. 5C

COMPOSITIONS AND METHODS FOR NEURALGENESIS

CROSS REFERENCE TO RELATED APPLICATIONS

This application is a national stage application, filed under 35 U.S.C. § 371, of International Application No. PCT/US2017/017464, filed on Feb. 10, 2017, which claims the benefit of priority under 35 U.S.C. § 119 (e) to U.S. Provisional Application No. 62/294,112, filed Feb. 11, 2016, which is incorporated herein by reference in its entirety.

STATEMENT AS TO FEDERALLY SPONSORED RESEARCH

The invention was made with government support under the following grant awarded by the National Institute of Health (NIH): U18TR000547. The government has certain rights in the invention.

SEQUENCE LISTING

The instant application contains a Sequence Listing which has been submitted electronically in ASCII format and is hereby incorporated by reference in its entirety. Said ASCII copy, created on Mar. 21, 2017, is named 48317-518001WO_SL.txt and is 329,024 bytes in size.

BACKGROUND OF THE INVENTION

Simple neural in vitro systems do not reflect the physiology, cellular interactions, or genetics of mammalian brain tissue. Accordingly, there is an unmet need to develop human models of brain disorders and/or diseases.

SUMMARY OF THE INVENTION

The present invention provides brain microphysiological systems (BMPS) that can be produced from induced pluripotent stem cells (iPSCs). Furthermore, the invention provides for reproducible BMPS that differentiate into mature neurons and glial cells (astrocytes and oligodendrocytes) in the central nervous system. This model is electrophysiologically active in a spontaneous manner and may be reproduced with patient cells. The derivation of 3D BMPS from iPSCs has applications in the study and treatment of neurological diseases.

In an aspect, the disclosure provides an in vitro brain microphysiological system (BMPS), comprising two or more neural cell types aggregated into a spheroid mass, wherein the spheroid mass has a diameter that is less than about 500 µm and the in vitro BMPS is electrophysiologically active in a spontaneous manner.

In an embodiment, the two or more neural cell types comprise at least a mature neuron and glial cell.

In an embodiment, the two or more neural cell types further comprise cells selected from the group consisting of astrocytes, polydendrocytes, oligodendrocytes, and combinations thereof.

In an embodiment, the in vitro BMPS has neural characteristics selected from the group consisting of synaptogenesis, neuron-neuron interactions, neuronal-glial interactions, axon myelination, and combinations thereof.

In an embodiment, two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an aspect, the disclosure provides a synthetic neurological organ comprising two or more neural cell types aggregated into a spheroid mass, wherein the spheroid mass has a diameter that is less than 500 µm and the in vitro BMPS is electrophysiologically active in a spontaneous manner.

In an embodiment, the two or more neural cell types comprise at least a mature neuron and glial cells.

In an embodiment, the mature neuron and glial cells further comprise cells selected from the group consisting of astrocytes, polydendrocytes, oligodendrocytes, and combinations thereof.

In an embodiment, the synthetic neurological organ further comprises neural characteristics selected from the group consisting of synaptogenesis, neuron-neuron interactions, neuronal-glial interactions, axon myelination, and combinations thereof.

In an embodiment, the synthetic neurological organ mimics the microenvironment of the central nervous system (CNS).

In an aspect, the disclosure provides a method of reproducibly producing an in vitro brain microphysiological system (BMPS), comprising: inducing one or more pluripotent stem cell (PSC) types; differentiating the one or more PSC types to form one or more neural progenitor cell (NPC) types; exposing the one or more NPC types to gyratory shaking or stirring; and differentiating the one or more NPC types into one or more neural cell types aggregated into a spheroid mass, wherein the spheroid mass has a diameter that is less than 500 µm.

In an embodiment, the one or more pluripotent stem cells are selected from the group consisting of human or animal embryonic stem cells, iPSC, adult stem cells, fibroblasts, embryonic fibroblasts, peripheral blood mononuclear cells, neuronal precursor cells, mesenchymal stem cells, and combinations thereof.

In an embodiment, inducing further comprises: adding micro-glia or micro-glia precursor cells.

In an embodiment, the micro-glia or micro-glia precursor cells are selected from the group consisting of monocytes, human monocytes, pro-monocyte cell lines, iPSC-derived monocytes, hematopoetic stem cells, isolated microglia, immortalized microglia, and combinations thereof.

In an embodiment, gyratory shaking comprises constant or regular gyratory shaking or stirring for 2 or more, 3 or more, 4 or more, 5 or more, 6 or more, 7 or more, or 8 or more weeks.

In an embodiment, the one or more growth factors are selected from the group consisting of GDNF, BDNF, GM-CSF, B27, basic FGF, basic EGF, NGF, CNTF, and any combination thereof.

In an aspect, the disclosure provides a method of cryopreserving an in vitro brain microphysiological system (BMPS), comprising: differentiating BMPS aggregates into one or more mature neurons; incubating the aggregates in a cryopreserving medium; and exposing the aggregates to freezing temperatures of −60° C. or colder.

In an embodiment, differentiating further comprises: inducing differentiation of one or more pluripotent stem cell types by incubation with one or more growth factors.

In an embodiment, the one or more pluripotent stem cells are selected from a group consisting of human or animal embryonic stem cells, iPSC, adult stem cells, fibroblasts, embryonic fibroblasts, peripheral blood mononuclear cells, neuronal precursor cells, mesenchymal stem cells, and combinations thereof.

In an embodiment, inducing further comprises: adding micro-glia precursor cells.

In an embodiment, micro-glia precursor cells are selected from the group consisting of monocytes, human monocytes, iPSC-derived monocytes, hematopoetic stem cells, promonocyte cell lines, isolated microglia, immortalized microglia, and combinations thereof.

In an embodiment, the one or more growth factors are selected from the group consisting of GDNF, BDNF, GM-CSF, B27, basic FGF, basic EGF, NGF, CNTF, and any combination thereof.

In an embodiment, the cryopreserving medium is a medium selected from the group consisting of regular cryopreservation medium (95% FBS and 5% DMSO), STEMdiff Neural Progenitor Freezing Medium (Stem Cells Technologies), solutions with cryoprotectants, and combinations thereof.

In an embodiment, exposing the aggregates to freezing temperatures further comprises freezing aggregates over a temperature gradient of about 1° C. per hour to below-60° C. over up to 48 hours.

In an embodiment, cryopreserving further comprises additives selected from the group consisting of DMSO, HES, glycerol, serum, and any combination or derivative thereof.

In an aspect, the disclosure provides a method of transporting a brain microphysiological system (BMPS) or minibrain, comprising: producing the BMPS or mini-brain of claim 1, incubating the BMPS or mini-brain at 37° C., and maintaining the temperature at 37° C. with constant application of heat while moving the BMPS or mini-brain.

In an embodiment, maintaining the temperature comprises use of heating pads, heaters, insulation, insulated boxes, heat packs, electric blankets, chemical pads, and combinations thereof.

In an aspect, the disclosure provides a method of studying a neurological disease or disorder comprising: producing an in vitro brain microphysiological system (BMPS); exposing the in vitro BMPS to conditions that replicate or induce the neurological disease or disorder; adding an agent to treat the neurological disease or disorder; and assessing the effect of the agent on the neurological disease or disorder.

In an embodiment, the neurological disease or disorder is selected from the group consisting of neurodegenerative disorder, muscular dystrophy, Parkinson's Disease, Huntington's Disease, Autism Spectrum Disorder and other neurodevelopmental disorders, Down's Syndrome, Multiple Sclerosis, Amyotrophic lateral sclerosis, brain cancer, encephalitis, infection, trauma, stroke, and paralysis.

In an aspect, the disclosure provides a method of treating a patient having a neurological disease or disorder, comprising: extracting a stem cell from the patient with a genetic background pre-disposed for the neurological disease or disorder; producing a brain microphysiological system (BMPS) or mini-brain with the genetic background; treating the BMPS or mini-brain with an agent targeting the neurological disease or disorder; and assessing the effect of the agent on the BMPS or mini-brain.

In an embodiment, the neurological disease or disorder is selected from the group consisting of neurodegenerative disorder, muscular dystrophy, Parkinson's Disease, Huntington's Disease, Autism Spectrum Disorder and other neurodevelopmental disorders, Down's Syndrome, Multiple Sclerosis, Amyotrophic lateral sclerosis, brain cancer, encephalitis, infection, trauma, stroke, and paralysis.

In an embodiment, the BMPS includes two or more neuronal cell types that include one or more genetically modified cells. The BMPS wherein the one or more genetically modified cells include one or more reporter genes. The BMPS further comprises one or more endothelial cells capable of forming a blood-brain-barrier.

In an embodiment, the synthetic neurological organ may include two or more neural cell types that include one or more genetically modified cells. The synthetic neurological organ including one or more genetically modified cells that include one or more reporter genes. The synthetic neurological organ further comprising one or more endothelial cells capable of forming a blood-brain-barrier.

In an aspect, the disclosure provides a method of reproducibly producing an in vitro brain microphysiological system (BMPS), comprising: exposing one or more NPC types to gyratory shaking or stirring; and differentiating the one or more NPC types into one or more neural cell types aggregated into a spheroid mass, wherein the spheroid mass has a diameter that is less than 500 µm.

In an embodiment, the spheroid mass has a diameter that is less than about 450 µm, 400 µm, 350 µm, or 300 µm, or a diameter that is between about 350 µm and about 300 µm, or a diameter that is between about 330 µm and about 300 µm, or a diameter that is about 310 µm.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, inducing comprises a single PSC.

In an embodiment, the an in vitro brain microphysiological system (BMPS) may be produced according to the above described method.

It is also contemplated within the scope of the invention that the addition of other cells inside (see e.g., FIG. 6) and outside (see e.g., FIG. 7) the BMPS may be used to modify the structure/composition of the BMPS, such as, e.g., by forming a blood-brain-barrier. It is also contemplated that the BMPS described herein may include genetically modified pluripotent stem cells, or be combined with other organoids (see e.g., Example 11).

Definitions

By "agent" is meant any small compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

In this disclosure, "comprises," "comprising," "containing," and "having" and the like may have the meaning ascribed to them in U.S. Patent law and may mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "effective amount" is meant the amount of an agent needed to ameliorate the symptoms of a neurological disease relative to an untreated patient. The effective amount of active agent(s) used to practice the present invention for therapeutic treatment of a neurological disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, 100, 200, 300, 400, 500, 600, 700, 800, 900, or 1000 nucleotides or amino acids, or more.

By "gene" is meant a locus (or region) of DNA that encodes a functional RNA or protein product, and is the molecular unit of heredity.

By "marker" is meant any protein or polynucleotide having an alteration in expression level or activity that is associated with a disease or disorder.

By "modulate" is meant alter (increase or decrease). Such alterations are detected by standard art known methods such as those described herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

By "reference" is meant a standard or control condition.

By "pluripotency" is meant stem cells with the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). However, one of skill in the art will understand that cell pluripotency is a continuum, ranging from the completely pluripotent cell that can form every cell of the embryo proper, e.g., embryonic stem cells and iPSCs (see below), to the incompletely or partially pluripotent cell that can form cells of all three germ layers but that may not exhibit all the characteristics of completely pluripotent cells. Induced pluripotent stem cells, commonly abbreviated as iPS cells or iPSCs are a type of pluripotent stem cell artificially derived from a non-pluripotent cell, typically an adult somatic cell, by inducing a "forced" expression of certain genes and transcription factors. These transcription factors play a key role in determining the state of these cells and also highlight the fact that these somatic cells do preserve the same genetic information as early embryonic cells. The ability to induce cells into a pluripotent state was initially pioneered using mouse fibroblasts and four transcription factors, Oct4, Sox2, Klf4 and c-Myc;—a process called reprogramming. The successful induction of human iPSCs derived from human dermal fibroblasts has been performed using methods similar to those used for the induction of mouse cells. These induced cells exhibit similar traits to those of embryonic stem cells (ESCs) but do not require the use of embryos. Some of the similarities between ESCs and iPSCs include pluripotency, morphology, self-renewal ability, a trait that implies that they can divide and replicate indefinitely, and gene expression.

By "stem cells" is meant undifferentiated biological cells that can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells—ectoderm, endoderm and mesoderm (see induced pluripotent stem cells)—but also maintain the normal turnover of regenerative organs, such as blood, skin, or intestinal tissues. There are three known accessible sources of autologous adult stem cells in humans: 1. Bone marrow, which requires extraction by harvesting, that is, drilling into bone (typically the femur or iliac crest). 2. Adipose tissue (lipid cells), which requires extraction by liposuction. 3. Blood, which requires extraction through apheresis, wherein blood is drawn from the donor (similar to a blood donation), and passed through a machine that extracts the stem cells and returns other portions of the blood to the donor. Stem cells can also be taken from umbilical cord blood just after birth. Of all stem cell types, autologous harvesting involves the least risk. By definition, autologous cells are obtained from one's own body.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a neurological disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "or" is understood to be inclusive.

Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

A "therapeutically effective amount" is an amount sufficient to effect beneficial or desired results, including clinical results. An effective amount can be administered in one or more administrations.

By "GRIN1 polypeptide" (or glutamate ionotropic receptor NMDA type subunit 1) is meant a polypeptide or fragment thereof having at least about 85% amino acid identity to NCBI Accession No. Q05586.

```
  1 mstmrlltla llfscsvara acdpkivnig avlstrkheq mfreavnqan krhgswkiql
 61 natsvthkpn aiqmalsvce dlissqvyai lvshpptpnd hftptpvsyt agfyripvlg
121 lttrmsiysd ksihlsflrt vppyshqssv wfemmrvysw nhiillvsdd hegraaqkrl
181 etlleeresk aekvlqfdpg tknvtallme akelearvii lsaseddaat vyraaamlnm
241 tgsgyvwlvg ereisgnalr yapdgilglq lingknesah isdavgvvaq avhelleken
301 itdpprgcvg ntniwktgpl fkrvlmssky adgvtgrvef nedgdrkfan ysimnlqnrk
361 lvqvgiyngt hvipndrkii wpggetekpr gyqmstrlki vtihqepfvy vkptlsdgtc
421 keeftvngdp vkkvictgpn dtspgsprht vpqccygfci dlliklartm nftyevhlva
481 dgkfgtqerv nnsnkkewng mmgellsgqa dmivapltin neraqyiefs kpfkyqglti
541 lvkkeiprst ldsfmqpfqs tlwllvglsv hvvavmlyll drfspfgrfk vnseeeeeda
601 ltlssamwfs wgvllnsgig egaprsfsar ilgmvwagfa miivasytan laaflvldrp
661 eeritgindp rlrnpsdkfi yatvkqssvd iyfrrqvels tmyrhmekhn yesaaeaiqa
721 vrdnklhafi wdsavlefea sqkcdlvttg elffrsgfgi gmrkdspwkq nvslsilksh
781 engfmedldk twvryqecds rsnapatltf enmagvfmlv aggivagifl ifieiaykrh
841 kdarrkqmql afaavnvwrk nlqdrksgra epdpkkkatf raitstlass fkrrrsskdt
901 stgggrgalq nqkdtvlprr aiereegqlq lcsrhres
```

By "GRIN1 nucleic acid molecule" (or glutamate ionotropic receptor NMDA type subunit 1) is meant a polynucleotide encoding an GRIN1 polypeptide. An exemplary GRIN1 nucleic acid molecule (e.g., mRNA) is provided at NCBI Accession No. NM_007327.

```
  1 gtcgccgcag cgtccggacc ggaaccagcg ccgtccgcgg agccgccgcc gccgccgccg
 61 ggccctttcc aagccgggcg ctcggagctg tgcccgccc cgcttcagca ccgcggacag
121 cgccggccgc gtggggctga gccccgagcc cccgcgcacg cttcagcgcc ccttccctcg
181 gccgacgtcc cggaccgcc gctccggggg agacgtggcg tccgcagccc gcggggccgg
241 gcgagcgcag gacggcccgg aagccccgcg ggggatgcgc cgagggcccc gcgttcgcgc
301 cgcgcagagc caggcccgcg gcccgagccc atgagcacca tgcgcctgct gacgctcgcc
361 ctgctgttct cctgctccgt cgccgtgcc gcgtgcgacc ccaagatcgt caacattggc
421 gcggtgctga gcacgcggaa gcacgagcag atgttccgcg aggccgtgaa ccaggccaac
```

-continued

```
 481 aagcggcacg gctcctggaa gattcagctc aatgccacct ccgtcacgca caagcccaac
 541 gccatccaga tggctctgtc ggtgtgcgag gacctcatct ccagccaggt ctacgccatc
 601 ctagttagcc atccacctac ccccaacgac cacttcactc ccacccctgt ctcctacaca
 661 gccggcttct accgcatacc cgtgctgggg ctgaccaccc gcatgtccat ctactcggac
 721 aagagcatcc acctgagctt cctgcgcacc gtgccgccct actcccacca gtccagcgtg
 781 tggtttgaga tgatgcgtgt ctacagctgg aaccacatca tcctgctggt cagcgacgac
 841 cacgagggcc gggcggctca gaaacgcctg agacgctgc tggaggagcg tgagtccaag
 901 gcagagaagg tgctgcagtt tgacccaggg accaagaacg tgacggccct gctgatggag
 961 gcgaaagagc tggaggcccg ggtcatcatc ctttctgcca gcgaggacga tgctgccact
1021 gtataccgcg cagccgcgat gctgaacatg acgggctccg ggtacgtgtg gctggtcggc
1081 gagcgcgaga tctcggggaa cgccctgcgc tacgccccag acggcatcct cgggctgcag
1141 ctcatcaacg gcaagaacga gtcggcccac atcagcgacg ccgtgggcgt ggtgcccag
1201 gccgtgcacg agctcctcga aggagaaac atcaccgacc cgccgcgggg ctgcgtgggc
1261 aacaccaaca tctggaagac cgggccgctc ttcaagagag tgctgatgtc ttccaagtat
1321 gcggatgggg tgactggtcg cgtggagttc aatgaggatg gggaccggaa gttcgccaac
1381 tacagcatca tgaacctgca gaaccgcaag ctggtgcaag tgggcatcta caatggcacc
1441 cacgtcatcc ctaatgacag gaagatcatc tggccaggcg gagagacaga gaagcctcga
1501 gggtaccaga tgtccaccag actgaagatt gtgacgatcc accaggagcc cttcgtgtac
1561 gtcaagccca cgctgagtga tgggacatgc aaggaggagt tcacagtcaa cggcgaccca
1621 gtcaagaagg tgatctgcac cgggcccaac gacacgtcgc cgggcagccc ccgccacacg
1681 gtgcctcagt gttgctacgg cttttgcatc gacctgctca tcaagctggc acggaccatg
1741 aacttcacct acgaggtgca cctggtggca gatggcaagt tcggcacaca ggagcgggtg
1801 aacaacagca acaagaagga gtggaatggg atgatgggcg agctgctcag cgggcaggca
1861 gacatgatcg tggcgccgct aaccataaac aacgagcgcg cgcagtacat cgagttttcc
1921 aagcccttca gtaccagggg cctgactatt ctggtcaaga aggagattcc ccggagcacg
1981 ctggactcgt tcatgcagcc gttccagagc acactgtggc tgctggtggg gctgtcggtg
2041 cacgtggtgg ccgtgatgct gtacctgctg gaccgcttca gccccttcgg ccggttcaag
2101 gtgaacagcg aggaggagga ggaggacgca ctgaccctgt cctcggccat gtggttctcc
2161 tgggcgtcc tgctcaactc cggcatcggg gaaggcgccc ccagaagctt ctcagcgcgc
2221 atcctgggca tggtgtgggc cggctttgcc atgatcatcg tggcctccta caccgccaac
2281 ctggcggcct tcctggtgct ggaccggccg gaggagcgca tcacgggcat caacgacccc
2341 cggctgagga acccctcgga caagtttatc tacgccacgg tgaagcagag ctccgtggat
2401 atctacttcc ggcgccaggt ggagctgagc accatgtacc ggcatatgga gaagcacaac
2461 tacgagagtg cggcggaggc catccaggcc gtgagagaca acaagctgca tgccttcatc
2521 tgggactcgg cggtgctgga gttcgaggcc tcgcagaagt gcgacctggt gacgactgga
2581 gagctgtttt tccgctcggg cttcggcata ggcatgcgca agacagccc ctggaagcag
2641 aacgtctccc tgtccatcct caagtcccac gagaatggct tcatgaaga cctggacaag
2701 acgtgggttc ggtatcagga atgtgactcg cgcagcaacg cccctgcgac ccttactttt
2761 gagaacatgg ccggggtctt catgctggta gctgggggca tcgtggccgg gatcttcctg
2821 attttcatcg agattgccta caagcggcac aaggatgctc gccggaagca gatgcagctg
```

```
-continued
2881 gcctttgccg ccgttaacgt gtggcggaag aacctgcagg atagaaagag tggtagagca 2941 gagcctgacc ctaaaaagaa agccacattt agggctatca cctccaccct ggcttccagc 3001 ttcaagaggc gtaggtcctc caaagacacg agcaccgggg gtggacgcgg cgctttgcaa 3061 aaccaaaaag acacagtgct gccgcgacgc gctattgaga gggaggaggg ccagctgcag 3121 ctgtgttccc gtcataggga gagctgagac tccccgcccg ccctcctctg cccctcccc 3181 cgcagacaga cagacagacg gacgggacag cggcccggcc cacgcagagc cccggagcac 3241 cacggggtcg ggggaggagc accccagcc tcccccaggc tgcgcctgcc cgcccgccgg 3301 ttggccggct ggccggtcca ccccgtcccg gccccgcgcg tgccccagc gtggggctaa 3361 cgggcgcctt gtctgtgtat ttctattttg cagcagtacc atcccactga tatcacgggc 3421 ccgctcaacc tctcagatcc ctcggtcagc accgtggtgt gaggccccg gaggcgccca 3481 cctgcccagt tagcccggcc aaggacactg atgggtcctg ctgctcggga aggcctgagg 3541 gaagcccacc cgccccagag actgcccacc ctgggcctcc cgtccgtccg cccgcccacc 3601 ccgctgcctg cgggcagcc cctgctggac caaggtgcgg accggagcgg ctgaggacgg 3661 ggcagagctg agtcggctgg caggggccgc agggcgctcc ggcagaggca gggccctggg 3721 gtctctgagc agtggggagc gggggctaac tggccccagg cggaggggct tggagcagag 3781 acggcagccc catccttccc gcagcaccag cctgagccac agtggggccc atggccccag 3841 ctggctgggt cgcccctcct cgggcgcctg cgctcctctg cagcctgagc tccaccctcc 3901 cctcttcttg cggcaccgcc cacccacacc ccgtctgccc cttgacccca cacgccgggg 3961 ctggccctgc cctcccccac ggccgtccct gacttcccag ctggcagcgc ctcccgccgc 4021 ctcgggccgc ctcctccaga ctcgagaggg ctgagcccct cctctcctcg tccggcctgc 4081 agcccagaac gggcctcccc gggggtcccc ggacgctggc tcgggactgt cttcaaccct 4141 gccctgcacc ttgggcacgg gagagcgcca cccgcccgcc cccgccctcg ctccgggtgc 4201 gtgaccggcc cgccaccttg tacagaacca gcactcccag ggcccgagcg cgtgccttcc 4261 ccgtgcggcc cgtgcgcagc cgcgctctgc ccctccgtcc ccagggtgca ggcgcgcacc 4321 gcccaacccc cacctcccgg tgtatgcagt ggtgatgcct aaaggaatgt cacgcagttt 4381 tcaaaaaaaa aaaaaaaaa
```

By "GAD1 polypeptide" (or glutamate decarboxylase 1) is meant a polypeptide or fragment thereof having at least about 85% amino acid identity to NCBI Accession No. Q99259.

```
  1 masstpsssa tssnagadpn ttnlrpttyd twcgvahgct rklglkicgf lqrtnsleek 61 srlvsafker qssknllsce nsdrdarfrr tetdfsnlfa rdllpaknge eqtvqfllev 121 vdillnyvrk tfdrstkvld fhhphqlleg megfnlelsd hpesleqilv dcrdtlkygv 181 rtghprffnq lstgldiigl agewltstan tnmftyeiap vfvlmeqitl kkmreivgws 241 skdgdgifsp ggaisnmysi maarykyfpe vktkgmaavp klvlftseqs hysikkagaa 301 lgfgtdnvil ikcnergkii padfeakile akqkgyvpfy vnatagttvy gafdpiqeia 361 dicekynlwl hvdaawgggl lmsrkhrhkl ngieransvt wnphkmmgvl lqcsailvke 421 kgilqgcnqm cagylfqpdk qydvsydtgd kaiqcgrhvd ifkfwlmwka kgtvgfenqi 481 nkclelaeyl yakiknreef emvfngepeh tnvcfwyipq slrgvpdspq rreklhkvap 541 kikalmmesg ttmvgyqpqg dkanffrmvi snpaatqsdi dflieeierl gqdl
```

By "GAD1 nucleic acid molecule" (or glutamate decarboxylase 1) is meant a polynucleotide encoding an GAD1 polypeptide. An exemplary GAD1 nucleic acid molecule (e.g., mRNA) is provided at NCBI Accession No. BC036552.

```
   1 agcgtgtggt agaggagaaa cgctgaaacc ggaccgaaac ctcgccctag gcttagcgat
  61 ggctaaaaac cggctgggac aagagggagg caagcaacat tccgactcgc tgctttctgg
 121 ctgtctggag tgcaaggtga ctgtggttct tctctggcca agtccgaggg agaacgtaaa
 181 gatatgggcc ttttccccc tctcaccttg tctcaccaaa gtccctagtc cccggagcag
 241 ttagcctctt tctttccagg gaattagcca gacacaacaa cgggaaccag acaccgaacc
 301 agacatgccc gccccgtgcg cctccccc gctggcccac acgccggctg ctgagtgccc
 361 aatggggctt gtagcggctc ggctggaaaa tcgctcactg agcgctcccc tgtgctccta
 421 gcccagtccc ccacacccctt gcgtcttgta ctggccttgg accccaccc cgaccccgac
 481 cccgcctcgt ctcggcgctt cactccaggt cgcgccgatg caccgccaga ctcgagagcg
 541 gcccagggct acgctccctg cgcccagta ccggagctag cgcgcacgtc tcctccgctg
 601 ccccacccc tgcgcacccc taccaggcag gctcgctgcc tttcctccct cttgtctctc
 661 cagagccgga tcttcaaggg gagcctccgt gcccccggct gctcagtccc tccggtgtgc
 721 aggacccccgg aagtcctccc cgcacagctc tcgcttctct ttgcagcctg tttctgcgcc
 781 ggaccagtcg aggactctgg acagtagagg ccccgggacg accgagctga tggcgtcttc
 841 gaccccatct tcgtccgcaa cctcctcgaa cgcgggagcg acccccaata ccactaaccct
 901 gcgccccaca acgtacgata cctggtgcgg cgtggcccat ggatgcacca gaaaactggg
 961 gctcaagatc tgcggcttct tgcaaaggac caacagcctg gaagagaaga gtcgccttgt
1021 gagtgccttc aaggagaggc aatcctccaa gaacctgctt tcctgtgaaa acagcgaccg
1081 ggatgcccgc ttccggcgca cagagactga cttctctaat ctgtttgcta gagatctgct
1141 tccggctaag aacggtgagg agcaaaccgt gcaattcctc ctggaagtgg tggacatact
1201 cctcaactat gtccgcaaga catttgatcg ctccaccaag gtgctggact ttcatcaccc
1261 acaccagttg ctggaaggca tggagggctt caacttggag ctctctgacc accccgagtc
1321 cctggagcag atcctggttg actgcagaga caccttgaag tatggggttc gcacaggtca
1381 tcctcgattt tcaaccagc tctccactgg attggatatt attggcctag ctggagaatg
1441 gctgacatca acggccaata ccaacatgtt tacatatgaa attgcaccag tgtttgtcct
1501 catggaacaa ataacactta agaagatgag agagatagtt ggatggtcaa gtaaagatgg
1561 tgatgggata ttttctcctg ggggcgccat atccaacatg tacagcatca tggctgctcg
1621 ctacaagtac ttcccggaag ttaagacaaa gggcatggcg gctgtgccta aactggtcct
1681 cttcacctca gaacagagtc actattccat aaagaaagct ggggctgcac ttggctttgg
1741 aactgacaat gtgattttga taaagtgcaa tgaaagggg aaaataattc cagctgattt
1801 tgaggcaaaa attcttgaag ccaaacagaa gggatatgtt cccttttatg tcaatgcaac
1861 tgctggcacg actgtttatg gagcttttga tccgatacaa gagattgcag atatatgtga
1921 gaaatataac ctttggttgc atgtcgatgg atttaacttc tcacaattgg ccaataggat
1981 catctgccct tgctactgaac taatgactaa caaaggctgt gtcacgtggc atcccaacta
2041 ttcagtaaac atgcatcatg gctgcctggg gaggtgggct gctcatgtcc aggaagcacc
2101 accataaact caacggcata gaaagggcca actcagtcac ctggaaccct cacaagatga
2161 tgggcgtgct gttgcagtgc tctgccattc tcgtcaagga aaagggtata ctccaaggat
```

```
-continued
2221 gcaaccagat gtgtgcagga tacctcttcc agccagacaa gcagtatgat gtctcctacg 2281 acaccgggga caaggcaatt cagtgtggcc gccacgtgga tatcttcaag ttctggctga 2341 tgtggaaagc aaagggcaca gtgggatttg aaaaccagat caacaaatgc ctggaactgg 2401 ctgaatacct ctatgccaag attaaaaaca gagaagaatt tgagatggtt ttcaatggcg 2461 agcctgagca cacaaacgtc tgttttggt atattccaca aagcctcagg ggtgtgccag 2521 acagccctca cgacgggaa aagctacaca aggtggctcc aaaaatcaaa gccctgatga 2581 tggagtcagg tacgaccatg gttggctacc agccccaagg ggacaaggcc aacttcttcc 2641 ggatggtcat ctccaaccca gccgctaccc agtctgacat tgacttcctc attgaggaga 2701 tagaaagact gggccaggat ctgtaatcat ccttcgcaga acatgagttt atgggaatgc 2761 cttttccctc tggcactcca gaacaaacct ctatatgttg ctgaaacaca caggccattt 2821 cattgaggga aaacataata tcttgaagaa tattgttaaa accttactta aagcttgttt 2881 gttctagtta gcaggaaata gtgttctttt taaaagttg cacattagga acagagtata 2941 tatgtacagt tatacatacc tctctctata tatacatgta tagtgagtgt ggcttagtaa 3001 tagatcacgg catgtttccc gctccaagag aattcacttt accttcagca gttaccgagg 3061 agctaaacat gctgccaacc agcttgtcca acaactccag gaaaactgtt tttcaaaacg 3121 ccatgtccta ggggccaagg gaaatgctgt tggtgagaat cgacctcact gtcagcgttt 3181 ctccacctga agtgatgatg gatgagaaaa acaccacca aatgacaagt cacaccctcc 3241 ccattagtat cctgttaggg gaaaatagta gcagagtcat tgttacaggt gtactatggc 3301 tgtattttta gagattaatt tgtgtagatt gtgtaaattc ctgttgtctg accttggtgg 3361 tgggagggggg agactatgtg tcatgatttc aatgattgtt taattgtagg tcaatgaaat 3421 atttgcttat ttatattcag agatgtacca tgttaaagag gcgtcttgta ttttcttccc 3481 atttgtaatg tatcttattt atatatgaag taagttctga aaactgttta tggtattttc 3541 gtgcatttgt gagccaaaga gaaaagatta aaattagtga gatttgtatt tatattagag 3601 tgcccttaaa ataatgattt aagcatttta ctgtctgtaa gagaattcta agattgtaca 3661 taaagtcata tatatggaaa tcctgttact taaatagcat ctgctcttct cttacgctct 3721 ctgtctggct gtacgtctgg tgttctcaat gcttttctag caactgttgg ataataacta 3781 gatctcctgt aattttgtag tagttgatga ccaatctctg ttactcgctt agctgaaacc 3841 taaggcaaca tttccgaaga ccttctgaag atctcagata aagtgaccag gctcacaact 3901 gtttttgaag aagggaaatt cacactgtgc gttttagagt atgcaagaag aatataaata 3961 aataaaaata ttctccatgg agaatttgaa caaaaaaaa aaaaaaa
```

By "GABA polypeptide" (or gamma-Aminobutyric acid) is meant a polypeptide or fragment thereof having at least about 85% amino acid identity to NCBI Accession No. P30531.

```
  1 matngskvad gqistevsea pvandkpktl vvkvqkkaad lpdrdtwkgr fdflmscvgy 61 aiglgnvwrf pylcgknggg aflipyfltl ifagvplfll ecslgqytsi gglgvwklap 121 mfkgvglaaa vlsfwlniyy iviiswaiyy lynsfttttlp wkqcdnpwnt drcfsnysmv 181 nttnmtsavv efwernmhqm tdgldkpgqi rwplaitlai awilvyfciw kgvgwtgkvv 241 yfsatypyim liilffrgvt lpgakegilf yitpnfrkls dsevvwldaat qiffsyglgl 301 gslialgsyn sfhnnvyrds iivccinsct smfagfvifs ivgfmahvtk rsiadvaasg 361 pglaflaype avtqlpispl wailffsmll mlgidsqfct vegfitalvd eyprllrnrr
```

```
421 elfiaavcii syliglsnit qggiyvfklf dyysasgmsl lflvffecvs iswfygvnrf 481 ydniqemvgs rpciwwklcw sfftpiivag vfifsavqmt pltmgnyvfp kwgqgvgwlm 541 alssmvlipg ymaymfltlk gslkqriqvm vqpsedivrp engpeqpqag sstskeayi
```

By "GABA nucleic acid molecule" (or gamma-Aminobutyric acid) is meant a polynucleotide encoding an GABA polypeptide. An exemplary GABA nucleic acid molecule (e.g., mRNA) is provided at NCBI Accession No. U76343.

```
   1 gtagcttcac taaggtggga tggatagcag ggtctcaggc acaaccagta atggagagac
  61 aaaaccantg tatcacaaga tggagtttgt gctgtcagtg gctggggaga tcattggctt
 121 aggcaacgtc tggaggtttc cctatctctg ctacaaaaat gggggaggtg ccttcttcat
 181 cccctacctc gtcttcctct ttacctgtgg cattcctgtc ttccttctgg agacagcact
 241 aggccagtac actagccagg gaggcgtcac agcctggagg aagatctgcc ccatctttga
 301 gggcattggc tatgcctccc agatgatcgt catcctcctc aacgtctact acatcattgt
 361 gttggcctgg gccctgttct acctcttcag cagcttcacc atcgacctgc cctggggcgg
 421 ctgctaccat gagtggaaca cagaacactg tatggagttc cagaagacca acggctccct
 481 gaatggtacc tctgagaatg ccacctctcc tgtcatcgag ttctgggagc ggcgggtctt
 541 gaagatctct gatgggatcc agcacctggg ggccctgcgc tgggagctgg ctctgtgcct
 601 cctgctggcc tgggtcatct gctacttctg catctggaag ggggtgaagt ccacaggcaa
 661 ggtggtgtac ttcacggcca catttcctta cctcatgctg gtggtcctgt taattcgagg
 721 ggtgacgttg cctggggcag cccaaggaat tcagttttac ctgtacccaa acctcacgcg
 781 tctgtgggat ccccaggtgt ggatggatgc aggcacccag atattcttct ccttcgccat
 841 ctgtcttggg tgcctgacag ccctgggcag ctacaacaag taccacaaca actgctacag
 901 cggcaccagc tttgtggccg gctttgccat cttctccatc ctgggcttca tgtctcagga
 961 gcaggggtg cccatttctg aggtggccga gtcaggccct ggcctggctt tcatcgctta
1021 cccgcgggct gtggtgatgc tgcccttctc tcctctctgg gcctgctgtt tcttcttcat
1081 ggtcgttctc ctgggactgg atagccagtt tgtgtgtgta gaaagcctgg tgacagcgct
1141 ggtggacatg taccctcacg tgttccgcaa gaagaaccgg agggaagtcc tcatccttgg
1201 agtatctgtc gtctccttcc ctgtggggct gatcatgctc acagagggcg gaatgtacgt
1261 gttccagctc tttgactact atgcggccaa tggcatgtgc ctcctgttcg tggccatctt
1321 cgagtccctc tgtgtggctt gggtttacgg agccaagcgc ttctacgaca acatcgaaga
1381 catgattggg tacaggccat ggcctcttat caaatactgt tggctcttcc tcacaccagc
1441 tgtgtgcaca gccacctttc tcttctccct gataaagtac actccgctga cctacaacaa
1501 gaagtacacg tacccgtggt ggggcgatgc cctgggctgg ctcctggctc tgtcctcctg
1561 gtctgcattc ctgcctggag cctctacaga ctcggaaccc tcaagggccc cttcagagag
1621 agaatccgtc agctcatgtg cccagccgag gacctgcccc agcggaaccc agcaggaccc
1681 tcggctcccg ccaccccag gacctcactg ctcagactca cagagctaga gtctcactgc
1741 taggggcag gcccttggat ggtgcctgtg tgcctggcct tggggatggc tgtggaggga
1801 acgtggcaga agcagcccca tgtgttccct gccccgacc tggagtggat aagacaagag
1861 gggtattttg gagtccacct gctgagctgg aggcctccca ctgcaacttt tcagctcagg
1921 ggttgttgaa cagatgtgaa aaggccagtg ccaagagtgt ccctcggaga cccttgaagg
1981 c
```

By "TH polypeptide" (or Tyrosine Hydroxylase) is meant a polypeptide or fragment thereof having at least about 85% amino acid identity to NCBI Accession No. NP_002692.

```
  1 mptpdattpq akgfrravse ldakqaeaim vrgqgapgps ltgspwpgta apaasytptp
 61 rsprfigrrq sliedarker eaavaaaaaa vpsepgdple avafeekegk avlnllfspr
121 atkpsalsra vkvfetfeak ihhletrpaq rpraggphle yfvrlevrrg dlaallsgvr
181 qvsedvrspa gpkvpwfprk vseldkchhl vtkfdpdldl dhpgfsdqvy rqrrkliaei
241 afqyrhgdpi prveytaeei atwkevyttl kglyathacg ehleafalle rfsgyredni
301 pqledvsrfl kertgfqlrp vagllsardf laslafrvfq ctqyirhass pmhspepdcc
361 hellghvpml adrtfaqfsq diglaslgas deeieklstl ywftvefglc kqngevkayg
421 agllssygel lhclseepei rafdpeaaav qpyqdqtyqs vyfvsesfsd akdklrsyas
481 riqrpfsvkf dpytlaidvl dspqavrrsl egvqdeldtl ahalsaig
```

By "TH nucleic acid molecule" (or Tyrosine Hydroxylase) is meant a polynucleotide encoding an TH polypeptide. An exemplary TH nucleic acid molecule is provided at NCBI Accession No. NG_008128.

```
   1 gcgggggggc agtgtgtgct ccagcatgtg tgtgtgtgtg tgcatgtaca cgtgtgcacc
  61 tgtatcgcct gtgtgtgtgc atgtgatgtg tacacgtgtc atgcatgcac gcacatgtgt
 121 agtgtgtgct cgtgtgtggt gtgtgcctgt gtcatgtatg agcacacttg tatatgttgt
 181 gtgtactgtg tcatatatga gtgtgtttgc ctgtgtagtg catgcacatc cgtgtgtgca
 241 tctggtgtgt ccgtgggtca ttacgagtgc atcgtatgtg tatcgtgtac atgagtacac
 301 ttgtatgtgt ggtgtgtaca ggtgccatgt aagtgtgctt gtacatatat gcatgcatgt
 361 gtcatatgca tctgtgtgtg catgtgtgtg gtgcacacat gtgttatgtc tgagtgtgcc
 421 tgtatgtgtg ctatgtacac gtcatgtgtg agtgtgcttg catgtgcagt gtgtggatgc
 481 tgcttgtacc tgtggtgtgt acctgtgtca tgggtgctca cacgtgcatg gagtgttgtg
 541 tgtgtgcttg tgtgccccat gtgtgcatgt gtgtgtgcct cacacagatg cctgcatttg
 601 cctaggcact tgcaagagga ccatgctg gctctcaaag atcacagggc cacctgagcc
 661 ctgtgcacac cacagccagg ccatggctag accctgcaga gccacagggc gatgcctgtc
 721 agccagggga cccagaacac ctcctgggct cctccccagc acatggctgg gctcctccag
 781 caggcctgga tttgggaagg gcccgtggtg ggcaaggctg gtgctgggga gcaggcctgg
 841 tggcctcaga gactcgccct gtgggcggag cagcctcaca gccaggtcga agtcagcact
 901 ctgacctgc cccacgcggg gagtgggcac cagtcccagg gcacagacgt gctgggtgat
 961 taatctgggt gattaagcct cgggctgaga ggctgttgag agagaacacg ctccattgtg
1021 gagctggctc agcattcctt acggccatgg tggcaggggc tgtaaccaca gggacggcgg
1081 aagtggtgga gggtggtggg gtatggaggg aagcccagag ggctccgtgc aggaaggtgg
1141 agcctggtgc aatggagggg acagcaaggg ctcctcagac ctctgcgggg ccccccactcc
1201 cctggtcacc tgttttgtct ctgatctggc ctgggtcggc cctcactcct ggccccacct
1261 catagccccc cctggtgggg ctccgctcca gcccttctcc ttcccagggg ccagtatgct
1321 ggccccaggg gtctcttggg gcgtgacctc ggcctccaga gaaccctgtc ccagctctgc
1381 ccttccctct ggggtctctg tagatgggac gctggtcaca gcagcctgtc tgatttgttc
1441 cctgtggcct aggttcctga gccccacagt gccagggat ggatgccacc ggatctttga
1501 aagaccagtg tcaggccggg cgcagtggct cacgcctgta atcccagcac tttgggaggc
```

-continued

```
1561  cgaggtgggc ggatcacgaa gtcaggagat cgagaccatc ctggctaaca cagtgaaacc
1621  ccgtctccac taaaaataca aaaagttagc tgggcgtggt ggtgggcgcc tgtagtccca
1681  gctacttggg aggctgaggc aggagaatgg cgtgaaccgg ggaggcggag cttgcagtga
1741  gccgagatcg cgccattgca ctccagcctg ggtgacagag cgagactcgg tctcaaaaaa
1801  aaagaaaaaa aggaaagacc agtgtcttgg agttgggaa  acctgggctg agactcact
1861  gcatgacccc tgagaagttg cacctcagaa cctcagtcct cgcatctgca gaatgggtct
1921  gtgaacacct cagctgcccg aacgtggatg ccgcaggctg acccagcact gagctctacc
1981  aagaccaggg gccagccgtg tgctcccctcc aggcctgtgc cagcgtgga  gaggcctcgt
2041  cccgtgggcg ctggagtgga gccttcctgg tgtttgtgga catctctgga gagggccaga
2101  ggcaggtggg tgacacgggg catggctcaa tcatgggtgg tccagactgg agaggtaccc
2161  tcgggctggg agcggggagg ctggccaggg tagactttttg gggcctccat ggataccctc
2221  accatctgga atcggagagg ggcacggcac aaaggagggc ggggccaggg ccaggactgg
2281  agtcgggggc acctctgtgc caacaggggc cttggatctg gggtacagca tggttccccg
2341  gccctgaagg ggctggcgtg tgggacaggc ttcccaggaa tggataggca gggatggatg
2401  ctgcctgatt ggggcgggag gctggaggca gggcaggtgc aggcacctga gggcagcact
2461  cacctccaca ggggtccagg ggcctcccca gcctcagcac ctggcctggg ctcctgcctc
2521  cagagagcct ggccccaagg aagagtctag taagcttagt tcccatcggg cttccatgaa
2581  agcacaactg cccggcagg  aaaccgaatt aaaaagcaat atttgtatca gtggaagaca
2641  tttgctgaaa ggttaaatcc acatccggca gtgtgggcca tgagcctccg gcgtggtgtt
2701  catcaggcat gtctctcctc ctggcctggg cacctgagca ctggggccgc cctgggcaga
2761  gctggggcgg ggtgctgggg ggcctggagc tgcctcaccg agggatcctc agcagccgac
2821  cctggggggag gcaaatgaga ctctttctgg ggaccttgag gggagctcgg gggagccatg
2881  cagagcttca ccaggcctgg acactgggca tggaggctgg gccacccaag ggccatcacc
2941  agggactcag gtgggtgggc ctcagccctg ggtgacagaa gctcacgggc gcagggcga
3001  ggccagaggc tgagccttca ggctgaggtc ttggaggcaa atccctccaa cgcccttctg
3061  agcaggcacc cagacctact gtgggcagga cccacaggag gtggaggcct ttggggaaca
3121  ctgtggaggg gcatagcatc tccagagag  gacagggtct gcactgggtg ctgagagaca
3181  gcaggggccg agcggtaggc ttccctgccc ccagggatgt tccagaggag cgcaagggag
3241  gggcattaat atcgtggcaa gaaagggcag gcattgcaga gtgagcagcg acggaactgg
3301  gttttgtggg atgcatagga gttcacccgg ataagaggtg ggtgaggaat gacactgcaa
3361  accggggatc acggagcccc aaatccttct gggccaggaa gtgggaaggg ttgggggtc
3421  ttcccttttgc tttgactgag cactcagcct gcctgcagag ggcagcgagg agccacggag
3481  gggtgtggga cagggatgcc atggctgaag cagttttagg aaaggtccca ggggctattg
3541  ttgaagagag aacggggagc ggggagtccc acagctgaca ggagcagagt gggccctgag
3601  agatgccagc tctggctgcc acagtgacca gccggggtag gccttcgaga agtcagggag
3661  cgtctagggc ttctggctcc tgctgggccc agggtgtcat cttgggctgc caacaccaga
3721  aagcccagca gatacaggaa gccccaagcc ctgtcggaaa cggttcttct ccaggaggga
3781  cagcggtggc agcgttcagc cgcaggccat gcactctggg ccacgtcct  tccctctgta
3841  cagtccagca ttgtcaaggc aggctctggc catctctgct gaccccagag ggatggggag
3901  gcctcccctt ccaccagaag ggccagaagc caccctgggc aggggcatca ctctccctgg
```

```
-continued
3961  gtggggcagc ggctgggagc aggaggtgcc agtgggcgtg ggctggatgc gggtgcctgc
4021  ggggcggaca tggaacttgg gggaggctct aggctggggt tgtcctcaag ggagttctca
4081  ggtcacccca gggtcaccct caacccgggg cctggtgggg tagaggagaa actgcaaagg
4141  tctctccaag gggaaggcat cagggccctc agcactgagg acgtgcgtg ctctttaaag
4201  aaggggccac aggaccccga gggaagccag gagctagcag tgggccatag aggggctgag
4261  tggggtgggt ggaagccgtc cctggccctg gtcgccctgg caaccctggt ggggactgtg
4321  atgcaggagg tggcagccat ttggaaacgc gtggcgtctc cttagagatg tcttcttcag
4381  cctcccaggg tcctccacac tggacaggtg ggccctcctg ggacattctg accccacgg
4441  ggcgagcttg ggaagccgct gcaagggcca cacctgcagg gcccggggc tgtgggcaga
4501  tggcactcct aggaaccacg tctatgagac acacggcctg gaatcttctg gagaagcaaa
4561  caaattgcct cctgacatct gaggctggag gctggattcc ccgtcttggg gctttctggg
4621  tcggtctgcc acgaggttct ggtgttcatt aaaagtgtgc ccctgggctg ccagaaagcc
4681  cctccctgtg tgctctcttg agggctgtgg ggccaagggg accctggctg tctcagcccc
4741  ccgcagagca cgagcccctg gtccccgcaa gcccgcgggc tgaggatgat tcagacaggg
4801  ctggggagtg aaggcaatta gattccacgg acgagccctt tctcctgcgc ctccctcctt
4861  cctcacccac ccccgcctcc atcaggcaca gcaggcaggg gtgggggatg taaggagggg
4921  aaggtggggg acccagaggg ggctttgacg tcagctcagc ttataagagg ctgctgggcc
4981  agggctgtgg agacggagcc cggacctcca cactgagcca tgcccacccc cgacgccacc
5041  acgccacagg ccaagggctt ccgcagggcc gtgtctgagc tggacgccaa gcaggcagag
5101  gccatcatgg taagagggca ggtaggtgcc cggcggccgc agtggaccgg agcccagggc
5161  tggtgccagc tgcctctgct actccccagc ctggctggca gccccaggct cagggtccat
5221  gcaaaccct gggacgcggc gtggatgtgg aggcctgggc acagcggcat ccctgtgcc
5281  tggtgtttga gtccctgttg ggggagggtg aggtgatgcc tgtccctgtg tgtgcccctc
5341  ttaggccgac ctctctcggg ggtcgtgtgg gtctctgtgt cttgtttcat cttgaatctt
5401  aacgatcgga atgtggaaac aaatccatcc aaaaaatcca agatggccag aggtccccgg
5461  ctgctgcacc cagcccccac cctactccca cctgcccctg cctccctctg ccccagctgc
5521  cctagtcagc acccccaacca gcctgcctgc ttggggaggc agccccaagg cccttcccag
5581  gctctagcag cagctcatgg tgggggtcc tgggcaaata gggggcaaaa ttcaaagggt
5641  atctgggctc tggggtgatt cccattggcc tgttcctccc ttatttccct cattcattca
5701  ttcattcatt cattcattca ccatggagtc tgtgttccct gtgacctgca ctcggaagcc
5761  ctgtgtacag gggactgtgt gggccaggct ggataatcgg gagcttttca gcccacagga
5821  ggggtcttcg gtgcctcctt gggcactcag aaccttgggc tccctggcac atttaaaatg
5881  ggttttatt tatggacctt gattgaaatg tggtgtgagt tgtagcagtg tcatttccag
5941  gtaccttctc agggacacag ggcgccctcc ccgtcctcc ccgccctcc cctaccctcc
6001  cccaccagc tcccatcag gcatccctc cagggcgc ccgggcc agcctcacag
6061  gctctccgtg gcctggaact gcagccccag ctgcatccta caccccacc ccaagggtaa
6121  gtaagagggg actctgggag gggcttctgc tgctccctt catgttccac aaccctggaa
6181  gctcaggatg aagctgattc ttctcttaca aggggccag agccttcttg ggagttcagc
6241  tccaagggat gagccccagg tgtctgccaa gtccccctct gtccaggcct gggacggctc
6301  tgggatcgag gggtcagagg cgctgagccc agggagagac acctgcgccc agagctatga
6361  caaagggtgg agggatgaca aggcagccag gagcgggcgc ctgcggggtg gcacagaggg
```

-continued

```
6421  gcagggcccg aggacaggtg tcctgatggg agtgtgagaa agggtcccct gtgcggcagc
6481  caggagggta gggggggttgt tcactggggc cctgtggggg cagctccttc ctgagctgcc
6541  gttccctccc cggcagccga tgccactgtc catcaagaca tcgccctctt cccatcacta
6601  atccagttag cgcctggcct ggggatgagt gacacagcgt ctctgtctgt ctgctcgcca
6661  cagagtgggg agcaggcgag caccttccca gcccccactc ctcccccacc accactgctt
6721  ctgactgggc tgcccccatc gggaagggcg tgcaatgccc gcaggcacct cggctagcat
6781  ctgccccagc aggcacacag taggcgctca aaaacgtgct ctcatcccct gcctctgtgt
6841  gccatcagcg ctgcccgact gtgggaccag ctgtgggtgg aggtccccgg gtctcagcag
6901  gtggaggagg catgggtgcc ccttgtcccc acagtccccg cggttcattg ggcgcaggca
6961  gagcctcatc gaggacgccc gcaaggagcg ggaggcgcg gtggcagcag cggccgctgc
7021  agtcccctcg gagcccgggg accccctgga ggctgtggcc tttgaggaga aggaggggaa
7081  ggccgtgcta aacctgctct tctccccgag ggccaccaag ccctcggcgc tgtcccgagc
7141  tgtgaaggtg tttgaggtga gctggtggcc ttcgtgtccc tggggcaagt tcacctgtgg
7201  gtggggctgt gtgggctgag ttcctgaccc ctctatagca gaggtgcagc tgcccaggcc
7261  cccgaggccg gcacaggatg cagcagggga gtctcaggcc tcagctcagc ccccatggca
7321  tctagccaca ccccgtgtt tttgagggat cctgagccca cccctagggc tgaggctacc
7381  aagccccact gtgcctcttg ccttgcccat cccctggatc cccctcaccc accatttccc
7441  acgtgggggg ctcccagcag ggcagcacaa gaggcagggg cagggcagtg tgccctctcc
7501  cacccaccca gcacagtggc tcaggtgacc actgattgca ttagtcactc cggccccact
7561  gtgccccggg aggcaggtga cccagctccc ggaagaagct cccaaatgac attaaagcca
7621  gactccccgc cccccagctc ccagagccag ttttgtggcc cgagggccac tgcgacccac
7681  cgcccttgtt gctaggcaac aggaggtggg ggtggagcgg acccttctgg ccagtgtcct
7741  ggacgctcag gggccagtga gactcagggc ccatcctaca aacctggatg aggccaccag
7801  ggttgggggc accttctgac cagtggctga ggagccggac tgtgtggcat ggccttggga
7861  cacacacacc gagccgccca gaaccaggtt aagcctcaag cggtgacaac tcctggttag
7921  gcacgtaaca caaaatccaa cttgccagtg caaaccctg gcctggtggc cgacagctga
7981  cctgagcctg gaagaacggg atcgtgtgc tgctagcaca aaagtcaagg gcagggcctg
8041  gccagccagc cagatgtgcc tcctccccgc ccaccccacc ctctctctcc atctctgtct
8101  ctttctcctt ctctctctct tcctgctttt gctccctaag acgtttgaag ccaaaatcca
8161  ccatctagag acccggcccg cccagaggcc gcgagctggg ggcccccacc tggagtactt
8221  cgtgcgcctc gaggtgcgcc gaggggacct ggccgccctg ctcagtggtg tgcgccaggt
8281  gtcagaggac gtgcgcagcc ccgcggggcc caagggtgag gcggttttct gtccttgagg
8341  gccaccaaat gaccttgaga ggctggggtg caggggctcc tgcaggggga ccctacagtg
8401  accacgtggt ggtggcctgg ttccctctct gcgggctcca ctccgcaccc cgttttgcta
8461  cacatccgtg tccgggcctg gggccactcc aggatccccc cgcagctctc acagcccgg
8521  ctgcctctgc cccccggaag tcttgtaggg gaggctgctt caaggtgggt gacacagccc
8581  cacggctccg agctcaccaa gatctcttcc tccatcaccc ataaagtccc ctggttccca
8641  agaaaagtgt cagagctgga caagtgtcat cacctggtca ccaagttcga ccctgacctg
8701  gacttggacc acccggtgag tggtgcgccc ctcactcagg cctcctgccc ctgatcacat
8761  cccctaccct tagcccaacc ctggacagga gtctgtcggc tccaggagcc tccgtggcct
```

```
-continued
 8821 gtgccccac cccagcacag cctcctgacc cgtgcatccc ctctgccctc agggcttctc
 8881 ggaccaggtg taccgccagc gcaggaagct gattgctgag atcgccttcc agtacaggca
 8941 gtgagggggcc cctgcgctcg ggacccagac tccgtcctgc aggctgacgc tggacctggg
 9001 gggtgggagg gaaggacaaa ggggaggacc catcttgtca ccagcatcag tgcctcctgc
 9061 caggcagctc tgctccaggg ctttccatgt ccccaaatcc cagtggggaa actgaggccc
 9121 aggggggcta gagcaacctg ccgaggccac atagccggct cacggcacag tcagctgggg
 9181 tgcaccctcc tgtccatcct ccaacccaaa ggcctcgctg cactaggcgg gtgtggacct
 9241 gtgcccagtg aagctccctc cctccctcct gcccttctca ctccccgagg ggacctgctg
 9301 accactggcc ccctccccag cggcgacccg attccccgtg tggagtacac cgccgaggag
 9361 attgccacct ggtgagacct ccgtgcagct aggggctggg gaggagcccg ggggatgcct
 9421 cctggaatcc tggcgtgtga gggccgcctc cagggacctt ggcacaacag gagagactaa
 9481 ggccgggaag aagagggact tgcagggctc agaatgttgg gttgggagga agaggctacc
 9541 catcctgtcg ggccatcccc agtgtgctga gggaccgccc ctcatggccc cctatcccct
 9601 gggattccct aaagccacca gcaaaagccc ctcccggggg cctgggtctt caggggtccc
 9661 caagaggcct gcgttggtag gggctcaggc aggcagaggc acccacagtt caggagggggg
 9721 gtttcgggca ctggggtggg gcattagagg gccctgagcc tggctgcccg caggaaggag
 9781 gtctacacca cgctgaaggg cctctacgcc acgcacgcct gcggggagca cctggaggcc
 9841 tttgctttgc tggagcgctt cagcggctac cgggaagaca atatcccca gctggaggac
 9901 gtctcccgct tcctgaaggg tgtgcccaga cgggaggggc gcagagccgg ggggccgggg
 9961 atggtcagcc aagcgcccca ccccagcgcg gctccagccc gtcccggctc ggcagtgacc
10021 cgcgtggccc cttgcagagc gcacgggctt ccagctgcgg cctgtggccg gctgctgtc
10081 cgcccgggac ttcctggcca gcctggcctt ccgcgtgttc cagtgcaccc agtatatccg
10141 ccacgcgtcc tcgcccatgc actcccctga gccgtgagtg cgcgccctgg ccgccagccc
10201 gagggtgggg ggtgcgacgg gcggcccctc agccccttc tccctcctac gcgcagggac
10261 tgctgccacg agctgctggg gcacgtgccc atgctggccg accgcacctt cgcgcagttc
10321 tcgcaggtac gccgcggcct cggagggagc cggggtcacc caggggctgg cttggcgccg
10381 ggggcgggcg gggatcgatg tgcgggtggg tgaagtgtgc tgcctgctcc cgggcccccgc
10441 caaggaggct cggcgccccg agggtcgcgc ggcatagggc ggggctggag cggagcctcc
10501 cacggcctgt gctgccacct gccggctacc tgggaacggc gcccacgggc ttaggaatgt
10561 ggtcaaggag ggctgcctgg aggaggaggc ccggtggagg tgcggatcct gggcggccag
10621 ggaaggtctc tgccgccagg gaagtgtccc agagacccct ggaggggctg ctgacacccc
10681 cggtgccccc acctcgagca tgacccaggg ctgcctctcc ccatccttca tcctccctgc
10741 tccacaggac attggcctgg cgtccctggg ggcctcggat gaggaaattg agaagctgtc
10801 cacggtgggt tgaccccctcc ctgcagggcc tggggtgtgg gtttgggggt ctgaatccag
10861 gcctcaccct cttgccgtcc aggctgaggc ctctccttcc acccacgaat tgtgaccctc
10921 accctggcct gcctgcatcc tggcctggcc tccctggggg tggtatcctg gtcacgggtg
10981 accaggggct gcccggtggg cggcagctgt ctctgggctg atgctgcccg gcttccccgc
11041 agctgtactg gttcacggtg gagttcgggc tgtgtaagca gaacggggag gtgaaggcct
11101 atggtgccgg gctgctgtcc tcctacgggg agctcctggt gagagtctct ccttgctgca
11161 gccccagca gaggggcagg gctgggggac ggtgcaggga ggggacaggc tcccagtggg
11221 aggaaactga ggcctggacc tccaggactc aggctctgtt tgggagaagg cttgtctctg
```

```
11281 cccagtcctc accccacatt atcccaggcc tccgaaggcc cggcggggga gatggggtg
11341 actctaccca aggaacccac ccagcgtcag gccacggtgc cccagttccc tcggggacct
11401 gggtgcagtg gagtcagtga tgccattggc ctcctgccag cactgcctgt ctgaggagcc
11461 tgagattcgg gccttcgacc ctgaggctgc ggccgtgcag ccctaccaag accagacgta
11521 ccagtcagtc tacttcgtgt ctgagagctt cagtgacgcc aaggacaagc tcaggtgggc
11581 taggctgcta gggcaagccc cccatggtgc ccccaaactg ggccagccag gccttccttc
11641 tggccttgag cagggctgga cctgtgagcc caggtcacag atgagaaaac cgacccctgg
11701 ttgcagcagc ccccacacag cagggacacc atccgtgaga aggaccccag cgtctgggga
11761 ggggcagacc tacaggactg ggggctgctg ggtggccggg tcaaggccag tcttggaggt
11821 gctgacagag cctgagcttt gtgaggacgt cctgtggaac ctgtcccggc ccctgccct
11881 gggatgggga gaagtcaggg ggatagacag agtcaaggtg ggggacaggg cgggagtggg
11941 gtccccaggg ctgggggcct ttggtgcagt gaccagagtg tcaggagagg ggagcaaagc
12001 cctctagcct catcctcata aaaggtctca tcattttccc tccagcctct tatgcactgg
12061 ggaaactgag gccaggggct atgtgtccag cggacagggg tgctgaattc cacccacagg
12121 cttagggata tggtcaagga aagcttcctg gaggaggccc agtggaggtt cagggaggga
12181 tggggtgccc ggcagtctct agtggaaaag cgcctagcc tatctccccc atgaaccccc
12241 tcacccagcc ctggaagagg cctcagtgtc ccgcctgtga ccagttggct cagaaaagcc
12301 ctgggagctc tgagccactg tgaaggtgga aacgcggccc ctggcctccc ctctcctgga
12361 ggctgcagac tctgcccgcc agttgacgag ggctctgccg ctctcctccc caggagctat
12421 gcctcacgca tccagcgccc cttctccgtg aagttcgacc cgtacacgct ggccatcgac
12481 gtgctggaca gcccccaggc cgtgcggcgc tccctggagg gtgtccagga tgagctggac
12541 acccttgccc atgcgctgag tgccattggc taggtgcacg gcgtccctga gggcccttcc
12601 caacctcccc tggtcctgca ctgtcccgga gctcaggccc tggtgagggg ctgggtcccg
12661 ggtgccccc atgccctccc tgctgccagg ctcccactgc ccctgcacct gcttctcagc
12721 gcaacagctg tgtgtgcccg tggtgaggtt gtgctgcctg tggtgaggtc ctgtcctggc
12781 tcccagggtc ctgggggctg ctgcactgcc ctccgccctt ccctgacact gtctgctgcc
12841 ccaatcaccg tcacaataaa agaaactgtg gtctctacac ctgcctggcc ccacatctgt
12901 gccacagaga cagaccctgg gatcctcaga ctcccacacc cccaccccag cctcactcag
12961 aggtttcgcc ctggcctcct tcctcctctg ggagatggct ggccgccctg gccaggcagc
13021 tggcccctcc gggcctggtt tccccgctca ccctgaggcc ccgcccagct ctgagcccca
13081 agcagctcca gaggctcggg caccctggcc gagctgcccc atctccgtgg ggtgccctcc
13141 caaggtgggg agccacgtga cagtgggagg gcctctctca ggcctggcag ggagcagggg
13201 tcacaaactg tgctggctgg gggtggtctc agaggtgggc ctgcaggcct aaccctccct
13261 gctgacaggg ctcccagccc ttgagagaaa cagggatgga ggaacagctg ccctgatgcc
13321 ctcacccacc cggagcaggc cctgcgaacc aaggggaacc tcagtgtggc ccccagcatg
13381 tgtgctgatg gggagggtct ggctgagctg gtgcccaggc agatggtctg ggcctgtctc
13441 cccagcgagg caggatgggg gctggatttc agactctgta agatgcccct ggcttactcg
13501 aggggctgg acattgccct ccagagagag cacccaacac cctccaggct tgaccggcca
13561 gggtgtcccc ttcctacctt ggagagagca gccccagggc atcctgcagg gggtgctggg
13621 acaccagctg gccttcaagg tctctgcctc cctccagcca ccccactaca cgctgctggg
```

```
13681 atcctggatc tcagctcccc ggccgacaac actggcaaac tcctactcat ccacgaaggc 13741 cctcctgggc atggtggtcc ttcccagcct ggcagtctgt tcctcacaca ccttgttagt 13801 gcccagcccc tgaggttgca gctgggggtg tctctgaagg gctgtgagcc cccaggaagc 13861 cctggggaag tgcctgcctt gcctccccccc ggccctgcca gcgcctggct ctgccctcct 13921 acctgggctc ccccatcca gcctccctcc ctacacactc ctctcaagga ggcacccatg 13981 tcctctccag ctgccgggcc tcagagcact gtggcgtcct ggggcagcca ccgcatgtcc 14041 tgctgtggca tggctcaggg tggaaagggc ggaagggagg ggtcctgcag atagctggtg 14101 cccactacca aacccgctcg gggcaggaga gccaaaggct gggtgtgtgc agagcggccc 14161 cgagaggttc cgaggctgag gccagggtgg gacatacggga tgcgagggc cggggcacag 14221 gatactccaa cctgcctgcc cccatggtct catcctcctg cttctgggac ctcctgatcc 14281 tgccctggt gctaagaggc aggtaggggc tgcaggcagc agggctcgga gcccatgccc 14341 cctcaccatg ggtcaggctg gacctccagg tgcctgttct ggggagctgg gagggccgga 14401 ggggtgtacc ccaggggctc agcccagatg acactatggg ggtgatggtg tcatgggacc 14461 tggccaggag agggagatg ggctcccaga agaggagtgg gggctgagag ggtgcctggg 14521 gggccaggac ggagctgggc cagtgcacag cttcccacac ctgcccaccc ccagagtcct 14581 gccgccaccc ccagatcaca cggaagatga ggtccgagtg gcctgctgag gacttgctgc 14641 ttgtcccag gtccccaggt catgccctcc ttctgccacc ctggggagct gagggcctca 14701 gctgggctg ctgtcctaag gcagggtggg aactaggcag ccagcaggga ggggaccct 14761 ccctcactcc cactctccca ccccaccac cttggcccat ccatggcggc atcttgggcc 14821 atccgggact ggggacaggg gtcctgggga cagggtgtg gggacagggg tcctggg
```

By "LMX1A polypeptide" (or LIM homeobox transcription factor 1-alpha) is meant a polypeptide or fragment thereof having at least about 85% amino acid identity to NCBI Accession No. Q8TE12.

```
  1 mldglkmeen fqsaidtsas fssllgravs pksvcegcqr vildrfllrl ndsfwheqcv 61 qcasckeple ttcfyrdkkl yckydyeklf avkcggcfea iapnefvmra qksvyhlscf 121 cccvcerqlq kgdefvlkeg qllckgdyek erellslvsp aasdsgksdd eeslcksahg 181 agkgtaeegk dhkrpkrprt ilttqqrraf kasfevsskp crkvretlaa etglsvrvvq 241 vwfqnqrakm kklarrqqqq qqdqqntqrl ssaqtnggqs agmegimnpy talptpqqll 301 aieqsvyssd pfrqgltppq mpgdhmhpyg aeplfhdlds ddtslsnlgd cflatseagp 361 lqsrvgnpid hlysmqnsyf ts
```

By "LMX1A nucleic acid molecule" (or LIM homeobox transcription factor 1-alpha) is meant a polynucleotide encoding an LMX1A polypeptide. An exemplary LMX1A nucleic acid molecule is provided at NCBI Accession No. AH011517.

```
  1 gtataggttg gggcggagtc ggattcggga tggaaaacct ggggcaaggg atgtaggtgg 61 gggtgagggg ggcaggagaa ggagaaacgc agttgggggg cggaggccta agtacataac 121 gtgttgactt caagtgaaat cagatcagcc agagcagttc gctgtgactg atctctcctc 181 ccaccctaca ttctcttggc tggaccctat cctcctggct gattctggtc gccctggaca 241 ctcccctcagt tctttcccag gagtgcggtg gctgctggcg ccgagtccca gcgggcacgg
```

-continued

```
301 acgtcagacg catcgtttct tctcctctac aggtcctccc ggcccggccc gaacatgctg 361 gacggcctaa agatggagga gaacttccaa agcgcgatcg acacctcggc ctccttctcc 421 tcgctgctgg gtgagtgttc aggccgtgcg tcctgggcgc actctctttc cgcttggcgc 481 tgagctctgg agccccgctc tctgggacct ggtccgcgat agggaagcta gcgcccctct 541 tcatacacta aattgagccc catcactatc tgtccgtcag tgcttgtggg tcgtccctac 601 ccaaataaat ccaacaagcc gccccaggcc tcacgcactg gcaccgaat tcccaaagc 661 cgcgaggggc gggcgagctt gttcgtaggc gtctgagtgg caagtgatta aaaatacca 721 gggctggatt tttaatctcg gagctgatcg acgtctcata aatgccgccc tcttctcgcg 781 gcctagaggc aatagcatcc gagacccgag gcctggagcg cccaagttcg aggaggcttc 841 tctccccac caactccagc cccaatttca gccatgggca aggccgagag actttttct 901 nnnnnnnnnn nnnnnnnnnn nnnnnnnnnn nnnnnnnnnn nnnnnnnnnn nnnnnnnnnn 961 nnnnnnnnnn nnnnnnnnnn nnnnnnnnnn nnnnnnnnnn gggtcccggc caggtttggc 1021 atggtctacc tgcccgggct gctcacccgc caacgtctgt tgtggctaca ggcagagcgg 1081 tgagccccaa gtctgtctgc gagggctgtc agcgggtcat cttggacagg tttctgctgc 1141 ggctcaacga cagcttctgg catgagcagt gcgtgcagtg cgcctcctgc aaagagcccc 1201 tggagaccac ctgcttctac cgggacaaga agctgtactg caagtatgac tacgagaagt 1261 aagtggccgc accccgcag cgctccccgc gcactggcat nnnnnnnnnn nnnnnnnnnn 1321 nnnnnnnnnn nnnnnnnnnn nnnnnnnnnn nnnnnnnnnn nnnnnnnnnn nnnnnnnnnn 1381 nnnnnnnnnn nnnnnnnnnn atcccagttc ttgaagttcc ttttgctgtt gacttcaggg 1441 gagacccagg accaagccag attttactca tggtgcatgt acttcctttc tccctgctgc 1501 caggctgttt gctgttaaat gtgggggctg cttcgaggcc atcgctccca atgagtttgt 1561 tatgcgggcc cagaagagtg tataccacct gagctgcttc tgctgctgtg tctgcgagcg 1621 acagcttcag aagggtgatg agtttgtcct gaaggagggg cagctgctct gcaaagggga 1681 ctatgagaag gagcgggagc tgctcagcct ggtgagccca gcagcctcag actcaggtga 1741 gtgccaggtg gtgggcaggg ctgcggtggg gtgggtagag tggagttggg tggctgtctg 1801 cattgtttct tccctagatg nnnnnnnnnn nnnnnnnnnn nnnnnnnnnn nnnnnnnnnn 1861 nnnnnnnnnn nnnnnnnnnn nnnnnnnnnn nnnnnnnnnn nnnnnnnnnn nnnnnnnnnn 1921 catacagctc caggaactgg ctttcaggga ctcacaacat tgtcttttgc ttctttcagg 1981 taaaagtgat gatgaagaaa gtctctgcaa gtcagcccat ggggcaggga aaggaactgc 2041 tgaggaaggc aaggaccata agcgcccaa acgtccgaga accatcttga caactcaaca 2101 gaggcgagca ttcaaggcct catttgaagt atcctccaag ccctgcagga aggtatagga 2161 gggagcaggg aggaaaagga gctgggcccc acttctctgt gtgcactcag acccctctgg 2221 gatctcagtg ggcattgggg gtcacagtgg tgaggaaggc tgttcagaca gagcctgcac 2281 aggcggctca agcctgttgg agactccaga gatcactaag ctgtgccag ggtgtgatag 2341 actctcctga agctttcatg catgcacacc aactccaaat ggcccctgtc acacctttca 2401 tttcatagag cacaatggga acagtaataa tgataggtgt ccattgtggt gtagacccag 2461 atgctgtaaa gcaaagagta taaaaacaca gtggcttgca gtactctttt ttgagtctgg 2521 cttttccac ttggtgtggt ggtttggga ttcattcatt cctatttcag cattccactg 2581 tataggtgtg ccatgattgg tttgtccatg cacctgttga tgggtgtttg gggttgtttc 2641 tagtttggga ctgtttcaaa taggactgct atggacatta atgtaaaaaa aaatacagtg 2701 gtttaatgag acaggagttt attctcttct gtcacagtcc agaggtgagc aaggcaaggc
```

-continued

```
2761 tggtgggtgg ctctgttatc catctcctgt gtccaagcga ctgctccagt tgtcaccatg
2821 tttccagtca ccaggtagag aaagaggaaa tggaggggcaa gcgccctgct ttttaaggat
2881 nnnnnnnnnn nnnnnnnnnn nnnnnnnnnn nnnnnnnnnn nnnnnnnnnn nnnnnnnnnn
2941 nnnnnnnnnn nnnnnnnnnn nnnnnnnnnn nnnnnnnnnn atgcatatgc atggcttata
3001 gctaaagcac aacaatagac taaagtctaa accacttgaa ggcctaattt ccagagcaag
3061 agaaatccag aaacacctct tgggaatgca catgtaaatt aataattatt attttgtttc
3121 tttacctggt gaaggacttt cttttctacct gaagggaagc aatgttctcg tgtttgtgtg
3181 tatgctcaac attaaaaact attcagctcc taaagcagat acagtctttt ggcctcctca
3241 agtattatat aggagatgtt ctacctccta ccctgagatg ccagtgtgtc tacatttctc
3301 gttcaatttt tccaaggtga gagagactct ggctgcagag acagggctga gtgtccgtgt
3361 cgtccaggtg tggttccaaa accagagagc gaaggtaacc tgcttcttac ttttatctgt
3421 ccccatgttg ctggtttcct gaaataatca cagtaggaca nnnnnnnnnn nnnnnnnnnn
3481 nnnnnnnnnn nnnnnnnnnn nnnnnnnnnn nnnnnnnnnn nnnnnnnnnn nnnnnnnnnn
3541 nnnnnnnnnn nnnnnnnnnn agccctctcc cggggaaggt gtcacttcca ggcccccct
3601 tactttgtga acatgctgca ggccacctga cttctaatcc tatggtcctc tccttatcag
3661 atgaagaagc tggccaggcg acagcagcag cagcagcaag atcagcagaa cacccagagg
3721 ctgagctctg gtaagctggt gcctcctccc aggcagttct ggctggaatc caggctgttc
3781 ctaccagagg cctcccacta cccagctctt tggatgacat atctggactc agtgaagcct
3841 agaccacacc cactggagaa ataaggcctt caagggaaga ctgagccacg aggaacttgt
3901 gagagggttg agggctcctg agctgcaggc ttagaactgc tgattgggga tggcactgac
3961 cttatccaca gcgtccaggc ctggatccca ccacagcgtc agggactgct tgcagagtca
4021 cagatacgtt cagtttctca tcttgcttag ttctccttcc aggctaattg atttaataga
4081 agacacctcg gtgacttggc tctttccaaa ataacataaa gtagtaaaaa taatgatagt
4141 aaaataacaa tgccttcctt tgttgaacac tcttatagat tggtgttctc atacatgctg
4201 acttgacttt tacaacaccc attcctggag gcgagtggga aagttgttat tatccctatg
4261 tcacagatga gcaaacaaag gctctgcaag attgaatgtg ccctagatc ggtaagggca
4321 gggggctggg actagaactc taactgtgtt ccacaggcca tgggccttct catctctacc
4381 cagatgtgct tttgaaaaag nnnnnnnnnn nnnnnnnnnn nnnnnnnnnn nnnnnnnnnn
4441 nnnnnnnnnn nnnnnnnnnn nnnnnnnnnn nnnnnnnnnn nnnnnnnnnn nnnnnnnnnn
4501 cacgttgaga atgacctggc ttcttctttg ttccacagct cagacaaacg gtggtgggag
4561 tgctgggatg gaaggaatca tgaacccta cacggctctg cccacccac agcagctcct
4621 ggccatcgag cagagtgtct acagctcaga tcccttccga cagggtctca ccccacccca
4681 gatgcctgga gaccacatgc acccttatgg taagagggac ttaagcccct cgggccctct
4741 cataacttgt gtgggtttct cattccctcc taaacacatc taggcagttc ccagatgctc
4801 nnnnnnnnnn nnnnnnnnnn nnnnnnnnnn nnnnnnnnnn nnnnnnnnnn nnnnnnnnnn
4861 nnnnnnnnnn nnnnnnnnnn nnnnnnnnnn nnnnnnnnnn aaatgagtca cttcttcaag
4921 accctcatgc cagtgtttca tctccatttc aggtgccgag cccctttttcc atgacctgga
4981 tagcgacgac acctccctca gtaacctggg tgattgtttc ctagcaacct cagaagctgg
5041 gcctctgcag tccagagtgg gaaacccat tgaccatctg tactccatgc agaattctta
5101 cttcacatct tgagtcttcc cctagagttc tgtgactagg ctcccatatg gaacaaccat
```

```
5161 attctttgag gggtcactgg ctttaggaca gggaggccag ggaagaggtg ggttggggag 5221 ggagttttgt tggggatgct gttgtataat gatatggtgt agctcagcat ttccaaagac 5281 tgaatacatt atgattgca tagtttaatg
```

By "FOXO1 polypeptide" (or Forkhead box protein 01) is meant a polypeptide or fragment thereof having at least about 85% amino acid identity to NCBI Accession No. Q12778.

```
  1 maeapqvvei dpdfeplprp rsctwplprp efsqsnsats spapsgsaaa npdaaaglps 61 asaaavsadf msnlsllees edfpqapgsv aaavaaaaaa aatgglcgdf qgpeagclhp 121 appqpppppgp lsqhppvppa aagplagqpr kssssrrnaw gnlsyadlit kaiessaekr 181 ltlsqiyewm vksvpyfkdk gdsnssagwk nsirhnlslh skfirvqneg tgksswwmln 241 peggksgksp rrraasmdnn skfaksrsra akkkaslqsg qegagdspgs qfskwpaspg 301 shsnddfdnw stfrprtssn astisgrlsp imteqddlge gdvhsmvypp saakmastlp 361 slseisnpen menlldnlnl lssptsltvs tqsspgtmmq qtpcysfapp ntslnspspn 421 yqkytygqss msplpqmpiq tlqdnkssyg gmsqyncapg llkelltsds pphndimtpv 481 dpgvaqpnsr vlgqnvmmgp nsvmstygsq ashnkmmnps shthpghaqq tsavngrplp 541 htvstmphts gmnrltqvkt pvqvplphpm qmsalggyss vsscngygrm gllhqeklps 601 dldgmfierl dcdmesiirn dlmdgdtldf nfdnvlpnqs fphsvkttth swvsg
                                                             30
```

By "FOXO1 nucleic acid molecule" (or Forkhead box protein 01) is meant a polynucleotide (e.g., mRNA) encoding an FOXO1 polypeptide. An exemplary FOXO1 nucleic acid molecule is provided at NCBI Accession No. NM_002015.

```
   1 gcagccgcca cattcaacag gcagcagcgc agcgggcgcg ccgctgggga gagcaagcgg 61 cccgcggcgt ccgtccgtcc ttccgtccgc ggccctgtca gctggagcgc ggcgcaggct 121 ctgccccggc ccggcggctc tggccggccg tccagtccgt gcggcggacc ccgaggagcc 181 tcgatgtgga tggccccgcg aagttaagtt ctgggctcgc gcttccactc cgccgcgcct 241 tcctcccagt ttccgtccgc tcgccgcacc ggcttcgttc ccccaaatct cggaccgtcc 301 cttcgcgccc cctcccgtc cgcccccagt gctgcgttct ccccctcttg gctctcctgc 361 ggctgggga ggggcggggg tcaccatggc cgaggcgcct caggtggtgg agatcgaccc 421 ggacttcgag ccgctgcccc ggccgcgctc gtgcacctgg ccgctgccca ggccggagtt 481 tagccagtcc aactcggcca cctccagccc ggcgccgtcg ggcagcgcgg ctgccaaccc 541 cgacgccgcg gcgggcctgc cctcggcctc ggctgccgct gtcagcgccg acttcatgag 601 caacctgagc ttgctggagg agagcgagga cttcccgcag gcgcccggct ccgtggcggc 661 ggcggtggcg gcggcggccg ccgcggccgc caccgggggg ctgtgcgggg acttccaggg 721 cccggaggcg ggctgcctgc acccagcgcc accgcagccc ccgccgcccg gccgctgtc 781 gcagcacccg ccggtgcccc ccgccgccgc tgggccgctc gcggggcagc cgcgcaagag 841 cagctcgtcc cgccgcaacg cgtggggcaa cctgtcctac gccgacctca tcaccaaggc 901 catcgagagc tcggcggaga gcggctcac gctgtcgcag atctacgagt ggatggtcaa 961 gagcgtgccc tacttcaagg ataagggtga cagcaacagc tcggcgggct ggaagaattc 1021 aattcgtcat aatctgtccc tacacagcaa gttcattcgt gtgcagaatg aaggaactgg
```

-continued

```
1081 aaaaagttct tggtggatgc tcaatccaga gggtggcaag agcgggaaat ctcctaggag 1141 aagagctgca tccatggaca acaacagtaa atttgctaag agccgaagcc gagctgccaa 1201 gaagaaagca tctctccagt ctggccagga gggtgctggg acagccctg gatcacagtt 1261 ttccaaatgg cctgcaagcc ctggctctca cagcaatgat gactttgata actggagtac 1321 atttcgccct cgaactagct caaatgctag tactattagt gggagactct cacccattat 1381 gaccgaacag gatgatcttg gagaagggga tgtgcattct atggtgtacc cgccatctgc 1441 cgcaaagatg gcctctactt tacccagtct gtctgagata agcaatcccg aaaacatgga 1501 aaatcttttg gataatctca accttctctc atcaccaaca tcattaactg tttcgaccca 1561 gtcctcacct ggcaccatga tgcagcagac gccgtgctac tcgtttgcgc caccaaacac 1621 cagtttgaat tcacccagcc caaactacca aaaatataca tatggccaat ccagcatgag 1681 cccttttgccc cagatgccta tacaaacact tcaggacaat aagtcgagtt atggaggtat 1741 gagtcagtat aactgtgcgc ctggactctt gaaggagttg ctgacttctg actctcctcc 1801 ccataatgac attatgacac cagttgatcc tggggtagcc cagcccaaca gccgggttct 1861 gggccagaac gtcatgatgg cccctaattc ggtcatgtca acctatggca gccaggcatc 1921 tcataacaaa atgatgaatc ccagctccca tacccaccct ggacatgctc agcagacatc 1981 tgcagttaac gggcgtcccc tgccccacac ggtaagcacc atgccccaca cctcgggtat 2041 gaaccgcctg acccaagtga agacacctgt acaagtgcct ctgccccacc ccatgcagat 2101 gagtgccctg gggggctact cctccgtgag cagctgcaat ggctatggca gaatgggcct 2161 tctccaccag gagaagctcc caagtgactt ggatggcatg ttcattgagc gcttagactg 2221 tgacatggaa tccatcattc ggaatgacct catggatgga gatacattgg attttaactt 2281 tgacaatgtg ttgcccaacc aaagcttccc acacagtgtc aagacaacga cacatagctg 2341 ggtgtcaggc tgagggttag tgagcaggtt acacttaaaa gtacttcaga ttgtctgaca 2401 gcaggaactg agagaagcag tccaaagatg tcttcacca actcccttt agttttcttg 2461 gttaaaaaaa aaacaaaaa aaaaaaccct ccttttttcc tttcgtcaga cttggcagca 2521 aagacatttt tcctgtacag gatgtttgcc caatgtgtgc aggttatgtg ctgctgtaga 2581 taaggactgt gccattggaa atttcattac aatgaagtgc caaactcact acaccatata 2641 attgcagaaa agattttcag atcctggtgt gctttcaagt tttgtatata agcagtagat 2701 acagattgta tttgtgtgtg tttttggttt ttctaaatat ccaattggtc caaggaaagt 2761 ttatactctt tttgtaatac tgtgatgggc ctcatgtctt gataagttaa acttttgttt 2821 gtactacctg ttttctgcgg aactgacgga tcacaaagaa ctgaatctcc attctgcatc 2881 tccattgaac agccttggac ctgttcacgt tgccacagaa ttcacatgag aaccaagtag 2941 cctgttatca atctgctaaa ttaatggact tgttaaactt ttggaaaaaa aaagattaaa 3001 tgccagcttt gtacaggtct tttctatttt tttttgttta ttttgttatt tgcaaatttg 3061 tacaaacatt taaatggttc taatttccag ataaatgatt tttgatgtta ttgttgggac 3121 ttaagaacat ttttgaaata gatattgaac tgtaataatg ttttcttaaa actagagtct 3181 actttgttac atagtcagct tgtaaatttt gtggaaccac aggtatttgg ggcagcattc 3241 ataattttca ttttgtattc taactggatt agtactaatt ttatacatgc ttaactggtt 3301 tgtacacttt gggatgctac ttagtgatgt ttctgactaa tcttaaatca ttgtaattag 3361 tacttgcata ttcaacgttt caggccctgg ttgggcagga aagtgatgta tagttatgga 3421 cactttgcgt ttcttattta ggataactta atatgttttt atgtatgtat tttaaagaaa 3481 tttcatctgc ttctactgaa ctatgcgtac tgcatagcat caagtcttct ctagagacct
```

-continued

```
3541 ctgtagtcct gggaggcctc ataatgtttg tagatcagaa aagggagatc tgcatctaaa 3601 gcaatggtcc tttgtcaaac gagggatttt gatccacttc accattttga gttgagcttt 3661 agcaaaagtt tcccctcata attctttgct cttgtttcag tccaggtgga ggttggtttt 3721 gtagttctgc cttgaggaat tatgtcaaca ctcatacttc atctcattct cccttctgcc 3781 ctgcagatta gattacttag cacactgtgg aagtttaagt ggaaggaggg aatttaaaaa 3841 tgggacttga gtggtttgta gaatttgtgt tcataagttc agatgggtag caaatggaat 3901 agaacttact taaaaattgg ggagatttat ttgaaaacca gctgtaagtt gtgcattgag 3961 attatgttaa aagccttggc ttaagaattt gaaaatttct ttagcctgta gcaacctaaa 4021 ctgtaattcc tatcattatg ttttattact ttccaattac ctgtaactga cagaccaaat 4081 taattggctt tgtgtcctat ttagtccatc agtattttca agtcatgtgg aaagcccaaa 4141 gtcatcacaa tgaagagaac aggtgcacag cactgttcct cttgtgttct tgagaaggat 4201 ctaattttc tgtatatagc ccacatcaca cttgctttgt cttgtatgtt aattgcatct 4261 tcattggctt ggtatttcct aaatgtttaa caagaacaca agtgttcctg ataagatttc 4321 ctacagtaag ccagctctat tgtaagcttc ccactgtgat gatcattttt ttgaagattc 4381 attgaacagc caccactcta tcatcctcat tttggggcag tccaagacat agctggtttt 4441 agaaacccaa gttcctctaa gcacagcctc ccgggtatgt aactgaactt ggtgccaaag 4501 tacttgtgta ctaatttcta ttactacgta ctgtcacttt cctcccgtgc cattactgca 4561 tcataataca aggaacctca gagcccccat ttgttcatta aagaggcaac tacagccaaa 4621 atcactgtta aaatcttact acttcatgga gtagctctta ggaaaatata tcttcctcct 4681 gagtctgggt aattataccct ctcccaagcc cccattgtgt gttgaaatcc tgtcatgaat 4741 ccttggtagc tctctgagaa cagtgaagtc cagggaaagg catctggtct gtctggaaag 4801 caaacattat gtggcctctg gtagtttttt tcctgtaaga atactgactt tctggagtaa 4861 tgagtatata tcagttattg tacatgattg ctttgtgaaa tgtgcaaatg atatcaccta 4921 tgcagccttg tttgatttat tttctctggt ttgtactgtt attaaaagca tattgtatta 4981 tagagctatt cagatatttt aaatataaag atgtattgtt tccgtaatat agacgtatgg 5041 aatatattta ggtaatagat gtattacttg gaaagttctg ctttgacaaa ctgacaaagt 5101 ctaaatgagc acatgtatcc cagtgagcag taaatcaatg gaacatccca agaagaggat 5161 aaggatgctt aaaatggaaa tcattctcca acgatataca aattggactt gttcaactgc 5221 tggatatatg ctaccaataa ccccagcccc aacttaaaat tcttacattc aagctcctaa 5281 gagttcttaa tttataacta atttttaaaag agaagtttct tttctggttt tagtttggga 5341 ataatcattc attaaaaaaa atgtattgtg gtttatgcga acagaccaac ctggcattac 5401 agttggcctc tccttgaggt gggcacagcc tggcagtgtg gccaggggtg gccatgtaag 5461 tcccatcagg acgtagtcat gcctcctgca tttcgctacc cgagtttagt aacagtgcag 5521 attccacgtt cttgttccga tactctgaga agtgcctgat gttgatgtac ttacagacac 5581 aagaacaatc tttgctataa ttgtataaag ccataaatgt acataaatta tgtttaaatg 5641 gcttggtgtc tttctttctct aattatgcag aataagctct ttattaggaa ttttttgtga 5701 agctattaaa tacttgagtt aagtcttgtc agccacaa
```

By "FOXA2 polypeptide" (or Forkhead box protein A2) is meant a polypeptide or fragment thereof having at least about 85% amino acid identity to NCBI Accession No. Q9Y261.

```
  1 mlgavkmegh epsdwssyya epegyssvsn mnaglgmngm ntymsmsaaa mgsgsgnmsa 61 gsmnmssyvg agmspslagm spgagamagm ggsagaagva gmgphlspsl splggqaaga 121 mgglapyanm nsmspmygqa glsrardpkt yrrsythakp pysyislitm aiqqspnkml 181 tlseiyqwim dlfpfyrqnq qrwqnsirhs lsfndcflkv prspdkpgkg sfwtlhpdsg 241 nmfengcylr rqkrfkcekq lalkeaagaa gsgkkaaaga qasqaqlgea agpasetpag 301 tesphssasp cqehkrgglg elkgtpaaal sppepapspg qqqqaaahll gpphhpglpp 361 eahlkpehhy afnhpfsinn lmsseqqhhh shhhhqphkm dlkayeqvmh ypgygspmpg 421 slamgpvtnk tgldasplaa dtsyyqgvys rpimnss
```

By "FOXA2 nucleic acid molecule" (or Forkhead box protein A2) is meant a polynucleotide (e.g., mRNA) encoding an FOXA2 polypeptide. An exemplary FOXA2 nucleic acid molecule is provided at NCBI Accession No. NM_021784.

```
   1 cccgcccact tccaactacc gcctccggcc tgcccaggga gagagaggga gtggagccca 61 gggagaggga gcgcgagaga gggagggagg aggggacggt gctttggctg acttttttt 121 aaaagagggt gggggtgggg ggtgattgct ggtcgtttgt tgtggctgtt aaattttaaa 181 ctgccatgca ctcggcttcc agtatgctgg gagcggtgaa gatggaaggg cacgagccgt 241 ccgactggag cagctactat gcagagcccg agggctactc ctccgtgagc aacatgaacg 301 ccggcctggg gatgaacggc atgaacacgt acatgagcat gtcggcggcc gccatgggca 361 gcggctcggg caacatgagc gcgggctcca tgaacatgtc gtcgtacgtg ggcgctggca 421 tgagcccgtc cctggcgggg atgtcccccg gcgcgggcgc catggcgggc atgggcggct 481 cggccggggc ggccggcgtg gcgggcatgg gccgcacttt gagtccagc ctgagcccgc 541 tcgggggggca ggcggccggg gccatgggcg gcctggcccc ctacgccaac atgaactcca 601 tgagccccat gtacgggcag gcgggcctga ccgcgcccg cgaccccaag acctacaggc 661 gcagctacac gcacgcaaag ccgccctact cgtacatctc gctcatcacc atggccatcc 721 agcagagccc caacaagatg ctgacgctga gcgagatcta ccagtggatc atggaccctc 781 tccccttcta ccggcagaac cagcagcgct ggcagaactc catccgccac tcgctctcct 841 tcaacgactg tttcctgaag gtgccccgct cgcccgacaa gcccggcaag ggctccttct 901 ggaccctgca ccctgactcg ggcaacatgt tcgagaacgg ctgctacctg cgccgccaga 961 agcgcttcaa gtgcgagaag cagctggcgc tgaaggaggc cgcaggcgcc gccggcagcg 1021 gcaagaaggc ggccgccgga gcccaggcct cacaggctca actcggggag gccgccgggc 1081 cggcctccga gactccggcg gcaccgagt cgcctcactc gagcgcctcc ccgtgccagg 1141 agcacaagcg aggggggcctg ggagagctga agggacgcc ggctgcggcg ctgagccccc 1201 cagagccggc gccctctccc gggcagcagc agcaggccgc ggcccacctg ctgggcccgc 1261 cccaccaccc gggcctgccg cctgaggccc acctgaagcc ggaacaccac tacgccttca 1321 accacccgtt ctccatcaac aacctcatgt cctcggagca gcagcaccac cacagccacc 1381 accaccacca accccacaaa atggaccctca aggcctacga acaggtgatg cactaccccg 1441 gctacggttc cccatgcct ggcagcttgg ccatgggccc ggtcacgaac aaaacgggcc
```

-continued

```
1501 tggacgcctc gcccctggcc gcagatacct cctactacca gggggtgtac tcccggccca 1561 ttatgaactc ctcttaagaa gacgacggct tcaggcccgg ctaactctgg caccccggat 1621 cgaggacaag tgagagagca agtgggggtc gagactttgg ggagacggtg ttgcagagac 1681 gcaagggaga agaaatccat aacacccccca ccccaacacc cccaagacag cagtcttctt 1741 cacccgctgc agccgttccg tcccaaacag agggccacac agataccccca cgttctatat 1801 aaggaggaaa acgggaaaga atataaagtt aaaaaaaagc ctccggtttc cactactgtg 1861 tagactcctg cttcttcaag cacctgcaga ttctgattt ttttgttgttg ttgttctcct 1921 ccattgctgt tgttgcaggg aagtcttact taaaaaaaaa aaaaaatttt gtgagtgact 1981 cggtgtaaaa ccatgtagtt ttaacagaac cagagggttg tactattgtt taaaaacagg 2041 aaaaaaaata atgtaagggt ctgttgtaaa tgaccaagaa aaagaaaaaa aaagcattcc 2101 caatcttgac acggtgaaat ccaggtctcg ggtccgatta atttatggtt tctgcgtgct 2161 ttattatgg cttataaatg tgtattctgg ctgcaagggc cagagttcca caaatctata 2221 ttaaagtgtt atacccggtt ttatcccttg aatcttttct tccagatttt tcttttcttt 2281 acttggctta caaatatac aggcttggaa attatttcaa gaaggaggga gggatacccct 2341 gtctggttgc aggttgtatt ttattttggc ccagggagtg ttgctgtttt cccaacattt 2401 tattaataaa attttcagac ataaaaaa
```

By "FOXO4 polypeptide" (or Forkhead box protein 04) is meant a polypeptide or fragment thereof having at least about 85% amino acid identity to NCBI Accession No. P98177.

```
1 mdpgnensat eaaaiidldp dfepqsrprs ctwplprpei anqpseppev epdlgekvht 61 egrsepillp srlpepaggp qpgilgavtg prkggsrrna wgnqsyaeli sqaiesapek 121 rltlaqiyew mvrtvpyfkd kgdsnssagw knsirhnlsl hskfikvhne atgksswwml 181 npeggksgka prrraasmds sskllrgrsk apkkkpsvlp appegatpts pvghfakwsg 241 spcsrnreea dmwttfrprs ssnassvstr lsplrpesev laeeipasvs syaggvpptl 301 neglelldgl nltsshslls rsglsgfslq hpgvtgplht yssslfspae gplsagegcf 361 sssqaleall tsdtppppad vlmtqvdpil sqaptllllg glpsssklat gvglcpkple 421 apgpsslvpt lsmiapppvm asapipkalg tpvltpptea asqdrmpqdl dldmymenle 481 cdmdniisdl mdegegldfn fepdp
```

By "FOXO4 nucleic acid molecule" (or Forkhead box protein 04) is meant a polynucleotide (e.g., mRNA) encoding an FOXO4 polypeptide. An exemplary FOXO4 nucleic acid molecule is provided at NCBI Accession No. NM_005938.

```
1 aaaaggggga gggaactgcg gctaaggaga cgttcggtga tgggagcgca atatatgagg 61 ggatacagtg cctcaggttt aaaagagcag gaagctgagt gagaggttgc agaaaaagtg 121 tcttcgctcg gcagaggtta caggtggcat ctcagaaaga gctttgaggc tacaggctgt 181 agtcgggaag gggatcggag aactgtgtga agggacagct tagggactag cgtcctggga 241 ctaggggaa gttcgcgact ttctgaagac tggcaggaat gtgcctcctg gccctcgatg 301 cttccccct gaggggaggc atcgtgaggg actgtggcag gcttcactga acgctgagcc 361 ggggaggtcc aactccacgt atggatccgg ggaatgagaa ttcagccaca gaggctgccg
```

-continued

```
 421 cgatcataga cctagatccc gacttcgaac cccagagccg tccccgctcc tgcacctggc
 481 cccttcccccg accagagatc gctaaccagc cgtccgagcc gcccgaggtg gagccagatc
 541 tgggggaaaa ggtacacacg gaggggcgct cagagccgat cctgttgccc tctcggctcc
 601 cagagccggc cggggggcccc cagcccggaa tcctggggggc tgtaacaggt cctcggaagg
 661 gaggctcccg ccggaatgcc tgggggaaatc agtcatatgc agaactcatc agccaggcca
 721 ttgaaagcgc cccggagaag cgactgcac ttgcccagat ctacgagtgg atggtccgta
 781 ctgtacccta cttcaaggac aagggtgaca gcaacagctc agcaggatgg aagaactcga
 841 tccgccacaa cctgtccctg cacagcaagt tcatcaaggt tcacaacgag gccaccggca
 901 aaagctcttg gtggatgctg aaccctgagg gaggcaagag cggcaaagcc ccccgccgcc
 961 gggccgcctc catggatagc agcagcaagc tgctccgggg ccgcagtaaa gcccccaaga
1021 agaaaccatc tgtgctgcca gctccacccg aaggtgccac tccaacgagc cctgtcggcc
1081 actttgccaa gtggtcaggc agcccttgct ctcgaaaccg tgaagaagcc gatatgtgga
1141 ccaccttccg tccacgaagc agttcaaatg ccagcagtgt cagcacccgg ctgtccccct
1201 tgaggccaga gtctgaggtg ctggcggagg aaataccagc ttcagtcagc agttatgcag
1261 ggggtgtccc tcccacccctc aatgaaggtc tagagctgtt agatgggctc aatctcacct
1321 cttcccattc cctgctatct cggagtggtc tctctggctt ctctttgcag catcctgggg
1381 ttaccggccc cttacacacc tacagcagct ccctttcag cccagcagag ggcccctgt
1441 cagcaggaga agggtgcttc tccagctccc aggctctgga ggccctgctc acctctgata
1501 cgccaccacc ccctgctgac gtcctcatga cccaggtaga tcccattctg tcccaggctc
1561 cgactcttct gttgctgggg gggcttcctt cctccagtaa gctggccacg ggcgtcggcc
1621 tgtgtcccaa gccccctagag gctccaggcc ccagcagtct ggttcccacc ctttctatga
1681 tagcaccacc tccagtcatg gcaagtgccc ccatccccaa ggctctgggg actcctgtgc
1741 tcacacccccc tactgaagct gcaagccaag acagaatgcc tcaggatcta gatcttgata
1801 tgtatatgga gaacctggag tgtgacatgg ataacatcat cagtgacctc atggatgagg
1861 gcgagggact ggacttcaac tttgagccag atccctgagt catgcctgga agctttgtcc
1921 cctgcttcag atgtggagcc aggcgtgttc atatctactc tttacccttg agccctcccc
1981 aggaatttgg gaccctgctt tagagctagg gtggggtctg gtcacacaca ggtgttgaag
2041 aaattataaa gataaagctg ccccatctgg ggacgatatg gggagggaga tgggagggga
2101 aagggagag ggttttttctc actgtgccaa ttaggggggta aggccccctc tcaggagcca
2161 tcatcggctt tccccattcc tacccactta ggctttgtag caagatgagc aatgctgttg
2221 gaaatgtgaa gtcaccagtg gccttacccc tgccttttggg agcaggattt ttttgtagag
2281 agtcttatct gagctgagcc aggctagctg gagcctggga tttctatgca gtggcccctt
2341 aggccagtga tgtgcggtgg gtgggctgtt tagggatct ggaagggcca aggtctgagc
2401 actggagtgg ctcgccaggc caaatcaccc ttagaaggct gcagataaca gaaaggcttt
2461 ttataaactt ttaaagaaat ataaacacaa atatagagat ttttttaacca tggcagggtg
2521 ctagtggtgg gcagaatgct ttttttttctt tctgaaggct ttgtgatagt gacatgatac
2581 aaacactaca gacaataaat attaggagac acagggaagt ggggagaggt ggggagtaat
2641 agtaaacaca gggaagagct cccctacgga ccaggtatag agaaaggtct atgcagaaat
2701 aggttagagt ttccctaaca aaaaagctaa cccaggtccc ctcattcctt caacttgtgc
2761 ctgggagtgt gtggtgttag ggtgcagcca cactcttcta tgacccagca tgggttagtg
2821 ctatggtggg agagtacatt gaaggcctgg aattagcttg gggccaggga agggactggg
```

-continued

```
2881 aggggagaga agagaaggag ggaaggattt aggatggtaa agttaggtac agagacctcc 2941 ctgttcaagg cccctgacag ctgtccctgc ccttcttccc cttccctgac tgcaggggtt 3001 atgtggaagt gtgtgtggca gcaggcagcg gggaggggag gaacagggaa gggggagctg 3061 gggagcttgg ctgagggtct gggaaatgag cagggatggg gggggatgtg gatcaggttt 3121 actagcacct gccagggagg ccatctgggg ctccttctcc accccagccc ccaaagcagc 3181 ccttccccca gtgccctttg catcgtcccc tcccccaccc ctgctgtggg ttcccatcat 3241 ttcctgtgtc agcgcctggc ctacccagat tgtatcatgt gctagattgg agtggggaag 3301 tgtgtcaaat caataaatga ataaattcaa taaatgccta taaccagcaa aaaaaaaaaa 3361 aaaaa
```

By "CNP polypeptide" (or 2',3'-cyclic-nucleotide 3'-phosphodiesterase) is meant a polypeptide or fragment thereof having at least about 85% amino acid identity to NCBI Accession No. P09543.

```
  1 mnrgfsrksh tflpkiffrk msssgakdkp elqfpflqde dtvatlleck tlfilrglpg 61 sgkstlarvi vdkyrdgtkm vsadaykitp gargafseey krldedlaay crrrdirilv 121 lddtnherer leqlfemadq yqyqvvlvep ktawrldcaq lkeknqwqls addlkklkpg 181 lekdflplyf gwfltkksse tlrkagqvfl eelgnhkafk kelrqfvpgd eprekmdlvt 241 yfgkrppgvl hcttkfcdyg kapgaeeyaq qdvlkksysk aftltisalf vtpkttgarv 301 elseqqlqlw psdvdklspt dnlprgsrah itlgcaadve avqtgldlle ilrqekggsr 361 geevgelsrg klyslgngrw mltlaknmev raiftgyygk gkpvptqgsr kggalqscti 421 i
```

By "CNP nucleic acid molecule" (or 2',3'-cyclic-nucleotide 3'-phosphodiesterase) is meant a polynucleotide (e.g., mRNA) encoding an CNP polypeptide. An exemplary CNP nucleic acid molecule is provided at NCBI Accession No. BC011046.

```
  1 ctccgcgcag gcgggcggcc ccggagcgct ggtgccggca gaggcggcga cggtggcgcc 61 cctcctcatc atgaggcttc tcccgaaaaa gccacacatt cctgcccaag atcttcttcc 121 gcaagatgtc atcctcaggg gccaaggaca agcctgagct gcagtttccc ttccttcagg 181 atgaggacac agtggccacg ctgctagagt gcaagacgct cttcatcttg cgcggcctgc 241 caggaagcgg caagtccacg ctggcacggg tcatcgtgga caagtaccgt gatggcacca 301 agatggtgtc ggctgacgct tacaagatca cccccggcgc tcgaggagcc ttctccgagg 361 agtacaagcg gctcgatgag gacctggctg cctactgccg ccgccgggac atcagaattc 421 ttgtgcttga tgacaccaac cacgaacggg aacggctgga gcagctcttt gaaatggccg 481 accagtacca gtaccaggtg gtgctggtgg agcccaagac ggcgtggcgg ctggactgtg 541 cccagctcaa ggagaagaac cagtggcagc tgtcggctga tgacctgaag aagctgaagc 601 ctgggctgga aaggacttc ctgccgctct acttcggctg gttcctgacc aagaagagct 661 ctgagaccct ccgcaaagcc ggccaggtct tcctggaaga gctggggaac cacaaggcct 721 tcaagaagga gctgcgacaa ttcgtccctg gggatgagcc cagggagaag atggacttgg 781 tcacctactt tggaaagaga ccccaggcg tgctgcattg cacaaccaag ttttgtgact 841 acgggaaggc tccggggca gaggagtacg ctcaacaaga tgtgttaaag aaatcttact
```

-continued

```
 901 ccaaggcctt cacgctgacc atctctgccc tctttgtgac acccaagacg actggggccc
 961 gggtggagtt aagcgagcag caactgcagt tgtggccgag tgatgtggac aagctgtcac
1021 ccactgacaa cctgccgcgg gggagccgcg cccacatcac cctcggctgt gcagctgacg
1081 tagaggccgt gcagacgggc cttgacctct tagagattct gcggcaggag aagggggggca
1141 gccgaggcga ggaggtgggc gagctaagcc ggggcaagct ctattccttg gcaatgggc
1201 gctggatgct gaccctggcc aagaacatgg aggtcagggc catcttcacg gggtactacg
1261 ggaaaggcaa acctgtgccc acgcaaggta gccggaaggg gggcgccttg cagtcctgca
1321 ccatcatatg agtgttctca ccaccactta tgcccctaga agggaagggg agagggaaac
1381 gtgccctctg tttgatcctt gttttgtgac attttttttt ttttttttt tactcaaagt
1441 taacctacct gtaactttt aaaaacttgt aaaataactg accctccctt cctgtccgcc
1501 ctcttcccct ctaatgctca cgctcccaac acaaggtggg cagggaggca ccattcagga
1561 acctggacca aagctgacga ggctgggcca agccagggat ggggccacag ccagaaccc
1621 gagccctact tccaggttct ggttagctca gccccagccc agcccagctg ctctgcccag
1681 agctgggtga gtggggagac acctcagagc cccgcaaaac ccactgaccg gaggcaaaag
1741 gcagtggggc tgggggtagt tttccatggt cacagagaac tagtggtggc tctgagaagg
1801 ggaggacctc tgggctttga ttccatctcc ttgtctttt tctttgtttt tagagacagg
1861 gtcctgctat ttcccaagct ggagtgcagt ggtgcgatca tggctcactg cagcctcgaa
1921 ctcctgggct caagcaatcc tcctgagtga tcccatttct taatcagtgt agccccaaga
1981 aggctggggc tatttaccag ggtagaaaaa ggagcttacc tcccaccttt ggtcctaagt
2041 ccctgccccc tccccttcac accataacta ggtaacagtt tgataactag ggaagaaagc
2101 agaacagtta agcagccgcc acatccccgc tggctggggg cctcactcca ggaaggggct
2161 ggactgctg tcctttccag tggcctggct ccgctgtgtg gatggggaga tcggggccag
2221 aggcagaacc ctggtgagga agctccagtc ctgctctcta cccagcccat cttgcctcca
2281 tggtgcctct ggaggcctct gggcctcctc taacaggggc tggtgggcac caagagccaa
2341 tggagtagac ccctggctgg taagggccaa gtcccaccgg ttgcttctgg gaaggggttt
2401 ctaacactag tctgtgtgct gtggttcctg gggtgccctc cactgccctc tgttcagtaa
2461 cagggccttg ctaatcgggt tgtcactcaa caaaagtgct ttggatttaa gttactatcc
2521 tggctttgcc caacctcagc aacctgtaag actgataatg aaataaatca tgttaatcct
2581 agcaaaaaaa aaaaaaaa
```

By "MBP polypeptide" (or myelin basic protein) is meant a polypeptide or fragment thereof having at least about 85% amino acid identity to NCBI Accession No. P02686.

```
  1mgnhagkrel naekastnse tnrgesekkr nlgelsrtts ednevfgead anqnngtssq
 61dtavtdskrt adpknawqda hpadpgsrph lirlfsrdap gredntfkdr psesdelqti
121qedsaatses ldvmasqkrp sqrhgskyla tastmdharh gflprhrdtg ildsigrffg
181gdrgapkrgs gkdshhpart ahygslpqks hgrtqdenpv vhffknivtp rtpppsqgkg
241rglslsrfsw gaegqrpgfg yggrasdyks ahkgfkgvda qgtlskifkl ggrdsrsgsp
301marr
```

By "MBP nucleic acid molecule" (or myelin basic protein) is meant a polynucleotide (e.g., mRNA) encoding an MBP polypeptide. An exemplary MBP nucleic acid molecule is provided at NCBI Accession No. M13577.

```
   1 gaaaacagtg cagccacctc cgagagcctg gatgtgatgg cgtcacagaa gagaccctcc
  61 cagaggcacg gatccaagta cctggccaca gcaagtacca tggaccatgc caggcatggc
 121 ttcctcccaa ggcacagaga cacgggcatc cttgactcca tcgggcgctt ctttggcggt
 181 gacaggggtg cgccaaagcg gggctctggc aaggactcac accacccggc aagaactgct
 241 cactatggct ccctgcccca gaagtcacac ggccggaccc aagatgaaaa ccccgtagtc
 301 cacttcttca agaacattgt gacgcctcgc acaccacccc cgtcgcaggg aaaggggaga
 361 ggactgtccc tgagcagatt tagctggggg gccgaaggcc agagaccagg atttggctac
 421 ggaggcagag cgtccgacta taaatcggct cacaagggat tcaagggagt cgatgcccag
 481 ggcacgcttt ccaaaatttt taagctggga ggaagagata gtcgctctgg atcacccatg
 541 gctagacgct gaaaacccac ctggttccgg aatcctgtcc tcagcttctt aatataactg
 601 ccttaaaact ttaatcccac ttgcccctgt tacctaatta gagcagatga cccctcccct
 661 aatgcctgcg gagttgtgca cgtagtaggg tcaggccacg gcagcctacc ggcaatttcc
 721 ggccaacagt taaatgagaa catgaaaaca gaaaacggtt aaaactgtcc ctttctgtgt
 781 gaagatcacg ttccttcccc cgcaatgtgc ccccagacgc acgtgggtct tcaggggggcc
 841 aggtgcacag acgtccctcc acgttcaccc ctccacccct tggactttctt ttcgccgtgg
 901 ctcggcaccc ttgcgctttt gctggtcact gccatggagg cacacagctg cagagacaga
 961 gaggacgtgg gcggcagaga ggactgttga catccaagct tcctttgttt tttttttcctg
1021 tccttctctc acctcctaaa gtagacttca ttttttcctaa caggattaga cagtcaagga
1081 gtggcttact acatgtggga gcttttttggt atgtgacatg cgggctgggc agctgttaga
1141 gtccaacgtg gggcagcaca gagagggggc cacctcccca ggccgtggct gcccacacac
1201 cccaattagc tgaattcgcg tgtggcagag ggaggaaaag gaggcaaacg tgggctgggc
1261 aatggcctca cataggaaac agggtcttcc tggagatttg gtgatggaga tgtcaagcag
1321 gtggcctctg gacgtcaccg ttgccctgca tggtggcccc agagcagcct ctatgaacaa
1381 cctcgtttcc aaaccacagc ccacagccgg agagtccagg aagacttgcg cactcagagc
1441 agaagggtag gagtcctcta gacagcctcg cagccgcgcc agtcgcccat agacactggc
1501 tgtgaccggg cgtgctggca gcggcagtgc acagtggcca gcactaaccc tccctgagaa
1561 gataaccggc tcattcactt cctcccagaa gacgcgtggt agcgagtagg cacaggcgtg
1621 cacctgctcc cgaattactc accgagacac acgggctgag cagacggccc ctgtgatgga
1681 gacaaagagc tcttctgacc atatccttct taacacccgc tggcatctcc tttcgcgcct
1741 ccctccctaa cctactgacc cacctttttga ttttagcgca cctgtgattg ataggccttc
1801 caaagagtcc cacgctggca tcaccctccc cgaggacgga gatgaggagt agtcagcgtg
1861 atgccaaaac gcgtcttctt aatccaattc taattctgaa tgtttcgtgt gggcttaata
1921 ccatgtctat taatatatag cctcgatgat gagagagtta caaagaacaa aactccagac
1981 acaaacctcc aaatttttca gcagaagcac tctgcgtcgc tgagctgagg tcggctctgc
2041 gatccatacg tggccgcacc cacacagcac gtgctgtgac gatggctgaa cggaaagtgt
2101 acactgttcc tgaatattga aataaaacaa taaacttttt
```

By "TUBIII polypeptide" (or TUBB3, tubulin beta chain 3) is meant a polypeptide or fragment thereof having at least about 85% amino acid identity to NCBI Accession No. NP_001184110.

```
  1 mdsvrsgafg hlfrpdnfif gqsgagnnwa kghytegael vdsvldvvrk ecencdclqg
 61 fqlthslggg tgsgmgtlli skvreeypdr imntfsvvps pkvsdtvvep ynatlsihql
121 ventdetyci dnealydicf rtlklatpty gdlnhlvsat msgvttslrf pgqlnadlrk
181 lavnmvpfpr lhffmpgfap ltargsqqyr altvpeltqq mfdaknmmaa cdprhgrylt
241 vatvfrgrms mkevdeqmla iqsknssyfv ewipnnvkva vcdipprglk msstfignst
301 aiqelfkris eqftamfrrk aflhwytgeg mdemefteae snmndlvsey qqyqdataee
361 egemyeddee eseaqgpk
```

By "TUBIII nucleic acid molecule" (or TUBB3, tubulin beta chain 3) is meant a polynucleotide (e.g., mRNA) encoding an TUBIII polypeptide. An exemplary TUBIII nucleic acid molecule is provided at NCBI Accession No. BC000748.

```
   1 gcccggcccg cccgcgcccg tccgcagccg cccgccagac gcgcccagta tgagggagat
  61 cgtgcacatc caggccggcc agtgcggcaa ccagatcggg gccaagttct gggaagtcat
 121 cagtgatgag catggcatcg accccagcgg caactacgtg ggcgactcgg acttgcagct
 181 ggagcggatc agcgtctact acaacgaggc ctcttctcac aagtacgtgc ctcgagccat
 241 tctggtggac ctggaacccg gaaccatgga cagtgtccgc tcaggggcct ttggacatct
 301 cttcaggcct gacaatttca tctttggtca gagtggggcc ggcaacaact gggccaaggg
 361 tcactacacg gaggggcgg agctggtgga ttcggtcctg gatgtggtgc ggaaggagtg
 421 tgaaaactgc gactgcctgc agggcttcca gctgacccac tcgctggggg gcggcacggg
 481 ctccggcatg ggcacgttgc tcatcagcaa ggtgcgtgag gagtatcccg accgcatcat
 541 gaacaccttc agcgtcgtgc cctcacccaa ggtgtcagac acggtggtgg agccctacaa
 601 cgccacgctg tccatccacc agctggtgga gaacacggat gagacctact gcatcgacaa
 661 cgaggcgctc tacgacatct gcttccgcac cctcaagctg gccacgccca ctacgggga
 721 cctcaaccac ctggtatcgg ccaccatgag cggagtcacc acctccttgc gcttcccggg
 781 ccagctcaac gctgacctgc gcaagctggc cgtcaacatg gtgcccttcc cgcgcctgca
 841 cttcttcatg cccggcttcg cccccctcac agcccggggc agccagcagt accgggccct
 901 gaccgtgccc gagctcaccc agcagatgtt cgatgccaag aacatgatgg ccgcctgcga
 961 cccgcgccac ggccgctacc tgacggtggc caccgtgttc cggggccgca tgtccatgaa
1021 ggaggtggac gagcagatgc tggccatcca gcaagaac agcagctact cgtggagtg
1081 gatccccaac aacgtgaagg tggccgtgtg tgacatcccg ccccgcggcc tcaagatgtc
1141 ctccaccttc atcgggaaca gcacggccat ccaggagctg ttcaagcgca tctccgagca
1201 gttcacggcc atgttccggc gcaaggcctt cctgcactgg tacacgggcg agggcatgga
1261 cgagatggag ttcaccgagg ccgagagcaa catgaacgac ctggtgtccg agtaccagca
1321 gtaccaggac gccacggccg aggaagaggg cgagatgtac gaagacgacg aggaggagtc
1381 ggaggcccag ggccccaagt gaagctgctc gcagctggag tgagaggcag gtggcggccg
1441 gggccgaagc cagcagtgtc taaaccccg gagccatctt gctgccgaca ccctgctttc
1501 ccctcgcccct agggctccct tgccgccctc ctgcagtatt tatggcctcg tcctcccac
```

-continued

```
1561 ctaggccacg tgtgagctgc tcctgtctct gtcttattgc agctccaggc ctgacgtttt 1621 acggttttgt tttttactgg tttgtgttta tattttcggg gatacttaat aaatctattg 1681 ctgtcagata cccttaaaaa aaaaaaaaaa aaaaaaaaa
```

By "NEUN polypeptide" (or Feminizing Locus on X-3, Fox-3, RNA-binding protein fox-1 homolog 3, or Hexaribonucleotide Binding Protein-3) is meant a polypeptide or fragment thereof having at least about 85% amino acid identity to NCBI Accession No. NP_001076044.

```
  1 maqpyppaqy pppppqngipa eyappphpt qdysgqtpvp tehgmtlytp aqthpeqpgs 61 eastqpiagt qtvpqtdeaa qtdsqplhps dptekqqpkr lhvsnipfrf rdpdlrqmfg 121 qfgkildvei ifnergskgf gfvtfetssd adrareklng tivegrkiev nnatarvmtn 181 kktgnpytng wklnpvvgav ygpefyavtg fpypttgtav ayrgahlrgr gravyntfra 241 apppppipty gavvyqdgfy gaeiyggyaa yryaqpaaaa aaysdsygrv yaaadpyhht 301 igpaatysig tm
```

By "NEUN nucleic acid molecule" (or Feminizing Locus on X-3, Fox-3, RNA-binding protein fox-1 homolog 3, or Hexaribonucleotide Binding Protein-3) is meant a polynucleotide (e.g., mRNA) encoding an NEUN polypeptide. An exemplary NEUN nucleic acid molecule is provided at NCBI Accession No. NM_001082575.

```
   1 gatacagcag cagctggtgc tcctggccag gctgtgcgtg ctctctctgc ctctctctct 61 cggactctct gctctctctc tctgactctc tcctctctct ctgttggcct ggtgaaatgt 121 tcttggctgt aggcacacag agccttggac tcaaggctgt tggagtcgag gacaccttga 181 cttcggtcct ggaggttgaa attctgcctc tgagaagcta acagtcttcc tgtggtcgcc 241 actcctcccc agcagccccc tccttgccaa ggacggtcca gaaggagccc cactggggcc 301 tccccgctca gcaaagcaga cctcacctcc cactaccagc ttgaagtcac agcagccaga 361 ggaaattctg ccaccatttt cccaggtctg cagcccctcc agctgggaac ctgctcctgg 421 agccatccct ctgcaaacag agagcccaga gtgcctcggg gaaaattggc tgaataaaag 481 agcgatcagg acgccacggc tccgcctgaa gcgatggccc agcccctaccc ccccgcccag 541 tacccccctc cgccacagaa cggcatccct gccgagtacg ccccgccccc accgcacccc 601 acgcaggact actccggcca gaccccggtc ccacagagc atggcatgac cctgtacaca 661 ccagcacaga cccaccccga gcagccaggc tccgaggcca gcacacagcc catcgccggg 721 acccagacag tgccgcagac agacgaggcg gcacagacgg acagccagcc gctccacccc 781 tccgacccta cagagaagca gcagcccaag cggctacacg tctccaacat ccccttccgg 841 ttcagggacc ccgacttgcg gcaaatgttc gggcaattcg gaaaaatttt agacgtggag 901 atcattttta acgagcgggg ctccaagggt tttgggtttg taacttttga aactagctca 961 gatgctgacc gagcccggga gaagctgaat gggacgatcg tagagggacg gaaaattgag 1021 gtcaataatg ccacggcccg agtgatgacc aacaagaaga cggggaaccc ctacaccaac 1081 ggctggaagc taaatccagt ggtcggcgca gtctacgggc ctgaattcta tgcagtgacg 1141 gggttcccct accccaccac cggcacagcc gttgcctacc ggggcgcaca tcttcggggc 1201 cggggccggg ccgtgtataa tacatttcgg gctgcgccac ccccacccc catcccgact 1261 tacggagcgg tcgtgtatca ggatggattt tatggtgctg agatttatgg aggctacgca
```

-continued

```
1321 gcctacagat acgctcagcc cgctgcagcg gcggcagcct acagcgacag ttacggcaga
1381 gtctacgcag ctgccgaccc gtaccatcac accatcgggc ccgcggcgac ctacagcatt
1441 ggaaccatgt gaaaccttcc accgtttcct tctcggacca tgaagggcaa aaacaaaaaa
1501 acaaaaaaaa tcacaaaaca aaaaaaacaa aaaaagatgt taagatccaa gcaacaaaaa
1561 aaaaaccaac caaaccaaga ggcatccaac caagtccaag tcccgcgtcc tggccacacg
1621 cccgcaccga gggagcacgc cggcaggggc gccgaggagc ggcccaggga caggacggcc
1681 ccaccgcgtc ctggctggca gcacagtggg aacacgcccc tcgtctcag gcagtggggg
1741 agttggaggg gaaggggcct cccttgtggg acccgtgggg ggctctgttt tccatccagt
1801 cttcctttcc cagcccccaa ctcccaagac agacagtgtg gagcccagcg gcggcggagc
1861 aggcccgggc ctgagcaggc aggcgctgct agcaagactt gatctttgtg gccagctgtg
1921 ccaggggggcc ggcggggctg aggggtgcgg gcagctttca tcccaggggc tccactgggc
1981 cccgtcaccc tcctgtcgcg tcccctgcgt cccacctccc tcctgcccgg cagtcccgcc
2041 cgtgccccca gcctggcgag gaagccgtcc aacagtagcc ccggggccag ctcccaacag
2101 aaagggctga cgtggctcca ggactcaggg gcgctccatg ggaggacgaa ggaagcccag
2161 ccagccagga gccactcctc acacctccaa gtgtggccaa gtgggccctg aggccaagga
2221 cttacttgct cttcctggcc atctctccct ttctggagga ggcccgggggc ctgtgtacac
2281 caaggctgac ctcgtgctgc ctgctgggac ccagccctcc ctgccgctcc cctgtgagcc
2341 cagtccaccg tgggcgccca gggccaggga cgggccagcg cccggctgca tcgcgaggtt
2401 gggagtcaca gtggctgtgg gcctggacgg gcacagccag agcaggggcc catgggaagg
2461 gcaagggatg gggaagcctg ggccggcccc ttccctgctc ccaaggcagg tgtccaggtg
2521 gcgggagcag caccaaggac agccaggctt acccggtggg aggagcagga gcagagcagg
2581 tggcagggag gaaccccctgg cgaggcaggg agcactgaag tagggaagca gcaaaaaata
2641 caggctccca acgtggctcc actgtctcat gaagtgtcaa aaatttaaaa atacacctca
2701 ctttctattc agcatcagct attgaaatgg aattctcctt ttctattccc gttgtacata
2761 gccccacgcc ctgcctccgg ctttgtcctc tgtacagagc ccctgtccc ctctgctgtt
2821 ccggacccctt tcttgcagc agctcaaccc cccgactcac tcagatcccc aggactgcag
2881 ccgagccccg ggcttccttt cttaccattc tgtatgcttc caaggtgtga ccattcaaac
2941 taacagtatt attaagatta ttaataaaga tttctttctt caaaccagga aaaaaaaaaa
3001 aaaaaaa
```

By "SLC1A6 polypeptide" (or Excitatory amino acid transporter 4; Sodium-dependent glutamate/aspartate transporter; Solute carrier family 1 member 6) is meant a polypeptide or fragment thereof having at least about 85% amino acid identity to NCBI Accession No. P48664.

```
  1 msshgnslfl resgqrlgrv gwlqrlqesl qqralrtrlr lqtmtlehvl rflrrnafil
 61 ltvsavvigv slafalrpyq ltyrqikyfs fpgellmrml qmlvlplivs slvtgmasld
121 nkatgrmgmr aavyymvtti iavfigilmv tiihpgkgsk eglhregrie tiptadafmd
181 lirnmfppnl veacfkqfkt qystrvvtrt mvrtengsep gasmpppfsv engtsflenv
241 tralgtlqem lsfeetvpvp gsanginalg lvvfsvafgl viggmkhkgr vlrdffdsln
301 eaimrlvgii iwyapvgilf liagkileme dmavlggqlg mytltvivgl flhagivlpl
361 iyflvthrnp fpfiggmlqa litamgtsss satlpitfrc leeglgvdrr itrfvlpvga
```

```
421 tvnmdgtaly ealaaifiaq vnnyelnlgq ittisitata asvgaagipq aglvtmvivl
481 tsvglptedi tliiavdwfl drlrtmtnvl gdsigaavie hlsqrelelq eaeltlpslg
541 kpykslmaqe kgasrgrggn esam
```

By "SLC1A6 nucleic acid molecule" (or Excitatory amino acid transporter 4; Sodium-dependent glutamate/aspartate transporter; Solute carrier family 1 member 6) is meant a polynucleotide (e.g., mRNA) encoding an SLC1A6 polypeptide. An exemplary SLC1A6 nucleic acid molecule is provided at NCBI Accession No. BC040604.

```
   1 ggcatagcgc gtcccggctc cgcgccggtg cctccacggt ccggtccccg cgccggtgct
  61 gcacagtccc tggcgggtcc ccgcggcccc ggccgggcgc ttcgccgggc tccggctcct
 121 gcatccgggc gcagcgcgca ggccgaggcg cgggcaggcc gccccgccg ctccggacgc
 181 cgggatgtaa gaggctccga aaagcagccc acgcatctca tcagatctaa gtgtctagag
 241 gtcgggagaa ccaagtggga aagacccacc ctcacccctc accttgtaga aactgggaac
 301 actagaaggg acattttctg agcaggaaac ccaagagaca gggttttacg ctgtcaccca
 361 agttggagtg cagtggtacg atcatagctc attgcagcct caaactcctg ggttcaagcg
 421 atcctcctgc tttagcctct tgagtagcta ggactacagg cacaggccac cgtgcctggc
 481 taatttttaa tttttaaaaa agagacaggg tctggctatg ttgcccaggc tggccatgaa
 541 ctcctgggct caagcggttc tccagccttc acctcccaaa gtgttgggat tgcaggcatg
 601 agccactgcg tctggcccac agatgctaag tgctgtctgc cttctccag gggtcagcaa
 661 atttttttcag caaatggccc aagagtaaat attttgagct ttgtggcccg tacaatctct
 721 gtcccaacaa ctcaactcag gcattgtagc ttgaaagcag ctgtagacaa taggtaatcc
 781 atgagtgtgg ctgtgtgcca ataaaacttt atttacaaaa acaagcagta ggctgaattt
 841 gactagcaga ccatagtttg tcaataccgt attatgtctt gtaaggaaga gaaaggaacc
 901 agacaaaact ctagcctcgg gagttttcct gactgttcag atcttagctg aatgatctcc
 961 cttggtatct acaggcaact tcctgctgtg gcttagggac tggaaacata atatcccaga
1021 gggattccct gtgtagtctg tggttcactc tttgggattt tttttttttt tttcacagca
1081 aggagaagca gcattgtggt ttcaggagat gggtccattt ggagcaggat cctaagtggg
1141 gcttggcatt gggaatttgg attagctcta gaggacgcag gatctggaaa atcagggcag
1201 atttcccatc ccttggatat ggtggggagt tgaggagggc aaggaagatc ccagaaaagc
1261 cagtggcagc aaaacacaaa ggccagggac ctacgtactg gtaaaactga gacctccaag
1321 aaacctgcag ctcgacctgg ttgaattcag atagaccatg agcagccatg caacagcct
1381 gttccttcgg gagagcggcc agcggctggg ccgggtgggc tggctgcagc ggctgcagga
1441 aagcctgcag cagagagcac tgcgcacgcg cctgcgcctg cagaccatga ccctcgagca
1501 cgtgctgcgc ttcctgcgcc gaaacgcctt cattctgctg acggtcagcg ccgtggtcat
1561 tggggtcagc ctggcctttg ccctgcgccc atatcagctc acctaccgcc agatcaagta
1621 cttctctttt cctggagagc ttctgatgag gatgctgcag atgctggtgt tacctctcat
1681 tgtctccagc ctggtcacag gtatggcatc cctggacaac aaggccacgg gcggatggg
1741 gatgcgggca gctgtgtact acatggtgac caccatcatc gcggtcttca tcggcatcct
1801 catggtcacc atcatccatc ccgggaaggg ctccaaggag gggctgcacc gggagggccg
1861 gatcgagacc atccccacag ctgatgcctt catggacctg atcagaaata tgtttccacc
1921 aaaccttgtg gaggcctgct tcaaacagtt caagacgcag tacagcacga gggtggtaac
1981 caggaccatg gtgaggacag agaacgggtc tgagccgggt gcctccatgc ctcctccatt
```

-continued

```
2041 ctcagtggag aacggaacca gcttcctgga aaatgtcact cgggccttgg gtaccctgca
2101 ggagatgctg agctttgagg agactgtacc cgtgcctggc tccgccaatg gcatcaacgc
2161 cctgggcctc gtggtcttct ctgtggcctt tgggctggtc attggtggca tgaaacacaa
2221 gggcagagtc ctcagggact tcttcgacag cctcaatgag ctattatga ggctggtggg
2281 catcattatc tggtgagtcc tggtctgtgc ccacgggaag gtggagccag agctgggaag
2341 tcaggctgtg gggaagctgc cgaagggctt gctggggacc tttggtcatt catttacgta
2401 ttgggtgatt cacttaccca ctcaccaact cattcattca tgtctttctg ggatgatttc
2461 atcactagtt cacttccttg ttcatctgtt cattcattca ttcttctatg cattggttag
2521 ttcatggaat atctcactct ttcattcatt catgtccttc tgcaatgatt cattcactgc
2581 tttgttcatc tgttcattca ctcattcttc tatgcattga tgaaatcact cattcagtga
2641 tttattcatc tatactcatg cttcaatgca ttgatttact catttcctca tgcatttatt
2701 cattcatcta tgcattggtt aaatcactgg ccaactcact aactcattca ttcattcaca
2761 cttttctgca atgatttgtt cacttgttca ctcccttgct tatctgttca ttcactcatt
2821 cttcaataca ttgaccaagc cattcactga catttattca gctacattta ttctttcatg
2881 cattggtctg gatttatttg gtcattcatt tatttatttt gcaaaattaa tgtatttta
2941 attgacaaat aaaaactgta tatttttca tgtgcaaaaa aaaaaaaaa
```

By "NOGOA polypeptide" (or neurite outgrowth inhibitor A; neurite outgrowth inhibitor isoform A; human reticulon-4; human reticulon-4 isoform A) is meant a polypeptide or fragment thereof having at least about 85% amino acid identity to NCBI Accession No. NP_065393.

```
   1 medldqsplv sssdspprpq pafkyqfvre pedeeeeee eeedededle elevlerkpa
  61 aglsaapvpt apaagaplmd fgndfvppap rgplpaappv aperqpswdp spvsstvpap
 121 splsaaavsp sklpeddepp arpppppas vspqaepvwt ppapapaapp stpaapkrrg
 181 ssgsvdetlf alpaasepvi rssaenmdlk eqpgntisag qedfpsvlle taaslpslsp
 241 lsaasfkehe ylgnlstvlp tegtlqenvs easkevseka ktllidrdlt efseleysem
 301 gssfsvspka esavivanpr eeiivknkde eeklvsnnil hnqqelptal tklvkedevv
 361 ssekakdsfn ekrvaveapm reeyadfkpf ervwevkdsk edsdmlaagg kiesnleskv
 421 dkkcfadsle qtnhekdses snddtsfpst pegikdrsga yitcapfnpa atesiatnif
 481 pllgdptsen ktdekkieek kaqivteknt stktsnpflv aaqdsetdyv ttdnltkvte
 541 evvanmpegl tpdlvqeace selnevtgtk iayetkmdlv qtsevmqesl ypaaqlcpsf
 601 eeseatpspv lpdivmeapl nsavpsagas viqpsssple assvnyesik hepenpppye
 661 eamsvslkkv sgikeeikep eninaalqet eapyisiacd liketklsae papdfsdyse
 721 makveqpvpd hselvedssp dsepvdlfsd dsipdvpqkq detvmlvkes ltetsfesmi
 781 eyenkeklsa lppeggkpyl esfklsldnt kdtllpdevs tlskkekipl qmeelstavy
 841 snddlfiske aqiretetfs dsspieiide fptlissktd sfsklareyt dlevshksei
 901 anapdgagsl pctelphdls lkniqpkvee kisfsddfsk ngsatskvll lppdvsalat
 961 qaeiesivkp kvlvkeaekk lpsdtekedr spsaifsael sktsvvdlly wrdikktgvv
1021 fgaslfllls ltvfsivsvt ayialallsv tisfriykgv iqaiqksdeg hpfraylese
1081 vaiseelvqk ysnsalghvn ctikelrrlf lvddlvdslk favlmwvfty vgalfngltl
1141 lilalislfs vpviyerhqa qidhylglan knvkdamaki qakipglkrk ae
```

By "NOGOA nucleic acid molecule" (or neurite outgrowth inhibitor A; neurite outgrowth inhibitor isoform A; human reticulon-4; human reticulon-4 isoform A) is meant a polynucleotide encoding an NOGOA polypeptide. An exemplary NOGOA nucleic acid molecule (e.g., mRNA) is provided at NCBI Accession No. NM_020532.

```
   1 agtccctgcc ctccctggg gagggtgagt cacgccaaac tgggcggaga gtccgctggc
  61 ctcactccta gctcatctgg gcggcggcgg caagtgggga cagggcgggt ggcgcatcac
 121 cggcgcggag gcaggaggag cagtctcatt gttccgggag ccgtcaccac agtaggtccc
 181 tcggctcagt cggcccagcc cctctcagtc ctccccaacc cccacaaccg cccgcggctc
 241 tgagacgcgg ccccggcggc ggcggcagca gctgcagcat catctccacc ctccagccat
 301 ggaagacctg gaccagtctc ctctggtctc gtcctcggac agcccacccc ggccgcagcc
 361 cgcgttcaag taccagttcg tgagggagcc cgaggacgag gaggaagaag aggaggagga
 421 agaggaggac gaggacgaag acctggagga gctggaggtg ctggagagga gcccgccgc
 481 cgggctgtcc gcggcccag tgccaccgc ccctgccgcc ggcgcgcccc tgatggactt
 541 cggaaatgac ttcgtgccgc cggcgccccg ggacccctg ccggccgctc ccccgtcgc
 601 cccggagcgg cagccgtctt gggacccgag cccggtgtcg tcgaccgtgc ccgcgccatc
 661 cccgctgtct gctgccgcag tctcgcccctc caagctccct gaggacgacg agcctccggc
 721 ccggcctccc cctcctcccc cggccagcgt gagccccag gcagagcccg tgtggacccc
 781 gccagccccg gctcccgccg cgccccctc caccccggcc gcgcccaagc gcagggggctc
 841 ctcgggctca gtggatgaga cccttttgc tcttcctgct gcatctgagc ctgtgatacg
 901 ctcctctgca gaaaatatgg acttgaagga gcagccaggt aacactattt cggctggtca
 961 agaggatttc ccatctgtcc tgcttgaaac tgctgcttct cttccttctc tgtctcctct
1021 ctcagccgct tctttcaaag aacatgaata ccttggtaat ttgtcaacag tattacccac
1081 tgaaggaaca cttcaagaaa atgtcagtga agcttctaaa gaggtctcag agaaggcaaa
1141 aactctactc atagatagag atttaacaga gttttcagaa ttagaatact cagaaatggg
1201 atcatcgttc agtgtctctc caaaagcaga atctgccgta atagtagcaa atcctaggga
1261 agaaataatc gtgaaaaata agatgaaga agagaagtta gttagtaata acatccttca
1321 taatcaacaa gagttaccta cagctcttac taaattggtt aaagaggatg aagttgtgtc
1381 ttcagaaaaa gcaaaagaca gtttaatga aaagagagtt gcagtggaag ctcctatgag
1441 ggaggaatat gcagacttca accatttga gcgagtatgg gaagtgaaag atagtaagga
1501 agatagtgat atgttggctg ctggaggtaa aatcgagagc aacttggaaa gtaaagtgga
1561 taaaaaatgt tttgcagata gccttgagca aactaatcac gaaaaagata gtgagagtag
1621 taatgatgat acttctttcc ccagtacgcc agaaggtata aaggatcgtt caggagcata
1681 tatcacatgt gctccctta acccagcagc aactgagagc attgcaacaa acattttttcc
1741 tttgttagga gatcctactt cagaaaataa gaccgatgaa aaaaaatag aagaaagaa
1801 ggcccaaata gtaacagaga gaatactag caccaaaaca tcaaaccctt ttcttgtagc
1861 agcacaggat tctgagacag attatgtcac aacagataat ttaacaaagg tgactgagga
1921 agtcgtggca aacatgcctg aaggcctgac tccagattta gtacaggaag catgtgaaag
1981 tgaattgaat gaagttactg gtacaaagat tgcttatgaa acaaaaatgg acttggttca
2041 aacatcagaa gttatgcaag agtcactcta tcctgcagca cagctttgcc catcatttga
2101 agagtcagaa gctactcctt caccagtttt gcctgacatt gttatggaag caccattgaa
2161 ttctgcagtt cctagtgctg gtgcttccgt gatacagccc agctcatcac cattagaagc
2221 ttcttcagtt aattatgaaa gcataaaaca tgagcctgaa aaccccccac catatgaaga
```

-continued

```
2281 ggccatgagt gtatcactaa aaaaagtatc aggaataaag gaagaaatta aagagcctga
2341 aaatattaat gcagctcttc aagaaacaga agctccttat atatctattg catgtgattt
2401 aattaaagaa acaaagcttt ctgctgaacc agctccggat ttctctgatt attcagaaat
2461 ggcaaaagtt gaacagccag tgcctgatca ttctgagcta gttgaagatt cctcacctga
2521 ttctgaacca gttgacttat ttagtgatga ttcaatacct gacgttccac aaaaacaaga
2581 tgaaactgtg atgcttgtga agaaagtct cactgagact tcatttgagt caatgataga
2641 atatgaaaat aaggaaaaac tcagtgcttt gccacctgag ggaggaaagc catatttgga
2701 atcttttaag ctcagtttag ataacacaaa agatacctg ttacctgatg aagtttcaac
2761 attgagcaaa aaggagaaaa ttcctttgca gatggaggag ctcagtactg cagtttattc
2821 aaatgatgac ttatttattt ctaaggaagc acagataaga gaaactgaaa cgttttcaga
2881 ttcatctcca attgaaatta tagatgagtt ccctacattg atcagttcta aaactgattc
2941 attttctaaa ttagccaggg aatatactga cctagaagta tcccacaaaa gtgaaattgc
3001 taatgccccg gatggagctg ggtcattgcc ttgcacagaa ttgccccatg acctttcttt
3061 gaagaacata caacccaaag ttgaagagaa aatcagtttc tcagatgact tttctaaaaa
3121 tgggtctgct acatcaaagg tgctcttatt gcctccagat gtttctgctt tggccactca
3181 agcagagata gagagcatag ttaaacccaa agttcttgtg aaagaagctg agaaaaaact
3241 tccttccgat acagaaaaag aggacagatc accatctgct atattttcag cagagctgag
3301 taaaacttca gttgttgacc tcctgtactg gagagacatt aagaagactg gagtggtgtt
3361 tggtgccagc ctattcctgc tgcttttcatt gacagtattc agcattgtga gcgtaacagc
3421 ctacattgcc ttggccctgc tctctgtgac catcagcttt aggatataca agggtgtgat
3481 ccaagctatc cagaaatcag atgaaggcca cccattcagg gcatatctgg aatctgaagt
3541 tgctatatct gaggagttgg ttcagaagta cagtaattct gctcttggtc atgtgaactg
3601 cacgataaag gaactcaggc gcctcttctt agttgatgat ttagttgatt ctctgaagtt
3661 tgcagtgttg atgtgggtat ttacctatgt tggtgccttg tttaatggtc tgacactact
3721 gatttttggct ctcatttcac tcttcagtgt tcctgttatt tatgaacggc atcaggcaca
3781 gatagatcat tatctaggac ttgcaaataa gaatgttaaa gatgctatgg ctaaaatcca
3841 agcaaaaatc cctggattga agcgcaaagc tgaatgaaaa cgcccaaaat aattagtagg
3901 agttcatctt taaaggggat attcatttga ttatacgggg gagggtcagg gaagaacgaa
3961 ccttgacgtt gcagtgcagt ttcacagatc gttgttagat ctttattttt agccatgcac
4021 tgttgtgagg aaaaattacc tgtcttgact gccatgtgtt catcatctta agtattgtaa
4081 gctgctatgt atggatttaa accgtaatca tatctttttc ctatctatct gaggcactgg
4141 tggaataaaa aacctgtata ttttactttg ttgcagatag tcttgccgca tcttggcaag
4201 ttgcagagat ggtggagcta gaaaaaaaaa aaaaaagcc cttttcagtt tgtgcactgt
4261 gtatggtccg tgtagattga tgcagatttt ctgaaatgaa atgtttgttt agacgagatc
4321 ataccggtaa agcaggaatg acaaagcttg cttttctggt atgttctagg tgtattgtga
4381 cttttactgt tatattaatt gccaatataa gtaaatatag attatatatg tatagtgttt
4441 cacaaagctt agacctttac cttccagcca ccccacagtg cttgatattt cagagtcagt
4501 cattggttat acatgtgtag ttccaaagca cataagctag aagaagaaat atttctagga
4561 gcactaccat ctgttttcaa catgaaatgc cacacacata gaactccaac atcaatttca
4621 ttgcacagac tgactgtagt taattttgtc acagaatcta tggactgaat ctaatgcttc
4681 caaaaatgtt gtttgtttgc aaatatcaaa cattgttatg caagaaatta ttaattacaa
```

```
4741 aatgaagatt tataccattg tggtttaagc tgtactgaac taaatctgtg gaatgcattg 4801 tgaactgtaa aagcaaagta tcaataaagc ttatagactt aaaaaaaaaa aaaaaaaaa 4861 aaaaaaaaaa a
```

By "oligodendrocyte O1 polypeptide" (or oligodendrocyte marker O1; oligodendrocyte transcription factor 1: olig1) is meant a polypeptide or fragment thereof having at least about 85% amino acid identity to NCBI Accession No. Q8TAK6.

```
1 myyavsqarv navpgtmlrp qrpgdlqlga slyelvgyrq ppsssssts stsstsssst 61 tapllpkaar ekpeapaepp gpgpgsgahp ggsarpdake eqqqqlrrki nsrerkrmqd 121 nlnlamdalre vilpysaahc qgapgrklsk iatllllarny illlgsslqe lrralgegag 181 paaprlllag lpllaaapgs vllapgavgp pdalrpakyl slaldeppcg qfalpgggag 241 gpglctcavc kfphlvpasl glaavqaqfs k
```

By "oligodendrocyte O1 nucleic acid molecule" (or oligodendrocyte marker O1; oligodendrocyte transcription factor 1; olig1) is meant a polynucleotide encoding an oligodendrocyte O1 polypeptide. An exemplary oligodendrocyte O1 nucleic acid molecule (e.g., mRNA) is provided at NCBI Accession No. NM_138983.

```
1    gttctagatc gtttcccgc gcgcaggtcc gcggggaggg gcggcctgcc gaccggccca 61   ccccagggcg ttcctgaagg gcgtcctcgg ccgcccccac cgcctcccag atgtactatg 121  cggtttccca ggcgcgcgtg aacgcggtcc ccgggaccat gctgcggcca cagcggcccg 181  gagacttgca gctcggggcc tccctctacg agctggtggg ctacaggcag ccgccctcct 241  cctcctcctc ctccacctcc tccacctcct ccacttcctc ctcctccacg acggccccc 301  tcctccccaa ggctgcgcgc gagaagccgg aggcgccggc cgagcctcca ggccccgggc 361  ccgggtcagg cgcgcacccg ggcggcagcg cccggccgga cgccaaggag gagcagcagc 421  agcagctgcg gcgcaagatc aacagccgcg agcggaagcg catgcaggac ctgaacctgg 481  ccatggacgc cctgcgcgag gtcatcctgc cctactcagc ggcgcactgc cagggcgcgc 541  ccggccgcaa gctctccaag atagccacgc tgctgctcgc ccgcaactac atcctactgc 601  tgggcagctc gctgcaggag ctgcgccgcg cgctgggcga gggcgccggg cccgccgcgc 661  cgcgcctgct gctggccggg ctgcccctgc tcgccgccgc gcccggctcc gtgctgctgg 721  cgccccggcgc cgtaggaccc cccgacgcgc tgcgccccgc caagtacctg tcgctggcgc 781  tggacgagcc gccgtgcggc cagttcgctc tccccggcgg cggcgcaggc ggccccggcc 841  tctgcacctg cgccgtgtgc aagttcccgc acctggtccc ggccagcctg ggcctggccg 901  ccgtgcaggc gcaattctcc aagtgagggc gggtctgggc ctggggcgcg acctcggccc 961  ggcctcccctt cgctcagctt ctccgcgccc ctgctccctg cgtctgggag agcgaggccg 1021 agcaaggaaa gcatttcgaa ccttccagtc cagaggaagg gactgtcggg caccccttc 1081 cccgccccca ccctgggac gttaaagtga ccagagcgga tgttcgatgg cgcctcgggg 1141 cagtttgggg ttctgggtcg gttccagcgg ctttaggcag aaagtgctcg ctctcaccca 1201 gcacatctct ctccttgtcc ctggagttgc gcgcttcgcg gggccgatgt agaacttagg 1261 gcgccttgcc gtggttggcg cgccccgggt gcagcgagag gccatccccg agcgctacct
```

-continued

```
1321 ccccggagcg gagcacgcgg gctcccagta ctaggggctg cgctcgagca gtggcggggg 1381 cggaggggtg gttcttttcc ttctcctccg ccagaggcca cgggcgccct tgttcccgcc 1441 ggccaggtcc tatcaaagga ggctgccgga actcaagagg cagaaaaaga ccagttaggc 1501 ggtgcagacg gtctgggacg tgcagacgg acggaccctc ggcggacagg tggtcggcgt 1561 cggggtgcgg tgggtagggg cgaggacaac gcagggtgcg ctgggttggg acgtgggtcc 1621 acttttgtag accagctgtt tggagagctg tatttaagac tcgcgtatcc agtgttttgt 1681 cgcagagagt tttcactctt aaatcctggg ggtttcttag aaagcaactt agaactcgag 1741 attcacctttt cgtttccctt tccccaaaag tagcgtaacc aacatttaag cttgcttaaa 1801 aacgaaaacc aaccgccttg catccagtgt tcccgattta ctaaaatagg taaccaggcg 1861 tctcacagtc gccgtcctgt caagagcgct aatgaacgtt ctcattaaca cgcaggagta 1921 ccgggagccc tgaaccgccc gctgctcggc ggatcccagc tgcggtggcg acggcgggaa 1981 ggcgctttcc gctgttcctc agcgggccgg gcccttgacc agcgcggccc gcaggtcttc 2041 cttctcgccg tcttgcagtt gaagagctac atacgtagtc agtttcgatt tgttacagac 2101 gttaacaaat tcctttaccc aaggttatgc tatgaccttt ccgcagttta ctttgatttt 2161 ctatgtttaa ggttttggtt gttggtagta gccgaattta actggcactt tattttactt 2221 ctaaccttgt ttcctgacgg tgtacagaat caacaaaata aaacatttaa agtctgattt 2281 tttaaaaaaa aaaaaaa
```

By "oligodendrocyte O2 polypeptide" (or oligodendrocyte marker O2; oligodendrocyte transcription factor 2; olig2) is meant a polypeptide or fragment thereof having at least about 85% amino acid identity to NCBI Accession No. Q13516.

```
  1 mdsdaslvss rpsspepddl flparskgss gsaftggtvs sstpsdcppe lsaelrgamg 61 sagahpgdkl ggsgfkssss stssstssaa asstkkdkkq mtepelqqlr lkinsrerkr 121 mhdlniamdg lrevmpyahg psvrklskia tllllarnyil mltnsleemk rlvseiyggh 181 hagfhpsacg glahsaplpa atahpaaaah aahhpavhhp ilppaaaaaa aaaaaavss 241 aslpgsglps vgsirpphgl lkspsaaaaa plgggggggsg asggfqhwgg mpcpcsmcqv 301 ppphhhvsam gagslprlts dak
```

By "oligodendrocyte O2 nucleic acid molecule" (or oligodendrocyte marker O2; oligodendrocyte transcription factor 2; olig2) is meant a polynucleotide encoding an oligodendrocyte O2 polypeptide. An exemplary oligodendrocyte O2 nucleic acid molecule (e.g., mRNA) is provided at NCBI Accession No. NM_005806.

```
  1 gggtgcttat tatagatcga cgcgacacca gcgcccggtg ccaggttctc ccctgaggct 61 tttcggagcg agctcctcaa atcgcatcca gagtaagtgt ccccgcccca cagcagccgc 121 agcctagatc ccagggacag actctcctca actcggctgt gacccagaat gctccgatac 181 aggggggtctg gatccctact ctgcgggcca tttctccaga gcgactttgc tcttctgtcc 241 tccccacact caccgctgca tctccctcac caaaagcgag aagtcggagc gacaacagct 301 ctttctgccc aagccccagt cagctggtga gctccccgtg gtctccagat gcagcacatg 361 gactctgggc cccgcgccgg ctctgggtgc atgtgcgtgt gcgtgtgttt gctgcgtggt 421 gtcgatggag ataaggtgga tccgtttgag gaaccaaatc attagttctc tatttagatc
```

-continued

```
 481 tccattctcc ccaaagaaag gccctcactt cccactcgtt tattccagcc cgggggctca
 541 gttttcccac acctaactga aagcccgaag cctctagaat gccacccgca ccccgagggt
 601 caccaacgct ccctgaaata acctgttgca tgagagcaga ggggagatag agagagctta
 661 attataggta cccgcgtgca gctaaaagga gggccagaga tagtagcgag ggggacgagg
 721 agccacgggc cacctgtgcc gggaccccgc gctgtggtac tgcggtgcag gcgggagcag
 781 cttttctgtc tctcactgac tcactctctc tctctctccc tctctctctc tctcattctc
 841 tctcttttct cctcctctcc tggaagtttt cgggtccgag ggaaggagga ccctgcgaaa
 901 gctgcgacga ctatcttccc ctggggccat ggactcggac gccagcctgg tgtccagccg
 961 cccgtcgtcg ccagagcccg atgaccttt tctgccggcc cggagtaagg gcagcagcgg
1021 cagcgccttc actgggggca ccgtgtcctc gtccaccccg agtgactgcc cgccggagct
1081 gagcgccgag ctgcgcggcg ctatgggctc tgcgggcgcg catcctgtgg acaagctagg
1141 aggcagtggc ttcaagtcat cctcgtccag cacctcgtcg tctacgtcgt cggcggctgc
1201 gtcgtccacc aagaaggaca agaagcaaat gacagagccg gagctgcagc agctgcgtct
1261 caagatcaac agccgcgagc gcaagcgcat gcacgacctc aacatcgcca tggatggcct
1321 ccgcgaggtc atgccgtacg cacacggccc ttcggtgcgc aagcttttcca agatcgccac
1381 gctgctgctg gcgcgcaact acatcctcat gctcaccaac tcgctggagg agatgaagcg
1441 actggtgagc gagatctacg ggggccacca cgctggcttc caccgtcgg cctgcggcgg
1501 cctggcgcac tccgcgcccc tgcccgccgc caccgcgcac ccggcagcag cagcgcacgc
1561 cgcacatcac cccgcggtgc accacccat cctgccgccc gccgccgcag cggctgctgc
1621 cgccgctgca gccgcggctg tgtccagcgc ctctctgccc ggatccgggc tgccgtcggt
1681 cggctccatc cgtccaccgc acggcctact caagtctccg tctgctgccg cggccgcccc
1741 gctgggggc ggggcggcg gcagtggggc gagcgggggc ttccagcact ggggcggcat
1801 gccctgcccc tgcagcatgt gccaggtgcc gccgccgcac caccacgtgt cggctatggg
1861 cgccggcagc ctgccgcgcc tcacctccga cgccaagtga gcctactggc gccggcgcgt
1921 tctggcgaca ggggagccag gggccgcggg gaagcgagga ctggcctgcg ctgggctcgg
1981 gagctctgtc gcgaggaggg gcgcaggacc atggactggg ggtggggcat ggtggggatt
2041 tcagcatctg cgaacccaag caatgggggc gcccacagag cagtggggag tgaggggatg
2101 ttctctccgg gacctgatcg agcgctgtct ggctttaacc tgagctggtc cagtagacat
2161 cgttttatga aaaggtaccg ctgtgtgcat tcctcactag aactcatccg accccccgacc
2221 cccacctccg ggaaaagatt ctaaaaactt cttcccctga gagcgtggcc tgacttgcag
2281 actcggcttg gcagcactt cggggggga gggggtgtta tggaggggg acacattggg
2341 gccttgctcg tcttcctcct ttcttggcgg gtgggagact ccgggtagcc gcactgcaga
2401 agcaacagcc cgaccgcgcc ctccagggtc gtccctggcc caaggccagg ggccacaagt
2461 tagttggaag ccggcgttcg gtatcagaag cgctgatggt catatccaat ctcaatatct
2521 gggtcaatcc acaccctctt agaactgtgg ccgttcctcc ctgtctctcg ttgatttggg
2581 agaatatggt tttctaataa atctgtggat gttccttctt caacagtatg agcaagttta
2641 tagacattca gagtagaacc acttgtggat tggaataacc caaaactgcc gatttcaggg
2701 gcgggtgcat tgtagttatt attttaaaat agaaactacc ccaccgactc atctttcctt
2761 ctctaagcac aaagtgattt ggttattttg gtacctgaga acgtaacaga attaaaaggc
2821 agttgctgtg gaaacagttt gggttatttg ggggttctgt tggcttttta aaatttctt
```

```
-continued
2881 ttttggatgt gtaaatttat caatgatgag gtaagtgcgc aatgctaagc tgtttgctca 2941 cgtgactgcc agcccatcg gagtctaagc cggctttcct ctattttggt ttatttttgc 3001 cacgtttaac acaaatggta aactcctcca cgtgcttcct gcgttccgtg caagccgcct 3061 cggcgctgcc tgcgttgcaa actgggcttt gtagcgtctg ccgtgtaaca cccttcctct 3121 gatcgcaccg cccctcgcag agagtgtatc atctgtttta tttttgtaaa aacaaagtgc 3181 taaataatat ttattacttg tttggttgca aaaacggaat aaatgactga gtgttgagat 3241 tttaaataaa atttaaagca aaaaaaaaaa aaaaa
```

By "oligodendrocyte O4 polypeptide" (or oligodendrocyte marker O4; oligodendrocyte transcription factor 4; olig4) is meant a polypeptide or fragment thereof having at least about 85% amino acid identity to NCBI Accession No. Q05586.

By "oligodendrocyte O4 nucleic acid molecule" (or oligodendrocyte marker O4; oligodendrocyte transcription factor 4; olig4) is meant a polynucleotide encoding an oligodendrocyte O4 polypeptide. An exemplary oligodendrocyte O4 nucleic acid molecule (e.g., mRNA) is provided at NCBI Accession No. NM_007327.

By "GFAP" (or Glial fibrillary acidic protein) is meant a polypeptide or fragment thereof having at least about 85% amino acid identity to NCBI Accession No. P14136.

```
  1 merrritsaa rrsyvssgem mvgglapgrr lgpgtrlsla rmppplptrv dfslagalna 61 gfketraser aemmelndrf asyiekvrfl eqqnkalaae lnqlrakept kladvyqael 121 relrlrldql tansarleve rdnlaqdlat vrqklqdetn lrleaennla ayrqeadeat 181 larldlerki esleeeirfl rkiheeevre lqeqlarqqv hveldvakpd ltaalkeirt 241 qyeamassnm heaeewyrsk fadltdaaar naellrqakh eandyrrqlq sltcdleslr 301 gtneslerqm reqeerhvre aasyqealar leeegqslkd emarhlqeyq dllnvklald 361 ieiatyrkll egeenritip vqtfsnlqir etsldtksvs eghlkrnivv ktvemrdgev 421 ikeskqehkd vm
```

By "GFAP nucleic acid molecule" (or Glial fibrillary acidic protein) is meant a polynucleotide encoding an GFAP polypeptide. An exemplary GFAP nucleic acid molecule (e.g., mRNA) is provided at NCBI Accession No. NM_002055.

```
  1 gcaggatgga gaggagacgc atcacctccg ctgctcgccg ctcctacgtc tcctcagggg 61 agatgatggt gggggggcctg gctcctggcc gccgtctggg tcctggcacc cgcctctccc 121 tggctcgaat gccccctcca ctcccgaccc gagtggattt ctccctggct ggggcactca 181 atgctggctt caaggagacc cgggccagtg agcgggcaga gatgatggag ctcaatgacc 241 gctttgccag ctacatcgag aaggttcgct tcctggaaca gcaaaacaag gcgctggctg 301 ctgagctgaa ccagctgcgg gccaaggagc ccaccaagct ggcagacgtc taccaggctg 361 agctgcgaga gctgcggctg cggctcgatc aactcaccgc caacagcgcc cggctggagg 421 ttgagaggga caatctggca caggacctgg ccactgtgag gcagaagctc caggatggaa 481 ccaacctgag gctggaagcc gagaacaacc tggctgccta tagacaggaa gcagatgaag 541 ccacccctggc ccgtctggat ctggagagga gattgagtc gctggaggag gagatccggt 601 tcttgaggaa gatccacgag gaggaggttc gggaactcca ggagcagctg gcccgacagc
```

-continued

```
 661 aggtccatgt ggagcttgac gtggccaagc cagacctcac cgcagccctg aaagagatcc
 721 gcacgcagta tgaggcaatg gcgtccagca acatgcatga agccgaagag tggtaccgct
 781 ccaagtttgc agacctgaca gacgctgctg cccgcaacgc ggagctgctc cgccaggcca
 841 agcacgaagc caacgactac cggcgccagt tgcagtcctt gacctgcgac ctggagtctc
 901 tgcgcggcac gaacgagtcc ctggagaggc agatgcgcga gcaggaggag cggcacgtgc
 961 gggaggcggc cagttatcag gaggcgctgg cgcggctgga ggaagagggg cagagcctca
1021 aggacgagat ggcccgccac ttgcaggagt accaggacct gctcaatgtc aagctggccc
1081 tggacatcga gatcgccacc tacaggaagc tgctagaggg cgaggagaac cggatcacca
1141 ttcccgtgca gaccttctcc aacctgcaga ttcgagaaac cagcctggac accaagtctg
1201 tgtcagaagg ccacctcaag aggaacatcg tggtgaagac cgtgggagatg cgggatggag
1261 aggtcattaa ggagtccaag caggagcaca aggatgtgat gtgaggcagg acccacctgg
1321 tggcctctgc cccgtctcat gaggggcccg agcagaagca ggatagttgc tccgcctctg
1381 ctggcacatt tccccagacc tgagctcccc accacccag ctgctcccct ccctcctctg
1441 tccctaggtc agcttgctgc cctaggctcc gtcagtatca ggcctgcc
```

By "s100b" (or S-100 protein beta chain; S-100 protein subunit beta; S100 calcium-binding protein B) is meant a polypeptide or fragment thereof having at least about 85% amino acid identity to NCBI Accession No. P04271.

```
  1 mselekamva lidvfhqysg regdkhklkk selkelinne lshfleeike qevvdkvmet
 61 ldndgdgecd fqefmafvam vttacheffe he
```

By "s100b nucleic acid molecule" (or S-100 protein beta chain; S-100 protein subunit beta; S100 calcium-binding protein B) is meant a polynucleotide encoding an s100b polypeptide. An exemplary s100b nucleic acid molecule (e.g., mRNA) is provided at NCBI Accession No. NM_006272.

```
  1 gggcagaggg aataagaggc tgcctctgcc caccagtcct gccgcccagg acccgcagca
 61 gagacgacgc ctgcagcaag gagaccagga aggggtgaga caaggaagag gatgtctgag
121 ctggagaagg ccatggtggc cctcatcgac gttttccacc aatattctgg aagggaggga
181 gacaagcaca agctgaagaa atccgaactg aaggagctca tcaacaatga gctttcccat
241 ttcttagagg aaatcaaaga gcaggaggtt gtggacaaag tcatggaaac actggacaat
301 gatggagacg gcgaatgtga cttccaggaa ttcatggcct tgttgccat ggttactact
361 gcctgccacg agttctttga acatgagtga gattagaaag cagccaaacc tttcctgtaa
421 cagagacggt catgcaagaa agcagacagc aagggcttgc agcctagtag gagctgagct
481 ttccagccgt gttgtagcta attaggaagc ttgatttgct ttgtgattga aaaattgaaa
541 acctcttttcc aaaggctgtt ttaacggcct gcatcattct ttctgctata ttaggcctgt
601 gtgtaagctg actggcccca gggactcttg ttaacagtaa cttaggagtc aggtctcagt
661 gataaagcgt gcaccgtgca gcccgccatg gccgtgtaga ccctaacccg gagggaaccc
721 tgactacaga aattaccccg gggcacccstt aaaacttcca ctacctttaa aaaacaaagc
781 cttatccagc attatttgaa aacactgctg ttctttaaat gcgttcctca tccatgcaga
841 taacagctgg ttggccggtg tggccctgca agggcgtggt ggcttcggcc tgcttcccgg
```

```
 901 gatgcgcctg atcaccaggt gaacgctcag cgctggcagc gctcctggaa aaagcaactc 961 catcagaact cgcaatccga gccagctctg ggggctccag cgtggcctcc gtgacccatg 1021 cgattcaagt cgcggctgca ggatccttgc ctccaacgtg cctccagcac atgcggcttc 1081 cgagggcact accgggggct ctgagccacc gcgagggcct gcgttcaata aaaag
```

By "SOX10 polypeptide" (or SRY-related HMG-box transcription factor) is meant a polypeptide or fragment thereof having at least about 85% amino acid identity to NCBI Accession No. NP_008872.1.

MAEEQDLSEVELSPVGSEEPRCLSPGSAPSLGPDGGGGGSGLRASPGPGE

LGKVKKEQQDGEADDDKFPVCIREAVSQVLSGYDWTLVPMPVRVNGASKS

KPHVKRPMNAFMVWAQAARRKLADQYPHLHNAELSKTLGKLWRLLNESDK

RPFIEEAERLRMQHKKDHPDYKYQPRRRKNGKAAQGEAECPGGEAEQGGT

AAIQAHYKSAHLDHRHPGEGSPMSDGNPEHPSGQSHGPPTPPTTPKTELQ

SGKADPKRDGRSMGEGGKPHIDFGNVDIGEISHEVMSNMETFDVAELDQY

LPPNGHPGHVSSYSAAGYGLGSALAVASGHSAWISKPPGVALPTVSPPGV

DAKAQVKTETAGPQGPPHYTDQPSTSQIAYTSLSLPHYGSAFPSISRPQF

DYSDHQPSGPYYGHSGQASGLYSAFSYMGPSQRPLYTAISDPSPSG

PQSHSPTHWEQPVYTTLSRP

By "SOX10 nucleic acid molecule" (or SRY-related HMG-box transcription factor) is meant a polynucleotide encoding an SOX10 polypeptide. An exemplary SOX10 nucleic acid molecule (e.g., mRNA) is provided at NCBI Accession No. NM_006941.3.

```
   1 gtccggccag ggtggttggt ggtaaggatt caggctccgt cctaacgagg ccgtggcctg 61 aggctcaggg cccccgccc ctccctccca gccaccagc gtcacctccc agcccgagc 121 tggaccgcac accttgggac acggttttcc acttcctaag gacgagcccc agactggagg 181 agaggtccga ggaggtgggc gttggactct ttgcgaggac cccggcggct ggcccggggg 241 aggcggccga ggcggcggcg gcggcggccg ggggcgacat ggcggaggag caggacctat 301 cggaggtgga gctgagcccc gtgggctcgg aggagccccg ctgcctgtcc ccggggagcg 361 cgccctcgct agggcccgac ggcggcggcg gcggatcggg cctgcgagcc agcccggggc 421 caggcgagct gggcaaggtc aagaaggagc agcaggacgg cgaggcggac gatgacaagt 481 tccccgtgtg catccgcgag gccgtcagcc aggtgctcag cggctacgac tggacgctgg 541 tgcccatgcc cgtgcgcgtc aacggcgcca gcaaaagcaa gccgcacgtc aagcggccca 601 tgaacgcctt catggtgtgg gctcaggcag cgcgcaggaa gctcgcggac cagtacccgc 661 acctgcacaa cgctgagctc agcaagacgc tgggcaagct ctggaggctg ctgaacgaaa 721 gtgacaagcg ccccttcatc gaggaggctg agcggctccg tatgcagcac aagaaagacc 781 acccggacta caagtaccag cccaggcggc ggaagaacgg gaaggccgcc cagggcgagg 841 cggagtgccc cggtggggag gccgagcaag tgggaccgc cgccatccag gcccactaca 901 agagcgccca cttggaccac cggcacccag gagagggctc ccccatgtca gatgggaacc 961 ccgagcaccc ctcaggccag agccatggcc cacccacccc tccaaccacc ccgaagacag 1021 agctgcagtc gggcaaggca gacccgaagc gggacgggcg ctccatgggg gagggcggga 1081 agcctcacat cgacttcggc aacgtggaca ttggtgagat cagccacgag gtaatgtcca 1141 acatggagac ctttgatgtg gctgagttgg accagtacct gccgcccaat gggcacccag 1201 gccatgtgag cagctactca gcagccggct atgggctggg cagtgccctg gccgtggcca 1261 gtggacactc cgcctggatc tccaagccac caggcgtggc tctgcccacg gtctcaccac 1321 ctggtgtgga tgccaaagcc caggtgaaga cagagaccgc ggggccccag gggcccccac 1381 actacaccga ccagccatcc acctcacaga tcgcctacac ctccctcagc ctgccccact 1441 atggctcagc cttcccctcc atctcccgcc ccagtttga ctactctgac catcagccct 1501 caggaccta ttatggccac tcgggccagg cctctggcct ctactcggcc ttctcctata
```

```
1561 tggggccctc gcagcggccc ctctacacgg ccatctctga ccccagcccc tcagggcccc 1621 agtcccacag ccccacacac tgggagcagc cagtatatac gacactgtcc cggccctaaa 1681 gggggccctg tcgccaccac ccccgccca gcccctgccc ccagcctgtg tgccctgttc 1741 cttgcccacc tcaggcctgg tggtggcagt ggaggaggct gaggaggctg aagaggctga 1801 caggtcgggg ggctttctgt ctggctcact gccctgatga cccacccgcc ccatccaggc 1861 tccagcagca aagccccagg agaacaggct ggacagagga gaaggaggtt gactgttgca 1921 cccacactga aagatgaggg gctgcacctt cccccaggaa tgaccctcta tcccaggacc 1981 tgagaagggc ctgctcaccc tcctcgggga ggggaagcac cagggttggt ggcatcggag 2041 gccttaccac tcctatgact cctgttttct ctctcacaga tagtgagggt ctgacatgcc 2101 catgccacct atgccacagt gcctaagggc taggccaccc agagactgtg cccggagctg 2161 gccgtgtctc ccactcaggg gctgagagta gctttgagga gcctcattgg ggagtggggg 2221 gttcgaggga cttagtggag ttctcatccc ttcaatgccc cctccctttc tgaaggcagg 2281 aaggagttgg cacagaggcc ccctgatcca attctgtgcc aataacctca ttctttgtct 2341 gagaaacagc ccccagtcct cctccactac aacctccatg accttgagac gcatcccagg 2401 aggtgacgag gcagggctc caggaaagga atcagagaca attcacagag cctccctccc 2461 tgggctcctt gccagctccc tcttcccta ctaggctcta tggcccctgc tcagtcagcc 2521 ccactccctg ggcttcccag agagtgacag ctgctcaggc cctaacccctt ggctccagga 2581 gacacagggc ccagcaccca ggttgctgtc ggcaggctga agacactaga atcctgacct 2641 gtacattctg cccttgcctc ttaccccttg cctcccagtg gtatttgaat aaagtatgta 2701 gctatatctg cccctatttt cctgttctgc agccccccaa atccacatgt aactcattac 2761 tgtctcctgt tatttatctc agtagtcccc tctcctagcc actctagccc ctattaactc 2821 tgcattaagc attccacata ataaaattaa aggttccggt taaaaaaaaa aaaaaaaaa 2881 aa
```

By "SYN1 protein" (or Synaptin I protein) is meant a polypeptide or fragment thereof having at least about 85% amino acid identity to GenBank: AH006533.2.

MNYLRRRLSDSNFMANLPNGYMTDLQRPQPPPPPPGAHSPGATPGPGTAT

AERSSGVAPAASPAAPSPGSSGGGGFFSSLSNAVKQTTAAAAATFSEQVG

GGSGGAGRGGAASRVLLVIDEPHTDWAKYFKGKKIHGGIDIKVEQAEFSD

LNLVAHANGGFSVDMEVLRNGVKVVRSLKPDFVLIRQHAFSMARNGDYRS

LVIGLQYAGIPSVNSLHSVYNFCDKPWVFAQMVRLHKKLGTEEFPLIDQT

FYPNHKEMLSSTTYPVVVKMGHAHSGMGKVKVDNQHDFQDIASVVALTKT

YATAEPFIDAKYDVRVQKIGQNYKAYMRTSVSGNWKTNTGSAMLEQIAMS

DRYKLWVDTCSEIFGGLDICAVEALHGKDGRDHIIEVVGSSMPLIGDHQD

EDKQLIVELVVNKMAQALPRQRQRDASPGRGSHGQTPSPGALPLGRQTSQ

QPAGPPAQQRPPPQGGPPQPGPGPQRQGPPLQQRPPPQGGQQHLSGLGPPA

GSPLPQRLPSPTSAPQQPASQAAPPTQGQGRQSRPVAGGPGAPPAARPPA

SPSPQRQAGPPQATRQTSVSGPAPPKASGAPPGGQQRQGPPQKPPGPAGP

TRQASQAGPVPRTGPPTTQQPRPSGPGPAGAPKPQLAQKPSQDVPPPATA

AAGGPPHPQLNKSQSLTNAFNLPEPAPPRPSLSQDEVKAETIRSLRKSFA

SLFSD

By "SYN1 nucleic acid molecule" (or synapsin I gene) is meant a polynucleotide encoding an SYN1 polypeptide. An exemplary SYN1 nucleic acid molecule (e.g., mRNA) is provided at GenBank: AH006533.2.

```
  1 ctcgagagag aaggagagga cattcctggc agaagttaca acacatgcaa aggtacagag 61 gttgcccct tcctacccct ctccttagag gtgggttaga gatgtatcct ttttacagat 121 gaggaaacca aatctcagaa agattaagtc actttcccaa gtgtatggtg gaggcccac 181 ttgaacccag gcactgtgtc tccagacccc acactattac tgccttgttt aaaccagcca 241 actgatttaa tgaataaagg atgaacaaat gaataagtgg atgagtcacc tgaaaattct
```

-continued

```
 301 gcaggcaaag agactccata tctacttact tcttgcctat cttctgccac ctctcctagt 361 ccaccatcac tgctcactat ggtcaaggtc ctacccaatc tggcccctgc taccacaacc 421 cccttcagct tgttccagcc acattggcac tggatgtttc ctcttcctgg cacattctta 481 aaaaaatgtg ttgatcataa agtgaacatg acccttggg aattaactgg agttcttgta 541 ttccctcatc tgtaaaatag acattatatt atccacccca ctggattgtt gtgagggtgg 601 gatgaaatga tgcatgtaaa cacgcttagc ttaagagttg ggtacaatca gtgaacaaat 661 gattatgaat tagtgctttt attgtagtca gaatcataaa gatttgacag gttcccatat 721 cccacctctg cttggactac ctcatttgct catatgcaaa gattatttgg tacctactgt 781 gtgtgcacca tgggatgggc ctgcctctgt ggaaagttct tgggtgcagg gggagacagc 841 catgggcact gatgacatca ggtagttatc gtgagttttg gcggtgtcca gagcaaaggg 901 atggtggcgt ataccaag tgtgttctgg tgtgggggtg gacacgcacc agggctaggg 961 ctgcagagaa tgtctgtgtt gcagatctag gtttctccat gatcatcggt gggaatgtgt 1021 tttgtctgca agtgtatgct catatgagtt tccctgggtc tctgtgtgtc agtgtgttac 1081 ctgtgtgtgt gggggtatgg gtgtatgcat gcatgtatgt aacatgccca tgtgtgttac 1141 tctggacttg tatgtctgta tgtataccta gattggcgtg tgttctgtct gtacatgccc 1201 tcgtatgttt cctcactttt gtgtgtgttt atatgtgtgt catttcttgt gtgccctcca 1261 ggcccccctt gccaccttgg gcaagggtgt gtacaccacc caagtgtcca cctccgcttg 1321 tctgatgctg tctgtgacgc ccccgctctc tgcctagctg agcctgtgtg gatgtgggag 1381 actaatctcc ccgcgggcac tgcgtgtgac ctcaccccc tctgtgaggg ggttatttct 1441 ctactttcgt gtctctgagt gtgcttccag tgcccccctc cccccaaaaa atgccttctg 1501 agttgaatat caacactaca aaccgagtat ctgcagactg cagagggccc tgcgtatgag 1561 tgcaagtggg ttttaggacc aggatgaggc ggggtggggg tgcctacctg acgaccgacc 1621 ccgacccact ggacaagcac ccaacccccca ttccccaaat tgcgcatccc ctatcagaga 1681 gggggagggg aaacaggatg cggcgaggcg cgtcgcgact gccagcttca gcaccgcgga 1741 cagtgccttc gcccccgcct ggcggcgcgc gccaccgccg cctcagcact gaaggcgcgc 1801 tgacgtcact cgccggtccc ccgcaaactc cccttccgg ccaccttggt cgcgtccgcg 1861 ccgccgccgg cccagccgga ccgcaccacg cgaggcgcga gataggggg cacgggcgcg 1921 accatctgcg ctgcggcgcc ggcgactcag cgctgcctca gtctgcggtg ggcagcggag 1981 gagtcgtgtc gtgcctgaga gcgcagctgt gctcctgggc accgcgcagt ccgccccgc 2041 ggctcctggc cagaccaccc ctaggacccc ctgccccaag tcgcagccat gaactacctg 2101 cggcgccgcc tgtcggacag caactttatg gccaatctgc caaatgggta catgacagac 2161 ctgcagcgtc cgcagccgcc cccaccgccg cccggtgccc acagccccgg agccacgccc 2221 ggtcccggga ccgccactgc cgagaggtcc tccggggtcg ccccagcggc ctctccggcc 2281 gcccctagcc ccgggtcctc gggggcggt ggcttcttct cgtcgctgtc caacgcggtc 2341 aagcagacca cggcggcggc agctgccacc ttcagcgagc aggtgggcgg cggctctggg 2401 ggcgcaggcc gcggggagc cgcctccagg gtgctgctgg tcatcgacga gccgcacacc 2461 gactggtaag
```

By "SYP protein" (or synaptophysin protein) is meant a polypeptide or fragment thereof having at least about 85% amino acid identity to NCBI Reference Sequence: NM_003179.2.

MLLLADMDVVNQLVAGGQFRVVKEPLGFVKVLQWVFAIFAFATCGSYSGE
LQLSVDCANKTESDLSIEVEFEYPFRLHQVYFDAPTCRGGTTKVFLVGDY
SSSAEFFVTVAVFAFLYSMGALATYIFLQNKYRENNKGPMLDFLATAVFA

-continued
FMWLVSSSAWAKGLSDVKMATDPENIIKEMPVCRQTGNTCKELRDPVTSG
LNTSVVFGFLNLVLWVGNLWFVFKETGWAAPFLRAPPGAPEKQPAPGDAY
GDAGYGQGPGGYGPQDSYGPQGGYQPDYGQPAGSGGSGYGPQGDYGQQGY
GPQGAPTSFSNQM By "SYP nucleic acid molecule" (or synaptophysin gene) is meant a polynucleotide encoding an SYN1polypeptide. An exemplary SYP nucleic acid molecule (e.g., mRNA) is provided at NCBI Reference Sequence: NM_003179.2.

```
   1 gccccctgca ttgctgatgc tgctgctggc ggacatggac gtggtgaatc agctggtggc
  61 tggggtcag ttccgggtgg tcaaggagcc cctcggcttt gtgaaggtgc tgcaatgggt
 121 cttcgccatc ttcgcctttg ccacatgcgg cagctacagt ggggagctcc agctgagcgt
 181 ggattgtgcc aacaagaccg agagtgacct cagcatcgag gtcgagttcg agtacccctt
 241 caggctgcac caagtgtact ttgatgcacc cacctgccga gggggcacca ccaaggtctt
 301 cttagttggg gactactcct cgtcagccga attctttgtc accgtggccg tgtttgcctt
 361 cctctactcc atgggggctc tggccaccta catcttcctg cagaacaagt accgagagaa
 421 taacaaaggg cccatgctgg actttctggc cacggctgtg ttcgccttca tgtggctagt
 481 tagctcatcg gcatgggcca aggggctgtc agatgtgaag atgccacag acccagaa
 541 cattatcaag gagatgcctg tctgccgcca gacaggaac acatgcaagg agctgagaga
 601 ccctgtgacc tcgggactca acacctcggt ggtgttcggc ttcctgaacc tggtgctctg
 661 ggtcggcaac ctgtggttcg tgtttaagga gacaggctgg gccgcccgt cctgcgcgc
 721 gcctccggc gccccgaga aacaaccggc acccggggac gcctacggcg atgcaggcta
 781 cgggcagggc cccggcgggt acgggcccca ggattcctac gggcctcagg cggctacca
 841 gcctgactat ggtcaaccag ccggcagcgg tggcagtggc tacgggcctc agggcgacta
 901 tgggcagcaa ggctacgcc cgcagggtgc acccacctcc ttctccaatc agatgtagtc
 961 tggtcagtga agcccaggag gacctggggg gggcaagagc tcaggagaag gcctgccccc
1021 cttcccaccc ctatcccta ggtctccacc cctcaagcca ggagaccctg tctttgctgt
1081 ttatatatat atatattata tataaatatc tatttatctg tctgagccct gccctcactc
1141 cactccctc atccactagg tgcccagtct tgagtgggcc ccctctctta cccgtccct
1201 ttccctgcat cccttggccc ctctctgttt accctccctg tccctgagg ttaaggggat
1261 ctaaaaggag gacagggagg gaacagacct cggctgtgtg gggagggtgg gcgtgacttc
1321 agactctctc ctctctctcc ctccactcct cccaactctg gccttggttc ctccagcaat
1381 gcctgctga acaaaggccg ttagggaaat ccaactccag ggttaaagaa aggcagagat
1441 tgggggggct tggggtagag aggacagttt aggacccaag gtggtcttgg agaggaggtg
1501 tggagtggag gggtcagcag gggggttggg ttccagacag agtggatctg gagtctgaag
1561 gagaggagtg cgctagagca ttctggggtg gggcttggaa gggcgctgag gcagggttc
1621 tagaagggc gaggctttaa gcgaggcaga atggtgggct ccagagtagg tgggtcttgg
1681 attggtacca gagcctatgg aaagggtgtg gcttggaaca tttgggagac tgagcttgat
1741 tctaaagggg acagatcttg agcaaggcaa gaagtgggat tcaggaatgg gccaagccag
1801 ggttccagac agggtggggc ttagaatggg gcttccatgg tggtttcaga aagggcagcc
1861 cctccccatg gtgcagtgaa gaaaatgttt tacaatggct gggtttgggc agtggagagg
1921 ggacttggat aggagcttcc agatgggttt tgttaggggt gggggagaat ggctctggct
```

```
1981 acgacttggg acggaagtgg cctgagaaga gtcgagtgat atggcttgta gggtgaggcg 2041 tgggatccag agagaagcac cccaccacac acacccttcc ccactcccgt gatgaaacag 2101 ctaggttaat aggaggacag aaccaacggg tctgtgggac tggcccaccc ctcttccccc 2161 ttccctgcg ccctccctcc ctccacacct cacccgtcc tggggtggtt ggaggcctgg 2221 tctggagccc ctatcctgca ccctctgcta tgtctgtgat gtcagtagtg cctgtgatcg 2281 tgtgttgcca ttttgtctgg ctgtggcccc tccttctccc ctccagaccc ctacccttc 2341 ccaaaccctt cggtattgtt caaagaaccc ccctcccaa ggaagaacaa atatgattct 2401 cctctcccaa ataaactcct taaccaccta gtcaaaaaaa aaaaaaaaa
```

By "NOGOA polypeptide" (or neurite outgrowth inhibitor A; neurite outgrowth inhibitor isoform A; human reticulon-4; human reticulon-4 isoform A) is meant a polypeptide or fragment thereof having at least about 85% amino acid identity to NCBI Accession No. NP_065393.

```
   1 medldqsplv sssdspprpq pafkyqfvre pedeeeeeee eeedededle elevlerkpa 61 aglsaapvpt apaagaplmd fgndfvppap rgplpaappv aperqpswdp spvsstvpap 121 splsaaavsp sklpeddepp arpppppas vspqaepvwt ppapapaapp stpaapkrrg 181 ssgsvdetlf alpaasepvi rssaenmdlk eqpgntisag qedfpsvlle taaslpslsp 241 lsaasfkehe ylgnlstvlp tegtlqenvs easkevseka ktllidrdlt efseleysem 301 gssfsvspka esavivanpr eeiivknkde eeklvsnnil hnqqelptal tklvkedevv 361 ssekakdsfn ekrvaveapm reeyadfkpf ervwevkdsk edsdmlaagg kiesnleskv 421 dkkcfadsle qtnhekdses snddtsfpst pegikdrsga yitcapfnpa atesiatnif 481 pllgdptsen ktdekkieek kaqivteknt stktsnpflv aaqdsetdyv ttdnltkvte 541 evvanmpegl tpdlvqeace selnevtgtk iayetkmdlv qtsevmqesl ypaaqlcpsf 601 eeseatpspv lpdivmeapl nsavpsagas viqpssspe assvnyesik hepenpppye 661 eamsvslkkv sgikeeikep eninaalqet eapyisiacd liketklsae papdfsdyse 721 makveqpvpd hselvedssp dsepvdlfsd dsipdvpqkq detvmlvkes ltetsfesmi 781 eyenkeklsa lppeggkpyl esfklsldnt kdtllpdevs tlskkekipl qmeelstavy 841 snddlfiske aqiretetfs dsspieiide fptlissktd sfsklareyt dlevshksei 901 anapdgagsl pctelphdls lkniqpkvee kisfsddfsk ngsatskvll lppdvsalat 961 qaeiesivkp kvlvkeaekk lpsdtekedr spsaifsael sktsvvdlly wrdikktgvv 1021 fgaslfllls ltvfsivsvt ayialallsv tisfriykgv iqaiqksdeg hpfraylese 1081 vaiseelvqk ysnsalghvn ctikelrrlf lvddlvdslk favlmwvfty vgalfngltl 1141 lilalislfs vpviyerhqa qidhylglan knvkdamaki qakipglkrk ae
```

By "NOGOA nucleic acid molecule" (or neurite outgrowth inhibitor A; neurite outgrowth inhibitor isoform A; human reticulon-4; human reticulon-4 isoform A) is meant a polynucleotide encoding an NOGOA polypeptide. An exemplary NOGOA nucleic acid molecule (e.g., mRNA) is provided at NCBI Accession No. NM_020532.

```
  1 agtccctgcc ctcccctggg gagggtgagt cacgccaaac tgggcggaga gtccgctggc 61 ctcactccta gctcatctgg gcggcggcgg caagtgggga cagggcgggt ggcgcatcac
```

-continued

```
 121 cggcgcggag gcaggaggag cagtctcatt gttccgggag ccgtcaccac agtaggtccc
 181 tcggctcagt cggcccagcc cctctcagtc ctccccaacc cccacaaccg cccgcggctc
 241 tgagacgcgg ccccggcggc ggcggcagca gctgcagcat catctccacc ctccagccat
 301 ggaagacctg gaccagtctc ctctggtctc gtcctcggac agcccacccc ggccgcagcc
 361 cgcgttcaag taccagttcg tgagggagcc cgaggacgag gaggaagaag aggaggagga
 421 agaggaggac gaggacgaag acctggagga gctggaggtg ctggagagga agcccgccgc
 481 cgggctgtcc gcggccccag tgcccaccgc ccctgccgcc ggcgcgcccc tgatggactt
 541 cggaaatgac ttcgtgccgc cggcgccccg gggaccctg ccggccgctc ccccgtcgc
 601 cccggagcgg cagccgtctt gggacccgag cccggtgtcg tcgaccgtgc ccgcgccatc
 661 cccgctgtct gctgccgcag tctcgccctc caagctccct gaggacgacg agcctccggc
 721 ccggcctccc cctcctcccc cggccagcgt gagcccccag gcagagcccg tgtggacccc
 781 gccagccccg gctcccgccg cgccccctc caccccggcc gcgcccaagc gcagggggctc
 841 ctcgggctca gtggatgaga ccctttttgc tcttcctgct gcatctgagc ctgtgatacg
 901 ctcctctgca gaaaatatgg acttgaagga gcagccaggt aacactattt cggctggtca
 961 agaggatttc ccatctgtcc tgcttgaaac tgctgcttct cttccttctc tgtctcctct
1021 ctcagccgct tctttcaaag aacatgaata ccttggtaat ttgtcaacag tattacccac
1081 tgaaggaaca cttcaagaaa atgtcagtga agcttctaaa gaggtctcag agaaggcaaa
1141 aactctactc atagatagag atttaacaga gttttcagaa ttagaatact cagaaatggg
1201 atcatcgttc agtgtctctc caaaagcaga atctgccgta atagtagcaa atcctaggga
1261 agaaataatc gtgaaaaata agatgaaga agagaagtta gttagtaata acatccttca
1321 taatcaacaa gagttaccta cagctcttac taaattggtt aaagaggatg aagttgtgtc
1381 ttcagaaaaa gcaaaagaca gttttaatga aaagagagtt gcagtggaag ctcctatgag
1441 ggaggaatat gcagacttca aaccatttga gcgagtatgg gaagtgaaag atagtaagga
1501 agatagtgat atgttggctg ctggaggtaa aatcgagagc aacttggaaa gtaaagtgga
1561 taaaaaatgt tttgcagata gccttgagca aactaatcac gaaaaagata gtgagagtag
1621 taatgatgat acttcttttcc ccagtacgcc agaaggtata aaggatcgtt caggagcata
1681 tatcacatgt gctccctta acccagcagc aactgagagc attgcaacaa acatttttcc
1741 tttgttagga gatcctactt cagaaaataa gaccgatgaa aaaaaaatag aagaaaagaa
1801 ggcccaaata gtaacagaga agaatactag caccaaaaca tcaaacccctt ttcttgtagc
1861 agcacaggat tctgagacag attatgtcac aacagataat ttaacaaagg tgactgagga
1921 agtcgtggca acatgcctg aaggcctgac tccagattta gtacaggaag catgtgaaag
1981 tgaattgaat gaagttactg gtacaaagat tgcttatgaa acaaaaatgg acttggttca
2041 aacatcagaa gttatgcaag agtcactcta tcctgcagca cagctttgcc catcatttga
2101 agagtcagaa gctactccctt caccagtttt gcctgacatt gttatggaag caccattgaa
2161 ttctgcagtt cctagtgctg gtgcttccgt gatacagccc agctcatcac cattagaagc
2221 ttcttcagtt aattatgaaa gcataaaaca tgagcctgaa accccccac catatgaaga
2281 ggccatgagt gtatcactaa aaaagtatc aggaataaag gaagaaatta aagagcctga
2341 aaatattaat gcagctcttc aagaaacaga agctccttat atatctattg catgtgatttt
2401 aattaaagaa acaaagcttt ctgctgaacc agctccggat ttctctgatt attcagaaat
2461 ggcaaaagtt gaacagccag tgcctgatca ttctgagcta gttgaagatt cctcacctga
2521 ttctgaacca gttgacttat ttagtgatga ttcaatacct gacgttccac aaaaacaaga
```

-continued

```
2581 tgaaactgtg atgcttgtga aagaaagtct cactgagact tcatttgagt caatgataga
2641 atatgaaaat aaggaaaaac tcagtgcttt gccacctgag ggaggaaagc catatttgga
2701 atcttttaag ctcagtttag ataacacaaa agatacctg ttacctgatg aagtttcaac
2761 attgagcaaa aaggagaaaa ttcctttgca gatggaggag ctcagtactg cagtttattc
2821 aaatgatgac ttatttattt ctaaggaagc acagataaga gaaactgaaa cgttttcaga
2881 ttcatctcca attgaaatta tagatgagtt ccctacattg atcagttcta aaactgattc
2941 attttctaaa ttagccaggg aatatactga cctagaagta tcccacaaaa gtgaaattgc
3001 taatgccccg gatggagctg ggtcattgcc ttgcacagaa ttgccccatg acctttcttt
3061 gaagaacata caacccaaag ttgaagagaa aatcagtttc tcagatgact tttctaaaaa
3121 tgggtctgct acatcaaagg tgctcttatt gcctccagat gtttctgctt tggccactca
3181 agcagagata gagagcatag ttaaacccaa agttcttgtg aaagaagctg agaaaaaact
3241 tccttccgat acagaaaaag aggacagatc accatctgct atattttcag cagagctgag
3301 taaaacttca gttgttgacc tcctgtactg gagagacatt aagaagactg gagtggtgtt
3361 tggtgccagc ctattcctgc tgctttcatt gacagtattc agcattgtga gcgtaacagc
3421 ctacattgcc ttggccctgc tctctgtgac catcagcttt aggatataca agggtgtgat
3481 ccaagctatc cagaaatcag atgaaggcca cccattcagg gcatatctgg aatctgaagt
3541 tgctatatct gaggagttgg ttcagaagta cagtaattct gctcttggtc atgtgaactg
3601 cacgataaag gaactcaggc gcctcttctt agttgatgat ttagttgatt ctctgaagtt
3661 tgcagtgttg atgtgggtat ttacctatgt tggtgccttg tttaatggtc tgacactact
3721 gattttggct ctcatttcac tcttcagtgt tcctgttatt tatgaacggc atcaggcaca
3781 gatagatcat tatctaggac ttgcaaataa gaatgttaaa gatgctatgg ctaaaatcca
3841 agcaaaaatc cctggattga agcgcaaagc tgaatgaaaa cgcccaaaat aattagtagg
3901 agttcatctt taaaggggat attcatttga ttatacgggg gagggtcagg gaagaacgaa
3961 ccttgacgtt gcagtgcagt ttcacagatc gttgttagat ctttatttt agccatgcac
4021 tgttgtgagg aaaaattacc tgtcttgact gccatgtgtt catcatctta agtattgtaa
4081 gctgctatgt atggattta accgtaatca tatcttttc ctatctatct gaggcactgg
4141 tggaataaaa aacctgtata ttttactttg ttgcagatag tcttgccgca tcttggcaag
4201 ttgcagagat ggtggagcta gaaaaaaaaa aaaaaaagcc cttttcagtt tgtgcactgt
4261 gtatggtccg tgtagattga tgcagatttt ctgaaatgaa atgtttgttt agacgagatc
4321 ataccggtaa agcaggaatg acaaagcttg cttttctggt atgttctagg tgtattgtga
4381 cttttactgt tatattaatt gccaatataa gtaaatatag attatatatg tatagtgttt
4441 cacaaagctt agacctttac cttccagcca ccccacagtg cttgatattt cagagtcagt
4501 cattggttat acatgtgtag ttccaaagca cataagctag aagaagaaat atttctagga
4561 gcactaccat ctgttttcaa catgaaatgc cacacacata gaactccaac atcaatttca
4621 ttgcacagac tgactgtagt taattttgtc acagaatcta tggactgaat ctaatgcttc
4681 caaaaatgtt gtttgtttgc aaatatcaaa cattgttatg caagaaatta ttaattacaa
4741 aatgaagatt tataccattg tggtttaagc tgtactgaac taaatctgtg gaatgcattg
4801 tgaactgtaa aagcaaagta tcaataaagc ttatagactt aaaaaaaaaa aaaaaaaaa
4861 aaaaaaaaa a
```

By "GFAP" (or Glial fibrillary acidic protein) is meant a polypeptide or fragment thereof having at least about 85% amino acid identity to NCBI Accession No. P14136.

```
  1 merrritsaa rrsyvssgem mvgglapgrr lgpgtrlsla rmppplptrv dfslagalna
 61 gfketraser aemmelndrf asyiekvrfl eqqnkalaae lnqlrakept kladvyqael
121 relrlrldql tansarleve rdnlaqdlat vrqklqdetn lrleaennla ayrqeadeat
181 larldlerki esleeeirfl rkiheeevre lqeqlarqqv hveldvakpd ltaalkeirt
241 qyeamassnm heaeewyrsk fadltdaaar naellrqakh eandyrrqlq sltcdleslr
301 gtneslerqm reqeerhvre aasyqealar leeegqslkd emarhlqeyq dllnvklald
361 ieiatyrkll egeenritip vqtfsnlqir etsldtksvs eghlkrnivv ktvemrdgev
421 ikeskqehkd vm
```

By "GFAP nucleic acid molecule" (or Glial fibrillary acidic protein) is meant a polynucleotide encoding an GFAP polypeptide. An exemplary GFAP nucleic acid molecule (e.g., mRNA) is provided at NCBI Accession No. NM_002055.

```
   1 atcgccagtc tagcccactc cttcataaag ccctcgcatc ccaggagcga gcagagccag
  61 agcaggatgg agaggagacg catcacctcc gctgctcgcc gctcctacgt ctcctcaggg
 121 gagatgatgg tggggggcct ggctcctggc cgccgtctgg gtcctggcac ccgcctctcc
 181 ctggctcgaa tgccccctcc actcccgacc cgggtggatt tctccctggc tggggcactc
 241 aatgctggct tcaaggagac ccgggccagt gagcgggcag agatgatgga gctcaatgac
 301 cgctttgcca gctacatcga gaaggttcgc ttcctggaac agcaaaacaa ggcgctggct
 361 gctgagctga accagctgcg ggccaaggag cccaccaagc tggcagacgt ctaccaggct
 421 gagctgcgag agctgcggct gcggctcgat caactcaccg ccaacagcgc ccggctggag
 481 gttgagaggg acaatctggc acaggacctg gccactgtga ggcagaagct ccaggatgaa
 541 accaacctga ggctggaagc cgagaacaac ctggctgcct atagacagga agcagatgaa
 601 gccaccctgg cccgtctgga tctggagagg aagattgagt cgctggagga ggagatccgg
 661 ttcttgagga agatccacga ggaggaggtt cgggaactcc aggagcagct ggcccgacag
 721 caggtccatg tggagcttga cgtggccaag ccagacctca ccgcagccct gaaagagatc
 781 cgcacgcagt atgaggcaat ggcgtccagc aacatgcatg aagccgaaga gtggtaccgc
 841 tccaagtttg cagacctgac agacgctgct gcccgcaacg cggagctgct ccgccaggcc
 901 aagcacgaag ccaacgacta ccggcgccag ttgcagtcct tgacctgcga cctggagtct
 961 ctgcgcggca cgaacgagtc cctggagagg cagatgcgcg agcaggagga gcggcacgtg
1021 cgggaggcgg ccagttatca ggaggcgctg gcgcggctgg aggaagaggg gcagagcctc
1081 aaggacgaga tggcccgcca cttgcaggag taccaggacc tgctcaatgt caagctggcc
1141 ctggacatcg agatcgccac ctacaggaag ctgctagagg gcgaggagaa ccggatcacc
1201 attcccgtgc agaccttctc caacctgcag attcgagaaa ccagcctgga caccaagtct
1261 gtgtcagaag gccacctcaa gaggaacatc gtggtgaaga ccgtggagat gcgggatgga
1321 gaggtcatta aggagtccaa gcaggagcac aaggatgtga tgtgaggcag gacccacctg
1381 gtggcctctg ccccgtctca tgagggccc gagcagaagc aggatagttg ctccgcctct
1441 gctggcacat tccccagac ctgagctccc caccacccca gctgctcccc tccctcctct
1501 gtccctaggt cagcttgctg ccctaggctc cgtcagtatc aggcctgcca gacggcaccc
```

-continued

```
1561 acccagcacc cagcaactcc aactaacaag aaactcaccc ccaaggggca gtctggaggg 1621 gcatggccag cagcttgcgt tagaatgagg aggaaggaga gaaggggagg agggcggggg 1681 gcacctacta catcgccctc cacatccctg attcctgttg ttatggaaac tgttgccaga 1741 gatggaggtt ctctcggagt atctgggaac tgtgcctttg agtttcctca ggctgctgga 1801 ggaaaactga gactcagaca ggaaagggaa ggcccacag acaaggtagc cctggccaga 1861 ggcttgtttt gtcttttggt ttttatgagg tgggatatcc ctatgctgcc taggctgacc 1921 ttgaactcct gggctcaagc agtctaccca cctcagcctc ctgtgtagct gggattatag 1981 attggagcca ccatgcccag ctcagagggt tgttctccta gactgacccct gatcagtcta 2041 agatgggtgg ggacgtcctg ccacctgggg cagtcacctg cccagatccc agaaggacct 2101 cctgagcgat gactcaagtg tctcagtcca cctgagctgc catccaggga tgccatctgt 2161 gggcacgctg tgggcaggtg ggagcttgat tctcagcact tgggggatct gttgtgtacg 2221 tggagaggga tgaggtgctg ggagggatag aggggggctg cctggccccc agctgtgggt 2281 acagagaggt caagcccagg aggactgccc cgtgcagact ggaggggacg ctggtagaga 2341 tggaggagga ggcaattggg atggcgctag gcatacaagt aggggttgtg ggtgaccagt 2401 tgcacttggc ctctggattg tgggaattaa ggaagtgact catcctcttg aagatgctga 2461 aacaggagag aaaggggatg tatccatggg ggcagggcat gactttgtcc catttctaaa 2521 ggcctcttcc ttgctgtgtc ataccaggcc gccccagcct ctgagcccct gggactgctg 2581 cttcttaacc ccagtaagcc actgccacac gtctgaccct ctccacccca tagtgaccgg 2641 ctgcttttcc ctaagccaag ggcctcttgc ggtcccttct tactcacaca caaaatgtac 2701 ccagtattct aggtagtgcc ctattttaca attgtaaaac tgaggcacga gcaaagtgaa 2761 gacactggct catattcctg cagcctggag gccgggtgct cagggctgac acgtccaccc 2821 cagtgcaccc actctgcttt gactgagcag actggtgagc agactggtgg gatctgtgcc 2881 cagagatggg actgggaggg cccacttcag ggttctcctc tcccctctaa ggccgaagaa 2941 gggtccttcc ctctccccaa gacttggtgt cctttccctc cactccttcc tgccacctgc 3001 tgctgctgct gctgctaatc ttcagggcac tgctgctgcc tttagtcgct gaggaaaaat 3061 aaagacaaat gctgcgccct tccccaaaaa aaaaaaa
```

By "s100b" (or S-100 protein beta chain; S-100 protein subunit beta; S100 calcium-binding protein B) is meant a polypeptide or fragment thereof having at least about 85% amino acid identity to NCBI Accession No. P04271.

```
  1 mselekamva lidvfhqysg regdkhklkk selkelinne lshfleeike qevvdkvmet 61 ldndgdgecd fqefmafvam vttacheffe he
```

By "s100b nucleic acid molecule" (or S-100 protein beta chain; S-100 protein subunit beta; S100 calcium-binding protein B) is meant a polynucleotide encoding an s100b polypeptide. An exemplary s100b nucleic acid molecule (e.g., mRNA) is provided at NCBI Accession No. NM_006272.

```
  1 gggcagaggg aataagaggc tgcctctgcc caccagtcct gccgcccagg acccgcagca 61 gagacgacgc ctgcagcaag gagaccagga aggggtgaga caaggaagag gatgtctgag 121 ctggagaagg ccatggtggc cctcatcgac gttttccacc aatattctgg aagggaggga
```

-continued

```
 181 gacaagcaca agctgaagaa atccgaactg aaggagctca tcaacaatga gctttcccat 241 ttcttagagg aaatcaaaga gcaggaggtt gtggacaaag tcatggaaac actggacaat 301 gatggagacg gcgaatgtga cttccaggaa ttcatggcct ttgttgccat ggttactact 361 gcctgccacg agttctttga acatgagtga gattagaaag cagccaaacc tttcctgtaa 421 cagagacggt catgcaagaa agcagacagc aagggcttgc agcctagtag gagctgagct 481 ttccagccgt gttgtagcta attaggaagc ttgatttgct ttgtgattga aaaattgaaa 541 acctctttcc aaaggctgtt ttaacggcct gcatcattct ttctgctata ttaggcctgt 601 gtgtaagctg actggcccca gggactcttg ttaacagtaa cttaggagtc aggtctcagt 661 gataaagcgt gcaccgtgca gcccgccatg gccgtgtaga ccctaacccg gagggaaccc 721 tgactacaga aattacccecg gggcacccett aaaacttcca ctacctttaa aaaacaaagc 781 cttatccagc attatttgaa aacactgctg ttctttaaat gcgttcctca tccatgcaga 841 taacagctgg ttggccggtg tggccctgca agggcgtggt ggcttcggcc tgcttcccgg 901 gatgcgcctg atcaccaggt gaacgctcag cgctggcagc gctcctggaa aaagcaactc 961 catcagaact cgcaatccga gccagctctg ggggctccag cgtggcctcc gtgacccatg 1021 cgattcaagt cgcggctgca ggatccttgc ctccaacgtg cctccagcac atgcggcttc 1081 cgagggcact accgggggct ctgagccacc gcgagggcct gcgttcaata aaaag
```

By "PAX6 polypeptide" (or paired box protein PAX6) is meant a polypeptide or fragment thereof having at least about 85% amino acid identity to NCBI Accession No. AAK95849.1.

MQNSHSGVNQLGGVFVNGRPLPDSTRQKIVELAHSGARPCDISR

ILQVSNGCVSKILGRYYETGSIRPRAIGGSKPRVATPEVVSKIAQYKREC

PSIFAWEI

RDRLLSEGVCTNDNIPSVSSINRVLRNLASEKQQMGADGMYDKLRMLNGQ

TGSWGTRP

GWYPGTSVPGQPTQDGCQQQEGGGENTNSISSNGEDSDEAQMRLQLKRKL

QRNRTSFT

QEQIEALEKEFERTHYPDVFARERLAAKIDLPEARIQVWFSNRRAKWRRE

EKLRNQRR

QASNTPSHIPISSSFSTSVYQPIPQPTTPVSSFTSGSMLGRTDTALTNTY

SALPPMPS

FTMANNLPMQPPVPSQTSSYSCMLPTSPSVNGRSYDTYTPPHMQTHMNSQ

PMGTSGTT

STGLISPGVSVPVQVPGSEPDMSQYWPRLQ

By "PAX6 polynucleotide" (or paired box protein PAX6) is meant a polynucleotide encoding an PAX6 polypeptide. An exemplary PAX6 nucleic acid molecule (e.g., mRNA) is provided at NCBI Accession No. AY047583.

```
   1 aggggggaaga ctttaactag gggcgcgcag atgtgtgagg ccttttattg tgagagtgga 61 cagacatccg agatttcaga gccccatatt cgagccccgt ggaatcccgc ggccccagc 121 cagagccagc atgcagaaca gtcacagcgg agtgaatcag ctcggtggtg tctttgtcaa 181 cgggcggcca ctgccggact ccacccggca gaagattgta gagctagctc acagcggggc 241 ccggccgtgc gacatttccc gaattctgca ggtgtccaac ggatgtgtga gtaaaattct 301 gggcaggtat tacgagactg gctccatcag acccagggca atcggtggta gtaaaccgag 361 agtagcgact ccagaagttg taagcaaaat agcccagtat aagcgggagt gcccgtccat 421 ctttgcttgg gaaatccgag acagattact gtccgagggg gtctgtacca acgataacat 481 accaagcgtg tcatcaataa acagagttct tcgcaacctg ctagcgaaa gcaacagat 541 gggcgcagac ggcatgtatg ataaactaag gatgttgaac gggcagaccg gaagctgggg 601 cacccgccct ggttggtatc cggggacttc ggtgccaggg caacctacg aagatggctg 661 ccagcaacag gaaggagggg gagagaatac caactccatc agttccaacg gagaagattc
```

```
-continued
 721 agatgaggct caaatgcgac ttcagctgaa gcggaagctg caaagaaata gaacatcctt 781 tacccaagag caaattgagg ccctggagaa agagtttgag agaacccatt atccagatgt 841 gtttgcccga gaaagactag cagccaaaat agatctacct gaagcaagaa tacaggtatg 901 gttttctaat cgaagggcca aatggagaag agaagaaaaa ctgaggaatc agagaagaca 961 ggccagcaac acacctagtc atattcctat cagcagtagt ttcagcacca gtgtctacca 1021 accaattcca caacccacca caccggtttc ctccttcaca tctggctcca tgttgggccg 1081 aacagacaca gccctcacaa acacctacag cgctctgccg cctatgccca gcttcaccat 1141 ggcaaataac ctgcctatgc aaccccagt ccccagccag acctcctcat actcctgcat 1201 gctgcccacc agcccttcgg tgaatgggcg gagttatgat acctacaccc ccccacatat 1261 gcagacacac atgaacagtc agccaatggg cacctcgggc accacttcaa caggactcat 1321 ttcccctggt gtgtcagttc cagttcaagt tcccggaagt gaacctgata tgtctcaata 1381 ctggccaaga ttacagtaa
```

By "Nestin polypeptide" is meant a polypeptide or fragment thereof having at least about 85% amino acid identity to NCBI Accession No. NP_006608.1.

MEGCMGEESFQMWELNRRLEAYLARVKALEEQNELLSAELGGLR

AQSADTSWRAHADDELAALRALVDQRWREKHAAEVARDNLAEELEGVAGRCQQL

RLAR

ERTTEEVARNRRAVEAEKCARAWLSSQVAELERELEALRVAHEEERVGLNAQAAC

APR

CPAPPRGPPAPAPEVEELARRLGEAWRGAVRGYQERVAHMETSLGQARERLGRAV

QGA

REGRLELQQLQAERGGLLERRAALEQRLEGRWQERLRATEKFQLAVEALEQEKQGL

QS

QIAQVLEGRQQLAHLKMSLSLEVATYRTLLEAENSRLQTPGGGSKTSLSFQDPKLELQ

FPRTPEGRRLGSLLPVLSPTSLPSPLPATLETPVPAFLKNQEFLQARTPTLASTPIPP

TPQAPSPAVDAEIRAQDAPLSLLQTQGGRKQAPEPLRAEARVAIPASVLPGPEEPGGQ

RQEASTGQSPEDHASLAPPLSPDHSSLEAKDGESGGSRVFSICRGEGEGQIWGLVEKE

TAIEGKVVSSLQQEIWEEEDLNRKEIQDSQVPLEKETLKSLGEEIQESLKTLENQSHE

TLERENQECPRSLEEDLETLKSLEKENKELLKDVEVVRPLEKEAVGQLKPTGKEDTQT

LQSLQKENQELMKSLEGNLETFLFPGTENQELVSSLQENLESLTALEKENQEPLRSPE

VGDEEALRPLTKENQEPLRSLEDENKEAFRSLEKENQEPLKTLEEEDQSIVRPLETEN

HKSLRSLEEQDQETLRTLEKETQQRRRSLGEQDQMTLRPPEKVDLEPLKSLDQEIARP

LENENQEFLKSLKEESVEAVKSLETEILESLKSAGQENLETLKSPETQAPLWTPEEIN

QGAMNPLEKEIQEPLESVEVNQETFRLLEEENQESLRSLGAWNLENLRSPEEVDKESQ

RNLEEEENLGKGEYQESLRSLEEEGQELPQSADVQRWEDTVEKDQELAQESPPGMA

GV

ENEDEAELNLREQDGFTGKEEVVEQGELNATEEVWIPGEGHPESPEPKEQRGLVEGAS

VKGGAEGLQDPEGQSQQVGAPGLQAPQGLPEAIEPLVEDDVAPGGDQASPEVMLGS

EP

-continued

AMGESAAGAEPGPGQGVGGLGDPGHLTREEVMEPPLEEESLEAKRVQGLEGPRKDLEE

AGGLGTEFSELPGKSRDPWEPPREGREESEAEAPRGAEEAFPAETLGHTGSDAPSPWP

LGSEEAEEDVPPVLVSPSPTYTPILEDAPGPQPQAEGSQEASWGVQGRAEALGKVESE

QEELGSGEIPEGPQEEGEESREESEEDELGETLPDSTPLGFYLRSPTSPRWDPTGEQR

PPPQGETGKEGWDPAVLASEGLEAPPSEKEEGEEGEEECGRDSDLSEEFEDLGTEAPF

LPGVPGEVAEPLGQVPQLLLDPAAWDRDGESDGFADEEESGEEGEEDQEEGREPGAGR

WGPGSSVGSLQALSSSQRGEFLESDSVSVSVPWDDSLRGAVAGAPKTALETESQDSAE

PSGSEEESDPVSLEREDKVPGPLEIPSGMEDAGPGADIIGVNGQGPNLEGKSQHVNGG

VMNGLEQSEEVGQGMPLVSEGDRGSPFQEEEGSALKTSWAGAPVHLGQGQFLKFTQRE

GDRESWSSGED

By "Nestin polynucleotide" is meant a polynucleotide encoding an Nestin polypeptide. An exemplary Nestin nucleic acid molecule (e.g., mRNA) is provided at NCBI Accession No. NM_006617.

```
   1 gctactccca ccccgccccg ccccgtcatt gtcccgtcg gtctcttttc tcttccgtcc
  61 taaaagctct gcgagccgct cccttctccc ggtgccccgc gtctgtccat cctcagtggg
 121 tcagacgagc aggatggagg gctgcatggg ggaggagtcg tttcagatgt gggagctcaa
 181 tcggcgcctg gaggcctacc tggcccgggt caaggcgctg gaggagcaga atgagctgct
 241 cagcgcggag ctcggggggc tccgggcaca atccgcggac acctcctggc gggcgcatgc
 301 cgacgacgag ctggcggccc tgcgggccct cgttgaccaa cgctggcggg agaagcacgc
 361 ggccgaggtg cgcgcgcgaca acctggctga agagctggag ggcgtggcag gccgatgcca
 421 gcagctgcgg ctggcccggg agcggacgac ggaggaggta gcccgcaacc ggcgcgccgt
 481 cgaggcagag aaatgcgccc gggcctggct gagtagccag gtggcagagc tggagcgcga
 541 gctagaggct ctacgcgtgg cgcacgagga ggagcgcgtc ggcctgaacg cgcaggctgc
 601 ctgtgccccc cgctgccccg cgccgccccg cgggcctccc gcgccggccc cggaggtaga
 661 ggagctggca aggcgactgg gcgaggcgtg gcgcggggca gtgcgcggct accaggagcg
 721 cgtggcacac atggagacgt cgctgggcca ggcccgcgag cggctgggcc gggcggtgca
 781 gggtgcccgc gagggccgcc tggagctgca gcagctccag gctgagcgcg gaggcctcct
 841 ggagcgcagg gcagcgttgg aacagaggtt ggagggccgc tggcaggagc ggctgcgggc
 901 tactgaaaag ttccagctgg ctgtggaggc cctggagcag gagaaacagg gcctacagag
 961 ccagatcgct caggtcctgg aaggtcggca gcagctggcg cacctcaaga tgtccctcag
1021 cctggaggtg gccacgtaca ggaccctcct ggaggctgag aactcccggc tgcaaacacc
1081 tggcggtggc tccaagactt ccctcagctt tcaggacccc aagctggagc tgcaattccc
1141 taggacccca gagggccggc gtcttggatc tttgctccca gtcctgagcc caacttccct
1201 cccctcaccc ttgcctgcta cccttgagac acctgtgcca gcctttctta agaaccaaga
1261 attcctccag gcccgtaccc ctaccttggc cagcaccccc atccccccca cacctcaggc
1321 accctctcct gctgtagatg cagagatcag agcccaggat gctcctctct ctctgctcca
1381 gacacagggt gggaggaaac aggctccaga gcccctgcgg gctgaagcca gggtggccat
```

-continued

```
1441 tcctgccagc gtcctgcctg gaccagagga gcctgggggc cagcggcaag aggccagtac
1501 aggccagtcc ccagaggacc atgcctcctt ggcaccaccc ctcagccctg accactccag
1561 tttagaggct aaggatggag aatccggtgg gtctagagtg ttcagcatat gccgagggga
1621 aggtgaaggg caaatctggg ggttggtaga gaaagaaaca gccatagagg caaagtggt
1681 aagcagcttg cagcaggaaa tatgggaaga agaggatcta aacaggaagg aaatccagga
1741 ctcccaggtt cctttggaaa aagaaaccct gaagtctctg ggagaggaga ttcaagagtc
1801 actgaagact ctggaaaacc agagccatga gacactagaa agggagaatc aagaatgtcc
1861 gaggtcttta aagaagact tagaaacact aaaaagtcta gaaaaggaaa ataaagagct
1921 attaaaggat gtggaggtag tgagacctct agaaaaagag gctgtaggcc aacttaagcc
1981 tacaggaaaa gaggacacac agacattgca atccctgcaa aaggagaatc aagaactaat
2041 gaaatctctt gaaggtaatc tagagacatt tttatttcca ggaacggaaa atcaagaatt
2101 agtaagttct ctgcaagaga acttagagtc attgacagct ctggaaaagg agaatcaaga
2161 gccactgaga tctccagaag taggggatga ggaggcactg agacctctga caaaggagaa
2221 tcaggaaccc ctgaggtctc ttgaagatga gaacaaagag gcctttagat ctctagaaaa
2281 agagaaccag gagccactga agactctaga agaagaggac cagagtattg tgagacctct
2341 agaaacagag aatcacaaat cactgaggtc tttagaagaa caggaccaag agacattgag
2401 aactcttgaa aaagagactc aacagcgacg gaggtctcta ggggaacagg atcagatgac
2461 attaagaccc ccagaaaaag tggatctaga accactgaag tctcttgacc aggagatagc
2521 tagacctctt gaaaatgaga atcaagagtt cttaaagtca ctcaaagaag agagcgtaga
2581 ggcagtaaaa tctttagaaa cagagatcct agaatcactg aagtctgcgg acaagagaa
2641 cctggaaaca ctgaaatctc cagaaactca agcaccactg tggactccag aagaaataaa
2701 tcaggggggca atgaatcctc tagaaaagga aattcaagaa ccactggagt ctgtggaagt
2761 gaaccaagag acattcagac tcctggaaga ggagaatcag gaatcattga gatctctggg
2821 agcatggaac ctggagaatt tgagatctcc agaggaggta gacaaggaaa gtcaaaggaa
2881 tctggaaagag gaagagaacc tgggaaaggg agagtaccaa gagtcactga ggtctctgga
2941 ggaggaggga caggagctgc cgcagtctgc agatgtgcag aggtgggaag atacggtgga
3001 gaaggaccaa gaactggctc aggaaaagccc tcctgggatg gctggagtgg aaaatgagga
3061 tgaggcagag ctgaatctga gggagcagga tggcttcact gggaaggagg aggtggtaga
3121 gcagggagag ctgaatgcca cagaggaggt ctggatccca ggcgaggggc acccagagag
3181 ccctgagccc aaagagcaga gaggcctggt tgagggcagcc agtgtgaagg gaggggctga
3241 gggcctccag gaccctgaag gcaatcaca acaggtgggg gccccaggcc tccaggctcc
3301 ccaggggctg ccagaggcga tagagcccct ggtggaagat gatgtggccc caggggtga
3361 ccaagcctcc ccagaggtca tgttgggtc agagcctgcc atgggtgagt ctgctgcggg
3421 agctgagcca ggcccggggc agggggtggg agggctgggg gacccaggcc atctgaccag
3481 ggaagaggtg atggaaccac ccctggaaga ggagagtttg gaggcaaaga gggttcaggg
3541 cttggaaggg cctagaaagg acctagagga ggcaggtggt ctggggacag agttctccga
3601 gctgcctggg aagagcagag acccttggga gcctcccagg gagggtaggg aggagtcaga
3661 ggctgaggcc cccaggggag cagaggaggc gttccctgct gagaccctgg gccacactgg
3721 aagtgatgcc ccttcacctt ggcctctggg gtcagaggaa gctgaggagg atgtaccacc
3781 agtgctggtc tcccccagcc caacgtacac cccgatcctg gaagatgccc ctgggcctca
```

-continued
```
3841 gcctcaggct gaagggagtc aggaggctag ctgggggtg caggggaggg ctgaagccct
3901 gggaaagta gagagcgagc aggaggagtt gggttctggg gagatcccg agggccccca
3961 ggaggaaggg gaggagagca gagaagagag cgaggaggat gagctcgggg agaccctttcc
4021 agactccact cccctgggct tctacctcag gtcccccacc tcccccaggt gggaccccac
4081 tggagagcag aggccacccc ctcaagggga gactggaaag gagggctggg atcctgctgt
4141 cctggcttcc gagggccttg aggccccacc ctcagaaaag gaggaggggg aggagggaga
4201 agaggagtgt ggccgtgact ctgacctgtc agaagaattt gaggacctgg ggactgaggc
4261 accttttctt cctggggtcc ctggggaggt ggcagaacct ctgggccagg tgccccagct
4321 gctactggat cctgcagcct gggatcgaga tggggagtcc gatgggtttg cagatgagga
4381 agaaagtggg gaggagggag aggaggatca ggaggagggg agggagccag gggctgggcg
4441 gtgggggcca gggtcttctg ttggcagcct ccaggccctg agtagctccc agagagggga
4501 attcctggag tctgattctg tgagtgtcag tgtcccctgg gatgacagct gaggggtgc
4561 agtggctggt gcccccaaga ctgccctgga acggagtcc caggacagtg ctgagccttc
4621 tggctcagag gaagagtctg accctgtttc cttggagagg gaggacaaag tccctggccc
4681 tctagagatc cccagtggga tggaggatgc aggcccaggg gcagacatca ttggtgttaa
4741 tggccagggt cccaacttgg aggggaagtc acagcatgtg aatggggag tgatgaacgg
4801 gctggagcag tctgaggaag tggggcaagg aatgccgcta gtctctgagg gagaccgagg
4861 gagcccttt caggaggagg aggggagtgc tctgaagacc tcttgggcag gggctcctgt
4921 tcacctgggc cagggtcagt tcctgaagtt cactcagagg gaaggagata gagagtcctg
4981 gtcctcaggg gaggactagg aaaagaccat ctgcccggca ctgggactt aggggtgcgg
5041 ggagggaag gacgcctcca agcccgctcc ctgctcagga gcagcactct taacttacga
5101 tctcttgaca tatggtttct ggctgagagg cctggcccgc taaggtgaaa aggggtgtgg
5161 caaaggagcc tactccaaga atggaggctg taggaatata acctcccacc ctgcaaaggg
5221 aatctcttgc ctgctccatc tcataggcta agtcagctga atcccgatag tactaggtcc
5281 ccttccctcc gcatcccgtc agctggaaaa ggcctgtggc ccagaggctt ctccaaggg
5341 agggtgacat gctggctttt gtgcccaagc tcaccagccc tgcgccacct cactgcagta
5401 gtgcaccatc tcactgcagt agcacgcct cctgggccgt ctggcctgtg gctaatggag
5461 gtgacggcac tccatgtgc tgactccccc catcccctgcc acgctgtggc cctgcctggc
5521 tagtccctgc ctgaataaag taatgcctcc gcttcaaaaa aaaaaaaaa aaaaaaaaaa
5581 aaaaaaaaaa a
```

By "LHX6 polypeptide" (or LIM homeobox 6) is meant a polypeptide or fragment thereof having at least about 85% amino acid identity to NCBI Accession No. AAI03937.1.

MAQPGSGCKATTRCLEGTAPPAMAQSDAEALAGALDKDEGQASP

CTPSTPSVCSPPSAASSVPSAGKNICSSCGLEILDRYLLKVNNLIWHVRC

LECSVCRT

SLRQQNSCYIKNKEIFCKMDYFSRFGTKCARCGRQIYASDWVRRARGNAY

HLACFACF

SCKRQLSTGEEFGLVEEKVLCRIHYDTMIENLKRAAENGNGLTLEGAVPS

EQDSQPKP

-continued

AKRARTSFTAEQLQVMQAQFAQDNNPDAQTLQKLADMTGLSRRVIQVWFQ

NCRARHKK

HTPQHPVPPSGAPPSRLPSALSDDIHYTPFSSPERARMVTLHGYIESHPF

SVLTLPAL

PHLPVGAPQLPLSR

By "LHX6 polynucleotide" (or LIM homeobox 6) is meant a polynucleotide encoding an LHX6 polypeptide. An exemplary LHX6 nucleic acid molecule (e.g., mRNA) is provided at NCBI Accession No. BC103936.

```
   1 cccgccaccg accaggtgat ggcccagcca gggtccggct gcaaagcgac cacccgctgt
  61 cttgaaggga ccgcgccgcc cgccatggct cagtctgacg ccgaggccct ggcaggagct
 121 ctggacaagg acgagggtca ggcctcccca tgtacgccca gcacgccatc tgtctgctca
 181 ccgccctctg ccgcctcctc cgtgccgtct gcaggcaaga acatctgctc cagctgcggc
 241 ctcgagatcc tggaccgata tctgctcaag gtcaacaacc tcatctggca cgtgcggtgc
 301 ctcgagtgct ccgtgtgtcg cacgtcgctg aggcagcaga acagctgcta catcaagaac
 361 aaggagatct tctgcaagat ggactacttc agccgattcg ggaccaagtg tgcccggtgc
 421 ggccgacaga tctacgccag cgactgggtg cggagagctc gcggcaacgc ctaccacctg
 481 gcctgcttcg cctgcttctc gtgcaagcgc cagctgtcca ctggtgagga gttcggcctg
 541 gtcgaggaga aggtgctctg ccgcatccac tacgacacca tgattgagaa cctcaagagg
 601 gccgccgaga acgggaacgg cctcacgttg gagggggcag tgccctcgga acaggacagt
 661 caacccaagc cggccaagcg cgcgcggacg tccttcaccg cggaacagct gcaggttatg
 721 caggcgcagt tcgcgcagga caacaacccc gacgctcaga cgctgcagaa gctggcggac
 781 atgacgggcc tcagccggag agtcatccag gtgtggtttc aaaactgccg ggcgcgtcat
 841 aaaaagcaca cgccgcaaca cccagtgccg ccctcggggg cgccccgtc ccgccttccc
 901 tccgccctgt ccgacgacat ccactacacc ccgttcagca gccccgagcg ggcgcgcatg
 961 gtcaccctgc acgctacat tgagagtcat cctttttcag tactaacgct gccggcactt
1021 ccgcatctgc ccgtgggcgc cccacagctg cccctcagcc gctgagatcc agtgtccaag
1081 ctgcggccag gagtccaccc acctccgcat ccaccccgt ccgccatcct gcccaccacc
1141 aggtcggttc ccgaggcctg gccttccct ctcctgctga gaaccagaac ccaccaggag
1201 caccacagag tcctcctctt ggaaggcaga actccctgaa atctggaatc agggtggaaa
1261 cagcctgttt ttcccattta aacaggagtc ctcttcaact tcagctgatt acaataacaa
1321 aaggcggaat tgaattgtgc gatgccaacg gccttctcat ttacaggttt ttttccccca
1381 cattggcctt tatttactac ttccttggaa ccatctctga attctgaata gctgacaacc
1441 cccaatgtta tccactctgt tgcttttgtc tggaaaactc tacagtgttt gtgggatgtc
1501 cccaaaggta agctatgttc taattttatc atttccatct gtctggttat gtcaagttaa
1561 ttcagaaaga gaagagacag tgaccaaccc tgagaggcct aatagggcag agatggaggc
1621 ctgcccagac taggaggcag cggggataga cagggaatgg ggagaagaaa gacccccatt
1681 ggtttggaaa tcaaggagag ggcggtgaca tattggacca gaagaggcac tagccatttt
1741 aaggagagga aagagaaaac tctggggtca gggagagacc ctaccccccac ctaattatcc
1801 agcatatatg taagaaacat agcagcgatg gtattcgatc tgtgccatga ctcttctgaa
1861 tgtttggaca ggttagagtt ggggaccccct gttggccact tgttgacctc tcatagtggt
1921 gcttgggcca ggtcttctca atggaagggg aatcccttat aggggagagg gaacagagcc
1981 cagtgaaatg gcagtcagaa tgttaaccct ggatccatct ctaagtagag agagggtgcc
2041 cattgcctag gtgagtgtgc caagctcagg attccaactg gtgcctctga gcttcccaat
2101 caatacttcc tggagccagc cccacccacc cctgagaaca gaggtcagac acagctgcgt
2161 aacatccatc ctgctacaac tcttccaccc caaacaaaag ggctcaggct acacacgacc
2221 atgatttatg ttttcagggg atgcccattt gtcccaagct tatcctgtaa ttctagaatt
2281 acctggtgtc ctgatgcatt ttccactaga ggttgctaat cagcatgttt tagcccaagt
2341 ccaccttcct gctgtggtta acctgttatg ttgcttttgg aaggagactc taagacaggg
2401 aaagcaagtt catggtacat acgcagccat tgtctctgtt tttacccatg gcagacattg
```

```
2461 ctaatcaatg gcagctctat ttcactgagt ctggataagg tttcagagtt caaatgcttg 2521 acgttggcac ttaacatgaa agcctatagg tcattcttgc tctgggatct acaggcaggg 2581 taggcacagg tgcagcctaa gaagggaacc tgcttcctct cccttccaaa gacagtgaca 2641 gctgactgag ggcaaagagc aggcaccact cagaacgtgg tgagtacagc tcagctcagc 2701 actcagtcag tggtaacttg tgcccagccc tgtgctaggc gctgacatta acaggagcaa 2761 ccagggccca attcctggcc ttggagctca aatctttcct ttgattttg ctcctgatca 2821 tcaaggcccc agtgg
```

By "LHX8 polypeptide" (or LIM homeobox 8) is meant a polypeptide or fragment thereof having at least about 85% amino acid identity to NCBI Accession No. AAH40321.1.

MQILSRCQGLMSEECGRTTALAAGRTRKGAGEEGLVSPEGAGDE

DSCSSSAPLSPSSSPRSMASGSGCPPGKCVCNSCGLEIVDKYLLKVNDLC

WHVRCLSC

SVCRTSLGRHTSCYIKDKDIFCKLDYFRRYGTRCSRCGRHIHSTDWVRRA

KGNVYHLA

CFACFSCKRQLSTGEEFALVEEKVLCRVHYDCMLDNLKREVENGNGISVE

GALLTEQD

VNHPKPAKRARTSFTADQLQVMQAQFAQDNNPDAQTLQKLAERTGLSRRV

IQVWFQNC

RARHKKHVSPNHSSSTPVTAAPPSRLSPPMLEEMAYSAYVPQDGTMLTAL

HSYMDAHS

PTTLGLQPLLPHSMTQLPISHT

By "LHX8 polynucleotide" (or LIM homeobox 8) is meant a polynucleotide encoding an LHX8 polypeptide. An exemplary LHX8 nucleic acid molecule (e.g., mRNA) is provided at NCBI Accession No. BC040321.

```
   1 agcggcaaga ggctagcggc tggaccactt gtgctggagt ggtaaagaac tatcatgaat 61 ccatttactg aaagtgtcca tttctgaact caccctaaag aggacaaaca ccgcaaagta 121 gttaaaagtc aggcattcgc gtcgacgtc tgggtttgaa ttctgccctg gcttgactgg 181 aaacgcttcc cctatttctt ccgtagcgga ccgggagagc ttactggcgc tctgcgaacc 241 ggctggaaag aaacaccgag tcactcgtac agactcttgg tcgcagaact tggctttccg 301 ctattggtcc tccagaaccg cttgaaacaa ctggccccag ctggcgcatc agaccgcagt 361 gaggaatgcc gcggggcggg tggcgaaggc agggtctgcc cgccagtgga ttcccgggtg 421 tcccgcgtgg agcaggcttg cccagctggg aagcccatca aacctcagtc ttggcccaca 481 gtgggagaga gaccagtggg tcccagacgg aggccatcgc ccgcttttgg cgacctccac 541 tggcgtgaat aaaagcaccc ctctcttacc ctcagaaact gtgggtagca aggtataaaa 601 cggagtctgg gaccggtaag tcccaaggtg agcccgtata cagctctgcc atctctgagg 661 ggttatgcag attctgagca ggtgtcaggg gctcatgtca gaggagtgcg ggcggactac 721 agccctggcg gccgggagga ctcgcaaagg cgccggggaa gagggactgg tgagccccga 781 gggagcgggg gacgaggact cgtgctcctc ctcggccccg ctgtcccgt cgtcctcgcc 841 ccggtccatg gcctcgggct ccggctgccc tcctggcaag tgtgtgtgca acagttgcgg 901 cctggagatc gtggacaaat accttctcaa ggtgaatgac ctatgctggc atgtccggtg 961 tctctcctgc agtgtttgca gaacctccct aggaaggcac accagctgtt atattaaaga 1021 caaagacatt ttctgcaaac ttgattattt cagaaggtat ggaactcgct gctctcgatg 1081 tgggagacac atccattcta ctgactgggt ccggagagcc aaggggaatg tctatcactt 1141 ggcatgcttt gcctgctttt cctgcaaaag caactttcc acaggagagg agtttgcttt 1201 ggtggaagag aaagtcctct gcagagtaca ttatgactgc atgctggata atttaaaaag 1261 agaagtagaa aatgggaatg ggattagtgt ggaaggtgcc ctcctcacag agcaagatgt
```

```
1321 taaccatcca aaaccagcaa aaagagctcg gaccagcttt acagcagatc agcttcaggt 1381 tatgcaagca caatttgctc aggacaacaa cccagatgca cagacactcc agaaattggc 1441 agaaaggaca ggcttgagca gacgtgtgat acaggtgtgg tttcagaatt gtagagcacg 1501 ccacaagaaa cacgtcagtc ctaatcactc atcctccacc ccagtcacag cagcccacc 1561 ctccaggctg tctccaccca tgttagaaga aatggcttat tctgcctacg tgccccaaga 1621 tggaacgatg ttaactgcgc tgcatagtta tatggatgct cattccaa caactcttgg 1681 actccagccc ttgttacccc attcaatgac acaactgcca ataagtcata cctaattctt 1741 ttttcaggga tagacttgat taaggatata aatttgtcat ttattatgta taaaatacca 1801 ttgaaaagat attactgtta attttttatt taacacctaa agcatttcca acatcacttt 1861 gctgcccagg tatgtatcta tagttggcct gcaagacact tttattaatt cttcattttt 1921 tgtaaaactt atgtttacaa gaagaaaaca aatcaaaaca ttttttgtat tgtctggaaa 1981 tagttcactc tagtgtgtat ctgttaattt atttgtcatc aaaagagcac tttgcctaaa 2041 agaaaggact gacaagtgtg caaaatgttt acaatctttt gtgaaattgt agtttatcat 2101 tagtttgtat ctgtaagtta ttgtaataaa tattacctgt attttttgtt atatacaact 2161 ttatactttg aagcttgtat ctgtgaattt gcaactgaaa tttattttgc caatgttttc 2221 tgaatgaact gaataaagct tctgttgtag catgccatgc aaacacatta ttgtgtttgt 2281 ggttgatgaa ttatggctgt aaataacact atagtttaat aagcccacca ttctgagttt 2341 attaaacatt ttccattctt gtgaaaattt caaaaaaaaa aaaaaaaaaa aaagaaaaaa 2401 aaaaaaaaaa a
```

By "TBR1 polypeptide" (or T-box, brain 1 (TBR1)) is meant a polypeptide or fragment thereof having at least about 85% amino acid identity to NCBI Accession No. NP_006584.1.

MQLEHCLSPSIMLSKKFLNVSSSYPHSGGSELVLHDHPIISTTD

NLERSSPLKKITRGMTNQSDTDNFPDSKDSPGDVQRSKLSPVLDGVSELR

HSFDGSAA

DRYLLSQSSQPQSAATAPSAMFPYPGQHGPAHPAFSIGSPSRYMAHHPVI

TNGAYNSL

LSNSSPQGYPTAGYPYPQQYGHSYQGAPFYQFSSTQPGLVPGKAQVYL

CNRPLWLKFH

RHQTEMIITKQGRRMFPFLSFNISGLDPTAHYNIFVDVILADPNHWRFQG

GKWVPCGK

ADTNVQGNRVYMHPDSPNTGAHWMRQEISFGKLKLTNNKGASNNNGQMVV

LQSLHKYQ

PRLHVVEVNEDGTEDTSQPGRVQTFTFPETQFIAVTAYQNTDITQLKIDH

NPFAKGFR

DNYDTIYTGCDMDRLTPSPNDSPRSQIVPGARYAMAGSFLQDQFVSNYAK

ARFHPGAG

AGPGPGTDRSVPHTNGLLSPQQAEDPGAPSPQRWFVTPANNRLDFAASAY

DTATDFAG

NAATLLSYAAAGVKALPLQAAGCTGRPLGYYADPSGWGARSPPQYCGTKS

GSVLPCWP

NSAAAAARMAGANPYLGEEAEGLAAERSPLPPGAAEDAKPKDLSDSSWIE

TPSSIKSI

DSSDSGIYEQAKRRRISPADTPVSESSSPLKSEVLAQRDCEKNCAKDISG

YYGFYSHS

By "TBR1 polynucleotide" (or T-box, brain 1 (TBR1)) is meant a polynucleotide encoding an TBR1 polypeptide. An exemplary TBR1 nucleic acid molecule (e.g., mRNA) is provided at NCBI Accession No. NM_006593.

```
  1 gtcgctacca ggagccaggt gattatccta attaatgtct atctaattaa attactgtca 61 gcagctaacc aatggcagga gccgtttcat cggctgcaca agcagcaaga tcaaaagtga 121 gccttttctg attgctgcat agtgtcaatt ggccaatctc ttctcccagg gaaaaaaaa 181 agtaaatcaa acctttgaga agcatttgct ggttgaagtg ctttctgtct agtgagggg
```

-continued

```
 241 tctgtggatt tctagtttat gataaatagg acttaaaaa ccagggacgg gagggcgagt
 301 gttcaggttc tagagctatg cagctggagc actgcctttc tccttctatc atgctctcca
 361 agaaatttct caatgtgagc agcagctacc cacattcagg cggatccgag cttgtcttgc
 421 acgatcatcc cattatctcg accactgaca acctggagag aagttcacct ttgaaaaaaa
 481 ttaccagggg gatgacgaat cagtcagata cagacaattt tcctgactcc aaggactcac
 541 caggggacgt ccagagaagt aaactctctc ctgtcttgga cggggtctct gagcttcgtc
 601 acagtttcga tggctctgct gcagatcgct acctcctctc tcagtccagc cagccacagt
 661 ctgcggccac tgctcccagt gccatgttcc cgtaccccgg ccagcacgga ccggcgcacc
 721 ccgccttctc catcggcagc cctagccgct acatggccca ccacccggtc atcaccaacg
 781 gagcctacaa cagcctcctg tccaactcct cgccgcaggg ataccccacg gccggctacc
 841 cctacccaca gcagtacggc cactcctacc aaggagctcc gttctaccag ttctcctcca
 901 cccagccggg gctggtgccc ggcaaagcac aggtgtacct gtgcaacagg cccctttggc
 961 tgaaatttca ccggcaccaa acggagatga tcatcaccaa acaggaagg cgcatgtttc
1021 ctttttttaag ttttaacatt tctggtctcg atcccacggc tcattacaat attttgtgg
1081 atgtgattt ggcggatccc aatcactgga ggtttcaagg aggcaaatgg gttccttgcg
1141 gcaaagcgga caccaatgtg caaggaaatc gggtctatat gcatccggat tcccccaaca
1201 ctggggctca ctggatgcgc caagaaatct cttttggaaa attaaaactt acgaacaaca
1261 aaggagcttc aaataacaat gggcagatgg tggttttaca gtccttgcac aagtaccagc
1321 cccgcctgca tgtggtggaa gtgaacgagg acggcacgga ggacactagc cagcccggcc
1381 gcgtgcagac gttcactttc cctgagactc agttcatcgc cgtcaccgcc taccagaaca
1441 cggatattac acaactgaaa atagatcaca accccttttgc aaaaggattt cgggataatt
1501 atgacacgat ctacaccggc tgtgacatgg accgcctgac ccctcgccc aacgactcgc
1561 cgcgctcgca gatcgtgccc ggggcccgct acgccatggc cggctctttc ctgcaggacc
1621 agttcgtgag caactacgcc aaggcccgct ccacccgggg cgcgggcgcg ggccccgggc
1681 cgggtacgga ccgcagcgtg ccgcacacca acgggctgct gtcgccgcag caggccgagg
1741 acccgggcgc gccctcgccg caacgctggt tgtgacgcc ggccaacaac cggctggact
1801 tcgcggcctc ggcctatgac acggccacgg acttcgcggg caacgcggcc acgctgctct
1861 cttacgcggc ggcgggcgtg aaggcgctgc cgctgcaggc tgcaggctgc actggccgcc
1921 cgctcggcta ctacgccgac ccgtcgggct ggggcgcccg cagtccccg cagtactgcg
1981 gcaccaagtc gggctcggtg ctgccctgct ggcccaacag cgccgcggcc gccgcgcgca
2041 tggccgcgc caatccctac ctgggcgagg aggccgaggg cctggccgcc gagcgctcgc
2101 cgctgccgcc cggcgccgcc gaggacgcca agcccaagga cctgtccgat tccagctgga
2161 tcgagacgcc ctcctcgatc aagtccatcg actccagcga ctcggggatt tacgagcagg
2221 ccaagcggag gcggatctcg ccggccgaca cgcccgtgtc cgagagttcg tccccgctca
2281 agagcgaggt gctggcccag cgggactgcg agaagaactg cgccaaggac attagcggct
2341 actatggctt ctactcgcac agctaggccg ccccctgcccg cccggcccg ccgcggcccg
2401 gaccccagc cagcccctca cagctcttcc ccagctccgc ctcccacac tcctccttgc
2461 gcacccactc attttatttg accctcgatg gccgtctgca gcgaataagt gcaggtctcc
2521 gagcgtgatt ttaacctttt ttgcacagca gtctctgcaa ttagctcacc gaccttcaac
2581 tttgctgtaa acctttggt ttccctactt actcttcttc tgtggagtta tcctcctaca
2641 attcccctcc ccctcgtctt tctcttacct cctacttctc tttcttgtaa tgaaactctt
```

```
2701 cacctttagg agacctgggc agtcctgtca ggcagcagcg attccgaccc gccaagtctc 2761 ggcctccaca ttaaccatag gatgttgact ctagaacctg gacccaccca gcgcgtcctt 2821 tcttatcccc gagtggatgg atggatggat ggatggtagg gatgttaata attttagtgg 2881 aacaaagcct gtgaaatgat tgtacatagt gttaatttat tgtaacgaat ggctagtttt 2941 tattctcgtc aaggcacaaa accagttcat gcttaacctt tttttccttt cctttctttg 3001 cttttctttc tctcctctca tactttctct tctctctctt ttaattttct tgtgagataa 3061 tattctaaga ggctctagaa acatgaaata ctcagtagtg atgggtttcc cacttctcct 3121 caatccgttg catgaaataa ttactatgtg ccctaatgca cacaaatagc taaggagaat 3181 ccacccaaac acctttaaag gataggtgtc tgttcatagg caagtcgatt aagtggcatg 3241 atgcctgcaa agcaaagtca actggagttg tatgttcccc ccaccttcta aatagaatag 3301 ctcgacatca gcaatattat tttgccttat ttgttttttcc ccaaagtgcc aaatccatta 3361 ctggtctgtg caggtgccaa atatgctgac aaactgtttc tgaatatctt tcagtaccccc 3421 ttcacccttta tatgctgtaa atctttgtaa tgaatactct attaatgata tagatgactg 3481 aattgttggt aactatagtg tagtctagtg aagatgaatt gtgtgagttg tatattttac 3541 tgcattttag ttttgaaaat gacttcccca ccacctagaa acagctgaaa tttgacttcc 3601 ttgggagaac actagcatta atgcaagtaa gactgatttt cccctaagtc ttgttatatt 3661 tgataaggag cattaatccc cctggaaata gattagtagg atttctaatg ttgtgtagca 3721 aacctatact tttttgtatt taaaaattaa tgtgaaatat gcatcataca caatattcaa 3781 tctagattcc agtccatggg gggattttc ctaataggaa ttcagggtct aaacgtgtgt 3841 atattttggc tcttctgtaa atctaatgtt gtgattttta tatttgtttc gttttgtctg 3901 tgaactgaat aatttataca agaacacact ccattgagaa acgttttgtt ttttgctcgt 3961 ttgtatcgtc tgtgtataac aagtaaaata aacctggtaa aaacgc
```

By "SLC1A3 polypeptide" (or solute carrier family 1; glial high affinity glutamate transporter member 3 (SLC1A3)) is meant a polypeptide or fragment thereof having at least about 85% amino acid identity to NCBI Accession No. BAG35230.1.

MTKSNGEEPKMGGRMERFQQGVRKRTLLAKKKVQNITKEDVKSYLFRNAF

VLLTVTAVIVGTILGFTLRPYRMSYREVKYFSFPGELLMRMLQMLVLPLI

ISSLVTGMAALDSKASGKMGMRAVVYYMTTTIIAVVIGIIIVIIIHPGKG

TKENMHREGKIVRVTAADAFLDLIRNMFPPNLVEACFKQFKTNYEKRSFK

VPIQANETLVGAVINNVSEAMETLTRITEELVPVPGSVNGVNALGLVVFS

MCFGFVIGNMKEQGQALREFFDSLNEAIMRLVAVIMWYAPVGILFLIAGK

IVEMEDMGVIGGQLAMYTVTVIVGLLIHAVIVLPLLYFLVTRKNPWVFIG

GLLQALITALGTSSSSATLPITFKCLEENNGVDKRVTRFVLPVGATINMD

GTALYEALAAIFIAQVNNFELNFGQIITISITATAASIGAAGIPQAGLVT

MVIVLTSVGLPTDDITLIIAVDWFLDRLRTTTNVLGDSLGAGIVEHLSRH

ELKNRDVEMGNSVIEENEMKKPYQLIAQDNETEKPIDSETKM

By "SLC1A3 polynucleotide" (or solute carrier family 1; glial high affinity glutamate transporter member 3 (SLC1A3)) is meant a polynucleotide encoding an SLC1A3 polypeptide. An exemplary SLC1A3 nucleic acid molecule (e.g., mRNA) is provided at NCBI Accession No. AK312304.

```
  1 gatagtaact tgcagtttca gagcacatgc acactgtcag ggctagcctg cctgcttacg 61 cgcgctgcgg attgttgctc cgttgtacct gctggggaat tcacctcgtt actgcttgat 121 atcttccacc ccttacaaaa tcagaaaagt tgtgttttct aataccaaag aggaggtttg 181 gcttctgtg ggtgattccc agacactgaa gtgcaaagaa gagaccctcc tagaaaagta 241 aaatatgact aaaagcaatg gagaagagcc caagatgggg gcaggatgg agagattcca 301 gcagggagtc cgtaaacgca cactttttggc caagaagaaa gtgcagaaca ttacaaagga 361 ggatgttaaa agttacctgt ttcggaatgc ttttgtgctg ctcacagtca ccgctgtcat
```

```
 421 tgtgggtaca atccttggat ttaccctccg accatacaga atgagctacc gggaagtcaa 481 gtacttctcc tttcctgggg aacttctgat gaggatgtta cagatgctgg tcttaccact 541 tatcatctcc agtcttgtca caggaatggc ggcgctagat agtaaggcat cagggaagat 601 gggaatgcga gctgtagtct attatatgac taccaccatc attgctgtgg tgattggcat 661 aatcattgtc atcatcatcc atcctgggaa gggcacaaag gaaaacatgc acagagaagg 721 caaaattgta cgagtgacag ctgcagatgc cttcctggac ttgatcagga acatgttccc 781 tccaaatctg gtagaagcct gctttaaaca gtttaaaacc aactatgaga agagaagctt 841 taaagtgccc atccaggcca acgaaacgct tgtgggtgct gtgataaaca atgtgtctga 901 ggccatggag actcttaccc gaatcacaga ggagctggtc ccagttccag gatctgtgaa 961 tggagtcaat gccctgggtc tagttgtctt ctccatgtgc ttcggttttg tgattggaaa 1021 catgaaggaa caggggcagg ccctgagaga gttctttgat tctcttaacg aagccatcat 1081 gagactggta gcagtaataa tgtggtatgc ccccgtgggg attctcttcc tgattgctgg 1141 gaagattgtg gagatggaag acatgggtgt gattggggggg cagcttgcca tgtacaccgt 1201 gactgtcatt gttggcttac tcattcacgc agtcatcgtc ttgccactcc tctacttctt 1261 ggtaacacgg aaaaacccttt gggttttttat tggagggttg ctgcaagcac tcatcaccgc 1321 tctggggacc tcttcaagtt ctgccaccct acccatcacc ttcaagtgcc tggaagagaa 1381 caatggcgtg gacaagcgcg tcaccagatt cgtgctcccc gtaggagcca ccattaacat 1441 ggatgggact gccctctatg aggctttggc tgccattttc attgctcaag ttaacaactt 1501 tgaactgaac ttcggacaaa ttattacaat cagcatcaca gccacagctg ccagtattgg 1561 ggcagctgga attcctcagg cgggcctggt cactatggtc attgtgctga catctgtcgg 1621 cctgcccact gacgacatca cgctcatcat cgcggtggac tggttcctgg atcgcctccg 1681 gaccaccacc aacgtactgg gagactccct gggagctggg attgtggagc acttgtcacg 1741 acatgaactg aagaacagag atgttgaaat gggtaactca gtgattgaag agaatgaaat 1801 gaagaaacca tatcaactga ttgcacagga caatgaaact gagaaaccca tcgacagtga 1861 aaccaagatg tag
```

By "TH polypeptide" (or tyrosine hydroxylase) is meant a polypeptide or fragment thereof having at least about 85% amino acid identity to NCBI Accession No. AAI43612.1.

MPTPDATTPQAKGFRRAVSELDAKQAEAIMSPRFIGRRQSLIEDARKERE

AAVAAAAAAVPSEPGDPLEAVAFEEKEGKAVLNLLFSPRATKPSALSRAV

KVFETFEAKIHHLETRPAQRPRAGGPHLEYFVRLEVRRGDLAALLSGVRQ

VSEDVRSPAGPKVPWFPRKVSELDKCHHLVTKFDPDLDLDHPGFSDQVYR

QRRKLIAEIAFQYRHGDPIPRVEYTAEEIATWKEVYTTLKGLYATHACGE

HLEAFALLERFSGYREDNIPQLEDVSRFLKERTGFQLRPVAGLLSARDFL

ASLAFRVFQCTQYIRHASSPMHSPEPDCCHELLGHVPMLADRTFAQFSQD

IGLASLGASDEEIEKLSTLYWFTVEFGLCKQNGEVKAYGAGLLSSYGELL

HCLSEEPEIRAFDPEAAAVQPYQDQTYQSVYFVSESFSDAKDKLRSYASR

IQRPFSVKFDPYTLAIDVLDSPQAVRRSLEGVQDELDTLAHALSAIG

By "TH polynucleotide" (or tyrosine hydroxylase) is meant a polynucleotide encoding an TH polypeptide. An exemplary TH nucleic acid molecule (e.g., mRNA) is provided at NCBI Accession No. BC143611.

```
   1 acccagaggg ggctttgacg tcagctcagc ttataagagg ctgctgggcc agggctgtgg 61 agacggagcc cggacctcca cactgagcca tgcccacccc cgacgccacc acgccacagg 121 ccaagggctt ccgcagggcc gtgtctgagc tggacgccaa gcaggcagag gccatcatgt 181 ccccgcggtt cattgggcgc aggcagagcc tcatcgagga cgcccgcaag gagcgggagg 241 cggcggtggc agcagcggcc gctgcagtcc cctcggagcc cggggacccc ctggaggctg
```

-continued

```
 301 tggcctttga ggagaaggag gggaaggccg tgctaaacct gctcttctcc ccgagggcca
 361 ccaagccctc ggcgctgtcc cgagctgtga aggtgtttga cacgtttgaa gccaaaatcc
 421 accatctaga gacccggccc gcccagaggc cgcgagctgg gggcccccac ctggagtact
 481 tcgtgcgcct cgaggtgcgc cgaggggacc tggccgccct gctcagtggt gtgcgccagg
 541 tgtcagagga cgtgcgcagc cccgcggggc ccaaggtccc ctggttccca agaaaagtgt
 601 cagagctgga caagtgtcat cacctggtca ccaagttcga ccctgacctg gacttggacc
 661 acccgggctt ctcggaccag gtgtaccgcc agcgcaggaa gctgattgct gagatcgcct
 721 tccagtacag gcacggcgac ccgattcccc gtgtggagta caccgccgag gagattgcca
 781 cctggaagga ggtctacacc acgctgaagg gcctctacgc cacgcacgcc tgcggggagc
 841 acctggaggc ctttgctttg ctggagcgct tcagcggcta ccgggaagac aatatccccc
 901 agctggagga cgtctcccgc ttcctgaagg agcgcacggg cttccagctg cggcctgtgg
 961 ccggcctgct gtccgcccgg gacttcctgg ccagcctggc cttccgcgtg ttccagtgca
1021 cccagtatat ccgccacgcg tcctcgccca tgcactcccc tgagccggac tgctgccacg
1081 agctgctggg gcacgtgccc atgctggccg accgcacctt cgcgcagttc tcgcaggaca
1141 ttggcctggc gtccctgggg gcctcggatg aggaaattga gaagctgtcc acgctgtact
1201 ggttcacggt ggagttcggg ctgtgtaagc agaacgggga ggtgaaggcc tatggtgccg
1261 ggctgctgtc ctcctacggg gagctcctgc actgcctgtc tgaggagcct gagattcggg
1321 ccttcgaccc tgaggctgcg gccgtgcagc cctaccaaga ccagacgtac cagtcagtct
1381 acttcgtgtc tgagagcttc agtgacgcca aggacaagct caggagctat gcctcacgca
1441 tccagcgccc cttctccgtg aagttcgacc cgtacacgct ggccatcgac gtgctggaca
1501 gcccccaggc cgtgcggcgc tccctggagg gtgtccagga tgagctggac acccttgccc
1561 atgcgctgag tgccattggc taggtgcacg gcgtccctga gggccttcc caacctcccc
1621 tggtcctgc
```

By "Neurofilament 200 polypeptide" (or neurofilament heavy (NEFH)) is meant a polypeptide or fragment thereof having at least about 85% amino acid identity to NCBI Accession No. NP_066554.2.

MMSFGGADALLGAPFAPLHGGGSLHYALARKGGAGGTRSAAGSSSGFHSW
TRTSVSSVSASPSRFRGAGAASSTDSLDTLSNGPEGCMVAVATSRSEKEQ
LQALNDRFAGYIDKVRQLEAHNRSLEGEAAALRQQQAGRSAMGELYEREV
REMRGAVLRLGAARGQLRLEQEHLLEDIAHVRQRLDDEARQREEAEAAAR
ALARFAQEAEAARVDLQKKAQALQEECGYLRRHHQEEVGELLGQIQGSGA
AQAQMQAETRDALKCDVTSALREIRAQLEGHAVQSTLQSEEWFRVRLDRL
SEAAKVNTDAMRSAQEEITEYRRQLQARTTELEALKSTKDSLERQRSELE
DRHQADIASYQEAIQQLDAELRNTKWEMAAQLREYQDLLNVKMALDIEIA
AYRKLLEGEECRIGFGPIPFSLPEGLPKIPSVSTHIKVKSEEKIKVVEKS
EKETVIVEEQTEETQVTEEVTEEEEKEAKEEEGKEEEGGEEEEAEGGEEE
TKSPPAEEAASPEKEAKSPVKEEAKSPAEAKSPEKEEAKSPAEVKSPEKA
KSPAKEEAKSPPEAKSPEKEEAKSPAEVKSPEKAKSPAKEEAKSPAEAKS
PEKAKSPVKEEAKSPAEAKSPVKEEAKSPAEVKSPEKAKSPTKEEAKSPE
KAKSPEKEEAKSPEKAKSPVKAEAKSPEKAKSPVKAEAKSPEKAKSPVKE
EAKSPEKAKSPVKEEAKSPEKAKSPVKEEAKTPEKAKSPVKEEAKSPEKA
KSPEKAKTLDVKSPEAKTPAKEEARSPADKFPEKAKSPVKEEVKSPEKAK
SPLKEDAKAPEKEIPKKEEVKSPVKEEEKPQEVKVKEPPKKAEEEKAPAT
PKTEEKKDSKKEEAPKKEAPKPKVEEKKEPAVEKPKESKVEAKKEEAEDK
KKVPTPEKEAPAKVEVKEDAKPKEKTEVAKKEPDDAKAKEPSKPAEKKEA
APEKKDTKEEKAKKPEEKPKTEAKAKEDDKTLSKEPSKPKAEKAEKSSST
DQKDSKPPEKATEDKAAKGK

By "Neurofilament 200 polynucleotide" (or neurofilament heavy (NEFH)) is meant a polynucleotide encoding an Neurofilament 200 polypeptide. An exemplary Neurofilament 200 nucleic acid molecule (e.g., mRNA) is provided at NCBI Accession No. NM_021076.

```
   1 aaaagggccg gcgccctggt gctgccgcag tgcctcccgc cccgtccsgg cctcgcgcac
  61 ctgctcaggc catgatgagc ttcggcggcg cggacgcgct gctgggcgcc ccgttcgcgc
 121 cgctgcatgg cggcggcagc ctccactacg cgctagcccg aaagggtggc gcaggcggga
 181 cgcgctccgc cgctggctcc tccagcggct tccactcgtg gacacggacg tccgtgagct
 241 ccgtgtccgc ctcgcccagc cgcttccgtg gcgcaggcgc cgcctcaagc accgactcgc
 301 tggacacgct gagcaacggg ccggagggct gcatggtggc ggtggccacc tcacgcagtg
 361 agaaggagca gctgcaggcg ctgaacgacc gcttcgccgg gtacatcgac aaggtgcggc
 421 agctggaggc gcacaaccgc agcctggagg gcgaggctgc ggcgctgcgg cagcagcagg
 481 cgggccgctc cgctatgggc gagctgtacg agcgcgaggt ccgcgagatg cgcggcgcgg
 541 tgctgcgcct gggcgcggcg cgcggtcagc tacgcctgga gcaggagcac ctgctcgagg
 601 acatcgcgca cgtgcgccag cgcctagacg acgaggcccg gcagcgagag gaggccgagg
 661 cggcggcccg cgcgctggcg cgcttcgcgc aggaggccga ggcggcgcgc gtggacctgc
 721 agaagaaggc gcaggcgctg caggaggagt gcggctacct gcggcgccac caccaggaag
 781 aggtgggcga gctgctcggc cagatccagg gctccggcgc cgcgcaggcg cagatgcagg
 841 ccgagacgcg cgacgccctg aagtgcgacg tgacgtcggc gctgcgcgag attcgcgcgc
 901 agcttgaagg ccacgcggtg cagagcacgc tgcagtccga ggagtggttc cgagtgaggc
 961 tggaccgact gtcggaggca gccaaggtga acacagacgc tatgcgctca gcgcaggagg
1021 agataactga gtaccggcgt cagctgcagg ccaggaccac agagctggag gcactgaaaa
1081 gcaccaagga ctcactggag aggcagcgct ctgagctgga ggaccgtcat caggccgaca
1141 ttgcctccta ccaggaagcc attcagcagc tggacgctga gctgaggaac accaagtggg
1201 agatggccgc ccagctgcga gaataccagg acctgctcaa tgtcaagatg gctctggata
1261 tagagatagc cgcttacaga aaactcctgg aaggtgaaga gtgtcggatt ggctttggcc
1321 caattccttt ctcgcttcca gaaggactcc ccaaaattcc ctctgtgtcc actcacataa
1381 aggtgaaaag cgaagagaag atcaaagtgg tggagaagtc tgagaaagaa actgtgattg
1441 tggaggaaca gacagaggag acccaagtga ctgaagaagt gactgaagaa gaggagaaag
1501 aggccaaaga ggaggagggc aaggaggaag aaggggggtga agaagaggag gcagaagggg
1561 gagaagaaga aacaaagtct cccccagcag aagaggctgc atcccagag aaggaagcca
1621 agtcaccagt aaaggaagag gcaaagtcac cggctgaggc caagtcccca gagaaggagg
1681 aagcaaaatc cccagccgaa gtcaagtccc ctgagaaggc caagtctcca gcaaggaag
1741 aggcaaagtc accgcctgag gccaagtccc cagagaagga ggaagcaaaa tctccagctg
1801 aggtcaagtc ccccgagaag gccaagtccc cagcaaagga gaggcaaag tcaccggctg
1861 aggccaagtc tccagagaag gccaagtccc cagtgaagga gaagcaaag tcaccggctg
1921 aggccaagtc cccagtgaag gaagaagcaa atctccagc tgaggtcaag tccccggaaa
1981 aggccaagtc tccaacgaag gaggaagcaa agtcccctga aaggccaag tccccagaga
2041 aggaagaggc caagtcccct gagaaggcca gtccccagt gaaggcagaa gcaaagtccc
2101 ctgagaaggc caagtcccca gtgaaggcag aagcaaagtc ccctgagaag gccaagtccc
2161 cagtgaagga agaagcaaag tcccctgaga aggccaagtc cccagtgaag gaagaagcaa
2221 agtcccctga aaggccaag tccccagtga aggaagaagc aaagaccccc gagaaggcca
2281 agtccccagt gaaggaagaa gctaagtccc cagagaaggc caagtcccca gagaaggcca
2341 agactcttga tgtgaagtct ccagaagcca agactccagc gaaggaggaa gcaaggtccc
2401 ctgcagacaa attcccctgaa aaggccaaaa gccctgtcaa ggaggaggtc aagtccccag
```

```
2461 agaaggcgaa atctccoctg aaggaggatg ccaaggcccc tgagaaggag atcccaaaaa 2521 aggaagaggt gaagtcccca gtgaaggagg aggagaagcc ccaggaggtg aaagtcaaag 2581 agccccoaaa gaaggcagag gaagagaaag ccoctgccac accaaaaaca gaggagaaga 2641 aggacagcaa gaaagaggag gcacccaaga aggaggctcc aaagcccaag gtggaggaga 2701 agaaggaacc tgctgtcgaa aagcccaaag aatccaaagt tgaagccaag aaggaagagg 2761 ctgaagataa gaaaaaagtc cccaccccag agaaggaggc tcctgccaag gtggaggtga 2821 aggaagacgc taaacccaaa gaaaagacag aggtagccaa gaggaaccca gatgatgcca 2881 aggccaagga acccagcaaa ccagcagaga agaaggaggc agcaccggag aaaaaagaca 2941 ccaaggagga gaaggccaag aagcctgagg agaaacccaa gacagaggcc aaagccaagg 3001 aagatgacaa gaccctctca aaagagccta gcaagcctaa ggcagaaaag gctgaaaaat 3061 cctccagcac agaccaaaaa gacagcaagc ctccagagaa ggccacagaa gacaaggccg 3121 ccaaggggaa gtaaggcagg gagaaaggaa catccggaac agccaaagaa actcagaaga 3181 gtcccggagc tcaaggatca gagtaacaca attttcactt tttctgtctt tatgtaagaa 3241 gaaactgctt agatgacggg gcctccttct tcaaacagga atttctgtta gcaatatgtt 3301 agcaagagag ggcactccca ggcccctgcc cccaggccct ccccaggcga tggacaatta 3361 tgatagctta tgtagctgaa tgtgatacat gccgaatgcc acacgtaaac acttgactat 3421 aaaaactgcc cccctccttt ccaaataagt gcatttattg cctctatgtg caactgacag 3481 atgaccgcaa taatgaatga gcagttagaa atacattatg cttgagatgt cttaacctat 3541 tcccaaatgc cttctgtttt ccaaaggagt ggtcaagccc ttgcccagag ctctctattc 3601 tggaagagcg gtccaggtgg ggccgggac tggccactga attatgccag ggcgcacttt 3661 ccactggagt tcactttcaa ttgcttctgt gcaataaaac caagtgctta taaaatgaaa 3721 a
```

By "Map2" (or microtubule-associated protein 2) is meant a polypeptide or fragment thereof having at least about 85% amino acid identity to NCBI Accession No. AAH38857.1.

MADERKDEAKAPHWTSAPLTEASAHSHPPEIKDQGGAGEGLVRSANGFPY
REDEEGAFGEHGSQGTYSNTKENGINGELTSADRETAEEVSARIVQVVTA
EAVAVLKGEQEKEAQHKDQTAALPLAAEETANLPPSPPPSPASEQTVTVE
EAAGGESALAPSVFKQAKDKVSNSTLSKIPALQGSTKSPRYSSACPSTTK
RATFSDSLLIQPTSAGSTDRLPYSKSGNKDGVTKSPEKRSSLPRPSSILP
PRRGVSGDRDENSFSLNSSISSSARRTTRSEPIRRAGKSGTSTPTTPGST
AITPGTPPSYSSRTPGTPGTPSYPRTPHTPGTPKSAILVPSEKKVAIIRT
PPKSPATPKQLRLINQPLPDLKNVKSKIGSTDNIKYQPKGGQVRILNKKI
DFSKVQSRCGSKDNIKHSAGGGNVQIVTKKIDLSHVTSKCGSLKNIRHRP
GGGRVKIESVKLDFKEKAQAKVGSLDNAHHVPGGGNVKIDSQKLNFREHA
KARVDHGAEIITQSPGRSSVASPRRLSNVSSSGSINLLESPQLATLAEDV
TAALAKQGL

By "Map2 polynucleotide" (or microtubule-associated protein 2) is meant a polynucleotide encoding an Map2 polypeptide. An exemplary Map2 nucleic acid molecule (e.g., mRNA) is provided at NCBI Accession No. BC038857.

```
  1 ggcgctcggg ctgcgcgggc tctgggcagc agcagcagca gcagcagcat cctctcttcc 61 tttacttccc ttccgcttct ttctcttcct tctccttctt tttccccccc ctcccctttct 121 tccoctaacc cttctacccc tctccttttt ctccggaggg cgctaagtcc gtgagcggtg 181 gcagtcgcga ccgcgggtgc atccagtttc tgcgcccaga ttttattgat ctaatccaaa 241 gtatcttata acttctggct ggaattaaga ttcttcagct tgtctctaac cgaggaagca 301 ttgattggga gctactcatt cagaaaatta aagaaagaa gccagaaaat attatcaacc 361 ctttgagaac acgacacaac gaactttata ttttaccact tccttgaata gttgcaggag
```

-continued

```
 421 aaataacaag gcattgaaga atggcagatg aacggaaaga cgaagcaaag gcacctcact
 481 ggacctcagc accgctaaca gaggcatctg cacactcaca tccacctgag attaaggatc
 541 aaggcggagc aggggaagga cttgtccgaa gcgccaatgg attcccatac agggaggatg
 601 aagagggtgc ctttggagag catgggtcac agggcaccta ttcaaatacc aaagagaatg
 661 ggatcaacgg agagctgacc tcagctgaca gagaaacagc agaggaggtg tctgcaagga
 721 tagttcaagt agtcactgct gaggctgtag cagtcctgaa aggtgaacaa gagaaagaag
 781 ctcaacataa agaccagact gcagctctgc ctttagcagc tgaagaaaca gctaatctgc
 841 ctccttctcc accccatca cctgcctcag aacagactgt cacagtggag gaagcagcag
 901 gtggggaatc agctctggct cccagtgtat ttaaacaggc aaaggacaaa gtctctaatt
 961 ctaccttgtc aaagattcct gctttacagg gtagcacaaa gtccccaaga tacagctcag
1021 cctgccctag cacgactaaa agggctacat tttctgacag tttattaata cagcccacct
1081 cagcaggctc cacagaccgt ttgccatact caaaatcagg gaacaaggac ggagtaacca
1141 agagcccaga aaagcgctct tctctcccaa gaccttcctc cattctccct cctcggcgag
1201 gtgtgtcagg agacagagat gagaattcct tctctctcaa cagttctatc tcttcttcag
1261 cacggcggac caccaggtca gagccaattc gcagagcagg aagagtggt acctcaacac
1321 ccactacccc tgggtctact gccatcactc ctggcacccc accaagttat tcttcacgca
1381 caccaggcac tcctggaacc cctagctatc caggacccc tcacacacca ggaaccccca
1441 agtctgccat cttggtgccg agtgagaaga aggtcgccat catacgtact cctccaaaat
1501 ctcctgcgac tcccaagcag cttcggctta ttaaccaacc actgccagac ctgaagaatg
1561 tcaaatccaa aatcggatca acagacaaca tcaaatacca gcctaaaggg gggcaggtta
1621 ggattttaaa caagaagatc gattttagca aagttcagtc cagatgtggt tccaaggata
1681 acatcaaaca ttcggctggg ggcggaaatg tacaaattgt taccaagaaa atagacctaa
1741 gccatgtgac atccaaatgt ggctctctga gaacatccg ccacaggcca ggtggcggac
1801 gtgtgaaaat tgagagtgta aaactagatt tcaaagaaaa ggcccaagct aaagttggtt
1861 ctcttgataa tgctcatcat gtacctggag gtggtaatgt caagattgac agccaaaagt
1921 tgaacttcag agagcatgct aaagcccgtg tggaccatgg ggctgagatc attacacagt
1981 ccccaggcag atccagcgtg gcatcacccc gacgactcag caatgtctcc tcgtctggaa
2041 gcatcaacct gctcgaatct cctcagcttg ccactttggc tgaggatgtc actgctgcac
2101 tcgctaagca gggcttgtga atatttctca tttagcattg aaataataat atttaggcat
2161 gagctcttgg caggagtggg ctctgagcag ttgttatatt cattctttat aaaccataaa
2221 ataaataatc tcatccccaa aaaaaaaaaa aaaaaaaaa aaaaaaaaa aaaaaaaaa
2281 aaaaaa
```

By "DCX" (or doublecortin) is meant a polypeptide or fragment thereof having at least about 85% amino acid identity to NCBI Accession No. NP_835366.1.

MELDFGHFDERDKTSRNMRGSRMNGLPSPTHSAHCSFYRTRTLQALSNEK

KAKKVRFYRNGDRYFKGIVYAVSSDRFRSFDALLADLTRSLSDNINLPQG

VRYIYTIDGSRKIGSMDELEEGESYVCSSDNFFKKVEYTKNVNPNWSVNV

KTSANMKAPQSLASSNSAQARENKDFVRPKLVTIIRSGVKPRKAVRVLLN

KKTAHSFEQVLTDITEAIKLETGVVKKLYTLDGKQVTCLHDFFGDDDVFI

ACGPEKFRYAQDDFSLDENECRVMKGNPSATAGPKASPTPQKTSAKSPGP

MRRSKSPADSANGTSSSQLSTPKSKQSPISTPTSPGSLRKHKDLYLPLSL

DDSDSLGDSM

By "DCX polynucleotide" (or doublecortin) is meant a polynucleotide encoding an DCX polypeptide. An exemplary DCX nucleic acid molecule (e.g., mRNA) is provided at NCBI Accession No. NM_178153.

```
   1 ctggcaggaa tttcttgctt ggagctcaga caacaaaggc atagagagat tggttttctt
  61 tctctcagca tctccaccca accagcagaa aaccggtctc tgaggttcca ccaaaatatg
 121 gaacttgatt ttggacactt tgacgaaaga gataagacat ccaggaacat gcgaggctcc
 181 cggatgaatg ggttgcctag ccccactcac agcgcccact gtagcttcta ccgaaccaga
 241 accttgcagg cactgagtaa tgagaagaaa gccaagaagg tacgtttcta ccgcaatggg
 301 gaccgctact tcaaggggat tgtgtacgct gtgtcctctg accgttttcg cagctttgac
 361 gccttgctgg ctgacctgac gcgatctctg tctgacaaca tcaacctgcc tcagggagtg
 421 cgttacattt acaccattga tggatccagg aagatcggaa gcatggatga actggaggaa
 481 ggggaaagct atgtctgttc ctcagacaac ttctttaaaa aggtggagta caccaagaat
 541 gtcaatccca actggtctgt caacgtaaaa acatctgcca atatgaaagc cccccagtcc
 601 ttggctagca gcaacagtgc acaggccagg agaacaagg actttgtgcg ccccaagctg
 661 gttaccatca tccgcagtgg ggtgaagcct cggaaggctg tgcgtgtgct tctgaacaag
 721 aagacagccc actctttga gcaagtcctc actgatatca cagaagccat caaactggag
 781 accggggttg tcaaaaaact ctacactctg gatggaaaac aggtaacttg tctccatgat
 841 ttctttggtg atgatgatgt gtttattgcc tgtggtcctg aaaaatttcg ctatgctcag
 901 gatgattttt ctctggatga aaatgaatgc cgagtcatga agggaaaccc atcagccaca
 961 gctggcccaa aggcatcccc aacacctcag aagacttcag ccaagagccc tggtcctatg
1021 cgccgaagca agtctccagc tgactcagca aacggaacct ccagcagcca gctctctacc
1081 cccaagtcta gcagtctcc catctctacg cccaccagtc ctggcagcct ccggaagcac
1141 aaggacctgt acctgcctct gtccttggat gactcggact cgcttggtga ttccatgtaa
1201 aggaggggag agtgctcaga gtccagagta caaatccaag cctatcattg tagtagggta
1261 cttctgctca agtgtccaac agggctattg gtgctttcaa gttttttattt tgttgttgtt
1321 gttatttttga aaacacatt gtaatatgtt gggtttattt tcctgtgatt tctcctctgg
1381 gccactgatc cacagttacc aattatgaga gatagattga taaccatcct ttggggcagc
1441 attccaggga tgcaaaatgt gctagtccat gacctttcaa tggaaagctt aggtgcctgc
1501 gttatatttg ccctgtctaa ttttgcccat acagtcttcc ttctgtagag ggctgtttac
1561 atatacagca cttaaaatgt ttgtgtggga aaaaaaaac tcattggcag atccaagaat
1621 gacaaacaca agtgcccctt ttctctggat ctcaagaatg gtggaggacc ctggaaggac
1681 agcaaggcag ctccccagcc tcactcttca ctcctgattg aggccgggt tgttgtcca
1741 gcaccaattc tggctgtcaa tggggagaaa taaaccaaca acttataatt gtgacaccag
1801 atgcttagga tcctggtgct gggttagcta agagaataga cagaattgga aaatactgca
1861 gacatttccg aagagtttat aaagcacagt gaattcctgg tcaatctctc cactgaggca
1921 atttggaatc aataagcaat tgataatagt ttggagtaag ggacttcata tacctgattc
1981 ctctagaagg ctgtctaaca taccacatga ttacatgaac tgtatggtat ccatctatct
2041 ctgttctatt gaatgccttg ttaacagcca acactgaaaa cactgtgaga atttgttttc
2101 aggtctgaca ccttttcagtc tcttttttata gcaagaaatc aatatccttt ttataaaat
2161 tcatgtctgt atttcaggag caaactcttc aggctccttt tttataaact ggtgatttttt
2221 cttttgtcta aaaacacat gaagaaaatt taccaaaaaa aaaaaaaaa gcagaagaat
2281 aatgtagttt agaaattatg ctgtcactgc caaacagtaa cctccaggag aaaacaagat
2341 gaatagcaga ggccaattca atagaatcag tttttttgata gcttttttaac agttatgctt
2401 gcattaataa tttcaatgtg gaccagacat tctaattata ttttaaatga aatgttacag
```

-continued

```
2461 catatttttaa gcaactctttt ttatctataa tcctaatatt tcatactgaa gacacagaaa
2521 tctttcactt gtctttaaca ttagaaagga tttctcttta ctaaggactg atcatttgaa
2581 atagttttca gtcttttgag atacaggttt ataacactgc ttttttttt ctgtaatcat
2641 agcccataat ggcaaagaca actaaattta agtgaaggtc atgcatgcca attctgtgtt
2701 tgcttttagc agatatgaag atttccttat ttctttgtaa ttgtgcagat attttgaaag
2761 gcacagcatt cgaagccaag ctgctgtttg gctactgaat ggcttgcagt tgttcctcca
2821 ctctaaatgg aatgagcttg ctgtgtgtgt gtgtggtggt ggtgggaggg ggtggtgcat
2881 gtgtgtgtgt gtgtgtgcat ctgcagctgc ttcaaaatta ggaaatacta caggacaccc
2941 ctgtaatgga ttggtggcaa ctgggtggca ctgctgatgt gcactgtgta gggggggaacc
3001 cagtggtggt ggggtagctc agatgcccct agacaagctt cagatgtctg tagctaccag
3061 aaacattttc ggttcaggaa aagtgagatg atggtagtac tggtttctgg tgaaattgaa
3121 gaacccccaaa tgatgaggat ctcttttgc cccctctcct tttttgtag acccattcaa
3181 aaccattaat aagcccattt tactaagccc ctatttcttt ctagaagctc agggttttct
3241 tagtgcctcc cagaacattt tgtagttaat tgggaaaaag tgatacttgg attaggggt
3301 gtgggcataa agaatggtgg gaggcctgat tttaaacttc aggccagaac ccccaatgac
3361 tccacccata gtctcacttt aggtctcatt tagtccatca cctttatttt aagttgagga
3421 agtggaggct ggtaaagagc aggaccagag gaagaatcca gatttcctta tgcttgggcc
3481 tcacactagc tctctgagta tttccttgat tgcggtatat gtactactag aaaataccaa
3541 atggatatat tttctttagg ataaccttg aaccaacaat cttcaataac aatagtacat
3601 cttccatctt acttttaatc gagtataagg aaatgtttct ttatggccat tttggaggga
3661 gcagggatg aggcttggca tagtccaaaa tttaagtctc caataattaa ttgcatttta
3721 aattggccca ctttcaaggc aattttttt gtgtgtctgt aactgagctc ctccaccccct
3781 gtcattcact tccaattta cccaatccaa ttttagcact caagttccat tgtgttaatt
3841 tctgcacggt caacaaacat caagtcagca agcatttgcc accactccct atacttctcc
3901 ctccttctta cacacacaca cacacacaca cacacaatcc atctcttgct tgttcctacc
3961 tcctgatttt tcttccctac agaaatagaa atagggacaa agaagggggaa aatgtatata
4021 ttggggctgg gctgaacaac taacttcata agtagtatta actagggta aattgagaga
4081 aaagctcctt ttctcttcac tgttttggaa aggatagcca ttagcatgac tgctttgtgt
4141 ccttatggac tttagtatta gcctagattg aattatagcg ttttctagct ggaaggaacc
4201 ttaagatcac atcatctact cctctactcc aaatttctca ttcttcaggc caggaaaccg
4261 agacacagag gtaaagtaat ttccccaagg tcacacagct ggctggggca ggattgggtt
4321 tacaacccac atctcctggc tcttattcca gggcctttc ccactaagta gtattgcctt
4381 ccattaggct cctgagagtt atttctcagg gtcatgttgc atcttggagc acatgctgc
4441 tgccctgatc tcagtgggaa atccacccag caacctaata cagccccttt tccctgcatt
4501 cacctggttc ccatccacat gggttgcaga tgtccttgaa gagagtgagg cattgagggc
4561 caataggagc aatggggtcc ctggccttgt ccatctgatt caggagatca ctgctccatc
4621 gtgaggagcc ctctgaatag cccccccactg aatgcttgcc ttgcccaaat ggaatggagg
4681 aagattgatt ttctccatca gttcaccttg tgtcatctca taatggttgg tctttccagg
4741 ctgagggaaa tgtttcttgt ttccagagta gaaaaagaaa gagtggaaca atagctttgt
4801 tcatcctaac tttctgagat ggcttttcaa catttttaaaa aaactagtgt ggctaccatt
```

-continued

```
4861 cactggcaat gatttctttt agaatatggg agtaagatga gctagagaaa ataacctggt
4921 ctcactgtgg ttgccctcat ccacaatgtc cccaaagcca tcctgctctg atgaggacaa
4981 tttccaggta taagcaaggg gctttgtgac aaaaatgtac cctggctgat gttaaacatt
5041 ggctcctgtg tttgcaccaa aatagcaagc tgtgtgctct atacactctt cccatcgtct
5101 tgtgtacact gctcctgtgg ccttccacag cagaaaccag ggcaaaaggg tccaaacaca
5161 tggttttcct tgctgcaagg ctcttcctgg gaactaaggg ggtatttatt agttcagttc
5221 taagagacct ccttctgggc ttaccccact cctcaggtac ttctctctcc ttcctccttc
5281 tcctccacag tcacaagtaa ccaaggaacc tgaaagtgga tgtgtagcta tttgaagaag
5341 gcaaggaacc ctgagattct tctttgaatc ctctagtcca agtcttagac cagtgattgg
5401 tgcttacctt gaacaaaatt ttgtctgtgt tcctaatccc ttcaatactc tgggtacaat
5461 gctcccaatc accctgcaca tttgattcta aatggctttt attttttaaa aatccatatc
5521 cctaggacaa gagaacagga tgcctatatc cccaaaatga gctccaggac actgatggga
5581 atgatcccaa agatcacccc acctcagaaa cgtctgtgcc aagagacttc cccagataga
5641 aacactggga cagtggtttg aacgacttct tttatggttg tccagtttgc tatggaaata
5701 aaaggcattg atttttttaaa aagatgattg gaacctgtct ttggccacat agggccactt
5761 ggatccattt ccaggcctta ctcatatatt gccttcactg aagggctttg gctttaagtc
5821 ccagactggt ctcccaagtg aaccataagt gttttggagc tcatctgggg tgaggcatga
5881 gaatgttgcc ccatctatcc cttcaggaaa aggtgccttc cctcccttc tcctaaagcc
5941 tggtccccag aaattgtttt tgtctccaaa agtctagtat ggtctttata cacccagact
6001 cttagtgttg cgtcctgcct tgtttccttg ttaaggatct atgcagacct cccgctttgg
6061 cttagctagc gtgacattgg ctatcatttg acaagactaa cttttttttt tttttttttt
6121 tgactgagtc tccctctgtc acctaggctg gagtgcagtg gcacaatctt ggctcgctgc
6181 aaccttcacc cttcacctcc caggtcgaag cgattctcct gcctcagtct cccgagtagc
6241 tgggattaca ggcgtgcgcc accaaatctg gctatttttt tattattatt attttttagta
6301 gagatggggt ttcaccatgt tggccagact ggtcttgaac tcttggcctc aaattatctg
6361 cccacctcgg cctcccaaag tgctgggatt acaggcatga gccaccatgc ccagctgaca
6421 agactaattt tttatccctt ggtttattgg cttcaacatc ttctggaatc agaggtgatt
6481 ttttcttacc ttggatgcct gagactaggg gagtatagaa ttccaattgg taattaaggc
6541 atctttctgc tcctgatcag aagggcaggt tagttgggag aggtcagatg gcacaacaga
6601 agtcaccttg taagtaaggc aaagacttga aggcattagc gtttctcatt actaggtcaa
6661 taacctgagg gaatcaatgg cttttttgccg ctctacctct tgtgtatctc tttgacttt
6721 ctttctctgt ctagtttcct ctgttctcag tttatattct atgttatcag tctctctttc
6781 cacagtacaa acatccatcc tttctcctgt gcaattctgt ctctccctct tattatcttt
6841 atttgtactt tttccttcct ccctgtctag gcattgggca tgtgcctctt cttagcctgt
6901 gattttgcct tgggactgat gataaattat ttccagattc aatcagccct ggtcctaccc
6961 cagtccaatc agaagtatgt tggtgggaat caacctgatc ctggccctttt cttcttctcc
7021 attttcattc gtaatccccc tcagcagatc tttacaagca gtttccttat agctcatgta
7081 tctttaggtc tttgccttcc aagcactgta cagaatactt tgtggttcct ttttagtctg
7141 acattttgtg gagcagtgaa gcgtgctcag agacataatc agctgaagag aaaaaatcca
7201 cccatggatt tatatcagct aaatactaat aattgatttt gtttgatgtg cccataattt
7261 ttaaagctgc aatataatat aatgagggac cacaggtaat ttctcctgtc atttgttttg
```

-continued

```
7321 gctggatggg ggtggggag taattgctta aagttttacc attacacatt aaactctcta 7381 taataatctt gtttgggct tgctaactgt tgagctgttt taactaaact ggtaggcaat 7441 cggagttgat ttaaatgaaa agataattta acaaatctat actataaaaa gagacatttg 7501 cttaattgac atgtattttt tccttctgag tcacctaaac atttactctt gacaccaact 7561 gttcatgata ctgaatagac agtccatata agagaaatta gtggacctaa agaagccaga 7621 ttgtaggtgt taatttatta aacagagtgc aaagcccttg gaaatgtcac tgcttggcaa 7681 taccatatgg aatgccaaaa tttacaatga cttttcttta taagttatcc aaaagggatt 7741 tgaacaagta agaggttatg ccaaaatgtc tccaatgtat ggtcctgtaa tatattgcag 7801 cttgaagcca atgatccctt atgacttgta tacaactaat gcatgtttta ttgaattttg 7861 catttcccac gtgtggtaag ttctttaaaa tgttttttgat cacctttttg tgccattaaa 7921 cttgtacaga aaatgttttt atggccattt tcaaagggag aaagtttaaa atggaaacag 7981 cccacccttt ctgccctata gctgtagtta gaattgagta cctgtagcaa aacagctgta 8041 attggtggtt gtagtgttag aggtgttagc ttgctagtga ctagctttgg agagtaaatg 8101 catggtattg tacatcacat ttcttaactc gttttaacct ctgaaaagaa tatattcttc 8161 tttgtagtcc ttcttcccac cccttgccc tctccctctc cctgctccca gttgtcttac 8221 agttgtaaat atctgatttg aggcccaata actcttgcca agtaaagtca gcaaacaaca 8281 aacaaaccaa aatgtgggga aaaggcattt ctcaaccatc tctcagcagt tattgatcat 8341 ttcttaagga acagcattgt gatcaaagac tcaactttac gtaaaaatca gtggtaaatt 8401 ggggttgtat ttggccattt gattacattt caggattgaa tagttttcag aatcacatgt 8461 aatccaaaga cagtaggtag tgatgtccct tatccctgca gctgttttaa gatagagacc 8521 tcagaagact ctgcttgacc gatgaccaat aattatttga aaaaaaaaga aaaaatgaga 8581 gaaataaaac agatatttaa gaactttagc cacctattta gaatagttat agccagaaaa 8641 aaaaacaagg gcatgagttc aaatgcatta ctatcagtgt cctaggcaat acctaaccta 8701 ctctgaaatt gtgattcaaa agcagtattt caagaggcat tctccttttt tggtttgctg 8761 accccacttg gactggtagg tttggtgagg ccccccataaa ccagctggag cagaccctt 8821 tcatctcctg tgcctgtaac acccctcttc ccccacccc tccgcaattc aatgagggct 8881 ttcttgggtc agaggacttc aaggttgtct agagaagttt gccatgtgtg taaggtgctg 8941 tgaactgtga gtgctgaaga ttcgcagcat tcaataccag gcagccaaag agctgctctt 9001 gcaattattt tggctctcaa gctctgttct tcatcgcatt ctcatttctg tgtacatttg 9061 caagatgtgt gtaatgtcat tttccaaaaa taaaatttga tttcaataaa aaaaaaaaaa 9121 aaaaaaaaaa aaaaa
```

By "GABRA1" (or gamma-aminobutyric acid (GABA) A receptor) is meant a polypeptide or fragment thereof having at least about 85% amino acid identity to NCBI Accession No. AAH30696.1.

MRKSPGLSDCLWAWILLLSTLTGRSYGQPSLQDELKDNTTVFTRILDRLL

DGYDNRLRPGLGERVTEVKTDIFVTSFGPVSDHDMEYTIDVFFRQSWKDE

RLKFKGPMTVLRLNNLMASKIWTPDTFFHNGKKSVAHNMTMPNKLLRITE

DGTLLYTMRLTVRAECPMHLEDFPMDAHACPLKFGSYAYTRAEVVYEWTR

EPARSVVVAEDGSRLNQYDLLGQTVDSGIVQSSTGEYVVMTTHFHLKRKI

GYFVIQTYLPCIMTVILSQVSFWLNRESVPARTVFGVTTVLTMTTLSISA

RNSLPKVAYATAMDWFIAVCYAFVFSALIEFATVNYFTKRGYAWDGKSVV

PEKPKKVKDPLIKKNNTYAPTATSYTPNLARGDPGLATIAKSATIEPKEV

KPETKPPEPKKTFNSVSKIDRLSRIAFPLLFGIFNLVYWATYLNREPQLK

APTPHQ

By "GABRA1 polynucleotide" (or gamma-aminobutyric acid (GABA) A receptor) is meant a polynucleotide encoding an GABRA1 polypeptide. An exemplary GABRA1 nucleic acid molecule (e.g., mRNA) is provided at NCBI Accession No. BC030696.

```
   1 agcggagcgg gcgagcaagg gagcgagcag gacaggagcc tgatcccaca gctgctgctc
  61 cagcccgcga tgaggaaaag tccaggtctg tctgactgtc tttgggcctg gatcctcctt
 121 ctgagcacac tgactggaag aagctatgga cagccgtcat tacaagatga acttaaagac
 181 aataccactg tcttcaccag gattttggac agactcctag atggttatga caatcgcctg
 241 agaccaggat tgggagagcg tgtaaccgaa gtgaagactg atatcttcgt caccagtttc
 301 ggacccgttt cagaccatga tatggaatat acaatagatg tattttttccg tcaaagctgg
 361 aaggatgaaa ggttaaaatt taaaggacct atgacagtcc tccggttaaa taacctaatg
 421 gcaagtaaaa tctggactcc ggacacattt ttccacaatg gaaagaagtc agtggcccac
 481 aacatgacca tgcccaacaa actcctgcgg atcacagagg atggcacctt gctgtacacc
 541 atgaggctga cagtgagagc tgaatgtccg atgcatttgg aggacttccc tatggatgcc
 601 catgcttgcc cactaaaatt tggaagttat gcttatacaa gagcagaagt tgtttatgaa
 661 tggaccagag agccagcacg ctcagtggtt gtagcagaag atggatcacg tctaaaccag
 721 tatgaccttc ttgacaaaac agtagactct ggaattgtcc agtcaagtac aggagaatat
 781 gttgttatga ccactcattt ccacttgaag agaaagattg ctactttgt tattcaaaca
 841 tacctgccat gcataatgac agtgattctc tcacaagtct ccttctggct caacagagag
 901 tctgtaccag caagaactgt ctttggagta caactgtgc tcaccatgac aacattgagc
 961 atcagtgcca gaaactccct ccctaaggtg gcttatgcaa cagctatgga ttggtttatt
1021 gccgtgtgct atgcctttgt gttctcagct ctgattgagt ttgccacagt aaactatttc
1081 actaagagag gttatgcatg ggatggcaaa agtgtggttc agaaaagcc aaagaaagta
1141 aaggatcctc ttattaagaa aaacaacact tacgctccaa cagcaaccag ctacacccct
1201 aatttggcca ggggcgaccc gggcttagcc accattgcta aaagtgcaac catagaacct
1261 aaagaggtca gcccgaaac aaaaccacca gaacccaaga aaacctttaa cagtgtcagc
1321 aaaattgacc gactgtcaag aatagccttc ccgctgctat ttggaatctt taacttagtc
1381 tactgggcta cgtatttaaa cagagagcct cagctaaaag cccccacacc acatcaatag
1441 atcttttact cacattctgt tgttcagtcc tctgcactgg gaatttattt atgttctcaa
1501 cgcagtaatt cccatctgct ttattgcctc tgtcttaaag aatttgaaag tttccttatt
1561 ttcataattc atttaagaac aagagacccc tgtctggcag tctggagcaa agcagactat
1621 gcagcttgga gacaggattc tgacagagca agcgaaagag caaagtcatg tcagaaggag
1681 acagaatgag agagaaaaga gggggaagat ggttcaaaga tacaagaaaa agtagaaaaa
1741 aaaataacac ttaactaaaa cccctaggtc atttgtagat atatatttcc aaatattcta
1801 aaaaagatac tgtatatgtc aaaaatattt ttatgtgaag gtgtttcaaa gggtaaatta
1861 taaatgtttc atgaagaaaa aattttaaaa atctacgtct ttattacaca aactatggtg
1921 tgcttatgtt tttgttttgc tttttaaact gatgtatagc tttaacatttt tgtttccaaa
1981 gctgaagatc cccattcttt ctctttgaaa aaaaaaagg cctaatgcat tattttgtca
2041 taaaatgcta ttttaaaatt catgaacttt tcatacgtaa aggtgcagtt gctcattgta
2101 gagcacattt agtccaatga agataaatgc tttaaatagt ttacttcact ttcatctgag
2161 cttttaccac tagactcaag gaagaataat tttaacagac atgtatactc catagaaact
2221 aaattaaaat agtttaaaaa tattcccttt ttcaccctat tttcagatag cacatgagcc
2281 caacactcac ttaattctca ttatgaagat gttttagag gggcaaaaat attttgcaag
2341 ctctggaatt gttgaatgta ttcttttata taactacatt aaaagcttta gattgaaatt
2401 tatgactagc aaacaaaaat agaatatata aacgatatat gtaaatatac agcatgagat
```

```
-continued 2461 tgtacatttt ttactttttt aaaattgtgt tcttaaaata ttgtgtaaga atcactgcac 2521 ttagctgttg gaatgttgtt aaatgctatg gaaatacatt tagaacctgc atttaagaac 2581 agaacagcaa gtatgaacca catggaactt aaaacatatg ggtgtgaagt ccacttatgt 2641 agacaaaact tataatttcc aaactgttgt ctagtataca gtgatcagtt gctctctgtt 2701 caagtcattc cacacatttc cctattttag gctattataa tatagaaaga aaatgggaag 2761 cattagttgg agctagaaaa tgaactgtat attattgcta tatttgctaa taccaactat 2821 ttcaataagt gttgtaccat atgtagcatt aaatataaaa tacataaaag aatgtacaga 2881 aaatagcttt tattgagtaa tattacattt catttatact gtagcaatat atttgtaggt 2941 atactatgta agggctttaa ataaaagagg tccattaata cttccttata aaaattctag 3001 tctgtttcat tactgcccag atgttttaga gataaatatt tatgcagaag gtattttga 3061 agtctccttt tgtctgatag agtttaacag atatttaaat ttagtgctca gaatccacaa 3121 gtcacggtct aaacacactt agaatactac agcataaatc tgttagcatt attgccaaat 3181 aagacagttg ggatccaaac ccaagtcttg agcaatgttt ttctcaaaaa gctgctatcc 3241 aatgatatag gaaaatacat tgtgttttcc taaacacact tttctttta aatgtgcttc 3301 attgtttgat ttggtcctgc ctaaatttca caagctaggc caatgaaggc tgaatcaaag 3361 acatttcatc caccaatatc atgtgtagat attatgtata gaaaataaaa taaattatgg 3421 ctccaaaaaa aaaaaaaaaa
```

Other features and advantages of the invention will be apparent to those skilled in the art from the following detailed description and claims.

BRIEF DESCRIPTION OF THE DRAWINGS

FIGS. 1A-1D depict characterization of BMPS during differentiation. FIG. 1A depicts a diagram of a differentiation protocol. FIG. 1B depicts size of aggregates measured during the 3D neuronal differentiation. Negative days on the x-axis represent 3D cells cultured in NPC medium while positive days represent 3D cells cultured in differentiation medium. FIG. 1C1-C5 depicts BMPS mRNA and miRNA expression of different markers during differentiation. FIG. 1D depicts flow cytometry population analysis of BMPS at different stages of differentiation.

FIG. 2A depicts co-immunostaining of neurons with markers. MAP2+ neurons were co-immunostained with the maturation marker Nestin at 2, 4, and 8 weeks of differentiation, which showed progressive increase of MAP2+ neurons and decrease of Nestin+ cells over time (panels a, b, c), demonstrating neuronal maturation. Co-immunostaining of neurons (NF-H) with the myelin marker MBP at 2, 4, and 8 weeks of differentiation (d,e,f, respectively) showed progressive increase of MBP+ cells in association with axonal processes. An increasing number of MBP+ cells (oligodendrocytes) was observed in association with axons (panels d, e, f). FIG. 2B depicts neuronal and glial cell diversity was evaluated at 8 weeks. Neurons (MAP2, NF, SYP and SMI32) were visualized interacting with glia (GFAP and NOGOA). Neurons disclosed characteristic perykaria, dendrites (MAP2, panels a, b) and axons (NF, SMI32, panels c-f) associated with glia. Neurons exhibited diverse neurotransmitter identities shown by identification of glutamatergic VGLUT1+ (panels g, h), GABAergic CALB+ (panels i, j) and dopaminergic TH (panels k, l) neurons. FIG. 2C depicts that GFAP+ astroglia and CNPase+, O1+ and MBP+ oligodendroglia were identified.

Oligodendroglia appeared mixed among astrocytes (panels a, b). O1+ (panels c, d) and MBP+ (panels e, f) oligodendrocytes were associated with axonal processes. Astrocytes established relationships with oligodendrocytes and exhibited characteristic multipolar processes (panels g, h). MBP+ oligodendrocytes issued processes in association with axons (panel i) 3D-reconstruction demonstrated myelinating processes resembling human myelination (panels j, k). Electron microscopy analysis of BMPS at 4 and 8 weeks of differentiation identified morphology of axonal structures and cells (e.g., oligodendrocytes) (panel l). Myelinating-like processes, which closely resembled cross-sections of myelinated axons of the CNS were identified at 8 weeks of differentiation (panel m).

FIGS. 3A-3F depict electrical activity of BMPS. Cells were cultured in 3D for 8 weeks and then cultured in 12-well and 48-well MEA plates for 4 more weeks. FIG. 3A depicts heat map recordings from a 48-well plate. FIG. 3B depicts illustration of an active well showing spike morphology and FIG. 3C depicts spike activity. FIGS. 3D and 3E depicts phase-contrast imaging of the mini-brains on MEAs, electrode diameter is 40-50 µm and inter-electrode space is 350 µm. FIG. 3F depicts activity pattern recordings over 0.05 spikes/sec of the electrode over 10 min.

FIG. 4A depicts viability (resazurin assay) of BMPS after 24 hours rotenone exposure. FIG. 4B depicts ROS (OxiSelect™ In Vitro ROS/RNS Assay Kit) production of BMPS after 12 and 24 hours rotenone exposure. FIG. 4C depicts viability (resazurin assay) of BMPS after 24 hours MPP+ exposure. FIG. 4D depicts ROS (OxiSelect™ In Vitro ROS/RNS Assay Kit) production of BMPS after 12 and 24 hours MPP+ exposure. FIGS. 4E and 4F depict confocal images of BMPS exposed to different concentrations of rotenone and MPP+ for NF200 (Red), TH (Green) and Hoechst nucleus staining (Blue). FIG. 4G depicts expression of genes associated with oxidative stress and PD by real time RT-PCR. Graphs represent the relative expression of different markers compared to control (cells not treated) after 24 hours exposure to 5 µM rotenone and 1 mM MPP+. Genes of interest: mitochondrial complex 5 (ATP5O, ATP5C1), mitochondrial complex 1 (NDUFB1), oxidative stress (KEAP1) and genes related to PD (TH, SNCA, TBR1, CASP1). Data are presented as mean±SD, of 3 independent experiments performed in 3 replicates. * $P<0.05$ comparing to control (untreated).

FIG. 5A depicts morphological characterization with immunostaining of neurons (MAP2, Syn1, TH, SYP), neural precursor cells (nestin) and glial cells (GFAP) at 8 weeks of differentiation. FIG. 5B depicts expression of genes in healthy BMPS vs. Down's Syndrome BMPS before and after treatment with 5 µM rotenone, after 24 hours exposure. Genes of interest include CNS markers (TH, OLIG2, NEFH), mitochondrial markers (ATP5C1, ATP5J, ATP5O) and ROS markers (NFE2L2, SOD1) which were measured by comparing control with exposed cells to rotenone on both healthy and Down syndrome derived mini-brains. FIGS. 5C and 5D depict karyotyping of iPSCs derived from the patient with Down's Syndrome. aCGH+ SNP results for Down syndrome iPSC line are shown.

FIG. 8A shows at 8 weeks, neuronal populations exhibited a diversity of neurotransmitter identities as shown by identification of dopaminergic TH+ (a,b), glutamatergic VGLUT1+ (c,d) and gabaergic calbindin+ (c,f) neurons. Neurons disclosed characteristic axons (NF) and synaptic proteins (SYN) (g,h). FIG. 8B depicts two distinctive glial populations were identified in close interaction with neuronal populations, GFAP+ astroglia and CNPasc+, O1+, NOGOA+ oligodendroglia. O1+ oligodendrocytes were closely associated with axonal processes (NF) (a,b), CNPase+ oligodendroglia appeared mixed among GFAP+ astroglia (c,d) and exhibited the characteristic multipolar glial processes, which extended from the perykaria (e,f). NOGOA+ cells were associated with MAP+ neurons (g,h). FIG. 8C depicts example of custom algorithm created using the Cellomics Target Activation image-analysis software package to study astrocytes and oligodendrocytes (a,b,c,d). Quantification of cell populations as a percentage of the total nuclei count showed 3% NOGOA+ positive cells, 9% CNPase+ cells and 19% GFAP+ cells at 8 weeks (e). FIG. 8D shows Co-expression of mature oligodendroglia markers (MBP and O2). FIG. 8E shows expression of neuronal markers (VGLUT, TUJ1, SYN). Scale Bar: 10 µm.

DETAILED DESCRIPTION OF THE INVENTION

Figure 1A:
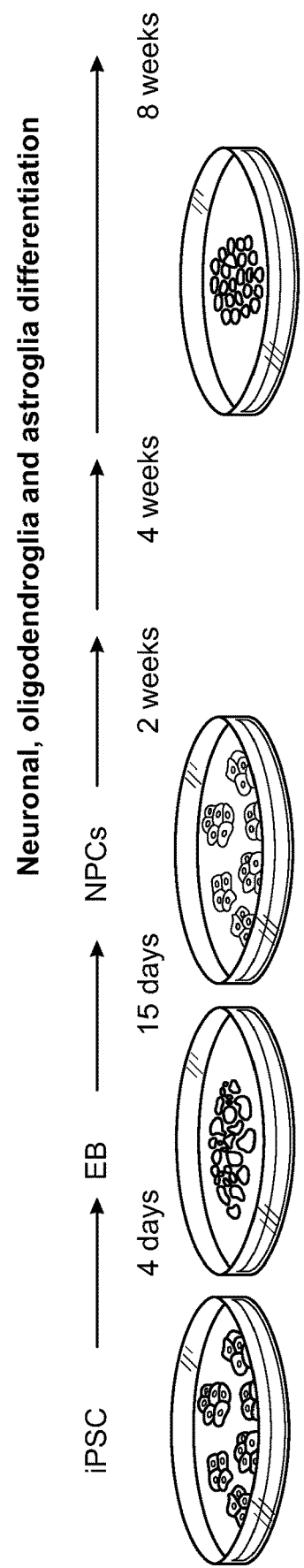

The present invention is based, at least in part, upon the discovery that brain microphysiological systems (BMPS) can be produced from induced pluripotent stem cells (iPSCs). Furthermore, the invention provides for reproducible BMPS that differentiate into mature neurons and glial cells (astrocytes and oligodendrocytes) in the central nervous system. This model is spontaneously electrophysiological active and may be reproduced with patient or genetically modified cells. The derivation of 3D BMPS from iPSCs has applications in the study and treatment of neurological and neurodevelopmental diseases. In some embodiments, the present disclosure provides for compositions and methods to study and/or treat neurodevelopmental and neurodegenerative disorders. In some cases, the neurodevelopmental and neurodegenerative disorders treated and/or studied by the present disclosure include, but are not limited to, autism, encephalitis, trauma, brain cancer, stroke, Amyotrophic lateral sclerosis, Huntington's Disease, muscular dystrophy, neurodegenerative disorder, neurodevelopmental disorder, Multiple Sclerosis, infection, Parkinson's Disease and Alzheimer's Disease.

As described herein, the present disclosure provides for the derivation of a multitude of identical brain microphysiological systems (BMPS) from stem cells, preferably of human origin, but including stem cells from animal origin.

The preferred starting material are human induced pluripotent stem cells or embryonic stem cells, although other pluripotent stem cells such as, for example, neuronal precursor cells and mesenchymal stem cells may also be employed. Human in-vitro models of brain neurophysiology are needed to investigate molecular and cellular mechanisms associated with neurological disorders and neurotoxicity.

The techniques herein provide a reproducible iPSC-derived human 3D BMPS that includes differentiated mature neurons and glial cells (astrocytes and oligodendrocytes) that reproduce neuronal-glial interactions and connectivity. BMPS mature over about eight weeks and show the critical elements of neuronal function including, but not limited to, synaptogenesis and neuron-to-neuron (e.g. spontaneous electric field potentials) and neuronal-glial interactions (e.g. myelination). Advantageously, the BMPS described herein include mature neurons (e.g., glutamatergic, dopaminergic and GABAergic neurons) and glial cells (e.g., astrocytes and oligodendrocytes). Quantification of the different cell types exhibited high reproducibility between experiments. Moreover, the BMPS disclosed herein present neuron and glial functions such as spontaneous electrical activity and axon myelination. The BMPS described herein are able to mimic the microenvironment of the central nervous system, which is a significant advance in the field of neurobiology as this ability has not been achieved at this level of functionality, reproducibility, and consistency in prior art in vitro systems.

In particular, the high amount of myelination of axons (up to 40%) in the disclosed BMPS represents a significant improvement over the prior art. Myelin pathology is a rather frequent condition in demyelinating and inflammatory disorders such as multiple sclerosis and post-infection diseases as well as other neurological diseases such as acute and post-traumatic brain injury, stroke and neurodegenerative disorders (see e.g., Fumagalli et al., 2016; Tse and Herrup, 2016). Moreover, the myelination process can be perturbed by exposure to chemicals and drugs (see e.g., Garcia et al., 2005; Brubaker et al., 2009; Creeley et al., 2013) during brain development and adulthood. For example, the BMPS disclosed herein show 40% overall myelination after 8 weeks of differentiation. Myelin was observed by immunohistochemistry and confirmed by confocal microscopy 3D reconstruction and electron microscopy. These findings are of particular relevance since myelin is crucial for proper neuronal function and development. The ability to assess oligodendroglia function and mechanisms associated with myelination in this BMPS model provide an excellent tool for future studies of neurological disorders such as multiple sclerosis and other demyelinating diseases. Thus, the BMPS provides a suitable and reliable model to investigate neuron-neuroglia function in neurotoxicology or other pathogenic mechanisms that has heretofore not been available in the prior art.

The method disclosed combines gyratory shaking or regular stirring and the addition of growth factors to obtain the basic model. Suitable conditions as to how to achieve reproducible brain composition are disclosed herein. In contrast to earlier models, identical units of BMPS are produced, which allow comparative testing for the purpose of product development or safety assessments.

According to the techniques herein, a number of additional measures complement the basic BMPS to increase their completeness in modeling the human brain and improve its usefulness for such testing, for example:

1. The addition of microglia: All stem-cell-derived brain models described so far lack micro-glia. The techniques herein provide that the addition of micro-glia precursor cells and suitable growth factors may allow microglia to be added to the model. Suitable cells may be monocytes (e.g., human monocytes), hematopoetic stem cells, respective (pro-) monocyte cell lines, and isolated microglia.

2. The addition of a blood-brain-barrier: The human brain is protected by a tight blood-brain-barrier that excludes many substances from the brain. For the first time, the techniques herein provide a method to form a blood-brain-barrier to the BMPS via cells such as, for example, human endothelial cells.

3. Addition of reporter and reporter cells: During the generation of the BMPS, cells carrying reporter for testing purposes may be used or added. These include, but are not limited to, fluorescent or luminescent markers to indicate a certain cell lineage or cell response. Genetic transient or permanent transfections are the primary, but not only, method of choice.

4. The BMPS may also be produced, entirely or in its components, from cells from a specific genetic background, e.g. from patients with a specific disease or after selective genetic manipulation of the cells.

5. The versatility of the BMPS may be improved by combining it with electrodes including, but not limited to, micro-electrode arrays (MEA).

6. The versatility of the BMPS may be improved by combining it with other MPS (organ models) platforms such as, for example, microfluidic human-on-chip systems, perfusion chambers and others.

7. Transportability of BMPS: Methods to cryopreserve BMPS were developed, which allow transport to other laboratories and testing or integration into multi-MPS platforms.

Simplified neural in vitro systems do not reflect physiology, interactions between different cell types, or human genetics. Induced pluripotent stem cells (iPSC)-derived human-relevant microphysiological systems (MPS) better mimic the organ level, but are too complex for chemical and drug screening. As described herein, a reproducible 3D brain MPS (BMPS) that differentiates into mature neurons and glial cells (astrocytes and oligodendrocytes), which reproduces the topology of neuronal-glial interactions and connectivity in the central nervous system was developed. BMPS from healthy donors or patients evolve from a period of differentiation to maturity over about 8 weeks, including synaptogenesis, neuron-neuron interactions (e.g. spontaneous electric field potentials) and neuronal-glial interactions (e.g. myelination of axons), which mimic the microenvironment of the central nervous system. Effects of substances on neurodevelopment may be studied during this phase of BMPS development. In an exemplary embodiment, the techniques herein were used to study Parkinson's disease (PD) by evaluating neurotoxicants with a link to PD pathogenesis. Exposure to 5 μM rotenone or 100 μM 1-methyl-4-phenylpyridinium (MPP+) (or 1 mM 1-methyl-4-phenylpyridinium (MPP+) for gene expression studies) disrupted dopaminergic neurons, as observed by immunohistochemistry and altered expression of PD-related genes (TH, TBR1, SNCA, KEAP1, NDUFB1, ATP5C1, ATP5O and CASP1), thus recapitulating hallmarks of PD pathogenesis linked to toxicant compounds in the respective animal models. The BMPS, as described herein, provide a suitable and reliable model to investigate neuron-neuroglia function in neurotoxicity or other pathogenic mechanisms.

There is growing concern about the continuing increase in neurodevelopmental and-degenerative disorders such as autism [1, 2], Parkinson's [3] and Alzheimer disease [4]. Although genetic factors play an important role, environmental factors such as pesticides, air pollution, cigarette smoke, and dietary toxicants appear to contribute [5, 6, 7]. Due to a lack of mechanistic understanding, it is difficult to study their contributions and interactions with respect to neurotoxicity and neurological disorders. The complexity of the CNS makes it challenging to find appropriate in vitro human-relevant models, ideally from different genetic backgrounds, that are able to recapitulate the relevant pathophysiology. The poor predictive ability of animal-based models for human health, which may fail to mimic human pathology as outlined in the costly and time-consuming current developmental neurotoxicity (DNT) guidelines, contributes to the lack of reliable information on DNT mechanisms [8]. At the same time, more than 90% of all drugs fail clinical trials after extensive animal testing [9] due, in part, to the fact that animal studies often do not reflect human physiology and inter-individual differences. Simple in vitro systems do not represent physiology and organ function [10], which creates a critical demand for better models in drug development, study of disease mechanisms and progression, bioengineering and toxicological testing.

Attempts to generate more complex organotypic cultures or microphysiological systems (MPS) [11, 12, 13, 14] have resulted in more physiological multicellular 3D co-culture models able to simulate a functional part of the brain [15, 16]. 3D MPS have shown increased cell survival, differentiation, cell-cell interactions and can reproduce the complexity of the organ more closely [18]. Recent US research programs by NIH, FDA, DARPA, and DTRA have initiated the systematic development of MPS, including the model presented here, and their combinations to human-on-a-chip technologies to assess the safety and efficacy of countermeasures to biological and chemical terrorism and warfare [19].

The discovery of induced pluripotent stem cells (iPSC) and new protocols to differentiate them into various cell types have boosted the development of human in vitro models [20, 21]. iPSC from healthy or patient donors with a specific disease [22, 23, 24, 12] used in MPS promise more human-representative models, e.g. the brain organoids by Lancaster et al. and Kadoshima et al., have been able to recapitulate features of human cortical development [15, 16]. These complex systems present novel tools to study biological mechanisms in the CNS, however, they have certain limitations: 1) an elaborate and complex protocol, 2) size differences between organoids, 3) necrosis in the center of the organoid, 4) low reproducibility in cell differentiation. The human BMPS described herein overcomes these limitations. The reproducible in vitro iPSC-derived human 3D brain microphysiological system (BMPS) is comprised of differentiated and mature neurons and glial cells (astrocytes and oligodendrocytes).

The techniques herein provide a reproducible BMPS that contains several different cell types of the human brain, such as glutamatergic, dopaminergic and GABAergic neurons, astrocytes and oligodendrocytes. Moreover, the system has shown neural functionality as observed by spontaneous electrical activity and myelination of axons. Furthermore, the BMPS is reproducible from batch to batch and displays differences between healthy and patient donors. In addition, the obtained results demonstrate the application of such BMPS to the study of neurological disorders such as, for example, Parkinson's Disease (PD).

The brain MPS described herein is a versatile tool for more complex testing platforms and strategies as well as research into neurotoxicity (e.g., developmental), CNS physiology and pathology. Some stem cell-derived brain microphysiological systems have been developed in the latest years showing the capability to recapitulate some of the in vivo biological process [36, 37, 38]. These models have an enormous advantage over the classical in vitro models to study various differentiation mechanisms, developmental processes and diseases [15]. However, they are mostly based on human embryonic stem cells raising ethical concerns and not allowing the use of patient cells. Moreover, they require complicated protocols that may reduce the reproducibility of the system and make it difficult to use in other fields such as chemical and drug screening. Some of these complex organoids have a large diameter, which can lead to extensive cell death, visible in the core of these tissues [15]. This may be due to insufficient diffusion of nutrients and oxygen in these non-vascularized systems, which may generate artifacts in toxicological and disease measurements and make it difficult to study different endpoints in a medium- to high-throughput manner. In addition, it will be challenging to adapt endpoints, established for relative simple 2D cultures, to such complex models. In the study described herein, the ability to generate a high number of viable (about 800 per batch), BMPS that are homogeneous in size (e.g., about 300 μm) and shape using iPSC by applying a constant or regular gyratory shaking or stirring technique as described earlier for rat re-aggregating brain cell cultures is shown. Control of the size using specific shaker speed allowed the aggregates to be maintained below 350 μM in diameter (FIG. 1B) and avoid disparate morphology and/or necrosis in the middle of the organoids. Moreover, a spherical homogeneous shape facilitates fluorescent quantification and further imaging-based endpoints as well as reproducibility between aggregates. The BMPS had reproducible cell composition by immunomorphological quantification, assessment of imaging-based endpoints and neurophysiological testing.

Figure 1B:
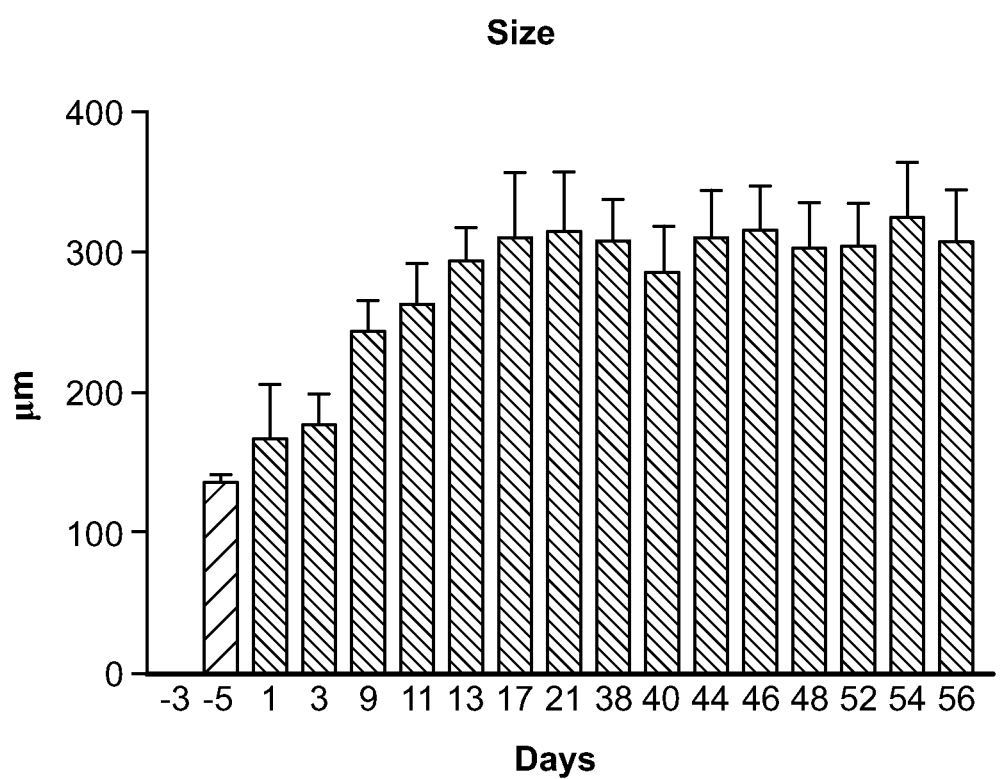
Figure 1D:
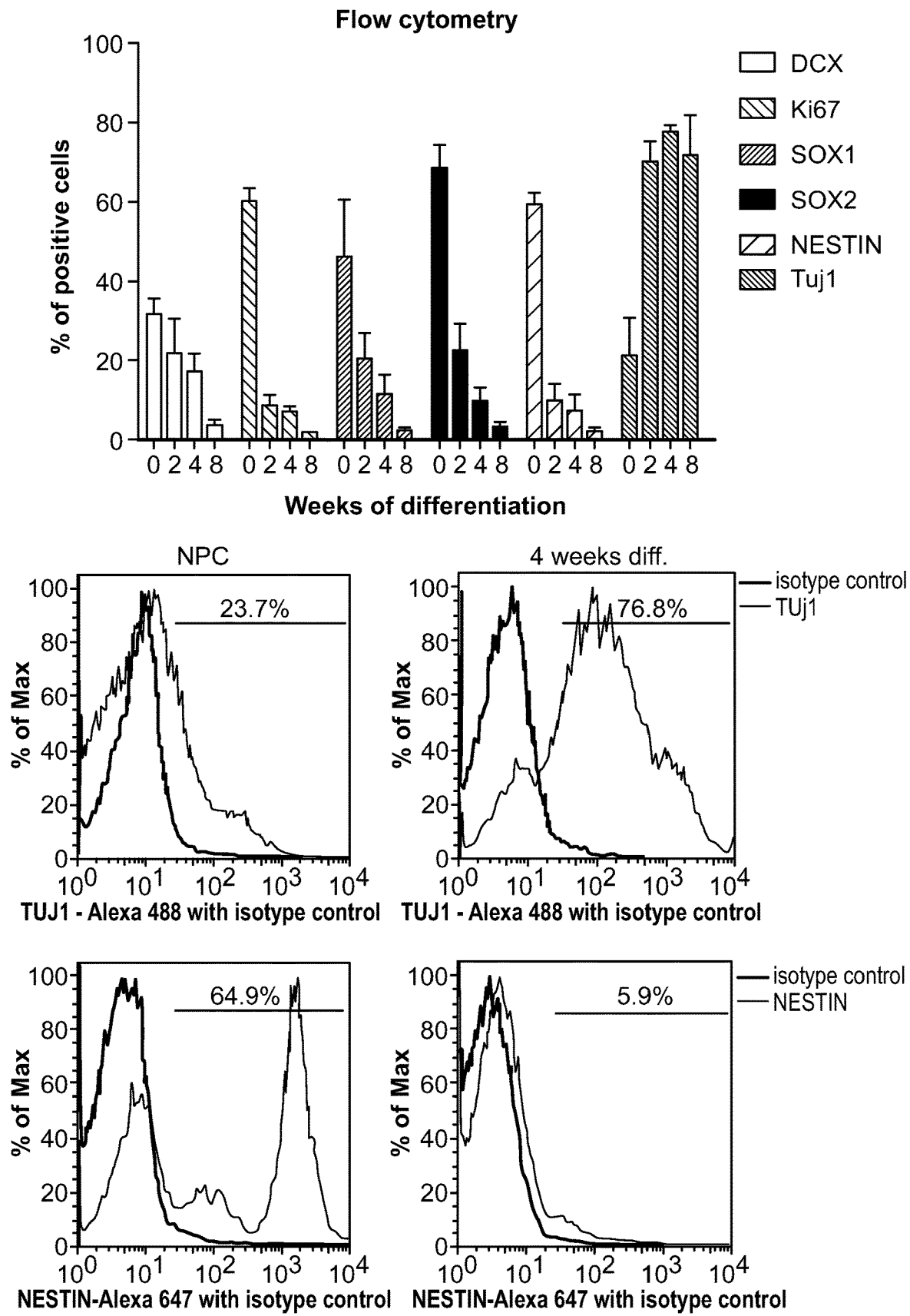
Figure 2A:
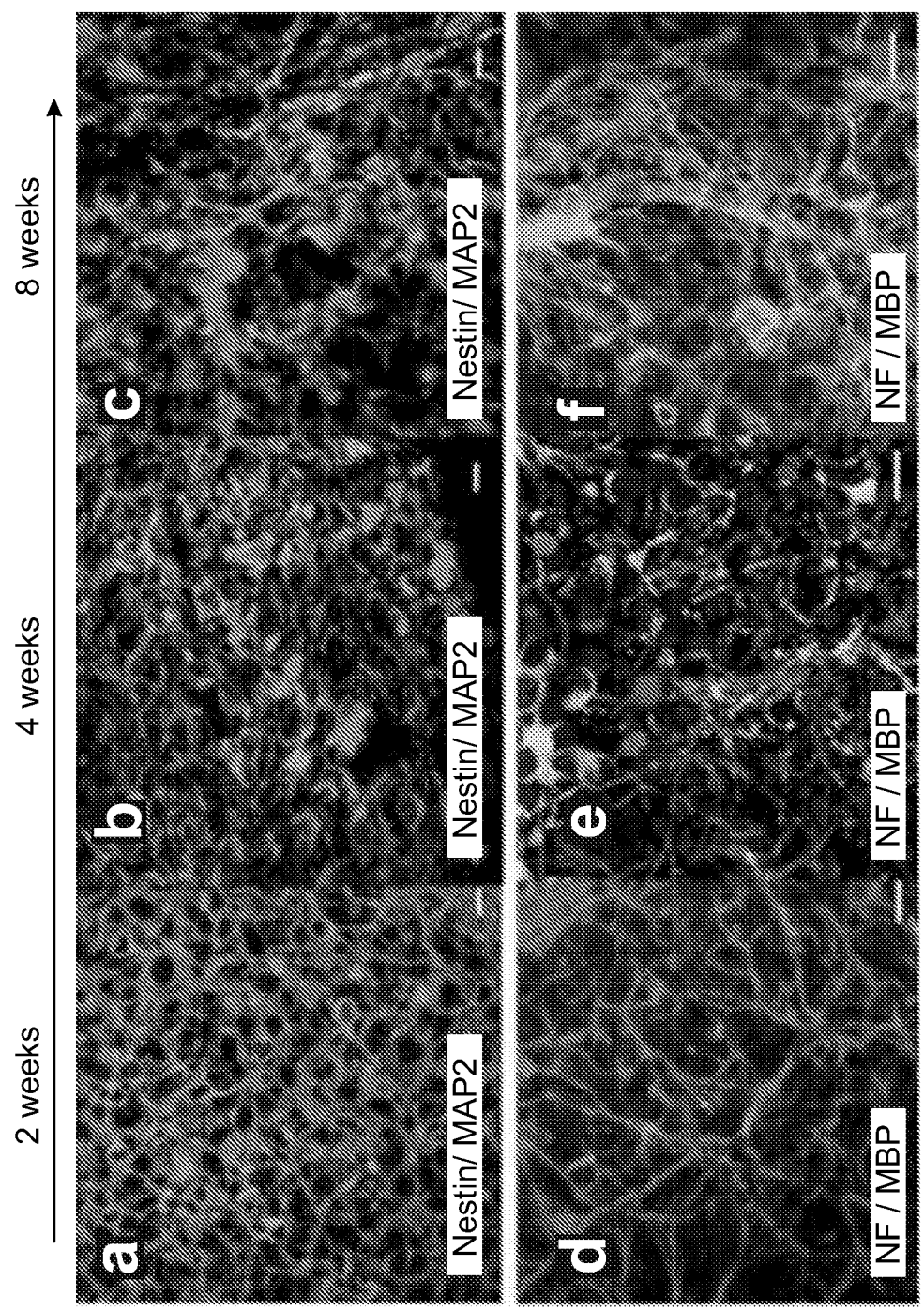
FIGS. 2A-2C depict morphological characterization of BMPS.
Figure 2B:
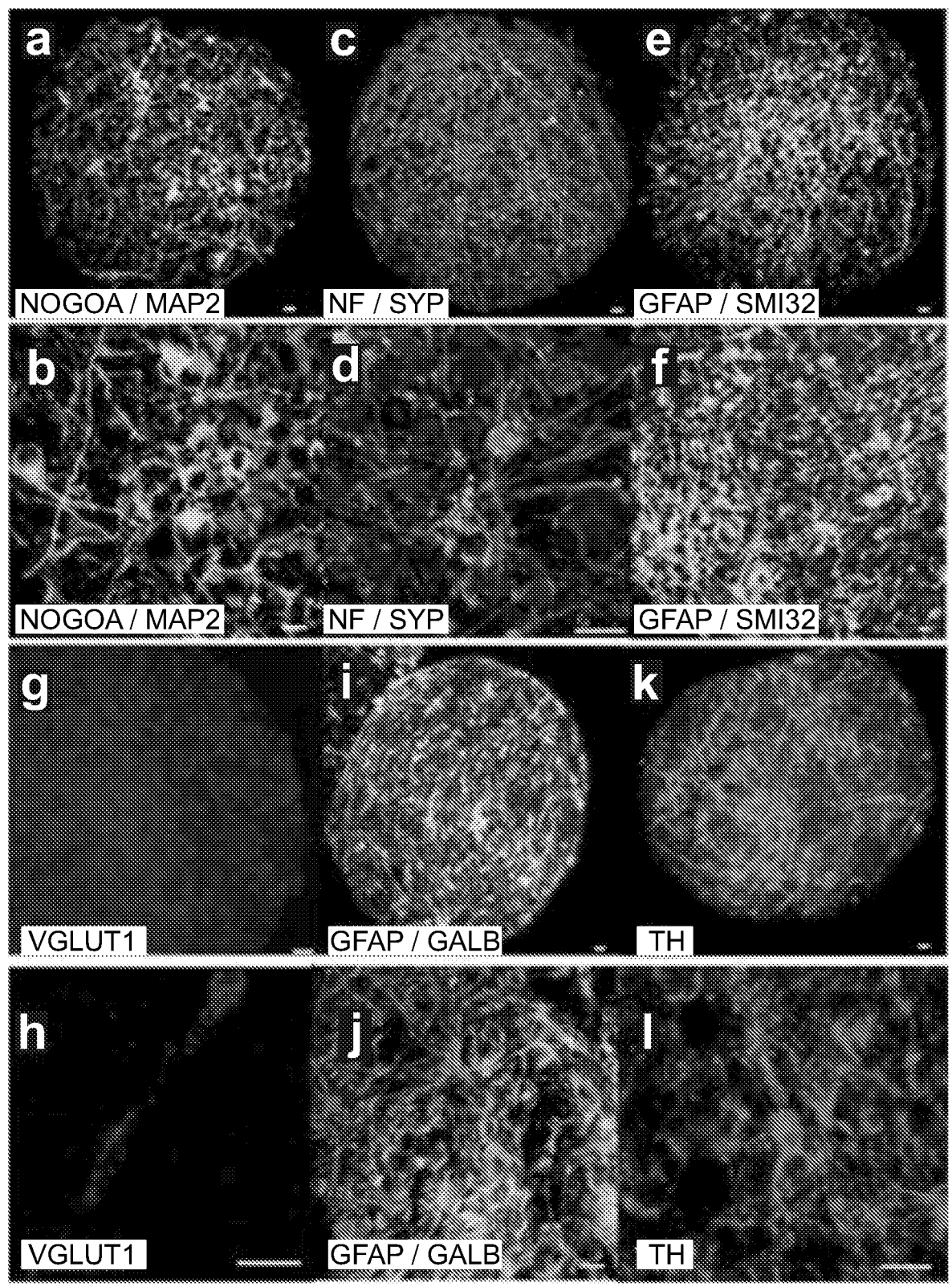

The 3D differentiation protocol described herein covered stages from neuronal precursors to different cell types of the mature CNS. After 2 weeks, BMPS consisted of an immature population of cells, showing minimal neuronal networks, low percentage of mature astrocytes and oligodendrocytes, with no myelin basic protein expression (FIG. 1C). Cell populations in the BMPS were further differentiated and matured over time (FIG. 2A). Evidence of iPSC differentiation into mature BMPS was supported by decreased Nestin expression over time. Nestin is normally expressed in embryonic tissue and its expression decreases with age in humans, therefore its decrement is a sign of maturation towards the adult phenotype [41, 42]. Also, the increasing presence of mature neuronal and glial markers such as MAP2, GFAP, Olig1 and MBP corroborate differentiation of the system. Different markers of pluripotency and proliferation decreased during the differentiation process, indicating maturing of the in vitro system (FIGS. 1C and 1D). Neuronal precursor markers such as Nestin, SOX1, SOX2 and the proliferation marker Ki67 decreased at the gene expression level and in flow cytometry measurements during the differentiation process (FIGS. 1C and 1D). Gene expression studies, flow cytometry, image analysis, immunostaining and miRNA studies have demonstrated an increase of cell maturation markers, which follows the BMPS differentiation (FIGS. 1A-1D, 2A-2H and 9A-9C). Obtained data demonstrate that this simple protocol is sufficient to generate representative CNS cell phenotypes that can reproduce various stages of differentiation. The presence of GABAergic neurons, dopaminergic neurons and glutamatergic neurons was observed by immunohistochemistry and real-time-PCR data (FIG. 1C and FIG. 2B). In addition, miRNAs such as mir-124, mir-132, mir-128, mir-137 and mir133b with a role in nervous system differentiation and neuronal degeneration [43, 44] increased during differentiation in patterns consistent with the in vivo situation. Moreover, the BMPS described herein produced spontaneous electrical activity (FIG. 3) confirming neuronal functionality of the system. However, further optimizations of the electrophysiological measurements using MEAs in 3D systems are needed.

Figure 2C:
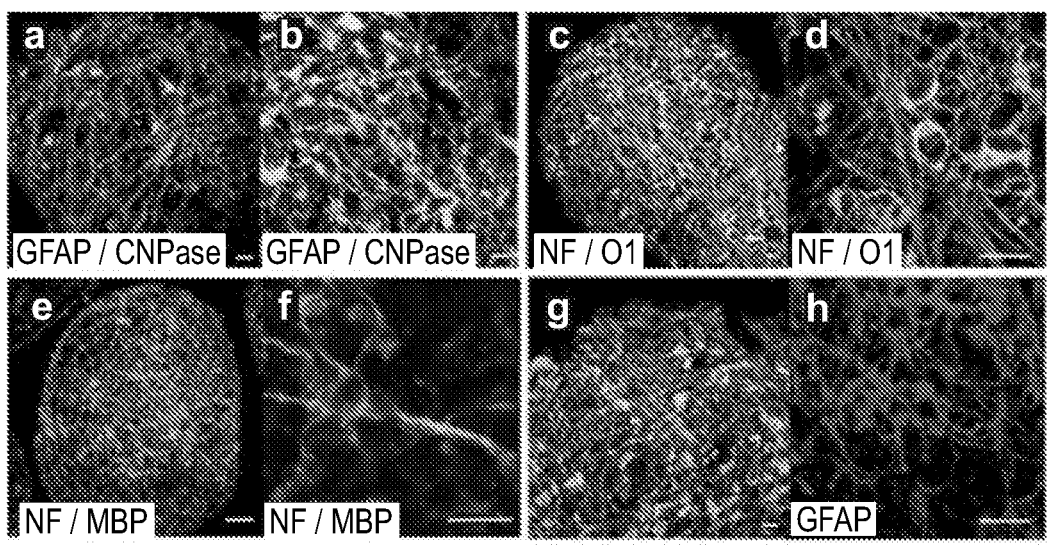
Figure 2C:
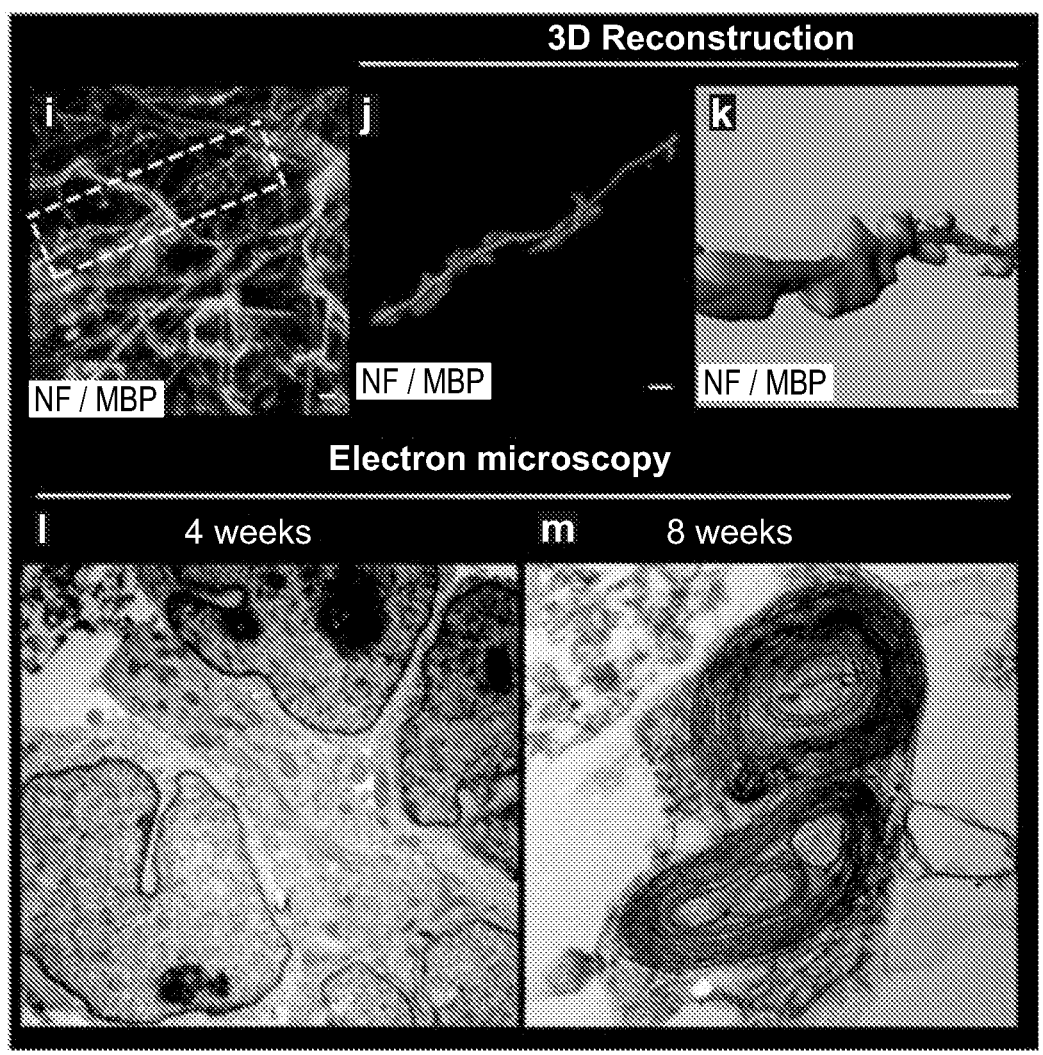

Most of the brain MPS published so far are entirely focused on neurons and not glia populations [45, 46]; the brain MPS described herein is the first 3D model with fully characterized mature human oligodendrocytes, astrocytes and neurons, derived from iPSC. Astrocytes and oligodendrocytes play an important role during neuronal development, plasticity and neuronal injury. Astrocytes have a role in protecting neurons, increasing neuronal viability and mitochondrial biogenesis from both exogenous (e.g. chemicals) or endogenous (such as glutamate-induced excitotoxicity or the Alzheimer related Aβ1-42) toxicity [47, 48, 49, 50]. Astrocytes have an especially important role in neuroprotection from oxidative stress. Oxidative stress is known to be involved in a number of neuropathological conditions (such as neurodegenerative diseases) [51, 52, 53]. Thus, the presence of astrocytes in a biological system to study disease is crucial due to their role in detoxification and neuronal protection. Immunochemistry results from the iPSC-derived BMPS showed low numbers of astrocytes (GFAP-positive cells) at 2 weeks of differentiation, which increased continuously throughout differentiation (FIG. 2F-2H, and FIG. 2A). Real-time RT-PCR data supports these findings, as a continuous increase in both s100b and GFAP mRNA levels could be observed from 2 weeks up to 8 weeks old BMPS. Immunohistochemistry and RT-PCR data results showed increasing numbers of astrocytes (GFAP-positive cells) in the BMPS model, reaching 19% astrocytes of the total cell population at 8 weeks. After 4 weeks of differentiation, astrocytes demonstrated increased positive staining for GFAP and the presence of glial network was observed (FIG. 2C, panels g, h). At the same time, the presence of oligodendrocytes and myelination of axons could be observed in the system described herein. This process is highly important, since it is known to be involved in many degenerative diseases such as multiple sclerosis [54], congenital hypomyelination [55], progressive multifocal leukoencephalopathy caused by JC virus infection [56], periventricular leukomalacia (PVL) and Alzheimer's disease [58]. Moreover, several chemicals such as ethanol [59], tellurium and lead [(61, 62, 63, 64, 65] have shown to have an effect on the myelination process.

The presence of astroglia and oligodendroglia in the model described herein brings the system closer to the in vivo brain physiology, which is a crucial component to study neurodegeneration and neurotoxicity. In addition, the system has shown functionality as seen by imaging of cell-cell junctions, myelination, a rich astroglial network and electrical activity (FIG. 3). These characteristics make the BMPS described herein a promising tool to study interactions between human neuronal cells in neurological diseases. The use of iPSCs makes it possible to study genetic factors and gene/environment interactions.

An assessment of the myelination process by quantification of MBP immunostaining along axons showed an increase over time reaching 42% of myelinated axons at 8 weeks (FIG. 2D). 3D reconstruction of confocal z-stacks images (FIGS. 2C and 2E) and electron microscopy confirmed the wrapping of axonal structures after 8 weeks of differentiation (FIG. 2C). These findings are of particular relevance since myelin is a critical element for proper neuronal function and development, the ensheathment of axons by myelin allows faster action potential transmission, reduces axonal energy consumption and protects the axons from degeneration [79]. Furthermore, recent evidence suggests that oligodendrocytes and myelin have a role in the metabolic support of axons independent of their role in action potential conduction, highlighting their importance in neuronal survival [80]. The ability of assessing oligodendroglia function and mechanisms associated with myelination in the BMPS model provide an excellent tool for future studies of neurological disorders such as multiple sclerosis and other demyelinating disorders.

Figure 3A:
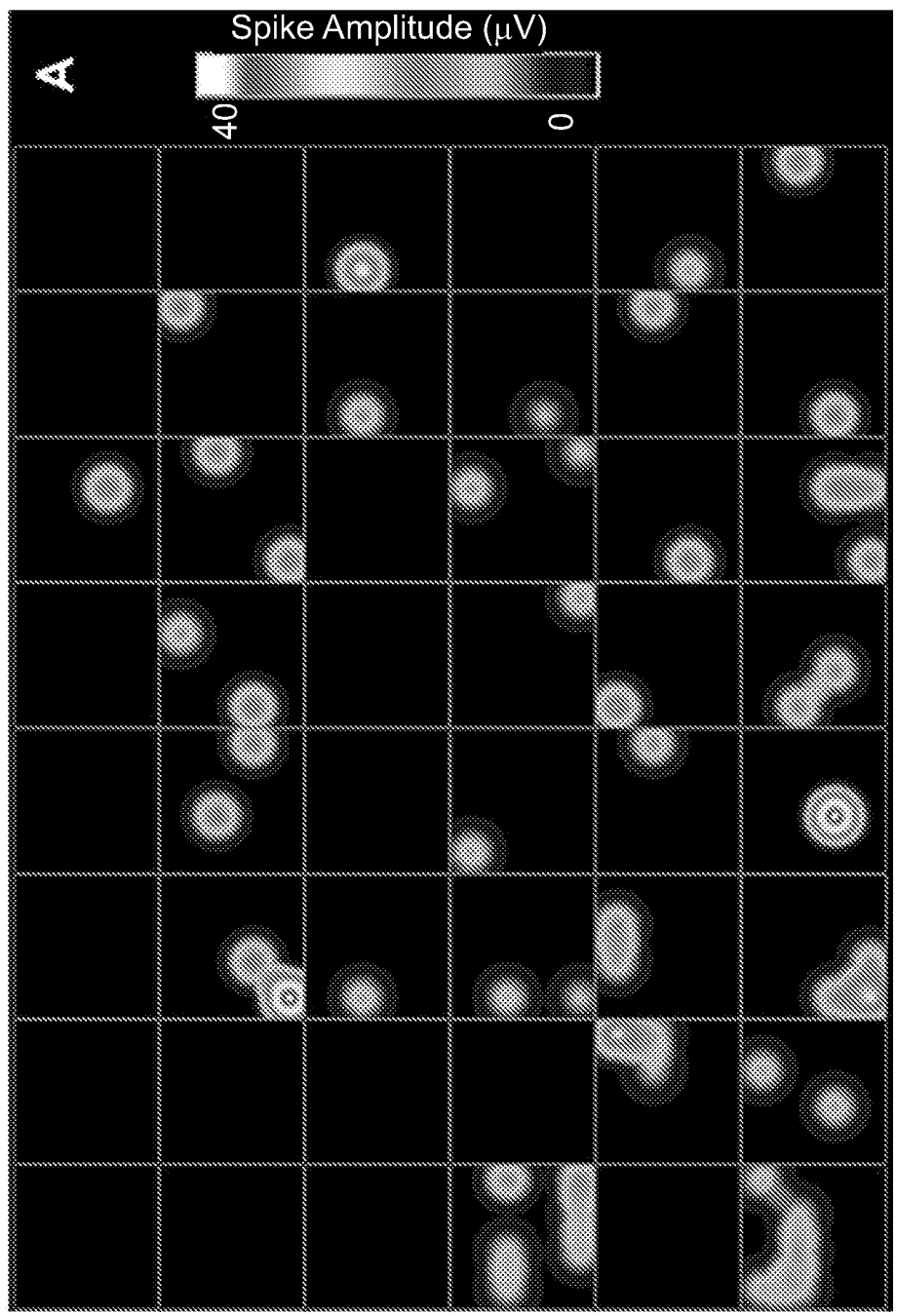
Figure 4A:
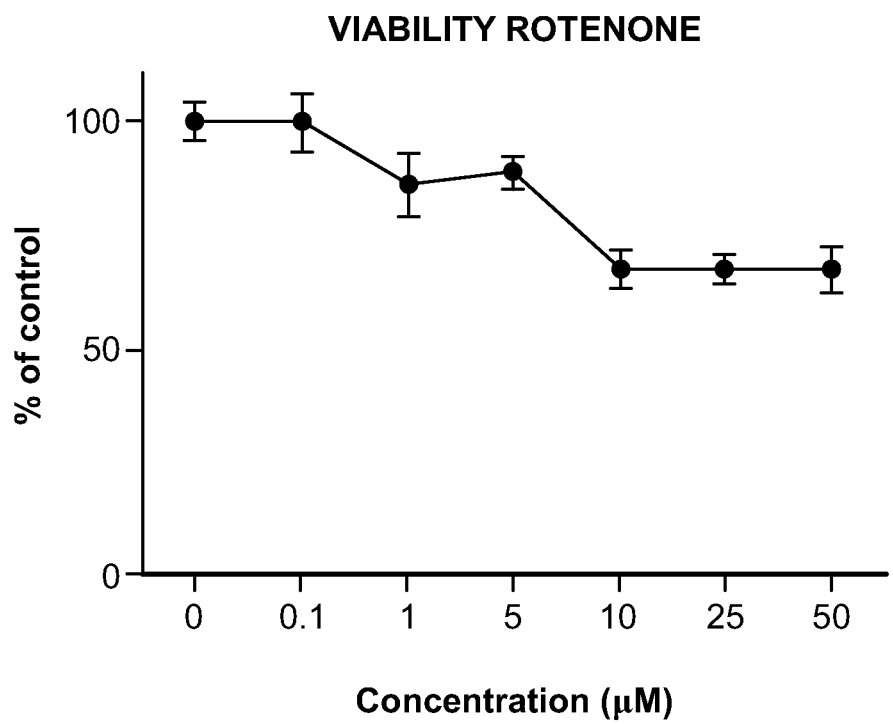
FIGS. 4A-4G depict Parkinson's disease (PD) application of BMPS. BMPS were differentiated for 4 weeks and exposed to rotenone and MPP+ for 12 and 24 hours.
Figure 4B:
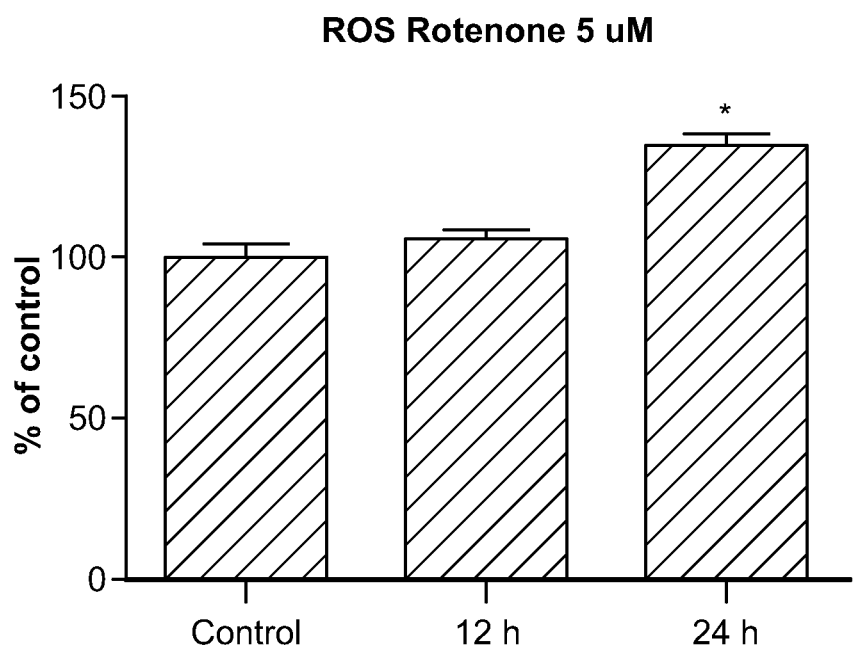
Figure 4C:
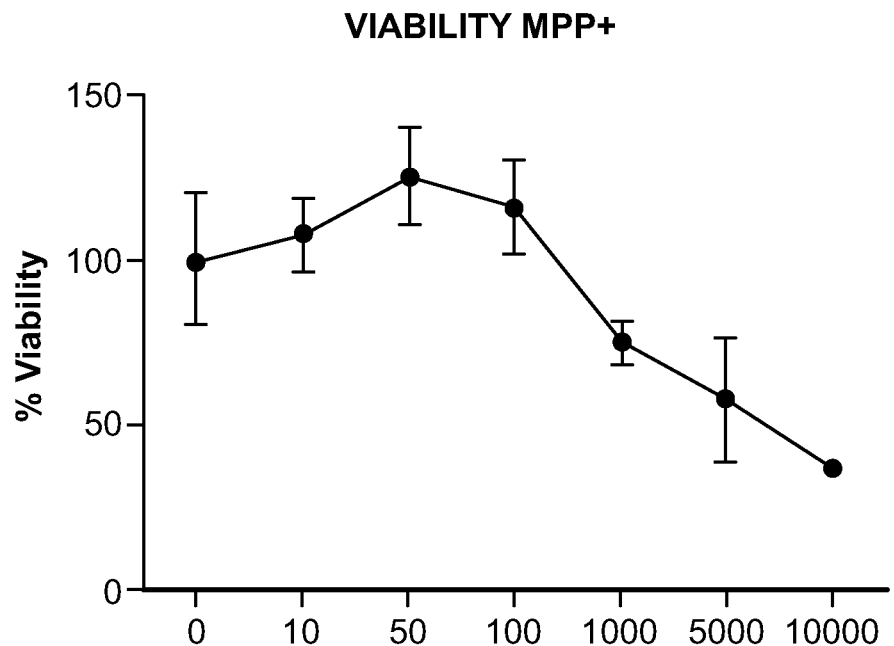
Figure 4D:
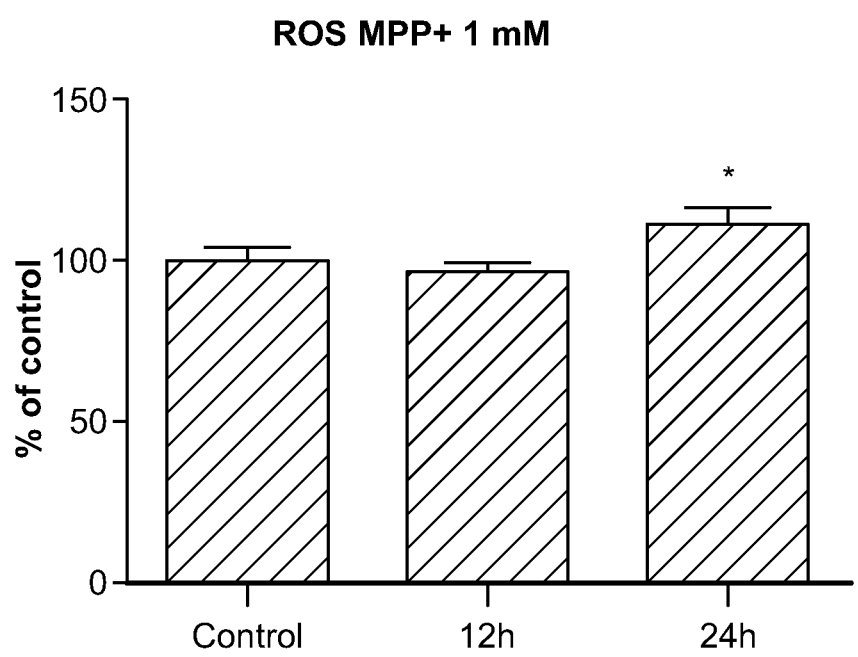
Figure 4E:
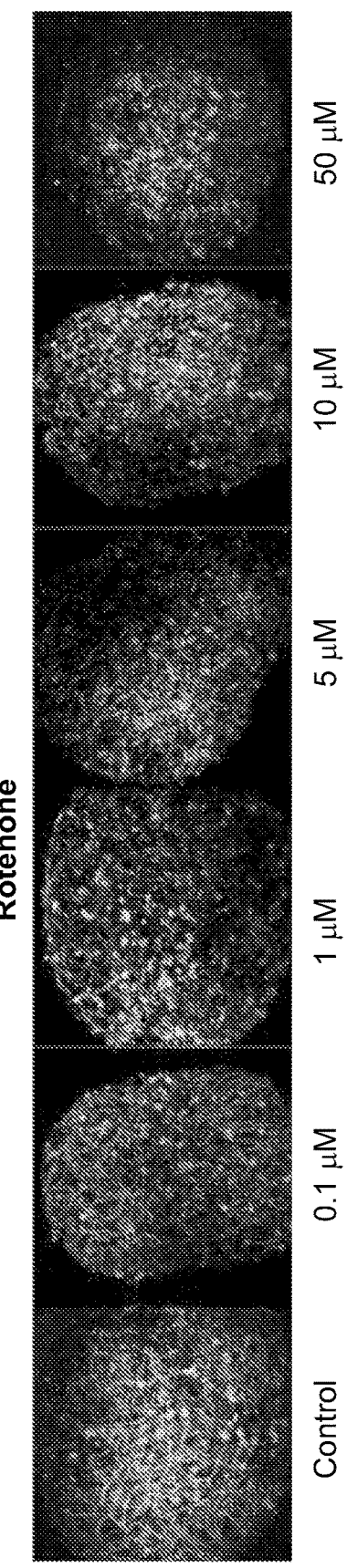
Figure 4F:
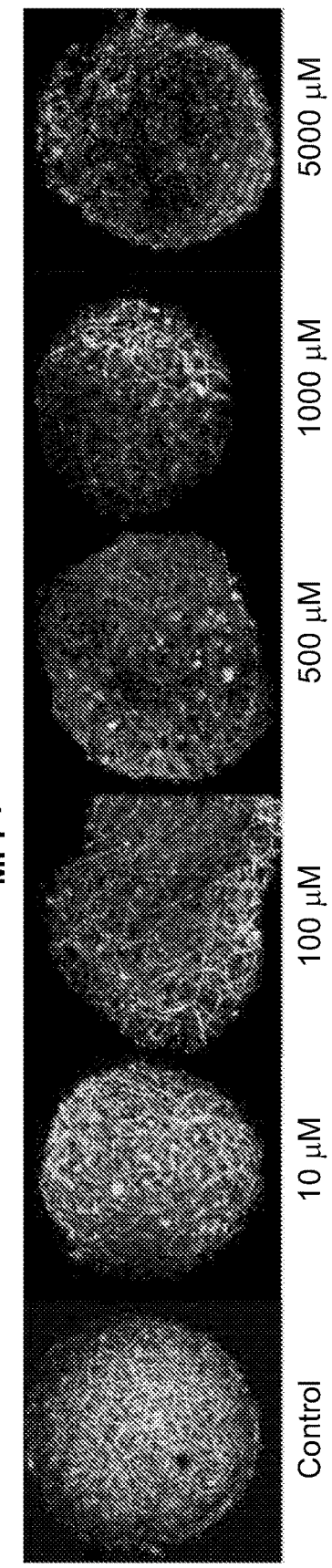
Figure 4G:
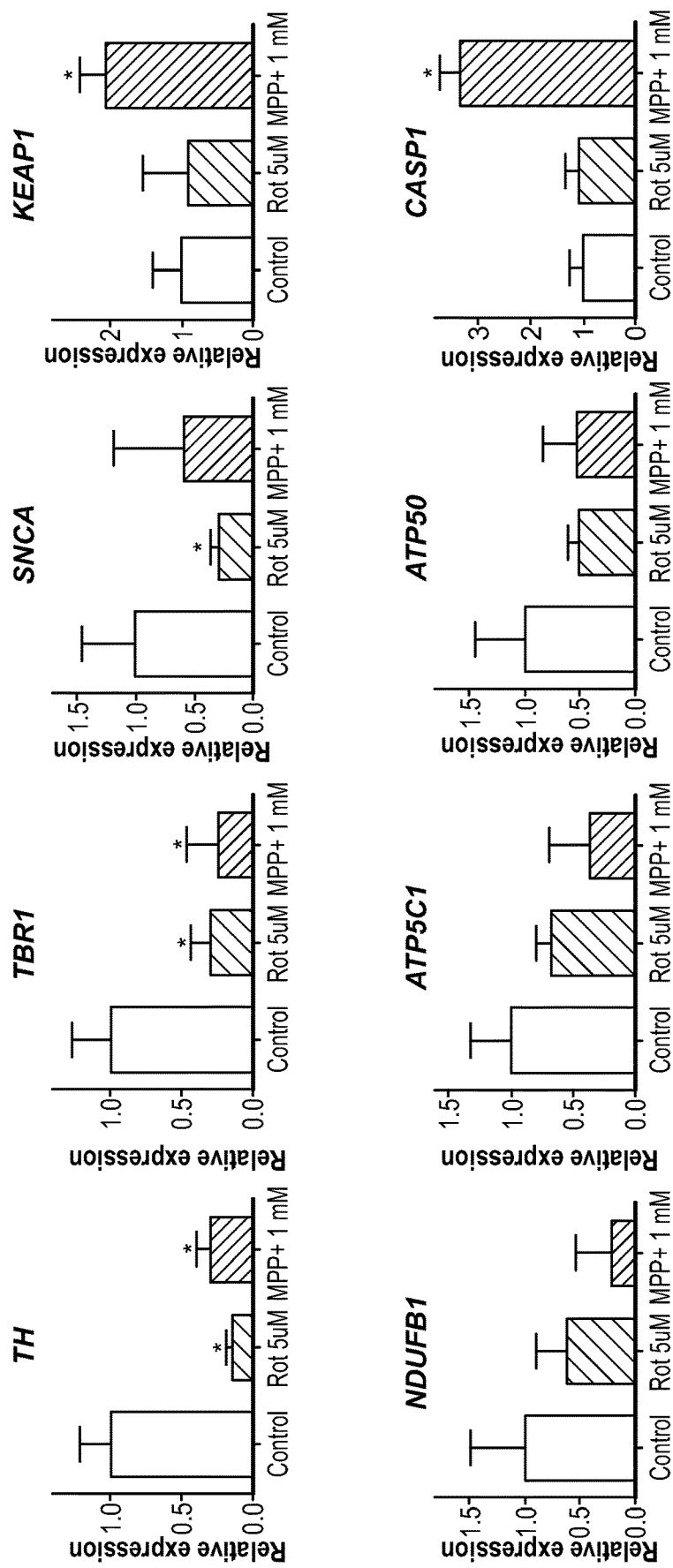
Figure 5A:
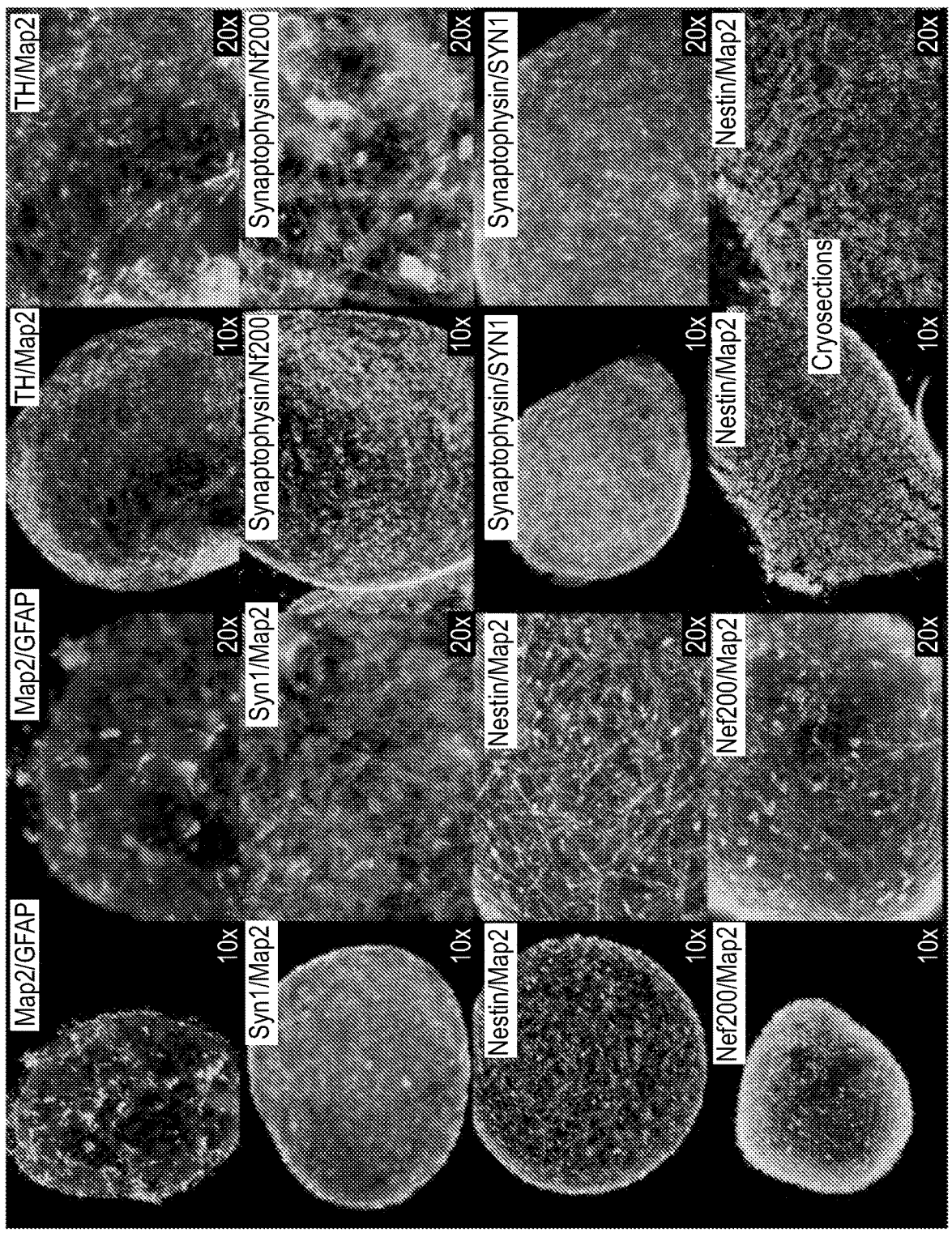
FIGS. 5A-5D depict Down's Syndrome application of BMPS. BMPS were produced with iPSCs derived from a patient with Down's Syndrome.
Figure 5B:
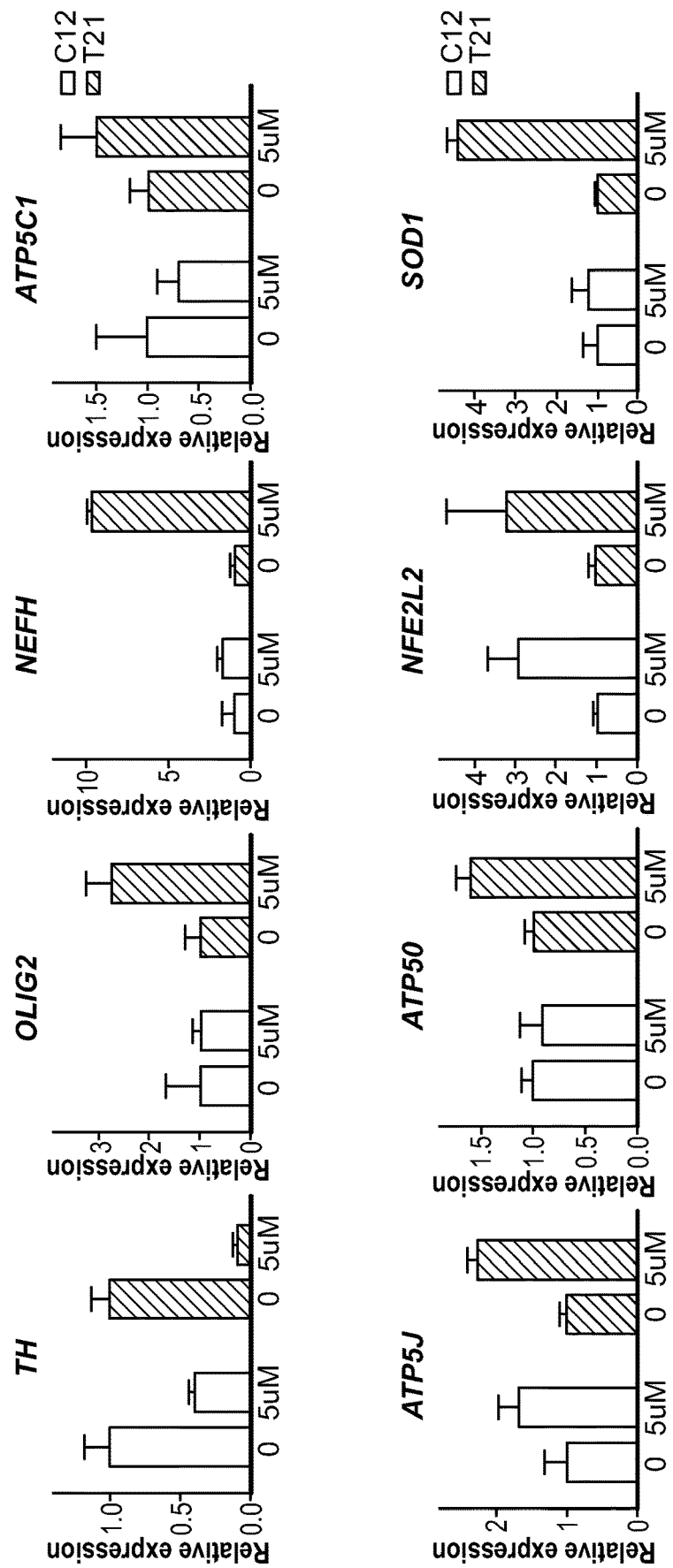
Figure 5C:
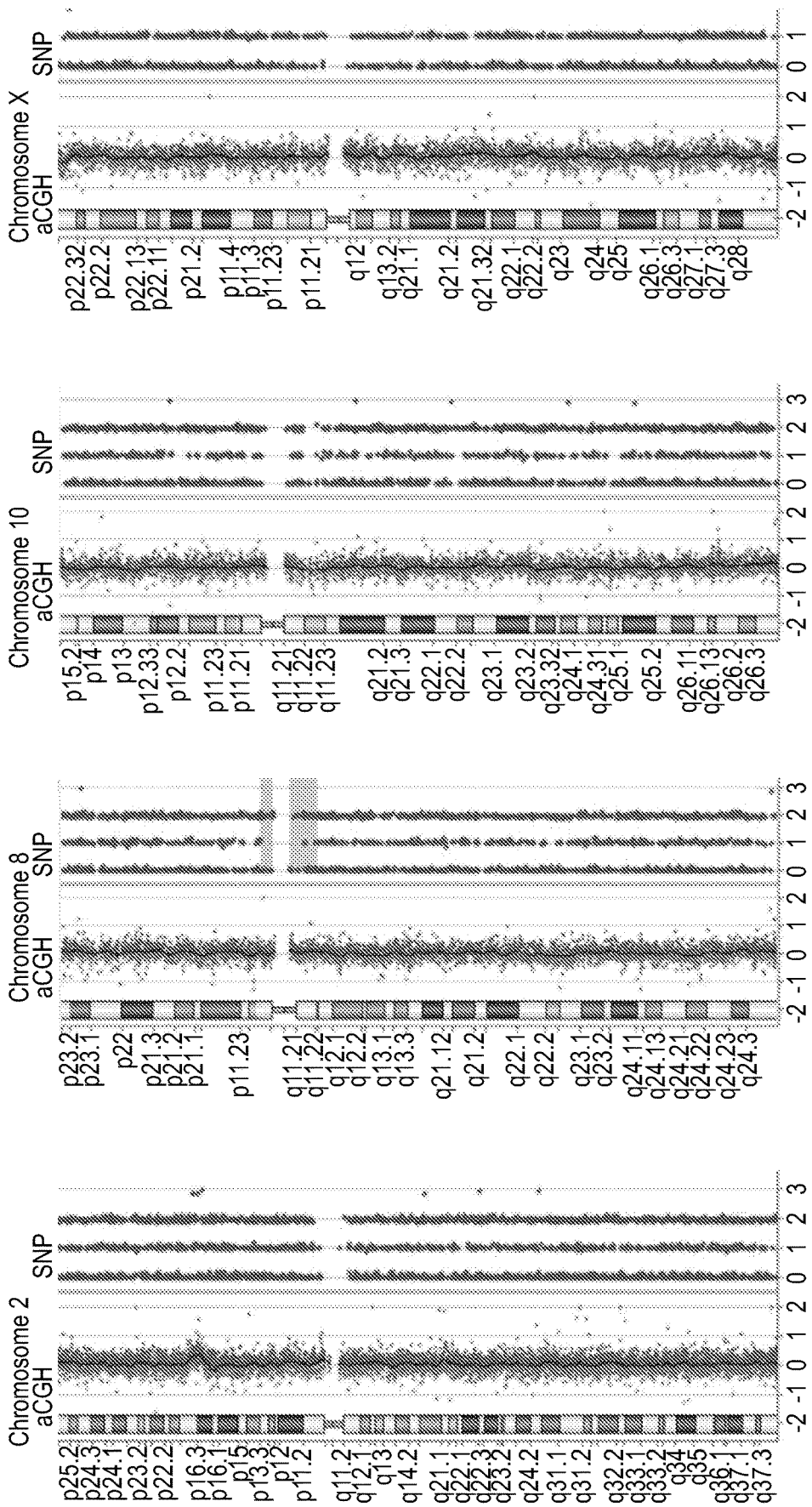
Figure 5D:
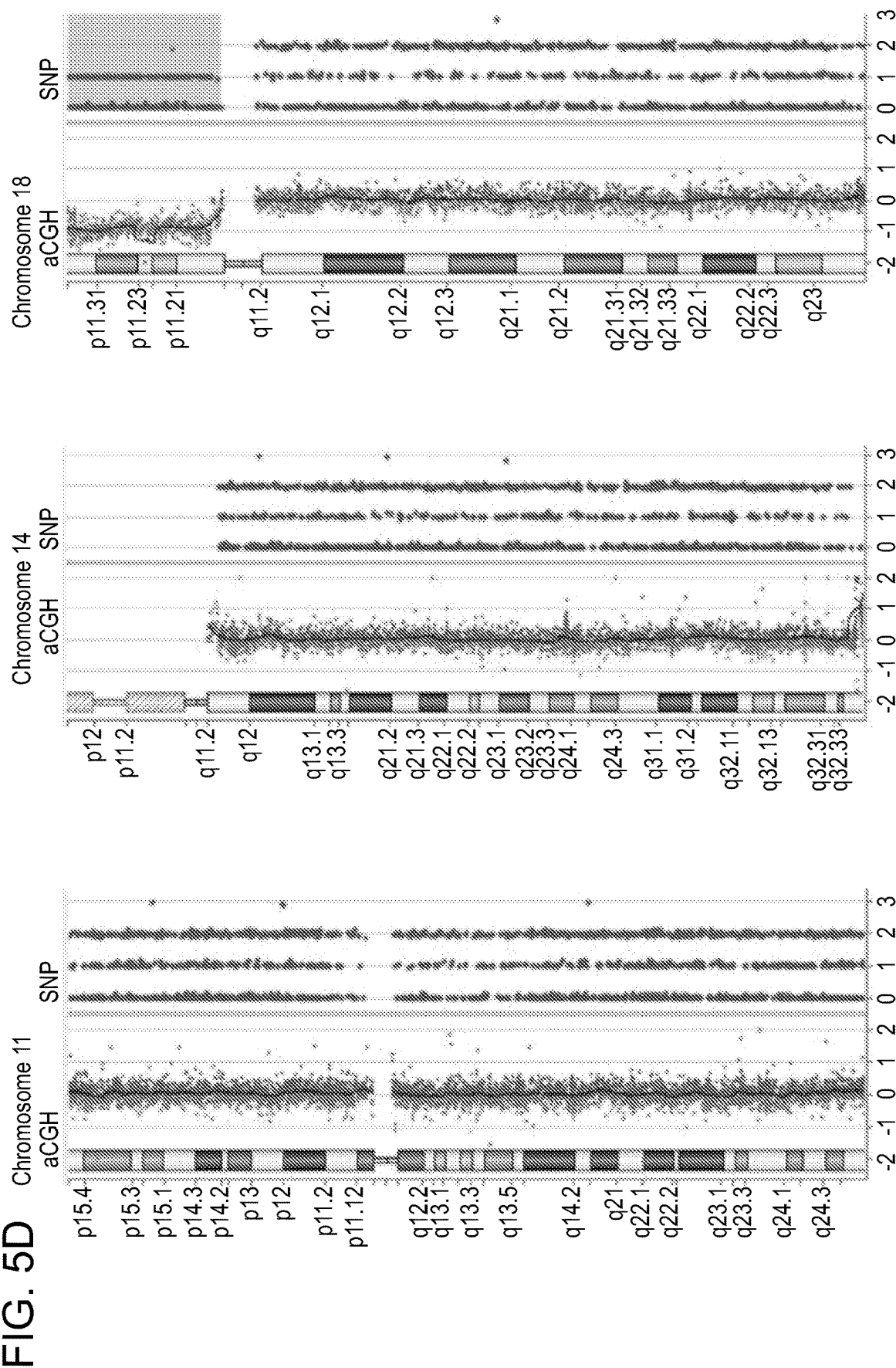

In one embodiment, the model described herein is useful for studying Parkinson's disease (PD). Traditionally, PD has been described as a pre-synaptic degenerative process that affects dopaminergic neurons and induces a fundamental motor disorder [66], however, non-motor symptoms can also be present [67]. Research in Parkinson's disease is experiencing an upswing at the moment, owing to a lack of curative drugs for the large number of patients. Drug testing is nearly exclusively performed in vivo in the so-called MPTP (the parent compound to the metabolite MPP+ used here), rotenone, methamphetamine and 6-hydroxydopamine models requiring tens of thousands of animals [68, 69, 70]. These model toxins are mainly used in mice and primates (and less in cell cultures) to model a disease state resembling PD. Human neurons, which would be most relevant, are not usually available and existing cell lines are only very poor substitutes. The model described herein shows that treatment with MPP+ or rotenone induced specific degeneration of dopaminergic neurons in agreement with Parkinson patients and current animal models of the disease (FIGS. 4E and 4F). The BMPS PD model has shown to recapitulate some of the molecular mechanisms of the human disease, e.g. increase in ROS production (FIGS. 4B and 3D) and changes in genes related to PD (FIG. 4G). BMPS treated with rotenone or MPP+ had decreased TH gene expression compared to controls, supporting the results presented in FIGS. 4E and 4F where the dopaminergic neuronal phenotype is altered after treatment with the two chemicals. TBR1 encodes a transcription factor involved in the regulation of developmental processes. It also plays a role in major neurological diseases such as Alzheimer Disease and PD [71]. This gene was down-regulated after treatment with non-cytotoxic concentrations of MPP+ and rotenone. At the same time, mRNA levels of SNAC were altered. α-Synucleinopathy (common in Parkinson) is a neurodegenerative disease, which consists of the abnormal accumulation of aggregates of alpha-synuclein protein in neurons, nerve fibers or glial cells [72]. Alpha-synuclein plays regulatory roles such as synaptic maintenance, mitochondrial homeostasis, proteasome function, dopamine metabolism [73]. Reduction of SNCA (the alpha-synuclein encoding gene) after treatment with 5 μM rotenone and to a lesser extent after 1 mM MPP+ exposure could be explained by the alteration of alpha-synuclein protein metabolism. However, it may be that longer exposure times are required to produce an increase in gene expression. Caspase-1 (CASP1) expression increased significantly after 24h exposure to 1 μM MPP+. Recently, some studies have identified human enzyme caspase-1 as the protease that cleaves α-synuclein in vivo [74]. This cleavage generates α-synuclein fragments that are prone to toxic aggregate formation. Finally, effects upon genes related with mitochondrial function (such as NDUFB1, ATP5C1 and ATP50) were down-regulated, more strongly in BMPS treated with MPP+ than rotenone.

Changes in NDUFB1, indicate an alteration in mitochondrial function, agreeing with the phenomena already described in Parkinson's disease. This downregulation is linked to the increase in KEAP1 expression (oxidative stress marker) after 24h exposure to 1 mM MPP+. The high variability in some of the genes may be explained by the selective effects of these chemicals (especially MPP+) to dopaminergic neurons, which represent only a subpopulation within the BMPS. While rotenone and MPP+ alter gene expression of this cell population, the other populations presented in BMPS appear not to be affected. Further studies using cell sorting could identify cell-specific effects.

This disclosure provides for a description of a brain microphysiological system aiming to study various aspects of brain development, pathophysiology and disturbance by genetic and environmental factors. The possibilities to study developmental and neurodegenerative disorders, infections, toxicity and trauma are emerging with such a system. Furthermore, the potential to use iPSC from different donors adds a personalized component to these studies. The high reproducibility and relatively easy protocol, enables future higher throughput testing of chemicals, and drugs and their potential to induce or treat diseases.

Autism

Autism is a highly variable neurodevelopmental disorder that first appears during infancy or childhood, and generally follows a steady course without remission. Patients with autism may be severely impaired in some respects but normal, or even superior, in others. Overt symptoms gradually begin after the age of six months, become established by age two or three years, and tend to continue through adulthood, although often in more muted form. It is distinguished not by a single symptom, but by a characteristic triad of symptoms: impairments in social interaction; impairments in communication; and restricted interests and repetitive behavior. Other aspects, such as atypical eating, are also common but are not essential for diagnosis. Autism's individual symptoms occur in the general population and appear not to associate highly, without a sharp line separating pathologically severe from common traits.

While autism is highly heritable, researchers suspect both environmental and genetic factors as causes. In rare cases, autism is strongly associated with agents that cause birth defects. Controversies surround other proposed environmental causes; for example, the vaccine hypotheses have been disproven. Autism affects information processing in the brain by altering how nerve cells and their synapses connect and organize; how this occurs is not well understood. It is one of three recognized disorders in the autism spectrum (ASDs), the other two being Asperger syndrome, which lacks delays in cognitive development and language, and pervasive developmental disorder, not otherwise specified (commonly abbreviated as PDD-NOS), which is diagnosed when the full set of criteria for autism or Asperger syndrome are not met.

Globally, autism is estimated to affect 21.7 million people as of 2013. As of 2010, the number of people affected is estimated at about 1-2 per 1,000 worldwide. It occurs four to five times more often in boys than girls. About 1.5% of children in the United States (one in 68) are diagnosed with ASD as of 2014, a 30% increase from one in 88 in 2012. The rate of autism among adults aged 18 years and over in the United Kingdom is 1.1%. The number of people diagnosed has been increasing dramatically since the 1980s, partly due to changes in diagnostic practice and government-subsidized financial incentives for named diagnoses; the question of whether actual rates have increased is unresolved.

Autism has a strong genetic basis, although the genetics of autism are complex and it is unclear whether ASD is explained more by rare mutations with major effects, or by rare multigene interactions of common genetic variants. Complexity arises due to interactions among multiple genes, the environment, and epigenetic factors which do not change DNA but are heritable and influence gene expression. Studies of twins suggest that heritability is 0.7 for autism and as high as 0.9 for ASD, and siblings of those with autism are about 25 times more likely to be autistic than the general population. However, most of the mutations that increase autism risk have not been identified. Typically, autism cannot be traced to a Mendelian (single-gene) mutation or to a single chromosome abnormality, and none of the genetic syndromes associated with ASDs have been shown to selectively cause ASD. Numerous candidate genes have been located, with only small effects attributable to any particular gene. The large number of autistic individuals with unaffected family members may result from copy number variations-spontaneous deletions or duplications in genetic material during meiosis. Hence, a substantial fraction of autism cases may be traceable to genetic causes that are highly heritable but not inherited: that is, the mutation that causes the autism is not present in the parental genome.

Several lines of evidence point to synaptic dysfunction as a cause of autism. Some rare mutations may lead to autism by disrupting some synaptic pathways, such as those involved with cell adhesion. Gene replacement studies in mice suggest that autistic symptoms are closely related to later developmental steps that depend on activity in synapses and on activity-dependent changes. All known teratogens (agents that cause birth defects) related to the risk of autism appear to act during the first eight weeks from conception, and though this does not exclude the possibility that autism can be initiated or affected later, there is strong evidence that autism arises very early in development.

Exposure to air pollution during pregnancy, especially heavy metals and particulates, may increase the risk of autism. Environmental factors that have been claimed to contribute to or exacerbate autism, or may be important in future research, include certain foods, infectious diseases, solvents, diesel exhaust, PCBs, phthalates and phenols used in plastic products, pesticides, brominated flame retardants, alcohol, smoking, illicit drugs, vaccines, and prenatal stress, although no links have been found, and some have been completely disproven.

Autism does not have a clear unifying mechanism at either the molecular, cellular, or systems level; it is not known whether autism is a few disorders caused by mutations converging on a few common molecular pathways, or is (like intellectual disability) a large set of disorders with diverse mechanisms. Autism appears to result from developmental factors that affect many or all functional brain systems, and to disturb the timing of brain development more than the final product. Neuroanatomical studies and the associations with teratogens strongly suggest that autism's mechanism includes alteration of brain development soon after conception. This anomaly appears to start a cascade of pathological events in the brain that are significantly influenced by environmental factors. Just after birth, the brains of children with autism tend to grow faster than usual, followed by normal or relatively slower growth in childhood. It is not known whether early overgrowth occurs in all children with autism. It seems to be most prominent in brain areas underlying the development of higher cognitive specialization. Hypotheses for the cellular and molecular bases of pathological early overgrowth include the following: an excess of neurons that causes local over connectivity in key brain regions, disturbed neuronal migration during early gestation, unbalanced excitatory-inhibitory networks, and abnormal formation of synapses and dendritic spines, for example, by modulation of the neurexin-neuroligin cell-adhesion system, or by poorly regulated synthesis of synaptic proteins.

The immune system is thought to play an important role in autism. Children with autism have been found by researchers to have inflammation of both the peripheral and central immune systems as indicated by increased levels of pro-inflammatory cytokines and significant activation of microglia. Biomarkers of abnormal immune function have also been associated with increased impairments in behaviors that are characteristic of the core features of autism such as deficits in social interactions and communication. Interactions between the immune system and the nervous system begin early during the embryonic stage of life, and successful neurodevelopment depends on a balanced immune response. It is thought that activation of a pregnant mother's immune system such as from environmental toxicants or infection can contribute to causing autism through causing a disruption of brain development. This is supported by recent studies that have found that infection during pregnancy is associated with an increased risk of autism.

The relationship of neurochemicals to autism is not well understood; several have been investigated, with the most evidence for the role of serotonin and of genetic differences in its transport. The role of group I metabotropic glutamate receptors (mGluR) in the pathogenesis of fragile X syndrome, the most common identified genetic cause of autism, has led to interest in the possible implications for future autism research into this pathway. Some data suggests neuronal overgrowth potentially related to an increase in several growth hormones or to impaired regulation of growth factor receptors. Also, some inborn errors of metabolism are associated with autism, but probably account for less than 5% of cases.

The mirror neuron system (MNS) theory of autism hypothesizes that distortion in the development of the MNS interferes with imitation and leads to autism's core features of social impairment and communication difficulties. The MNS operates when an animal performs an action or observes another animal perform the same action. The MNS may contribute to an individual's understanding of other people by enabling the modeling of their behavior via embodied simulation of their actions, intentions, and emotions. Several studies have tested this hypothesis by demonstrating structural abnormalities in MNS regions of individuals with ASD, delay in the activation in the core circuit for imitation in individuals with Asperger syndrome, and a correlation between reduced MNS activity and severity of the syndrome in children with ASD. However, individuals with autism also have abnormal brain activation in many circuits outside the MNS and the MNS theory does not explain the normal performance of children with autism on imitation tasks that involve a goal or object.

The under connectivity theory of autism hypothesizes that autism is marked by under functioning high-level neural connections and synchronization, along with an excess of low-level processes. Evidence for this theory has been found in functional neuroimaging studies on autistic individuals and by a brainwave study that suggested that adults with ASD have local over connectivity in the cortex and weak functional connections between the frontal lobe and the rest of the cortex. Other evidence suggests the under connectivity is mainly within each hemisphere of the cortex and that autism is a disorder of the association cortex.

From studies based on event-related potentials, transient changes to the brain's electrical activity in response to stimuli, there is considerable evidence for differences in autistic individuals with respect to attention, orientation to auditory and visual stimuli, novelty detection, language and face processing, and information storage; several studies have found a preference for nonsocial stimuli. For example, magnetoencephalography studies have found evidence in children with autism of delayed responses in the brain's processing of auditory signals.

Relations have been found between autism and schizophrenia based on duplications and deletions of chromosomes; research showed that schizophrenia and autism are significantly more common in combination with 1q21.1 deletion syndrome. Research on autism/schizophrenia relations for chromosome 15 (15q13.3), chromosome 16 (16p13.1) and chromosome 17 (17p12) are inconclusive.

Diagnosis is based on behavior, not cause or mechanism. Under the DSM-5, autism is characterized by persistent deficits in social communication and interaction across multiple contexts, as well as restricted, repetitive patterns of behavior, interests, or activities. These deficits are present in early childhood, typically before age three, and lead to clinically significant functional impairment. Sample symptoms include lack of social or emotional reciprocity, stereotyped and repetitive use of language or idiosyncratic language, and persistent preoccupation with unusual objects. The disturbance must not be better accounted for by Rett syndrome, intellectual disability or global developmental delay. ICD-10 uses essentially the same definition. A pediatrician commonly performs a preliminary investigation by taking developmental history and physically examining the child. If warranted, diagnosis and evaluations are conducted with help from ASD specialists, observing and assessing cognitive, communication, family, and other factors using standardized tools, and taking into account any associated medical conditions. A pediatric neuropsychologist is often asked to assess behavior and cognitive skills, both to aid diagnosis and to help recommend educational interventions.

Clinical genetics evaluations are often done once ASD is diagnosed, particularly when other symptoms already suggest a genetic cause. Although genetic technology allows clinical geneticists to link an estimated 40% of cases to genetic causes, consensus guidelines in the US and UK are limited to high-resolution chromosome and fragile X testing. Metabolic and neuroimaging tests are sometimes helpful, but are not routine.

Many medications are used to treat ASD symptoms that interfere with integrating a child into home or school when behavioral treatment fails. More than half of US children diagnosed with ASD are prescribed psychoactive drugs or anticonvulsants, with the most common drug classes being antidepressants, stimulants, and antipsychotics. Antipsychotics, such as risperidone and aripiprazole, have been found to be useful for treating some conditions associated with autism, including irritability, repetitive behavior, and sleeplessness. A person with ASD may respond atypically to medications, the medications can have adverse effects, and no known medication relieves autism's core symptoms of social and communication impairments. Experiments in mice have reversed or reduced some symptoms related to autism by replacing or modulating gene function, suggesting the possibility of targeting therapies to specific rare mutations known to cause autism. Although many alternative therapies and interventions are available, few are supported by scientific studies. Some alternative treatments may place the child at risk. A 2008 study found that compared to their peers, autistic boys have significantly thinner bones if on casein-free diets; in 2005, botched chelation therapy killed a five-year-old child with autism. There has been early research looking at hyperbaric treatments in children with autism.

Parkinson's Disease

Parkinson's disease (PD, also known as idiopathic or primary parkinsonism, hypokinetic rigid syndrome (HRS), or paralysis agitans) is a degenerative disorder of the central nervous system mainly affecting the motor system. The motor symptoms of Parkinson's disease result from the death of dopamine-generating cells in the substantia nigra, a region of the midbrain. The causes of this cell death are poorly understood. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease, and depression is the most common psychiatric symptom. Other symptoms include sensory, sleep and emotional problems. Parkinson's disease is more common in older people, with most cases occurring after the age of 50; when it is seen in young adults, it is called young onset PD (YOPD).

The main motor symptoms are collectively called "parkinsonism," or a "parkinsonian syndrome." The disease can be either primary or secondary. Primary Parkinson's disease is referred to as idiopathic (having no known cause), although some atypical cases have a genetic origin, while secondary parkinsonism is due to known causes like toxins. The pathology of the disease is characterized by the accumulation of a protein into Lewy bodies in neurons, and insufficient formation and activity of dopamine in certain parts of the midbrain. Where the Lewy bodies are located is often related to the expression and degree of the symptoms of an individual. Diagnosis of typical cases is mainly based on symptoms, with tests such as neuroimaging being used for confirmation.

Diagnosis of Parkinson's disease involves a physician taking a medical history and performing a neurological examination. There is no lab test that will clearly identify the disease, but brain scans are sometimes used to rule out disorders that could give rise to similar symptoms. People may be given levodopa and resulting relief of motor impairment tends to confirm diagnosis. The finding of Lewy bodies in the midbrain on autopsy is usually considered proof that the person had Parkinson's disease. The progress of the illness over time may reveal it is not Parkinson's disease, and some authorities recommend that the diagnosis be periodically reviewed. Other causes that can secondarily produce a parkinsonian syndrome are Alzheimer's disease, multiple cerebral infarction and drug-induced parkinsonism. Parkinson plus syndromes such as progressive supranuclear palsy and multiple system atrophy must be ruled out. Anti-Parkinson's medications are typically less effective at controlling symptoms in Parkinson plus syndromes. Faster progression rates, early cognitive dysfunction or postural instability, minimal tremor or symmetry at onset may indicate a Parkinson plus disease rather than PD itself. Genetic forms are usually classified as PD, although the terms familial Parkinson's disease and familial parkinsonism are used for disease entities with an autosomal dominant or recessive pattern of inheritance.

The PD Society Brain Bank criteria require slowness of movement (bradykinesia) plus either rigidity, resting tremor, or postural instability. Other possible causes for these symptoms need to be ruled out prior to diagnosis with PD. Finally, three or more of the following features are required during onset or evolution: unilateral onset, tremor at rest, progression in time, asymmetry of motor symptoms, response to levodopa for at least five years, clinical course of at least ten years and appearance of dyskinesias induced by the intake of excessive levodopa. Accuracy of diagnostic criteria evaluated at autopsy is 75-90%, with specialists such as neurologists having the highest rates. Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, diffusion MRI, has been reported to be useful at discriminating between typical and atypical parkinsonism, although its exact diagnostic value is still under investigation. Dopaminergic function in the basal ganglia can be measured with different PET and SPECT radiotracers. Examples are ioflupane (123I) (trade name DaTSCAN) and iometopane (Dopascan) for SPECT or fluorodeoxyglucose (18F) and DTBZ for PET. A pattern of reduced dopaminergic activity in the basal ganglia can aid in diagnosing PD.

Treatments, typically the medications L-DOPA and dopamine agonists, improve the early symptoms of the disease. As the disease progresses and dopaminergic neurons continue to be lost, these drugs eventually become ineffective at treating the symptoms and at the same time produce a complication marked by involuntary writhing movements. Surgery and deep brain stimulation have been used to reduce motor symptoms as a last resort in severe cases where drugs are ineffective. Although dopamine replacement alleviates the symptomatic motor dysfunction, its effectiveness is reduced as the disease progresses, leading to unacceptable side effects such as severe motor fluctuations and dyskinesias. Furthermore, there is no therapy that will halt the progress of the disease. Moreover, this palliative therapeutic approach does not address the underlying mechanisms of the disease.

The term parkinsonism is used for a motor syndrome whose main symptoms are tremor at rest, stiffness, slowing of movement and postural instability. Parkinsonian syndromes can be divided into four subtypes according to their origin: primary or idiopathic, secondary or acquired, hereditary parkinsonism, and Parkinson plus syndromes or multiple system degeneration. Usually classified as a movement disorder, PD also gives rise to several non-motor types of symptoms such as sensory deficits, cognitive difficulties or sleep problems. Parkinson plus diseases are primary parkinsonisms which present additional features. They include multiple system atrophy, progressive supranuclear palsy, corticobasal degeneration and dementia with Lewy bodies.

In terms of pathophysiology, PD is considered a synucleinopathy due to an abnormal accumulation of alpha-synuclein protein in the brain in the form of Lewy bodies, as opposed to other diseases such as Alzheimer's disease where the brain accumulates tau protein in the form of neurofibrillary tangles. Nevertheless, there is clinical and pathological overlap between tauopathies and synucleinopathies. The most typical symptom of Alzheimer's disease, dementia, occurs in advanced stages of PD, while it is common to find neurofibrillary tangles in brains affected by PD. Dementia with Lewy bodies (DLB) is another synucleinopathy that has similarities with PD, and especially with the subset of PD cases with dementia. However, the relationship between PD and DLB is complex and still has to be clarified. They may represent parts of a continuum or they may be separate diseases.

Mutations in specific genes have been conclusively shown to cause PD. These genes encode alpha-synuclein (SNCA), parkin (PRKN), leucine-rich repeat kinase 2 (LRRK2 or dardarin), PTEN-induced putative kinase 1 (PINK1), DJ-1 and ATP13A2. In most cases, people with these mutations will develop PD. With the exception of LRRK2, however, they account for only a small minority of cases of PD. The most extensively studied PD-related genes are SNCA and LRRK2. Mutations in genes including SNCA, LRRK2 and glucocerebrosidase (GBA) have been found to be risk factors for sporadic PD. Mutations in GBA are known to cause Gaucher's disease. Genome-wide association studies, which search for mutated alleles with low penetrance in sporadic cases, have now yielded many positive results.

The role of the SNCA gene is important in PD because the alpha-synuclein protein is the main component of Lewy bodies. The histopathology (microscopic anatomy) of the substantia nigra and several other brain regions shows neuronal loss and Lewy bodies in many of the remaining nerve cells. Neuronal loss is accompanied by death of astrocytes (star-shaped glial cells) and activation of the microglia (another type of glial cell). Lewy bodies are a key pathological feature of PD.

Alzheimer's Disease

Alzheimer's disease (AD) accounts for 60% to 70% of cases of dementia. It is a chronic neurodegenerative disease that often starts slowly, but progressively worsens over time. The most common early symptom is short-term memory loss. As the disease advances, symptoms include problems with language, mood swings, loss of motivation, disorientation, behavioral issues, and poorly managed self-care. Gradually, bodily functions are lost, ultimately leading to death. Although the speed of progression can vary, the average life expectancy following diagnosis is three to nine years. The cause of Alzheimer's disease is poorly understood. About 70% of the risk is believed to be genetic with many genes involved. Other risk factors include a history of head injuries, hypertension, or depression. The disease process is associated with plaques and tangles in the brain.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Alzheimer's disease has been hypothesized to be a protein misfolding disease (proteopathy), caused by accumulation of abnormally folded A-beta and tau proteins in the brain. Plaques are made up of small peptides, 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques.

A probable diagnosis is based on the history of the illness and cognitive testing with medical imaging and blood tests to rule out other possible causes. Initial symptoms are often mistaken for normal ageing. Examination of brain tissue is needed for a definite diagnosis. Alzheimer's disease is diagnosed through a complete medical assessment. There is no one clinical test that can determine whether a person has Alzheimer's. Usually several tests are performed to rule out any other cause of dementia. The only definitive method of diagnosis is examination of brain tissue obtained from a biopsy or autopsy. Tests (such as blood tests and brain imaging) are used to rule out other causes of dementia-like symptoms. Laboratory tests and screening include: complete blood cell count; electrolyte panel; screening metabolic panel; thyroid gland function tests; vitamin B-12 folate levels; tests for syphilis and, depending on history, for human immunodeficiency antibodies; urinalysis; electrocardiogram (ECG); chest X-ray; computerized tomography (CT) head scan; and an electroencephalogram (EEG). A lumbar puncture may also be informative in the overall diagnosis.

There are no known medications or supplements that decrease risk of Alzheimer's. Additionally, no known treatments stop or reverse Alzheimer's progression, although some may temporarily improve symptoms.

This invention is further illustrated by the following examples, which should not be construed as limiting. The contents of all references, patents, and published patent applications cited throughout this application, as well as the figures, are incorporated herein by reference.

EXAMPLES

Example 1: Characterization of BMPS by Expression of Neural Specific Genes During Differentiation According to the techniques herein, the BMPS model established herein follows a stepwise differentiation protocol (FIG. 1A). In the final step, cells were differentiated into various neuronal and glial cell types during constant gyratory shaking. Briefly, the BMPS were established as follows: cells were differentiated, by addition of B27, GDNF and BDNF and withdrawal of stempro, basic FGF and EGF, into different neuronal and glial cell types with CNS functions during constant gyratory shaking. Advantageously, the techniques herein provide that the BMPS that were produced were of a spherical shape and a consistent size. For example, the BMPS showed spherical shapes and controlled sizes that were below 350 µm after 17 days in culture, a size that avoids necrosis in the center of the aggregate (FIG. 1B) that occurs in larger spheroids (e.g., >350 µm) due to nutrient and oxygen deprivation. Nutrient and oxygen deprivation-induced necrosis could produce artifacts in the different endpoints measured, especially in disease and toxicity studies. Five days after initiation of aggregation in NPC medium, spheres were on average 130±5 µm in diameter; the size increased to 300±40 µm during the first 17 days in differentiation medium. From day 17 onwards size remained constant around 310 µm. Advantageously, this technique significantly increases throughput of BMPS production by allowing simultaneous production of several batches with different conditions. Without the shaking condition, aggregates tend to stick together, grow in different shapes, attach to the bottom and in some point get necrotic in the middle of the sphere. Thus, constant gyratory shaking technology is a suitable method to control the shape and size of BMPS.

In order to characterize different stages of the differentiation and maturation process, BMPS were collected every week up to 8 weeks of differentiation (FIGS. 1C1-C5). Analysis of different neuronal and glial cell-specific genes by real-time reverse transcription polymerase chain reaction (RT-PCR) was performed to characterize the presence of neurons, astrocytes, oligodendrocytes and neural precursor cells (NPC). NPC are self-renewing and proliferating multipotent cells able to generate different cell types of the central nervous system. The differentiation of NPC in 3D was initiated by changing the medium to differentiation medium. Gene expression of the cell proliferation marker Ki67 decreased 95% after 2 weeks of differentiation (FIG. 1C1, proliferation and stem cell markers). The remaining Ki67 expression appears to be due to the presence of a small population of NPC and other proliferating cell types such as oligodendrocytes and astrocytes (FIG. 1C2, astroglia and oligodendroglia). Astrocyte-specific genes (S100B and GFAP) showed a constant increase after two weeks, while, differentiation of oligodendrocytes was induced later, after six weeks of differentiation as shown by OLIG2 gene expression (FIG. 1C2).

Gene expression of specific neurotransmitters or their receptors was used to characterize the identity of different neuronal populations and the differentiation patterns of the human iPSC derived BMPS (FIG. 1C4, neuronal markers; right y-axis relative quantification of GRIN1 and GABRA1; MBP, FOXA2, and SLC1A3). GRIN1 encodes the essential Glutamate [NMDA] receptor subunit zeta-1 was increased at very early stages of differentiation (one week after induction of differentiation) and continued to increase up to 5 weeks when it reached a plateau (FIG. 1C4). Similarly, GAD1, a GABAergic neuronal gene marker which encodes the Glutamate decarboxylase 1, and catalyzes decarboxylation of glutamate to GABA, showed an increase in expression during the first 4 weeks of differentiation, reaching a plateau thereafter (FIG. 1C4). The expression of tyrosine hydroxylase (TH) a gene, which identifies dopaminergic neurons, was observed first after three weeks, showing delayed differentiation compared to glutamatergic neurons. The expression of TH increased constantly thereafter reaching an 86-fold increase at seven weeks compared to NPC (week 0; FIG. 1C4). GABRA1, which encodes the gamma-aminobutyric acid (GABA) receptor, showed a steady increase of expression after 2 weeks and reached its maximum increase of a 150-fold change at 8 weeks compared to week 0 (FIG. 1C4). Moreover other markers for specific part of the brain, such as ventral midbrain neuron marker LMX1A, FOXO1 and FOXA2 (Hedlund et al., 2016; Stott et al., 2013), cerebral cortex marker FOXO4, or markers for myelination CNP and MBP (Li and Richardson, 2008; Agrawal et al., 1994) and L-glutamate transport SLC1A6 (Sery et al., 2015) has been studied (FIG. 1D d). Based on the patterns of expression of neuronal genes, the iPSC-derived BMPS model closely represents the different neuronal populations of different cortical and subcortical areas of the human CNS, suggesting that some of the mechanisms implicated in the early stages of nervous system development are reflected.

To prove that BMPS can be generated from different IPCs, another healthy line (IPS IMR90) and Down syndrome line (DYP0730) were used (FIG. 1C5). Both lines were able to generate BMPS and differentiated to neurons (MAP2 marker), astrocytes (GFAP marker) and oligodendrocytes (OLIG1 marker).

Example 2: Characterization of BMPS by Flow Cytometry Analysis Shows Neuronal Maturation of the Human Induced Pluripotent Stem Cells Over Time In order to quantify cell populations in the iPSC-derived BMPS and verify the reproducibility between experiments and batches of the cell line (C1, CRL-2097), flow cytometry was performed using CNS-specific antibodies for identification of neural markers (Table 1). Flow cytometry allowed quantifying 60% of cells with proliferation marker (Ki67) at the NPCs stage (week 0), which was reduced during differentiation down to 9% at 2 weeks, 7% at 4 weeks and 1% at 8 weeks (FIG. 1D), indicating a fast reduction of proliferating cells after induction of differentiation. This confirms the gene expression data and indicates a fast reduction of proliferating cells after induction of differentiation. This result was confirmed by further analysis of NPC markers such as SOX1, SOX2 and Nestin. SOX1 and SOX2 are known to be involved in the maintenance of neural progenitor cell identity. The number of SOX1-, SOX2- and NES-positive (NPC marker) cells in the NPC population (week 0) was 46%, 68% and 60%, respectively. SOX1, SOX2 and NES expression was reduced dramatically with differentiation, showing very low positive populations at eight weeks (2%, 3% and 2%, respectively). This loss in the NPC population during differentiation was corroborated by Doublecortin (DCX), a microtubule-associated protein expressed in neuroblasts and immature neurons: the number of DCX-positive cells in NPC (week o) was around 30%, which reduced to 22% at two, 17% at four and 4% at eight weeks, respectively. On the other hand, the marker for mature neurons, Tuj1 (Neuron-specific class III beta-tubulin) presented the opposite pattern. Analysis showed low levels of Tuj1-positive cells at the NPC stage (week 0). The expression of this marker in the cell population increased to 70% after 2 weeks of differentiation and remained constant up to 8 weeks. These flow cytometry experiments indicate differentiation and maturation of the BMPS over time. Quantification of the cell population in at least three independent experiments showed low variability between cultures, demonstrating the reproducibility of the system. The variation (standard deviation, SD) between experiments decreased with the cell differentiation process and was very small at the latest maturation stage (eight weeks); DCX SD 0.9%, Ki67 SD 0.2%, SOX1 SD 0.7%, SOX2 SD 1.2%, NES SD 0.7% and Tuj1 SD 9,8% (FIG. 1E). These results indicate that after eight weeks of differentiation the cellular composition is similar and shows high reproducibility between different BMPS experiments.

TABLE 1

Gene and miRNAs Taqman Assays. List of the primers used for the experiments.

| Assay ID | Assay Type | Availability | Catalog Number | Assay Name |
|---|---|---|---|---|
| Gene Expression Taqman Primers | | | | |
| Hs01060665 | TaqMan ® Gene Expression Assay | Inventoried | 4331182 | BACT |
| Hs99999901 | TaqMan ® Gene Expression Assay | Inventoried | 4331182 | 18S |
| Hs04187831 | TaqMan ® Gene Expression Assay | Inventoried | 4331182 | NES |
| Hs01032443 | TaqMan ® Gene Expression Assay | Inventoried | 4331182 | Ki67 |
| Hs01088112 | TaqMan ® Gene Expression Assay | Inventoried | 4331182 | PAX6 |

TABLE 1-continued

Gene and miRNAs Taqman Assays. List of the primers used for the experiments.

| Assay ID | Assay Type | Availability | Catalog Number | Assay Name |
|---|---|---|---|---|
| Hs00909233 | TaqMan ® Gene Expression Assay | Inventoried | 4331182 | GFAP |
| Hs00300164 | TaqMan ® Gene Expression Assay | Inventoried | 4331182 | OLIG2 |
| Hs00902901 | TaqMan ® Gene Expression Assay | Inventoried | 4331182 | S100B |
| Hs00609557 | TaqMan ® Gene Expression Assay | Inventoried | 4331182 | GRIN1 |
| Hs00165941 | TaqMan ® Gene Expression Assay | Inventoried | 4331182 | TH |
| Hs00971228 | TaqMan ® Gene Expression Assay | Inventoried | 4331182 | GABRA1 |
| Hs01065893 | TaqMan ® Gene Expression Assay | Inventoried | 4331182 | GAD1 |
| Hs00199577 | TaqMan ® Gene Expression Assay | Inventoried | 4331182 | SYN1 |
| Hs00232429 | TaqMan ® Gene Expression Assay | Inventoried | 4331182 | TBR1 |
| Hs01003383 | TaqMan ® Gene Expression Assay | Inventoried | 4331182 | SNCA |
| Hs01003430 | TaqMan ® Gene Expression Assay | Inventoried | 4331182 | KEAP1 |
| Hs00929425 | TaqMan ® Gene Expression Assay | Inventoried | 4331182 | NDUFB1 |
| Hs01101219 | TaqMan ® Gene Expression Assay | Inventoried | 4331182 | ATP5C1 |
| Hs00919163 | TaqMan ® Gene Expression Assay | Inventoried | 4331182 | ATP5O |
| Hs00354836 | TaqMan ® Gene Expression Assay | Inventoried | 4331182 | CASP1 |
| Hs00263981 | TaqMan ® Gene Expression Assay | Inventoried | 4331182 | CNP |
| Hs01054576 | TaqMan ® Gene Expression Assay | Inventoried | 4331182 | FOXO1 |
| Hs00188193 | TaqMan ® Gene Expression Assay | Inventoried | 4331182 | SLC1A3 |
| Hs00936217 | TaqMan ® Gene Expression Assay | Inventoried | 4331182 | FOXO4 |
| Hs00892663 | TaqMan ® Gene Expression Assay | Inventoried | 4331182 | LMX1A |
| Hs00232764 | TaqMan ® Gene Expression Assay | Inventoried | 4331182 | FOXA2 |
| miRNA Taqman Assays | | | | |
| 1182 | TaqMan ® microRNA Assay | Inventoried | 4427975 | mmu-miR-124a |
| 2216 | TaqMan ® microRNA Assay | Inventoried | 4427975 | hsa-miR-128a |
| 457 | TaqMan ® microRNA Assay | Inventoried | 4427975 | hsa-miR-132 |
| 2247 | TaqMan ® microRNA Assay | Inventoried | 4427975 | hsa-miR-133b |
| 1129 | TaqMan ® microRNA Assay | Inventoried | 4427975 | mmu-miR-137 |
| 1094 | Control miRNA Assay | Inventoried | 4427975 | RNU44 |

Example 3: MicroRNAs as Neuronal Differentiation Markers in Human iPSC-Derived BMPS MicroRNAs (miRNA), known as posttranscriptional regulators of developmental timing, have recently been established as markers to study the differentiation process [26]. Expression of neural-specific miRNAs showed strong induction of miRNAs involved in neurogenesis (FIG. 1C3, miRNA). mir-124, the most abundant brain miRNA, was strongly induced in the earlier stages of differentiation, then slightly down-regulated at eight weeks of differentiation. This finding correlates with previous studies, where mir-124 was shown to promote neuronal lineage commitment at earlier stages of neural stem cells specification by targeting anti-neuronal factors [26]. mir-128, a modulator of late neural differentiation, was strongly up-regulated after 5 weeks of differentiation. mir-137, the most induced miRNA over time in the system described herein, is known as a regulator of neural differentiation of embryonic stem cells (ESCs) [27]. mir-132 and mir-133b which are involved in regulation of dopaminergic neuron maturation and function, were induced in week three of differentiation, a finding which correlates with the expression pattern of TH. Moreover, mir-132 is involved in dendritic spine formation [28]. These results support the view of a coordinated mechanism of neuronal differentiation as reflected by the patterns of neuronal gene and miRNA expression and neuronal and neurotransmitter identity.

Figure 8A:
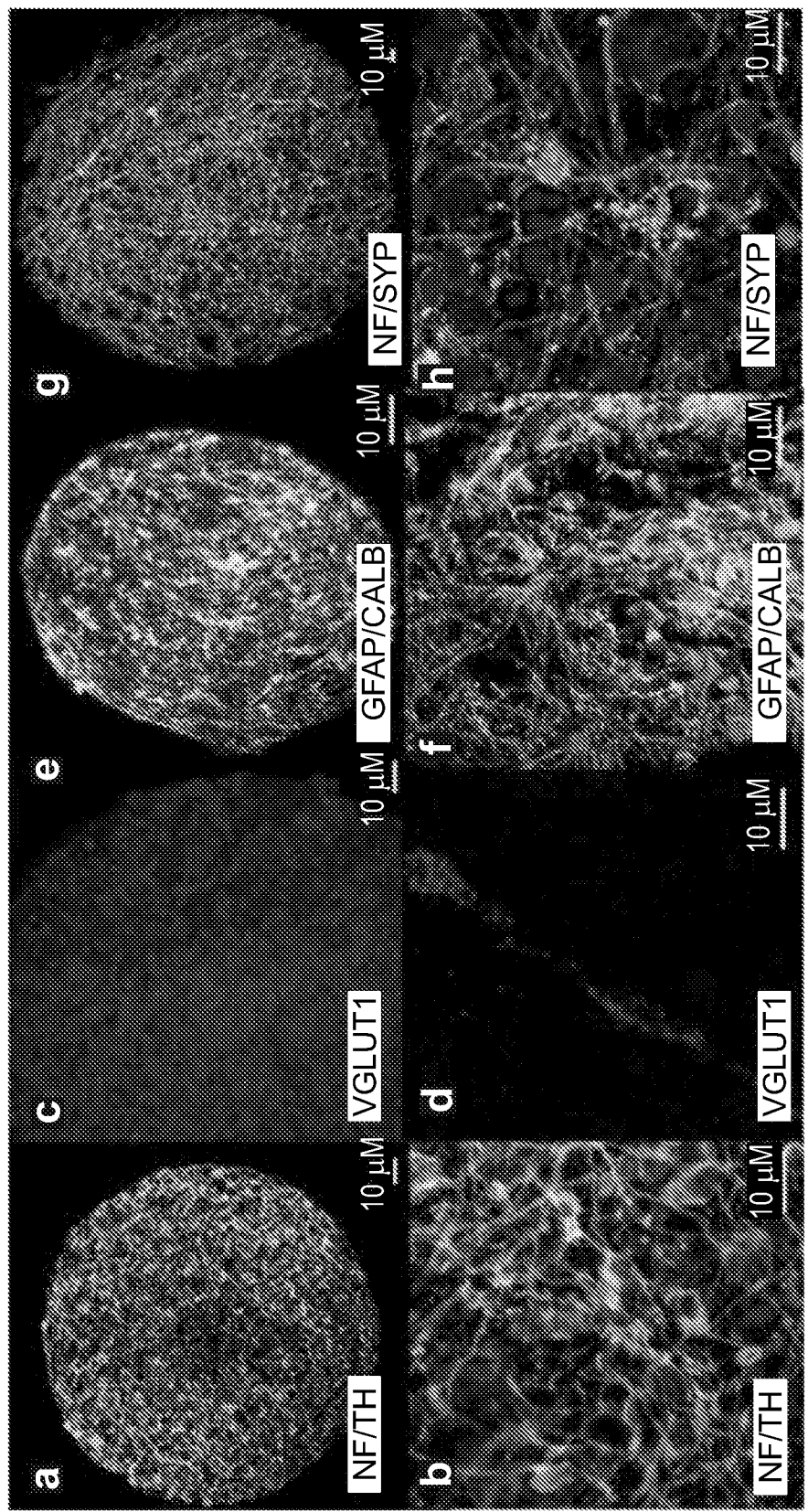
FIGS. 8A-8E depict morphologic characterization of mature human BMPS.

Example 4: Characterization of Human BMPS by Immunohistochemistry and Electron Microscopy Shows Evidence of Differentiation into Mature Brain Cell Types In order to assess the cellular composition and the process of maturation of the cells within the human BMPS, the expression of markers for different CNS cell populations including neurons and glial cells at 2, 4 and 8 weeks of differentiation were evaluated using immunohistochemistry and electron microscopy techniques. A reproducible pattern of expression consistent with maturation of the BMPS towards mature neural phenotypes was found. After 4 weeks of differentiation, the BMPS showed positive staining for mature neuronal markers such as microtubule-associated protein 2 (MAP2), neurofilament-heavy chain (NF, SMI32) and synaptophysin (FIG. 2A, 2B). Furthermore, different neuronal subtypes in the BMPS including dopaminergic (TH-positive neurons), glutamatergic (VGLUT1-positive neurons) and GABAergic interneurons (calbindin-positive neurons) (FIG. 2B, FIG. 8A) were observed. Moreover, the BMPS matured over time of differentiation as seen by decreased NES-positive cells (FIG. 2A) and increased cell-cell interactions (neuron-neuron and neuron glia) as subsets of neurons showed several processes, which resembled dendritic and axonal projections (FIG. 8A).

Figure 8B:
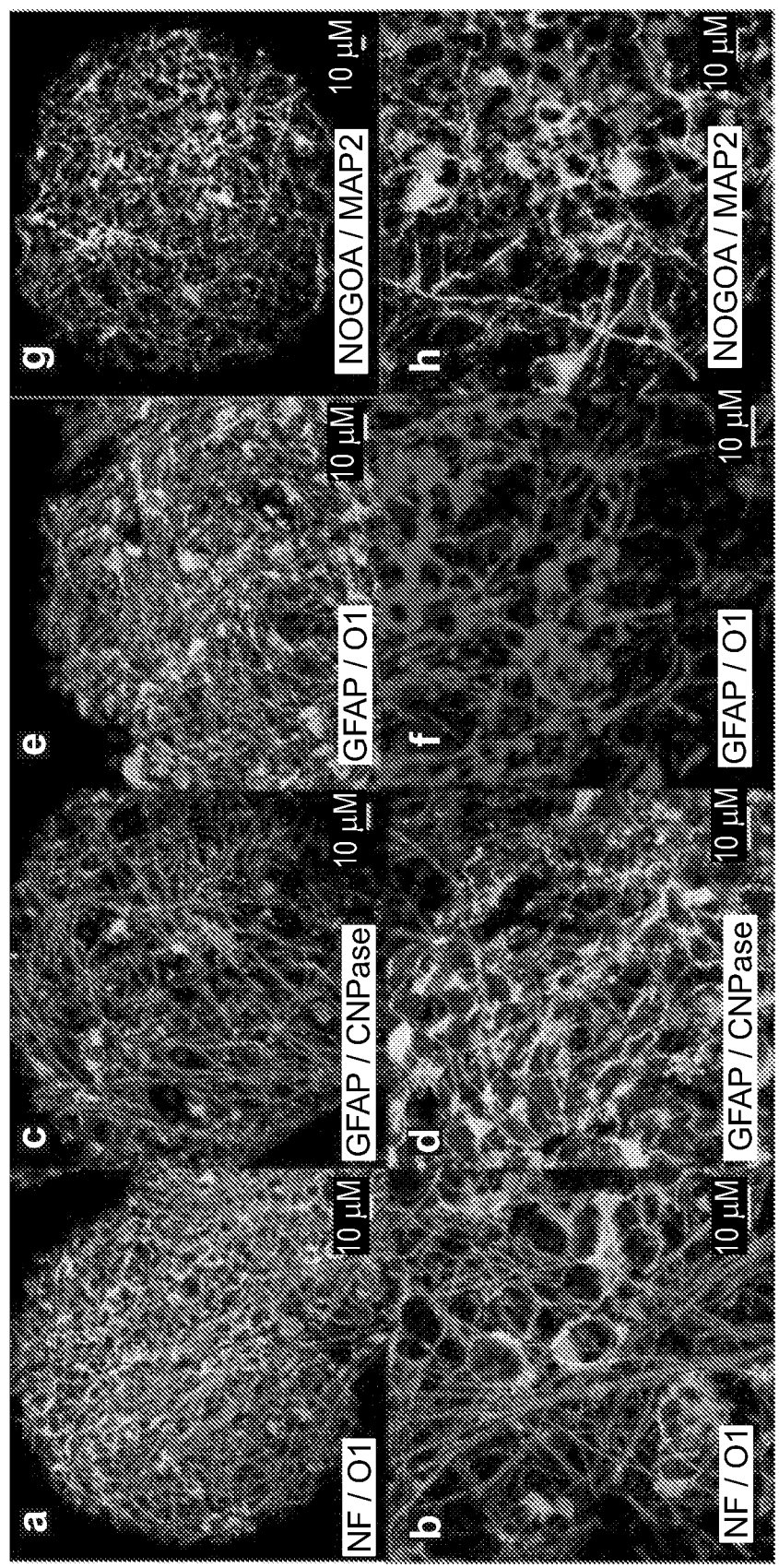

A subset of neuronal cells exhibited immunoreactivity for markers such as NOGOA, O1, O2, and CNPase (FIG. 8B, panels a-j; FIG. 1C5), which identifies the presence of mature oligodendrocytes in the BMPS [31, 33]. Automatic image quantification showed that oligodendrocytes (CNPase, NOGOA, and Olig1) comprised 3, 9, and 11% of the total cell population, respectively, at 8 weeks of differentiation (FIG. 8C; FIG. 1C5). Similar to the in vivo physiology, these cells were immunoreactive for myelin basic protein (MBP) (FIG. 2), which characterizes myelinating oligodendrocytes [32]. Moreover, they had morphological features of normal human oligodendrocytes in vivo and appeared in close contact with neuronal processes (FIG. 8a-b, FIG. 2C, 2D)

Figure 2D:
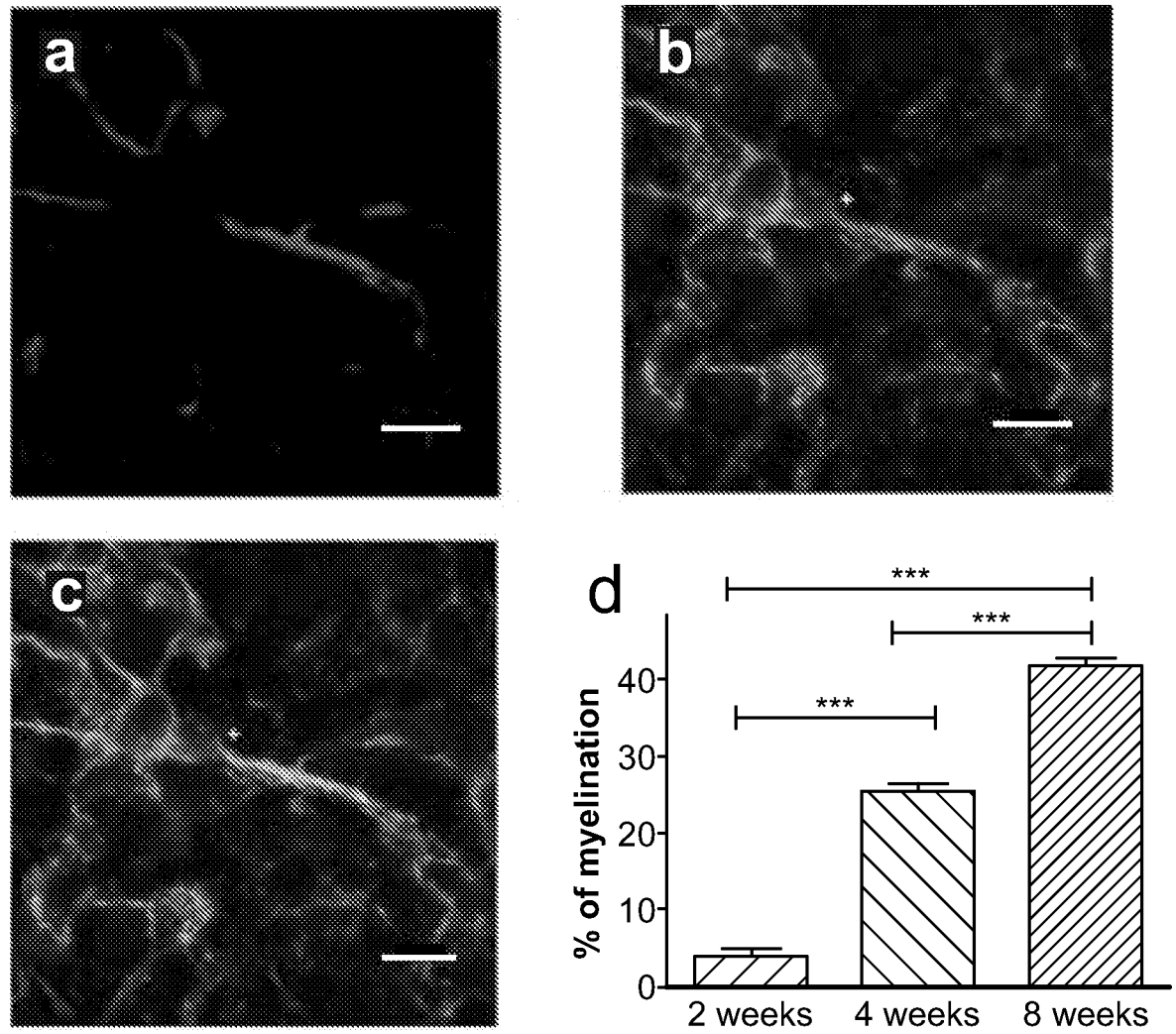
FIG. 2D depicts MBP+ oligodendrocytes issued processes in close association with axons and seemed to enwrap them at 8 weeks (a,b,c). Myelination calculated as the mean percentage MBP positive oligodendrocyte processes coverage of NF-H-positive axons (a,b,c) at 2, 4 and 8 weeks in at least 2 independent experiments showed significant increase of myelination observed with time of differentiation ($p<0.001$) (d).
Figure 2E:
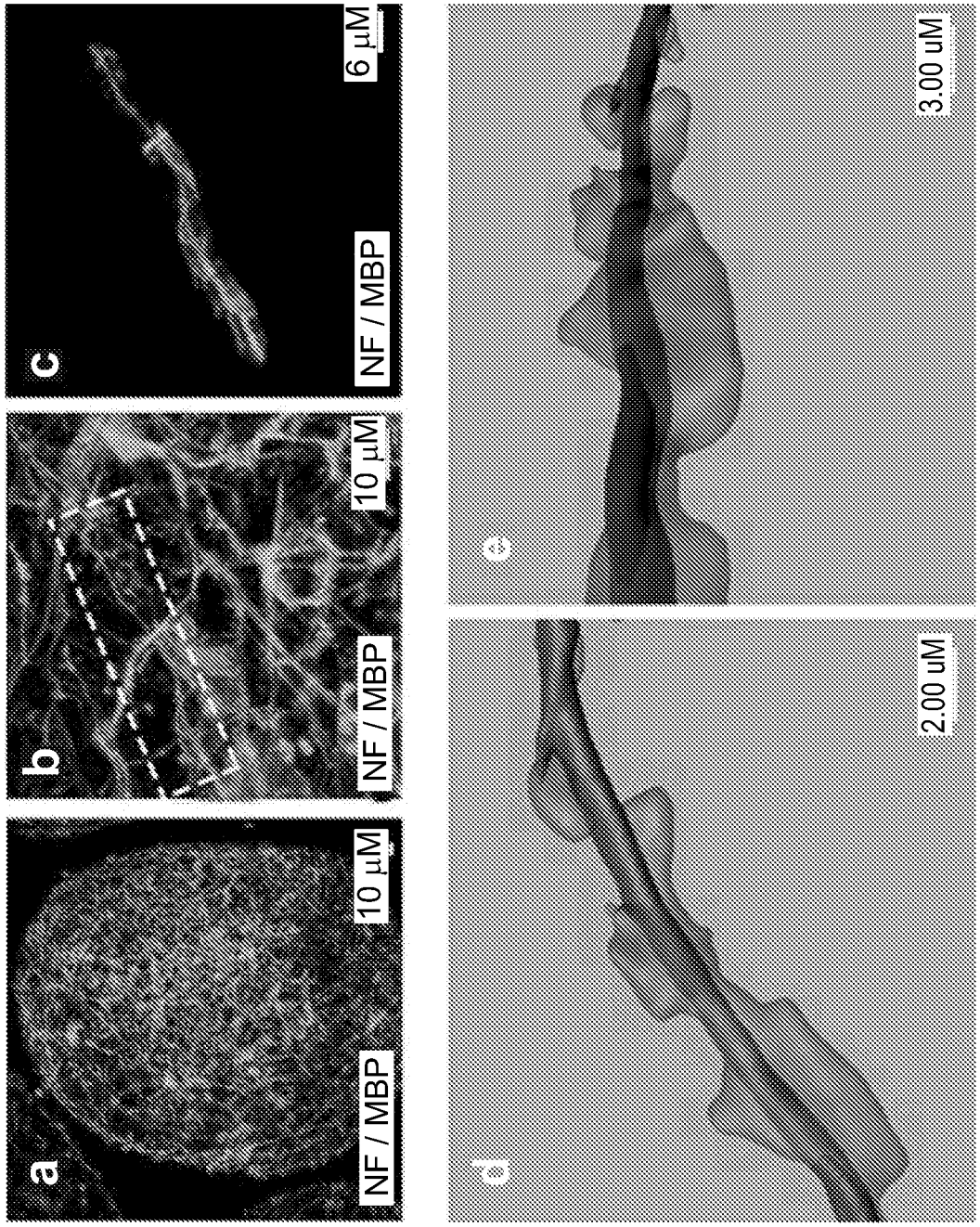
FIG. 2E depicts 3D-reconstruction based on confocal z-stacks at 8 weeks demonstrating a "wrapping" myelinating process, which resembled the myelination of axons in human CNS.
Figure 2F:
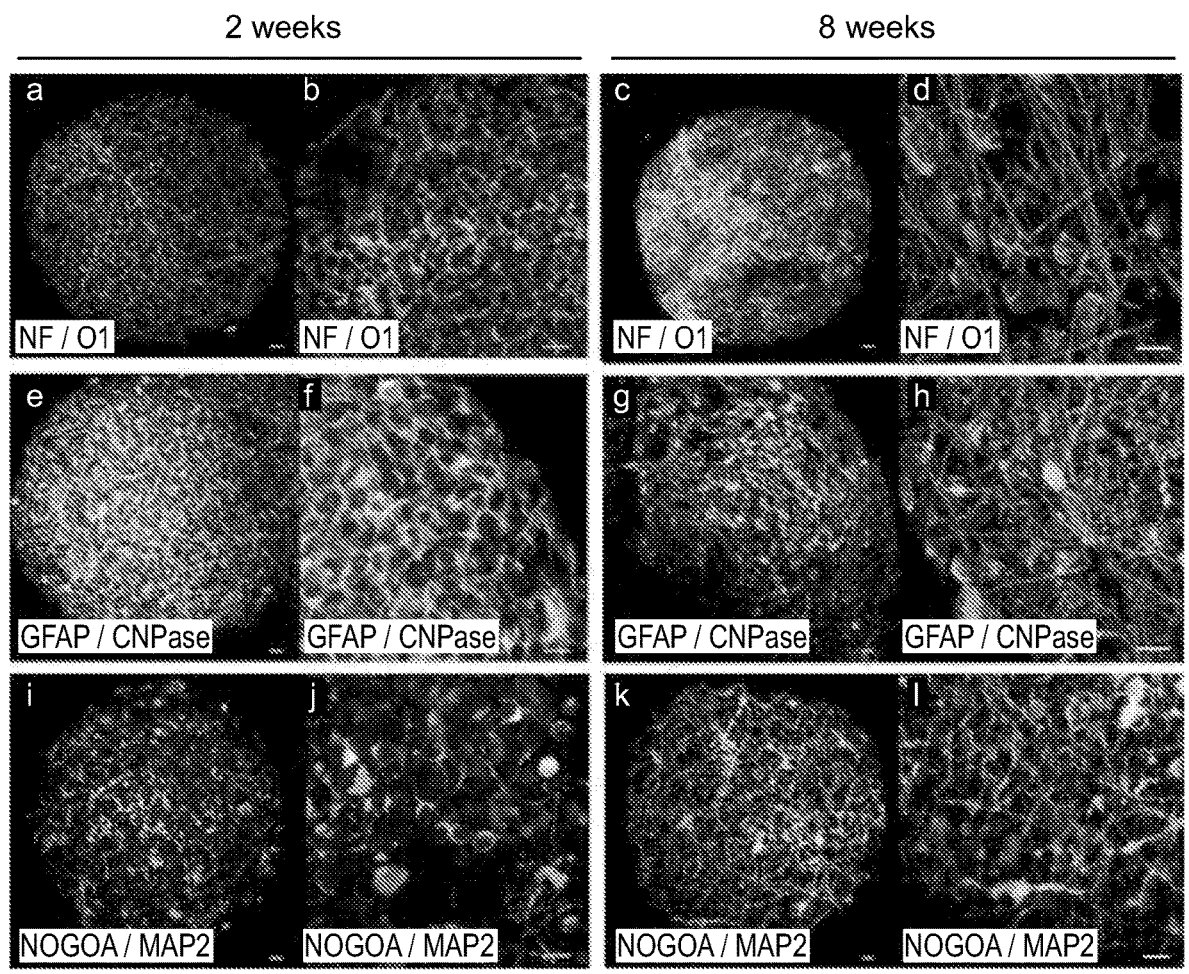
FIG. 2F depicts a comparison of expression of neuronal and glial markers at 2 and 8 weeks. At 2 weeks, oligodendrocytes (O1, CNPase, NOGOA) were identified without a preferential localization (a,b,c,f,i), later they resemble human oligodendrocytes and localize in close proximity with axons (c,d, g,h, k,l). At 2 weeks there are few MAP2-positive cells without identifiable neuronal shape (I,j) whereas at 8 weeks, the MAP2+ cells acquire a well-defined dendritic network (k,l). The amount of astrocytes and density of the astroglial network increases with time of differentiation (GFAP, g,h).

Similarly, populations of neuroglia such as astrocytes and oligodendrocytes were identified using specific antibody markers. A subset of neuroglial cells exhibit immunoreactivity for markers such as NOGOA, Olig1 and CNPase (FIG. 2C, panels a-f and 2C, panel i), which identify the presence of mature oligodendrocytes in the BMPS [29, 30, 31, 32]. This pattern of immunostaining suggests that oligodendrocytes within the BMPS are functional and myelinate axons. Similar to the in vivo physiology, these cells were also immunoreactive for myelin basic protein (MBP) (FIG. 2C panel i and 2C panel j), which characterizes myelinating oligodendrocytes [33, 30]. These cells had morphological features of normal human oligodendrocytes and appeared in close contact with neuron processes, which resemble axonal structures (FIG. 2C, panels j-m). In addition, a high number of mature astrocytes (FIGS. 2Ca, 2Cb, 2Cg, 2Ch and 2F) at 4 and 8 weeks of differentiation were observed. Morphometric studies of neuronal processes identified by immunostaining with NF antibodies and MBP markers were used to estimate the percentage of myelinated axons within the BMPS with an average of 4% at 2 weeks, 25% at 4 weeks and 42% at 8 weeks of differentiation (p<0.001) (FIG. 2D). All analyzed BMPS showed similar extent of myelination at the same differentiation window. Percentages were calculated as the mean of at least 18 microscopy fields from at least 3 individual BMPS in 2 different experiments. Ultrastructural analysis by electron microscopy demonstrated cell projections, which enwrapped cell processes resembling axons after 8 weeks of differentiation (FIG. 2C).

Figure 8C:
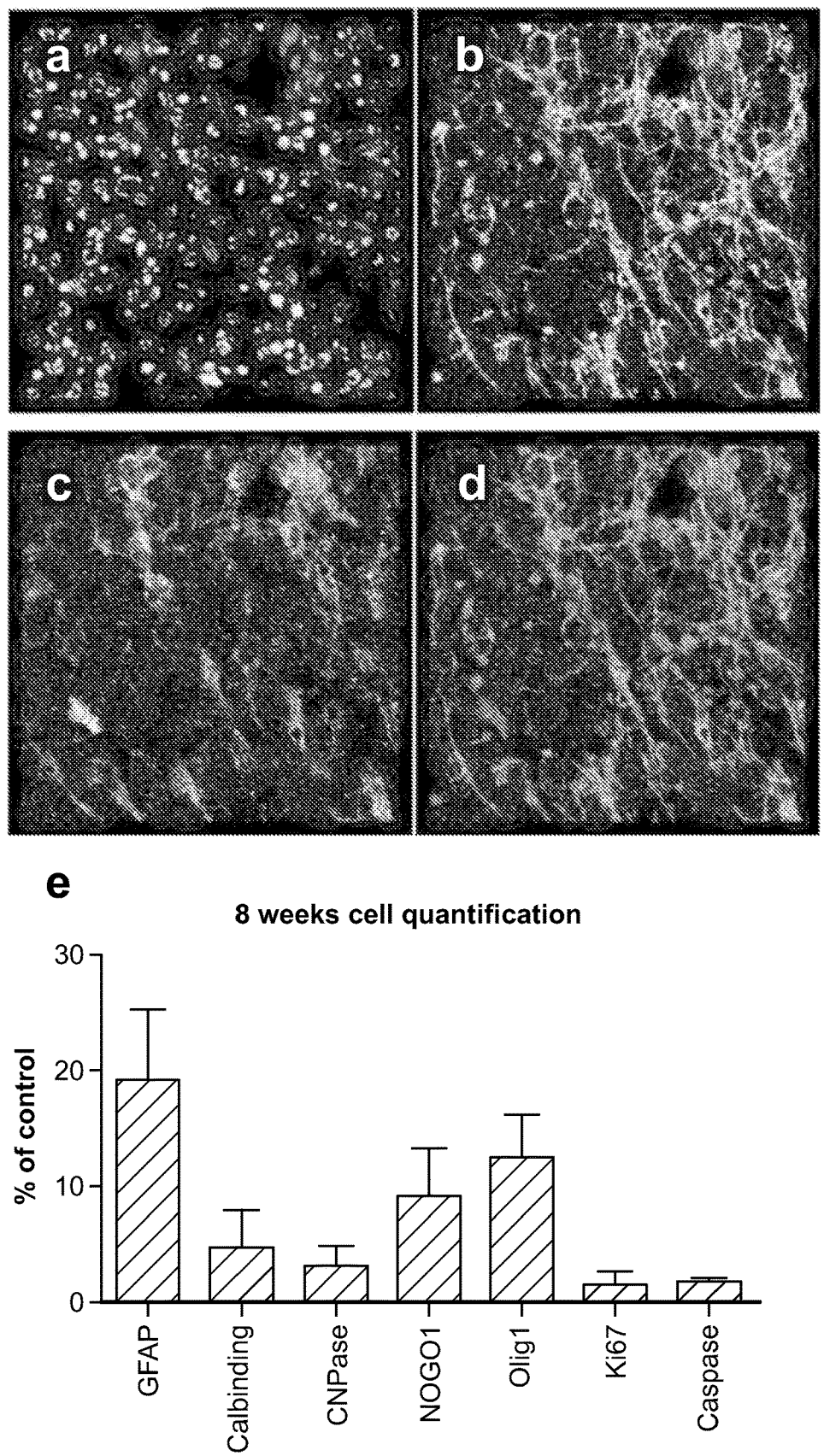

GFAP-positive cells formed numerous cell processes organized in a network typical for human astrocyte glial processes in vivo, which established contacts with other glial cells and neurons (FIG. 2Cg, 2Ch, 2F, and FIG. 8B). Image quantification revealed 19% of astrocytes in the total population (FIG. 8C). Altogether, the patterns of cell morphology, immunostaining and cell-cell interactions shown by neuronal and glial cell populations demonstrates that the BMPS recapitulates the cellular types and pattern of interactions seen in the human CNS and is, therefore, considered organotypic.

Figure 2G:
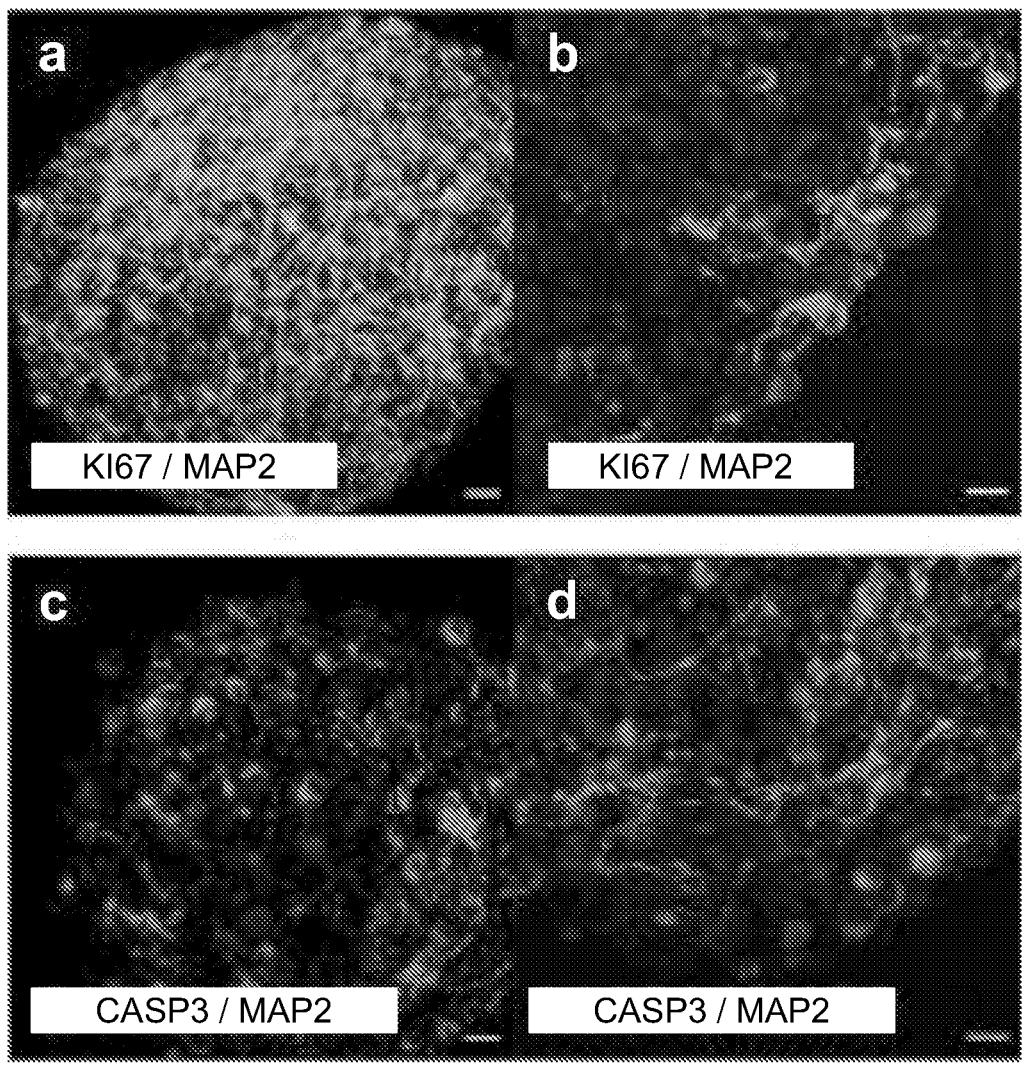
FIG. 2G depicts variation in the nuclear morphology. Co-immunostaining of neurons (MAP2) with cell-division marker KI67 showed that some cells are dividing (a,b), there was also a small degree of apoptosis demonstrated by positive staining with CASP3 (c). CASP 3-positive nuclei did not co-localize with mature neurons (d).
Figure 2H:
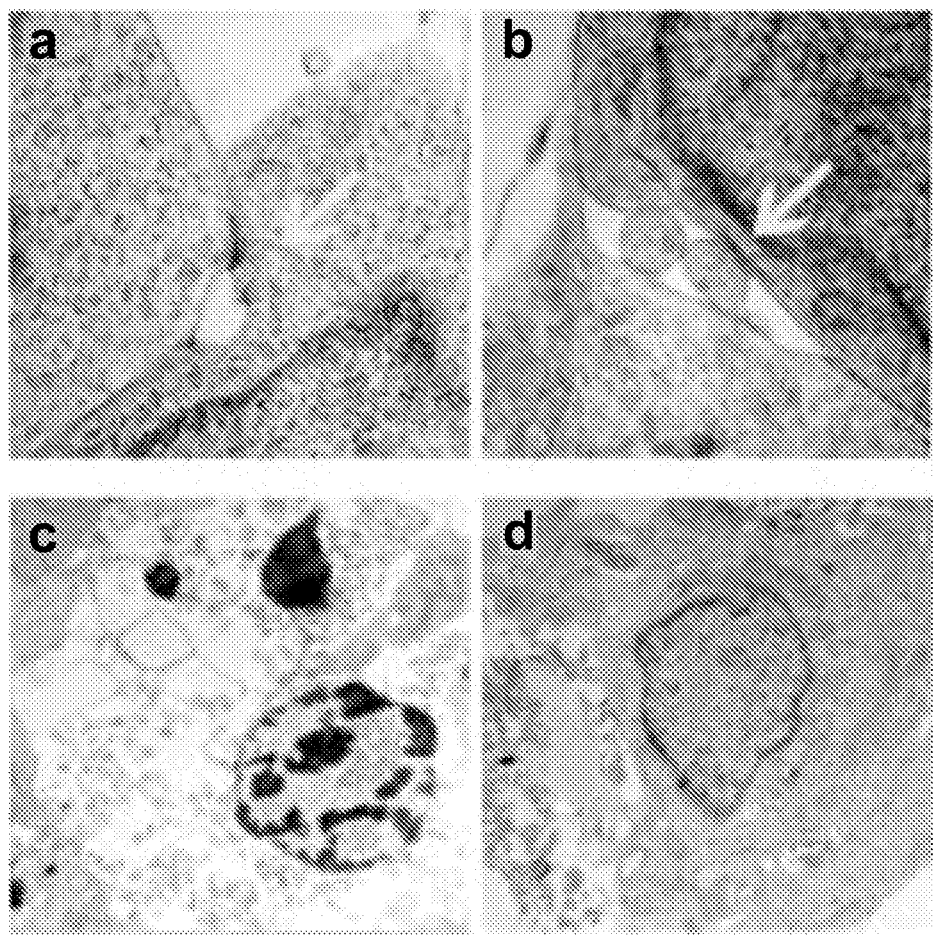
FIG. 2H depicts ultrastructure analysis by electron microscopy of 4 week BMPS showed evidence of cell to cell junctions demonstrating functional interactions between the cells (arrows, a,b). Nuclear variation was confirmed by the presence of a few apoptotic nuclei (c) and normal healthy nuclei (d). NF: Neurofilament-heavy-chain, MAP2: Microtubule-associated-protein 2, MBP: myelin-basic-protein, VGLUT1: Vesicular-glutamate-transporter 1, GFAP: Glial-fibrillary-acidic-protein, CALB: Calbindin, NOGOA: Neurite-outgrowth-inhibitor, SYP: Synaptophysin, SMI32: Non-phosphorylated-neurofilament, TH: Tyrosine-hydroxylase, O1: Olig1, CNPase: 2',3'-Cyclic-nucleotide-3'-phosphodiesterase. Scale Bar: 10 µm.
Figure 8D:
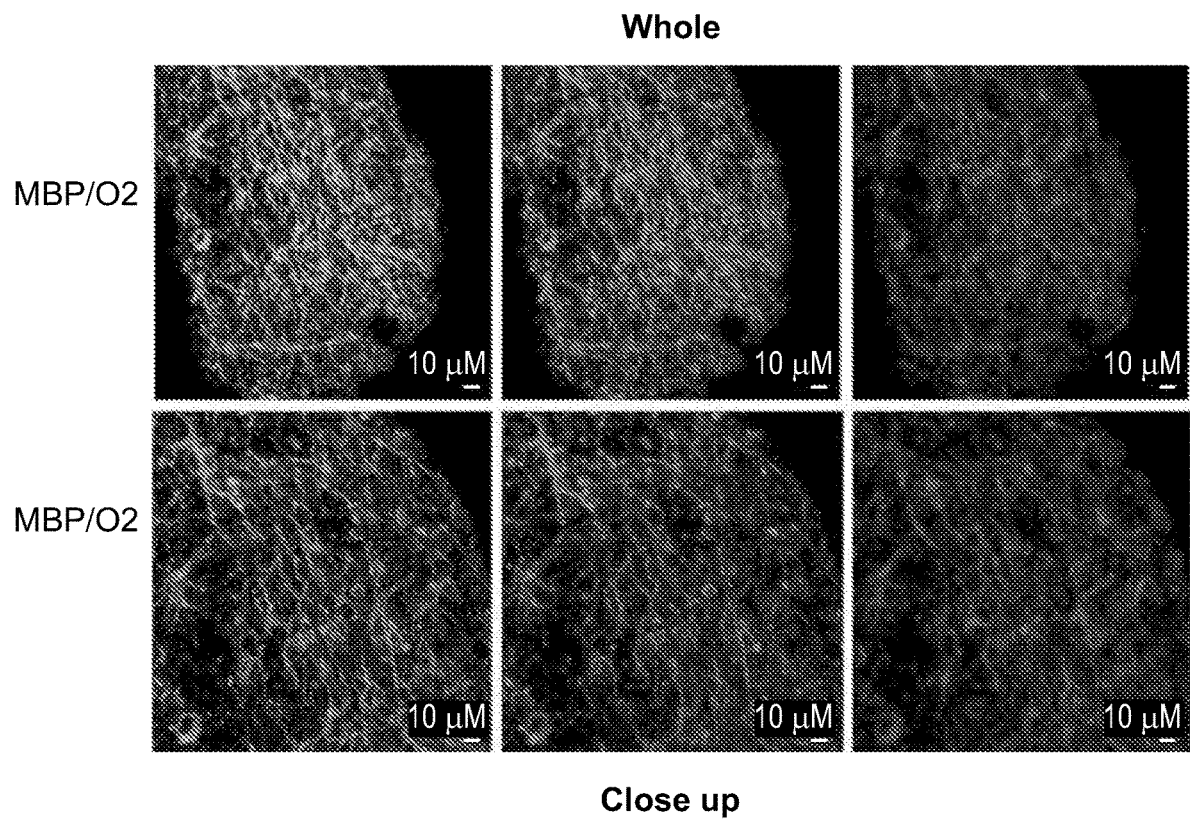
Figure 8E:
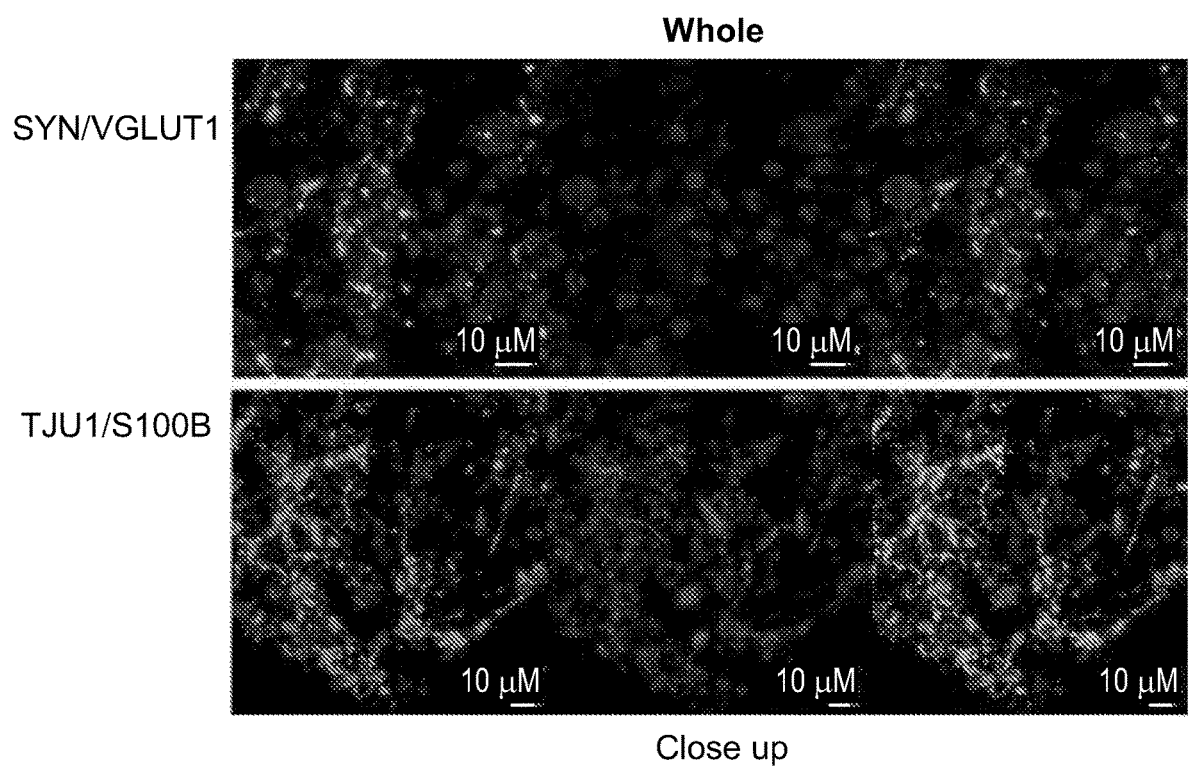

The morphology of cell nuclei observed by immunocytochemistry and electron microscopy showed some variation in nuclear morphology attributed to (i) cell proliferation as seen by positive staining for Ki67 and Nestin markers, and (ii) nuclear fragmentation likely associated with apoptosis as indicated by caspase 3 staining (FIG. 2G, 2H) was observed. These observations were also confirmed by electron microscopy studies at 4 and 8 weeks of differentiation (FIG. 2H). The variation of nuclei morphology likely reflects the active stages of cell differentiation that BMPS exhibited during all stages of development. The presence of apoptotic nuclei likely resemble stages of cell death seen in normal neurodevelopment [34, 35]. Importantly, Caspase 3-positive nuclei did not concentrate in the center of the spheres and BMPS did not present necrosis in the center of the 3D structures (FIG. 2G). Thus, Caspase3-positive nuclei do not appear linked to deprivation of oxygen or nutrients. Caspase has been quantified at eight weeks in BMPS (FIG. 8C). Additionally, FIGS. 8D and 8E depict co-expression of mature oligodendroglia markers (MBP and 02) and expression of neuronal markers (VGLUT, TUJ1, SYN), respectively.

Further analysis of neuronal cell populations and morphology presented a pattern of evolution that suggests BMPS maturation as seen by Nestin-positive cells decreasing over time of differentiation while MBP expressing cells increased (FIG. 2A). There was also evidence of cell-cell interactions as subsets of neurons showed several processes, which resemble dendritic and axonal projections that interact with other neurons as well as glial cells (FIG. 2B, FIG. 2H). Furthermore, cells immunostained with myelin binding protein (MBP) antibodies issued projections, which appear to enwrap neuronal processes, which resemble axons (FIG. 2C, panels i-k, 2C, panel m). The pattern of immunostaining with MBP and its association with neuronal processes suggests that oligodendrocytes within the BMPS exhibit myelinating properties such as in the human CNS in vivo. Ultrastructural analysis by electron microscopy demonstrated cell projections, which enwrapped cell processes resembling axons (FIG. 2C, panel m).

Example 5: Microelectrode Array Recording of Spontaneous Electrical Activity of BMPS To test the neurophysiological properties of the cells within the BMPS model, spontaneous electrical activity in BMPS was analyzed by micro-electrode array (MEA) (see FIG. 3 generally). BMPS were plated in 12-well or 48-well MEA plates at 8 weeks of differentiation. The aggregates were attached to the MEAs using Matrigel coating. Spontaneous electrical activity was measured starting one week after plating up to two weeks. The activity was measured for 20 minutes on 7 different days. Electrodes were considered active when the recorded activity was above 0.05 spikes/sec. FIG. 3A shows a representative heatmap of a 48-well MEA plate measurement from one 20 minute recording. The heatmap represents the spike amplitude ($\mu V$) with a minimum of 0 $\mu V$ and maximum of 40 $\mu V$ (FIG. 3A). The spikes showed a common waveform between different electrodes and measurements (FIG. 3B) and neurons were repeatedly firing. 25 electrodes, distributed over 19 wells, were included after the first step of data analysis. 20 to 40% of these 25 electrodes reached the threshold of 0.05 spikes/sec during each recording. FIG. 3F shows the spike events of active electrodes from one representative 20 minutes recording. These data show potential for the use of MEA to measure electrical activity of the 3D BMPS. Further optimization of the protocol may increase the measurement of the neuronal activity on the electrodes.

Example 6: A Human 3D Model to Study Parkinson's Disease

Due to the presence of TH-positive dopaminergic neurons in the iPSC-derived BMPS (FIG. 2B, panels k, 1, and FIG. 8), the possibility of using this model to study Parkinson's Disease (PD), a neurodegenerative disorder known to specifically affect dopaminergic neurons, was further explored. Two well-known neurotoxicants, which induce pathogenic processes resembling the mechanism associated with neurodegeneration in PD: the illicit drug MPTP's toxic metabolite MPP+ and the broadly used pesticide rotenone, were selected. Both MPP+ and rotenone interfere with oxidative phosphorylation in mitochondria by inhibiting complex I [36]. Initially, cytotoxicity experiments were performed to estimate sub-cytotoxic concentrations of these two compounds affecting only dopaminergic neurons (FIGS. 4A and 4C). Selective disruption of dopaminergic neurons but not of any other cell types in the systems described herein were observed with immunohistochemistry after exposure to 1 $\mu M$ rotenone and 100 $\mu M$ MPP+ for 24 h (FIGS. 4E and 4F). This effect was likely selective even at cytotoxic concentrations of 10 $\mu M$ rotenone and 1000 $\mu M$ MPP+ as these concentrations did not show any alterations in other neurofilament 200-positive neurons. Lower concentrations of these compounds may induce effects in dopaminergic neurons, however, the effect was not as obvious by immunocytochemistry. Higher concentrations of rotenone and MPP+

(up to 50 μM and 5000 μM, respectively) led to general cytotoxicity and affected also other neuronal types stained positive for neurofilament 200 (FIGS. 4E and F). 5 μM of rotenone and 1000 μM of MPP+ were selected for further studies as these concentrations induced clear and selective dopaminergic effects. Reactive oxygen species (ROS) were measured in the cellular medium using the OxiSelect™ In Vitro ROS/RNS Assay Kit (Cellbiolabs, San Diego, CA) as an indication of oxidative stress. Exposure to rotenone at 5 μM and MPP+ at 1000 μM showed an increase in ROS production after 24 hours exposure, while 12 hours showed no statistically significant changes. Real time RT-PCR was performed in order to determine effects of both chemicals on genes related to PD, mitochondrial dysfunction and oxidative stress. Tyrosine hydroxylase (TH, Dopaminergic neuronal marker) mRNA expression decreased by 84%±11 after exposure to 5 μM rotenone and 70%±9 after exposure to 1000 μM MPP+ for 24 hours. Additional genes related to PD also showed changes at sub-cytotoxic concentrations of MPP+ and rotenone. The expression of genes that encode T-box brain 1 (TBR1) and Alpha-synuclein (SNCA) protein decreased after 24 hours exposure. The reduction of TBR1 was 70±13% (rotenone) and 76±22% (MPP+) and the reduction of SNCA was 72±6% (rotenone) and 41±40% (MPP, however, BMPS exposed to 1 mM MPP+ led to no statistically significant changes in SNCA expression). Expression of genes related to mitochondrial function complex I (NDUFB1) or complex 0 (ATP5C1 or ATP50) tended to decrease in expression but these changes were not statistically significant. Caspase-1 gene expression, which has been related to SNCA, increased after 24 hours exposure to MPP+. These results demonstrate the potential of BMPS for studies elucidating molecular mechanisms of PD, lending itself to PD drug and neurotoxicity screening.

Example 7: Addition of Microglia

Peripheral blood mononuclear cells (PBMCs) are isolated from fresh or commercially available cryo-preserved whole blood of pooled healthy donors by Ficoll or Percoll gradient centrifugation. Monocyte populations are obtained by negative magnet-antibody selection after Ficoll or Percoll gradient and then re-suspend in RPMI 1640. Monocytes are cultured in macrophage serum-free medium, stimulated with a cocktail of cytokines, GM-CSF and IL-34. Monocytes may also be obtained by differentiation of iPSCs, hematopoetic or other stem cells. The microglia-like cells are combined with neuronal precursor cells in shaker cultures to preferably arrive at a final concentration of 5-8% microglia.

Primary monocytes or iPSC-derived monocytes may be incorporated into the system, both at early and later stages of BMPS differentiation. For the early stages, a number of $2 \times 10^6$ NPCs mixed with $2 \times 10^4$ monocytes are plated per 1 well (6 well-plate). Gyratory shaking is used at 88 rpms to generate spheres. After 2 days media are replaced with ½ CNS differentiation medial (Neurobasal® electro Medium (Gibco) supplemented with 5% B-27® Electrophysiology (Gibco), 1% glutamax (Gibco), 10 μg human recombinant GDNF (Gemini), 10 μg human recombinant BDNF (Gemini)) and ½ macrophage differentiation media (Dulbecco's modified Eagle's medium (Invitrogen) supplemented with 10% FCS, 0.055 mM B-mercaptoethanol, M-CSF (50 ng/ml), and IL-3 (25 ng/ml) (R&D Systems). The medium is replaced every 3 days.

Monocytes can also be incorporated after BMPS differentiation. For that, BMPS are differentiated up to 8 weeks. BMPS spheres are separated in 500 μl Eppendorf tubes. $2 \times 10^4$ monocytes are added to the Eppendorf with the BMPS. Tubes are shaking manually every hour, up to 8 hours. After that, BMPS-monocytes are collected and plated in 6 well plates. Cells are kept on constant shaking until use.

The characterization of the immune-competent human organoids can be carried out by immunocytochemically assessing the presence of markers such as HLA-DR, and the ionized calcium-binding adapter molecule 1 (Iba1), specific microglial markers. Measures of cytokines and chemokines release and expression of receptors associated with microglia function (e.g., CCL2 and CX3CL) demonstrates successful engrafting of the microglia cells. This modified model is more suitable to investigate the neuroimmunological component associated with many substance exposures and diseases.

Example 8: Addition of a Blood Brain Barrier

The blood brain barrier (BBB) has a crucial role in neurotoxicity, being the last barrier for substances before reaching the brain. Moreover, the BBB is the bottleneck in brain drug development and is the single most important factor limiting the future growth of neurotherapeutics [81]. Most of the in vitro models do not incorporate BBB.

Figure 7:
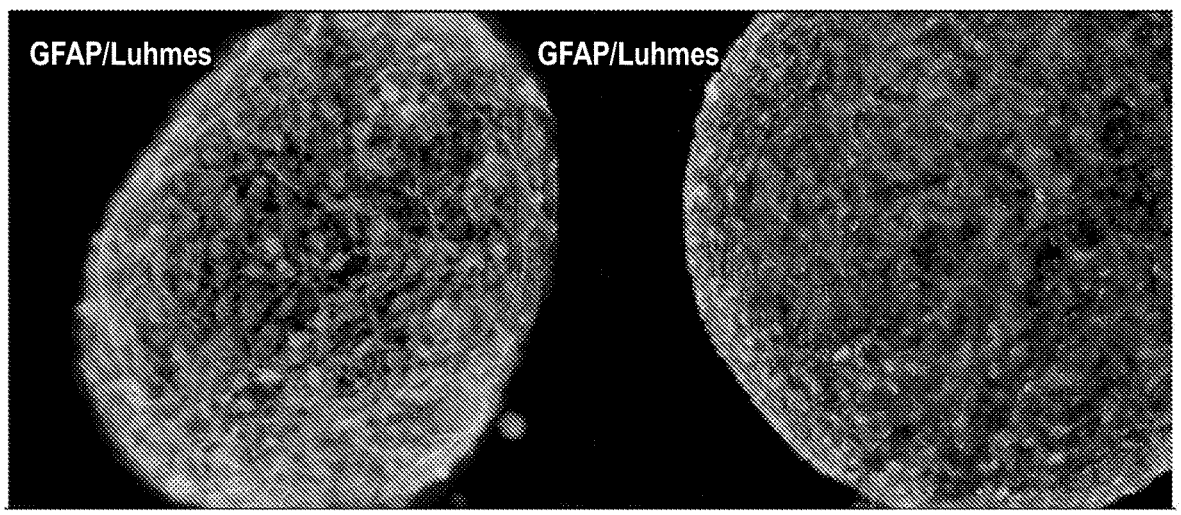
FIG. 7 depicts an example of a BMPS covered with other cell types. LUHMES fluorescent cells (red) were incorporated to a BMP using gravity systems to cover the surface of the aggregate.

Human brain microvascular endothelial cells (hBMECs) from human iPSCs are incorporated into the BMPS by two techniques. In the first approach, mature BBB endothelial cells and neuronal precursors cells (NPCs) are combined in a single cells suspension in a ratio of 1:5, gyratory shaking or stirring are used to generated spheroids and aggregates are cultured up to 8 weeks. In the second technique, mature BMPS (8 weeks of differentiation) are covered by BBB endothelial cells using gravity systems (aggrewell, gravity well or hanging drops). Cells may be covered as well with other cell types, such as fluorescent LUHMES cells (FIG. 7).

Example 9: Addition of Reporters

The BMPS gives the opportunity to develop cell-based assays allowing for high-content imaging (HCI) that can be adapted to high-throughput platforms, to evaluate the effects of toxicants on key cellular processes of neural development and physiology in the culture system.

Example of establishing fluorescent iPSC cell line: Creation of reporter cells lines greatly assists imaging efforts by allowing us to avoid complications associated with staining 3D cultures, to image subsets of cells, and to perform functional assays. Differentiated 3D aggregates from iPSC cultures spiked with 1-2% of iPSCs ubiquitously expressing fluorescent protein allow visualizing individual cells within the aggregates aiding quantification of phenotypic parameters, including neurite outgrowth and migration. Lines expressing markers allow measurement of synapse formation (PSD95, Synapsin 1), proliferation (Ki67), glial maturation (GFAP), and calcium signaling (GCaMP). Clustered Regularly Interspaced Short Palindromic Repeats/Cas (CRISPR) were used to create the various lines. Similar in function to the well-established zinc-finger (ZFNs) and TALEN nucleases, the Cas9-CRISPR system is a new entrant into the rapidly emerging field of genome engineering and has been quickly adopted and validated across a wide array of human stem cells. Gene-editing in hiPSCs has traditionally been a technically difficult task but with these advances it is now possible to generate reporter and mutant cell lines with genetically matched controls [83, 84, 85, 86]; essential tools not only for this project but also for the future success of using human iPSC-derived cells in quantitative live-cell phenotypic assays of toxicant testing.

Using the CRISPR-Cas9 system, fluorescent protein (FxP) reporter cell lines were generated by generating gRNAs targeting the gene of interested. In this system as described herein, an RNA guided Cas9 endonuclease is used in conjunction with customizable small guide RNAs (gRNAs) to target and cleave any DNA template with a GN21GG sequence; the first G is for the U6 polymerase promoter while the N21GG is for the protospacer adjacent motif (PAM) sequence requirement of Cas9 [86, 87, 89].

For reporter cell generation, homology-directed repair (HDR) guides the insertion of the appropriate DNA donor fragment into a target site at regions of homology between the donor fragment and the genomic DNA target. An ES line that ubiquitously expresses GFP was created by introducing CAG promoter-driven GFP into the AAVS1 safe harbor locus, and can use these constructs to transfect iPSC cells. For other reporters, constructs may be created that will direct the integration of a self-cleaving P2A peptide sequence targeted fluorescent protein cassette in frame at the stop codon of the gene of interest. The P2A sequence engineered between the C-terminus of the endogenous protein and the fluorescent protein may minimize possible fusion protein functional defects. Plasmids encoding the Cas9 nuclease, the targeting gRNA, and appropriate donor DNA will be introduced by electroporation, recombinant hiPSC clones will be manually selected and screened for the desired insertion by PCR, and the genotype may be verified by sequencing. Reporter hiPSCs will be subjected to a differentiation protocol and expression of the reporter validated by examining expression patterns and through immunohistochemistry experiments where it may be determined whether the FxP expressing cells co-label with known markers.

Example 10: Using Cells with Specific Genetic Backgrounds

The use of iPSCs, as described herein, has created new opportunities to study human diseases and gene/environment interaction [20, 21]. Fibroblasts or other somatic cells from healthy and diseased individuals can be reprogrammed into iPSCs, and subsequently be differentiated into all neural cell types. Similarly, iPSC can be genetically modified before creating the BMPS. As a proof-of-principle, iPSCs were obtained from patients with Down's syndrome (FIGS. 1C5 and 5A-D), Rett Syndrome and from individuals with mutations in disrupted in schizophrenia 1 (DISC1). DISC1 may have some functional overlap with TSC-iPSCs as both are involved in the mTOR cell signaling pathway.

The Down's syndrome model is further characterized (see FIGS. 5A-5D). Down's syndrome iPSCs have been successfully differentiated into neural precursor cells (NPCs). Currently the cells are differentiated in 3D and characterization by gene expression and immunohistochemistry is being performed. The Down's syndrome model has been exposed to compounds that induce oxidative stress (rotenone and paraquat). The response was compared to the model from healthy donors, which were more sensitive to these compounds than the healthy model.

Example 11: Combining the BMPS with Other Organoids

In some embodiments, BMPS may be combined with other organs and/or organ model systems. Several groups have been developing organ-on-a-chip platforms for different organs by using microfluidic techniques. Those platforms are designed to mimic in-vivo fluidic flows in the organs by separating cell culture chambers and perfusion channels, and successfully demonstrate recapitulation of iPSC-based organ functions. Together with other organ models on these platforms, the BMPS can be integrated, which allow us to untwine the complex toxicology from organ interactions. Such platforms allow (1) in-situ and high-throughput production of mini-brains on chip, (2) in-vivo like fluidic flow around mini-brains with enough supply of nutrient and small molecule through diffusion, (3) a large number of parallel test of toxic materials, and (4) a real-time monitoring of electrophysiological activities from BMPS with integrated electrodes. Companies such as TissUse GmbH have designed microfluidics platform that allow culture of floating spheres like the BMPS as described herein.

Example 12: Cryopreservation and Other Modes of Transportability

Figure 6:
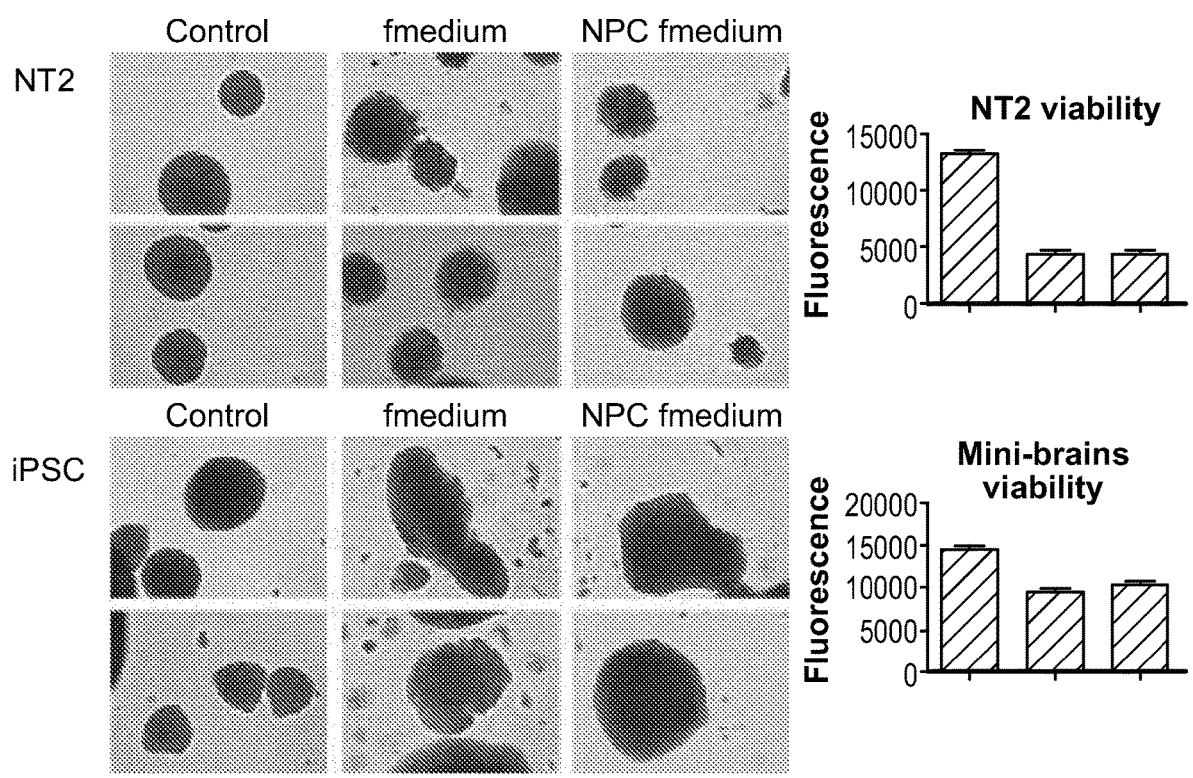
FIG. 6 depicts viability of pre-frozen NT2 human teratocarcinoma cell line and iPSC derived mini-brains. Fmedium corresponds to 95% FBS and 5% DMSO. NPC fmedium corresponds to STEMdiff™ Neural Progenitor Freezing Medium. Viability was measured by resazurin cell viability assay. Non-frozen cells at the same stage of differentiation were used as control aggregates.

In order to e.g. incorporate the BMPS into platforms or enable any use in other laboratories, transportability of the system was optimized. Preliminary studies have shown possible recovery of the neuronal 3D aggregates after cryopreservation (FIG. 6). A human embryonal carcinoma stem cell line, (hNT2), and iPSC derived-aggregates were differentiated into mature neurons (8 weeks of differentiation for each cell line) and then cryopreserved with regular cryopreservation medium (95% FBS and 5% DMSO) or STEMdiff™ Neural Progenitor Freezing Medium (Stem cells technologies). After 2 days in liquid nitrogen, cells were thawed. Freezing media was removed and fresh media was added. One day later, viability was measured using the resazurin cell viability assay. hNT2 aggregates presented a 70% decrease in viability in both freezing medias while iPSC derived mini-brains showed a 20%-35% reduction in viability (FIG. 6). However, viability recovery of the 3D aggregates is currently optimized using other viability and functional assays. Optimization of this protocol will vary additives (DMSO, HES, glycerol, serum etc.), the cooling temperature gradient as well as thawing protocol.

Human iPSC derived mini-brains are kept in culture at 37° C. In order to transport the live mini-brains, temperature must be controlled. Different methods can be used to control temperature during transport. Heating pads combined with an insulated box have been used to transport live biological material. Disposable chemical pads employ a one-time exothermic chemical reaction such as catalyzed rusting of iron, or dissolving calcium chloride. The most common reusable heat pads are based on a chemical reaction that transforms a liquid into a solid thus releasing energy. Some new heating pads (such as Deltaphase Isothermal Pad 3SET, from Braintree Scientific, Inc.) have been able to maintain 37° C. for more than 6 hours. 3D mini-brains cultured up to 8 weeks are sent in an insulated material box with heating pads. After transport, viability may be measured.

Example 13: Overview

The techniques herein provide a human BMPS model that is a versatile tool for more complex testing platforms, as well as for research into CNS physiology, mechanisms associated with (developmental) neurotoxicity, and pathogenesis of neurological disorders. Prior art stem cell-derived brain model systems developed in the past few years have shown the capability to recapitulate some of the in vivo biological processes (Juraver-Geslin and Durand, 2015; Nakano et al., 2012; Krug et al., 2014) and have an advantage over other classical in vitro models as they facilitate the study of various differentiation mechanisms, developmental processes and diseases (Lancaster et al., 2013). Unfortunately, these prior art systems require complicated protocols that reduce the reproducibility of the system and make it difficult to use in other fields such as chemical toxicity and drug screening. Additionally, these prior art models are also limited by large diameters, which lead to extensive cell death in the interior regions due to insufficient diffusion of oxygen and nutrients (Lancaster et al., 2013) and other artifacts.

The techniques herein overcome the limitations of the prior art by developing a human in vitro model by the gyratory shaking technique that enables reliably generation of a high number (about 500 per six-well plate) of viable BMPS that are homogeneous in size and shape. Control of size makes it possible to keep cell aggregates below 350 µM in diameter (FIG. 1C) and thereby avoid disparate morphology and/or necrosis in the center of the spheres. Moreover, the BMPS showed reproducible cell composition by immunomorphological quantification, assessment of imaging-based endpoints and flow cytometry analysis.

As described herein, the 3D differentiation protocol for the BMPS covers stages from neuronal precursors to different cell types of the mature CNS. As discussed in detail above, at two weeks, BMPS consisted of an immature population of cells, showing minimal neuronal networks, a low percentage of mature astrocytes and oligodendrocytes, and minimal but early stages of myelin basic protein (MBP) expression. iPSC differentiation into mature BMPS was indicated by decreasing NES expression over time and a progressive expression of mature neuronal and glial markers such as MAP2, GFAP, 01 and MBP. Gene expression studies, flow cytometry, image analysis, immunostaining and miRNA studies have shown increase of cell maturation markers, which follow the BMPS differentiation. The presence of GABAergic neurons, dopaminergic neurons and glutamatergic neurons was documented by immunohistochemistry and real-time PCR data. Moreover, the BMPS showed spontaneous electrical activity, indicating neuronal functionality of the system.

Since astrocytes and oligodendrocytes play important roles during neuronal development, plasticity and injury, the presence of glial cell populations in the presently disclosed BMPS model provides an excellent opportunity for the evaluation of neuronal-glial interactions and the role of glia in pathogenesis and toxicity processes. Astrocytes have an important role in protecting neurons, increasing neuronal viability and mitochondrial biogenesis from both exogenous (e.g. chemicals) and endogenous toxicity (Shinozaki et al., 2014; Aguirre-Rueda et al., 2015), especially against oxidative stress (Shao et al., 1997; Schwab and McGeer, 2008). Thus, their presence in a biological system to study disease and neurotoxicity is crucial. Immunohistochemistry and RT-PCR results showed increasing numbers of astrocytes (GFAP-positive cells) in the BMPS model reaching 19% astrocytes of the total cell population at eight weeks, which is earlier than in previously described cortical spheroids, where similar proportions of GFAP-positive cells were observed first at day 181. at day 86 the number of GFAP+ cells was below 10% (Pasca et al., 2015).

The most novel element of this BMPS is the presence of mature human oligodendrocytes with myelination properties, which has not been achieved in the prior art. Immunocytochemical and ultrastructural studies confirmed the morphological identity of these cells (FIG. 2D) as multiple markers for mature oligodendrocytes were expressed by rounded cells with branching processes and membrane sheaths that are similar to the ones found in humans in vivo. The structure and morphology was further confirmed by electron microscopy. Quantitative assessment of the myelination process of MBP immunostaining along axons showed an increase over time of differentiation reaching 42% of myelinated axons at eight weeks (FIG. 2D). 3D reconstruction of confocal z-stacks images (FIG. 2A) and electron microscopy confirmed the wrapping of axonal structures after eight weeks of differentiation (FIG. 2C). These findings are of particular relevance since myelin is a critical element for proper neuronal function and development, and the covering of axons by myelin allows faster action potential transmission, reduces axonal energy consumption and protects the axons from degeneration (Nave, 2010). Furthermore, recent evidence suggests that oligodendrocytes and myelin have a role in the metabolic support of axons independent of their role in action potential conduction, highlighting their importance in neuronal survival (Saab et al., 2013). This is the first time that a 3D human microphysiological system, consisting of different types of neurons and glial cells, has achieved such a high percentage of myelination. The ability to assess oligodendroglia function and mechanisms associated with myelination in this BMPS model provides an excellent tool for future studies of neurological disorders such as multiple sclerosis and other demyelinating disorders. As an illustration it was recently discovered that astroglia cells could promote oligodendrogenesis via secreted molecules (Jiang et al., 2016). A human BMPS that consist of neurons, astrocytes and oligodendrocytes is essential to evaluate this mechanism further and to develop a potential therapy for demyelinating disorders.

In conclusion, the techniques herein provide a BMPS that replicates crucial aspects of brain physiology and functionality. The potential for studying developmental and neurodegenerative disorders, brain infections, toxicity and trauma with such a system is growing. Furthermore, the potential to use iPSCs from different donors adds a personalized component to these studies. The high reproducibility and relatively simple protocol, enables future medium-throughput (96-well format) testing of chemicals, drugs and their potential to induce or treat diseases.

Methods and Materials

Chemicals

Rotenone and MPP+ were supplied from Sigma-Aldrich (St. Louis, MO). A 10 mM rotenone stock was prepared in DMSO Hybri-Max (Sigma) while MPP+ was diluted in water to a concentration of 30 mM.

iPSC Generation

CCD1079Sk (ATCC® CRL2097™), IPS IMR90 (WiCELL) and ATCCDYP0730 Human (IPS) Cells (ATCC® ACS1003™) fibroblasts were originally purchased from ATCC. All studies followed institutional IRB protocols approved by the Johns Hopkins University School of Medicine. Human fibroblasts and mouse embryonic fibroblasts (MEFs) were cultured in Dulbecco's modified Eagle's medium (DMEM, Mediatech Inc.) supplemented with 10% fetal bovine serum (FBS, HyClone) and 2 mM L-glutamine (Invitrogen). MEFs were derived from E13.5 CF-1 mouse embryos. Human iPCS cells were generated with the EBV-based vectors as previously described [75]. iPSC from other sources were used as well. Colonies of iPSCs were manually picked after 3-6 weeks for further expansion and characterization. iPSCs (passage≤20) were cultured on irradiated MEFs in human embryonic stem cell (hESC) medium comprising D-MEM/F12 (Invitrogen), 20% Knockout Serum Replacement (KSR, Invitrogen), 2 mM L-glutamine (Invitrogen), 100 µM MEM NEAA (Invitrogen), 100 µM β-mercaptoethanol (Invitrogen), and 10 ng/mL human basic FGF (bFGF, PeproTech). Media were changed daily and iPSC lines were passaged using collagenase (Invitrogen, 1 mg/ml in D-MEM/F12 for 1 hr at 37° C.). These iPSC lines have been previously fully characterized [75].

Neuronal Progenitor Cells (NPC) Production

NPC generated followed the previous published protocol [75]. Briefly, iPSCs colonies were detached from the feeder layer with collagenase (1 mg/ml) treatment for 1 hr and suspended in EB medium, comprising of FGF-2-free hESC medium supplemented with Dorsomorphin (2 µM) and A-83 (2 µM), in non-treated polystyrene plates for 4 days with a daily medium change. After 4 days, EB medium was replaced by neural induction medium (hNPC medium) comprising of DMEM/F12, N2 supplement, NEAA, heparin (2 µg/ml) for 15 more days. The floating neurospheres were then dissociated to single cells in Accutase and plated in 175 mm flasks and were allowed to expand for 7 days. NPCs were expanded in poly-1-ornithine and laminin-coated 175 mm flask on StemPro® NSC SFM (Life Technologies). Half of the media was changed every day. Cultures were maintained at 37° C. in an atmosphere of 5% $CO_2$. After NPC generation, iPSCs colonies were detached and NPCs were expanded in poly-1-ornithine and laminin-coated 175 mm flask in StemPro® NSC SFM (Life Technologies). Half of the media was changed every day. Cultures were maintained at 37° C. in an atmosphere of 5% $CO_2$.

BMPS Differentiation

At 100% confluence NPCs were detached mechanically and counted. $2 \times 10^6$ cells per well were plated in 2 ml of medium in non-treated 6 well-plates. Cells were grown in NPC media for two days under constant gyratory shaking. Subsequently, medium was changed to differentiation medium (Neurobasal® electro Medium (Gibco) supplemented with 5% B-27® Electrophysiology (Gibco), 1% glutamax (Gibco), 0.02 µg/ml human recombinant GDNF (Gemini), 0.02 µg/ml human recombinant BDNF (Gemini)). Cultures were maintained at 37° C. 5% $CO_2$ under constant gyratory shaking for up to 8 weeks. Differentiation medium was routinely changed every 2 days.

Size Measurement

Aggregates (n=20) from 3 independent experiments were randomly selected per time point for obtaining pictures and measuring size using SPOT software 5.0. Results were expressed as mean±SD. Cells were kept two days in NPC medium, indicated as NPC med. 2d in FIG. 1B.

RNA and miRNA Extraction

Total RNA was extracted from aggregates every week up to 8 weeks of differentiation using Tripure (Roche, Switzerland) according to Chomczynski and Sacchi (1987) [76]. The same RNA extraction method was used to isolate RNA after toxicant treatment. RNA quantity and purity was determined using NanoDrop 2000c (Thermo Scientific). One microgram of RNA was reverse-transcribed using the M-MlV Promega Reverse Transcriptase (Promega) according to the manufacturer's recommendations. For miRNA reverse-transcription 60 ng of RNA were reverse transcribed using TaqMan microRNA Reverse transcription kit in combination with miRNA specific stem-loop primers, which are a part of TaqMAn microRNA expression assay. Upto eight stem-loop primers were multiplexed in one reaction.

Quantitative RT-PCR

The expression of genes was evaluated using specific Taqman® gene expression assays (Life Technologies). miRNA expression was analyzed using TaqMAn microRNA expression assay in combination with TaqMan miRNA Reverse Transcription kit using protocol described in [77]. Table 1 shows a summary of the genes assayed. Real time RT-PCRs were performed using a 7500 Fast Real Time system machine (Applied Biosystems). Fold changes were calculated using the 2 $(-\Delta\Delta Ct)$ method [78]. B-actin and 18s were used as a housekeeping genes for mRNA and RNU44 for miRNA. There were no statistically significant differences in expression for β-actin, 18s, and RNU44. Data were presented as mean±SD, normalized to housekeeping genes and week 0.

Immunocytochemistry of the BMPS

BMPS aggregates were collected at 2, 4 and 8 weeks. BMPS were fixed in 4% paraformaldehyde for 1 hour, washed 3 times in PBS, then incubated for 1 hour in blocking solution consisting of 5% normal goat serum (NGS) in PBS with 0.4% TritonX (Sigma). BMPS were then incubated at 4° C. for 48 hours with a combination of primary antibodies (Table 2) diluted in PBS containing 3% NGS and 0.1% TritonX. BMPS were washed in PBS 3 times after which they were incubated with the appropriate fluorophore-tagged secondary antibody for 1 hour in PBS with 3% NGS at room temperature. Double immunostaining was visualized using the proper combination of secondary antibodies (e.g., goat anti-rabbit secondary antibody conjugated with Alexa 594 and goat anti-mouse secondary antibody conjugated with Alexa 488 (Molecular Probes). Nuclei were counterstained with DRAQ5 dye (Cell Signaling; 1:5000 in 1×PBS) or NucRed Live (Molecular Probes) for 15 minutes before mounted on slides with coverslips and Prolong Gold antifade reagent (Molecular Probes); BMPS used as negative controls for immunostaining were processed omitting the primary antibody. Images were taken using a Zeiss UV-LSM 510 confocal microscope. The experiments were performed in duplicates; at least three different fields of view were analyzed for each combination of antibodies. 3D reconstruction was done using Imaris 7.6.4 software for scientific imaging.

TABLE 2

Primary Antibodies.

| Antibody | Host | Type | Source | Dilution |
|---|---|---|---|---|
| NF-H | Rabbit | Polyclonal | Enzo | 1:1000 |
| GFAP | Rabbit | Polyclonal | Dako | 1:500 |
| Olig 1 | Mouse | Monoclonal | Millipore | 1:500 |
| CNPase | Mouse | Monoclonal | Millipore | 1:500 |
| Calbindin | Mouse | Monoclonal | SIGMA | 1:500 |
| NOGO-A | Rabbit | Polyclonal | Santa Cruz | 1:500 |
| Map2 | Mouse | Monoclonal | Chemicon | 1:1000 |
| MBP/SMI99 | Mouse | Monoclonal | COVANCE | 1:1000 |
| SMI-32 | Mouse | Monoclonal | Stenberger Monoclonals | 1:2000 |
| Synaptophysin | Mouse | Monoclonal | SIGMA | 1:500 |
| VGLUT1 | Rabbit | Polyclonal | Alpha Diagnostic | 1:500 |
| TH | Mouse | Monoclonal | Millipore | 1:250 |
| Nestin | Rabbit | Polyclonal | Millipore | 1:200 |
| Ki67 | Rabbit | Polyclonal | abcam | 1:100 |
| Caspase3 | Rabbit | Polyclonal | R&D | 0.2 µg/ml |
| OLIG1 | Mouse | Monoclonal | Millipore | 1:200 |
| TUJ1 | Mouse | Monoclonal | Stemcell technologies | 1:200 |
| S100B | Rabbit | Polyclonal | Santa Cruz | 1:200 |

Automated Quantitation of Cell Types

BMPS was differentiated for 8 weeks. Randomly selected pictures from three experiments were acquired by confocal imaging and then analyzed with a custom algorithm created with the Cellomics TargetActivation (Thermo Fisher Scientific, Pittsburgh, PA) image-analysis software package. With this algorithm, cells were identified based on DRAQ5 stained nucleus and quantified oligodendrocytes and astrocytes based on staining of CNPase, NOGO1 and GFAP.

Myelination Assessment and Quantification

To calculate the percentage of axonal myelination, a semi-automated computer platform was used, termed computer-assisted evaluation of myelin formation (CEM) [82], which uses NIH Image J built-in tools as well as a Math lab processing functions. The results were generated as pixel counts and percent values. The percent of myelinated axons was calculated by dividing the pixel count for myelin by the pixel count for axons after cell body removal and multiplying by 100. For each time point at least 18 fields from at least two independent experiments were analyzed.

Electron Microscopy

BMPS aggregates were collected at 2, 4 and 8 weeks and were fixed in 2% glutaraldehyde and 4% formaldehyde in 0.1M Sodium Cacodylate buffer (EMS, electron microscopy sciences) pH 7.4 with 3% sucrose and 3 mM $CaCl_2$). Post-fixation was done with 2% osmium for 2 hours. The BMPS aggregates were then stained en bloc with 2% uranyl acetate in distilled water for 30 min and subsequently dehydrated in graded ethanol. Embed 812 (EMS) was used as the embedding media. Thin sections (70-80 nm) were cut on a Reichert Jung Ultracut E microtome and placed on formvar coated 100 mesh copper grids. The grids were stained with uranyl acetate and followed by lead citrate. All imaging was performed on a Zeiss Libra 120 electron microscope with a Veleta (Olympus) camera.

Treatment and Cytotoxicity Assay

BMPS was exposed to different concentrations of rotenone and MPP+ for 24 and 48 hours after 4 weeks of differentiation. Rotenone working solutions were prepared in differentiation medium from 10 nM or 100 µM stocks to reach final concentrations of 0.1, 1. 10, 25 and 50 µM. DMSO was used as vehicle control. MPP+ working solutions were prepared in differentiation medium from 30 mM stocks to reach final concentrations of 10, 50, 100, 500, 1,000, 5,000 and 10,000 µM. Four independent experiments in 3 replicates were performed for each experimental condition (control and toxicant exposure for the different time points). Resazurin reduction assay was performed in order to determine cell viability after rotenone and MPP+ treatment. Resazurin (7-Hydroxy-3H-phenoxazin-3-one 10-oxide) is a blue dye that is reduced into red fluorescent resorufin by redox reactions in viable cells. 100 µl Resazurin (2 mg/ml stock) were added directly to the 6 well plates (2 ml/well). Plates were incubated for 3 h at 37° C., 5% $CO_2$. Subsequently, 50 µl of medium were transferred from each well in triplicates to a 96-well plate and fluorescence was measured at 530 nm/590 nm (excitation/emission) using a multi-well fluorometric reader CytoFluor series 4000 (PerSeptive Biosystems, Inc). Data were presented as mean±SD. Statistical analysis was performed using Dunnett's test.

Reactive Oxygen Species Measurement

Reactive oxygen species (ROS) were measured in cell media collected 24 hours after treatment with 5 µM rotenone or 1,000 µM MPP+ using the OxiSelect™ In Vitro ROS/RNS Assay Kit (Cell Biolabs, San Diego, CA). This is a fluorescence-based assay measuring the presence of total free radicals within a sample and was used according to the manufacturer's protocol. The quenched fluorogenic dye dichlorodihydrofluorescin-DiOxyQ (DCFH-DiOxyQ) which is similar to the popular 2',7'-dichlorodihydrofluorescein diacetate (DCFH-DA) is first primed with a quench removal reagent. The resulted highly reactive non-fluorescent DCFH can react with present ROS species in the cell supernatant and is then oxidized to the highly fluorescent DCF (2',7'-dichlorodihydroxyfluorescein). At every time point, 50 µl of the cell supernatant was added to a 96-well plate in triplicates and was mixed and incubated with the DCFH-DiOxyQ for 45 minutes. The fluorescence intensity was measured with a fluorescence microplate reader at 480 nm/530 nm (excitation/emission) and was proportional to the total ROS/RNS levels within the sample.

Flow Cytometry

In order to quantify percentage of NPCs, and neurons within the aggregates, flow cytometry with NPC and neuronal markers was performed. Flow cytometry was performed according to previously published protocol with some optimization steps for 3D cultures. Aggregates were washed once with PBS/1 mM EDTA and trypsinized directly in the well using TrypLE Express containing 4 units/ml DNAse for 30 min at 37° C. on the shaker. Pipetting the aggregates up and down with a 1 ml syringe and a 26G3/8 needle ensured generation of single cell suspension. Cells were counted, washed once with PBS/1 mM EDTA, fixed with 2% PFA for 20 min at 4° C., washed twice with PBS/1% BSA (wash solution I, WS I) and blocked for 30 min in blocking solution (PBS/1% BSA/0.15% saponin/10% NGS). $1 \times 10^6$ cells were stained for one hour at 4° C. with fluorochrome-conjugated antibodies dissolved in blocking solution (Table 3). Unstained cells as well as cells incubated with isotype controls were used as negative controls to set the gates for measurements. Cells were washed twice with PBS/1% BSA/0.15% saponin, once with PBS/1% BSA. Flow cytometry was performed using a Becton Dickinson FACSCalibur system by measuring $10^4$ gating events per measurement. Data was analyzed using FlowJo v10 software.

TABLE 3

Antibodies for flow cytometry analysis

| Antibodies | Host | type | Source | Dilution |
|---|---|---|---|---|
| Alexa Fluor ® 647 Nestin | Mouse | Monoclonal, clone 25 | BD Pharmingen | 1:05 |
| Alexa Fluor ® 488 β-III-Tubulin | Mouse | Monoclonal, clone TUJ1 | BD Pharmingen | 1:05 |
| PerCP-Cy ™ 5.5 Sox2 | Mouse | Monoclonal, clone 030-678 | BD Pharmingen | 1:20 |
| PerCP-Cy ™ 5.5 Sox1 | Mouse | Monoclonal, clone N23-844 | BD Pharmingen | 1:20 |
| PE Doublecortin | Mouse | Monoclonal, clone 30 | BD Pharmingen | 1:20 |
| Alexa Fluor ® 647 Ki67 | Mouse | Monoclonal, clone B56 | BD Pharmingen | 1:20 |

Microelectrode Array (MEA) Recordings

After 8 weeks of differentiation, BMPS were plated on 48-well MEA plates previously coated with Matrigel. During two weeks spontaneous electrical activity was recorded using the 'Maestro' MEA platform and Axion's Integraded Studio (AXIS) software [Axion Biosystems inc.; Atlanta, US]. Each well of the 48-well MEA plate contains 16 individual microelectrodes (~40-50 μm diameter, center-to-center spacing 350 μm) with integrated ground electrodes, resulting in a total of 768 electrodes/plate. The 'Maestro' MEA platform has an integrated heating system, which can be controlled by AXIS software. All recordings were performed at a constant temperature of 37° C. Prior to a twenty minutes recording, the MEA plates were placed in the Maestro MEA platform and equilibrated for five min. AXIS software was used to control heating system and monitor the recordings, which includes simultaneously sampling of the channels at 12.5 kHz/channel with a gain of 1200× and a band pass filter of 200-5000 Hz. The recordings were converted into RAW files. After a recording the RAW-files were re-recorded with AXIS to convert the data into a spike file, which includes spike timing and profile information. A variable threshold spike detector was used for the spike-file, it was set at 6 times standard deviations of the rms-noise on each channel. The spike file was later used for data analysis with NeuroExplorer® [Nex Technologies, Madison (AL), US] to convert data into Microsoft Excel files. Using the function rate histogram, a summary of the spikes of all electrodes of one plate was put into one Excel sheet. Only electrodes that recorded activity higher than 0.05 spikes/sec at least once over the time measured were included for data analysis.

Statistical Analysis

Statistical analysis was performed using GraphPad InStat 3. The Dunnett's test was applied to all the experiments shown here that compare to a control group. Statistically significant values (p<0.01) are marked with an asterisk (*). For myelination quantification at the different time points, a Kruskal-Wallis test was employed, statistical significance was considered for p values<0.05.

REFERENCES

1. K. Y. Liu, M. King, P. S. Bearman. Social influence and the autism epidemic. *AJS* 115, 1387-434 (2010).
2. M. Rutter. Incidence of autism spectrum disorders: changes over time and their meaning. *Acta. Paediatr.* 94, 2-15 (2005).
3. S. K. Van Den Eeden, C. M. Tanner, A. L. Bernstein, R. D. Fross, A. Leimpeter, D. A. Bloch, L. M. Nelson. Incidence of Parkinson's disease: variation by age, gender, and race/ethnicity. *Am. J. Epidemiol.* 157, 1015-22 (2003).
4. W, A. Kukull, R. Higdon, J. D. Bowen, W. C. McCormick, L. Teri, G. D. Schellenberg, G. van Belle, L. Jolley, E. B. Larson. Dementia and Alzheimer disease incidence: a prospective cohort study. *Arch. Neurol.* 59, 1737-46 (2002).
5. C. Mo, A. J. Hannan, T. Renoir. Environmental factors as modulators of neurodegeneration: Insights from gene-environment interactions in Huntington's disease. *Neurosci. Biobehav. Rev.* 52, 178-192 (2015).
6. S. Karama, S. Ducharme, J. Corley, F. Chouinard-Decorte, J. M. Starr, J. M. Wardlaw, M. E. Bastin, I. J. Deary. Cigarette smoking and thinning of the brain's cortex. *Mol. Psychiatry*. In press (2015).
7. O. van de Rest, A. A. Berendsen, A. Haveman-Nies, L.C. de Groot. Dietary Patterns, Cognitive Decline, and Dementia: A Systematic Review. *Adv. Nutr.* 13, 154-168. (2015)
8. L. Smirnova H. T. Hogberg, M. Leist and T. Hartung. Developmental neurotoxicity-challenges in the 21st century and in vitro opportunities. *ALTEX* 31, 129-156 (2014),
9. T. Hartung. Look back in anger-what clinical studies tell us about preclinical work. *ALTEX.* 30, 275-91 (2013)
10. T. Hartung. Food for thought . . . on cell culture. *ALTEX.* 24, 143-52 (2007)
11. D. Huh, D. C. Leslie, B. D. Matthews, J. P. Fraser, S. Jurek, G. A. Hamilton, K. S. Thorneloe, M. A. McAlexander, D. E. Ingber. A human disease model of drug toxicity-induced pulmonary edema in a lung-on-a-chip microdevice. *Sci. Transl. Med.* 7, 4 (159): 159ra147 (2012).
12. D. Pamies, T. Hartung, H. T. Hogberg. Biological and medical applications of a brain-on-a-chip. *Exp. Biol. Med.* 239,1096-107 (2014)
13. A. Agarwal, J. A. Goss, A. Cho, M. L. McCain, K. K. Parker. Microfluidic heart on a chip for higher throughput pharmacological studies. *Lab on a chip* 13, 3599-3608 (2013).
14. H. T. Hogberg, J. Bressler, K. M. Christian, G. Harris, G. Makri, C. O'Driscol, D. Pamies, L. Smirnova, Z. Wen, T. Hartung. Toward a 3D model of human brain development for studying gene/environment interactions. *Stem. Cell. Res. Ther.* 4 Suppl 1: S4 (2013).
15. M. A. Lancaster, M. Renner, C. A. Martin, D. Wenzel, L. S. Bicknell, M. E. Hurles, T. Homfray, J. M. Penninger, A. P. Jackson, J. A. Knoblich. Cerebral organoids model human brain development and microcephaly. *Nature* 19, 373-9 (2013).
16. Kadoshima T, Sakaguchi H, Nakano T, Soen M, Ando S, Eiraku M, Sasai Y. Self-organization of axial polarity, inside-out layer pattern, and species-specific progenitor dynamics in human ES cell-derived neocortex. *Proc. Natl. Acad. Sci. USA.* 110, 20284-9 (2013).
17. D. Huh, H. J. Kim, J. P. Fraser, D. E. Shea, M. Khan, A. Bahinski, G. A. Hamilton, D. E. Ingber. Microfabrication of human organs-on-chips. *Nat. Protoc.* 8, 2135-57 (2013).
18. N. Alépée, A. Bahinski, M. Daneshian, B. De Wever, E. Fritsche, A. Goldberg, J. Hansmann, T. Hartung, J. Haycock, H. Hogberg, L. Hoelting, J. M. Kelm, S. Kadereit, E. McVey, R. Landsiedel, M. Leist, M. Lübberstedt, F. Noor, C. Pellevoisin, D. Petersohn, U. Pfannenbecker, K. Reisinger, T. Ramirez, B. Rothen-Rutishauser, M. Schäfer-Korting, K. Zeilinger, M. G. Zurich. State-of-the-art of 3D cultures (organs-on-a-chip) in safety testing and pathophysiology. *ALTEX.* 31, 441-77 (2014).
19. T. Hartung, J. Zurlo. Alternative approaches for medical countermeasures to biological and chemical terrorism and warfare. *ALTEX.* 29, 251-60 (2012).
20. K. Takahashi, K. Tanabe, M. Ohnuki, M. Narita, T. Ichisaka, K. Tomoda, S. Yamanaka. Induction of pluripotent stem cells from adult human fibroblasts by defined factors. *Cell* 131:861-872 (2007).
21. J. Yu, M. A. Vodyanik, K. Smuga-Otto, J. Antosiewicz-Bourget, J. L. Frane, S. Tian, J. Nie, G. A. Jonsdottir, V. Ruotti, R. Stewart, I. I. Slukvin, J. A. Thomson. Induced pluripotent stem cell lines derived from human somatic cells. *Science* 318:1917-1920 (2007)
22. Y. Tsai, B. Lu, B. Bakondi, S. Girman, A. Sahabian, D. Sareen, C. N. Svendsen, S. Wang. Human iPSC-Derived Neural Progenitors Preserve Vision in an AMD-like Model. *Stem. Cells.* In press (2015).
23. K. Nieweg, A. Andreyeva, B. van Stegen, G. Tanriöver, K. Gottmann. Alzheimer's disease-related amyloid-β induces synaptotoxicity in human iPS cell-derived neurons. *Cell. Death. Dis.* In press. (2015)
24. S. Raitano, L. Ordovàs, L. De Muynck, W. Guo, I. Espuny-Camacho, M. Geraerts, S. Khurana, K. Vanuytsel, B. I. Tóth, T. Voets, R. Vandenberghe, T. Cathomen, L. Van Den Bosch, P. Vanderhaeghen, P. Van Damme, C. M. Verfaillie. Restoration of progranulin expression rescues cortical neuron generation in an induced pluripotent stem cell model of frontotemporal dementia. *Stem Cell Reports.* 13, 16-24 (2015).
25. H. Monyer, R. Sprengel, R. Schoepfer, A. Herb, M. Higuchi, H. Lomeli, N. Burnashev, B. Sakmann, P. H. Seeburg. Heteromeric NMDA receptors: molecular and functional distinction of subtypes. *Science* 256, 1217-1221 (1992).
26. X. Li, P. Jin. Roles of small regulatory RNAs in determining neuronal identity. *Nat. Rev. Neurosci.* 11, 329-38 (2010).
27. C. Tarantino, G. Paolella, L. Cozzuto, G. Minopoli, L. Pastore, S. Parisi, T. Russo. miRNA 34a, 100, and 137 modulate differentiation of mouse embryonic stem cells. *FASEB Journal* 24, 3255-3263 (2010).
28. D. Yang, T. Li, Y. Wang, Y. Tang, H. Cui, X. Zhang, D. Chen, N. Shen, W. Le W. miR-132 regulates the differentiation of dopamine neurons by directly targeting Nurr1 expression. *Journal of Cell Science* 125, 1673-1682 (2012).
29. D. Edbauer, J. R. Neilson, K. A. Foster, C. F. Wang, D. P. Seeburg, M. N. Batterton, T. Tada, B. M. Dolan, P. A. Sharp, M. Sheng. Regulation of synaptic structure and function by FMRP-associated microRNAs miR-125b and miR-132. *Neuron* 65, 373-384 (2010).
30. S. U. Kim, F. A. McMorris, T. J. Sprinkle. Immunofluorescence demonstration of 2': 3'-cyclic-nucleotide 3'-phosphodiesterase in cultured oligodendrocytes of mouse, rat, calf and human. *Brain Res.* 300, 195-9 (1984).
31. W. Deng, R. D. Poretz. Oligodendroglia in developmental neurotoxicity. *Neurotoxicology.* 24, 161-78 (2003).
32. S. P. Fancy, J. R. Chan, S. E. Baranzini, R. J. Franklin, D. H. Rowitch. Myelin Regeneration: A recapitulation of development? *Annu. Rev. Neurosci.* 34, 21-43 (2011)
33. M. E. Schwab. Functions of Nogo proteins and their receptors in the nervous system. *Nat. Rev. Neurosci.* 11, 799-811 (2010).
34. D. H. Meijer, M. F. Kane, S. Mentha, H. Liu, E. Harrington, C. M. Taylor, C. D. Stiles, D. H. Rowitch. Separated at birth? The functional and molecular divergence of OLIG1 and OLIG2. *Nat. Rev. Neurosci.* 13, 819-31 (2012).
35. Y. Yamaguchi, M. Miura. Programmed cell death in neurodevelopment. *Dev. Cell.* 32, 478-90 (2015).
36. H. A. Juraver-Geslin, B. C. Durand. Early development of the neural plate: new roles for apoptosis and for one of its main effectors caspase-3. Genesis. 53, 203-24 (2015).
37. A. K. Krug, S. Gutbier, L. Zhao, D. Pöltl, C. Kullmann, V. Ivanova, S. Förster, S. Jagtap, J. Meiser, G. Leparc, S. Schildknecht, M. Adam, K. Hiller, H. Farhan, T. Brunner, T. Hartung, A. Sachinidis, M. Leist. Transcriptional and metabolic adaptation of human neurons to the mitochondrial toxicant MPP (+). *Cell Death Dis.*5, e1222 (2014).
38. T. Nakano, S. Ando, N. Takata, M. Kawada, K. Muguruma, K. Sekiguchi, K. Saito, S. Yonemura, M. Eiraku, Y. Sasai. Self-formation of optic cups and storable stratified neural retina from human ESCs. *Cell Stem Cell.* 14, 771-85 (2012)
39. M. Eiraku, N. Takata, H. Ishibashi, M. Kawada, E. Sakakura, S. Okuda, K. Sekiguchi, T. Adachi, Y. Sasai. Self-organizing optic-cup morphogenesis in three-dimensional culture. *Nature.* 472, 51-6 (2012).
40. H. Suga, T. Kadoshima, M. Minaguchi, M. Ohgushi, M. Soen, T. Nakano, N. Takata, T. Wataya, K. Muguruma, H. Miyoshi, S. Yonemura, Y. Oiso, Y. Sasai. Self-formation of functional adenohypophysis in three-dimensional culture. *Nature.* 480, 57-62 (2011).
41. E. van Vliet, S. Morath, C. Eskes, J. Linge, J. Rappsilber, P. Honegger, T. Hartung, S. Coecke. A novel in vitro metabolomics approach for neurotoxicity testing, proof of principle for methyl mercury chloride and caffeine. *Neurotoxicology.* 29, 1-12 (2008).
42. J. Kim, K. Inoue, J. Ishii, W. B. Vanti, S. V. Voronov, E. Murchison, G. Hannon, A. Abeliovich. A MicroRNA feedback circuit in midbrain dopamine neurons. *Science* 317, 1220-1224 (2007).
43. C. Wiese, A. Rolletschek, G. Kania, P. Blyszczuk, K. V. Tarasov, Y. Tarasova, R. P. Wersto, K. R. Boheler, A. M. Wobus. Nestin expression—a property of multi-lineage progenitor cells? Cell. Mol. *Life. Sci.* 61, 2510-22 (2004).
44. C. Lépinoux-Chambaud, J. Eyer. Review on intermediate filaments of the nervous system and their pathological alterations. *Histochem. Cell. Biol.* 140, 13-22 (2013).
45. J. Park, B. K. Lee, G. S. Jeong, J. K. Hyun, C. J. Lee, S. H. Lee. Three-dimensional brain-on-a-chip with an interstitial level of flow and its application as an in vitro model of Alzheimer's disease. *Lab Chip.* 15, 141-50 (2015).
46. J. P. Dollé, B. Morrison, R. S. Schloss, M. L. Yarmush. Brain-on-a-chip microsystem for investigating traumatic brain injury: Axon diameter and mitochondrial membrane changes play a significant role in axonal response to strain injuries. *Technology (Singap. World. Sci.).* 2,106 (2014).
47. S. J. Mullett, D. A. Hinkle. DJ-1 knock-down in astrocytes impairs astrocyte-mediated neuroprotection against rotenone. *Neurobiol. Dis.* 33, 28-36 (2009).
48. Y. Shinozaki, M. Nomura, K. Iwatsuki, Y. Moriyama, C. Gachet, S. Koizumi. Microglia trigger astrocyte-mediated neuroprotection via purinergic gliotransmission. *Sci. Rep.* 4, 4329 (2014).
49. D. Aguirre-Rueda, S, Guerra-Ojeda, M. Aldasoro, A. Iradi, E. Obrador, A. Ortega, M. D. Mauricio, J. M. Vila, S. L. Valles. Astrocytes protect neurons from Aβ1-42 peptide-induced neurotoxicity increasing TFAM and PGC-1 and decreasing PPAR-γ and SIRT-1. *Int. J. Med. Sci.*12, 48-56. (2015).
50. R. Sattler, M. Tymianski. Molecular mechanisms of glutamate receptormediated excitotoxic neuronal cell death. *Mol. Neurobiol.* 24, 107-129 (2001).
51. Y. Shao, M. Gearing, S. S. Mirra. Astrocyte-apolipoprotein E associations in senile plaques in Alzheimer disease and vascular lesions: a regional immunohistochemical study. *J. Neuropathol. Exp. Neurol.* 56, 376-381 (1997)
52. C. Schwab, P. L. McGeer. Inflammatory aspects of Alzheimer disease and other neurodegenerative disorders. *J. Alzheimers. Dis.* 13, 359-369 (2008).
53. P. Damier, E. C. Hirsch, P. Zhang, Y. Agid, F. Javoy-Agid. Glutathione peroxidase, glial cells and Parkinson's disease. *Neuroscience* 52, 1-6 (1993).
54. C. Xie, Y. Q. Liu, Y. T. Guan, G. X. Zhang. Induced Stem Cells as a Novel Multiple Sclerosis Therapy. *Curr Stem Cell Res* Ther. In press (2015).
55. S. Wang, J. Bates, X. Li, S. Schanz, D. Chandler-Militello, C. Levine, N. Maherali, L. Studer, K. Hochedlinger, M. Windrem, S. A. Goldman. Human iPSC-derived oligodendrocyte progenitor cells can myelinate and rescue a mouse model of congenital hypomyelination. *Cell Stem Cell.* 12, 252-64 (2013)
56. M. Pinto, S. Dobson. BK and JC virus: a review. *J. Infect.* 68 Suppl 1: S2-8 (2014).
57. X. B. Liu, Y. Shen, J. M. Plane, W. Deng. Vulnerability of premyelinating oligodendrocytes to white-matter damage in neonatal brain injury. *Neurosci. Bull.* 29, 229-38 (2013).
58. G. Bartzokis. Age-related myelin breakdown: a developmental model of cognitive decline and Alzheimer's disease. *Neurobiol. Aging.* 25, 5-18 (2004).
59. H. Okamoto, T. Miki, K. Y. Lee, T. Yokoyama, H. Kuma, Z. Y. Wang, H. Gu, H. P. Li, Y. Matsumoto, S. Irawan, K. S. Bedi, Y. Nakamura, Y. Takeuchi. Oligodendrocyte myelin glycoprotein (OMgp) in rat hippocampus is depleted by chronic ethanol consumption. *Neurosci. Lett.* 406, 76-80 (2006).
60. T. W. Bouldin, G. Samsa, T. S. Earnhardt, M. R. Krigman. Schwann cell vulnerability to demyelination is associated with internodal length in tellurium neuropathy. *J. Neuropathol. Exp. Neurol.* 47, 41-47 (1988).
61. P. David, K. Subramaniam. Prenatal alcohol exposure and early postnatal changes in the developing nerve-muscle system. *Birth Defects Res. A. Clin. Mol. Teratol.* 73, 897-903 (2005).
62. G. J. Harry, A. D. Toews, M. R. Krigman, P. Morell. The effect of lead toxicity and milk deprivation of myelination in the rat. *Toxicol. Appl. Pharmacol.* 77, 458-464 (1985).
63. S. J. Rothenberg, A. Poblano, S. Garza-Morales. Prenatal and perinatal low level lead exposure alters brainstem auditory evoked responses in infants. *Neurotoxicology* 15, 695-699 (1994).
64. E. Tiffany-Castiglioni, J. Zmudzki, G. R. Bratton. Cellular targets of lead neurotoxicity: in vitro models. *Toxicology* 42, 303-315 (1986).
65. E. Tiffany-Castiglioni. Cell culture models for lead toxicity in neuronal and glial cells. *Neurotoxicology.* 14, 513-36 (1993).
66. J. Parkinson. An essay on the shaking palsy. 1817. *J. Neuropsychiatry Clin. Neurosci.* 14: 223-36 (2002)
67. K. R. Chaudhuri, P. Odin. The challenge of non-motor symptoms in Parkinson's disease. *Prog. Brain. Res.*184, 325-41 (2010).
68. P. McGonigle. Animal models of CNS disorders. *Biochem. Pharmacol.* 87, 140-9 (2014).
69. K. Tieu. A guide to neurotoxic animal models of Parkinson's disease. *Cold. Spring. Harb. Perspect. Med.* In press (2011).
70. S. E. Cavanaugh, J. J. Pippin, N. D. Barnard. Animal models of Alzheimer disease: historical pitfalls and a path forward. *ALTEX.* 31, 279-302 (2014).
71. A. Pombero, C. Bueno, L. Saglietti, M. Rodenas, J. Guimera, A. Bulfone, S. Martinez. Pallial origin of basal forebrain cholinergic neurons in the nucleus basalis of Meynert and horizontal limb of the diagonal band nucleus. *Development.* 138, 4315-26 (2011).
72. H. McCann, C. H. Stevens, H. Cartwright, G. M. Halliday. α-Synucleinopathy phenotypes. *Parkinsonism. Relat. Disord.* 20 Suppl 1, S62-7 (2014).
73. V. N. Uversky. A protein-chameleon: conformational plasticity of alphasynuclein, a disordered protein involved in neurodegenerative disorders. *J. Biomol. Struct. Dyn.* 21, 211-34 (2003)
74. G. A. Petsko and D. Ringer. Ice cleaved alpha-synuclein a biomarker. Patent WO2012061786 A1. (2012)
75. Wen Z, Nguyen H N, Guo Z, Lalli M A, Wang X, Su Y, Kim N S, Yoon K J, Shin J, Zhang C, Makri G, Nauen D, Yu H, Guzman E, Chiang C H, Yoritomo N, Kaibuchi K, Zou J, Christian K M, Cheng L, Ross C A, Margolis R L, Chen G, Kosik K S, Song H, Ming G L. Synaptic dysregulation in a human iPS cell model of mental disorders. *Nature.* 2014 Nov. 20;515 (7527): 414-8.
76. P. Chomczynski, N. Sacchi N. Single-step method of RNA isolation by acid guanidinium thiocyanate-phenol-chloroform extraction. *Ana.l Biochem.* 162, 156-9 (1987).
77. L. Smirnova, A. E. M. Seiler, A. Luch. microRNA profiling as tool for developmental neurotoxicity testing (DNT). *Toxicol.* 64:20.9.1-20.9.22, 2015
78. K. J. Livak, T. D. Schmittgen. Analysis of relative gene expression data using real-time quantitative PCR and the 2 (-Delta Delta C (T)) Method. *Methods.* 25, 402-8 (2001).
79. Nave, K. A. Myelination and support of axonal integrity by glia. *Nature* 468, 244-252, (2010).
80. Saab, A. S., Tzvetanova, I. D. & Nave, K. A. The role of myelin and oligodendrocytes in axonal energy metabolism. *Current opinion in neurobiology* 23, 1065-1072, (2013).
81. Pardridge, W. M. Crossing the blood brain barrier: are we getting it right? *Drug Disc. Today* January 1; 6 (1): 1-2, (2001).
82. Kerman, B. E. et al. In vitro myelin formation using embryonic stem cells. *Development* 142, 2213-2225, (2015)
83. Gaj T, Gersbach C A, Barbas C F 3rd. ZFN, TALEN, and CRISPR/Cas-based methods for genome engineering. *Trends Biotechnol.* July; 31 (7): 397-405, (2013).
84. Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, Jaenisch R. Efficient targeting of expressed and silent genes in human ESCs and iPSCs using zinc-finger nucleases. *Nat Biotechnol.* September; 27 (9): 851-7, (2009).
85. Hockemeyer D, Wang H, Kiani S, Lai C S, Gao Q, Cassady J P, Cost G J, Zhang L, Santiago Y, Miller J C, Zeitler B, Cherone J M, Meng X, Hinkley S J, Rebar E J, Gregory P D, Urnov F D, Jaenisch R. Genetic engineering of human pluripotent cells using TALE nucleases. *Nat Biotechnol.* July 7; 29 (8): 731-4, (2011).
86. Mali P, Aach J, Stranges P B, Esvelt K M, Moosburner M, Kosuri S, Yang L, Church G M. CAS9 transcriptional activators for target specificity screening and paired nickases for cooperative genome engineering. *Nat Biotechnol.* September; 31 (9): 833-8, (2013).
87. Chang N, Sun C, Gao L, Zhu D, Xu X, Zhu X, Xiong J W, Xi J J. Genome editing with RNA-guided Cas9 nuclease in zebrafish embryos. *Cell Res.* April; 23 (4): 465-72, (2013).
88. Cong L, Ran F A, Cox D, Lin S, Barretto R, Habib N, Hsu P D, Wu X, Jiang W, Marraffini L A, Zhang F. Multiplex genome engineering using CRISPR/Cas systems. *Science.* February 15; 339 (6121): 819-23, (2013).
89. Ran F A, Hsu P D, Wright J, Agarwala V, Scott D A, Zhang F. Genome engineering using the CRISPR-Cas9 system. *Nat Protoc.* November; 8 (11): 2281-308, (2013).
90. Kim W R, Sun W. 2011. Programmed cell death during postnatal development of the rodent nervous system. *Development, growth & differentiation* 53:225-235, (2011).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An in vitro brain microphysiological system (BMPS), comprising two or more neural cell types, derived from induced pluripotent stem cells, aggregated into a spheroid mass, and endothelial cells capable of forming a blood brain barrier, wherein the spheroid mass has a diameter that is between about 300 μm and about 350 μm, wherein the two or more neural cell types comprises at least a glial cell and the in vitro BMPS is electrophysiologically active in a spontaneous manner, wherein the BMPS exhibits detectable axon myelination.

2. The BMPS of claim 1, wherein the two or more neural cell types comprise at least a mature neuron and glial cell.

3. The BMPS of claim 2, wherein the two or more neural cell types further comprise cells selected from the group consisting of astrocytes, polydendrocytes, oligodendrocytes, and combinations thereof.

4. The BMPS of claim 1, wherein the in vitro BMPS has neural characteristics selected from the group consisting of synaptogenesis, neuron-neuron interactions, neuronal-glial interactions, axon myelination, and combinations thereof.

5. The BMPS of claim 1, wherein two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

6. A synthetic neurological organ comprising two or more neural cell types, derived from induced pluripotent stem cells, aggregated into a spheroid mass, and endothelial cells capable of forming a blood brain barrier, wherein the spheroid mass has a diameter that is between about 300 μm and about 350 μm, wherein the two or more neural cell types comprises at least a glial cell and the synthetic neurological organ is electrophysiologically active in a spontaneous manner, wherein the synthetic neurological organ exhibits detectable axon myelination.

7. The synthetic neurological organ of claim 6, wherein the two or more neural cell types comprise at least a mature neuron and glial cells.

8. The synthetic neurological organ of claim 7, wherein the mature neuron and glial cells further comprise cells selected from the group consisting of astrocytes, polydendrocytes, oligodendrocytes, and combinations thereof.

9. The synthetic neurological organ of claim 6, wherein synthetic neurological organ further comprises neural characteristics selected from the group consisting of synaptogenesis, neuron-neuron interactions, neuronal-glial interactions, axon myelination, and combinations thereof.

10. The synthetic neurological organ of claim 6, wherein the synthetic neurological organ mimics the microenvironment of the central nervous system (CNS).

11. A method of reproducibly producing an in vitro brain microphysiological system (BMPS), comprising:
    inducing one or more pluripotent stem cell (PSC) types;
    differentiating the one or more PSC types to form one or more neural progenitor cell (NPC) types;
    exposing the one or more NPC types to gyratory shaking or stirring; and
    differentiating the one or more NPC types into one or more neural cell types aggregated into a spheroid mass, wherein the spheroid mass has a diameter that is between about 300 μm and about 350 μm wherein the BMPS exhibits detectable axon myelination.

12. The method of claim 11, wherein the one or more pluripotent stem cells are selected from the group consisting of human or animal embryonic stem cells, iPSC, adult stem cells, fibroblasts, embryonic fibroblasts, peripheral blood mononuclear cells, neuronal precursor cells, mesenchymal stem cells, and combinations thereof.

13. The method of claim 11, wherein inducing further comprises:
    adding micro-glia or micro-glia precursor cells.

14. The method of claim 13, wherein the micro-glia precursor cells are selected from the group consisting of monocytes, human monocytes, pro-monocyte cell lines, iPSC-derived monocytes, hematopoetic stem cells, isolated microglia, immortalized microglia, and combinations thereof.

15. The method of claim 11, wherein gyratory shaking comprises constant or regular gyratory shaking or stirring for 2 or more, 3 or more, 4 or more, 5 or more, 6 or more, 7 or more, or 8 or more weeks.

16. The method of claim 11, wherein the one or more growth factors are selected from the group consisting of GDNF, BDNF, GM-CSF, B27, basic FGF, basic EGF, NGF, CNTF, and any combination thereof.

17. The BMPS of claim 1, wherein the two or more neural cell types include one or more genetically modified cells.

18. The BMPS of claim 17, wherein the one or more genetically modified cells include one or more reporter genes.

19. The synthetic neurological organ of claim 6, wherein the two or more neural cell types include one or more genetically modified cells.

20. The synthetic neurological organ of claim 19, wherein the one or more genetically modified cells include one or more reporter genes.

21. An in vitro brain microphysiological system (BMPS), comprising:
    a mature neuron and a glial cell, derived from human induced pluripotent stem cells (iPSCs), aggregated into a spheroid mass;
    wherein the spheroid mass has a diameter less than 500 μm; and
    wherein the BMPS is electrophysiologically active in a spontaneous manner, wherein the BMPS exhibits detectable axon myelination.

22. The in vitro BMPS of claim 21, wherein the glial cell comprises an astrocyte, an oligodendrocyte, or an astrocyte and an oligodendrocyte.

23. The in vitro BMPS of claim 21, wherein the oligodendrocyte has myelination properties.

24. The in vitro BMPS of claim 21, having neural characteristics selected from the group consisting of synaptogenesis, neuron-neuron interactions, neuronal-glial interactions and axon myelination.

25. An in vitro brain microphysiological system (BMPS), comprising:
    a mature neuron and a glial cell, derived from human induced pluripotent stem cells (iPSCs), aggregated into a spheroid mass;
    wherein the glial cell comprises an oligodendrocyte having myelination properties;
    wherein the spheroid mass has a diameter less than 500 μm; and
    wherein the BMPS is electrophysiologically active in a spontaneous manner and exhibits detectable axon myelination.

26. The in vitro BMPS of claim 25, having neural characteristics selected from the group consisting of synaptogenesis, neuron-neuron interactions, neuronal-glial interactions and axon myelination.

27. The in vitro BMPS of claim 25, additionally comprising one or more neural progenitor cell (NPC) types derived from the induced pluripotent stem cells (iPSCs).

28. An in vitro brain microphysiological system (BMPS), comprising:
    two or more neural cells, derived from induced pluripotent stem cells (iPSCs), aggregated into a spheroid mass;
    wherein the BMPS is electrophysiologically active in a spontaneous manner and exhibits detectable axon myelination; and
    wherein the two or more neural cells comprise a mature neuron and a glial cell.

\* \* \* \* \*

SEQUENCE LISTING

<160> NUMBER OF SEQ ID NOS: 70

<210> SEQ ID NO 1
<211> LENGTH: 938
<212> TYPE: PRT
<213> ORGANISM: Homo sapiens

<400> SEQUENCE: 1

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365
```

```
Gly Thr His Val Ile Pro Asn Asp Arg Lys Ile Ile Trp Pro Gly Gly
370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
                420                 425                 430

Lys Val Ile Cys Thr Gly Pro Asn Asp Thr Ser Pro Gly Ser Pro Arg
                435                 440                 445

His Thr Val Pro Gln Cys Cys Tyr Gly Phe Cys Ile Asp Leu Leu Ile
450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
                500                 505                 510

Ile Val Ala Pro Leu Thr Ile Asn Asn Glu Arg Ala Gln Tyr Ile Glu
                515                 520                 525

Phe Ser Lys Pro Phe Lys Tyr Gln Gly Leu Thr Ile Leu Val Lys Lys
530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
                580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
                755                 760                 765

Lys Gln Asn Val Ser Leu Ser Ile Leu Lys Ser His Glu Asn Gly Phe
770                 775                 780

Met Glu Asp Leu Asp Lys Thr Trp Val Arg Tyr Gln Glu Cys Asp Ser
```

```
                785                 790                 795                 800
Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
                900                 905                 910

Lys Asp Thr Val Leu Pro Arg Arg Ala Ile Glu Arg Glu Glu Gly Gln
                915                 920                 925

Leu Gln Leu Cys Ser Arg His Arg Glu Ser
    930                 935
```

<210> SEQ ID NO 2
<211> LENGTH: 4400
<212> TYPE: DNA
<213> ORGANISM: Homo sapiens

<400> SEQUENCE: 2

```
gtcgccgcag cgtccggacc ggaaccagcg ccgtccgcgg agccgccgcc gccgccgccg      60
ggccctttcc aagccgggcg ctcggagctg tgcccggccc cgcttcagca ccgcggacag     120
cgccggccgc gtgggctga gccccgagcc cccgcgcacg cttcagcgcc ccttccctcg      180
gccgacgtcc cggaccgcc gctcgggggg agacgtggcg tccgcagccc gcggggccgg      240
gcgagcgcag gacggcccgg aagccccgcg ggggatgcgc cgagggcccc gcgttcgcgc     300
cgcgcagagc caggcccgcg gcccgagccc atgagcacca tgcgcctgct gacgctcgcc     360
ctgctgttct cctgctccgt cgcccgtgcc gcgtgcgacc caagatcgt caacattggc      420
gcggtgctga gcacgcggaa gcacgagcag atgttccgcg aggccgtgaa ccaggccaac     480
aagcggcacg gctcctggaa gattcagctc aatgccacct ccgtcacgca aagcccaac      540
gccatccaga tggctctgtc ggtgtgcgag gacctcatct ccagccaggt ctacgccatc     600
ctagttagcc atccacctac ccccaacgac cacttcactc ccaccccgt ctcctacaca      660
gccggcttct accgcatacc cgtgctgggg ctgaccaccc gcatgtccat ctactcggac     720
aagagcatcc acctgagctt cctgcgcacc gtgccgccct actcccacca gtccagcgtg     780
tggtttgaga tgatgcgtgt ctacagctgg aaccacatca tcctgctggt cagcgacgac     840
cacgagggcc gggcggctca gaaacgcctg gagacgctgc tggaggagcg tgagtccaag     900
gcagagaagg tgctgcagtt tgacccaggg accaagaacg tgacggccct gctgatggag     960
gcgaaagagc tggaggcccg ggtcatcatc ctttctgcca gcaggacga tgctgccact    1020
gtataccgcg cagccgcgat gctgaacatg acgggctccg ggtacgtgtg gctggtcggc    1080
gagcgcgaga tctcggggaa cgccctgcgc tacgccccag acggcatcct cgggctgcag    1140
ctcatcaacg gcaagaacga gtcggcccac atcagcgacg ccgtgggcgt ggtgcccag    1200
gccgtgcacg agctcctcga aaggagaac atcaccgacc cgccgcgggg ctgcgtgggc    1260
```

-continued

```
aacaccaaca tctggaagac cgggccgctc ttcaagagag tgctgatgtc ttccaagtat    1320
gcggatgggg tgactggtcg cgtggagttc aatgaggatg gggaccggaa gttcgccaac    1380
tacagcatca tgaacctgca gaaccgcaag ctggtgcaag tgggcatcta caatggcacc    1440
cacgtcatcc ctaatgacag gaagatcatc tggccaggcg agagacaga gaagcctcga     1500
gggtaccaga tgtccaccag actgaagatt gtgacgatcc accaggagcc cttcgtgtac    1560
gtcaagccca cgctgagtga tgggacatgc aaggaggagt tcacagtcaa cggcgaccca    1620
gtcaagaagg tgatctgcac cgggcccaac gacacgtcgc cgggcagccc ccgccacacg    1680
gtgcctcagt gttgctacgg cttttgcatc gacctgctca tcaagctggc acggaccatg    1740
aacttcacct acgaggtgca cctggtggca gatggcaagt cggcacaca ggagcgggtg     1800
aacaacagca caagaagga gtggaatggg atgatgggcg agctgctcag cgggcaggca    1860
gacatgatcg tggcgccgct aaccataaac aacgagcgcg cgcagtacat cgagtttcc     1920
aagcccttca gtaccaggg cctgactatt ctggtcaaga aggagattcc ccggagcacg     1980
ctggactcgt tcatgcagcc gttccagagc acactgtggc tgctggtggg gctgtcggtg    2040
cacgtggtgg ccgtgatgct gtacctgctg daccgcttca gccccttcgg ccggttcaag    2100
gtgaacagcag aggaggagga ggaggacgca ctgaccctgt cctcggccat gtggttctcc    2160
tggggcgtcc tgctcaactc cggcatcggg gaaggcgccc ccagaagctt ctcagcgcgc    2220
atcctgggca tggtgtgggc cggctttgcc atgatcatcg tggcctccta caccgccaac    2280
ctggcggcct tcctggtgct ggaccggccg gaggagcgca tcacgggcat caacgaccct    2340
cggctgagga ccccctcgga caagtttatc tacgccacgg tgaagcagag ctccgtggat    2400
atctacttcc ggcgccaggt ggagctgagc accatgtacc ggcatatgga gaagcacaac    2460
tacgagagtg cggcggaggc catccaggcc gtgagagaca caagctgca tgccttcatc     2520
tgggactcgg cggtgctgga gttcgaggcc tcgcagaagt gcgacctggt gacgactgga    2580
gagctgtttt tccgctcggg cttcggcata ggcatgcgca aagacagccc ctggaagcag    2640
aacgtctccc tgtccatcct caagtcccac gagaatggct tcatggaaga cctggacaag    2700
acgtgggttc ggtatcagga atgtgactcg cgcagcaacg cccctgcgac ccttactttt    2760
gagaacatgg ccgggtctt catgctggta gctgggggca tcgtggccgg atcttcctg     2820
attttcatcg agattgccta caagcggcac aaggatgctc gccggaagca gatgcagctg    2880
gcctttgccg ccgttaacgt gtggcggaag aacctgcagg atagaaagag tggtagagca    2940
gagcctgacc ctaaaaagaa agccacattt agggctatca cctccaccct ggcttccagc    3000
ttcaagaggc gtaggtcctc caaagacacg agcaccgggg gtggacgcgg cgctttgcaa    3060
aaccaaaaag acacagtgct gccgcgacgc gctattgaga gggaggaggg ccagctgcag    3120
ctgtgttccc gtcataggga gagctgagac tccccgcccg ccctcctctg cccctcccc    3180
cgcagacaga cagacagacg gacgggacag cggcccggcc cacgcagagc cccggagcac    3240
cacggggtcg ggggaggagc accccagcc tcccccaggc tgcgcctgcc cgcccgccgg     3300
ttggccggct ggccggtcca ccccgtcccg gccccgcgcg tgcccccagc gtggggctaa    3360
cgggcgcctt gtctgtgtat ttctattttg cagcagtacc atcccactga tatcacgggc    3420
ccgctcaacc tctcagatcc ctcggtcagc accgtggtgt gaggccccg gaggcgccca     3480
cctgcccagt tagcccggcc aaggacactg atgggtcctg ctgctcggga aggcctgagg    3540
gaagcccacc cgccccagag actgcccacc ctggcctcc cgtccgtccg cccgcccacc    3600
ccgctgcctg gcgggcagcc cctgctggac caaggtgcgg accggagcgg ctgaggacgg    3660
```

```
ggcagagctg agtcggctgg gcagggccgc agggcgctcc ggcagaggca gggccctggg    3720
gtctctgagc agtggggagc gggggctaac tggccccagg cggaggggct tggagcagag    3780
acggcagccc catccttccc gcagcaccag cctgagccac agtggggccc atggccccag    3840
ctggctgggt cgcccctcct cgggcgcctg cgctcctctg cagcctgagc tccaccctcc    3900
cctcttcttg cggcaccgcc cacccacacc ccgtctgccc cttgacccca cacgccgggg    3960
ctggccctgc cctcccccac ggccgtccct gacttcccag ctggcagcgc ctcccgccgc    4020
ctcgggccgc ctcctccaga ctcgagaggg ctgagcccct cctctcctcg tccggcctgc    4080
agcccagaac gggcctcccc gggggtcccc ggacgctggc tcgggactgt cttcaaccct    4140
gccctgcacc ttgggcacgg gagagcgcca cccgcccgcc ccgccctcg ctccgggtgc    4200 gtgaccggcc cgccaccttg tacagaacca gcactcccag ggcccgagcg cgtgccttcc    4260
ccgtgcggcc cgtgcgcagc cgcgctctgc ccctccgtcc ccagggtgca ggcgcgcacc    4320
gcccaacccc cacctcccgg tgtatgcagt ggtgatgcct aaaggaatgt cacgcagttt    4380
tcaaaaaaaa aaaaaaaaa                                                 4400
```

<210> SEQ ID NO 3
<211> LENGTH: 594
<212> TYPE: PRT
<213> ORGANISM: Homo sapiens

<400> SEQUENCE: 3

```
Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240
```

Ser Lys Asp Gly Asp Gly Ile Phe Ser Pro Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
    290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
    370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu

<210> SEQ ID NO 4
<211> LENGTH: 4007
<212> TYPE: DNA
<213> ORGANISM: Homo sapiens

<400> SEQUENCE: 4
agcgtgtggt agaggagaaa cgctgaaacc ggaccgaaac ctcgccctag gcttagcgat     60

-continued

| | | | | | |
|---|---|---|---|---|---|
| ggctaaaaac | cggctgggac | aagagggagg | caagcaacat | tccgactcgc | tgctttctgg | 120 |
| ctgtctggag | tgcaaggtga | ctgtggttct | tctctggcca | agtccgaggg | agaacgtaaa | 180 |
| gatatgggcc | tttttccccc | tctcaccttg | tctcaccaaa | gtccctagtc | cccggagcag | 240 |
| ttagcctctt | tctttccagg | gaattagcca | gacacaacaa | cgggaaccag | acaccgaacc | 300 |
| agacatgccc | gccccgtgcg | ccctccccc  | gctggcccac | acgccggctg | ctgagtgccc | 360 |
| aatgggctt  | gtagcggctc | ggctggaaaa | tcgctcactg | agcgctcccc | tgtgctccta | 420 |
| gcccagtccc | ccacacccctt | gcgtcttgta | ctggccttgg | accccacccc | cgaccccgac | 480 |
| cccgcctcgt | ctcggcgctt | cactccaggt | cgcgccgatg | caccgccaga | ctcgagagcg | 540 |
| gcccagggct | acgctccctg | cgccccagta | ccggagctag | cgcgcacgtc | tcctccgctg | 600 |
| cccccacccc | tgcgcacccc | taccaggcag | gctcgctgcc | tttcctccct | cttgtctctc | 660 |
| cagagccgga | tcttcaaggg | gagcctccgt | gccccggct  | gctcagtccc | tccggtgtgc | 720 |
| aggaccccgg | aagtcctccc | cgcacagctc | tcgcttctct | ttgcagcctg | tttctgcgcc | 780 |
| ggaccagtcg | aggactctgg | acagtagagg | ccccgggacg | accgagctga | tggcgtcttc | 840 |
| gaccccatct | tcgtccgcaa | cctcctcgaa | cgcgggagcg | gacccca ta | ccactaacct | 900 |
| gcgcccca ca | acgtacgata | cctggtgcgg | cgtggcccat | ggatgcacca | gaaaactggg | 960 |
| gctcaagatc | tgcggcttct | tgcaaaggac | caacagcctg | aagagaaga  | gtcgccttgt | 1020 |
| gagtgccttc | aaggagaggc | aatcctccaa | gaacctgctt | tcctgtgaaa | acagcgaccg | 1080 |
| ggatgcccgc | ttccggcgca | cagagactga | cttctctaat | ctgtttgcta | gagatctgct | 1140 |
| tccggctaag | aacggtgagg | agcaaaccgt | gcaattcctc | ctggaagtgg | tggacatact | 1200 |
| cctcaactat | gtccgcaaga | catttgatcg | ctccaccaag | gtgctggact | tcatcacccc | 1260 |
| acaccagttc | ctgaaggca  | tggagggctt | caacttggag | ctctctgacc | accccgagtc | 1320 |
| cctggagcag | atcctggttg | actgcagaga | caccttgaag | tatggggttc | gcacaggtca | 1380 |
| tcctcgattt | tcaaccagc  | tctccactgg | attggatatt | ttggcctag  | ctggagaatg | 1440 |
| gctgacatca | acggccaata | ccaacatgtt | tacatatgaa | attgcaccag | tgtttgtcct | 1500 |
| catggaacaa | ataacactta | agaagatgag | agagatagtt | ggatggtcaa | gtaaagatgg | 1560 |
| tgatgggata | ttttctcctg | ggggcgccat | atccaacatg | tacagcatca | tggctgctcg | 1620 |
| ctacaagtac | ttcccggaag | ttaagacaaa | gggcatggcg | gctgtgccta | aactggtcct | 1680 |
| cttcacctca | gaacagagtc | actattccat | aaagaaagct | ggggctgcac | ttggctttgg | 1740 |
| aactgacaat | gtgattttga | taaagtgcaa | tgaaaggggg | aaaataattc | cagctgattt | 1800 |
| tgaggcaaaa | attcttgaag | ccaaacagaa | gggatatgtt | cccttttatg | tcaatgcaac | 1860 |
| tgctggcacg | actgttttatg | gagcttttga | tccgatacaa | gagattgcag | atatatgtga | 1920 |
| gaaatataac | ctttggttgc | atgtcgatgg | atttaacttc | tcacaattgg | ccaataggat | 1980 |
| catctgcctt | gctactgaac | taatgactaa | caaaggctgt | gtcacgtggc | atcccaacta | 2040 |
| ttcagtaaac | atgcatcatg | gctgcctggg | gaggtgggct | gctcatgtcc | aggaagcacc | 2100 |
| accataaact | caacggcata | gaaagggcca | actcagtcac | ctggaacccct | cacaagatga | 2160 |
| tgggcgtgct | gttgcagtgc | tctgccattc | tcgtcaagga | aaagggtata | ctccaaggat | 2220 |
| gcaaccagat | gtgtgcagga | tacctcttcc | agccagacaa | gcagtatgat | gtctcctacg | 2280 |
| acaccgggga | caaggcaatt | cagtgtggcc | gccacgtgga | tatcttcaag | ttctggctga | 2340 |
| tgtgaaaagc | aaagggcaca | gtgggatttg | aaaaccagat | caacaaatgc | ctggaactgg | 2400 |
| ctgaataacct | ctatgccaag | attaaaaaca | gagaagaatt | tgagatggtt | ttcaatggcg | 2460 |

-continued

```
agcctgagca cacaaacgtc tgttttggt atattccaca aagcctcagg ggtgtgccag      2520
acagccctca acgacgggaa aagctacaca aggtggctcc aaaaatcaaa gccctgatga      2580
tggagtcagg tacgaccatg gttggctacc agccccaagg ggacaaggcc aacttcttcc      2640
ggatggtcat ctccaaccca gccgctaccc agtctgacat tgacttcctc attgaggaga      2700
tagaaagact gggccaggat ctgtaatcat ccttcgcaga acatgagttt atgggaatgc      2760
cttttccctc tggcactcca gaacaaacct ctatatgttg ctgaaacaca caggccattt      2820
cattgaggga aaacataata tcttgaagaa tattgttaaa accttactta agcttgttt      2880 gttctagtta gcaggaaata tgttctttt taaaaagttg cacattagga acagagtata      2940
tatgtacagt tatacatacc tctctctata tatacatgta tagtgagtgt ggcttagtaa      3000
tagatcacgg catgtttccc gctccaagag aattcacttt accttcagca gttaccgagg      3060
agctaaacat gctgccaacc agcttgtcca acaactccag gaaaactgtt tttcaaaacg      3120
ccatgtccta ggggcaagg gaaatgctgt tggtgagaat cgacctcact gtcagcgttt      3180
ctccacctga agtgatgatg gatgagaaaa aacaccacca aatgacaagt cacaccctcc      3240
ccattagtat cctgttaggg gaaaatagta gcagagtcat tgttacaggt gtactatggc      3300
tgtattttta gagattaatt tgtgtagatt gtgtaaattc ctgttgtctg accttggtgg      3360
tgggaggggg agactatgtg tcatgatttc aatgattgtt taattgtagg tcaatgaaat      3420
atttgcttat ttatattcag agatgtacca tgttaaagag gcgtcttgta ttttcttccc      3480
atttgtaatg tatcttattt atatatgaag taagttctga aaactgttta tggtattttc      3540
gtgcatttgt gagccaaaga gaaaagatta aaattagtga gatttgtatt tatattagag      3600
tgcccttaaa ataatgattt aagcatttta ctgtctgtaa gagaattcta agattgtaca      3660
taaagtcata tatatggaaa tcctgttact taaaatagcat ctgctcttct cttacgctct      3720
ctgtctggct gtacgtctgg tgttctcaat gcttttctag caactgttgg ataataacta      3780
gatctcctgt aattttgtag tagttgatga ccaatctctg ttactcgctt agctgaaacc      3840
taaggcaaca tttccgaaga ccttctgaag atctcagata aagtgaccag gctcacaact      3900 gttttttgaag aagggaaatt cacactgtgc gttttagagt atgcaagaag aatataaata      3960
aataaaaata ttctccatgg agaatttgaa caaaaaaaa aaaaaaa                    4007
```

<210> SEQ ID NO 5
<211> LENGTH: 599
<212> TYPE: PRT
<213> ORGANISM: Homo sapiens

<400> SEQUENCE: 5

```
Met Ala Thr Asn Gly Ser Lys Val Ala Asp Gly Gln Ile Ser Thr Glu
1               5                   10                  15

Val Ser Glu Ala Pro Val Ala Asn Asp Lys Pro Lys Thr Leu Val Val
            20                  25                  30

Lys Val Gln Lys Lys Ala Ala Asp Leu Pro Asp Arg Asp Thr Trp Lys
        35                  40                  45

Gly Arg Phe Asp Phe Leu Met Ser Cys Val Gly Tyr Ala Ile Gly Leu
    50                  55                  60

Gly Asn Val Trp Arg Phe Pro Tyr Leu Cys Gly Lys Asn Gly Gly Gly
65                  70                  75                  80

Ala Phe Leu Ile Pro Tyr Phe Leu Thr Leu Ile Phe Ala Gly Val Pro
                85                  90                  95
```

```
Leu Phe Leu Leu Glu Cys Ser Leu Gly Gln Tyr Thr Ser Ile Gly Gly
            100                 105                 110

Leu Gly Val Trp Lys Leu Ala Pro Met Phe Lys Gly Val Gly Leu Ala
        115                 120                 125

Ala Ala Val Leu Ser Phe Trp Leu Asn Ile Tyr Tyr Ile Val Ile Ile
    130                 135                 140

Ser Trp Ala Ile Tyr Tyr Leu Tyr Asn Ser Phe Thr Thr Thr Leu Pro
145                 150                 155                 160

Trp Lys Gln Cys Asp Asn Pro Trp Asn Thr Asp Arg Cys Phe Ser Asn
                165                 170                 175

Tyr Ser Met Val Asn Thr Thr Asn Met Thr Ser Ala Val Val Glu Phe
            180                 185                 190

Trp Glu Arg Asn Met His Gln Met Thr Asp Gly Leu Asp Lys Pro Gly
        195                 200                 205

Gln Ile Arg Trp Pro Leu Ala Ile Thr Leu Ala Ile Ala Trp Ile Leu
    210                 215                 220

Val Tyr Phe Cys Ile Trp Lys Gly Val Gly Trp Thr Gly Lys Val Val
225                 230                 235                 240

Tyr Phe Ser Ala Thr Tyr Pro Tyr Ile Met Leu Ile Ile Leu Phe Phe
                245                 250                 255

Arg Gly Val Thr Leu Pro Gly Ala Lys Glu Gly Ile Leu Phe Tyr Ile
            260                 265                 270

Thr Pro Asn Phe Arg Lys Leu Ser Asp Ser Glu Val Trp Leu Asp Ala
        275                 280                 285

Ala Thr Gln Ile Phe Phe Ser Tyr Gly Leu Gly Leu Gly Ser Leu Ile
    290                 295                 300

Ala Leu Gly Ser Tyr Asn Ser Phe His Asn Asn Val Tyr Arg Asp Ser
305                 310                 315                 320

Ile Ile Val Cys Cys Ile Asn Ser Cys Thr Ser Met Phe Ala Gly Phe
                325                 330                 335

Val Ile Phe Ser Ile Val Gly Phe Met Ala His Val Thr Lys Arg Ser
            340                 345                 350

Ile Ala Asp Val Ala Ala Ser Gly Pro Gly Leu Ala Phe Leu Ala Tyr
        355                 360                 365

Pro Glu Ala Val Thr Gln Leu Pro Ile Ser Pro Leu Trp Ala Ile Leu
    370                 375                 380

Phe Phe Ser Met Leu Leu Met Leu Gly Ile Asp Ser Gln Phe Cys Thr
385                 390                 395                 400

Val Glu Gly Phe Ile Thr Ala Leu Val Asp Glu Tyr Pro Arg Leu Leu
                405                 410                 415

Arg Asn Arg Arg Glu Leu Phe Ile Ala Ala Val Cys Ile Ile Ser Tyr
            420                 425                 430

Leu Ile Gly Leu Ser Asn Ile Thr Gln Gly Gly Ile Tyr Val Phe Lys
        435                 440                 445

Leu Phe Asp Tyr Tyr Ser Ala Ser Gly Met Ser Leu Leu Phe Leu Val
    450                 455                 460

Phe Phe Glu Cys Val Ser Ile Ser Trp Phe Tyr Gly Val Asn Arg Phe
465                 470                 475                 480

Tyr Asp Asn Ile Gln Glu Met Val Gly Ser Arg Pro Cys Ile Trp Trp
                485                 490                 495

Lys Leu Cys Trp Ser Phe Phe Thr Pro Ile Ile Val Ala Gly Val Phe
            500                 505                 510

Ile Phe Ser Ala Val Gln Met Thr Pro Leu Thr Met Gly Asn Tyr Val
```

| | | | | | | | | | | | |
|---|---|---|---|---|---|---|---|---|---|---|---|
| | | 515 | | | | 520 | | | | 525 | |
| Phe | Pro | Lys | Trp | Gly | Gln | Gly | Val | Gly | Trp | Leu | Met | Ala | Leu | Ser | Ser |
| 530 | | | | | 535 | | | | | 540 | |

Met Val Leu Ile Pro Gly Tyr Met Ala Tyr Met Phe Leu Thr Leu Lys
545                 550                 555                 560

Gly Ser Leu Lys Gln Arg Ile Gln Val Met Val Gln Pro Ser Glu Asp
                565                 570                 575

Ile Val Arg Pro Glu Asn Gly Pro Glu Gln Pro Gln Ala Gly Ser Ser
            580                 585                 590

Thr Ser Lys Glu Ala Tyr Ile
        595

<210> SEQ ID NO 6
<211> LENGTH: 1981
<212> TYPE: DNA
<213> ORGANISM: Homo sapiens
<220> FEATURE:
<221> NAME/KEY: modified_base
<222> LOCATION: (68)..(68)
<223> OTHER INFORMATION: a, c, t, g, unknown or other

<400> SEQUENCE: 6

```
gtagcttcac taaggtggga tggatagcag ggtctcaggc acaaccagta atggagagac      60
aaaaccantg tatcacaaga tggagtttgt gctgtcagtg gctggggaga tcattggctt     120
aggcaacgtc tggaggtttc cctatctctg ctacaaaaat gggggaggtg ccttcttcat     180
cccctacctc gtcttcctct ttacctgtgg cattcctgtc ttccttctgg agacagcact     240
aggccagtac actagccagg gaggcgtcac agcctggagg aagatctgcc ccatctttga     300
gggcattggc tatgcctccc agatgatcgt catcctcctc aacgtctact acatcattgt     360
gttggcctgg gccctgttct acctcttcag cagcttcacc atcgacctgc cctggggcgg     420
ctgctaccat gagtggaaca cagaacactg tatggagttc cagaagacca acggctccct     480
gaatggtacc tctgagaatg ccacctctcc tgtcatcgag ttctgggagc ggcgggtctt     540
gaagatctct gatgggatcc agcacctggg ggccctgcgc tgggagctgg ctctgtgcct     600
cctgctggcc tgggtcatct gctacttctg catctggaag ggggtgaagt ccacaggcaa     660
ggtggtgtac ttcacggcca catttcctta cctcatgctg gtggtcctgt taattcgagg     720
ggtgacgttg cctggggcag cccaaggaat tcagttttac ctgtacccaa acctcacgcg     780
tctgtgggat ccccaggtgt ggatggatgc aggcacccag atattcttct ccttcgccat     840
ctgtcttggg tgcctgacag ccctgggcag ctacaacaag taccacaaca actgctacag     900
cggcaccagc tttgtggccg gctttgccat cttctccatc ctgggcttca tgtctcagga     960
gcaggggtg cccatttctg aggtggccga gtcaggccct ggcctggctt tcatcgctta    1020
cccgcgggct gtggtgatgc tgcccttctc tcctctctgg gcctgctgtt tcttcttcat    1080
ggtcgttctc ctgggactgg atagccagtt tgtgtgtgta gaaagcctgg tgacagcgct    1140
ggtggacatg taccctcacg tgttccgcaa gaagaaccgg agggaagtcc tcatccttgg    1200
agtatctgtc gtctccttcc ctgtggggct gatcatgctc acagagggcg gaatgtacgt    1260
gttccagctc tttgactact atgcggccag tggcatgtgc ctcctgttcg tggccatctt    1320
cgagtccctc tgtgtggctt gggtttacgg agccaagcgc ttctacgaca catcgaaga    1380
catgattggg tacaggccat ggcctcttat caaatactgt tggctcttcc tcacaccagc    1440
tgtgtgcaca gccacctttc tcttctcacct gataaagtac actccgctga cctacaacaa    1500
```

```
gaagtacacg tacccgtggt ggggcgatgc cctgggctgg ctcctggctc tgtcctcctg    1560
gtctgcattc ctgcctggag cctctacaga ctcggaaccc tcaagggccc cttcagagag    1620
agaatccgtc agctcatgtg cccagccgag gacctgcccc agcggaaccc agcaggaccc    1680
tcggctcccg ccaccccag gacctcactg ctcagactca cagagctaga gtctcactgc    1740
tagggggcag gcccttggat ggtgcctgtg tgcctggcct tggggatggc tgtggaggga    1800
acgtggcaga agcagcccca tgtgttccct gcccccgacc tggagtggat aagacaagag    1860
gggtattttg gagtccacct gctgagctgg aggcctccca ctgcaacttt tcagctcagg    1920
ggttgttgaa cagatgtgaa aaggccagtg ccaagagtgt ccctcggaga cccttgaagg    1980
c                                                                   1981
```

```
<210> SEQ ID NO 7
<211> LENGTH: 528
<212> TYPE: PRT
<213> ORGANISM: Homo sapiens

<400> SEQUENCE: 7

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
                20                  25                  30

Gly Gln Gly Ala Pro Gly Pro Ser Leu Thr Gly Ser Pro Trp Pro Gly
            35                  40                  45

Thr Ala Ala Pro Ala Ala Ser Tyr Thr Pro Thr Pro Arg Ser Pro Arg
        50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Val Pro Ser Glu Pro Gly
                85                  90                  95

Asp Pro Leu Glu Ala Val Ala Phe Glu Glu Lys Glu Gly Lys Ala Val
                100                 105                 110

Leu Asn Leu Leu Phe Ser Pro Arg Ala Thr Lys Pro Ser Ala Leu Ser
            115                 120                 125

Arg Ala Val Lys Val Phe Glu Thr Phe Glu Ala Lys Ile His His Leu
        130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp Leu Asp His Pro Gly
    210                 215                 220

Phe Ser Asp Gln Val Tyr Arg Gln Arg Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
            260                 265                 270

Leu Tyr Ala Thr His Ala Cys Gly Glu His Leu Glu Ala Phe Ala Leu
        275                 280                 285
```

```
Leu Glu Arg Phe Ser Gly Tyr Arg Glu Asp Asn Ile Pro Gln Leu Glu
        290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
                340                 345                 350

His Ser Pro Glu Pro Asp Cys Cys His Glu Leu Leu Gly His Val Pro
            355                 360                 365

Met Leu Ala Asp Arg Thr Phe Ala Gln Phe Ser Gln Asp Ile Gly Leu
        370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
                420                 425                 430

Cys Leu Ser Glu Glu Pro Glu Ile Arg Ala Phe Asp Pro Glu Ala Ala
            435                 440                 445

Ala Val Gln Pro Tyr Gln Asp Gln Thr Tyr Gln Ser Val Tyr Phe Val
450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
515                 520                 525

<210> SEQ ID NO 8
<211> LENGTH: 14877
<212> TYPE: DNA
<213> ORGANISM: Homo sapiens

<400> SEQUENCE: 8 gcggggggc agtgtgtgct ccagcatgtg tgtgtgtgtg tgcatgtaca cgtgtgcacc      60
tgtatcgcct gtgtgtgtgc atgtgatgtg tacacgtgtc atgcatgcac gcacatgtgt    120
agtgtgtgct cgtgtgtggt gtgtgcctgt gtcatgtatg agcacacttg tatatgttgt    180
gtgtactgtg tcatatatga gtgtgttttgc ctgtgtagtg catgcacatc cgtgtgtgca    240
tctggtgtgt ccgtgggtca ttacgagtgc atcgtatgtg tatcgtgtac atgagtacac    300
ttgtatgtgt ggtgtgtaca ggtgccatgt aagtgtgctt gtacatatat gcatgcatgt    360
gtcatatgca tctgtgtgtg catgtgtgtg gtgcacacat gttatgtc tgagtgtgcc      420
tgtatgtgtg ctatgtacac gtcatgtgtg agtgtgcttg catgtgcagt gtgtggatgc    480
tgcttgtacc tgtggtgtgt acctgtgtca tgggtgctca cacgtgcatg gagtgttgtg    540
tgtgtgcttg tgtgccccat gtgtgcatgt gtgtgtgcct cacacagatg cctgcatttg    600
cctaggcact tgcaagagga caccatgctg gctctcaaag atcacagggc cacctgagcc    660
ctgtgcacac cacagccagg ccatggctag acctgcaga gccacagggc gatgcctgtc     720
agccagggga cccagaacac ctcctgggct cctccccagc acatggctgg gctcctccag    780
```

```
caggcctgga tttgggaagg gcccgtggtg ggcaaggctg gtgctgggga gcaggcctgg    840
tggcctcaga gactcgccct gtgggcggag cagcctcaca gccaggtcga agtcagcact    900
ctgaccctgc cccacgcggg gagtgggcac cagtcccagg gcacagacgt gctgggtgat    960
taatctgggt gattaagcct cgggctgaga ggctgttgag agagaacacg ctccattgtg   1020
gagctggctc agcattcctt acggccatgg tggcaggggc tgtaaccaca gggacggcgg   1080
aagtggtgga gggtggtggg gtatggaggg aagcccagag ggctccgtgc aggaaggtgg   1140
agcctggtgc aatggagggg acagcaaggg ctcctcagac ctctgcgggg cccccactcc   1200
cctggtcacc tgttttgtct ctgatctggc ctgggtcggc cctcactcct ggccccacct   1260
catagccccc cctggtgggg ctccgctcca gcccttctcc ttcccagggg ccagtatgct   1320
ggccccaggg gtctcttggg gcgtgacctc ggcctccaga gaaccctgtc ccagctctgc   1380
ccttccctct ggggtctctg tagatgggac gctggtcaca gcagcctgtc tgatttgttc   1440
cctgtggcct aggttcctga gcccacagt gccaggggat ggatgccacc ggatctttga   1500
aagaccagtg tcaggccggg cgcagtggct cacgcctgta atcccagcac tttgggaggc   1560
cgaggtgggc ggatcacgaa gtcaggagat cgagaccatc ctggctaaca cagtgaaacc   1620
ccgtctccac taaaaataca aaaagttagc tgggcgtggt ggtgggcgcc tgtagtccca   1680
gctacttggg aggctgaggc aggagaatgg cgtgaaccgg ggaggcggag cttgcagtga   1740
gccgagatcg cgccattgca ctccagcctg ggtgacagag cgagactcgg tctcaaaaaa   1800
aaagaaaaaa aggaaagacc agtgtcttgg gagttgggaa acctgggctg gagactcact   1860
gcatgacccc tgagaagttg cacctcagaa cctcagtcct cgcatctgca gaatgggtct   1920
gtgaacacct cagctgcccg aacgtggatg ccgcaggctg acccagcact gagctctacc   1980
aagaccaggg gccagccgtg tgctccctcc aggcctgtgc ccagcgtgga gaggcctcgt   2040
cccgtgggcg ctggagtgga gccttcctgg tgtttgtgga catctctgga gagggccaga   2100
ggcaggtggg tgacacgggg catggctcaa tcatgggtgg tccagactgg agaggtaccc   2160
tcgggctggg agcggggagg ctggccaggg tagacttttg gggcctccat ggatacccctc  2220 accatctgga atcggagagg ggcacggcac aaaggagggc ggggccaggg ccaggactgg   2280 agtcggggc acctctgtgc caacagggc cttggatctg gggtacagca tggttccccg     2340
gccctgaagg ggctggcgtg tgggacaggc ttcccaggaa tggataggca gggatggatg   2400
ctgcctgatt ggggcgggag gctggaggca gggcaggtgc aggcacctga gggcagcact   2460
cacctccaca ggggtccagg ggcctcccca gcctcagcac ctggcctggg ctcctgcctc   2520
cagagagcct ggccccaagg aagagtctag taagcttagt tcccatcggg cttccatgaa   2580
agcacaactg gcccggcagg aaaccgaatt aaaaagcaat atttgtatca gtggaagaca   2640
tttgctgaaa ggttaaatcc acatccggca gtgtgggcca tgagcctccg gcgtggtgtt   2700
catcaggcat gtctctcctc ctggcctggg cacctgagca ctgggccgc cctgggcaga    2760 gctggggcgg ggtgctgggg ggcctggagc tgcctcaccg agggatcctc agcagccgac   2820 cctggggag gcaaatgaga ctctttctgg ggaccttgag gggagctcgg gggagccatg    2880
cagagcttca ccaggcctgg acactgggca tggaggctgg gccacccaag ggccatcacc   2940
agggactcag gtgggtgggc ctcagccctg ggtgacagaa gctcacgggc cgcagggcga   3000
ggccagaggc tgagccttca ggctgaggtc ttggaggcaa atccctccaa cgcccttctg   3060
agcaggcacc cagacctact gtgggcagga cccacaggag gtggaggcct ttggggaaca   3120
```

```
ctgtggaggg gcatagcatc tccgagagag acagggtct gcactgggtg ctgagagaca   3180
gcagggccg agcggtaggc ttccctgccc ccagggatgt tccagaggag cgcaagggag   3240
gggcattaat atcgtggcaa gaaagggcag gcattgcaga gtgagcagcg acggaactgg   3300
gttttgtggg atgcatagga gttcacccgg ataagaggtg ggtgaggaat gacactgcaa   3360
accgggatc acggagcccc aaatccttct gggccaggaa gtgggaaggg ttggggggtc    3420
ttcccttttgc tttgactgag cactcagcct gcctgcagag ggcagcgagg agccacggag  3480
gggtgtggga cagggatgcc atggctgaag cagttttagg aaaggtccca ggggctattg   3540
ttgaagagag aacggggagc ggggagtccc acagctgaca ggagcagagt gggccctgag   3600
agatgccagc tctggctgcc acagtgacca gccggggtag gccttcgaga agtcaggag   3660
cgtctagggc ttctggctcc tgctgggccc agggtgtcat cttgggctgc aacaccaga   3720
aagcccagca gatacaggaa gccccaagcc ctgtcggaaa cggttcttct ccaggaggga   3780
cagcggtggc agcgttcagc cgcaggccat gcactctggg gccacgtcct tccctctgta   3840
cagtccagca ttgtcaaggc aggctctggc catctctgct gaccccagag ggatggggag   3900
gcctccccctt ccaccagaag ggccagaagc caccctgggc aggggcatca ctctccctgg  3960
gtggggcagc ggctgggagc aggaggtgcc agtgggcgtg ggctggatgc gggtgcctgc   4020
ggggcggaca tggaacttgg gggaggctct aggctggggt tgtcctcaag ggagttctca   4080
ggtcacccca gggtcaccct caacccgggg cctggtgggg tagaggagaa actgcaaagg   4140
tctctccaag gggaaggcat cagggccctc agcactgagg gacgtgcgtg ctctttaaag   4200
aagggggccac aggaccccga gggaagccag gagctagcag tgggccatag aggggctgag  4260
tggggtgggt ggaagccgtc cctggccctg gtcgccctgg caaccctggt ggggactgtg   4320
atgcaggagg tggcagccat ttggaaacgc gtggcgtctc cttagagatg tcttcttcag   4380
cctcccaggg tcctccacac tggacaggtg ggccctcctg ggacattctg accccacgg    4440
ggcgagcttg gaagccgct gcaagggcca cacctgcagg gcccggggc tgtgggcaga    4500
tggcactcct aggaaccacg tctatgagac acacggcctg gaatcttctg gagaagcaaa  4560
caaattgcct cctgacatct gaggctggag gctggattcc ccgtcttggg gctttctggg  4620
tcggtctgcc acgaggttct ggtgttcatt aaaagtgtgc ccctgggctg ccagaaagcc   4680
cctccctgtg tgctctcttg agggctgtgg ggccaagggg accctggctg tctcagcccc   4740
ccgcagagca cgagcccctg gtccccgcaa gcccgcgggc tgaggatgat tcagacaggg   4800
ctggggagtg aaggcaatta gattccacgg acgagccctt tctcctgcgc ctccctcctt   4860
cctcacccac ccccgcctcc atcaggcaca gcaggcaggg gtggggatg taaggagggg   4920
aaggtggggg acccagaggg ggctttgacg tcagctcagc ttataagagg ctgctgggcc   4980
agggctgtgg agacggagcc cggacctcca cactgagcca tgcccacccc cgacgccacc   5040
acgccacagg ccaagggctt ccgcagggcc gtgtctgagc tggacgccaa gcaggcagag   5100
gccatcatgg taagagggca ggtaggtgcc cggcggccgc agtggaccgg agcccagggc   5160
tggtgccagc tgcctctgct actcccagc ctggctggca gcccaggct caggtccat     5220
gcaaacccct gggacgcggc gtggatgtgg aggcctgggc acagcggcat cccctgtgcc   5280
tggtgtttga gtccctgttg ggggagggtg aggtgatgcc tgtccctgtg tgtgcccctc   5340
ttaggccgac ctctctcggg ggtcgtgtgg gtctctgtgt cttgtttcat cttgaatctt   5400
aacgatcgga atgtggaaac aaatccatcc aaaaaatcca agatggccag aggtccccgg   5460
ctgctgcacc cagccccac cctactccca cctgcccctg cctccctctg ccccagctgc    5520
```

| | |
|---|---|
| cctagtcagc accccaacca gcctgcctgc ttggggaggc agccccaagg cccttcccag | 5580 |
| gctctagcag cagctcatgg tgggggtcc tgggcaaata gggggcaaaa ttcaaagggt | 5640 |
| atctgggctc tggggtgatt cccattggcc tgttcctccc ttatttccct cattcattca | 5700 |
| ttcattcatt cattcattca ccatggagtc tgtgttccct gtgacctgca ctcggaagcc | 5760 |
| ctgtgtacag gggactgtgt gggccaggct ggataatcgg gagcttttca gcccacagga | 5820 |
| ggggtcttcg gtgcctcctt gggcactcag aaccttgggc tccctggcac atttaaaatg | 5880 |
| ggtttttatt tatggacctt gattgaaatg tggtgtgagt tgtagcagtg tcatttccag | 5940 |
| gtaccttctc agggacacag gcgcccctcc cccgtcctcc cccgccctcc cctaccctcc | 6000 |
| cccaccaggc tccccatcag gcatcccctc ccagggcgc ccgggccc agcctcacag | 6060 |
| gctctccgtg gcctggaact gcagcccag ctgcatccta caccccacc caagggtaa | 6120 |
| gtaagagggg actctgggag gggcttctgc tgctccccctt catgttccac aaccctggaa | 6180 |
| gctcaggatg aagctgattc ttctcttaca aggggcccag agccttcttg ggagttcagc | 6240 |
| tccaagggat gagccccagg tgtctgccaa gtccccctct gtccaggcct gggacggctc | 6300 |
| tgggatcgag gggtcagagg cgctgagccc agggagagac acctgcgccc agagctatga | 6360 |
| caaagggtgg agggatgaca aggcagccag gagcgggcgc ctgcggggtg gcacagaggg | 6420 |
| gcagggcccg aggacaggtg tcctgatggg agtgtgagaa agggtcccct gtgcggcagc | 6480 |
| caggagggta gggggttgt tcactgggc cctgtggggg cagctccttc ctgagctgcc | 6540 |
| gttccctccc cggcagccga tgccactgtc catcaagaca tcgccctctt cccatcacta | 6600 |
| atccagttag cgcctggcct ggggatgagt gacacagcgt ctctgtctgt ctgctcgcca | 6660 |
| cagagtgggg agcaggcgag caccttccca gcccccactc ctcccccacc accactgctt | 6720 |
| ctgactgggc tgcccccatc gggaagggcg tgcaatgccc gcaggcacct cggctagcat | 6780 |
| ctgcccagc aggcacacag taggcgctca aaaacgtgct ctcatcccct gcctctgtgt | 6840 |
| gccatcagcg ctgcccgact gtgggaccag ctgtgggtgg aggtccccgg gtctcagcag | 6900 |
| gtggaggagg catgggtgcc ccttgtcccc acagtccccg cggttcattg ggcgcaggca | 6960 |
| gagcctcatc gaggacgccc gcaaggagcg ggaggcggcg gtggcagcag cggccgctgc | 7020 |
| agtcccctcg gagcccgggg accccctgga ggctgtggcc tttgaggaga aggaggggaa | 7080 |
| ggccgtgcta aacctgctct tctcccccgag gccaccaag cctcggcgc tgtcccgagc | 7140 |
| tgtgaaggtg tttgaggtga gctggtggcc ttcgtgtccc tggggcaagt tcacctgtgg | 7200 |
| gtggggctgt gtgggctgag ttcctgaccc ctctatagca gaggtgcagc tgcccaggcc | 7260 |
| cccgaggccg gcacaggatg cagcagggga gtctcaggcc tcagctcagc ccccatggca | 7320 |
| tctagccaca ccccgtgtt tttgagggat cctgagccca cccctagggc tgaggctacc | 7380 |
| aagccccact gtgcctcttg ccttgcccat ccctggatc cccctcaccc accatttccc | 7440 |
| acgtgggggg ctcccagcag ggcagcacaa gaggcagggg cagggcagtg tgccctctcc | 7500 |
| cacccaccca gcacagtggc tcaggtgacc actgattgca ttagtcactc cggccccact | 7560 |
| gtgcccggg aggcaggtga cccagctccc ggaagaagct cccaaatgac attaaagcca | 7620 |
| gactccccgc ccccagctc ccagagccag ttttgtggcc cgagggccac tgcgaccac | 7680 |
| cgcccttgtt gctaggcaac aggaggtggg ggtggagcgg accttctgg ccagtgtcct | 7740 |
| ggacgctcag gggccagtga gactcagggc ccatcctaca aacctggatg aggccaccag | 7800 |
| ggttggggc accttctgac cagtggctga ggagccggac tgtgtggcat ggccttggga | 7860 |

```
cacacacacc gagccgccca gaaccaggtt aagcctcaag cggtgacaac tcctggttag    7920
gcacgtaaca caaaatccaa cttgccagtg gcaaaccctg gcctggtggc cgacagctga    7980
cctgagcctg gaagaacggg atctgtgtgc tgctagcaca aaagtcaagg gcagggcctg    8040
gccagccagc cagatgtgcc tcctccccgc ccacccacc ctctctctcc atctctgtct     8100
ctttctcctt ctctctctct tcctgctttt gctccctaag acgtttgaag ccaaaatcca    8160
ccatctagag acccggcccg cccagaggcc gcgagctggg ggcccccacc tggagtactt    8220
cgtgcgcctc gaggtgcgcc gagggggacct ggccgccctg ctcagtggtg tgcgccaggt   8280
gtcagaggac gtgcgcagcc ccgcggggcc caagggtgag gcggttttct gtccttgagg    8340
gccaccaaat gaccttgaga ggctgggggtg caggggctcc tgcaggggga ccctacagtg   8400
accacgtggt ggtggcctgg ttccctctct gcggctccca ctccgcaccc cgttttgcta   8460
cacatccgtg tccgggcctg gggccactcc aggatccccc cgcagctctc acagcccgg    8520
ctgcctctgc cccccggaag tcttgtaggg gaggctgctt caaggtgggt gacacagccc    8580
cacggctccg agctcaccaa gatctcttcc tccatcaccc ataaagtccc ctggttccca    8640
agaaaagtgt cagagctgga caagtgtcat cacctggtca ccaagttcga ccctgacctg    8700
gacttggacc acccggtgag tggtgcgccc ctcactcagg cctcctgccc ctgatcacat    8760
cccctaccct tagcccaacc ctggacagga gtctgtcggc tccaggagcc tccgtggcct    8820
gtgccccac cccagcacag cctcctgacc cgtgcatccc ctctgccctc agggcttctc     8880
ggaccaggtg taccgccagc gcaggaagct gattgctgag atcgccttcc agtacaggca    8940
gtgagggcc cctgcgctcg ggacccagac tccgtcctgc aggctgacgc tggacctggg    9000
gggtgggagg gaaggacaaa ggggaggacc catcttgtca ccagcatcag tgcctcctgc    9060
caggcagctc tgctccaggg ctttccatgt ccccaaatcc cagtggggaa actgaggccc    9120
agggggggcta gagcaacctg ccgaggccac atagccggct cacggcacag tcagctgggg   9180
tgcaccctcc tgtccatcct ccaacccaaa ggcctgctg cactaggcgg gtgtggacct     9240
gtgcccagtg aagctccctc cctccctcct gccttctca ctccccgagg ggacctgctg     9300
accactggcc ccctccccag cggcgacccg attcccgtg tggagtacac cgccgaggag     9360
attgccacct ggtgagacct ccgtgcagct aggggctggg gaggagcccg ggggatgcct    9420
cctggaatcc tggcgtgtga gggccgcctc cagggacctt ggcacaacag gagagactaa    9480
ggccgggaag aagagggact tgcagggctc agaatgttgg gttgggagga agaggctacc    9540
catcctgtcg ggccatcccc agtgtgctga gggaccgccc ctcatggccc ctatcccct    9600
gggattccct aaagccacca gcaaaagccc ctccggggg cctgggtctt caggggtccc     9660
caagaggcct gcgttggtag gggctcaggc aggcagaggc acccacagtt caggaggggg    9720
gtttcgggca ctggggtggg gcattagagg gccctgagcc tggctgcccg caggaaggag    9780
gtctacacca cgctgaaggg cctctacgcc acgcacgcct gcggggagca cctgaggcc     9840
tttgctttgc tggagcgctt cagcggctac cgggaagaca atatccccca gctggaggac    9900
gtctcccgct tcctgaaggg tgtgcccaga cgggagggc gcagagccgg ggggccgggg    9960
atggtcagca aagcgcccca ccccagccgcg gctccagccc gtcccggctc ggcagtgacc   10020
cgcgtggccc cttgcagagc gcacgggctt ccagctgcgg cctgtggccg gcctgctgtc    10080
cgcccgggac ttcctggcca gcctggcctt ccgcgtgttc cagtgcaccc agtatatccg    10140
ccacgcgtcc tcgcccatgc actccccctga gccgtgagtg cgcgccctgg ccgccagccc   10200
gagggtgggg ggtgcgacgg gcggcccctc agccccttc tccctcctac gcgcagggac     10260
```

```
tgctgccacg agctgctggg gcacgtgccc atgctggccg accgcacctt cgcgcagttc   10320
tcgcaggtac gccgcggcct cggagggagc cggggtcacc caggggctgg cttggcgccg   10380
ggggcgggcg gggatcgatg tgcgggtggg tgaagtgtgc tgcctgctcc cgggccccgc   10440
caaggaggct cggcgccccg agggtcgcgc ggcatagggc ggggctggag cggagcctcc   10500
cacggcctgt gctgccacct gccggctacc tgggaacggc gcccacgggc ttaggaatgt   10560
ggtcaaggag ggctgcctgg aggaggaggc ccggtggagg tgcggatcct gggcggccag   10620
ggaaggtctc tgccgccagg gaagtgtccc agagacccct ggaggggctg ctgacacccc   10680
cggtgccccc acctcgagca tgacccaggg ctgcctctcc ccatccttca tcctccctgc   10740
tccacaggac attggcctgg cgtccctggg ggcctcggat gaggaaattg agaagctgtc   10800
cacggtgggt tgacccctcc ctgcaggggc tggggtgtgg gtttgggggt ctgaatccag   10860
gcctcaccct cttgccgtcc aggctgaggc ctctccttcc acccacgaat tgtgaccctc   10920
accctggcct gcctgcatcc tggcctggcc tccctggggg tggtatcctg gtcacgggtg   10980
accaggggct gcccggtggg cggcagctgt ctctgggctg atgctgcccg gcttccccgc   11040
agctgtactg gttcacggtg gagttcgggc tgtgtaagca gaacggggag gtgaaggcct   11100
atggtgccgg gctgctgtcc tcctacgggg agctcctggt gagagtctct ccttgctgca   11160
gcccccagca gaggggcagg gctggggac ggtgcaggga ggggacaggc tcccagtggg   11220
aggaaactga ggcctggacc tccaggactc aggctctgtt tgggagaagg cttgtctctg   11280
cccagtcctc accccacatt atcccaggcc tccgaaggcc cggcggggga gatggggtg   11340 actctaccca aggaacccac ccagcgtcag gccacggtgc cccagttccc tcggggacct   11400
gggtgcagtg gagtcagtga tgccattggc ctcctgccag cactgcctgt ctgaggagcc   11460
tgagattcgg gccttcgacc ctgaggctgc ggccgtgcag ccctaccaag accagacgta   11520
ccagtcagtc tacttcgtgt ctgagagctt cagtgacgcc aaggacaagc tcaggtgggc   11580
taggctgcta gggcaagccc cccatggtgc ccccaaactg gccagccag gccttccttc   11640 tggccttgag cagggctgga cctgtgagcc caggtcacag atgagaaaac cgacccctgg   11700
ttgcagcagc ccccacacag caggacacc atccgtgaga aggaccccag cgtctgggga   11760
ggggcagacc tacaggactg ggggctgctg ggtggccggg tcaaggccag tcttggaggt   11820
gctgacagag cctgagcttt gtgaggacgt cctgtgaaac ctgtcccggc ccctgcccct   11880
gggatgggga gaagtcaggg ggatagacag agtcaaggtg ggggacaggg cgggagtggg   11940
gtccccaggg ctgggggcct ttggtgcagt gaccagagtg tcaggagagg ggagcaaagc   12000
cctctagcct catcctcata aaaggtctca tcattttccc tccagcctct tatgcactgg   12060
ggaaactgag gccaggggct atgtgtccag cggacagggg tgctgaattc cacccacagg   12120
cttagggata tggtcaagga aagcttcctg gaggaggccc agtggaggtt cagggaggga   12180
tggggtgccc ggcagtctct agtggaaaag gcgcctagcc tatctccccc atgaaccccc   12240
tcacccagcc ctggaagagg cctcagtgtc ccgcctgtga ccagttggct cagaaaagcc   12300 ctggagctc tgagccactg tgaaggtgga aacgcggccc ctggcctccc ctctcctgga   12360
ggctgcagac tctgcccgcc agttgacgag ggctctgccg ctctcctccc caggagctat   12420
gcctcacgca tccagcgccc cttctccgtg aagttcgacc cgtacacgct ggccatcgac   12480
gtgctggaca gccccaggc cgtgcggcgc tccctggagg gtgtccagga tgagctggac   12540
acccttgccc atgcgctgag tgccattggc taggtgcacg gcgtccctga gggcccttcc   12600
```

```
caacctcccc tggtcctgca ctgtcccgga gctcaggccc tggtgagggg ctgggtcccg    12660
ggtgccccc  atgccctccc tgctgccagg ctcccactgc ccctgcacct gcttctcagc    12720
gcaacagctg tgtgtgcccg tggtgaggtt gtgctgcctg tggtgaggtc ctgtcctggc    12780
tcccagggtc ctgggggctg ctgcactgcc ctccgccctt ccctgacact gtctgctgcc    12840
ccaatcaccg tcacaataaa agaaactgtg gtctctacac ctgcctggcc ccacatctgt    12900
gccacagaga cagaccctgg gatcctcaga ctcccacacc cccacccag  cctcactcag    12960
aggtttcgcc ctggcctcct tcctcctctg ggagatggct ggccgccctg gccaggcagc    13020
tggcccctcc gggcctggtt tcccgctca  ccctgaggcc ccgcccagct ctgagcccca    13080
agcagctcca gaggctcggg caccctggcc gagctgcccc atctccgtgg ggtgccctcc    13140
caaggtgggg agccacgtga cagtgggagg gcctctctca ggcctggcag ggagcagggg    13200
tcacaaactg tgctggctgg gggtggtctc agaggtgggc ctgcaggcct aaccctccct    13260
gctgacaggg ctcccagccc ttgagagaaa cagggatgga ggaacagctg ccctgatgcc    13320
ctcacccacc cggagcaggc cctgcgaacc aaggggaacc tcagtgtggc ccccagcatg    13380
tgtgctgatg ggagggtct  ggctgagctg gtgcccaggc agatggtctg ggcctgtctc    13440
cccagcgagg caggatgggg gctggatttc agactctgta agatgcccct ggcttactcg    13500
aggggcctgg acattgccct ccagagagag cacccaacac cctccaggct tgaccggcca    13560
gggtgtcccc ttcctacctt ggagagagca gccccaggg  atcctgcagg gggtgctggg    13620
acaccagctg gccttcaagg tctctgcctc cctccagcca ccccactaca cgctgctggg    13680
atcctggatc tcagctcccc ggccgacaac actggcaaac tcctactcat ccacgaaggc    13740
cctcctgggc atggtggtcc ttcccagcct ggcagtctgt tcctcacaca ccttgttagt    13800
gcccagcccc tgaggttgca gctggggtg  tctctgaagg gctgtgagcc cccaggaagc    13860
cctggggaag tgcctgcctt gcctcccccc ggccctgcca gcgcctggct ctgccctcct    13920
acctgggctc cccccatcca gcctccctcc ctacacactc ctctcaagga ggcacccatg    13980
tcctctccag ctgccgggcc tcagagcact gtggcgtcct ggggcagcca ccgcatgtcc    14040
tgctgtggca tggctcaggg tggaaagggc ggaagggagg ggtcctgcag atagctggtg    14100
cccactacca aacccgctcg gggcaggaga gccaaaggct gggtgtgtgc agagcggccc    14160
cgagaggttc cgaggctgag gccagggtgg gacatagggga tgcgaggggc cggggcacag    14220
gatactccaa cctgcctgcc cccatggtct catcctcctg cttctgggac ctcctgatcc    14280
tgcccctggt gctaagaggc aggtagggc  tgcaggcagc agggctcgga gcccatgccc    14340
cctcaccatg ggtcaggctg gacctccagg tgcctgttct ggggagctgg gagggccgga    14400
ggggtgtacc ccaggggctc agcccagatg acactatggg ggtgatggtg tcatgggacc    14460
tggccaggag aggggagatg ggctcccaga agaggagtgg gggctgagag ggtgcctggg    14520
gggcaggac  ggagctgggc cagtgcacag cttcccacac ctgcccaccc ccagagtcct    14580
gccgccaccc ccagatcaca cggaagatga ggtccgagtg gcctgctgag gacttgctgc    14640
ttgtccccag gtcccaggt  catgccctcc ttctgccacc ctggggagct gagggcctca    14700
gctgggctc  ctgtcctaag gcagggtggg aactaggcag ccagcaggga ggggaccct    14760
ccctcactcc cactctccca cccccaccac cttggcccat ccatggcggc atcttgggcc    14820
atccgggact ggggacaggg gtcctgggga caggggtgtg gggacagggg tcctggg      14877
```

<210> SEQ ID NO 9
<211> LENGTH: 382

```
<212> TYPE: PRT
<213> ORGANISM: Homo sapiens

<400> SEQUENCE: 9

Met Leu Asp Gly Leu Lys Met Glu Glu Asn Phe Gln Ser Ala Ile Asp
1               5                   10                  15

Thr Ser Ala Ser Phe Ser Ser Leu Leu Gly Arg Ala Val Ser Pro Lys
            20                  25                  30

Ser Val Cys Glu Gly Cys Gln Arg Val Ile Leu Asp Arg Phe Leu Leu
        35                  40                  45

Arg Leu Asn Asp Ser Phe Trp His Glu Gln Cys Val Gln Cys Ala Ser
    50                  55                  60

Cys Lys Glu Pro Leu Glu Thr Thr Cys Phe Tyr Arg Asp Lys Lys Leu
65                  70                  75                  80

Tyr Cys Lys Tyr Asp Tyr Glu Lys Leu Phe Ala Val Lys Cys Gly Gly
                85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Val Cys Glu Arg Gln
        115                 120                 125

Leu Gln Lys Gly Asp Glu Phe Val Leu Lys Glu Gly Gln Leu Leu Cys
    130                 135                 140

Lys Gly Asp Tyr Glu Lys Glu Arg Glu Leu Leu Ser Leu Val Ser Pro
145                 150                 155                 160

Ala Ala Ser Asp Ser Gly Lys Ser Asp Asp Glu Glu Ser Leu Cys Lys
            165                 170                 175

Ser Ala His Gly Ala Gly Lys Gly Thr Ala Glu Glu Gly Lys Asp His
        180                 185                 190

Lys Arg Pro Lys Arg Pro Arg Thr Ile Leu Thr Thr Gln Gln Arg Arg
    195                 200                 205

Ala Phe Lys Ala Ser Phe Glu Val Ser Ser Lys Pro Cys Arg Lys Val
210                 215                 220

Arg Glu Thr Leu Ala Ala Glu Thr Gly Leu Ser Val Arg Val Val Gln
225                 230                 235                 240

Val Trp Phe Gln Asn Gln Arg Ala Lys Met Lys Lys Leu Ala Arg Arg
            245                 250                 255

Gln Gln Gln Gln Gln Gln Asp Gln Gln Asn Thr Gln Arg Leu Ser Ser
        260                 265                 270

Ala Gln Thr Asn Gly Gly Gly Ser Ala Gly Met Glu Gly Ile Met Asn
    275                 280                 285

Pro Tyr Thr Ala Leu Pro Thr Pro Gln Gln Leu Leu Ala Ile Glu Gln
290                 295                 300

Ser Val Tyr Ser Ser Asp Pro Phe Arg Gln Gly Leu Thr Pro Pro Gln
305                 310                 315                 320

Met Pro Gly Asp His Met His Pro Tyr Gly Ala Glu Pro Leu Phe His
            325                 330                 335

Asp Leu Asp Ser Asp Asp Thr Ser Leu Ser Asn Leu Gly Asp Cys Phe
        340                 345                 350

Leu Ala Thr Ser Glu Ala Gly Pro Leu Gln Ser Arg Val Gly Asn Pro
    355                 360                 365

Ile Asp His Leu Tyr Ser Met Gln Asn Ser Tyr Phe Thr Ser
370                 375                 380

<210> SEQ ID NO 10
```

```
<211> LENGTH: 5310
<212> TYPE: DNA
<213> ORGANISM: Homo sapiens
<220> FEATURE:
<221> NAME/KEY: modified_base
<222> LOCATION: (901)..(1000)
<223> OTHER INFORMATION: a, c, t, g, unknown or other
<220> FEATURE:
<221> NAME/KEY: modified_base
<222> LOCATION: (1301)..(1400)
<223> OTHER INFORMATION: a, c, t, g, unknown or other
<220> FEATURE:
<221> NAME/KEY: modified_base
<222> LOCATION: (1821)..(1920)
<223> OTHER INFORMATION: a, c, t, g, unknown or other
<220> FEATURE:
<221> NAME/KEY: modified_base
<222> LOCATION: (2881)..(2980)
<223> OTHER INFORMATION: a, c, t, g, unknown or other
<220> FEATURE:
<221> NAME/KEY: modified_base
<222> LOCATION: (3461)..(3560)
<223> OTHER INFORMATION: a, c, t, g, unknown or other
<220> FEATURE:
<221> NAME/KEY: modified_base
<222> LOCATION: (4401)..(4500)
<223> OTHER INFORMATION: a, c, t, g, unknown or other
<220> FEATURE:
<221> NAME/KEY: modified_base
<222> LOCATION: (4801)..(4900)
<223> OTHER INFORMATION: a, c, t, g, unknown or other

<400> SEQUENCE: 10
```

| | | | | | |
|---|---|---|---|---|---|
| gtataggttg | gggcggagtc | ggattcggga | tggaaaacct | ggggcaaggg | atgtaggtgg | 60 |
| gggtgagggg | ggcaggagaa | ggagaaacgc | agttgggggg | cggaggccta | agtacataac | 120 |
| gtgttgactt | caagtgaaat | cagatcagcc | agagcagttc | gctgtgactg | atctctcctc | 180 |
| ccaccctaca | ttctcttggc | tggaccctat | cctcctggct | gattctggtc | gccctggaca | 240 |
| ctccctcagt | tctttcccag | gagtgcggtg | gctgctggcg | ccgagtccca | gcgggcacgg | 300 |
| acgtcagacg | catcgtttct | tctcctctac | aggtcctccc | ggcccggccc | gaacatgctg | 360 |
| gacggcctaa | agatggagga | gaacttccaa | agcgcgatcg | acacctcggc | ctccttctcc | 420 |
| tcgctgctgg | gtgagtgttc | aggccgtgcg | tcctgggcgc | actctctttc | cgcttggcgc | 480 |
| tgagctctgg | agccccgctc | tctgggacct | ggtccgcgat | agggaagcta | gcgcccctct | 540 |
| tcatacacta | aattgagccc | catcactatc | tgtccgtcag | tgcttgtggg | tcgtccctac | 600 |
| ccaaataaat | ccaacaagcc | gccccaggcc | tcacgcactg | ggcaccgaat | tccccaaagc | 660 |
| cgcgaggggc | gggcgagctt | gttcgtaggc | gtctgagtgg | caagtgatta | aaaataccca | 720 |
| gggctggatt | tttaatctcg | gagctgatcg | acgtctcata | aatgccgccc | tcttctcgcg | 780 |
| gcctagaggc | aatagcatcc | gagacccgag | gcctggagcg | cccaagttcg | aggaggcttc | 840 |
| tctcccccac | caactccagc | cccaatttca | gccatgggca | aggccgagag | agactttcct | 900 |
| nnnnnnnnnn | nnnnnnnnnn | nnnnnnnnnn | nnnnnnnnnn | nnnnnnnnnn | nnnnnnnnnn | 960 |
| nnnnnnnnnn | nnnnnnnnnn | nnnnnnnnnn | nnnnnnnnnn | gggtcccggc | caggtttggc | 1020 |
| atggtctacc | tgcccgggct | gctcacccgc | caacgtctgt | tgtggctaca | ggcagagcgg | 1080 |
| tgagccccaa | gtctgtctgc | gagggctgtc | agcgggtcat | cttggacagg | tttctgctgc | 1140 |
| ggctcaacga | cagcttctgg | catgagcagt | gcgtgcagtg | cgcctcctgc | aaagagcccc | 1200 |
| tggagaccac | ctgcttctac | cgggacaaga | agctgtactg | caagtatgac | tacgagaagt | 1260 |
| aagtggccgc | accccgcag | cgctccccgc | gcactggcat | nnnnnnnnnn | nnnnnnnnnn | 1320 |
| nnnnnnnnnn | nnnnnnnnnn | nnnnnnnnnn | nnnnnnnnnn | nnnnnnnnnn | nnnnnnnnnn | 1380 |

```
nnnnnnnnnn nnnnnnnnnn atcccagttc ttgaagttcc ttttgctgtt gacttcaggg    1440
gagacccagg accaagccag attttactca tggtgcatgt acttcctttc tccctgctgc    1500
caggctgttt gctgttaaat gtggggctg cttcgaggcc atcgctccca atgagtttgt     1560
tatgcgggcc cagaagagtg tataccacct gagctgcttc tgctgctgtg tctgcgagcg    1620
acagcttcag aagggtgatg agtttgtcct gaaggagggg cagctgctct gcaaagggga    1680
ctatgagaag gagcgggagc tgctcagcct ggtgagccca gcagcctcag actcaggtga    1740
gtgccaggtg gtgggcaggg ctgcggtggg gtgggtagag tggagttggg tggctgtctg    1800
cattgtttct tccctagatg nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
catacagctc caggaactgg ctttcaggga ctcacaacat tgtcttttgc ttctttcagg    1980
taaaagtgat gatgaagaaa gtctctgcaa gtcagcccat ggggcaggga aaggaactgc    2040
tgaggaaggc aaggaccata agcgccccaa acgtccgaga accatcttga caactcaaca    2100
gaggcgagca ttcaaggcct catttgaagt atcctccaag ccctgcagga aggtatagga    2160
gggagcaggg aggaaaagga gctgggcccc acttctctgt gtgcactcag acccctctgg    2220
gatctcagtg ggcattgggg gtcacagtgg tgaggaaggc tgttcagaca gagcctgcac    2280
aggcggctca gcctgttgg agactccaga gatcactaag ctgtggccag ggtgtgatag     2340
actctcctga agctttcatg catgcacacc aactccaaat ggccctgtc acacctttca     2400
tttcatagag cacaatggga acagtaataa tgataggtgt ccattgtggt gtagacccag    2460
atgctgtaaa gcaaagagta taaaaacaca gtggcttgca gtactctttt ttgagtctgg    2520
cttttttccac ttggtgtggt ggtttgggga ttcattcatt cctatttcag cattccactg   2580
tataggtgtg ccatgattgg tttgtccatg cacctgttga tgggtgtttg gggttgtttc    2640
tagtttggga ctgtttcaaa taggactgct atggacattc atgtaaaaaa aaatacagtg    2700
gtttaatgag acaggagttt attctcttct gtcacagtcc agaggtgagc aaggcaaggc    2760
tggtgggtgg ctctgttatc catctcctgt gtccaagcga ctgctccagt tgtcaccatg    2820
tttccagtca ccaggtagag aaagaggaaa tggagggcaa cgcgccctgct ttttaaggat   2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn atgcatatgc atggcttata    3000
gctaaagcac aacaatagac taaagtctaa accacttgaa ggcctaattt ccagagcaag    3060
agaaatccag aaacacctct tgggaatgca catgtaaatt aataattatt attttgtttc    3120
tttacctggt gaaggacttt cttttctacct gaagggaagc aatgttctcg tgtttgtgtg    3180
tatgctcaac attaaaaact attcagctcc taaagcagat acagtctttt ggcctcctca    3240
agtattatat aggagatgtt ctacctccta ccctgagatg ccagtgtgtc tacatttctc    3300
gttcaattt tccaaggtga gagagactct ggctgcagag acagggctga gtgtccgtgt    3360
cgtccaggtg tggttccaaa accagagagc gaaggtaacc tgcttcttac ttttatctgt    3420
ccccatgttg ctggtttcct gaaataatca cagtaggaca nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn agccctctcc cggggaaggt gtcacttcca ggcccccct    3600
tactttgtga acatgctgca ggccacctga cttctaatcc tatggtcctc tccttatcag    3660
atgaagaagc tggccaggcg acagcagcag cagcagcaag atcagcagaa cacccagagg    3720
```

```
ctgagctctg gtaagctggt gcctcctccc aggcagttct ggctggaatc caggctgttc    3780
ctaccagagg cctcccacta cccagctctt tggatgacat atctggactc agtgaagcct    3840
agaccacacc cactggagaa ataaggcctt caagggaaga ctgagccacg aggaacttgt    3900
gagagggttg agggctcctg agctgcaggc ttagaactgc tgattgggga tggcactgac    3960
cttatccaca gcgtccaggc ctggatccca ccacagcgtc agggactgct tgcagagtca    4020
cagatacgtt cagtttctca tcttgcttag ttctccttcc aggctaattg atttaataga    4080
agacacctcg gtgacttggc tctttccaaa ataacataaa gtagtaaaaa taatgatagt    4140
aaaataacaa tgccttcctt tgttgaacac tcttatagat tggtgttctc atacatgctg    4200
acttgacttt tacaacaccc attcctggag gcgagtggag aagttgttat tatccctatg    4260
tcacagatga gcaaacaaag gctctgcaag attgaatgtg gccctagatc ggtaagggca    4320
gggggctggg actagaactc taactgtgtt ccacaggcca tgggccttct catctctacc    4380
cagatgtgct tttgaaaaag nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
cacgttgaga atgacctggc ttcttctttg ttccacagct cagacaaacg gtggtgggag    4560
tgctgggatg gaaggaatca tgaaccccta cacggctctg cccaccccac agcagctcct    4620
ggccatcgag cagagtgtct acagctcaga tcccttccga cagggtctca ccccacccca    4680
gatgcctgga gaccacatgc cccttatgg taagagggac ttaagcccct cgggccctct    4740
cataacttgt gtgggtttct cattccctcc taaacacatc taggcagttc ccagatgctc    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn aaatgagtca cttcttcaag    4920
accctcatgc cagtgtttca tctccatttc aggtgccgag ccccttttcc atgacctgga    4980
tagcgacgac acctccctca gtaacctggg tgattgtttc ctagcaacct cagaagctgg    5040
gcctctgcag tccagagtgg gaaaccccat tgaccatctg tactccatgc agaattctta    5100
cttcacatct tgagtcttcc cctagagttc tgtgactagg ctcccatatg gaacaaccat    5160
attctttgag gggtcactgg ctttaggaca gggaggccag ggaagaggtg ggttggggag    5220
ggagttttgt tggggatgct gttgtataat gatatggtgt agctcagcat ttccaaagac    5280
tgaatacatt atggattgca tagtttaatg                                    5310
```

<210> SEQ ID NO 11
<211> LENGTH: 655
<212> TYPE: PRT
<213> ORGANISM: Homo sapiens

<400> SEQUENCE: 11

```
Met Ala Glu Ala Pro Gln Val Val Glu Ile Asp Pro Asp Phe Glu Pro
1               5                   10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
        35                  40                  45

Ala Ala Asn Pro Asp Ala Ala Ala Gly Leu Pro Ser Ala Ser Ala Ala
    50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Val Ala Ala
                85                  90                  95
```

```
Ala Ala Ala Ala Ala Thr Gly Gly Leu Cys Gly Asp Phe Gln Gly
            100                 105                 110

Pro Glu Ala Gly Cys Leu His Pro Ala Pro Gln Pro Pro Pro Pro
        115                 120                 125

Gly Pro Leu Ser Gln His Pro Val Pro Ala Ala Ala Gly Pro
    130                 135                 140

Leu Ala Gly Gln Pro Arg Lys Ser Ser Ser Arg Arg Asn Ala Trp
145                 150                 155                 160

Gly Asn Leu Ser Tyr Ala Asp Leu Ile Thr Lys Ala Ile Glu Ser Ser
                165                 170                 175

Ala Glu Lys Arg Leu Thr Leu Ser Gln Ile Tyr Glu Trp Met Val Lys
        180                 185                 190

Ser Val Pro Tyr Phe Lys Asp Lys Gly Asp Ser Asn Ser Ser Ala Gly
            195                 200                 205

Trp Lys Asn Ser Ile Arg His Asn Leu Ser Leu His Ser Lys Phe Ile
    210                 215                 220

Arg Val Gln Asn Glu Gly Thr Gly Lys Ser Ser Trp Trp Met Leu Asn
225                 230                 235                 240

Pro Glu Gly Gly Lys Ser Gly Lys Ser Pro Arg Arg Arg Ala Ala Ser
                245                 250                 255

Met Asp Asn Asn Ser Lys Phe Ala Lys Ser Arg Ser Arg Ala Ala Lys
            260                 265                 270

Lys Lys Ala Ser Leu Gln Ser Gly Gln Glu Gly Ala Gly Asp Ser Pro
        275                 280                 285

Gly Ser Gln Phe Ser Lys Trp Pro Ala Ser Pro Gly Ser His Ser Asn
    290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
                325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
        355                 360                 365

Glu Asn Met Glu Asn Leu Leu Asp Asn Leu Asn Leu Leu Ser Ser Pro
    370                 375                 380

Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
                405                 410                 415

Pro Ser Pro Asn Tyr Gln Lys Tyr Thr Tyr Gly Gln Ser Ser Met Ser
            420                 425                 430

Pro Leu Pro Gln Met Pro Ile Gln Thr Leu Gln Asp Asn Lys Ser Ser
        435                 440                 445

Tyr Gly Gly Met Ser Gln Tyr Asn Cys Ala Pro Gly Leu Leu Lys Glu
    450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
                485                 490                 495

Met Met Gly Pro Asn Ser Val Met Ser Thr Tyr Gly Ser Gln Ala Ser
            500                 505                 510
```

```
His Asn Lys Met Met Asn Pro Ser Ser His Thr His Pro Gly His Ala
            515                 520                 525
Gln Gln Thr Ser Ala Val Asn Gly Arg Pro Leu Pro His Thr Val Ser
        530                 535                 540
Thr Met Pro His Thr Ser Gly Met Asn Arg Leu Thr Gln Val Lys Thr
545                 550                 555                 560
Pro Val Gln Val Pro Leu Pro His Pro Met Gln Met Ser Ala Leu Gly
                565                 570                 575
Gly Tyr Ser Ser Val Ser Ser Cys Asn Gly Tyr Gly Arg Met Gly Leu
            580                 585                 590
Leu His Gln Glu Lys Leu Pro Ser Asp Leu Asp Gly Met Phe Ile Glu
        595                 600                 605
Arg Leu Asp Cys Asp Met Glu Ser Ile Ile Arg Asn Asp Leu Met Asp
    610                 615                 620
Gly Asp Thr Leu Asp Phe Asn Phe Asp Asn Val Leu Pro Asn Gln Ser
625                 630                 635                 640
Phe Pro His Ser Val Lys Thr Thr Thr His Ser Trp Val Ser Gly
                645                 650                 655

<210> SEQ ID NO 12
<211> LENGTH: 5738
<212> TYPE: DNA
<213> ORGANISM: Homo sapiens

<400> SEQUENCE: 12
gcagccgcca cattcaacag gcagcagcgc agcgggcgcg ccgctgggga gagcaagcgg    60
cccgcggcgt ccgtccgtcc ttccgtccgc ggccctgtca gctggagcgc ggcgcaggct   120
ctgccccggc ccggcggctc tggccggccg tccagtccgt gcggcggacc ccgaggagcc   180
tcgatgtgga tggccccgcg aagttaagtt ctgggctcgc gcttccactc cgccgcgcct   240
tcctcccagt ttccgtccgc tcgccgcacc ggcttcgttc ccccaaatct cggaccgtcc   300
cttcgcgccc cctccccgtc cgcccccagt gctgcgttct cccctcttg gctctcctgc    360
ggctggggga ggggcggggg tcaccatggc cgaggcgcct caggtggtgg agatcgaccc   420
ggacttcgag ccgctgcccc ggccgcgctc gtgcacctgg ccgctgccca ggccggagtt   480
tagccagtcc aactcggcca cctccagccc ggcgccgtcg ggcagcgcgg ctgccaaccc   540
cgacgccgcg gcgggcctgc cctcggcctc ggctgccgct gtcagcgccg acttcatgag   600
caacctgagc ttgctggagg agagcgagga cttcccgcag gcgcccggct ccgtggcggc   660
ggcggtggcg gcggcggccg ccgcggccgc caccgggggg ctgtgcgggg acttccaggg   720
cccggaggcg ggctgcctgc acccagcgcc accgcagccc ccgccgcccg gccgctgtc    780
gcagcacccg ccggtgcccc cgccgccgc tgggccgctc gcggggcagc gcgcaagag    840
cagctcgtcc cgccgcaacg cgtggggcaa cctgtcctac gccgacctca tccaccaagge   900
catcgagagc tcggcggaga gcggctcac gctgtcgcag atctacgagt ggatggtcaa   960
gagcgtgccc tacttcaagg ataagggtga cagcaacagc tcggcgggct ggaagaattc   1020
aattcgtcat aatctgtccc tacacagcaa gttcattcgt gtgcagaatg aaggaactgg   1080
aaaaagttct tggtggatgc tcaatccaga gggtggcaag agcgggaaat ctcctaggag   1140
aagagctgca tccatggaca caacagtaa atttgctaag agccgaagcc gagctgccaa   1200
gaagaaagca tctctccagt ctggccagga gggtgctggg gacagccctg gatcacagtt   1260
ttccaaatgg cctgcaagcc ctggctctca cagcaatgat gactttgata actggagtac   1320
```

```
atttcgccct cgaactagct caaatgctag tactattagt gggagactct cacccattat   1380
gaccgaacag gatgatcttg gagaagggga tgtgcattct atggtgtacc cgccatctgc   1440
cgcaaagatg gcctctactt tacccagtct gtctgagata agcaatcccg aaaacatgga   1500
aaatcttttg gataatctca accttctctc atcaccaaca tcattaactg tttcgaccca   1560
gtcctcacct ggcaccatga tgcagcagac gccgtgctac tcgtttgcgc caccaaacac   1620
cagtttgaat tcacccagcc caaactacca aaaatataca tatggccaat ccagcatgag   1680 cccttttgccc cagatgccta tacaaacact tcaggacaat aagtcgagtt atggaggtat   1740
gagtcagtat aactgtgcgc ctggactctt gaaggagttg ctgacttctg actctcctcc   1800
ccataatgac attatgacac cagttgatcc tggggtagcc cagcccaaca gccgggttct   1860
gggccagaac gtcatgatgg gccctaattc ggtcatgtca acctatggca gccaggcatc   1920
tcataacaaa atgatgaatc ccagctccca tacccaccct ggacatgctc agcagacatc   1980
tgcagttaac gggcgtcccc tgccccacac ggtaagcacc atgccccaca cctcgggtat   2040
gaaccgcctg acccaagtga agacacctgt acaagtgcct ctgccccacc ccatgcagat   2100
gagtgccctg gggggctact cctccgtgag cagctgcaat ggctatggca gaatgggcct   2160
tctccaccag gagaagctcc caagtgactt ggatggcatg ttcattgagc gcttagactg   2220
tgacatggaa tccatcattc ggaatgacct catggatgga gatacattgg attttaactt   2280
tgacaatgtg ttgcccaacc aaagcttccc acacagtgtc aagacaacga cacatagctg   2340
ggtgtcaggc tgagggttag tgagcaggtt acacttaaaa gtacttcaga ttgtctgaca   2400
gcaggaactg agagaagcag tccaaagatg tctttcacca actccctttt agttttcttg   2460
gttaaaaaaa aaacaaaaa aaaaaaccct ccttttttcc tttcgtcaga cttggcagca   2520
aagacatttt tcctgtacag gatgtttgcc caatgtgtgc aggttatgtg ctgctgtaga   2580
taaggactgt gccattggaa atttcattac aatgaagtgc caaactcact acaccatata   2640
attgcagaaa agattttcag atcctggtgt gctttcaagt tttgtatata agcagtagat   2700
acagattgta tttgtgtgtg ttttttggttt ttctaaatat ccaattggtc caaggaaagt   2760
ttatactctt tttgtaatac tgtgatgggc ctcatgtctt gataagttaa acttttgttt   2820
gtactacctg ttttctgcgg aactgacgga tcacaaagaa ctgaatctcc attctgcatc   2880
tccattgaac agccttggac ctgttcacgt tgccacagaa ttcacatgag aaccaagtag   2940
cctgttatca atctgctaaa ttaatggact tgttaaactt ttggaaaaaa aaagattaaa   3000
tgccagcttt gtacaggtct tttctatttt ttttttgttta ttttgttatt tgcaaatttg   3060
tacaaacatt taaatggttc taatttccag ataaatgatt tttgatgtta ttgttgggac   3120
ttaagaacat ttttggaata gatattgaac tgtaataatg ttttcttaaa actagagtct   3180
actttgttac atagtcagct tgtaaatttt gtggaaccac aggtatttgg ggcagcattc   3240
ataattttca ttttgtattc taactggatt agtactaatt ttatacatgc ttaactggtt   3300
tgtacacttt gggatgctac ttagtgatgt ttctgactaa tcttaaatca ttgtaattag   3360
tacttgcata ttcaacgttt caggccctgg ttgggcagga aagtgatgta tagttatgga   3420
cactttgcgt ttcttattta ggataactta atatgttttt atgtatgtat tttaaagaaa   3480
tttcatctgc ttctactgaa ctatgcgtac tgcatagcat caagtcttct ctagagacct   3540
ctgtagtcct gggaggcctc ataatgtttg tagatcagaa aagggagatc tgcatctaaa   3600
gcaatggtcc tttgtcaaac gagggatttt gatccacttc accattttga gttgagcttt   3660
agcaaaagtt tcccctcata attctttgct cttgtttcag tccaggtgga ggttggtttt   3720
```

```
gtagttctgc cttgaggaat tatgtcaaca ctcatacttc atctcattct cccttctgcc    3780
ctgcagatta gattacttag cacactgtgg aagtttaagt ggaaggaggg aatttaaaaa    3840
tgggacttga gtggtttgta gaatttgtgt tcataagttc agatgggtag caaatggaat    3900
agaacttact taaaaattgg ggagatttat ttgaaaacca gctgtaagtt gtgcattgag    3960
attatgttaa aagccttggc ttaagaattt gaaaatttct ttagcctgta gcaacctaaa    4020
ctgtaattcc tatcattatg ttttattact ttccaattac ctgtaactga cagaccaaat    4080
taattggctt tgtgtcctat ttagtccatc agtattttca agtcatgtgg aaagcccaaa    4140
gtcatcacaa tgaagagaac aggtgcacag cactgttcct cttgtgttct tgagaaggat    4200 ctaattttc tgtatatagc ccacatcaca cttgctttgt cttgtatgtt aattgcatct    4260
tcattggctt ggtatttcct aaatgtttaa caagaacaca agtgttcctg ataagatttc    4320
ctacagtaag ccagctctat tgtaagcttc ccactgtgat gatcattttt ttgaagattc    4380
attgaacagc caccactcta tcatcctcat tttggggcag tccaagacat agctggtttt    4440
agaaacccaa gttcctctaa gcacagcctc ccgggtatgt aactgaactt ggtgccaaag    4500
tacttgtgta ctaatttcta ttactacgta ctgtcacttt cctcccgtgc cattactgca    4560
tcataataca aggaacctca gagcccccat tgttcatta aagaggcaac tacagccaaa    4620
atcactgtta aaatcttact acttcatgga gtagctctta ggaaaatata tcttcctcct    4680
gagtctgggt aattatacct ctcccaagcc cccattgtgt gttgaaatcc tgtcatgaat    4740
ccttggtagc tctctgagaa cagtgaagtc cagggaaagg catctggtct gtctggaaag    4800
caaacattat gtggcctctg gtagttttt tcctgtaaga atactgactt tctggagtaa    4860
tgagtatata tcagttattg tacatgattg ctttgtgaaa tgtgcaaatg atatcaccta    4920
tgcagccttg tttgatttat tttctctggt ttgtactgtt attaaaagca tattgtatta    4980
tagagctatt cagatatttt aaatataaag atgtattgtt tccgtaatat agacgtatgg    5040
aatatattta ggtaatagat gtattacttg gaaagttctg ctttgacaaa ctgacaaagt    5100
ctaaatgagc acatgtatcc cagtgagcag taaatcaatg gaacatccca agaagaggat    5160
aaggatgctt aaaatggaaa tcattctcca acgatataca aattggactt gttcaactgc    5220
tggatatatg ctaccaataa ccccagcccc aacttaaaat tcttacattc aagctcctaa    5280
gagttcttaa tttataacta atttttaaaag agaagtttct tttctggttt tagtttggga    5340
ataatcattc attaaaaaaa atgtattgtg gtttatgcga acagaccaac ctggcattac    5400
agttggcctc tccttgaggt gggcacagcc tggcagtgtg gccaggggtg gccatgtaag    5460
tcccatcagg acgtagtcat gcctcctgca tttcgctacc cgagtttagt aacagtgcag    5520
attccacgtt cttgttccga tactctgaga agtgcctgat gttgatgtac ttacagacac    5580
aagaacaatc tttgctataa ttgtataaag ccataaatgt acataaatta tgtttaaatg    5640
gcttggtgtc tttctttct aattatgcag aataagctct ttattaggaa tttttgtga    5700 agctattaaa tacttgagtt aagtcttgtc agccacaa                           5738
```

<210> SEQ ID NO 13
<211> LENGTH: 457
<212> TYPE: PRT
<213> ORGANISM: Homo sapiens

<400> SEQUENCE: 13

Met Leu Gly Ala Val Lys Met Glu Gly His Glu Pro Ser Asp Trp Ser
1               5                   10                  15

```
Ser Tyr Tyr Ala Glu Pro Glu Gly Tyr Ser Ser Val Ser Asn Met Asn
                20              25              30

Ala Gly Leu Gly Met Asn Gly Met Asn Thr Tyr Met Ser Met Ser Ala
            35              40              45

Ala Ala Met Gly Ser Gly Ser Gly Asn Met Ser Ala Gly Ser Met Asn
50              55              60

Met Ser Ser Tyr Val Gly Ala Gly Met Ser Pro Ser Leu Ala Gly Met
65              70              75              80

Ser Pro Gly Ala Gly Ala Met Ala Gly Met Gly Gly Ser Ala Gly Ala
                85              90              95

Ala Gly Val Ala Gly Met Gly Pro His Leu Ser Pro Ser Leu Ser Pro
            100             105             110

Leu Gly Gly Gln Ala Ala Gly Ala Met Gly Gly Leu Ala Pro Tyr Ala
            115             120             125

Asn Met Asn Ser Met Ser Pro Met Tyr Gly Gln Ala Gly Leu Ser Arg
130             135             140

Ala Arg Asp Pro Lys Thr Tyr Arg Arg Ser Tyr Thr His Ala Lys Pro
145             150             155             160

Pro Tyr Ser Tyr Ile Ser Leu Ile Thr Met Ala Ile Gln Gln Ser Pro
                165             170             175

Asn Lys Met Leu Thr Leu Ser Glu Ile Tyr Gln Trp Ile Met Asp Leu
            180             185             190

Phe Pro Phe Tyr Arg Gln Asn Gln Gln Arg Trp Gln Asn Ser Ile Arg
            195             200             205

His Ser Leu Ser Phe Asn Asp Cys Phe Leu Lys Val Pro Arg Ser Pro
210             215             220

Asp Lys Pro Gly Lys Gly Ser Phe Trp Thr Leu His Pro Asp Ser Gly
225             230             235             240

Asn Met Phe Glu Asn Gly Cys Tyr Leu Arg Arg Gln Lys Arg Phe Lys
                245             250             255

Cys Glu Lys Gln Leu Ala Leu Lys Glu Ala Ala Gly Ala Ala Gly Ser
            260             265             270

Gly Lys Lys Ala Ala Gly Ala Gln Ala Ser Gln Ala Gln Leu Gly
            275             280             285

Glu Ala Ala Gly Pro Ala Ser Glu Thr Pro Ala Gly Thr Glu Ser Pro
290             295             300

His Ser Ser Ala Ser Pro Cys Gln Glu His Lys Arg Gly Gly Leu Gly
305             310             315             320

Glu Leu Lys Gly Thr Pro Ala Ala Ala Leu Ser Pro Glu Pro Ala
                325             330             335

Pro Ser Pro Gly Gln Gln Gln Ala Ala Ala His Leu Leu Gly Pro
            340             345             350

Pro His His Pro Gly Leu Pro Pro Glu Ala His Leu Lys Pro Glu His
            355             360             365

His Tyr Ala Phe Asn His Pro Phe Ser Ile Asn Asn Leu Met Ser Ser
            370             375             380

Glu Gln Gln His His His Ser His His His Gln Pro His Lys Met
385             390             395             400

Asp Leu Lys Ala Tyr Glu Gln Val Met His Tyr Pro Gly Tyr Gly Ser
                405             410             415

Pro Met Pro Gly Ser Leu Ala Met Gly Pro Val Thr Asn Lys Thr Gly
            420             425             430
```

```
Leu Asp Ala Ser Pro Leu Ala Ala Asp Thr Ser Tyr Tyr Gln Gly Val
        435                 440                 445

Tyr Ser Arg Pro Ile Met Asn Ser Ser
    450                 455

<210> SEQ ID NO 14
<211> LENGTH: 2428
<212> TYPE: DNA
<213> ORGANISM: Homo sapiens

<400> SEQUENCE: 14
cccgcccact tccaactacc gcctccggcc tgcccaggga gagagaggga gtggagccca      60
gggagaggga gcgcgagaga gggagggagg aggggacggt gctttggctg acttttttt     120 aaaagagggt gggggtgggg ggtgattgct ggtcgtttgt tgtggctgtt aaattttaaa    180
ctgccatgca ctcggcttcc agtatgctgg gagcggtgaa gatggaaggg cacgagccgt    240
ccgactggag cagctactat gcagagcccg agggctactc ctccgtgagc aacatgaacg    300
ccggcctggg gatgaacggc atgaacacgt acatgagcat gtcggcggcc gccatgggca    360
gcggctcggg caacatgagc gcgggctcca tgaacatgtc gtcgtacgtg ggcgctggca    420
tgagcccgtc cctggcgggg atgtcccccg gcgcgggcgc catggcgggc atgggcggct    480
cggccggggc ggccggcgtg gcgggcatgg ggccgcactt gagtcccagc ctgagcccgc    540 tcgggggggca ggcggccggg gccatgggcg gcctggcccc ctacgccaac atgaactcca    600
tgagccccat gtacgggcag gcgggcctga ccgcgcccg cgaccccaag acctacaggc    660
gcagctacac gcacgcaaag ccgccctact cgtacatctc gctcatcacc atggccatcc    720
agcagagccc caacaagatg ctgacgctga gcgagatcta ccagtggatc atggacctct    780
tccccttcta ccggcagaac cagcagcgct ggcagaactc catccgccac tcgctctcct    840
tcaacgactg tttcctgaag gtgccccgct cgcccgacaa gccggcaag gctccttct     900 ggaccctgca ccctgactcg gcaacatgt tcgagaacgg ctgctacctg cgccgccaga    960
agcgcttcaa gtgcgagaag cagctggcgc tgaaggaggc cgcaggcgcc gccggcagcg   1020
gcaagaaggc ggccgccgga gcccaggcct cacaggctca actcggggag gccgccgggc   1080
cggcctccga gactccggcg ggcaccgagt cgcctcactc gagcgcctcc ccgtgccagg   1140
agcacaagcg agggggcctg ggagagctga agggacgcc ggctgcggcg ctgagccccc    1200
cagagccggc gccctctccc gggcagcagc agcaggccgc ggcccacctg ctgggccgc    1260 cccaccaccc gggcctgccg cctgaggccc acctgaagcc ggaacaccac tacgccttca   1320
accacccgtt ctccatcaac aacctcatgt cctcggagca gcagcaccac cacagccacc   1380
accaccacca accccacaaa atggaccctca aggcctacga acaggtgatg cactaccccg   1440
gctacggttc ccccatgcct ggcagcttgg ccatgggccc ggtcacgaac aaaacgggcc   1500
tggacgcctc gccctggcc gcagatacct cctactacca gggggtgtac tcccggccca   1560
ttatgaactc ctcttaagaa gacgacggct tcaggcccgg ctaactctgg cacccggat    1620 cgaggacaag tgagagagca agtgggggtc gagactttgg ggagacggtg ttgcagagac   1680
gcaagggaga agaaatccat aacacccca cccaacacc cccaagacag cagtcttctt     1740
cacccgctgc agccgttccg tcccaaacag agggccacac agatacccca cgttctatat   1800
aaggaggaaa acgggaaaga atataaagtt aaaaaaaagc ctccggtttc cactactgtg   1860
tagactcctg cttcttcaag cacctgcaga ttctgatttt tttgttgttg ttgttctcct   1920
ccattgctgt tgttgcaggg aagtcttact taaaaaaaaa aaaaattttt gtgagtgact   1980
```

```
cggtgtaaaa ccatgtagtt ttaacagaac cagagggttg tactattgtt taaaaacagg    2040
aaaaaaaata atgtaagggt ctgttgtaaa tgaccaagaa aaagaaaaaa aaagcattcc    2100
caatcttgac acggtgaaat ccaggtctcg ggtccgatta atttatggtt tctgcgtgct    2160
ttatttatgg cttataaatg tgtattctgg ctgcaaggc cagagttcca caaatctata     2220
ttaaagtgtt atacccggtt ttatcccttg aatcttttct tccagatttt tcttttcttt    2280
acttggctta caaatatac aggcttggaa attatttcaa gaaggaggga gggataccct     2340
gtctggttgc aggttgtatt ttattttggc ccagggagtg ttgctgtttt cccaacattt    2400
tattaataaa attttcagac ataaaaaa                                      2428
```

<210> SEQ ID NO 15
<211> LENGTH: 505
<212> TYPE: PRT
<213> ORGANISM: Homo sapiens

<400> SEQUENCE: 15

```
Met Asp Pro Gly Asn Glu Asn Ser Ala Thr Glu Ala Ala Ile Ile
1               5                   10                  15

Asp Leu Asp Pro Asp Phe Glu Pro Gln Ser Arg Pro Arg Ser Cys Thr
            20                  25                  30

Trp Pro Leu Pro Arg Pro Glu Ile Ala Asn Gln Pro Ser Glu Pro Pro
        35                  40                  45

Glu Val Glu Pro Asp Leu Gly Glu Lys Val His Thr Glu Gly Arg Ser
    50                  55                  60

Glu Pro Ile Leu Leu Pro Ser Arg Leu Pro Glu Ala Gly Gly Pro
65                  70                  75                  80

Gln Pro Gly Ile Leu Gly Ala Val Thr Gly Pro Arg Lys Gly Ser
            85                  90                  95

Arg Arg Asn Ala Trp Gly Asn Gln Ser Tyr Ala Glu Leu Ile Ser Gln
        100                 105                 110

Ala Ile Glu Ser Ala Pro Glu Lys Arg Leu Thr Leu Ala Gln Ile Tyr
    115                 120                 125

Glu Trp Met Val Arg Thr Val Pro Tyr Phe Lys Asp Lys Gly Asp Ser
130                 135                 140

Asn Ser Ser Ala Gly Trp Lys Asn Ser Ile Arg His Asn Leu Ser Leu
145                 150                 155                 160

His Ser Lys Phe Ile Lys Val His Asn Glu Ala Thr Gly Lys Ser Ser
            165                 170                 175

Trp Trp Met Leu Asn Pro Glu Gly Gly Lys Ser Gly Lys Ala Pro Arg
        180                 185                 190

Arg Arg Ala Ala Ser Met Asp Ser Ser Lys Leu Leu Arg Gly Arg
    195                 200                 205

Ser Lys Ala Pro Lys Lys Lys Pro Ser Val Leu Pro Ala Pro Pro Glu
210                 215                 220

Gly Ala Thr Pro Thr Ser Pro Val Gly His Phe Ala Lys Trp Ser Gly
225                 230                 235                 240

Ser Pro Cys Ser Arg Asn Arg Glu Glu Ala Asp Met Trp Thr Thr Phe
            245                 250                 255

Arg Pro Arg Ser Ser Asn Ala Ser Ser Val Ser Thr Arg Leu Ser
        260                 265                 270

Pro Leu Arg Pro Glu Ser Glu Val Leu Ala Glu Ile Pro Ala Ser
    275                 280                 285
```

Val Ser Ser Tyr Ala Gly Gly Val Pro Pro Thr Leu Asn Glu Gly Leu
        290                 295                 300

Glu Leu Leu Asp Gly Leu Asn Leu Thr Ser Ser His Ser Leu Leu Ser
305                 310                 315                 320

Arg Ser Gly Leu Ser Gly Phe Ser Leu Gln His Pro Gly Val Thr Gly
                325                 330                 335

Pro Leu His Thr Tyr Ser Ser Ser Leu Phe Ser Pro Ala Glu Gly Pro
            340                 345                 350

Leu Ser Ala Gly Glu Gly Cys Phe Ser Ser Gln Ala Leu Glu Ala
        355                 360                 365

Leu Leu Thr Ser Asp Thr Pro Pro Pro Ala Asp Val Leu Met Thr
370                 375                 380

Gln Val Asp Pro Ile Leu Ser Gln Ala Pro Thr Leu Leu Leu Gly
385                 390                 395                 400

Gly Leu Pro Ser Ser Ser Lys Leu Ala Thr Gly Val Gly Leu Cys Pro
                405                 410                 415

Lys Pro Leu Glu Ala Pro Gly Pro Ser Ser Leu Val Pro Thr Leu Ser
            420                 425                 430

Met Ile Ala Pro Pro Pro Val Met Ala Ser Ala Pro Ile Pro Lys Ala
        435                 440                 445

Leu Gly Thr Pro Val Leu Thr Pro Pro Thr Glu Ala Ala Ser Gln Asp
    450                 455                 460

Arg Met Pro Gln Asp Leu Asp Leu Asp Met Tyr Met Glu Asn Leu Glu
465                 470                 475                 480

Cys Asp Met Asp Asn Ile Ile Ser Asp Leu Met Asp Glu Gly Glu Gly
                485                 490                 495

Leu Asp Phe Asn Phe Glu Pro Asp Pro
                500                 505

<210> SEQ ID NO 16
<211> LENGTH: 3365
<212> TYPE: DNA
<213> ORGANISM: Homo sapiens

<400> SEQUENCE: 16

| | | | | | | |
|---|---|---|---|---|---|---|
| aaaagggga | gggaactgcg | gctaaggaga | cgttcggtga | tgggagcgca | atatatgagg | 60 |
| ggatacagtg | cctcaggttt | aaaagagcag | gaagctgagt | gagaggttgc | agaaaaagtg | 120 |
| tcttcgctcg | gcagaggtta | caggtggcat | ctcagaaaga | gctttgaggc | tacaggctgt | 180 |
| agtcgggaag | gggatcggag | aactgtgtga | agggacagct | tagggactag | cgtcctggga | 240 |
| ctaggggaa | gttcgcgact | ttctgaagac | tggcaggaat | gtgcctcctg | gccctcgatg | 300 |
| cttccccct | gagggaggc | atcgtgaggg | actgtggcag | gcttcactga | acgctgagcc | 360 |
| ggggaggtcc | aactccacgt | atggatccgg | ggaatgagaa | ttcagccaca | gaggctgccg | 420 |
| cgatcataga | cctagatccc | gacttcgaac | cccagagccg | tccccgctcc | tgcacctggc | 480 |
| cccttccccg | accagagatc | gctaaccagc | cgtccgagcc | gcccgaggtg | gagccagatc | 540 |
| tgggggaaaa | ggtacacacg | gagggcgct | cagagccgat | cctgttgccc | tctcggctcc | 600 |
| cagagccggc | cgggggcccc | cagcccggaa | tcctgggggc | tgtaacaggt | cctcggaagg | 660 |
| gaggctcccg | ccggaatgcc | tggggaaatc | agtcatatgc | agaactcatc | agccaggcca | 720 |
| ttgaaagcgc | cccggagaag | cgactgacac | ttgcccagat | ctacgagtgg | atggtccgta | 780 |
| ctgtacccta | cttcaaggac | aagggtgaca | gcaacagctc | agcaggatgg | aagaactcga | 840 |
| tccgccacaa | cctgtccctg | cacagcaagt | tcatcaaggt | tcacaacgag | gccaccggca | 900 |

```
aaagctcttg gtggatgctg aaccctgagg gaggcaagag cggcaaagcc ccccgccgcc      960
gggccgcctc catggatagc agcagcaagc tgctccgggg ccgcagtaaa gcccccaaga     1020
agaaaccatc tgtgctgcca gctccacccg aaggtgccac tccaacgagc cctgtcggcc     1080
actttgccaa gtggtcaggc agcccttgct ctcgaaaccg tgaagaagcc gatatgtgga     1140
ccaccttccg tccacgaagc agttcaaatg ccagcagtgt cagcacccgg ctgtccccct     1200
tgaggccaga gtctgaggtg ctggcggagg aaataccagc ttcagtcagc agttatgcag     1260
ggggtgtccc tcccacccte aatgaaggtc tagagctgtt agatgggctc aatctcacct     1320
cttcccattc cctgctatct cggagtggtc tctctggctt ctctttgcag catcctgggg     1380
ttaccggccc cttacacacc tacagcagct cccttttcag cccagcagag ggcccctgt      1440 cagcaggaga agggtgcttc tccagctccc aggctctgga ggccctgctc acctctgata     1500
cgccaccacc ccctgctgac gtcctcatga cccaggtaga tcccattctg tcccaggctc     1560
cgactcttct gttgctgggg gggcttcctt cctccagtaa gctggccacg ggcgtcggcc     1620
tgtgtcccaa gcccctagag gctccaggcc ccagcagtct ggttcccacc ctttctatga     1680
tagcaccacc tccagtcatg gcaagtgccc ccatccccaa ggctctgggg actcctgtgc     1740
tcacaccccc tactgaagct gcaagccaag acagaatgcc tcaggatcta gatcttgata     1800
tgtatatgga gaacctggag tgtgacatgg ataacatcat cagtgacctc atggatgagg     1860
gcgagggact ggacttcaac tttgagccag atccctgagt catgcctgga agctttgtcc     1920
cctgcttcag atgtggagcc aggcgtgttc atatctactc tttacccttg agccctcccc     1980
aggaatttgg gaccctgctt tagagctagg gtggggtctg gtcacacaca ggtgttgaag     2040
aaattataaa gataaagctg ccccatctgg ggacgatatg gggagggaga tgggagggga     2100
aaggggagag ggttttttctc actgtgccaa ttaggggta aggccccctc tcaggagcca     2160
tcatcggctt tccccattcc tacccactta ggctttgtag caagatgagc aatgctgttg     2220
gaaatgtgaa gtcaccagtg gccttacccc tgcctttggg agcaggattt ttttgtagag     2280
agtcttatct gagctgagcc aggctagctg gagcctggga tttctatgca gtggcccctt     2340
aggccagtga tgtgcggtgg gtgggctgtt tagggatct ggaagggcca aggtctgagc      2400
actggagtgg ctcgccaggc caaatcaccc ttagaaggct gcagataaca gaaaggcttt     2460
ttataaactt ttaaagaaat ataaacacaa atatagagat ttttttaacca tggcagggtg     2520 ctagtggtgg gcagaatgct ttttttttctt tctgaaggct ttgtgatagt gacatgatac     2580
aaacactaca gacaataaat attaggagac acagggaagt ggggagaggt ggggagtaat     2640
agtaaacaca gggaagagct cccctacgga ccaggtatag agaaaggtct atgcagaaat     2700
aggttagagt ttccctaaca aaaagctaa cccaggtccc ctcattcctt caacttgtgc      2760
ctgggagtgt gtggtgttag ggtgcagcca cactcttcta tgacccagca tgggttagtg     2820
ctatggtggg agagtacatt gaaggcctgg aattagcttg ggccaggga agggactggg      2880 aggggagaga agagaaggag ggaaggattt aggatggtaa agttaggtac agagacctcc     2940
ctgttcaagg cccctgacag ctgtccctgc ccttcttccc cttccctgac tgcagggtt      3000 atgtggaagt gtgtgtggca gcaggcagcg gggagggag gaacagggaa gggggagctg      3060
gggagcttgg ctgagggtct gggaaatgag cagggatggg gggggatgtg gatcaggttt     3120
actagcacct gccagggagg ccatctgggg ctccttctcc accccagccc caaaagcagc     3180
ccttccccca gtgcccttg catcgtcccc tcccccaccc ctgctgtggg ttcccatcat      3240
```

```
ttcctgtgtc agcgcctggc ctacccagat tgtatcatgt gctagattgg agtggggaag    3300
tgtgtcaaat caataaatga ataaattcaa taatgccta taaccagcaa aaaaaaaaaa    3360
aaaaa                                                                 3365
```

<210> SEQ ID NO 17
<211> LENGTH: 421
<212> TYPE: PRT
<213> ORGANISM: Homo sapiens

<400> SEQUENCE: 17

```
Met Asn Arg Gly Phe Ser Arg Lys Ser His Thr Phe Leu Pro Lys Ile
1               5                   10                  15

Phe Phe Arg Lys Met Ser Ser Ser Gly Ala Lys Asp Lys Pro Glu Leu
            20                  25                  30

Gln Phe Pro Phe Leu Gln Asp Glu Asp Thr Val Ala Thr Leu Leu Glu
        35                  40                  45

Cys Lys Thr Leu Phe Ile Leu Arg Gly Leu Pro Gly Ser Gly Lys Ser
    50                  55                  60

Thr Leu Ala Arg Val Ile Val Asp Lys Tyr Arg Asp Gly Thr Lys Met
65                  70                  75                  80

Val Ser Ala Asp Ala Tyr Lys Ile Thr Pro Gly Ala Arg Gly Ala Phe
                85                  90                  95

Ser Glu Glu Tyr Lys Arg Leu Asp Glu Asp Leu Ala Ala Tyr Cys Arg
            100                 105                 110

Arg Arg Asp Ile Arg Ile Leu Val Leu Asp Asp Thr Asn His Glu Arg
        115                 120                 125

Glu Arg Leu Glu Gln Leu Phe Glu Met Ala Asp Gln Tyr Gln Tyr Gln
    130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
            180                 185                 190

Phe Leu Thr Lys Lys Ser Ser Glu Thr Leu Arg Lys Ala Gly Gln Val
        195                 200                 205

Phe Leu Glu Glu Leu Gly Asn His Lys Ala Phe Lys Lys Glu Leu Arg
    210                 215                 220

Gln Phe Val Pro Gly Asp Glu Pro Arg Glu Lys Met Asp Leu Val Thr
225                 230                 235                 240

Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
    290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350
```

```
Arg Gln Glu Lys Gly Gly Ser Arg Gly Glu Val Gly Glu Leu Ser
        355                 360                 365
Arg Gly Lys Leu Tyr Ser Leu Gly Asn Gly Arg Trp Met Leu Thr Leu
370                 375                 380
Ala Lys Asn Met Glu Val Arg Ala Ile Phe Thr Gly Tyr Tyr Gly Lys
385                 390                 395                 400
Gly Lys Pro Val Pro Thr Gln Gly Ser Arg Lys Gly Gly Ala Leu Gln
                405                 410                 415
Ser Cys Thr Ile Ile
            420
```

<210> SEQ ID NO 18
<211> LENGTH: 2598
<212> TYPE: DNA
<213> ORGANISM: Homo sapiens

<400> SEQUENCE: 18

| | | | | | |
|---|---|---|---|---|---|
| ctccgcgcag | gcgggcggcc | ccggagcgct | ggtgccggca | gaggcggcga | cggtggcgcc | 60 |
| cctcctcatc | atgaggcttc | tcccgaaaaa | gccacacatt | cctgcccaag | atcttcttcc | 120 |
| gcaagatgtc | atcctcaggg | gccaaggaca | agcctgagct | gcagtttccc | ttccttcagg | 180 |
| atgaggacac | agtggccacg | ctgctagagt | gcaagacgct | cttcatcttg | cgcggcctgc | 240 |
| caggaagcgg | caagtccacg | ctggcacggg | tcatcgtgga | caagtaccgt | gatggcacca | 300 |
| agatggtgtc | ggctgacgct | tacaagatca | ccccggcgc | tcgaggagcc | ttctccgagg | 360 |
| agtacaagcg | gctcgatgag | gacctggctg | cctactgccg | ccgcgggac | atcagaattc | 420 |
| ttgtgcttga | tgacaccaac | cacgaacggg | aacggctgga | gcagctcttt | gaaatggccg | 480 |
| accagtacca | gtaccaggtg | gtgctggtgg | agcccaagac | ggcgtggcgg | ctggactgtg | 540 |
| cccagctcaa | ggagaagaac | cagtggcagc | tgtcggctga | tgacctgaag | aagctgaagc | 600 |
| ctgggctgga | gaaggacttc | ctgccgctct | acttcggctg | gttcctgacc | aagaagagct | 660 |
| ctgagaccct | ccgcaaagcc | ggccaggtct | tcctggaaga | gctggggaac | acaaggcct | 720 |
| tcaagaagga | gctgcgacaa | ttcgtccctg | gggatgagcc | cagggagaag | atggacttgg | 780 |
| tcacctactt | tggaaagaga | cccccaggcg | tgctgcattg | cacaaccaag | ttttgtgact | 840 |
| acggaaggc | tcccggggca | gaggagtacg | ctcaacaaga | tgtgttaaag | aaatcttact | 900 |
| ccaaggcctt | cacgctgacc | atctctgccc | tctttgtgac | acccaagacg | actggggccc | 960 |
| gggtggagtt | aagcgagcag | caactgcagt | tgtggccgag | tgatgtggac | aagctgtcac | 1020 |
| ccactgacaa | cctgccgcgg | gggagccgcg | cccacatcac | cctcggctgt | gcagctgacg | 1080 |
| tagaggccgt | gcagacgggc | cttgacctct | tagagattct | gcggcaggag | aagggggca | 1140 |
| gccgaggcga | ggaggtgggc | gagctaagcc | ggggcaagct | ctattccttg | ggcaatgggc | 1200 |
| gctggatgct | gaccctggcc | aagaacatgg | aggtcagggc | catcttcacg | gggtactacg | 1260 |
| ggaaaggcaa | acctgtgccc | acgcaaggta | gccggaaggg | gggcgccttg | cagtcctgca | 1320 |
| ccatcatatg | agtgttctca | ccaccactta | tgcccctaga | agggaagggg | agagggaaac | 1380 |
| gtgccctctg | tttgatcctt | gttttgtgac | atttttttt | tttttttttt | tactcaaagt | 1440 |
| taacctacct | gtaactttt | aaaaacttgt | aaaataactg | accctcccctt | cctgtccgcc | 1500 |
| ctcttcccct | ctaatgctca | cgctcccaac | acaaggtggg | cagggaggca | ccattcagga | 1560 |
| acctggacca | aagctgacga | ggctgggcca | agcagggat | ggggccacag | ccagaacccc | 1620 |
| gagccctact | tccaggttct | ggttagctca | gccccagccc | agcccagctg | ctctgcccag | 1680 |

```
agctgggtga gtggggagac acctcagagc cccgcaaaac ccactgaccg gaggcaaaag    1740 gcagtgggc tgggggtagt tttccatggt cacagagaac tagtggtggc tctgagaagg    1800
ggaggacctc tgggctttga ttccatctcc ttgtctttt tctttgtttt tagagacagg    1860
gtcctgctat ttcccaagct ggagtgcagt ggtgcgatca tggctcactg cagcctcgaa    1920
ctcctgggct caagcaatcc tcctgagtga tcccatttct taatcagtgt agccccaaga    1980
aggctggggc tatttaccag ggtagaaaaa ggagcttacc tcccaccttt ggtcctaagt    2040
ccctgccccc tccccttcac accataacta ggtaacagtt tgataactag ggaagaaagc    2100
agaacagtta agcagccgcc acatccccgc tggctggggg cctcactcca ggaagggggct   2160 ggactggctg tcctttccag tggcctggct ccgctgtgtg gatggggaga tcggggccag    2220
aggcagaacc ctggtgagga agctccagtc ctgctctcta cccagcccat cttgcctcca    2280
tggtgcctct ggaggcctct gggcctcctc taacaggggc tggtgggcac aagagccaa    2340 tggagtagac ccctggctgg taagggccaa gtcccaccgg ttgcttctgg aagggggttt    2400
ctaacactag tctgtgtgct gtggttcctg gggtgccctc cactgccctc tgttcagtaa    2460
cagggccttg ctaatcgggt tgtcactcaa caaaagtgct ttggatttaa gttactatcc    2520
tggctttgcc caacctcagc aacctgtaag actgataatg aaataaatca tgttaatcct    2580
agcaaaaaaa aaaaaaaa                                                  2598

<210> SEQ ID NO 19
<211> LENGTH: 304
<212> TYPE: PRT
<213> ORGANISM: Homo sapiens

<400> SEQUENCE: 19

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
        195                 200                 205
```

```
Lys Ser His Gly Arg Thr Gln Asp Glu Asn Pro Val Val His Phe Phe
    210                 215                 220
Lys Asn Ile Val Thr Pro Arg Thr Pro Pro Ser Gln Gly Lys Gly
225                 230                 235                 240
Arg Gly Leu Ser Leu Ser Arg Phe Ser Trp Gly Ala Glu Gly Gln Arg
                245                 250                 255
Pro Gly Phe Gly Tyr Gly Gly Arg Ala Ser Asp Tyr Lys Ser Ala His
            260                 265                 270
Lys Gly Phe Lys Gly Val Asp Ala Gln Gly Thr Leu Ser Lys Ile Phe
        275                 280                 285
Lys Leu Gly Gly Arg Asp Ser Arg Ser Gly Ser Pro Met Ala Arg Arg
    290                 295                 300
```

<210> SEQ ID NO 20
<211> LENGTH: 2139
<212> TYPE: DNA
<213> ORGANISM: Homo sapiens

<400> SEQUENCE: 20

```
gaaaacagtg cagccacctc cgagagcctg gatgtgatgg cgtcacagaa gagaccctcc      60
cagaggcacg gatccaagta cctggccaca gcaagtacca tggaccatgc caggcatggc     120
ttcctcccaa ggcacagaga cacgggcatc cttgactcca tcgggcgctt ctttggcggt     180
gacagggtgt cgccaaagcg gggctctggc aaggactcac accaccccgg caagaactgct    240
cactatggct ccctgcccca gaagtcacac ggccggaccc aagatgaaaa ccccgtagtc     300
cacttcttca gaacattgt gacgcctcgc acaccacccc cgtcgcaggg aaaggggaga      360
ggactgtccc tgagcagatt tagctggggg gccgaaggcc agagaccagg atttggctac     420
ggaggcagag cgtccgacta taaatcggct cacaagggat tcaagggagt cgatgcccag     480
ggcacgcttt ccaaaatttt taagctggga ggaagagata gtcgctctgg atcacccatg     540
gctagacgct gaaaacccac ctggttccgg aatcctgtcc tcagcttctt aatataactg     600
ccttaaaact ttaatcccac ttgccccctgt tacctaatta gagcagatga ccccctcccct   660
aatgcctgcg gagttgtgca cgtagtaggg tcaggccacg gcagcctacc ggcaatttcc     720
ggccaacagt taaatgagaa catgaaaaca gaaaacggtt aaaactgtcc ctttctgtgt     780
gaagatcacg ttccttcccc cgcaatgtgc ccccagacgc acgtgggtct tcaggggggcc    840
aggtgcacag acgtccctcc acgttcaccc ctccaccctt ggactttctt ttcgccgtgg     900
ctcggcaccc ttgcgctttt gctggtcact gccatggagg cacacagctg cagagacaga     960
gaggacgtgg gcggcagaga ggactgttga catccaagct tcctttgttt ttttttcctg    1020
tccttctctc acctcctaaa gtagacttca ttttttcctaa caggattaga cagtcaagga   1080
gtggcttact acatgtggga gcttttttggt atgtgacatg cgggctgggc agctgttaga   1140
gtccaacgtg gggcagcaca gagagggggc cacctcccca ggccgtggct gcccacacac   1200
cccaattagc tgaattcgcg tgtggcagag ggaggaaaag gaggcaaacg tgggctgggc   1260
aatggcctca cataggaaac agggtcttcc tggagatttg gtgatggaga tgtcaagcag   1320
gtggcctctg gacgtcaccg ttgccctgca tggtggcccc agagcagcct ctatgaacaa   1380
cctcgtttcc aaaccacagc ccacagccgg agagtccagg aagacttgcg cactcagagc   1440
agaagggtag gagtcctcta gacagcctcg cagccgcgcc agtcgcccat agacactggc   1500
tgtgaccggg cgtgctggca gcggcagtgc acagtggcca gcactaaccc tccctgagaa   1560
```

```
gataaccggc tcattcactt cctcccagaa gacgcgtggt agcgagtagg cacaggcgtg   1620
cacctgctcc cgaattactc accgagacac acgggctgag cagacggccc ctgtgatgga   1680
gacaaagagc tcttctgacc atatccttct taacacccgc tggcatctcc tttcgcgcct   1740
ccctccctaa cctactgacc caccttttga ttttagcgca cctgtgattg ataggccttc   1800
caaagagtcc cacgctggca tcaccctccc cgaggacgga gatgaggagt agtcagcgtg   1860
atgccaaaac gcgtcttctt aatccaattc taattctgaa tgtttcgtgt gggcttaata   1920
ccatgtctat taatatatag cctcgatgat gagagagtta caaagaacaa aactccagac   1980
acaaacctcc aaattttca gcagaagcac tctgcgtcgc tgagctgagg tcggctctgc   2040
gatccatacg tggccgcacc cacacagcac gtgctgtgac gatggctgaa cggaaagtgt   2100
acactgttcc tgaatattga aataaaacaa taaactttt                         2139
```

<210> SEQ ID NO 21
<211> LENGTH: 378
<212> TYPE: PRT
<213> ORGANISM: Homo sapiens

<400> SEQUENCE: 21

```
Met Asp Ser Val Arg Ser Gly Ala Phe Gly His Leu Phe Arg Pro Asp
1               5                   10                  15

Asn Phe Ile Phe Gly Gln Ser Gly Ala Gly Asn Asn Trp Ala Lys Gly
            20                  25                  30

His Tyr Thr Glu Gly Ala Glu Leu Val Asp Ser Val Leu Asp Val Val
        35                  40                  45

Arg Lys Glu Cys Glu Asn Cys Asp Cys Leu Gln Gly Phe Gln Leu Thr
    50                  55                  60

His Ser Leu Gly Gly Gly Thr Gly Ser Gly Met Gly Thr Leu Leu Ile
65                  70                  75                  80

Ser Lys Val Arg Glu Glu Tyr Pro Asp Arg Ile Met Asn Thr Phe Ser
                85                  90                  95

Val Val Pro Ser Pro Lys Val Ser Asp Thr Val Val Glu Pro Tyr Asn
            100                 105                 110

Ala Thr Leu Ser Ile His Gln Leu Val Glu Asn Thr Asp Glu Thr Tyr
        115                 120                 125

Cys Ile Asp Asn Glu Ala Leu Tyr Asp Ile Cys Phe Arg Thr Leu Lys
    130                 135                 140

Leu Ala Thr Pro Thr Tyr Gly Asp Leu Asn His Leu Val Ser Ala Thr
145                 150                 155                 160

Met Ser Gly Val Thr Thr Ser Leu Arg Phe Pro Gly Gln Leu Asn Ala
                165                 170                 175

Asp Leu Arg Lys Leu Ala Val Asn Met Val Pro Phe Pro Arg Leu His
            180                 185                 190

Phe Phe Met Pro Gly Phe Ala Pro Leu Thr Ala Arg Gly Ser Gln Gln
        195                 200                 205

Tyr Arg Ala Leu Thr Val Pro Glu Leu Thr Gln Gln Met Phe Asp Ala
    210                 215                 220

Lys Asn Met Met Ala Ala Cys Asp Pro Arg His Gly Arg Tyr Leu Thr
225                 230                 235                 240

Val Ala Thr Val Phe Arg Gly Arg Met Ser Met Lys Glu Val Asp Glu
                245                 250                 255

Gln Met Leu Ala Ile Gln Ser Lys Asn Ser Ser Tyr Phe Val Glu Trp
            260                 265                 270
```

```
Ile Pro Asn Asn Val Lys Val Ala Val Cys Asp Ile Pro Pro Arg Gly
                275                 280                 285
Leu Lys Met Ser Ser Thr Phe Ile Gly Asn Ser Thr Ala Ile Gln Glu
            290                 295                 300
Leu Phe Lys Arg Ile Ser Glu Gln Phe Thr Ala Met Phe Arg Arg Lys
305                 310                 315                 320
Ala Phe Leu His Trp Tyr Thr Gly Glu Gly Met Asp Glu Met Glu Phe
                325                 330                 335
Thr Glu Ala Glu Ser Asn Met Asn Asp Leu Val Ser Glu Tyr Gln Gln
            340                 345                 350
Tyr Gln Asp Ala Thr Ala Glu Glu Gly Glu Met Tyr Glu Asp Asp
                355                 360                 365
Glu Glu Glu Ser Glu Ala Gln Gly Pro Lys
    370                 375
```

<210> SEQ ID NO 22
<211> LENGTH: 1720
<212> TYPE: DNA
<213> ORGANISM: Homo sapiens

<400> SEQUENCE: 22

```
gcccggcccg cccgcgcccg tccgcagccg cccgccagac gcgcccagta tgagggagat    60
cgtgcacatc caggccggcc agtgcggcaa ccagatcggg gccaagttct gggaagtcat   120
cagtgatgag catggcatcg accccagcgg caactacgtg ggcgactcgg acttgcagct   180
ggagcggatc agcgtctact acaacgaggc ctcttctcac aagtacgtgc ctcgagccat   240
tctggtggac ctggaacccg gaaccatgga cagtgtccgc tcaggggcct ttggacatct   300
cttcaggcct gacaatttca tctttggtca gagtggggcc ggcaacaact gggccaaggg   360
tcactacacg gaggggcgg agctggtgga ttcggtcctg gatgtggtgc ggaaggagtg   420
tgaaaactgc gactgcctgc agggcttcca gctgacccac tcgctggggg gcggcacggg   480
ctccggcatg ggcacgttgc tcatcagcaa ggtgcgtgag gagtatcccg accgcatcat   540
gaacaccttc agcgtcgtgc cctcacccaa ggtgtcagac acggtggtgg agccctacaa   600
cgccacgctg tccatccacc agctggtgga gaacacggat gagacctact gcatcgacaa   660
cgaggcgctc tacgacatct gcttccgcac cctcaagctg gccacgccca cctacgggga   720
cctcaaccac ctggtatcgg ccaccatgag cggagtcacc acctccttgc gcttcccggg   780
ccagctcaac gctgacctgc gcaagctggc cgtcaacatg gtgcccttcc cgcgcctgca   840
cttcttcatg ccccggcttcg ccccccctcac agcccggggc agccagcagt accgggccct   900
gaccgtgccc gagctcaccc agcagatgtt cgatgccaag aacatgatgg ccgcctgcga   960
cccgcgccac ggccgctacc tgacggtggc caccgtgttc cggggccgca tgtccatgaa  1020
ggaggtggac gagcagatgc tggccatcca gagcaagaac agcagctact cgtggagtg   1080
gatccccaac aacgtgaagg tggccgtgtg tgacatcccg cccgcggcc tcaagatgtc  1140
ctccaccttc atcgggaaca gcacggccat ccaggagctg ttcaagcgca tctccgagca  1200
gttcacggcc atgttccggc gcaaggcctt cctgcactgg tacacgggcg agggcatgga  1260
cgagatggag ttcaccgagg ccgagagcaa catgaacgac ctggtgtccg agtaccagca  1320
gtaccaggac gccacggccg aggaagaggg cgagatgtac gaagacgacg aggaggagtc  1380
ggaggcccag ggccccaagt gaagctgctc gcagctggag tgagaggcag gtggcggccg  1440
gggccgaagc cagcagtgtc taaaccccg gagccatctt gctgccgaca ccctgctttc   1500
```

```
ccctcgccct agggctccct tgccgccctc ctgcagtatt tatggcctcg tcctccccac   1560
ctaggccacg tgtgagctgc tcctgtctct gtcttattgc agctccaggc ctgacgtttt   1620
acggttttgt tttttactgg tttgtgttta tattttcggg gatacttaat aaatctattg   1680
ctgtcagata cccttaaaaa aaaaaaaaaa aaaaaaaaa                          1720

<210> SEQ ID NO 23
<211> LENGTH: 312
<212> TYPE: PRT
<213> ORGANISM: Homo sapiens

<400> SEQUENCE: 23

Met Ala Gln Pro Tyr Pro Pro Ala Gln Tyr Pro Pro Pro Gln Asn
1               5                   10                  15

Gly Ile Pro Ala Glu Tyr Ala Pro Pro Pro His Pro Thr Gln Asp
            20                  25                  30

Tyr Ser Gly Gln Thr Pro Val Pro Thr Glu His Gly Met Thr Leu Tyr
            35                  40                  45

Thr Pro Ala Gln Thr His Pro Glu Gln Pro Gly Ser Glu Ala Ser Thr
        50                  55                  60

Gln Pro Ile Ala Gly Thr Gln Thr Val Pro Gln Thr Asp Glu Ala Ala
65                  70                  75                  80

Gln Thr Asp Ser Gln Pro Leu His Pro Ser Asp Pro Thr Glu Lys Gln
                85                  90                  95

Gln Pro Lys Arg Leu His Val Ser Asn Ile Pro Phe Arg Phe Arg Asp
            100                 105                 110

Pro Asp Leu Arg Gln Met Phe Gly Gln Phe Gly Lys Ile Leu Asp Val
        115                 120                 125

Glu Ile Ile Phe Asn Glu Arg Gly Ser Lys Gly Phe Gly Phe Val Thr
    130                 135                 140

Phe Glu Thr Ser Ser Asp Ala Asp Arg Ala Arg Glu Lys Leu Asn Gly
145                 150                 155                 160

Thr Ile Val Glu Gly Arg Lys Ile Glu Val Asn Asn Ala Thr Ala Arg
                165                 170                 175

Val Met Thr Asn Lys Lys Thr Gly Asn Pro Tyr Thr Asn Gly Trp Lys
            180                 185                 190

Leu Asn Pro Val Val Gly Ala Val Tyr Gly Pro Glu Phe Tyr Ala Val
        195                 200                 205

Thr Gly Phe Pro Tyr Pro Thr Thr Gly Thr Ala Val Ala Tyr Arg Gly
    210                 215                 220

Ala His Leu Arg Gly Arg Gly Arg Ala Val Tyr Asn Thr Phe Arg Ala
225                 230                 235                 240

Ala Pro Pro Pro Pro Ile Pro Thr Tyr Gly Ala Val Val Tyr Gln
                245                 250                 255

Asp Gly Phe Tyr Gly Ala Glu Ile Tyr Gly Gly Tyr Ala Ala Tyr Arg
            260                 265                 270

Tyr Ala Gln Pro Ala Ala Ala Ala Ala Tyr Ser Asp Ser Tyr Gly
        275                 280                 285

Arg Val Tyr Ala Ala Ala Asp Pro Tyr His His Thr Ile Gly Pro Ala
    290                 295                 300

Ala Thr Tyr Ser Ile Gly Thr Met
305                 310

<210> SEQ ID NO 24
<211> LENGTH: 3007
```

<212> TYPE: DNA
<213> ORGANISM: Homo sapiens

<400> SEQUENCE: 24

| | | | | | |
|---|---|---|---|---|---|
| gatacagcag | cagctggtgc | tcctggccag | gctgtgcgtg | ctctctctgc | ctctctctct | 60 |
| cggactctct | gctctctctc | tctgactctc | tcctctctct | ctgttggcct | ggtgaaatgt | 120 |
| tcttggctgt | aggcacacag | agccttggac | tcaaggctgt | tggagtcgag | gacaccttga | 180 |
| cttcggtcct | ggaggttgaa | attctgcctc | tgagaagcta | acagtcttcc | tgtggtcgcc | 240 |
| actcctcccc | agcagccccc | tccttgccaa | ggacggtcca | gaaggagccc | cactggggcc | 300 |
| tccccgctca | gcaaagcaga | cctcacctcc | cactaccagc | ttgaagtcac | agcagccaga | 360 |
| ggaaattctg | ccaccatttt | cccaggtctg | cagcccctcc | agctgggaac | ctgctcctgg | 420 |
| agccatccct | ctgcaaacag | agagcccaga | gtgcctcggg | gaaaattggc | tgaataaaag | 480 |
| agcgatcagg | acgccacggc | tccgcctgaa | gcgatggccc | agccctaccc | ccccgcccag | 540 |
| tacccccctc | cgccacagaa | cggcatccct | gccgagtacg | cccgccccc | accgcacccc | 600 |
| acgcaggact | actccggcca | gaccccggtc | cccacagagc | atggcatgac | cctgtacaca | 660 |
| ccagcacaga | cccaccccga | gcagccaggc | tccgaggcca | gcacacagcc | catcgccggg | 720 |
| acccagacag | tgccgcagac | agacgaggcg | gcacagacgg | acagccagcc | gctccacccc | 780 |
| tccgacccta | cagagaagca | gcagcccaag | cggctacacg | tctccaacat | cccctccgg | 840 |
| ttcagggacc | ccgacttgcg | gcaaatgttc | gggcaattcg | gaaaaatttt | agacgtggag | 900 |
| atcattttta | acgagcgggg | ctccaagggt | tttgggtttg | taactttga | aactagctca | 960 |
| gatgctgacc | gagcccggga | gaagctgaat | gggacgatcg | tagagggacg | gaaaattgag | 1020 |
| gtcaataatg | ccacggcccg | agtgatgacc | aacaagaaga | cggggaaccc | ctacaccaac | 1080 |
| ggctggaagc | taaatccagt | ggtcggcgca | gtctacgggc | ctgaattcta | tgcagtgacg | 1140 |
| gggttcccct | accccaccac | cggcacagcc | gttgcctacc | ggggcgcaca | tcttcggggc | 1200 |
| cggggccggg | ccgtgtataa | tacatttcgg | gctgcgccac | cccacccccc | catcccgact | 1260 |
| tacggagcgg | tcgtgtatca | ggatggattt | tatggtgctg | agatttatgg | aggctacgca | 1320 |
| gcctacagat | acgctcagcc | cgctgcagcg | gcggcagcct | acagcgacag | ttacggcaga | 1380 |
| gtctacgcag | ctgccgaccc | gtaccatcac | accatcgggc | ccgcggcgac | ctacagcatt | 1440 |
| ggaaccatgt | gaaaccttcc | accgtttcct | tctcggacca | tgaagggcaa | aaacaaaaaa | 1500 |
| acaaaaaaaa | tcacaaaaca | aaaaaaacaa | aaaagatgt | taagatccaa | gcaacaaaaa | 1560 |
| aaaaaccaac | caaaccaaga | ggcatccaac | caagtccaag | tccgcgtcc | tggcacacg | 1620 |
| cccgcaccga | gggagcacgc | cggcaggggc | gccgaggagc | ggcccagga | caggacggcc | 1680 |
| ccaccgcgtc | ctggctggca | gcacagtggg | aacacgcccc | tccgtctcag | gcagtggggg | 1740 |
| agttggaggg | gaaggggcct | cccttgtggg | accgtgggg | ggctctgttt | tccatccagt | 1800 |
| cttcctttcc | cagcccccaa | ctcccaagac | agacagtgtg | gagcccagcg | gcggcggagc | 1860 |
| aggcccgggc | ctgagcaggc | aggcgctgct | agcaagactt | gatctttgtg | ccagctgtg | 1920 |
| ccaggggggcc | ggcggggctg | agggggtgcg | gcagctttca | tcccagggc | tccactgggc | 1980 |
| cccgtcaccc | tcctgtcgcg | tcccctgcgt | cccacctccc | tcctgcccgg | cagtcccgcc | 2040 |
| cgtgccccca | gctggcgag | gaagccgtcc | aacagtagcc | ccggggccag | ctcccaacag | 2100 |
| aaagggctga | cgtggctcca | ggactcaggg | gcgctccatg | ggaggacgaa | ggaagccag | 2160 |
| ccagccagga | gccactcctc | acacctccaa | gtgtggccaa | gtgggccctg | aggccaagga | 2220 |

-continued

```
cttacttgct cttcctggcc atctctccct ttctggagga ggcccggggc ctgtgtacac   2280
caaggctgac ctcgtgctgc ctgctgggac ccagccctcc ctgccgctcc cctgtgagcc   2340
cagtccaccg tgggcgccca gggccaggga cgggccagcg cccggctgca tcgcgaggtt   2400
gggagtcaca gtggctgtgg gcctggacgg cacagccag agcaggggcc catgggaagg   2460
gcaagggatg gggaagcctg ggccggcccc ttccctgctc caaggcagg tgtccaggtg    2520 gcgggagcag caccaaggac agccaggctt acccggtggg aggagcagga gcagagcagg   2580
tggcagggag gaaccctgg cgaggcaggg agcactgaag tagggaagca gcaaaaaata    2640
caggctccca acgtggctcc actgtctcat gaagtgtcaa aaatttaaaa atacacctca   2700
ctttctattc agcatcagct attgaaatgg aattctcctt ttctattccc gttgtacata   2760
gccccacgcc ctgcctccgg ctttgtcctc tgtacagagc ccctgtccc ctctgctgtt    2820 ccggacccct ttcttgcagc agctcaaccc cccgactcac tcagatcccc aggactgcag   2880
ccgagccccg ggcttccttt cttaccattc tgtatgcttc caaggtgtga ccattcaaac   2940
taacagtatt attaagatta ttaataaaga tttctttctt caaaccagga aaaaaaaaa   3000 aaaaaaa                                                              3007
```

<210> SEQ ID NO 25
<211> LENGTH: 564
<212> TYPE: PRT
<213> ORGANISM: Homo sapiens

<400> SEQUENCE: 25

```
Met Ser Ser His Gly Asn Ser Leu Phe Leu Arg Glu Ser Gly Gln Arg
1               5                   10                  15

Leu Gly Arg Val Gly Trp Leu Gln Arg Leu Gln Glu Ser Leu Gln Gln
            20                  25                  30

Arg Ala Leu Arg Thr Arg Leu Arg Leu Gln Thr Met Thr Leu Glu His
        35                  40                  45

Val Leu Arg Phe Leu Arg Arg Asn Ala Phe Ile Leu Leu Thr Val Ser
    50                  55                  60

Ala Val Val Ile Gly Val Ser Leu Ala Phe Ala Leu Arg Pro Tyr Gln
65                  70                  75                  80

Leu Thr Tyr Arg Gln Ile Lys Tyr Phe Ser Phe Pro Gly Glu Leu Leu
                85                  90                  95

Met Arg Met Leu Gln Met Leu Val Leu Pro Leu Ile Val Ser Ser Leu
            100                 105                 110

Val Thr Gly Met Ala Ser Leu Asp Asn Lys Ala Thr Gly Arg Met Gly
        115                 120                 125

Met Arg Ala Ala Val Tyr Tyr Met Val Thr Thr Ile Ile Ala Val Phe
    130                 135                 140

Ile Gly Ile Leu Met Val Thr Ile Ile His Pro Gly Lys Gly Ser Lys
145                 150                 155                 160

Glu Gly Leu His Arg Glu Gly Arg Ile Glu Thr Ile Pro Thr Ala Asp
                165                 170                 175

Ala Phe Met Asp Leu Ile Arg Asn Met Phe Pro Pro Asn Leu Val Glu
            180                 185                 190

Ala Cys Phe Lys Gln Phe Lys Thr Gln Tyr Ser Thr Arg Val Val Thr
        195                 200                 205

Arg Thr Met Val Arg Thr Glu Asn Gly Ser Glu Pro Gly Ala Ser Met
    210                 215                 220

Pro Pro Pro Phe Ser Val Glu Asn Gly Thr Ser Phe Leu Glu Asn Val
```

```
                    225                 230                 235                 240
            Thr Arg Ala Leu Gly Thr Leu Gln Glu Met Leu Ser Phe Glu Glu Thr
                            245                 250                 255

Val Pro Val Pro Gly Ser Ala Asn Gly Ile Asn Ala Leu Gly Leu Val
                            260                 265                 270

Val Phe Ser Val Ala Phe Gly Leu Val Ile Gly Gly Met Lys His Lys
                            275                 280                 285

Gly Arg Val Leu Arg Asp Phe Phe Asp Ser Leu Asn Glu Ala Ile Met
                290                 295                 300

Arg Leu Val Gly Ile Ile Ile Trp Tyr Ala Pro Val Gly Ile Leu Phe
            305                 310                 315                 320

Leu Ile Ala Gly Lys Ile Leu Glu Met Glu Asp Met Ala Val Leu Gly
                            325                 330                 335

Gly Gln Leu Gly Met Tyr Thr Leu Thr Val Ile Val Gly Leu Phe Leu
                            340                 345                 350

His Ala Gly Ile Val Leu Pro Leu Ile Tyr Phe Leu Val Thr His Arg
                            355                 360                 365

Asn Pro Phe Pro Phe Ile Gly Gly Met Leu Gln Ala Leu Ile Thr Ala
                370                 375                 380

Met Gly Thr Ser Ser Ser Ser Ala Thr Leu Pro Ile Thr Phe Arg Cys
            385                 390                 395                 400

Leu Glu Glu Gly Leu Gly Val Asp Arg Arg Ile Thr Arg Phe Val Leu
                            405                 410                 415

Pro Val Gly Ala Thr Val Asn Met Asp Gly Thr Ala Leu Tyr Glu Ala
                            420                 425                 430

Leu Ala Ala Ile Phe Ile Ala Gln Val Asn Asn Tyr Glu Leu Asn Leu
                            435                 440                 445

Gly Gln Ile Thr Thr Ile Ser Ile Thr Ala Thr Ala Ala Ser Val Gly
                450                 455                 460

Ala Ala Gly Ile Pro Gln Ala Gly Leu Val Thr Met Val Ile Val Leu
            465                 470                 475                 480

Thr Ser Val Gly Leu Pro Thr Glu Asp Ile Thr Leu Ile Ile Ala Val
                            485                 490                 495

Asp Trp Phe Leu Asp Arg Leu Arg Thr Met Thr Asn Val Leu Gly Asp
                            500                 505                 510

Ser Ile Gly Ala Ala Val Ile Glu His Leu Ser Gln Arg Glu Leu Glu
                            515                 520                 525

Leu Gln Glu Ala Glu Leu Thr Leu Pro Ser Leu Gly Lys Pro Tyr Lys
                530                 535                 540

Ser Leu Met Ala Gln Glu Lys Gly Ala Ser Arg Gly Arg Gly Gly Asn
            545                 550                 555                 560

Glu Ser Ala Met

<210> SEQ ID NO 26
            <211> LENGTH: 2990
            <212> TYPE: DNA
            <213> ORGANISM: Homo sapiens

<400> SEQUENCE: 26
ggcatagcgc gtcccggctc cgcgccggtg cctccacggt ccggtccccg cgccggtgct      60
gcacagtccc tggcgggtcc ccgcggcccc ggccgggcgc ttcgccgggc tccggctcct     120
gcatccgggc gcagcgcgca ggccgaggcg cgggcaggcc gccccgccg ctccggacgc      180 cgggatgtaa gaggctccga aaagcagccc acgcatctca tcagatctaa gtgtctagag     240
```

```
gtcgggagaa ccaagtggga aagacccacc ctcacccctc accttgtaga aactgggaac    300
actagaaggg acattttctg agcaggaaac ccaagagaca gggttttacg ctgtcaccca    360
agttggagtg cagtggtacg atcatagctc attgcagcct caaactcctg ggttcaagcg    420
atcctcctgc tttagcctct tgagtagcta ggactacagg cacaggccac cgtgcctggc    480 taattttaa ttttaaaaa agagacaggg tctggctatg ttgcccaggc tggccatgaa    540
ctcctgggct caagcggttc tccagccttc acctcccaaa gtgttgggat tgcaggcatg    600
agccactgcg tctggcccac agatgctaag tgctgtctgc tcttctccag gggtcagcaa    660
attttttcag caaatggccc aagagtaaat attttgagct ttgtggcccg tacaatctct    720
gtcccaacaa ctcaactcag gcattgtagc ttgaaagcag ctgtagacaa taggtaatcc    780
atgagtgtgg ctgtgtgcca ataaaacttt atttacaaaa acaagcagta ggctgaattt    840
gactagcaga ccatagtttg tcaataccgt attatgtctt gtaaggaaga gaaaggaacc    900
agacaaaact ctagcctcgg gagttttcct gactgttcag atcttagctg aatgatctcc    960
cttggtatct acaggcaact tcctgctgtg gcttagggac tggaaacata atatcccaga   1020
gggattccct gtgtagtctg tggttcactc tttgggattt tttttttttt tttcacagca   1080
aggagaagca gcattgtggt ttcaggagat gggtccattt ggagcaggat cctaagtggg   1140
gcttggcatt gggaatttgg attagctcta gaggacgcag gatctggaaa atcagggcag   1200
atttcccatc ccttggatat ggtggggagt tgaggagggc aaggaagatc ccagaaaagc   1260
cagtggcagc aaaacacaaa ggccagggac ctacgtactg gtaaaactga gacctccaag   1320
aaacctgcag ctcgacctgg ttgaattcag atagaccatg agcagccatg caacagcct    1380 gttccttcgg gagagcggcc agcggctggg ccgggtgggc tggctgcagc ggctgcagga   1440
aagcctgcag cagagagcac tgcgcacgcg cctgcgcctg cagaccatga ccctcgagca   1500
cgtgctgcgc ttcctgcgcc gaaacgcctt cattctgctg acggtcagcg ccgtggtcat   1560
tggggtcagc ctggcctttg ccctgcgccc atatcagctc acctaccgcc agatcaagta   1620
cttctctttt cctggagagc ttctgatgag gatgctgcag atgctggtgt tacctctcat   1680
tgtctccagc ctggtcacag gtatggcatc cctggacaac aaggccacgg ggcggatggg   1740
gatgcgggca gctgtgtact acatggtgac caccatcatc gcggtcttca tcggcatcct   1800
catggtcacc atcatccatc ccgggaaggg ctccaaggag gggctgcacc gggagggccg   1860
gatcgagacc atccccacag ctgatgcctt catggacctg atcagaaata tgtttccacc   1920
aaaccttgtg gaggcctgct tcaaacagtt caagacgcag tacagcacga gggtggtaac   1980
caggaccatg gtgaggacag agaacgggtc tgagccgggt gcctccatgc ctcctccatt   2040
ctcagtggag aacggaacca gcttcctgga aaatgtcact cgggccttgg gtaccctgca   2100
ggagatgctg agctttgagg agactgtacc cgtgcctggc tccgccaatg catcaacgc    2160 cctgggcctc gtggtcttct ctgtggcctt gggctggtc attggtggca tgaaacacaa   2220
gggcagagtc ctcagggact tcttcgacag cctcaatgag gctattatga ggctggtggg   2280
catcattatc tggtgagtcc tggtctgtgc ccacgggaag gtggagccag agctggggaag   2340 tcaggctgtg gggaagctgc cgaagggctt gctgggaccc tttggtcatt catttacgta   2400
ttgggtgatt cacttaccca ctcaccaact cattcattca tgtctttctg ggatgatttc   2460
atcactagtt cacttccttg ttcatctgtt cattcattca ttcttctatg cattggttag   2520
ttcatggaat atctcactct ttcattcatt catgtccttc tgcaatgatt cattcactgc   2580
```

```
tttgttcatc tgttcattca ctcattcttc tatgcattga tgaaatcact cattcagtga    2640
tttattcatc tatactcatg cttcaatgca ttgatttact catttcctca tgcatttatt    2700
cattcatcta tgcattggtt aaatcactgg ccaactcact aactcattca ttcattcaca    2760
cttttctgca atgatttgtt cacttgttca ctcccttgct tatctgttca ttcactcatt    2820
cttcaataca ttgaccaagc cattcactga catttattca gctacattta ttctttcatg    2880
cattggtctg gatttatttg gtcattcatt tatttatttt gcaaaattaa tgtatttta     2940 attgacaaat aaaaactgta tatattttca gtgcaaaaa aaaaaaaaa                 2990
```

<210> SEQ ID NO 27
<211> LENGTH: 1192
<212> TYPE: PRT
<213> ORGANISM: Homo sapiens

<400> SEQUENCE: 27

```
Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro
                20                  25                  30

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Gly Ala Pro Leu Met Asp
65              70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
            195                 200                 205

Leu Lys Glu Gln Pro Gly Asn Thr Ile Ser Ala Gly Gln Glu Asp Phe
    210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
            275                 280                 285

Leu Thr Glu Phe Ser Glu Leu Glu Tyr Ser Glu Met Gly Ser Ser Phe
    290                 295                 300
```

```
Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
            325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
            355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
            435                 440                 445

Ser Thr Pro Glu Gly Ile Lys Asp Arg Ser Gly Ala Tyr Ile Thr Cys
450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Val Ala
            530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
    610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
            675                 680                 685

Glu Thr Glu Ala Pro Tyr Ile Ser Ile Ala Cys Asp Leu Ile Lys Glu
            690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
```

```
                725                 730                 735
Asp Ser Ser Pro Asp Ser Glu Pro Val Asp Leu Phe Ser Asp Asp Ser
                740                 745                 750
Ile Pro Asp Val Pro Gln Lys Gln Asp Glu Thr Val Met Leu Val Lys
                755                 760                 765
Glu Ser Leu Thr Glu Thr Ser Phe Glu Ser Met Ile Glu Tyr Glu Asn
                770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                805                 810                 815
Asp Glu Val Ser Thr Leu Ser Lys Lys Glu Lys Ile Pro Leu Gln Met
                820                 825                 830
Glu Glu Leu Ser Thr Ala Val Tyr Ser Asn Asp Asp Leu Phe Ile Ser
                835                 840                 845
Lys Glu Ala Gln Ile Arg Glu Thr Glu Thr Phe Ser Asp Ser Ser Pro
850                 855                 860
Ile Glu Ile Ile Asp Glu Phe Pro Thr Leu Ile Ser Ser Lys Thr Asp
865                 870                 875                 880
Ser Phe Ser Lys Leu Ala Arg Glu Tyr Thr Asp Leu Glu Val Ser His
                885                 890                 895
Lys Ser Glu Ile Ala Asn Ala Pro Asp Gly Ala Gly Ser Leu Pro Cys
                900                 905                 910
Thr Glu Leu Pro His Asp Leu Ser Leu Lys Asn Ile Gln Pro Lys Val
                915                 920                 925
Glu Glu Lys Ile Ser Phe Ser Asp Asp Phe Ser Lys Asn Gly Ser Ala
930                 935                 940
Thr Ser Lys Val Leu Leu Leu Pro Pro Asp Val Ser Ala Leu Ala Thr
945                 950                 955                 960
Gln Ala Glu Ile Glu Ser Ile Val Lys Pro Lys Val Leu Val Lys Glu
                965                 970                 975
Ala Glu Lys Lys Leu Pro Ser Asp Thr Glu Lys Glu Asp Arg Ser Pro
                980                 985                 990
Ser Ala Ile Phe Ser Ala Glu Leu  Ser Lys Thr Ser Val  Val Asp Leu
                995                 1000                1005
Leu Tyr  Trp Arg Asp Ile Lys  Lys Thr Gly Val Val  Phe Gly Ala
    1010                1015                1020
Ser Leu  Phe Leu Leu Leu Ser  Leu Thr Val Phe Ser  Ile Val Ser
    1025                1030                1035
Val Thr  Ala Tyr Ile Ala Leu  Ala Leu Leu Ser Val  Thr Ile Ser
    1040                1045                1050
Phe Arg  Ile Tyr Lys Gly Val  Ile Gln Ala Ile Gln  Lys Ser Asp
    1055                1060                1065
Glu Gly  His Pro Phe Arg Ala  Tyr Leu Glu Ser Glu  Val Ala Ile
    1070                1075                1080
Ser Glu  Glu Leu Val Gln Lys  Tyr Ser Asn Ser Ala  Leu Gly His
    1085                1090                1095
Val Asn  Cys Thr Ile Lys Glu  Leu Arg Arg Leu Phe  Leu Val Asp
    1100                1105                1110
Asp Leu  Val Asp Ser Leu Lys  Phe Ala Val Leu Met  Trp Val Phe
    1115                1120                1125
Thr Tyr  Val Gly Ala Leu Phe  Asn Gly Leu Thr Leu  Leu Ile Leu
    1130                1135                1140
```

```
Ala Leu Ile Ser Leu Phe Ser Val Pro Val Ile Tyr Glu Arg His
    1145                1150                1155

Gln Ala Gln Ile Asp His Tyr Leu Gly Leu Ala Asn Lys Asn Val
    1160                1165                1170

Lys Asp Ala Met Ala Lys Ile Gln Ala Lys Ile Pro Gly Leu Lys
    1175                1180                1185

Arg Lys Ala Glu
    1190

<210> SEQ ID NO 28
<211> LENGTH: 4871
<212> TYPE: DNA
<213> ORGANISM: Homo sapiens

<400> SEQUENCE: 28
agtccctgcc ctcccctggg gagggtgagt cacgccaaac tgggcggaga gtccgctggc      60
ctcactccta gctcatctgg gcggcggcgg caagtgggga cagggcgggt ggcgcatcac     120
cggcgcggag gcaggaggag cagtctcatt gttccgggag ccgtcaccac agtaggtccc     180
tcggctcagt cggcccagcc cctctcagtc tccccaacc cccacaaccg cccgcggctc      240
tgagacgcgg ccccggcggc ggcggcagca gctgcagcat catctccacc ctccagccat     300
ggaagacctg gaccagtctc tctggtctc gtcctcggac agcccacccc ggccgcagcc      360
cgcgttcaag taccagttcg tgagggagcc cgaggacgag gaggaagaag aggaggagga     420
agaggaggac gaggacgaag acctggagga gctggaggtg ctggagagga gcccgccgc      480 cgggctgtcc gcggccccag tgcccaccgc ccctgccgcc ggcgcgcccc tgatggactt     540
cggaaatgac ttcgtgccgc cggcgccccg gggaccctg ccggccgctc ccccgtcgc      600 cccggagcgg cagccgtctt gggacccgag cccggtgtcg tcgaccgtgc ccgcgccatc     660
cccgctgtct gctgccgcag tctcgccctc caagctccct gaggacgacg agcctccggc     720
ccggcctccc cctcctcccc cggccagcgt gagcccccag gcagagcccg tgtggacccc     780
gccagccccg gctcccgccg cgccccctc cacccccggcc gcgcccaagc gcaggggctc     840
ctcgggctca gtggatgaga cccttttttgc tcttcctgct gcatctgagc ctgtgatacg     900
ctcctctgca gaaatatgg acttgaagga gcagccaggt aacactattt cggctggtca     960
agaggatttc ccatctgtcc tgcttgaaac tgctgcttct cttccttctc tgtctcctct    1020
ctcagccgct tctttcaaag aacatgaata ccttggtaat ttgtcaacag tattacccac    1080
tgaaggaaca cttcaagaaa atgtcagtga agcttctaaa gaggtctcag agaaggcaaa    1140
aactctactc atagatagag atttaacaga gttttcagaa ttagaatact cagaaatggg    1200
atcatcgttc agtgtctctc caaaagcaga atctgccgta atagtagcaa atcctaggga    1260
agaaataatc gtgaaaaata agatgaaga agagaagtta gttagtaata acatccttca    1320
taatcaacaa gagttaccta cagctcttac taaattggtt aaagaggatg aagttgtgtc    1380
ttcagaaaaa gcaaaagaca gttttaatga aaagagagtt gcagtggaag ctcctatgag    1440
ggaggaatat gcagacttca aaccatttga gcgagtatgg gaagtgaaag atagtaagga    1500
agatagtgat atgttggctg ctggaggtaa aatcgagagc aacttggaaa gtaaagtgga    1560
taaaaaatgt tttgcagata gccttgagca aactaatcac gaaaaagata gtgagagtag    1620
taatgatgat acttctttcc ccagtacgcc agaaggtata aaggatcgtt caggagcata    1680
tatcacatgt gctccctta acccagcagc aactgagagc attgcaacaa acatttttcc    1740
```

```
tttgttagga gatcctactt cagaaaataa gaccgatgaa aaaaaaatag aagaaaagaa    1800
ggcccaaata gtaacagaga agaatactag caccaaaaca tcaaacccct ttcttgtagc    1860
agcacaggat tctgagacag attatgtcac aacagataat ttaacaaagg tgactgagga    1920
agtcgtggca acatgcctg aaggcctgac tccagattta gtacaggaag catgtgaaag    1980
tgaattgaat gaagttactg gtacaaagat tgcttatgaa acaaaaatgg acttggttca    2040
aacatcagaa gttatgcaag agtcactcta tcctgcagca cagctttgcc catcatttga    2100
agagtcagaa gctactcctt caccagtttt gcctgacatt gttatggaag caccattgaa    2160
ttctgcagtt cctagtgctg gtgcttccgt gatacagccc agctcatcac cattagaagc    2220
ttcttcagtt aattatgaaa gcataaaaca tgagcctgaa aaccccccac catatgaaga    2280
ggccatgagt gtatcactaa aaaagtatc aggaataaag gaagaaatta aagagcctga    2340
aaatattaat gcagctcttc aagaaacaga agctccttat atatctattg catgtgattt    2400
aattaaagaa acaaagcttt ctgctgaacc agctccggat ttctctgatt attcagaaat    2460
ggcaaaagtt gaacagccag tgcctgatca ttctgagcta gttgaagatt cctcacctga    2520
ttctgaacca gttgacttat ttagtgatga ttcaatacct gacgttccac aaaaacaaga    2580
tgaaactgtg atgcttgtga agaaagtct cactgagact tcatttgagt caatgataga    2640
atatgaaaat aaggaaaaac tcagtgcttt gccacctgag ggaggaaagc catatttgga    2700
atcttttaag ctcagtttag ataacacaaa agatacccctg ttacctgatg aagtttcaac    2760
attgagcaaa aaggagaaaa ttcctttgca gatggaggag ctcagtactg cagtttattc    2820
aaatgatgac ttatttattt ctaaggaagc acagataaga gaaactgaaa cgttttcaga    2880
ttcatctcca attgaaatta tagatgagtt ccctacattg atcagttcta aaactgattc    2940
attttctaaa ttagccaggg aatatactga cctagaagta tcccacaaaa gtgaaattgc    3000
taatgccccg gatggagctg ggtcattgcc ttgcacagaa ttgccccatg accttttcttt    3060 gaagaacata caacccaaag ttgaagagaa aatcagtttc tcagatgact tttctaaaaa    3120
tgggtctgct acatcaaagg tgctcttatt gcctccagat gtttctgctt tggccactca    3180
agcagagata gagagcatag ttaaacccaa agttcttgtg aaagaagctg agaaaaaact    3240
tccttccgat acagaaaaag aggacagatc accatctgct atattttcag cagagctgag    3300
taaaacttca gttgttgacc tcctgtactg gagagacatt aagaagactg gagtggtgtt    3360
tggtgccagc ctattcctgc tgcttcatt gacagtattc agcattgtga gcgtaacagc    3420
ctacattgcc ttggccctgc tctctgtgac catcagctt aggatataca agggtgtgat    3480
ccaagctatc cagaaatcag atgaaggcca cccattcagg gcatatctgg aatctgaagt    3540
tgctatatct gaggagttgg ttcagaagta cagtaattct gctcttggtc atgtgaactg    3600
cacgataaag gaactcaggc gcctcttctt agttgatgat ttagttgatt ctctgaagtt    3660
tgcagtgttg atgtgggtat ttacctatgt tggtgccttg tttaatggtc tgacactact    3720
gattttggct ctcatttcac tcttcagtgt tcctgttatt tatgaacggc atcaggcaca    3780
gatagatcat tatctaggac ttgcaaataa gaatgttaaa gatgctatgg ctaaaatcca    3840
agcaaaaatc cctggattga gcgcaaagc tgaatgaaaa cgcccaaaat aattagtagg    3900
agttcatctt taaggggat attcatttga ttatacgggg gagggtcagg gaagaacgaa    3960
ccttgacgtt gcagtgcagt ttcacagatc gttgttagat ctttattttt agccatgcac    4020
tgttgtgagg aaaaattacc tgtccttgact gccatgtgtt catcatctta agtattgtaa    4080
gctgctatgt atggatttaa accgtaatca tatctttttc ctatctatct gaggcactgg    4140
```

```
tggaataaaa aacctgtata ttttactttg ttgcagatag tcttgccgca tcttggcaag    4200
ttgcagagat ggtggagcta gaaaaaaaaa aaaaaaagcc cttttcagtt tgtgcactgt    4260
gtatggtccg tgtagattga tgcagatttt ctgaaatgaa atgtttgttt agacgagatc    4320
ataccggtaa agcaggaatg acaaagcttg cttttctggt atgttctagg tgtattgtga    4380
cttttactgt tatattaatt gccaatataa gtaaatatag attatatatg tatagtgttt    4440
cacaaagctt agacctttac cttccagcca ccccacagtg cttgatattt cagagtcagt    4500
cattggttat acatgtgtag ttccaaagca cataagctag aagaagaaat atttctagga    4560
gcactaccat ctgttttcaa catgaaatgc cacacacata gaactccaac atcaatttca    4620
ttgcacagac tgactgtagt taattttgtc acagaatcta tggactgaat ctaatgcttc    4680
caaaaatgtt gtttgtttgc aaatatcaaa cattgttatg caagaaatta ttaattacaa    4740
aatgaagatt tataccattg tggtttaagc tgtactgaac taaatctgtg gaatgcattg    4800
tgaactgtaa aagcaaagta tcaataaagc ttatagactt aaaaaaaaaa aaaaaaaaaa    4860
aaaaaaaaaa a                                                        4871
```

<210> SEQ ID NO 29
<211> LENGTH: 271
<212> TYPE: PRT
<213> ORGANISM: Homo sapiens

<400> SEQUENCE: 29

```
Met Tyr Tyr Ala Val Ser Gln Ala Arg Val Asn Ala Val Pro Gly Thr
1               5                   10                  15

Met Leu Arg Pro Gln Arg Pro Gly Asp Leu Gln Leu Gly Ala Ser Leu
            20                  25                  30

Tyr Glu Leu Val Gly Tyr Arg Gln Pro Ser Ser Ser Ser Ser Ser Ser
        35                  40                  45

Thr Ser Ser Thr Ser Ser Thr Ser Ser Ser Thr Thr Ala Pro Leu
    50                  55                  60

Leu Pro Lys Ala Ala Arg Glu Lys Pro Glu Ala Pro Ala Glu Pro Pro
65                  70                  75                  80

Gly Pro Gly Pro Gly Ser Gly Ala His Pro Gly Gly Ser Ala Arg Pro
                85                  90                  95

Asp Ala Lys Glu Glu Gln Gln Gln Leu Arg Arg Lys Ile Asn Ser
            100                 105                 110

Arg Glu Arg Lys Arg Met Gln Asp Leu Asn Leu Ala Met Asp Ala Leu
        115                 120                 125

Arg Glu Val Ile Leu Pro Tyr Ser Ala Ala His Cys Gln Gly Ala Pro
    130                 135                 140

Gly Arg Lys Leu Ser Lys Ile Ala Thr Leu Leu Leu Ala Arg Asn Tyr
145                 150                 155                 160

Ile Leu Leu Leu Gly Ser Ser Leu Gln Glu Leu Arg Arg Ala Leu Gly
                165                 170                 175

Glu Gly Ala Gly Pro Ala Ala Pro Arg Leu Leu Leu Ala Gly Leu Pro
            180                 185                 190

Leu Leu Ala Ala Ala Pro Gly Ser Val Leu Leu Ala Pro Gly Ala Val
        195                 200                 205

Gly Pro Pro Asp Ala Leu Arg Pro Ala Lys Tyr Leu Ser Leu Ala Leu
    210                 215                 220

Asp Glu Pro Pro Cys Gly Gln Phe Ala Leu Pro Gly Gly Gly Ala Gly
225                 230                 235                 240
```

Gly Pro Gly Leu Cys Thr Cys Ala Val Cys Lys Phe Pro His Leu Val
            245                 250                 255

Pro Ala Ser Leu Gly Leu Ala Ala Val Gln Ala Gln Phe Ser Lys
            260                 265                 270

<210> SEQ ID NO 30
<211> LENGTH: 2298
<212> TYPE: DNA
<213> ORGANISM: Homo sapiens

<400> SEQUENCE: 30

| | | | | | |
|---|---|---|---|---|---|
| gttctagatc | gtttccccgc | gcgcaggtcc | gcggggaggg | gcggcctgcc | gaccggccca | 60 |
| ccccagggcg | ttcctgaagg | gcgtcctcgg | ccgcccccac | cgcctcccag | atgtactatg | 120 |
| cggtttccca | ggcgcgcgtg | aacgcggtcc | ccgggaccat | gctgcggcca | cagcggcccg | 180 |
| gagacttgca | gctcggggcc | tccctctacg | agctggtggg | ctacaggcag | ccgccctcct | 240 |
| cctcctcctc | ctccacctcc | tccacctcct | ccacttcctc | ctcctccacg | acggcccccc | 300 |
| tcctccccaa | ggctgcgcgc | gagaagccgg | aggcgccggc | cgagcctcca | ggccccgggc | 360 |
| ccgggtcagg | cgcgcacccg | ggcggcagcg | cccggccgga | cgccaaggag | gagcagcagc | 420 |
| agcagctgcg | gcgcaagatc | aacagccgcg | agcggaagcg | catgcaggac | ctgaacctgg | 480 |
| ccatggacgc | cctgcgcgag | gtcatcctgc | cctactcagc | ggcgcactgc | cagggcgcgc | 540 |
| ccggccgcaa | gctctccaag | atagccacgc | tgctgctcgc | ccgcaactac | atcctactgc | 600 |
| tgggcagctc | gctgcaggag | ctgcgccgcg | cgctgggcga | gggcgccggg | ccgccgccgc | 660 |
| cgcgcctgct | gctggccggg | ctgccctgc | tcgccgccgc | gccggctcc | gtgctgctgg | 720 |
| cgccggcgc | cgtaggaccc | cccgacgcgc | tgcgccccgc | caagtacctg | tcgctggcgc | 780 |
| tggacgagcc | gccgtgcggc | cagttcgctc | tccccggcgg | cggcgcaggc | ggccccggcc | 840 |
| tctgcacctg | cgccgtgtgc | aagttcccgc | acctggtccc | ggccagcctg | ggcctggccg | 900 |
| ccgtgcaggc | gcaattctcc | aagtgagggc | gggtctgggc | ctggggcgcg | acctcggccc | 960 |
| ggcctccctt | cgctcagctt | ctccgcgccc | ctgctccctg | cgtctgggag | agcgaggccg | 1020 |
| agcaaggaaa | gcatttcgaa | ccttccagtc | cagaggaagg | gactgtcggg | cacccccttc | 1080 |
| cccgccccca | ccctgggac | gttaaagtga | ccagagcgga | tgttcgatgg | cgcctcgggg | 1140 |
| cagtttgggg | ttctgggtcg | gttccagcgg | ctttaggcag | aaagtgctcg | ctctcaccca | 1200 |
| gcacatctct | ctccttgtcc | ctggagttgc | gcgcttcgcg | gggccgatgt | agaacttagg | 1260 |
| gcgccttgcc | gtggttggcg | cgccccgggt | gcagcgagag | gccatccccg | agcgctacct | 1320 |
| ccccggagcg | gagcacgcgg | gctcccagta | ctaggggctg | cgctcgagca | gtggcggggg | 1380 |
| cggagggggtg | gttcttttcc | ttctcctccg | ccagaggcca | cgggcgccct | tgttcccgcc | 1440 |
| ggccaggtcc | tatcaaagga | ggctgccgga | actcaagagg | cagaaaaaga | ccagttaggc | 1500 |
| ggtgcagacg | gtctgggacg | tggcagacgg | acggaccctc | ggcggacagg | tggtcggcgt | 1560 |
| cggggtgcgg | tgggtagggg | cgaggacaac | gcagggtgcg | ctgggttggg | acgtgggtcc | 1620 |
| acttttgtag | accagctgtt | tggagagctg | tatttaagac | tcgcgtatcc | agtgttttgt | 1680 |
| cgcagagagt | tttcactctt | aaatcctggg | ggtttcttag | aaagcaactt | agaactcgag | 1740 |
| attcacctttt | cgtttcccctt | tccccaaaag | tagcgtaacc | aacatttaag | cttgcttaaa | 1800 |
| aacgaaaacc | aaccgccttg | catccagtgt | tcccgattta | ctaaaatagg | taaccaggcg | 1860 |
| tctcacagtc | gccgtcctgt | caagagcgct | aatgaacgtt | ctcattaaca | cgcaggagta | 1920 |

```
ccgggagccc tgaaccgccc gctgctcggc ggatcccagc tgcggtggcg acggcgggaa    1980
ggcgctttcc gctgttcctc agcgggccgg gcccttgacc agcgcggccc gcaggtcttc    2040
cttctcgccg tcttgcagtt gaagagctac atacgtagtc agtttcgatt tgttacagac    2100
gttaacaaat tcctttaccc aaggttatgc tatgaccttt ccgcagttta ctttgatttt    2160
ctatgtttaa ggttttggtt gttggtagta gccgaattta actggcactt tattttactt    2220
ctaaccttgt ttcctgacgg tgtacagaat caacaaaata aacatttaa agtctgattt    2280 tttaaaaaaa aaaaaaaa                                                  2298
```

```
<210> SEQ ID NO 31
<211> LENGTH: 323
<212> TYPE: PRT
<213> ORGANISM: Homo sapiens

<400> SEQUENCE: 31

Met Asp Ser Asp Ala Ser Leu Val Ser Ser Arg Pro Ser Ser Pro Glu
1               5                   10                  15

Pro Asp Asp Leu Phe Leu Pro Ala Arg Ser Lys Gly Ser Ser Gly Ser
            20                  25                  30

Ala Phe Thr Gly Gly Thr Val Ser Ser Thr Pro Ser Asp Cys Pro
        35                  40                  45

Pro Glu Leu Ser Ala Glu Leu Arg Gly Ala Met Gly Ser Ala Gly Ala
    50                  55                  60

His Pro Gly Asp Lys Leu Gly Gly Ser Gly Phe Lys Ser Ser Ser
65                  70                  75                  80

Ser Thr Ser Ser Ser Thr Ser Ser Ala Ala Ala Ser Ser Thr Lys Lys
                85                  90                  95

Asp Lys Lys Gln Met Thr Glu Pro Glu Leu Gln Gln Leu Arg Leu Lys
            100                 105                 110

Ile Asn Ser Arg Glu Arg Lys Arg Met His Asp Leu Asn Ile Ala Met
        115                 120                 125

Asp Gly Leu Arg Glu Val Met Pro Tyr Ala His Gly Pro Ser Val Arg
    130                 135                 140

Lys Leu Ser Lys Ile Ala Thr Leu Leu Leu Ala Arg Asn Tyr Ile Leu
145                 150                 155                 160

Met Leu Thr Asn Ser Leu Glu Glu Met Lys Arg Leu Val Ser Glu Ile
                165                 170                 175

Tyr Gly Gly His His Ala Gly Phe His Pro Ser Ala Cys Gly Gly Leu
            180                 185                 190

Ala His Ser Ala Pro Leu Pro Ala Ala Thr Ala His Pro Ala Ala Ala
        195                 200                 205

Ala His Ala Ala His His Pro Ala Val His Pro Ile Leu Pro Pro
    210                 215                 220

Ala Ala Ala Ala Ala Ala Ala Ala Ala Ala Ala Ala Val Ser Ser
225                 230                 235                 240

Ala Ser Leu Pro Gly Ser Gly Leu Pro Ser Val Gly Ser Ile Arg Pro
                245                 250                 255

Pro His Gly Leu Leu Lys Ser Pro Ser Ala Ala Ala Ala Pro Leu
            260                 265                 270

Gly Gly Gly Gly Gly Gly Ser Gly Ala Ser Gly Gly Phe Gln His Trp
        275                 280                 285

Gly Gly Met Pro Cys Pro Cys Ser Met Cys Gln Val Pro Pro Pro His
    290                 295                 300
```

His His Val Ser Ala Met Gly Ala Gly Ser Leu Pro Arg Leu Thr Ser
305                 310                 315                 320

Asp Ala Lys

<210> SEQ ID NO 32
<211> LENGTH: 3275
<212> TYPE: DNA
<213> ORGANISM: Homo sapiens

<400> SEQUENCE: 32

```
gggtgcttat tatagatcga cgcgacacca gcgcccggtg ccaggttctc ccctgaggct      60
tttcggagcg agctcctcaa atcgcatcca gagtaagtgt ccccgcccca cagcagccgc     120
agcctagatc ccagggacag actctcctca actcggctgt gacccagaat gctccgatac     180
aggggggtctg gatccctact ctgcgggcca tttctccaga cgactttgc tcttctgtcc     240
tccccacact caccgctgca tctccctcac caaaagcgag aagtcggagc gacaacagct     300
ctttctgccc aagccccagt cagctggtga gctccccgtg gtctccagat gcagcacatg     360
gactctgggc cccgcgccgg ctctgggtgc atgtgcgtgt gcgtgtgttt gctgcgtggt     420
gtcgatggag ataaggtgga tccgtttgag gaaccaaatc attagttctc tatttagatc     480
tccattctcc ccaaagaaag gccctcactt cccactcgtt tattccagcc cggggctca     540
gttttcccac acctaactga aagcccgaag cctctagaat gccacccgca ccccgagggt     600
caccaacgct ccctgaaata acctgttgca tgagagcaga ggggagatag agagagctta     660
attataggta cccgcgtgca gctaaaagga gggccagaga tagtagcgag ggggacgagg     720
agccacgggc cacctgtgcc gggacccgc gctgtggtac tgcggtgcag gcgggagcag     780
cttttctgtc tctcactgac tcactctctc tctctctccc tctctctctc tctcattctc     840
tctcttttct cctcctctcc tggaagtttt cgggtccgag ggaaggagga ccctgcgaaa     900
gctgcgacga ctatcttccc ctggggccat ggactcggac gccagcctgg tgtccagccg     960
cccgtcgtcg ccagagcccg atgacctttt tctgccggcc cggagtaagg gcagcagcgg    1020
cagcgccttc actgggggca ccgtgtcctc gtccaccccg agtgactgcc cgccggagct    1080
gagcgccgag ctgcgcggcg ctatgggctc tgcgggcgcg catcctgtgg acaagctagg    1140
aggcagtggc ttcaagtcat cctcgtccag cacctcgtcg tctacgtcgt cggcggctgc    1200
gtcgtccacc aagaaggaca agaagcaaat gacagagccg gagctgcagc agctgcgtct    1260
caagatcaac agccgcgagc gcaagcgcat gcacgacctc aacatcgcca tggatggcct    1320
ccgcgaggtc atgccgtacg cacacggccc ttcggtgcgc aagctttcca agatcgccac    1380
gctgctgctg gcgcgcaact acatcctcat gctcaccaac tcgctggagg agatgaagcg    1440
actggtgagc gagatctacg ggggccacca cgctggcttc cacccgtcgg cctgcggcgg    1500
cctggcgcac tccgcgcccc tgcccgccgc caccgcgcac ccggcagcag cagcgcacgc    1560
cgcacatcac cccgcggtgc accacccat cctgccgccc gccgccgcag cggctgctgc    1620
cgccgctgca gccgcggctg tgtccagcgc ctctctgccc ggatccgggc tgccgtcggt    1680
cggctccatc cgtccaccgc acggcctact caagtctccg tctgctgccg cggccgcccc    1740
gctgggggca gggggcggcg gcagtgggc gagcgggggc ttccagcact ggggcggcat    1800
gccctgcccc tgcagcatgt gccaggtgcc gccgccgcac caccacgtgt cggctatggg    1860
cgccggcagc ctgccgcgcc tcacctccga cgccaagtga gcctactggc gccgcgcgt    1920
tctggcgaca ggggagccag gggccgcggg gaagcgagga ctggcctgcg ctgggctcgg    1980
```

```
gagctctgtc gcgaggaggg gcgcaggacc atggactggg ggtggggcat ggtggggatt    2040
tcagcatctg cgaacccaag caatgggggc gcccacagag cagtggggag tgaggggatg    2100
ttctctccgg gacctgatcg agcgctgtct ggctttaacc tgagctggtc cagtagacat    2160
cgttttatga aaaggtaccg ctgtgtgcat tcctcactag aactcatccg accccccgacc   2220 cccacctccg ggaaaagatt ctaaaaactt cttttccctga gagcgtggcc tgacttgcag   2280
actcggcttg ggcagcactt cggggggggga ggggtgtta tgggaggggg acacattggg    2340
gccttgctcg tcttcctcct ttcttggcgg gtgggagact ccgggtagcc gcactgcaga    2400
agcaacagcc cgaccgcgcc ctccagggtc gtccctggcc caaggccagg ggccacaagt    2460
tagttggaag ccggcgttcg gtatcagaag cgctgatggt catatccaat ctcaatatct    2520
gggtcaatcc acaccctctt agaactgtgg ccgttcctcc ctgtctctcg ttgatttggg    2580
agaatatggt tttctaataa atctgtggat gttccttctt caacagtatg agcaagttta    2640
tagacattca gagtagaacc acttgtggat tggaataacc caaaactgcc gatttcaggg   2700
gcgggtgcat tgtagttatt attttaaaat agaaactacc ccaccgactc atctttcctt    2760
ctctaagcac aaagtgattt ggttattttg gtacctgaga acgtaacaga attaaaaggc    2820
agttgctgtg gaaacagttt gggttatttg ggggttctgt tggcttttta aaattttctt    2880
ttttggatgt gtaaatttat caatgatgag gtaagtgcgc aatgctaagc tgtttgctca    2940
cgtgactgcc agccccatcg gagtctaagc cggctttcct ctattttggt ttattttttgc   3000 cacgtttaac acaaatggta aactcctcca cgtgcttcct gcgttccgtg caagccgcct    3060
cggcgctgcc tgcgttgcaa actgggcttt gtagcgtctg ccgtgtaaca cccttcctct    3120
gatcgcaccg cccctcgcag agagtgtatc atctgtttta tttttgtaaa aacaaagtgc    3180
taaataatat ttattacttg tttggttgca aaaacggaat aaatgactga gtgttgagat    3240
tttaaataaa atttaaagca aaaaaaaaaa aaaaa                               3275

<210> SEQ ID NO 33
<211> LENGTH: 432
<212> TYPE: PRT
<213> ORGANISM: Homo sapiens

<400> SEQUENCE: 33

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
                20                  25                  30

Pro Gly Thr Arg Leu Ser Leu Ala Arg Met Pro Pro Leu Pro Thr
            35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140
```

| | | | | | | | | | | | | |
|---|---|---|---|---|---|---|---|---|---|---|---|---|
|Ala|Gln|Asp|Leu|Ala|Thr|Val|Arg|Gln|Lys|Leu|Gln|Asp|Glu|Thr|Asn|
|145| | | |150| | | | |155| | | | |160| |

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
                260                 265                 270

Glu Leu Leu Arg Gln Ala Lys His Glu Ala Asn Asp Tyr Arg Arg Gln
            275                 280                 285

Leu Gln Ser Leu Thr Cys Asp Leu Glu Ser Leu Arg Gly Thr Asn Glu
        290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
                340                 345                 350

Leu Asn Val Lys Leu Ala Leu Asp Ile Glu Ile Ala Thr Tyr Arg Lys
            355                 360                 365

Leu Leu Glu Gly Glu Glu Asn Arg Ile Thr Ile Pro Val Gln Thr Phe
        370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430

<210> SEQ ID NO 34
<211> LENGTH: 1488
<212> TYPE: DNA
<213> ORGANISM: Homo sapiens

<400> SEQUENCE: 34

```
gcaggatgga gaggagacgc atcacctccg ctgctcgccg ctcctacgtc tcctcagggg      60
agatgatggt gggggggcctg gctcctggcc gccgtctggg tcctggcacc cgcctctccc    120
tggctcgaat gccccctcca ctcccgaccc gagtggattt ctccctggct ggggcactca    180
atgctggctt caaggagacc cgggccagtg agcgggcaga gatgatggag ctcaatgacc    240
gctttgccag ctacatcgag aaggttcgct tcctggaaca gcaaaacaag gcgctggctg    300
ctgagctgaa ccagctgcgg gccaaggagc ccaccaagct ggcagacgtc taccaggctg    360
agctgcgaga gctgcggctg cggctcgatc aactcaccgc caacagcgcc cggctggagg    420
ttgagaggga caatctggca caggacctgg ccactgtgag gcagaagctc aggatggaa    480 ccaacctgag gctggaagcc gagaacaacc tggctgccta tagacaggaa gcagatgaag    540
```

```
ccaccctggc ccgtctggat ctggagagga agattgagtc gctggaggag gagatccggt      600
tcttgaggaa gatccacgag gaggaggttc gggaactcca ggagcagctg gcccgacagc      660
aggtccatgt ggagcttgac gtggccaagc cagacctcac cgcagccctg aaagagatcc      720
gcacgcagta tgaggcaatg gcgtccagca acatgcatga agccgaagag tggtaccgct      780
ccaagtttgc agacctgaca gacgctgctg cccgcaacgc ggagctgctc cgccaggcca      840
agcacgaagc caacgactac cggcgccagt tgcagtcctt gacctgcgac ctggagtctc      900
tgcgcggcac gaacgagtcc ctggagaggc agatgcgcga gcaggaggag cggcacgtgc      960
gggaggcggc cagttatcag gaggcgctgg cgcggctgga ggaagagggg cagagcctca     1020
aggacgagat ggcccgccac ttgcaggagt accaggacct gctcaatgtc aagctggccc     1080
tggacatcga gatcgccacc tacaggaagc tgctagaggg cgaggagaac cggatcacca     1140
ttcccgtgca gaccttctcc aacctgcaga ttcgagaaac cagcctggac accaagtctg     1200
tgtcagaagg ccacctcaag aggaacatcg tggtgaagac cgtggagatg cgggatggag     1260
aggtcattaa ggagtccaag caggagcaca aggatgtgat gtgaggcagg acccacctgg     1320
tggcctctgc cccgtctcat gaggggcccg agcagaagca ggatagttgc tccgcctctg     1380
ctggcacatt tccccagacc tgagctcccc accacccag ctgctcccct ccctcctctg     1440
tccctaggtc agcttgctgc cctaggctcc gtcagtatca ggcctgcc               1488

<210> SEQ ID NO 35
<211> LENGTH: 92
<212> TYPE: PRT
<213> ORGANISM: Homo sapiens

<400> SEQUENCE: 35

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
            85                  90

<210> SEQ ID NO 36
<211> LENGTH: 1135
<212> TYPE: DNA
<213> ORGANISM: Homo sapiens

<400> SEQUENCE: 36
gggcagaggg aataagaggc tgcctctgcc caccagtcct gccgcccagg acccgcagca       60
gagacgacgc ctgcagcaag gagaccagga agggtgaga caaggaagag gatgtctgag      120
ctggagaagg ccatggtggc cctcatcgac gttttccacc aatattctgg aagggaggga      180
gacaagcaca agctgaagaa atccgaactg aaggagctca tcaacaatga gctttcccat      240
ttcttagagg aaatcaaaga gcaggaggtt gtggacaaag tcatggaaac actggacaat      300
gatggagacg gcgaatgtga cttccaggaa ttcatggcct ttgttgccat ggttactact      360
```

```
gcctgccacg agttctttga acatgagtga gattagaaag cagccaaacc tttcctgtaa    420
cagagacggt catgcaagaa agcagacagc aagggcttgc agcctagtag gagctgagct    480
ttccagccgt gttgtagcta attaggaagc ttgatttgct ttgtgattga aaaattgaaa    540
acctctttcc aaaggctgtt ttaacggcct gcatcattct ttctgctata ttaggcctgt    600
gtgtaagctg actggcccca gggactcttg ttaacagtaa cttaggagtc aggtctcagt    660
gataaagcgt gcaccgtgca gcccgccatg gccgtgtaga ccctaacccg gagggaaccc    720
tgactacaga aattaccccg gggcacccett aaaacttcca ctacctttaa aaacaaagc    780
cttatccagc attatttgaa aacactgctg ttctttaaat gcgttcctca tccatgcaga    840
taacagctgg ttggccggtg tggccctgca agggcgtggt ggcttcggcc tgcttcccgg    900
gatgcgcctg atcaccaggt gaacgctcag cgctggcagc gctcctggaa aaagcaactc    960
catcagaact cgcaatccga gccagctctg ggggctccag cgtggcctcc gtgacccatg   1020
cgattcaagt cgcggctgca ggatccttgc ctccaacgtg cctccagcac atgcggcttc   1080
cgagggcact accggggget ctgagccacc gcgagggcct gcgttcaata aaaag        1135
```

<210> SEQ ID NO 37
<211> LENGTH: 466
<212> TYPE: PRT
<213> ORGANISM: Homo sapiens

<400> SEQUENCE: 37

Met Ala Glu Glu Gln Asp Leu Ser Glu Val Glu Leu Ser Pro Val Gly
1               5                   10                  15

Ser Glu Glu Pro Arg Cys Leu Ser Pro Gly Ser Ala Pro Ser Leu Gly
                20                  25                  30

Pro Asp Gly Gly Gly Gly Ser Gly Leu Arg Ala Ser Pro Gly Pro
            35                  40                  45

Gly Glu Leu Gly Lys Val Lys Lys Glu Gln Gln Asp Gly Glu Ala Asp
        50                  55                  60

Asp Asp Lys Phe Pro Val Cys Ile Arg Glu Ala Val Ser Gln Val Leu
65                  70                  75                  80

Ser Gly Tyr Asp Trp Thr Leu Val Pro Met Pro Val Arg Val Asn Gly
                85                  90                  95

Ala Ser Lys Ser Lys Pro His Val Lys Arg Pro Met Asn Ala Phe Met
            100                 105                 110

Val Trp Ala Gln Ala Ala Arg Arg Lys Leu Ala Asp Gln Tyr Pro His
        115                 120                 125

Leu His Asn Ala Glu Leu Ser Lys Thr Leu Gly Lys Leu Trp Arg Leu
    130                 135                 140

Leu Asn Glu Ser Asp Lys Arg Pro Phe Ile Glu Glu Ala Glu Arg Leu
145                 150                 155                 160

Arg Met Gln His Lys Lys Asp His Pro Asp Tyr Lys Tyr Gln Pro Arg
                165                 170                 175

Arg Arg Lys Asn Gly Lys Ala Ala Gln Gly Glu Ala Glu Cys Pro Gly
            180                 185                 190

Gly Glu Ala Glu Gln Gly Gly Thr Ala Ala Ile Gln Ala His Tyr Lys
        195                 200                 205

Ser Ala His Leu Asp His Arg His Pro Gly Glu Gly Ser Pro Met Ser
    210                 215                 220

Asp Gly Asn Pro Glu His Pro Ser Gly Gln Ser His Gly Pro Pro Thr
225                 230                 235                 240

```
Pro Pro Thr Thr Pro Lys Thr Glu Leu Gln Ser Gly Lys Ala Asp Pro
            245                 250                 255

Lys Arg Asp Gly Arg Ser Met Gly Glu Gly Lys Pro His Ile Asp
    260                 265                 270

Phe Gly Asn Val Asp Ile Gly Glu Ile Ser His Glu Val Met Ser Asn
            275                 280                 285

Met Glu Thr Phe Asp Val Ala Glu Leu Asp Gln Tyr Leu Pro Pro Asn
290                 295                 300

Gly His Pro Gly His Val Ser Ser Tyr Ser Ala Ala Gly Tyr Gly Leu
305                 310                 315                 320

Gly Ser Ala Leu Ala Val Ala Ser Gly His Ser Ala Trp Ile Ser Lys
                325                 330                 335

Pro Pro Gly Val Ala Leu Pro Thr Val Ser Pro Gly Val Asp Ala
            340                 345                 350

Lys Ala Gln Val Lys Thr Glu Thr Ala Gly Pro Gln Gly Pro Pro His
            355                 360                 365

Tyr Thr Asp Gln Pro Ser Thr Ser Gln Ile Ala Tyr Thr Ser Leu Ser
370                 375                 380

Leu Pro His Tyr Gly Ser Ala Phe Pro Ser Ile Ser Arg Pro Gln Phe
385                 390                 395                 400

Asp Tyr Ser Asp His Gln Pro Ser Gly Pro Tyr Tyr Gly His Ser Gly
                405                 410                 415

Gln Ala Ser Gly Leu Tyr Ser Ala Phe Ser Tyr Met Gly Pro Ser Gln
                420                 425                 430

Arg Pro Leu Tyr Thr Ala Ile Ser Asp Pro Ser Pro Ser Gly Pro Gln
            435                 440                 445

Ser His Ser Pro Thr His Trp Glu Gln Pro Val Tyr Thr Thr Leu Ser
450                 455                 460

Arg Pro
465

<210> SEQ ID NO 38
<211> LENGTH: 2882
<212> TYPE: DNA
<213> ORGANISM: Homo sapiens

<400> SEQUENCE: 38
gtccggccag ggtggttggt ggtaaggatt caggctccgt cctaacgagg ccgtggcctg      60
aggctcaggg ccccccgccc ctccctccca gcccaccagc gtcacctccc agccccgagc    120
tggaccgcac accttgggac acggttttcc acttcctaag gacgagcccc agactggagg    180
agaggtccga ggaggtgggc gttggactct ttgcgaggac cccggcggct ggcccggggg    240
aggcggccga ggcggcggcg gcggcggccg ggggcgacat ggcggaggag caggacctat    300
cggaggtgga gctgagcccc gtgggctcgg aggagccccg ctgcctgtcc ccggggagcg    360
cgccctcgct agggcccgac ggcggcggcg cggatcggg cctgcgagcc agcccggggc    420
caggcgagct gggcaaggtc aagaaggagc agcaggacgg cgaggcggac gatgacaagt    480
tccccgtgtg catccgcgag gccgtcagcc aggtgctcag cggctacgac tggacgctgg    540
tgcccatgcc cgtgcgcgtc aacggcgcca gcaaaagcaa gccgcacgtc aagcggccca    600
tgaacgcctt catggtgtgg gctcaggcag cgcgcaggaa gctcgcggac cagtacccgc    660
acctgcacaa cgctgagctc agcaagacgc tgggcaagct ctggaggctg ctgaacgaaa    720
gtgacaagcg ccccttcatc gaggaggctg agcggctccg tatgcagcac aagaaagacc    780
```

| | |
|---|---|
| acccggacta caagtaccag cccaggcggc ggaagaacgg gaaggccgcc cagggcgagg | 840 |
| cggagtgccc cggtggggag gccgagcaag gtgggaccgc cgccatccag gcccactaca | 900 |
| agagcgccca cttggaccac cggcacccag gagagggctc ccccatgtca gatgggaacc | 960 |
| ccgagcaccc ctcaggccag agccatggcc cacccacccc tccaaccacc ccgaagacag | 1020 |
| agctgcagtc gggcaaggca gacccgaagc gggacgggcg ctccatgggg gagggcggga | 1080 |
| agcctcacat cgacttcggc aacgtggaca ttggtgagat cagccacgag gtaatgtcca | 1140 |
| acatggagac ctttgatgtg gctgagttgg accagtacct gccgcccaat gggcacccag | 1200 |
| gccatgtgag cagctactca gcagccggct atgggctggg cagtgccctg gccgtggcca | 1260 |
| gtggacactc cgcctggatc tccaagccac caggcgtggc tctgcccacg gtctcaccac | 1320 |
| ctggtgtgga tgccaaagcc caggtgaaga cagagaccgc ggggcccag gggcccccac | 1380 |
| actacaccga ccagccatcc acctcacaga tcgcctacac ctccctcagc ctgccccact | 1440 |
| atggctcagc cttcccctcc atctcccgcc cccagtttga ctactctgac catcagccct | 1500 |
| caggacccta ttatggccac tcgggccagg cctctggcct ctactcggcc ttctcctata | 1560 |
| tggggccctc gcagcggccc ctctacacgg ccatctctga ccccagcccc tcagggcccc | 1620 |
| agtcccacag ccccacacac tgggagcagc cagtatatac gacactgtcc cggccctaaa | 1680 |
| gggggccctg tcgccaccac cccccgccca gcccctgccc ccagcctgtg tgccctgttc | 1740 |
| cttgcccacc tcaggcctgg tggtggcagt ggaggaggct gaggaggctg aagaggctga | 1800 |
| caggtcgggg ggctttctgt ctggctcact gccctgatga cccacccgcc ccatccaggc | 1860 |
| tccagcagca aagccccagg agaacaggct ggacagagga gaaggaggtt gactgttgca | 1920 |
| cccacactga aagatgaggg gctgcacctt cccccaggaa tgaccctcta tcccaggacc | 1980 |
| tgagaagggc ctgctcaccc tcctcgggga ggggaagcac cagggttggt ggcatcggag | 2040 |
| gccttaccac tcctatgact cctgttttct ctctcacaga tagtgagggt ctgacatgcc | 2100 |
| catgccacct atgccacagt gcctaagggc taggccaccc agagactgtg cccggagctg | 2160 |
| gccgtgtctc ccactcaggg gctgagagta gctttgagga gcctcattgg ggagtggggg | 2220 |
| gttcgaggga cttagtggag ttctcatccc ttcaatgccc cctccctttc tgaaggcagg | 2280 |
| aaggagttgg cacagaggcc ccctgatcca attctgtgcc aataacctca ttctttgtct | 2340 |
| gagaaacagc ccccagtcct cctccactac aacctccatg accttgagac gcatcccagg | 2400 |
| aggtgacgag gcaggggctc caggaaagga atcagagaca attcacagag cctccctccc | 2460 |
| tgggctcctt gccagctccc tcttccctta ctaggctcta tggcccctgc tcagtcagcc | 2520 |
| ccactccctg ggcttcccag agagtgacag ctgctcaggc cctaaccctt ggctccagga | 2580 |
| gacacagggc ccagcaccca ggttgctgtc ggcaggctga agacactaga atcctgacct | 2640 |
| gtacattctg cccttgcctc ttaccccttg cctcccagtg gtatttgaat aaagtatgta | 2700 |
| gctatatctg cccctatttt cctgttctgc agcccccaa atccacatgt aactcattac | 2760 |
| tgtctcctgt tatttatctc agtagtcccc tctcctagcc actctagccc ctattaactc | 2820 |
| tgcattaagc attccacata ataaaattaa aggttccggt taaaaaaaaa aaaaaaaaa | 2880 |
| aa | 2882 |

<210> SEQ ID NO 39
<211> LENGTH: 705
<212> TYPE: PRT
<213> ORGANISM: Homo sapiens

<400> SEQUENCE: 39

```
Met Asn Tyr Leu Arg Arg Arg Leu Ser Asp Ser Asn Phe Met Ala Asn
1               5                   10                  15

Leu Pro Asn Gly Tyr Met Thr Asp Leu Gln Arg Pro Gln Pro Pro
            20                  25                  30

Pro Pro Pro Gly Ala His Ser Pro Gly Ala Thr Pro Gly Pro Gly Thr
            35                  40                  45

Ala Thr Ala Glu Arg Ser Ser Gly Val Ala Pro Ala Ala Ser Pro Ala
50                  55                  60

Ala Pro Ser Pro Gly Ser Ser Gly Gly Gly Phe Phe Ser Ser Leu
65                  70                  75                  80

Ser Asn Ala Val Lys Gln Thr Thr Ala Ala Ala Ala Thr Phe Ser
                85                  90                  95

Glu Gln Val Gly Gly Gly Ser Gly Gly Ala Gly Arg Gly Gly Ala Ala
            100                 105                 110

Ser Arg Val Leu Leu Val Ile Asp Glu Pro His Thr Asp Trp Ala Lys
            115                 120                 125

Tyr Phe Lys Gly Lys Lys Ile His Gly Gly Ile Asp Ile Lys Val Glu
            130                 135                 140

Gln Ala Glu Phe Ser Asp Leu Asn Leu Val Ala His Ala Asn Gly Gly
145                 150                 155                 160

Phe Ser Val Asp Met Glu Val Leu Arg Asn Gly Val Lys Val Arg
                165                 170                 175

Ser Leu Lys Pro Asp Phe Val Leu Ile Arg Gln His Ala Phe Ser Met
            180                 185                 190

Ala Arg Asn Gly Asp Tyr Arg Ser Leu Val Ile Gly Leu Gln Tyr Ala
            195                 200                 205

Gly Ile Pro Ser Val Asn Ser Leu His Ser Val Tyr Asn Phe Cys Asp
            210                 215                 220

Lys Pro Trp Val Phe Ala Gln Met Val Arg Leu His Lys Lys Leu Gly
225                 230                 235                 240

Thr Glu Glu Phe Pro Leu Ile Asp Gln Thr Phe Tyr Pro Asn His Lys
                245                 250                 255

Glu Met Leu Ser Ser Thr Thr Tyr Pro Val Val Lys Met Gly His
            260                 265                 270

Ala His Ser Gly Met Gly Lys Val Lys Val Asp Asn Gln His Asp Phe
            275                 280                 285

Gln Asp Ile Ala Ser Val Val Ala Leu Thr Lys Thr Tyr Ala Thr Ala
            290                 295                 300

Glu Pro Phe Ile Asp Ala Lys Tyr Asp Val Arg Val Gln Lys Ile Gly
305                 310                 315                 320

Gln Asn Tyr Lys Ala Tyr Met Arg Thr Ser Val Ser Gly Asn Trp Lys
                325                 330                 335

Thr Asn Thr Gly Ser Ala Met Leu Glu Gln Ile Ala Met Ser Asp Arg
            340                 345                 350

Tyr Lys Leu Trp Val Asp Thr Cys Ser Glu Ile Phe Gly Gly Leu Asp
            355                 360                 365

Ile Cys Ala Val Glu Ala Leu His Gly Lys Asp Gly Arg Asp His Ile
            370                 375                 380

Ile Glu Val Val Gly Ser Ser Met Pro Leu Ile Gly Asp His Gln Asp
385                 390                 395                 400

Glu Asp Lys Gln Leu Ile Val Glu Leu Val Val Asn Lys Met Ala Gln
                405                 410                 415
```

```
Ala Leu Pro Arg Gln Arg Gln Arg Asp Ala Ser Pro Gly Arg Gly Ser
            420                 425                 430

His Gly Gln Thr Pro Ser Pro Gly Ala Leu Pro Leu Gly Arg Gln Thr
        435                 440                 445

Ser Gln Gln Pro Ala Gly Pro Ala Gln Arg Pro Pro Pro Gln
    450                 455                 460

Gly Gly Pro Pro Gln Pro Gly Pro Gln Arg Gln Gly Pro Pro
465                 470                 475                 480

Leu Gln Gln Arg Pro Pro Gln Gly Gln Gln His Leu Ser Gly Leu
                485                 490                 495

Gly Pro Pro Ala Gly Ser Pro Leu Pro Gln Arg Leu Pro Ser Pro Thr
            500                 505                 510

Ser Ala Pro Gln Gln Pro Ala Ser Gln Ala Ala Pro Pro Thr Gln Gly
        515                 520                 525

Gln Gly Arg Gln Ser Arg Pro Val Ala Gly Pro Gly Ala Pro Pro
    530                 535                 540

Ala Ala Arg Pro Pro Ala Ser Pro Ser Pro Gln Arg Gln Ala Gly Pro
545                 550                 555                 560

Pro Gln Ala Thr Arg Gln Thr Ser Val Ser Gly Pro Ala Pro Lys
            565                 570                 575

Ala Ser Gly Ala Pro Pro Gly Gly Gln Gln Arg Gln Gly Pro Pro Gln
                580                 585                 590

Lys Pro Pro Gly Pro Ala Gly Pro Thr Arg Gln Ala Ser Gln Ala Gly
            595                 600                 605

Pro Val Pro Arg Thr Gly Pro Pro Thr Thr Gln Pro Arg Pro Ser
    610                 615                 620

Gly Pro Gly Pro Ala Gly Ala Pro Lys Pro Gln Leu Ala Gln Lys Pro
625                 630                 635                 640

Ser Gln Asp Val Pro Pro Ala Thr Ala Ala Gly Gly Pro Pro
            645                 650                 655

His Pro Gln Leu Asn Lys Ser Gln Ser Leu Thr Asn Ala Phe Asn Leu
                660                 665                 670

Pro Glu Pro Ala Pro Pro Arg Pro Ser Leu Ser Gln Asp Glu Val Lys
            675                 680                 685

Ala Glu Thr Ile Arg Ser Leu Arg Lys Ser Phe Ala Ser Leu Phe Ser
    690                 695                 700
Asp
705

<210> SEQ ID NO 40
<211> LENGTH: 2470
<212> TYPE: DNA
<213> ORGANISM: Homo sapiens

<400> SEQUENCE: 40
ctcgagagag aaggagagga cattcctggc agaagttaca acacatgcaa aggtacagag     60
gttgccccct tcctacccct ctccttagag gtgggttaga gatgtatcct ttttacagat    120
gaggaaacca aatctcagaa agattaagtc actttcccaa gtgtatggtg gaggccccac    180
ttgaacccag gcactgtgtc tccagacccc acactattac tgccttgttt aaaccagcca    240
actgatttaa tgaataaagg atgaacaaat gaataagtgg atgagtcacc tgaaaattct    300
gcaggcaaag agactccata tctacttact tcttgcctat cttctgccac ctctcctagt    360
ccaccatcac tgctcactat ggtcaaggtc ctacccaatc tggcccctgc taccacaacc    420
```

```
cccttcagct tgttccagcc acattggcac tggatgtttc ctcttcctgg cacattctta      480
aaaaaatgtg ttgatcataa agtgaacatg acccttlggg aattaactgg agttcttgta      540
ttccctcatc tgtaaaatag acattatatt atccacccca ctggattgtt gtgagggtgg     600
gatgaaatga tgcatgtaaa cacgcttagc ttaagagttg ggtacaatca gtgaacaaat     660
gattatgaat tagtgctttt attgtagtca gaatcataaa gatttgacag gttcccatat     720
cccacctctg cttggactac ctcatttgct catatgcaaa gattatttgg tacctactgt     780
gtgtgcacca tgggatgggc ctgcctctgt ggaaagttct tgggtgcagg gggagacagc     840
catgggcact gatgacatca ggtagttatc gtgagttttg gcggtgtcca gagcaaaggg     900
atggtggcgt atataccaag tgtgttctgg tgtgggggtg gacacgcacc agggctaggg     960
ctgcagagaa tgtctgtgtt gcagatctag gttttctccat gatcatcggt gggaatgtgt    1020
tttgtctgca agtgtatgct catatgagtt tccctgggtc tctgtgtgtc agtgtgttac    1080
ctgtgtgtgt gggggtatgg gtgtatgcat gcatgtatgt aacatgccca tgtgtgttac    1140
tctggacttg tatgtctgta tgtataccta gattggcgtg tgttctgtct gtacatgccc    1200
tcgtatgttt cctcactttt gtgtgtgttt atatgtgtgt catttcttgt gtgccctcca    1260
ggcccccctt gccaccttgg gcaagggtgt gtacaccacc caagtgtcca cctccgcttg    1320
tctgatgctg tctgtgacgc ccccgctctc tgcctagctg agcctgtgtg gatgtgggag    1380
actaatctcc ccgcgggcac tgcgtgtgac ctcaccccccc tctgtgaggg ggttatttct    1440
ctactttcgt gtctctgagt gtgcttccag tgccccctc ccccaaaaa atgccttctg    1500
agttgaatat caacactaca aaccgagtat ctgcagactg cagagggccc tgcgtatgag    1560
tgcaagtggg ttttaggacc aggatgaggc ggggtggggg tgcctacctg acgaccgacc    1620
ccgacccact ggacaagcac ccaaccccca ttccccaaat tgcgcatccc ctatcagaga    1680
gggggagggg aaacaggatg cggcgaggcg cgtcgcgact gccagcttca gcaccgcgga    1740
cagtgccttc gccccccgcct ggcggcgcgc gccaccgccg cctcagcact gaaggcgcgc    1800
tgacgtcact cgccggtccc ccgcaaaactc cccttcccgg ccaccttggt cgcgtccgcg    1860
ccgccgccgg cccagccgga ccgcaccacg cgaggcgcga gatagggggg cacgggcgcg    1920
accatctgcg ctgcggcgcc ggcgactcag cgctgcctca gtctgcggtg ggcagcggag    1980
gagtcgtgtc gtgcctgaga gcgcagctgt gctcctgggc accgcgcagt ccgcccccgc    2040
ggctcctggc cagaccaccc ctaggacccc ctgccccaag tcgcagccat gaactacctg    2100
cggcgccgcg tgtcggacag caactttatg gccaatctgc caaatgggta catgacagac    2160
ctgcagcgtc cgcagccgcc cccaccgccg cccggtgccc acagcccgg agccacgccc    2220
ggtcccggga ccgccactgc cgagaggtcc tccggggtcg ccccagcggc ctctccggcc    2280
gcccctagcc ccgggtcctc ggggggcggt ggcttcttct cgtcgctgtc caacgcggtc    2340
aagcagacca cggcggcggc agctgccacc ttcagcgagc aggtgggcgg cggctctggg    2400
ggcgcaggcc gcggggagc cgcctccagg gtgctgctgg tcatcgacga gccgcacacc    2460
gactggtaag                                                           2470
```

<210> SEQ ID NO 41
<211> LENGTH: 313
<212> TYPE: PRT
<213> ORGANISM: Homo sapiens

<400> SEQUENCE: 41

Met Leu Leu Leu Ala Asp Met Asp Val Val Asn Gln Leu Val Ala Gly

```
1               5                  10                 15
Gly Gln Phe Arg Val Val Lys Glu Pro Leu Gly Phe Val Lys Val Leu
                20                 25                 30

Gln Trp Val Phe Ala Ile Phe Ala Phe Ala Thr Cys Gly Ser Tyr Ser
                35                 40                 45

Gly Glu Leu Gln Leu Ser Val Asp Cys Ala Asn Lys Thr Glu Ser Asp
    50                 55                 60

Leu Ser Ile Glu Val Glu Phe Glu Tyr Pro Phe Arg Leu His Gln Val
65                 70                 75                 80

Tyr Phe Asp Ala Pro Thr Cys Arg Gly Gly Thr Thr Lys Val Phe Leu
                85                 90                 95

Val Gly Asp Tyr Ser Ser Ser Ala Glu Phe Phe Val Thr Val Ala Val
                100                105                110

Phe Ala Phe Leu Tyr Ser Met Gly Ala Leu Ala Thr Tyr Ile Phe Leu
                115                120                125

Gln Asn Lys Tyr Arg Glu Asn Asn Lys Gly Pro Met Leu Asp Phe Leu
    130                135                140

Ala Thr Ala Val Phe Ala Phe Met Trp Leu Val Ser Ser Ser Ala Trp
145                150                155                160

Ala Lys Gly Leu Ser Asp Val Lys Met Ala Thr Asp Pro Glu Asn Ile
                165                170                175

Ile Lys Glu Met Pro Val Cys Arg Gln Thr Gly Asn Thr Cys Lys Glu
                180                185                190

Leu Arg Asp Pro Val Thr Ser Gly Leu Asn Thr Ser Val Val Phe Gly
                195                200                205

Phe Leu Asn Leu Val Leu Trp Val Gly Asn Leu Trp Phe Val Phe Lys
    210                215                220

Glu Thr Gly Trp Ala Ala Pro Phe Leu Arg Ala Pro Pro Gly Ala Pro
225                230                235                240

Glu Lys Gln Pro Ala Pro Gly Asp Ala Tyr Gly Asp Ala Gly Tyr Gly
                245                250                255

Gln Gly Pro Gly Gly Tyr Gly Pro Gln Asp Ser Tyr Gly Pro Gln Gly
                260                265                270

Gly Tyr Gln Pro Asp Tyr Gly Gln Pro Ala Gly Ser Gly Gly Ser Gly
                275                280                285

Tyr Gly Pro Gln Gly Asp Tyr Gly Gln Gln Gly Tyr Gly Pro Gln Gly
                290                295                300

Ala Pro Thr Ser Phe Ser Asn Gln Met
305                 310

<210> SEQ ID NO 42
<211> LENGTH: 2449
<212> TYPE: DNA
<213> ORGANISM: Homo sapiens

<400> SEQUENCE: 42 gcccctgca  ttgctgatgc  tgctgctggc  ggacatggac  gtggtgaatc  agctggtggc     60
tgggggtcag  ttccgggtgg  tcaaggagcc  cctcggcttt  gtgaaggtgc  tgcaatgggt    120
cttcgccatc  ttcgcctttg  ccacatgcgg  cagctacagt  ggggagctcc  agctgagcgt    180
ggattgtgcc  aacaagaccg  agagtgacct  cagcatcgag  gtcgagttcg  agtacccctt    240
caggctgcac  caagtgtact  ttgatgcacc  cacctgccga  gggggcacca  ccaaggtctt    300
cttagttggg  gactactcct  cgtcagccga  attctttgtc  accgtggccg  tgtttgcctt    360
```

```
cctctactcc atggggctc tggccaccta catcttcctg cagaacaagt accgagagaa    420
taacaaaggg cccatgctgg actttctggc cacggctgtg ttcgccttca tgtggctagt    480
tagctcatcg gcatgggcca aggggctgtc agatgtgaag atggccacag acccagagaa    540
cattatcaag gagatgcctg tctgccgcca gacaggaaac acatgcaagg agctgagaga    600
ccctgtgacc tcgggactca cacctcggt ggtgttcggc ttcctgaacc tggtgctctg    660
ggtcggcaac ctgtggttcg tgtttaagga gacaggctgg gccgcccgt tcctgcgcgc    720
gcctcccggc gccccgaga aacaaccggc acccgggac gcctacggcg atgcaggcta    780
cgggcagggc cccggcggt acgggcccca ggattcctac gggcctcagg gcggctacca    840
gcctgactat ggtcaaccag ccggcagcgg tggcagtggc tacgggcctc agggcgacta    900
tgggcagcaa ggctacggcc cgcagggtgc acccacctcc ttctccaatc agatgtagtc    960
tggtcagtga agcccaggag gacctggggg gggcaagagc tcaggagaag gcctgccccc   1020
cttcccaccc ctatacccta ggtctccacc cctcaagcca ggagaccctg tctttgctgt   1080
ttatatat atatattata tataaatatc tatttatctg tctgagccct gccctcactc   1140
cactcccctc atccactagg tgcccagtct tgagtgggcc ccctctctta ccccgtccct   1200
ttccctgcat cccttggccc ctctctgttt accctccctg tccctgagg ttaaggggat   1260
ctaaaaggag gacagggagg gaacagacct cggctgtgtg gggagggtgg gcgtgacttc   1320
agactctctc ctctctctcc ctccactcct cccaactctg gccttggttc ctccagcaat   1380
gcctgcctga acaaaggccg ttagggaaat ccaactccag ggttaaagaa aggcagagat   1440
tgggggggct tggggtagag aggacagttt aggacccaag gtggtcttgg agaggaggtg   1500
tggagtggag gggtcagcag gggggttggg ttccagacag agtggatctg gagtctgaag   1560
gagaggagtg cgctagagca ttctggggtg gggcttggaa gggcgctgag ggcagggttc   1620
tagaagggc gaggctttaa gcgaggcaga atggtgggct ccagagtagg tgggtcttgg   1680
attggtacca gagcctatgg aaagggtgtg gcttggaaca tttgggagac tgagcttgat   1740
tctaaagggg acagatcttg agcaaggcaa gaagtgggat tcaggaatgg gccaagccag   1800
ggttccagac agggtggggc ttagaatggg gcttccatgg tggtttcaga aagggcagcc   1860
cctcccccatg gtgcagtgaa gaaaatgttt tacaatggct gggtttgggc agtggagagg   1920
ggacttggat aggagcttcc agatgggttt tgttaggggt gggggagaat ggctctggct   1980
acgacttggg acggaagtgg cctgagaaga gtcgagtgat atggcttgta gggtgaggcg   2040
tgggatccag agagaagcac cccaccacac acacccttcc ccactcccgt gatgaaacag   2100
ctaggttaat aggaggacag aaccaacggg tctgtgggac tggcccaccc ctcttccccc   2160
ttccctgcg ccctccctcc ctccacacct ccacccgtcc tggggtggtt ggaggcctgg   2220
tctggagccc ctatcctgca ccctctgcta tgtctgtgat gtcagtagtg cctgtgatcg   2280
tgtgttgcca ttttgtctgg ctgtggcccc tccttctccc ctccagaccc ctacccttc   2340
ccaaaccctt cggtattgtt caagaaccc ccctccccaa ggaagaacaa atatgattct   2400
cctctcccaa ataaactcct taaccaccta gtcaaaaaaa aaaaaaaa                2449
```

<210> SEQ ID NO 43
<211> LENGTH: 1192
<212> TYPE: PRT
<213> ORGANISM: Homo sapiens

<400> SEQUENCE: 43

Met Glu Asp Leu Asp Gln Ser Pro Leu Val Ser Ser Asp Ser Pro

-continued

```
1               5                   10                  15
Pro Arg Pro Gln Pro Ala Phe Lys Tyr Gln Phe Val Arg Glu Pro Glu
                20                  25                  30
Asp Glu Glu Glu Glu Glu Glu Glu Glu Asp Glu Asp Glu Asp
        35                  40                  45
Leu Glu Glu Leu Glu Val Leu Glu Arg Lys Pro Ala Ala Gly Leu Ser
        50                  55                  60
Ala Ala Pro Val Pro Thr Ala Pro Ala Gly Ala Pro Leu Met Asp
65                  70                  75                  80
Phe Gly Asn Asp Phe Val Pro Pro Ala Pro Arg Gly Pro Leu Pro Ala
                85                  90                  95
Ala Pro Pro Val Ala Pro Glu Arg Gln Pro Ser Trp Asp Pro Ser Pro
                100                 105                 110
Val Ser Ser Thr Val Pro Ala Pro Ser Pro Leu Ser Ala Ala Ala Val
                115                 120                 125
Ser Pro Ser Lys Leu Pro Glu Asp Asp Glu Pro Pro Ala Arg Pro Pro
        130                 135                 140
Pro Pro Pro Pro Ala Ser Val Ser Pro Gln Ala Glu Pro Val Trp Thr
145                 150                 155                 160
Pro Pro Ala Pro Ala Pro Ala Ala Pro Pro Ser Thr Pro Ala Ala Pro
                165                 170                 175
Lys Arg Arg Gly Ser Ser Gly Ser Val Asp Glu Thr Leu Phe Ala Leu
                180                 185                 190
Pro Ala Ala Ser Glu Pro Val Ile Arg Ser Ser Ala Glu Asn Met Asp
        195                 200                 205
Leu Lys Glu Gln Pro Gly Asn Thr Ile Ser Ala Gly Gln Glu Asp Phe
        210                 215                 220
Pro Ser Val Leu Leu Glu Thr Ala Ala Ser Leu Pro Ser Leu Ser Pro
225                 230                 235                 240
Leu Ser Ala Ala Ser Phe Lys Glu His Glu Tyr Leu Gly Asn Leu Ser
                245                 250                 255
Thr Val Leu Pro Thr Glu Gly Thr Leu Gln Glu Asn Val Ser Glu Ala
                260                 265                 270
Ser Lys Glu Val Ser Glu Lys Ala Lys Thr Leu Leu Ile Asp Arg Asp
        275                 280                 285
Leu Thr Glu Phe Ser Glu Leu Glu Tyr Ser Glu Met Gly Ser Ser Phe
        290                 295                 300
Ser Val Ser Pro Lys Ala Glu Ser Ala Val Ile Val Ala Asn Pro Arg
305                 310                 315                 320
Glu Glu Ile Ile Val Lys Asn Lys Asp Glu Glu Lys Leu Val Ser
                325                 330                 335
Asn Asn Ile Leu His Asn Gln Gln Glu Leu Pro Thr Ala Leu Thr Lys
                340                 345                 350
Leu Val Lys Glu Asp Glu Val Val Ser Ser Glu Lys Ala Lys Asp Ser
        355                 360                 365
Phe Asn Glu Lys Arg Val Ala Val Glu Ala Pro Met Arg Glu Glu Tyr
        370                 375                 380
Ala Asp Phe Lys Pro Phe Glu Arg Val Trp Glu Val Lys Asp Ser Lys
385                 390                 395                 400
Glu Asp Ser Asp Met Leu Ala Ala Gly Gly Lys Ile Glu Ser Asn Leu
                405                 410                 415
Glu Ser Lys Val Asp Lys Lys Cys Phe Ala Asp Ser Leu Glu Gln Thr
                420                 425                 430
```

```
Asn His Glu Lys Asp Ser Glu Ser Ser Asn Asp Asp Thr Ser Phe Pro
            435                 440                 445

Ser Thr Pro Glu Gly Ile Lys Asp Arg Ser Gly Ala Tyr Ile Thr Cys
450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Val Ala
            530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
            610                 615                 620

Pro Ser Ala Gly Ala Ser Val Ile Gln Pro Ser Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
            675                 680                 685

Glu Thr Glu Ala Pro Tyr Ile Ser Ile Ala Cys Asp Leu Ile Lys Glu
            690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
            755                 760                 765

Glu Ser Leu Thr Glu Thr Ser Phe Glu Ser Met Ile Glu Tyr Glu Asn
770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
835                 840                 845
```

Lys Glu Ala Gln Ile Arg Glu Thr Glu Thr Phe Ser Asp Ser Ser Pro
    850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
    930                 935                 940

Thr Ser Lys Val Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

Ser Ala Ile Phe Ser Ala Glu Leu Ser Lys Thr Ser Val Val Asp Leu
        995                 1000                1005

Leu Tyr Trp Arg Asp Ile Lys Lys Thr Gly Val Val Phe Gly Ala
    1010                1015                1020

Ser Leu Phe Leu Leu Leu Ser Leu Thr Val Phe Ser Ile Val Ser
    1025                1030                1035

Val Thr Ala Tyr Ile Ala Leu Ala Leu Leu Ser Val Thr Ile Ser
    1040                1045                1050

Phe Arg Ile Tyr Lys Gly Val Ile Gln Ala Ile Gln Lys Ser Asp
    1055                1060                1065

Glu Gly His Pro Phe Arg Ala Tyr Leu Glu Ser Glu Val Ala Ile
    1070                1075                1080

Ser Glu Glu Leu Val Gln Lys Tyr Ser Asn Ser Ala Leu Gly His
    1085                1090                1095

Val Asn Cys Thr Ile Lys Glu Leu Arg Arg Leu Phe Leu Val Asp
    1100                1105                1110

Asp Leu Val Asp Ser Leu Lys Phe Ala Val Leu Met Trp Val Phe
    1115                1120                1125

Thr Tyr Val Gly Ala Leu Phe Asn Gly Leu Thr Leu Leu Ile Leu
    1130                1135                1140

Ala Leu Ile Ser Leu Phe Ser Val Pro Val Ile Tyr Glu Arg His
    1145                1150                1155

Gln Ala Gln Ile Asp His Tyr Leu Gly Leu Ala Asn Lys Asn Val
    1160                1165                1170

Lys Asp Ala Met Ala Lys Ile Gln Ala Lys Ile Pro Gly Leu Lys
    1175                1180                1185

Arg Lys Ala Glu
    1190

<210> SEQ ID NO 44
<211> LENGTH: 4871
<212> TYPE: DNA
<213> ORGANISM: Homo sapiens

<400> SEQUENCE: 44
agtccctgcc ctccccctggg gagggtgagt cacgccaaac tgggcggaga gtccgctggc    60

```
ctcactccta gctcatctgg gcggcggcgg caagtgggga cagggcgggt ggcgcatcac    120
cggcgcggag gcaggaggag cagtctcatt gttccgggag ccgtcaccac agtaggtccc    180
tcggctcagt cggcccagcc cctctcagtc ctccccaacc cccacaaccg cccgcggctc    240
tgagacgcgg ccccggcggc ggcggcagca gctgcagcat catctccacc ctccagccat    300
ggaagacctg gaccagtctc ctctggtctc gtcctcggac agcccacccc ggccgcagcc    360
cgcgttcaag taccagttcg tgagggagcc cgaggacgag gaggaagaag aggaggagga    420
agaggaggac gaggacgaag acctggagga gctggaggtg ctggagagga gcccgccgc    480
cgggctgtcc gcggcccag tgcccaccgc ccctgccgcc ggcgcgcccc tgatggactt    540
cggaaatgac ttcgtgccgc cggcgcccg gggaccctg ccggccgctc ccccgtcgc    600
cccggagcgg cagccgtctt gggacccgag cccggtgtcg tcgaccgtgc ccgcgccatc    660
cccgctgtct gctgccgcag tctcgccctc caagctccct gaggacgacg agcctccggc    720
ccggcctccc cctcctcccc cggccagcgt gagcccccag gcagagcccg tgtggacccc    780
gccagccccg gctcccgccg cgccccctc caccccggcc gcgcccaagc gcaggggctc    840
ctcgggctca gtggatgaga ccctttttgc tcttcctgct gcatctgagc ctgtgatacg    900
ctcctctgca gaaaatatgg acttgaagga gcagccaggt aacactattt cggctggtca    960
agaggatttc ccatctgtcc tgcttgaaac tgctgcttct cttccttctc tgtctcctct   1020
ctcagccgct tctttcaaag aacatgaata ccttggtaat ttgtcaacag tattacccac   1080
tgaaggaaca cttcaagaaa atgtcagtga agcttctaaa gaggtctcag agaaggcaaa   1140
aactctactc atagatagag atttaacaga gttttcagaa ttagaatact cagaaatggg   1200
atcatcgttc agtgtctctc caaaagcaga atctgccgta atagtagcaa atcctaggga   1260
agaaataatc gtgaaaaata agatgaaga agagaagtta gttagtaata acatccttca   1320
taatcaacaa gagttaccta cagctcttac taaattggtt aaagaggatg aagttgtgtc   1380
ttcagaaaaa gcaaaagaca gttttaatga aagagagtt gcagtggaag ctcctatgag   1440
ggaggaatat gcagacttca accatttga gcgagtatgg gaagtgaaag atagtaagga   1500
agatagtgat atgttggctg ctggaggtaa aatcgagagc aacttggaaa gtaaagtgga   1560
taaaaatgt tttgcagata gccttgagca aactaatcac gaaaaagata gtgagagtag   1620
taatgatgat acttctttcc ccagtacgcc agaaggtata aaggatcgtt caggagcata   1680
tatcacatgt gctcccttta acccagcagc aactgagagc attgcaacaa acatttttcc   1740
tttgttagga gatcctactt cagaaaataa gaccgatgaa aaaaaatag aagaaaagaa   1800
ggcccaaata gtaacagaga gaatactag caccaaaaca tcaaaccctt ttcttgtagc   1860
agcacaggat tctgagacag attatgtcac aacagataat ttaacaaagg tgactgagga   1920
agtcgtggca acatgcctg aaggcctgac tccagattta gtacaggaag catgtgaaag   1980
tgaattgaat gaagttactg gtacaaagat tgcttatgaa acaaaaatgg acttggttca   2040
aacatcagaa gttatgcaag agtcactcta tcctgcagca cagctttgcc catcatttga   2100
agagtcagaa gctactccctt caccagtttt gcctgacatt gttatggaag caccattgaa   2160
ttctgcagtt cctagtgctg gtgcttccgt gatacagccc agctcatcac cattagaagc   2220
ttcttcagtt aattatgaaa gcataaaaca tgagcctgaa accccccac catatgaaga   2280
ggccatgagt gtatcactaa aaaagtatc aggaataaag gaagaaatta aagagcctga   2340
aaatattaat gcagctcttc aagaaacaga agctccttat atatctattg catgtgattt   2400
aattaaagaa acaaagcttt ctgctgaacc agctccggat ttctctgatt attcagaaat   2460
```

```
ggcaaaagtt gaacagccag tgcctgatca ttctgagcta gttgaagatt cctcacctga   2520
ttctgaacca gttgacttat ttagtgatga ttcaatacct gacgttccac aaaaacaaga   2580
tgaaactgtg atgcttgtga aagaaagtct cactgagact tcatttgagt caatgataga   2640
atatgaaaat aaggaaaaac tcagtgcttt gccacctgag ggaggaaagc catatttgga   2700
atcttttaag ctcagtttag ataacacaaa agatacactg ttacctgatg aagtttcaac   2760
attgagcaaa aaggagaaaa ttcctttgca gatggaggag ctcagtactg cagtttattc   2820
aaatgatgac ttatttattt ctaaggaagc acagataaga gaaactgaaa cgttttcaga   2880
ttcatctcca attgaaatta tagatgagtt ccctacattg atcagttcta aaactgattc   2940
attttctaaa ttagccaggg aatatactga cctagaagta tcccacaaaa gtgaaattgc   3000
taatgccccg gatggagctg ggtcattgcc ttgcacagaa ttgccccatg acctttcttt   3060
gaagaacata caacccaaag ttgaagagaa aatcagtttc tcagatgact tttctaaaaa   3120
tgggtctgct acatcaaagg tgctcttatt gcctccagat gtttctgctt tggccactca   3180
agcagagata gagagcatag ttaaacccaa agttcttgtg aaagaagctg agaaaaaact   3240
tccttccgat acagaaaaag aggacagatc accatctgct atattttcag cagagctgag   3300
taaaacttca gttgttgacc tcctgtactg gagagacatt aagaagactg gagtggtgtt   3360
tggtgccagc ctattcctgc tgctttcatt gacagtattc agcattgtga gcgtaacagc   3420
ctacattgcc ttggccctgc tctctgtgac catcagcttt aggatataca agggtgtgat   3480
ccaagctatc cagaaatcag atgaaggcca cccattcagg gcatatctgg aatctgaagt   3540
tgctatatct gaggagttgg ttcagaagta cagtaattct gctcttggtc atgtgaactg   3600
cacgataaag gaactcaggc gcctcttctt agttgatgat ttagttgatt ctctgaagtt   3660
tgcagtgttg atgtgggtat ttacctatgt tggtgccttg tttaatggtc tgacactact   3720
gattttggct ctcatttcac tcttcagtgt tcctgttatt tatgaacggc atcaggcaca   3780
gatagatcat tatctaggac ttgcaaataa gaatgttaaa gatgctatgg ctaaaatcca   3840
agcaaaaatc cctggattga agcgcaaagc tgaatgaaaa cgcccaaaat aattagtagg   3900
agttcatctt taaaggggat attcatttga ttatacgggg gagggtcagg gaagaacgaa   3960
ccttgacgtt gcagtgcagt ttcacagatc gttgttagat cttttatttt agccatgcac   4020
tgttgtgagg aaaaattacc tgtcttgact gccatgtgtt catcatctta agtattgtaa   4080
gctgctatgt atggatttaa accgtaatca tatcttttc ctatctatct gaggcactgg   4140
tggaataaaa aacctgtata ttttactttg ttgcagatag tcttgccgca tcttggcaag   4200
ttgcagagat ggtggagcta gaaaaaaaaa aaaaaagcc ctttcagtt tgtgcactgt   4260 gtatggtccg tgtagattga tgcagatttt ctgaaatgaa atgtttgttt agacgagatc   4320
ataccggtaa agcaggaatg acaaagcttg cttttctggt atgttctagg tgtattgtga   4380
cttttactgt tatattaatt gccaatataa gtaaatatag attatatatg tatagtgttt   4440
cacaaagctt agacctttac cttccagcca ccccacagtg cttgatattt cagagtcagt   4500
cattggttat acatgtgtag ttccaaagca cataagctag aagaagaaat atttctagga   4560
gcactaccat ctgttttcaa catgaaatgc cacacacata gaactccaac atcaatttca   4620
ttgcacagac tgactgtagt aattttgtc acagaatcta tggactgaat ctaatgcttc   4680
caaaaatgtt gtttgtttgc aaatatcaaa cattgttatg caagaaatta ttaattacaa   4740
aatgaagatt tataccattg tggtttaagc tgtactgaac taaatctgtg gaatgcattg   4800
```

```
tgaactgtaa aagcaaagta tcaataaagc ttatagactt aaaaaaaaaa aaaaaaaaa      4860 aaaaaaaaaa a                                                           4871

<210> SEQ ID NO 45
<211> LENGTH: 432
<212> TYPE: PRT
<213> ORGANISM: Homo sapiens

<400> SEQUENCE: 45

Met Glu Arg Arg Arg Ile Thr Ser Ala Ala Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Leu Pro Thr
            35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
            195                 200                 205

Arg Glu Leu Gln Glu Gln Leu Ala Arg Gln Gln Val His Val Glu Leu
210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
            275                 280                 285

Leu Gln Ser Leu Thr Cys Asp Leu Glu Ser Leu Arg Gly Thr Asn Glu
290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
```

|  |  | 355 |  |  |  | 360 |  |  |  | 365 |  |
| --- | --- | --- | --- | --- | --- | --- | --- | --- | --- | --- | --- |

Leu Leu Glu Gly Glu Glu Asn Arg Ile Thr Ile Pro Val Gln Thr Phe
370            375              380

Ser Asn Leu Gln Ile Arg Glu Thr Ser Leu Asp Thr Lys Ser Val Ser
385                390              395                  400

Glu Gly His Leu Lys Arg Asn Ile Val Val Lys Thr Val Glu Met Arg
            405              410                  415

Asp Gly Glu Val Ile Lys Glu Ser Lys Gln Glu His Lys Asp Val Met
            420              425              430

<210> SEQ ID NO 46
<211> LENGTH: 3097
<212> TYPE: DNA
<213> ORGANISM: Homo sapiens

<400> SEQUENCE: 46

| | | | | | |
|---|---|---|---|---|---|
| atcgccagtc | tagcccactc | cttcataaag | ccctcgcatc | ccaggagcga | gcagagccag | 60 |
| agcaggatgg | agaggagacg | catcacctcc | gctgctcgcc | gctcctacgt | ctcctcaggg | 120 |
| gagatgatgg | tgggggggcct | ggctcctggc | cgccgtctgg | gtcctggcac | ccgcctctcc | 180 |
| ctggctcgaa | tgccccctcc | actcccgacc | cgggtggatt | tctccctggc | tggggcactc | 240 |
| aatgctggct | tcaaggagac | ccgggccagt | gagcgggcag | agatgatgga | gctcaatgac | 300 |
| cgcttttgcca | gctacatcga | gaaggttcgc | ttcctggaac | agcaaaacaa | ggcgctggct | 360 |
| gctgagctga | accagctgcg | ggccaaggag | cccaccaagc | tggcagacgt | ctaccaggct | 420 |
| gagctgcgag | agctgcggct | gcggctcgat | caactcaccg | ccaacagcgc | ccggctggag | 480 |
| gttgagaggg | acaatctggc | acaggacctg | gccactgtga | ggcagaagct | ccaggatgaa | 540 |
| accaacctga | ggctggaagc | cgagaacaac | ctggctgcct | atagacagga | agcagatgaa | 600 |
| gccaccctgg | cccgtctgga | tctggagagg | aagattgagt | cgctggagga | ggagatccgg | 660 |
| ttcttgagga | agatccacga | ggaggaggtt | cgggaactcc | aggagcagct | ggcccgacag | 720 |
| caggtccatg | tggagcttga | cgtggccaag | ccagacctca | ccgcagccct | gaaagagatc | 780 |
| cgcacgcagt | atgaggcaat | ggcgtccagc | aacatgcatg | aagccgaaga | gtggtaccgc | 840 |
| tccaagtttg | cagacctgac | agacgctgct | gcccgcaacg | cggagctgct | ccgccaggcc | 900 |
| aagcacgaag | ccaacgacta | ccggcgccag | ttgcagtcct | tgacctgcga | cctggagtct | 960 |
| ctgcgcggca | cgaacgagtc | cctggagagg | cagatgcgcg | agcaggagga | gcggcacgtg | 1020 |
| cgggaggcgg | ccagttatca | ggaggcgctg | gcgcggctgg | aggaagaggg | gcagagcctc | 1080 |
| aaggacgaga | tggcccgcca | cttgcaggag | taccaggacc | tgctcaatgt | caagctggcc | 1140 |
| ctggacatcg | agatcgccac | ctacaggaag | ctgctagagg | gcgaggagaa | ccggatcacc | 1200 |
| attcccgtgc | agaccttctc | caacctgcag | attcgagaaa | ccagcctgga | caccaagtct | 1260 |
| gtgtcagaag | gccacctcaa | gaggaacatc | gtggtgaaga | ccgtggagat | gcgggatgga | 1320 |
| gaggtcatta | aggagtccaa | gcaggagcac | aaggatgtga | tgtgaggcag | gacccacctg | 1380 |
| gtggcctctg | ccccgtctca | tgaggggccc | gagcagaagc | aggatagttg | ctccgcctct | 1440 |
| gctggcacat | ttccccagac | ctgagctccc | caccaccccca | gctgctcccc | tccctcctct | 1500 |
| gtccctaggt | cagcttgctg | ccctaggctc | cgtcagtatc | aggcctgcca | gacggcaccc | 1560 |
| acccagcacc | cagcaactcc | aactaacaag | aaactcaccc | ccaaggggca | gtctggaggg | 1620 |
| gcatggccag | cagcttgcgt | tagaatgagg | aggaaggaga | gaaggggagg | agggcgggg | 1680 |
| gcacctacta | catcgccctc | cacatccctg | attcctgttg | ttatggaaac | tgttgccaga | 1740 |

```
gatggaggtt ctctcggagt atctgggaac tgtgcctttg agtttcctca ggctgctgga    1800
ggaaaactga gactcagaca ggaaagggaa ggccccacag acaaggtagc cctggccaga    1860
ggcttgtttt gtcttttggt ttttatgagg tgggatatcc ctatgctgcc taggctgacc    1920
ttgaactcct gggctcaagc agtctaccca cctcagcctc ctgtgtagct gggattatag    1980
attggagcca ccatgcccag ctcagagggt tgttctccta gactgaccct gatcagtcta    2040
agatgggtgg ggacgtcctg ccacctgggg cagtcacctg cccagatccc agaaggacct    2100
cctgagcgat gactcaagtg tctcagtcca cctgagctgc atccaggga tgccatctgt     2160 gggcacgctg tgggcaggtg ggagcttgat tctcagcact tgggggatct gttgtgtacg    2220
tggagaggga tgaggtgctg ggagggatag agggggggctg cctggccccc agctgtgggt   2280
acagagaggt caagcccagg aggactgccc cgtgcagact ggaggggacg ctggtagaga    2340
tggaggagga ggcaattggg atggcgctag gcatacaagt aggggttgtg ggtgaccagt    2400
tgcacttggc ctctggattg tgggaattaa ggaagtgact catcctcttg aagatgctga    2460
aacaggagag aaaggggatg tatccatggg ggcagggcat gactttgtcc catttctaaa    2520
ggcctcttcc ttgctgtgtc ataccaggcc gccccagcct ctgagcccct gggactgctg    2580
cttcttaacc ccagtaagcc actgccacac gtctgaccct ctccacccca tagtgaccgg    2640
ctgcttttcc ctaagccaag ggcctcttgc ggtcccttct tactcacaca caaaatgtac    2700
ccagtattct aggtagtgcc ctattttaca attgtaaaac tgaggcacga gcaaagtgaa    2760
gacactggct catattcctg cagcctggag gccgggtgct cagggctgac acgtccaccc    2820
cagtgcaccc actctgcttt gactgagcag actggtgagc agactggtgg gatctgtgcc    2880
cagagatggg actgggaggg cccacttcag ggttctcctc tcccctctaa ggccgaagaa    2940
gggtccttcc ctctccccaa gacttggtgt cctttccctc cactccttcc tgccacctgc    3000
tgctgctgct gctgctaatc ttcagggcac tgctgctgcc tttagtcgct gaggaaaaat    3060
aaagacaaat gctgcgccct tccccaaaaa aaaaaaa                             3097
```

<210> SEQ ID NO 47
<211> LENGTH: 92
<212> TYPE: PRT
<213> ORGANISM: Homo sapiens

<400> SEQUENCE: 47

```
Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90
```

<210> SEQ ID NO 48
<211> LENGTH: 1135
<212> TYPE: DNA
<213> ORGANISM: Homo sapiens

<400> SEQUENCE: 48

```
gggcagaggg aataagaggc tgcctctgcc caccagtcct gccgcccagg acccgcagca    60
gagacgacgc ctgcagcaag gagaccagga aggggtgaga caaggaagag gatgtctgag   120
ctggagaagg ccatggtggc cctcatcgac gttttccacc aatattctgg aagggaggga   180
gacaagcaca agctgaagaa atccgaactg aaggagctca tcaacaatga gctttcccat   240
ttcttagagg aaatcaaaga gcaggaggtt gtggacaaag tcatggaaac actggacaat   300
gatggagacg gcgaatgtga cttccaggaa ttcatggcct ttgttgccat ggttactact   360
gcctgccacg agttctttga acatgagtga gattagaaag cagccaaacc tttcctgtaa   420
cagagacggt catgcaagaa agcagacagc aagggcttgc agcctagtag gagctgagct   480
ttccagccgt gttgtagcta attaggaagc ttgatttgct ttgtgattga aaaattgaaa   540
acctctttcc aaaggctgtt ttaacggcct gcatcattct ttctgctata ttaggcctgt   600
gtgtaagctg actggcccca gggactcttg ttaacagtaa cttaggagtc aggtctcagt   660
gataaagcgt gcaccgtgca gcccgccatg gccgtgtaga ccctaacccg gagggaaccc   720
tgactacaga aattaccccg gggcacccct aaaacttcca ctacctttaa aaaacaaagc   780
cttatccagc attatttgaa aacactgctg ttcttttaaat gcgttcctca tccatgcaga   840
taacagctgg ttggccggtg tggccctgca agggcgtggt ggcttcggcc tgcttcccgg   900
gatgcgcctg atcaccaggt gaacgctcag cgctggcagc gctcctggaa aaagcaactc   960
catcagaact cgcaatccga gccagctctg ggggctccag cgtggcctcc gtgacccatg  1020
cgattcaagt cgcggctgca ggatcccttgc ctccaacgtg cctccagcac atgcggcttc  1080
cgagggcact accgggggct ctgagccacc gcgagggcct gcgttcaata aaaag        1135
```

<210> SEQ ID NO 49
<211> LENGTH: 422
<212> TYPE: PRT
<213> ORGANISM: Homo sapiens

<400> SEQUENCE: 49

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
```

```
                    165                 170                 175
Cys Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Gln Ile Glu Ala
    210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
        275                 280                 285

Ser Ser Phe Ser Thr Ser Val Tyr Gln Pro Ile Pro Gln Pro Thr Thr
    290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
                420

<210> SEQ ID NO 50
<211> LENGTH: 1399
<212> TYPE: DNA
<213> ORGANISM: Homo sapiens

<400> SEQUENCE: 50 aggggggaaga ctttaactag gggcgcgcag atgtgtgagg ccttttattg tgagagtgga      60
cagacatccg agatttcaga gccccatatt cgagccccgt ggaatcccgc ggcccccagc     120
cagagccagc atgcagaaca gtcacagcgg agtgaatcag ctcggtggtg tctttgtcaa     180
cgggcggcca ctgccggact ccacccggca gaagattgta gagctagctc acagcggggc     240
ccggccgtgc gacatttccc gaattctgca ggtgtccaac ggatgtgtga gtaaaattct     300
gggcaggtat tacgagactg gctccatcag acccagggca atcggtggta gtaaaccgag     360
agtagcgact ccagaagttg taagcaaaat agcccagtat aagcgggagt gcccgtccat     420
ctttgcttgg gaaatccgag acagattact gtccgagggg gtctgtacca acgataacat     480
accaagcgtg tcatcaataa acagagttct tcgcaacctg gctagcgaaa agcaacagat     540
gggcgcagac ggcatgtatg ataaactaag gatgttgaac gggcagaccg gaagctgggg     600 caccccgccct ggttggtatc cggggacttc ggtgccaggg caacctacgc aagatggctg     660
```

```
ccagcaacag gaaggagggg gagagaatac caactccatc agttccaacg gagaagattc    720
agatgaggct caaatgcgac ttcagctgaa gcggaagctg caaagaaata gaacatcctt    780
tacccaagag caaattgagg ccctggagaa agagtttgag agaacccatt atccagatgt    840
gtttgcccga gaaagactag cagccaaaat agatctacct gaagcaagaa tacaggtatg    900
gttttctaat cgaagggcca atggagaag agaagaaaaa ctgaggaatc agagaagaca    960
ggccagcaac acacctagtc atattcctat cagcagtagt ttcagcacca gtgtctacca   1020
accaattcca caacccacca caccggtttc ctccttcaca tctggctcca tgttgggccg   1080
aacagacaca gccctcacaa acacctacag cgctctgccg cctatgccca gcttcaccat   1140
ggcaaataac ctgcctatgc aaccccagt ccccagccag acctcctcat actcctgcat    1200
gctgcccacc agcccttcgg tgaatgggcg gagttatgat acctacaccc cccacatat   1260 gcagacacac atgaacagtc agccaatggg cacctcgggc accacttcaa caggactcat   1320
ttcccctggt gtgtcagttc cagttcaagt tcccggaagt gaacctgata tgtctcaata   1380
ctggccaaga ttacagtaa                                                1399
```

```
<210> SEQ ID NO 51
<211> LENGTH: 1621
<212> TYPE: PRT
<213> ORGANISM: Homo sapiens

<400> SEQUENCE: 51
```

| | | | | | | | | | | | | | | |
|---|---|---|---|---|---|---|---|---|---|---|---|---|---|---|
Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
            20                  25                  30

Asn Glu Leu Leu Ser Ala Glu Leu Gly Gly Leu Arg Ala Gln Ser Ala
        35                  40                  45

Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Glu Leu Glu Gly Val Ala Gly Arg Cys Gln
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Val Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Ala Pro Glu Val Glu
                165                 170                 175

Glu Leu Ala Arg Arg Leu Gly Glu Ala Trp Arg Gly Ala Val Arg Gly
            180                 185                 190

Tyr Gln Glu Arg Val Ala His Met Glu Thr Ser Leu Gly Gln Ala Arg
        195                 200                 205

Glu Arg Leu Gly Arg Ala Val Gln Gly Ala Arg Glu Gly Arg Leu Glu
    210                 215                 220

Leu Gln Gln Leu Gln Ala Glu Arg Gly Gly Leu Leu Glu Arg Arg Ala
225                 230                 235                 240

-continued

```
Ala Leu Glu Gln Arg Leu Gly Arg Trp Gln Arg Leu Arg Ala
                245                 250                 255
Thr Glu Lys Phe Gln Leu Ala Val Glu Ala Leu Glu Gln Lys Gln
            260                 265                 270
Gly Leu Gln Ser Gln Ile Ala Gln Val Leu Glu Gly Arg Gln Gln Leu
            275                 280                 285
Ala His Leu Lys Met Ser Leu Ser Leu Glu Val Ala Thr Tyr Arg Thr
    290                 295                 300
Leu Leu Glu Ala Glu Asn Ser Arg Leu Gln Thr Pro Gly Gly Ser
305                 310                 315                 320
Lys Thr Ser Leu Ser Phe Gln Asp Pro Lys Leu Glu Leu Gln Phe Pro
                325                 330                 335
Arg Thr Pro Glu Gly Arg Arg Leu Gly Ser Leu Leu Pro Val Leu Ser
                340                 345                 350
Pro Thr Ser Leu Pro Ser Pro Leu Pro Ala Thr Leu Glu Thr Pro Val
            355                 360                 365
Pro Ala Phe Leu Lys Asn Gln Glu Phe Leu Gln Ala Arg Thr Pro Thr
    370                 375                 380
Leu Ala Ser Thr Pro Ile Pro Pro Thr Pro Gln Ala Pro Ser Pro Ala
385                 390                 395                 400
Val Asp Ala Glu Ile Arg Ala Gln Asp Ala Pro Leu Ser Leu Leu Gln
                405                 410                 415
Thr Gln Gly Gly Arg Lys Gln Ala Pro Glu Pro Leu Arg Ala Glu Ala
            420                 425                 430
Arg Val Ala Ile Pro Ala Ser Val Leu Pro Gly Pro Glu Glu Pro Gly
        435                 440                 445
Gly Gln Arg Gln Glu Ala Ser Thr Gly Gln Ser Pro Glu Asp His Ala
    450                 455                 460
Ser Leu Ala Pro Pro Leu Ser Pro Asp His Ser Ser Leu Glu Ala Lys
465                 470                 475                 480
Asp Gly Glu Ser Gly Gly Ser Arg Val Phe Ser Ile Cys Arg Gly Glu
                485                 490                 495
Gly Glu Gly Gln Ile Trp Gly Leu Val Glu Lys Glu Thr Ala Ile Glu
            500                 505                 510
Gly Lys Val Val Ser Ser Leu Gln Gln Glu Ile Trp Glu Glu Glu Asp
            515                 520                 525
Leu Asn Arg Lys Glu Ile Gln Asp Ser Gln Val Pro Leu Glu Lys Glu
    530                 535                 540
Thr Leu Lys Ser Leu Gly Glu Glu Ile Gln Glu Ser Leu Lys Thr Leu
545                 550                 555                 560
Glu Asn Gln Ser His Glu Thr Leu Glu Arg Glu Asn Gln Glu Cys Pro
                565                 570                 575
Arg Ser Leu Glu Glu Asp Leu Glu Thr Leu Lys Ser Leu Glu Lys Glu
            580                 585                 590
Asn Lys Glu Leu Leu Lys Asp Val Glu Val Val Arg Pro Leu Glu Lys
            595                 600                 605
Glu Ala Val Gly Gln Leu Lys Pro Thr Gly Lys Glu Asp Thr Gln Thr
    610                 615                 620
Leu Gln Ser Leu Gln Lys Glu Asn Gln Glu Leu Met Lys Ser Leu Glu
625                 630                 635                 640
Gly Asn Leu Glu Thr Phe Leu Phe Pro Gly Thr Glu Asn Gln Glu Leu
                645                 650                 655
```

```
Val Ser Ser Leu Gln Glu Asn Leu Glu Ser Leu Thr Ala Leu Glu Lys
            660                 665                 670

Glu Asn Gln Glu Pro Leu Arg Ser Pro Glu Val Gly Asp Glu Glu Ala
            675                 680                 685

Leu Arg Pro Leu Thr Lys Glu Asn Gln Glu Pro Leu Arg Ser Leu Glu
        690                 695                 700

Asp Glu Asn Lys Glu Ala Phe Arg Ser Leu Glu Lys Glu Asn Gln Glu
705                 710                 715                 720

Pro Leu Lys Thr Leu Glu Glu Glu Asp Gln Ser Ile Val Arg Pro Leu
                725                 730                 735

Glu Thr Glu Asn His Lys Ser Leu Arg Ser Leu Glu Glu Gln Asp Gln
            740                 745                 750

Glu Thr Leu Arg Thr Leu Glu Lys Glu Thr Gln Gln Arg Arg Arg Ser
            755                 760                 765

Leu Gly Glu Gln Asp Gln Met Thr Leu Arg Pro Pro Glu Lys Val Asp
        770                 775                 780

Leu Glu Pro Leu Lys Ser Leu Asp Gln Glu Ile Ala Arg Pro Leu Glu
785                 790                 795                 800

Asn Glu Asn Gln Glu Phe Leu Lys Ser Leu Lys Glu Glu Ser Val Glu
                805                 810                 815

Ala Val Lys Ser Leu Glu Thr Glu Ile Leu Glu Ser Leu Lys Ser Ala
            820                 825                 830

Gly Gln Glu Asn Leu Glu Thr Leu Lys Ser Pro Glu Thr Gln Ala Pro
            835                 840                 845

Leu Trp Thr Pro Glu Glu Ile Asn Gln Gly Ala Met Asn Pro Leu Glu
        850                 855                 860

Lys Glu Ile Gln Glu Pro Leu Glu Ser Val Glu Val Asn Gln Glu Thr
865                 870                 875                 880

Phe Arg Leu Leu Glu Glu Asn Gln Glu Ser Leu Arg Ser Leu Gly
                885                 890                 895

Ala Trp Asn Leu Glu Asn Leu Arg Ser Pro Glu Glu Val Asp Lys Glu
        900                 905                 910

Ser Gln Arg Asn Leu Glu Glu Glu Asn Leu Gly Lys Gly Glu Tyr
            915                 920                 925

Gln Glu Ser Leu Arg Ser Leu Glu Glu Glu Gly Gln Glu Leu Pro Gln
        930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Glu Asp
                965                 970                 975

Glu Ala Glu Leu Asn Leu Arg Glu Gln Asp Gly Phe Thr Gly Lys Glu
            980                 985                 990

Glu Val Val Glu Gln Gly Glu Leu Asn Ala Thr Glu Glu Val Trp Ile
        995                 1000                1005

Pro Gly Glu Gly His Pro Glu Ser Pro Glu Pro Lys Glu Gln Arg
    1010                1015                1020

Gly Leu Val Glu Gly Ala Ser Val Lys Gly Gly Ala Glu Gly Leu
    1025                1030                1035

Gln Asp Pro Glu Gly Gln Ser Gln Gln Val Gly Ala Pro Gly Leu
    1040                1045                1050

Gln Ala Pro Gln Gly Leu Pro Glu Ala Ile Glu Pro Leu Val Glu
    1055                1060                1065

Asp Asp Val Ala Pro Gly Gly Asp Gln Ala Ser Pro Glu Val Met
```

```
                    1070                1075                1080
Leu Gly Ser Glu Pro Ala Met Gly Glu Ser Ala Ala Gly Ala Glu
            1085                1090                1095
Pro Gly Pro Gly Gln Gly Val Gly Gly Leu Gly Asp Pro Gly His
            1100                1105                1110
Leu Thr Arg Glu Glu Val Met Glu Pro Pro Leu Glu Glu Glu Ser
            1115                1120                1125
Leu Glu Ala Lys Arg Val Gln Gly Leu Glu Gly Pro Arg Lys Asp
            1130                1135                1140
Leu Glu Glu Ala Gly Gly Leu Gly Thr Glu Phe Ser Glu Leu Pro
            1145                1150                1155
Gly Lys Ser Arg Asp Pro Trp Glu Pro Pro Arg Glu Gly Arg Glu
            1160                1165                1170
Glu Ser Glu Ala Glu Ala Pro Arg Gly Ala Glu Glu Ala Phe Pro
            1175                1180                1185
Ala Glu Thr Leu Gly His Thr Gly Ser Asp Ala Pro Ser Pro Trp
            1190                1195                1200
Pro Leu Gly Ser Glu Glu Ala Glu Glu Asp Val Pro Pro Val Leu
            1205                1210                1215
Val Ser Pro Ser Pro Thr Tyr Thr Pro Ile Leu Glu Asp Ala Pro
            1220                1225                1230
Gly Pro Gln Pro Gln Ala Glu Gly Ser Gln Glu Ala Ser Trp Gly
            1235                1240                1245
Val Gln Gly Arg Ala Glu Ala Leu Gly Lys Val Glu Ser Glu Gln
            1250                1255                1260
Glu Glu Leu Gly Ser Gly Glu Ile Pro Glu Gly Pro Gln Glu Glu
            1265                1270                1275
Gly Glu Glu Ser Arg Glu Glu Ser Glu Glu Asp Glu Leu Gly Glu
            1280                1285                1290
Thr Leu Pro Asp Ser Thr Pro Leu Gly Phe Tyr Leu Arg Ser Pro
            1295                1300                1305
Thr Ser Pro Arg Trp Asp Pro Thr Gly Glu Gln Arg Pro Pro Pro
            1310                1315                1320
Gln Gly Glu Thr Gly Lys Glu Gly Trp Asp Pro Ala Val Leu Ala
            1325                1330                1335
Ser Glu Gly Leu Glu Ala Pro Pro Ser Glu Lys Glu Glu Gly Glu
            1340                1345                1350
Glu Gly Glu Glu Glu Cys Gly Arg Asp Ser Asp Leu Ser Glu Glu
            1355                1360                1365
Phe Glu Asp Leu Gly Thr Glu Ala Pro Phe Leu Pro Gly Val Pro
            1370                1375                1380
Gly Glu Val Ala Glu Pro Leu Gly Gln Val Pro Gln Leu Leu Leu
            1385                1390                1395
Asp Pro Ala Ala Trp Asp Arg Asp Gly Glu Ser Asp Gly Phe Ala
            1400                1405                1410
Asp Glu Glu Glu Ser Gly Glu Glu Gly Glu Glu Asp Gln Glu Glu
            1415                1420                1425
Gly Arg Glu Pro Gly Ala Gly Arg Trp Gly Pro Gly Ser Ser Val
            1430                1435                1440
Gly Ser Leu Gln Ala Leu Ser Ser Gln Arg Gly Glu Phe Leu
            1445                1450                1455
Glu Ser Asp Ser Val Ser Val Ser Val Pro Trp Asp Asp Ser Leu
            1460                1465                1470
```

```
Arg Gly Ala Val Ala Gly Ala Pro Lys Thr Ala Leu Glu Thr Glu
1475                1480                1485

Ser Gln Asp Ser Ala Glu Pro Ser Gly Ser Glu Glu Ser Asp
    1490                1495                1500

Pro Val Ser Leu Glu Arg Glu Asp Lys Val Pro Gly Pro Leu Glu
1505                1510                1515

Ile Pro Ser Gly Met Glu Asp Ala Gly Pro Gly Ala Asp Ile Ile
1520                1525                1530

Gly Val Asn Gly Gln Gly Pro Asn Leu Glu Gly Lys Ser Gln His
1535                1540                1545

Val Asn Gly Gly Val Met Asn Gly Leu Glu Gln Ser Glu Glu Val
1550                1555                1560

Gly Gln Gly Met Pro Leu Val Ser Glu Gly Asp Arg Gly Ser Pro
1565                1570                1575

Phe Gln Glu Glu Glu Gly Ser Ala Leu Lys Thr Ser Trp Ala Gly
1580                1585                1590

Ala Pro Val His Leu Gly Gln Gly Gln Phe Leu Lys Phe Thr Gln
1595                1600                1605

Arg Glu Gly Asp Arg Glu Ser Trp Ser Ser Gly Glu Asp
1610                1615                1620

<210> SEQ ID NO 52
<211> LENGTH: 5591
<212> TYPE: DNA
<213> ORGANISM: Homo sapiens

<400> SEQUENCE: 52
gctactccca ccccgccccg ccccgtcatt gtccccgtcg gtctcttttc tcttccgtcc      60
taaaagctct gcgagccgct cccttctccc ggtgccccgc gtctgtccat cctcagtggg     120
tcagacgagc aggatggagg gctgcatggg ggaggagtcg tttcagatgt gggagctcaa     180
tcggcgcctg gaggcctacc tggcccgggt caaggcgctg gaggagcaga atgagctgct     240
cagcgcggag ctcggggggc tccgggcaca atccgcggac acctcctggc gggcgcatgc     300
cgacgacgag ctggcggccc tgcgggccct cgttgaccaa cgctggcggg agaagcacgc     360
ggccgaggtg gcgcgcgaca acctggctga agagctggag ggcgtggcag gccgatgcca     420
gcagctgcgg ctggcccggg agcggacgac ggaggaggta gcccgcaacc ggcgcgccgt     480
cgaggcagag aaatgcgccc gggcctggct gagtagccag gtggcagagc tggagcgcga     540
gctagaggct ctacgcgtgg cgcacgagga ggagcgcgtc ggcctgaacg cgcaggctgc     600
ctgtgccccc cgctgccccg cgccgccccg cgggcctccc gcgccggccc cggaggtaga     660
ggagctggca aggcgactgg gcgaggcgtg cgcgggggca gtgcgcggct accaggagcg     720
cgtggcacac atggagacgt cgctgggcca ggcccgcgag cggctgggcc gggcggtgca     780
gggtgcccgc gagggccgcc tggagctgca gcagctccag gctgagcgcg aggcctcct     840 ggagcgcagg gcagcgttgg aacagaggtt ggagggccgc tggcaggagc ggctgcgggc     900
tactgaaaag ttccagctgg ctgtggaggc cctggagcag gagaaacagg gcctacagag     960
ccagatcgct caggtcctgg aaggtcggca gcagctggcg cacctcaaga tgtccctcag    1020
cctggaggtg gccacgtaca ggaccctcct ggaggctgag aactcccggc tgcaaacacc    1080
tggcggtggc tccaagactt ccctcagctt tcaggacccc aagctggagc tgcaattccc    1140
taggacccca gagggccggc gtcttggatc tttgctccca gtcctgagcc caacttccct    1200
```

```
cccctcaccc ttgcctgcta cccttgagac acctgtgcca gcctttctta agaaccaaga    1260
attcctccag gcccgtaccc ctaccttggc cagcaccccc atccccccca cacctcaggc    1320
accctctcct gctgtagatg cagagatcag agcccaggat gctcctctct ctctgctcca    1380
gacacagggt gggaggaaac aggctccaga gcccctgcgg gctgaagcca gggtggccat    1440
tcctgccagc gtcctgcctg gaccagagga gcctggggc cagcggcaag aggccagtac    1500
aggccagtcc ccagaggacc atgcctcctt ggcaccaccc ctcagccctg accactccag    1560
tttagaggct aaggatggag aatccggtgg gtctagagtg ttcagcatat gccgagggga    1620
aggtgaaggg caaatctggg ggttggtaga gaaagaaaca gccatagagg gcaaagtggt    1680
aagcagcttg cagcaggaaa tatgggaaga agaggatcta aacaggaagg aaatccagga    1740
ctcccaggtt cctttggaaa aagaaaccct gaagtctctg ggagaggaga ttcaagagtc    1800
actgaagact ctggaaaacc agagccatga gacactagaa agggagaatc aagaatgtcc    1860
gaggtcttta agaagact tagaaacact aaaaagtcta gaaaaggaaa ataaagagct    1920
attaaaggat gtggaggtag tgagacctct agaaaaagag gctgtaggcc aacttaagcc    1980
tacaggaaaa gaggacacac agacattgca atccctgcaa aaggagaatc aagaactaat    2040
gaaatctctt gaaggtaatc tagagacatt tttatttcca ggaacggaaa atcaagaatt    2100
agtaagttct ctgcaagaga acttagagtc attgacagct ctggaaaagg agaatcaaga    2160
gccactgaga tctccagaag tagggggatga ggaggcactg agacctctga caaaggagaa    2220
tcaggaaccc ctgaggtctc ttgaagatga gaacaaagag gcctttagat ctctagaaaa    2280
agagaaccag gagccactga agactctaga agaagaggac cagagtattg tgagacctct    2340
agaaacagag aatcacaaat cactgaggtc tttagaagaa caggaccaag agacattgag    2400
aactcttgaa aaagagactc aacagcgacg gaggtctcta ggggaacagg atcagatgac    2460
attaagaccc ccagaaaaag tggatctaga accactgaag tctcttgacc aggagatagc    2520
tagacctctt gaaaatgaga atcaagagtt cttaaagtca ctcaaagaag agagcgtaga    2580
ggcagtaaaa tctttagaaa cagagatcct agaatcactg aagtctgcgg acaagagaa    2640 cctgaaaaca ctgaaatctc cagaaactca agcaccactg tggactccag aagaaataaa    2700 tcaggggca atgaatcctc tagaaaagga aattcaagaa ccactggagt ctgtggaagt    2760
gaaccaagag acattcagac tcctggaaga ggagaatcag gaatcattga gatctctggg    2820
agcatggaac ctgagaattt tgagatctcc agaggaggta gacaaggaaa gtcaaaggaa    2880
tctggaagag gaagagaacc tgggaaaggg agagtaccaa gagtcactga ggtctctgga    2940
ggaggaggga caggagctgc cgcagtctgc agatgtgcag aggtgggaag atacggtgga    3000
gaaggaccaa gaactggctc aggaaaagcc tcctgggatg gctggagtgg aaaatgagga    3060
tgaggcagag ctgaatctga gggagcagga tggcttcact gggaaggagg aggtggtaga    3120
gcagggagag ctgaatgcca cagaggaggt ctggatccca ggcgagggggc acccagagag    3180 ccctgagccc aaagagcaga gaggcctggt tgagggagcc agtgtgaagg gaggggctga    3240
gggcctccag gaccctgaag ggcaatcaca acaggtgggg gccccaggcc tccaggctcc    3300
ccaggggctg ccagaggcga tagagcccct ggtggaagat gatgtggccc caggggtga    3360 ccaagcctcc ccagaggtca tgttggggtc agagcctgcc atgggtgagt ctgctgcggg    3420
agctgagcca ggcccggggc aggggtggg agggctgggg gacccaggcc atctgaccag    3480
ggaagaggtg atgaaccac ccctggaaga ggagagtttg gaggcaaaga gggttcaggg    3540
cttggaaggg cctagaaagg acctagagga ggcaggtggt ctggggacag agttctccga    3600
```

```
gctgcctggg aagagcagag acccttggga gcctcccagg gagggtaggg aggagtcaga    3660
ggctgaggcc cccaggggag cagaggaggc gttccctgct gagaccctgg gccacactgg    3720
aagtgatgcc ccttcacctt ggcctctggg gtcagaggaa gctgaggagg atgtaccacc   3780
agtgctggtc tcccccagcc caacgtacac cccgatcctg gaagatgccc ctgggcctca    3840
gcctcaggct gaagggagtc aggaggctag ctgggggtg caggggaggg ctgaagccct     3900
ggggaaagta gagagcgagc aggaggagtt gggttctggg gagatccccg agggccccca    3960
ggaggaaggg gaggagagca gagaagagag cgaggaggat gagctcgggg agacccttcc    4020
agactccact cccctgggct tctacctcag gtcccccacc tcccccaggt gggacccac     4080
tggagagcag aggccacccc ctcaagggga gactggaaag gagggctggg atcctgctgt    4140
cctggcttcc gagggccttg aggccccacc ctcagaaaag gaggagggg aggagggaga     4200
agaggagtgt ggccgtgact ctgacctgtc agaagaattt gaggacctgg ggactgaggc    4260
accttttctt cctggggtcc ctggggaggt ggcagaacct ctgggccagg tgccccagct    4320
gctactggat cctgcagcct gggatcgaga tgggagtcc gatgggtttg cagatgagga     4380
agaaagtggg gaggagggag aggaggatca ggaggagggg agggagccag gggctgggcg    4440
gtgggggcca gggtcttctg ttggcagcct ccaggccctg agtagctccc agagagggga    4500
attcctggag tctgattctg tgagtgtcag tgtcccctgg gatgacagct tgagggtgc     4560
agtggctggt gcccccaaga ctgccctgga aacggagtcc caggacagtg ctgagccttc    4620
tggctcagag gaaagtctg acctgtttc cttggagagg gaggacaaag tccctggccc     4680
tctagagatc cccagtggga tggaggatgc aggcccaggg gcagacatca ttggtgttaa    4740
tggccagggt cccaacttgg aggggaagtc acagcatgtg aatggggag tgatgaacgg     4800
gctggagcag tctgaggaag tggggcaagg aatgccgcta gtctctgagg gagaccgagg    4860
gagcccctt caggaggagg aggggagtgc tctgaagacc tcttgggcag gggctcctgt     4920
tcacctgggc cagggtcagt tcctgaagtt cactcagagg aaggagata gagagtcctg     4980
gtcctcaggg gaggactagg aaaagaccat ctgcccggca ctgggacttt agggggtgcgg   5040
ggaggggaag gacgcctcca agcccgctcc ctgctcagga gcagcactct taacttacga    5100
tctcttgaca tatggtttct ggctgagagg cctggcccgc taaggtgaaa aggggtgtgg    5160
caaaggagcc tactccaaga atggaggctg taggaatata acctcccacc ctgcaaaggg    5220
aatctcttgc ctgctccatc tcataggcta agtcagctga atcccgatag tactaggtcc    5280
ccttccctcc gcatcccgtc agctggaaaa ggcctgtggc ccagaggctt ctccaaaggg    5340
agggtgacat gctggctttt gtgcccaagc tcaccagccc tgcgccacct cactgcagta    5400
gtgcaccatc tcactgcagt agcacgccct cctgggccgt ctggcctgtg gctaatggag    5460
gtgacggcac tcccatgtgc tgactccccc catccctgcc acgctgtggc cctgcctggc    5520
tagtccctgc ctgaataaag taatgcctcc gcttcaaaaa aaaaaaaaa aaaaaaaaa      5580
aaaaaaaaa a                                                          5591
```

<210> SEQ ID NO 53
<211> LENGTH: 348
<212> TYPE: PRT
<213> ORGANISM: Homo sapiens

<400> SEQUENCE: 53

Met Ala Gln Pro Gly Ser Gly Cys Lys Ala Thr Thr Arg Cys Leu Glu
1               5                   10                  15

Gly Thr Ala Pro Pro Ala Met Ala Gln Ser Asp Ala Glu Ala Leu Ala
            20                  25                  30

Gly Ala Leu Asp Lys Asp Glu Gly Gln Ala Ser Pro Cys Thr Pro Ser
        35                  40                  45

Thr Pro Ser Val Cys Ser Pro Ser Ala Ala Ser Ser Val Pro Ser
50                  55                  60

Ala Gly Lys Asn Ile Cys Ser Ser Cys Gly Leu Glu Ile Leu Asp Arg
65                  70                  75                  80

Tyr Leu Leu Lys Val Asn Asn Leu Ile Trp His Val Arg Cys Leu Glu
                85                  90                  95

Cys Ser Val Cys Arg Thr Ser Leu Arg Gln Gln Asn Ser Cys Tyr Ile
            100                 105                 110

Lys Asn Lys Glu Ile Phe Cys Lys Met Asp Tyr Phe Ser Arg Phe Gly
        115                 120                 125

Thr Lys Cys Ala Arg Cys Gly Arg Gln Ile Tyr Ala Ser Asp Trp Val
130                 135                 140

Arg Arg Ala Arg Gly Asn Ala Tyr His Leu Ala Cys Phe Ala Cys Phe
145                 150                 155                 160

Ser Cys Lys Arg Gln Leu Ser Thr Gly Glu Glu Phe Gly Leu Val Glu
                165                 170                 175

Glu Lys Val Leu Cys Arg Ile His Tyr Asp Thr Met Ile Glu Asn Leu
            180                 185                 190

Lys Arg Ala Ala Glu Asn Gly Asn Gly Leu Thr Leu Glu Gly Ala Val
        195                 200                 205

Pro Ser Glu Gln Asp Ser Gln Pro Lys Pro Ala Lys Arg Ala Arg Thr
210                 215                 220

Ser Phe Thr Ala Glu Gln Leu Gln Val Met Gln Ala Gln Phe Ala Gln
225                 230                 235                 240

Asp Asn Asn Pro Asp Ala Gln Thr Leu Gln Lys Leu Ala Asp Met Thr
                245                 250                 255

Gly Leu Ser Arg Arg Val Ile Gln Val Trp Phe Gln Asn Cys Arg Ala
            260                 265                 270

Arg His Lys Lys His Thr Pro Gln His Pro Val Pro Pro Ser Gly Ala
        275                 280                 285

Pro Pro Ser Arg Leu Pro Ser Ala Leu Ser Asp Asp Ile His Tyr Thr
290                 295                 300

Pro Phe Ser Ser Pro Glu Arg Ala Arg Met Val Thr Leu His Gly Tyr
305                 310                 315                 320

Ile Glu Ser His Pro Phe Ser Val Leu Thr Leu Pro Ala Leu Pro His
                325                 330                 335

Leu Pro Val Gly Ala Pro Gln Leu Pro Leu Ser Arg
            340                 345

<210> SEQ ID NO 54
<211> LENGTH: 2835
<212> TYPE: DNA
<213> ORGANISM: Homo sapiens

<400> SEQUENCE: 54
cccgccaccg accaggtgat ggcccagcca gggtccggct gcaaagcgac cacccgctgt     60
cttgaaggga ccgcgccgcc cgccatggct cagtctgacg ccgaggccct ggcaggagct    120
ctggacaagg acgagggtca ggcctcccca tgtacgccca gcacgccatc tgtctgctca    180
ccgccctctg ccgcctcctc cgtgccgtct gcaggcaaga acatctgctc cagctgcggc    240

```
ctcgagatcc tggaccgata tctgctcaag gtcaacaacc tcatctggca cgtgcggtgc    300
ctcgagtgct ccgtgtgtcg cacgtcgctg aggcagcaga acagctgcta catcaagaac    360
aaggagatct tctgcaagat ggactacttc agccgattcg ggaccaagtg tgcccggtgc    420
ggccgacaga tctacgccag cgactgggtg cggagagctc gcggcaacgc ctaccacctg    480
gcctgcttcg cctgcttctc gtgcaagcgc cagctgtcca ctggtgagga gttcggcctg    540
gtcgaggaga aggtgctctg ccgcatccac tacgacacca tgattgagaa cctcaagagg    600
gccgccgaga acgggaacgg cctcacgttg gaggggcag tgccctcgga acaggacagt     660
caacccaagc cggccaagcg cgcgcggacg tccttcaccg cggaacagct gcaggttatg    720
caggcgcagt tcgcgcagga caacaacccc gacgctcaga cgctgcagaa gctggcggac    780
atgacgggcc tcagccggag agtcatccag gtgtggtttc aaaactgccg ggcgcgtcat    840
aaaaagcaca cgccgcaaca cccagtgccg ccctcggggg cgccccgtc ccgccttccc     900 tccgccctgt ccgacgacat ccactacacc ccgttcagca gccccgagcg ggcgcgcatg    960
gtcaccctgc acggctacat tgagagtcat cctttttcag tactaacgct gccggcactt   1020
ccgcatctgc ccgtgggcgc cccacagctg cccctcagcc gctgagatcc agtgtccaag   1080
ctgcggccag gagtccaccc acctccgcat ccaccccgt ccgccatcct gcccaccacc    1140
aggtcggttc ccgaggcctg gccttccct tccctgctga gaaccagaac ccaccaggag     1200
caccacagag tcctcctctt ggaaggcaga actccctgaa atctggaatc agggtggaaa   1260
cagcctgttt ttcccattta acaggagtc ctcttcaact tcagctgatt acaataacaa     1320
aaggcggaat tgaattgtgc gatgccaacg gccttctcat ttacaggttt ttttccccca   1380
cattggcctt tatttactac ttccttggaa ccatctctga attctgaata gctgacaacc   1440
cccaatgtta tccactctgt tgcttttgtc tggaaaactc tacagtgttt gtgggatgtc   1500
cccaaaggta agctatgttc taattttatc atttccatct gtctggttat gtcaagttaa   1560
ttcagaaaga gaagagacag tgaccaaccc tgagaggcct aatagggcag agatggaggc   1620
ctgcccagac taggaggcag cggggataga cagggaatgg ggagaagaaa gaccccatt    1680 ggtttggaaa tcaaggagag ggcggtgaca tattggacca gaagaggcac tagccatttt   1740
aaggagagga aagagaaaac tctggggtca gggagagacc ctaccccac ctaattatcc    1800 agcatatatg taagaaacat agcagcgatg gtattcgatc tgtgccatga ctcttctgaa   1860
tgtttggaca ggttagagtt ggggaccct gttggccact tgttgacctc tcatagtggt    1920
gcttgggcca ggtcttctca atggaagggg aatcccttat aggggagagg gaacagagcc   1980
cagtgaaatg gcagtcagaa tgttaaccct ggatccatct ctaagtagag agagggtgcc   2040
cattgcctag gtgagtgtgc caagctcagg attccaactg gtgcctctga gcttcccaat   2100
caatacttcc tggagccagc cccacccacc cctgagaaca gaggtcagac acagctgcgt   2160
aacatccatc ctgctacaac tcttccaccc caaacaaaag ggctcaggct acacacgacc   2220
atgatttatg ttttcagggg atgcccattt gtcccaagct tatcctgtaa ttctagaatt   2280
acctggtgtc ctgatgcatt ttccactaga ggttgctaat cagcatgttt tagcccaagt   2340
ccaccttcct gctgtggtta acctgttatg ttgcttttgg aaggagactc taagacaggg   2400
aaagcaagtt catggtacat acgcagccat tgtctctgtt tttacccatg gcagacattg   2460
ctaatcaatg gcagctctat ttcactgagt ctggataagg tttcagagtt caaatgcttg   2520
acgttggcac ttaacatgaa agcctatagg tcattcttgc tctgggatct acaggcaggg   2580
```

-continued

```
taggcacagg tgcagcctaa gaagggaacc tgcttcctct cccttccaaa gacagtgaca    2640
gctgactgag ggcaaagagc aggcaccact cagaacgtgg tgagtacagc tcagctcagc    2700
actcagtcag tggtaacttg tgcccagccc tgtgctaggc gctgacatta acaggagcaa    2760
ccagggccca attcctggcc ttggagctca aatctttcct ttgattttg ctcctgatca     2820 tcaaggcccc agtgg                                                     2835

<210> SEQ ID NO 55
<211> LENGTH: 356
<212> TYPE: PRT
<213> ORGANISM: Homo sapiens

<400> SEQUENCE: 55

Met Gln Ile Leu Ser Arg Cys Gln Gly Leu Met Ser Glu Glu Cys Gly
1               5                   10                  15

Arg Thr Thr Ala Leu Ala Ala Gly Arg Thr Lys Gly Ala Gly Glu
            20                  25                  30

Glu Gly Leu Val Ser Pro Glu Gly Ala Gly Asp Glu Asp Ser Cys Ser
        35                  40                  45

Ser Ser Ala Pro Leu Ser Pro Ser Ser Pro Arg Ser Met Ala Ser
    50                  55                  60

Gly Ser Gly Cys Pro Pro Gly Lys Cys Val Cys Asn Ser Cys Gly Leu
65                  70                  75                  80

Glu Ile Val Asp Lys Tyr Leu Leu Lys Val Asn Asp Leu Cys Trp His
                85                  90                  95

Val Arg Cys Leu Ser Cys Ser Val Cys Arg Thr Ser Leu Gly Arg His
            100                 105                 110

Thr Ser Cys Tyr Ile Lys Asp Lys Asp Ile Phe Cys Lys Leu Asp Tyr
        115                 120                 125

Phe Arg Arg Tyr Gly Thr Arg Cys Ser Arg Cys Gly Arg His Ile His
    130                 135                 140

Ser Thr Asp Trp Val Arg Arg Ala Lys Gly Asn Val Tyr His Leu Ala
145                 150                 155                 160

Cys Phe Ala Cys Phe Ser Cys Lys Arg Gln Leu Ser Thr Gly Glu Glu
                165                 170                 175

Phe Ala Leu Val Glu Glu Lys Val Leu Cys Arg Val His Tyr Asp Cys
            180                 185                 190

Met Leu Asp Asn Leu Lys Arg Glu Val Glu Asn Gly Asn Gly Ile Ser
        195                 200                 205

Val Glu Gly Ala Leu Leu Thr Glu Gln Asp Val Asn His Pro Lys Pro
    210                 215                 220

Ala Lys Arg Ala Arg Thr Ser Phe Thr Ala Asp Gln Leu Gln Val Met
225                 230                 235                 240

Gln Ala Gln Phe Ala Gln Asp Asn Asn Pro Asp Ala Gln Thr Leu Gln
                245                 250                 255

Lys Leu Ala Glu Arg Thr Gly Leu Ser Arg Arg Val Ile Gln Val Trp
            260                 265                 270

Phe Gln Asn Cys Arg Ala Arg His Lys Lys His Val Ser Pro Asn His
        275                 280                 285

Ser Ser Ser Thr Pro Val Thr Ala Ala Pro Ser Arg Leu Ser Pro
    290                 295                 300

Pro Met Leu Glu Glu Met Ala Tyr Ser Ala Tyr Val Pro Gln Asp Gly
305                 310                 315                 320

Thr Met Leu Thr Ala Leu His Ser Tyr Met Asp Ala His Ser Pro Thr
```

```
                    325                 330                 335
Thr Leu Gly Leu Gln Pro Leu Leu Pro His Ser Met Thr Gln Leu Pro
            340                 345                 350
Ile Ser His Thr
        355

<210> SEQ ID NO 56
<211> LENGTH: 2411
<212> TYPE: DNA
<213> ORGANISM: Homo sapiens

<400> SEQUENCE: 56
agcggcaaga ggctagcggc tggaccactt gtgctggagt ggtaaagaac tatcatgaat      60
ccatttactg aaagtgtcca tttctgaact caccctaaag aggacaaaca ccgcaaagta     120
gttaaaagtc aggcattcgc gtcggacgtc tgggtttgaa ttctgccctg gcttgactgg     180
aaacgcttcc cctatttctt ccgtagcgga ccgggagagc ttactggcgc tctgcgaacc     240
ggctggaaag aaacaccgag tcactcgtac agactcttgg tcgcagaact ggctttccg     300 ctattggtcc tccagaaccg cttgaaacaa ctggccccag ctggcgcatc agaccgcagt     360
gaggaatgcc gcggggcggg tggcgaaggc agggtctgcc cgccagtgga ttcccgggtg     420
tcccgcgtgg agcaggcttg cccagctggg aagcccatca acctcagtc ttggcccaca     480 gtgggagaga ccagtgggg tcccagacgg aggccatcgc ccgcttttgg cgacctccac     540
tggcgtgaat aaaagcaccc ctctcttacc ctcagaaact gtgggtagca aggtataaaa     600
cggagtctgg gaccggtaag tcccaaggtg agcccgtata cagctctgcc atctctgagg     660
ggttatgcag attctgagca ggtgtcaggg gctcatgtca gaggagtgcg ggcggactac     720
agccctggcg gccgggagga ctcgcaaagg cgccggggaa gagggactgg tgagccccga     780
gggagcgggg gacgaggact cgtgctcctc ctcggccccg ctgtccccgt cgtcctcgcc     840
ccggtccatg gcctcgggct ccggctgccc tcctggcaag tgtgtgtgca acagttgcgg     900
cctggagatc gtggacaaat accttctcaa ggtgaatgac ctatgctggc atgtccggtg     960
tctctcctgc agtgtttgca gaaccctccct aggaaggcac accagctgtt atattaaaga    1020
caaagacatt ttctgcaaac ttgattattt cagaaggtat ggaactcgct gctctcgatg    1080
tgggagacac atccattcta ctgactgggt ccggagagcc aagggggaatg tctatcactt    1140 ggcatgcttt gcctgctttt cctgcaaaag gcaactttcc acaggagagg agtttgcttt    1200
ggtggaagag aaagtcctct gcagagtaca ttatgactgc atgctggata atttaaaaag    1260
agaagtagaa aatgggaatg ggattagtgt ggaaggtgcc ctcctcacag agcaagatgt    1320
taaccatcca aaaccagcaa aaagagctcg gaccagcttt acagcagatc agcttcaggt    1380
tatgcaagca caatttgctc aggacaacaa cccagatgca cagacactcc agaaattggc    1440
agaaaggaca ggcttgagca gacgtgtgat acaggtgtgg tttcagaatt gtagagcacg    1500
ccacaagaaa cacgtcagtc ctaatcactc atcctccacc ccagtcacag cagcccacc     1560 ctccaggctg tctccaccca tgttagaaga aatggcttat tctgcctacg tgccccaaga    1620
tggaacgatg ttaactgcgc tgcatagtta tggatgct cattcaccaa caactcttgg      1680
actccagccc ttgttacccc attcaatgac acaactgcca ataagtcata cctaattctt    1740
ttttcaggga tagacttgat taaggatata aatttgtcat ttattatgta taaaatacca    1800
ttgaaaagat attactgtta attttttatt taacacctaa agcatttcca acatcacttt    1860
gctgcccagg tatgtatcta tagttggcct gcaagacact tttattaatt cttcatttt     1920
```

```
tgtaaaactt atgtttacaa gaagaaaaca aatcaaaaca ttttttgtat tgtctggaaa    1980
tagttcactc tagtgtgtat ctgttaattt atttgtcatc aaaagagcac tttgcctaaa    2040
agaaaggact gacaagtgtg caaaatgttt acaatctttt gtgaaattgt agtttatcat    2100
tagtttgtat ctgtaagtta ttgtaataaa tattacctgt attttttgtt atatacaact    2160
ttatactttg aagcttgtat ctgtgaattt gcaactgaaa tttattttgc caatgttttc    2220
tgaatgaact gaataaagct tctgttgtag catgccatgc aaacacatta ttgtgtttgt    2280
ggttgatgaa ttatggctgt aaataacact atagtttaat aagcccacca ttctgagttt    2340
attaaacatt ttccattctt gtgaaaattt caaaaaaaaa aaaaaaaaaa aaagaaaaaa    2400
aaaaaaaaaa a                                                         2411

<210> SEQ ID NO 57
<211> LENGTH: 682
<212> TYPE: PRT
<213> ORGANISM: Homo sapiens

<400> SEQUENCE: 57

Met Gln Leu Glu His Cys Leu Ser Pro Ser Ile Met Leu Ser Lys Lys
1               5                   10                  15

Phe Leu Asn Val Ser Ser Ser Tyr Pro His Ser Gly Gly Ser Glu Leu
                20                  25                  30

Val Leu His Asp His Pro Ile Ile Ser Thr Thr Asp Asn Leu Glu Arg
            35                  40                  45

Ser Ser Pro Leu Lys Lys Ile Thr Arg Gly Met Thr Asn Gln Ser Asp
        50                  55                  60

Thr Asp Asn Phe Pro Asp Ser Lys Asp Ser Pro Gly Asp Val Gln Arg
65                  70                  75                  80

Ser Lys Leu Ser Pro Val Leu Asp Gly Val Ser Glu Leu Arg His Ser
                85                  90                  95

Phe Asp Gly Ser Ala Ala Asp Arg Tyr Leu Leu Ser Gln Ser Ser Gln
            100                 105                 110

Pro Gln Ser Ala Ala Thr Ala Pro Ser Ala Met Phe Pro Tyr Pro Gly
        115                 120                 125

Gln His Gly Pro Ala His Pro Ala Phe Ser Ile Gly Ser Pro Ser Arg
    130                 135                 140

Tyr Met Ala His His Pro Val Ile Thr Asn Gly Ala Tyr Asn Ser Leu
145                 150                 155                 160

Leu Ser Asn Ser Ser Pro Gln Gly Tyr Pro Thr Ala Gly Tyr Pro Tyr
                165                 170                 175

Pro Gln Gln Tyr Gly His Ser Tyr Gln Gly Ala Pro Phe Tyr Gln Phe
            180                 185                 190

Ser Ser Thr Gln Pro Gly Leu Val Pro Gly Lys Ala Gln Val Tyr Leu
        195                 200                 205

Cys Asn Arg Pro Leu Trp Leu Lys Phe His Arg His Gln Thr Glu Met
    210                 215                 220

Ile Ile Thr Lys Gln Gly Arg Arg Met Phe Pro Phe Leu Ser Phe Asn
225                 230                 235                 240

Ile Ser Gly Leu Asp Pro Thr Ala His Tyr Asn Ile Phe Val Asp Val
                245                 250                 255

Ile Leu Ala Asp Pro Asn His Trp Arg Phe Gln Gly Gly Lys Trp Val
            260                 265                 270

Pro Cys Gly Lys Ala Asp Thr Asn Val Gln Gly Asn Arg Val Tyr Met
```

```
                275                 280                 285
His Pro Asp Ser Pro Asn Thr Gly Ala His Trp Met Arg Gln Glu Ile
290                 295                 300
Ser Phe Gly Lys Leu Lys Leu Thr Asn Asn Lys Gly Ala Ser Asn Asn
305                 310                 315                 320
Asn Gly Gln Met Val Val Leu Gln Ser Leu His Lys Tyr Gln Pro Arg
                325                 330                 335
Leu His Val Val Glu Val Asn Glu Asp Gly Thr Glu Asp Thr Ser Gln
            340                 345                 350
Pro Gly Arg Val Gln Thr Phe Thr Phe Pro Glu Thr Gln Phe Ile Ala
            355                 360                 365
Val Thr Ala Tyr Gln Asn Thr Asp Ile Thr Gln Leu Lys Ile Asp His
370                 375                 380
Asn Pro Phe Ala Lys Gly Phe Arg Asp Asn Tyr Asp Thr Ile Tyr Thr
385                 390                 395                 400
Gly Cys Asp Met Asp Arg Leu Thr Pro Ser Pro Asn Asp Ser Pro Arg
                405                 410                 415
Ser Gln Ile Val Pro Gly Ala Arg Tyr Ala Met Ala Gly Ser Phe Leu
            420                 425                 430
Gln Asp Gln Phe Val Ser Asn Tyr Ala Lys Ala Arg Phe His Pro Gly
            435                 440                 445
Ala Gly Ala Gly Pro Gly Pro Gly Thr Asp Arg Ser Val Pro His Thr
450                 455                 460
Asn Gly Leu Leu Ser Pro Gln Gln Ala Glu Asp Pro Gly Ala Pro Ser
465                 470                 475                 480
Pro Gln Arg Trp Phe Val Thr Pro Ala Asn Asn Arg Leu Asp Phe Ala
                485                 490                 495
Ala Ser Ala Tyr Asp Thr Ala Thr Asp Phe Ala Gly Asn Ala Ala Thr
            500                 505                 510
Leu Leu Ser Tyr Ala Ala Ala Gly Val Lys Ala Leu Pro Leu Gln Ala
            515                 520                 525
Ala Gly Cys Thr Gly Arg Pro Leu Gly Tyr Tyr Ala Asp Pro Ser Gly
530                 535                 540
Trp Gly Ala Arg Ser Pro Pro Gln Tyr Cys Gly Thr Lys Ser Gly Ser
545                 550                 555                 560
Val Leu Pro Cys Trp Pro Asn Ser Ala Ala Ala Ala Arg Met Ala
                565                 570                 575
Gly Ala Asn Pro Tyr Leu Gly Glu Glu Ala Glu Gly Leu Ala Ala Glu
                580                 585                 590
Arg Ser Pro Leu Pro Pro Gly Ala Ala Glu Asp Ala Lys Pro Lys Asp
            595                 600                 605
Leu Ser Asp Ser Ser Trp Ile Glu Thr Pro Ser Ser Ile Lys Ser Ile
            610                 615                 620
Asp Ser Ser Asp Ser Gly Ile Tyr Glu Gln Ala Lys Arg Arg Ile
625                 630                 635                 640
Ser Pro Ala Asp Thr Pro Val Ser Glu Ser Ser Ser Pro Leu Lys Ser
                645                 650                 655
Glu Val Leu Ala Gln Arg Asp Cys Glu Lys Asn Cys Ala Lys Asp Ile
                660                 665                 670
Ser Gly Tyr Tyr Gly Phe Tyr Ser His Ser
            675                 680

<210> SEQ ID NO 58
```

```
<211> LENGTH: 4006
<212> TYPE: DNA
<213> ORGANISM: Homo sapiens

<400> SEQUENCE: 58
gtcgctacca ggagccaggt gattatccta attaatgtct atctaattaa attactgtca      60
gcagctaacc aatggcagga gccgtttcat cggctgcaca agcagcaaga tcaaaagtga     120
gccttttctg attgctgcat agtgtcaatt ggccaatctc ttctcccagg gaaaaaaaaa     180
agtaaatcaa acctttgaga agcatttgct ggttgaagtg ctttctgtct agtgagggg     240
tctgtggatt tctagtttat gataaatagg actttaaaaa ccaggacgg gagggcgagt     300
gttcaggttc tagagctatg cagctggagc actgcctttc tccttctatc atgctctcca     360
agaaatttct caatgtgagc agcagctacc cacattcagg cggatccgag cttgtcttgc     420
acgatcatcc cattatctcg accactgaca acctggagag aagttcacct ttgaaaaaaa     480
ttaccagggg gatgacgaat cagtcagata cagacaattt tcctgactcc aaggactcac     540
caggggacgt ccagagaagt aaactctctc ctgtcttgga cggggtctct gagcttcgtc     600
acagtttcga tggctctgct gcagatcgct acctcctctc tcagtccagc cagccacagt     660
ctgcggccac tgctcccagt gccatgttcc cgtaccccgg ccagcacgga ccggcgcacc     720
ccgccttctc catcggcagc cctagccgct acatggccca ccaccccggtc atcaccaacg     780
gagcctacaa cagcctcctg tccaactcct cgccgcaggg ataccccacg gccggctacc     840
cctacccaca gcagtacggc cactcctacc aaggagctcc gttctaccag ttctcctcca     900
cccagccggg gctggtgccc ggcaaagcac aggtgtacct gtgcaacagg ccccttggc     960
tgaaatttca ccggcaccaa acggagatga tcatcaccaa acagggaagg cgcatgtttc    1020
ctttttaag ttttaacatt tctggtctcg atcccacggc tcattacaat atttttgtgg    1080
atgtgatttt ggcggatccc aatcactgga ggtttcaagg aggcaaatgg gttccttgcg    1140
gcaaagcgga caccaatgtg caaggaaatc gggtctatat gcatccggat tcccccaaca    1200
ctgggctca ctggatgcgc caagaaatct cttttggaaa attaaaactt acgaacaaca    1260
aaggagcttc aaataacaat gggcagatgg tggttttaca gtccttgcac aagtaccagc    1320
cccgcctgca tgtggtggaa gtgaacgagg acggcacgga ggacactagc cagcccggcc    1380
gcgtgcagac gttcactttc cctgagactc agttcatcgc cgtcaccgcc taccagaaca    1440
cggatattac acaactgaaa atagatcaca acccttttgc aaaaggattt cgggataatt    1500
atgacacgat ctacaccggc tgtgacatgg accgcctgac cccctcgccc aacgactcgc    1560
cgcgctcgca gatcgtgccc ggggcccgct acgccatggc cggctctttc ctgcaggacc    1620
agttcgtgag caactacgcc aaggcccgct tccacccggg cgcggcgcg ggccccgggc    1680
cgggtacgga ccgcagcgtg ccgcacacca acgggctgct gtcgccgcag caggccgagg    1740
acccgggcgc gccctcgccg caacgctggt tgtgacgcc ggccaacaac cggctggact    1800
cgcggcctc ggcctatgac acggcacgg acttcgcggg caacgcggcc acgctgctct    1860
cttacgcggc ggcgggcgtg aaggcgctgc cgctgcaggc tgcaggctgc actggccgcc    1920
cgctcggcta ctacgccgac ccgtcggct ggggcgcccg cagtccccg cagtactgcg    1980
gcaccaagtc gggctcggtg ctgccctgct ggcccaacag cgccgcggcc gccgcgcgca    2040
tggccggcgc caatccctac ctgggcgagg aggccgaggg cctggccgcc gagcgctcgc    2100
cgctgccgcc cggcgccgcc gaggacgcca agccccaagga cctgtccgat tccagctgga    2160
tcgagacgcc ctcctcgatc aagtccatcg actccagcga ctcggggatt tacgagcagg    2220
```

-continued

```
ccaagcggag gcggatctcg ccggccgaca cgcccgtgtc cgagagttcg tccccgctca    2280
agagcgaggt gctggcccag cgggactgcg agaagaactg cgccaaggac attagcggct    2340
actatggctt ctactcgcac agctaggccg ccctgcccg ccggccccg ccgcggcccg      2400 gaccccagc cagcccctca cagctcttcc ccagctccgc ctccccacac tcctccttgc     2460
gcacccactc attttatttg accctcgatg gccgtctgca gcgaataagt gcaggtctcc    2520
gagcgtgatt ttaaccttt ttgcacagca gtctctgcaa ttagctcacc gaccttcaac    2580
tttgctgtaa accttttggt tttcctactt actcttcttc tgtggagtta tcctcctaca    2640
attcccctcc ccctcgtctt tctcttacct cctactctc tttcttgtaa tgaaactctt    2700
cacctttagg agacctgggc agtcctgtca ggcagcagcg attccgaccc gccaagtctc    2760
ggcctccaca ttaaccatag gatgttgact ctagaacctg gacccaccca gcgcgtcctt    2820
tcttatcccc gagtggatgg atggatggat ggatggtagg gatgttaata attttagtgg    2880
aacaaagcct gtgaaatgat tgtacatagt gttaatttat tgtaacgaat ggctagtttt    2940
tattctcgtc aaggcacaaa accagttcat gcttaacctt ttttcctttt cctttctttg    3000
cttttctttc tctcctctca tactttctct tctctctctt ttaattttct tgtgagataa    3060
tattctaaga ggctctagaa acatgaaata ctcagtagtg atgggtttcc cacttctcct    3120
caatccgttg catgaaataa ttactatgtg ccctaatgca cacaaatagc taaggagaat    3180
ccacccaaac acctttaaag gataggtgtc tgttcatagg caagtcgatt aagtggcatg    3240
atgcctgcaa agcaaagtca actggagttg tatgttcccc ccaccttcta aatagaatag    3300
ctcgacatca gcaatattat tttgccttat ttgttttcc ccaaagtgcc aaatccatta    3360
ctggtctgtg caggtgccaa atatgctgac aaactgtttc tgaatatctt tcagtacccc    3420
ttcaccttta tatgctgtaa atctttgtaa tgaatactct attaatgata tagatgactg    3480
aattgttggt aactatagtg tagtctagtg aagatgaatt gtgtgagttg tatattttac    3540 tgcatttag ttttgaaaat gacttcccca ccacctagaa acagctgaaa tttgacttcc    3600
ttgggagaac actagcatta atgcaagtaa gactgatttt cccctaagtc ttgttatatt    3660
tgataaggag cattaatccc cctggaaata gattagtagg atttctaatg ttgtgtagca    3720
aacctatact ttttgtatt taaaaattaa tgtgaaatat gcatcataca caatattcaa    3780
tctagattcc agtccatggg gggatttttc ctaataggaa ttcagggtct aaacgtgtgt    3840
atattttggc tcttctgtaa atctaatgtt gtgattttta tatttgtttc gttttgtctg    3900
tgaactgaat aatttataca agaacacact ccattgagaa acgttttgtt ttttgctcgt    3960
ttgtatcgtc tgtgtataac aagtaaaata aacctggtaa aaacgc                  4006
```

<210> SEQ ID NO 59
<211> LENGTH: 542
<212> TYPE: PRT
<213> ORGANISM: Homo sapiens

<400> SEQUENCE: 59

```
Met Thr Lys Ser Asn Gly Glu Glu Pro Lys Met Gly Gly Arg Met Glu
1               5                   10                  15

Arg Phe Gln Gln Gly Val Arg Lys Arg Thr Leu Leu Ala Lys Lys Lys
            20                  25                  30

Val Gln Asn Ile Thr Lys Glu Asp Val Lys Ser Tyr Leu Phe Arg Asn
        35                  40                  45

Ala Phe Val Leu Leu Thr Val Thr Ala Val Ile Val Gly Thr Ile Leu
```

```
            50                  55                  60
Gly Phe Thr Leu Arg Pro Tyr Arg Met Ser Tyr Arg Glu Val Lys Tyr
 65                  70                  75                  80

Phe Ser Phe Pro Gly Glu Leu Leu Met Arg Met Leu Gln Met Leu Val
                     85                  90                  95

Leu Pro Leu Ile Ile Ser Ser Leu Val Thr Gly Met Ala Ala Leu Asp
                100                 105                 110

Ser Lys Ala Ser Gly Lys Met Gly Met Arg Ala Val Val Tyr Tyr Met
                115                 120                 125

Thr Thr Thr Ile Ile Ala Val Val Ile Gly Ile Ile Val Ile Ile
                130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
                165                 170                 175

Met Phe Pro Pro Asn Leu Val Glu Ala Cys Phe Lys Gln Phe Lys Thr
                180                 185                 190

Asn Tyr Glu Lys Arg Ser Phe Lys Val Pro Ile Gln Ala Asn Glu Thr
                195                 200                 205

Leu Val Gly Ala Val Ile Asn Asn Val Ser Glu Ala Met Glu Thr Leu
                210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
                260                 265                 270

Ser Leu Asn Glu Ala Ile Met Arg Leu Val Ala Val Ile Met Trp Tyr
                275                 280                 285

Ala Pro Val Gly Ile Leu Phe Leu Ile Ala Gly Lys Ile Val Glu Met
                290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
                340                 345                 350

Leu Gln Ala Leu Ile Thr Ala Leu Gly Thr Ser Ser Ser Ala Thr
                355                 360                 365

Leu Pro Ile Thr Phe Lys Cys Leu Glu Glu Asn Asn Gly Val Asp Lys
                370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Glu Leu Asn Phe Gly Gln Ile Ile Thr Ile Ser Ile Thr
                420                 425                 430

Ala Thr Ala Ala Ser Ile Gly Ala Ala Gly Ile Pro Gln Ala Gly Leu
                435                 440                 445

Val Thr Met Val Ile Val Leu Thr Ser Val Gly Leu Pro Thr Asp Asp
                450                 455                 460

Ile Thr Leu Ile Ile Ala Val Asp Trp Phe Leu Asp Arg Leu Arg Thr
465                 470                 475                 480
```

```
Thr Thr Asn Val Leu Gly Asp Ser Leu Gly Ala Gly Ile Val Glu His
            485                 490                 495
Leu Ser Arg His Glu Leu Lys Asn Arg Asp Val Glu Met Gly Asn Ser
        500                 505                 510
Val Ile Glu Glu Asn Glu Met Lys Lys Pro Tyr Gln Leu Ile Ala Gln
    515                 520                 525
Asp Asn Glu Thr Glu Lys Pro Ile Asp Ser Glu Thr Lys Met
530                 535                 540

<210> SEQ ID NO 60
<211> LENGTH: 1873
<212> TYPE: DNA
<213> ORGANISM: Homo sapiens

<400> SEQUENCE: 60
gatagtaact tgcagtttca gagcacatgc acactgtcag ggctagcctg cctgcttacg     60
cgcgctgcgg attgttgctc cgttgtacct gctggggaat tcacctcgtt actgcttgat    120
atcttccacc ccttacaaaa tcagaaaagt gtgtttttct aataccaaag aggaggtttg    180
gctttctgtg ggtgattccc agacactgaa gtgcaaagaa gagaccctcc tagaaaagta    240
aaatatgact aaaagcaatg agaagagcc caagatgggg ggcaggatgg agagattcca    300
gcagggagtc cgtaaacgca cactttggc caagaagaaa gtgcagaaca ttacaaagga    360
ggatgttaaa agttacctgt ttcggaatgc ttttgtgctg ctcacagtca ccgctgtcat    420
tgtgggtaca atccttggat ttaccctccg accatacaga atgagctacc gggaagtcaa    480
gtacttctcc tttcctgggg aacttctgat gaggatgtta cagatgctgg tcttaccact    540
tatcatctcc agtcttgtca caggaatggc ggcgctagat agtaaggcat cagggaagat    600
gggaatgcga gctgtagtct attatatgac taccaccatc attgctgtgg tgattggcat    660
aatcattgtc atcatcatcc atcctgggaa gggcacaaag gaaaacatgc acagagaagg    720
caaaattgta cgagtgacag ctgcagatgc cttcctggac ttgatcagga catgttccc    780
tccaaatctg gtagaagcct gctttaaaca gtttaaaacc aactatgaga agagaagctt    840
taaagtgccc atccaggcca acgaaacgct tgtgggtgct gtgataaaca atgtgtctga    900
ggccatggag actcttaccc gaatcacaga ggagctggtc ccagttccag atctgtgaa    960
tggagtcaat gccctgggtc tagttgtctt ctccatgtgc ttcggttttg tgattggaaa   1020
catgaaggaa caggggcagg ccctgagaga gttctttgat tctcttaacg aagccatcat   1080
gagactggta gcagtaataa tgtggtatgc ccccgtgggg attctcttcc tgattgctgg   1140
gaagattgtg gagatggaag acatgggtgt gattgggggg cagcttgcca tgtacaccgt   1200
gactgtcatt gttggcttac tcattcacgc agtcatcgtc ttgccactcc tctacttctt   1260
ggtaacacgg aaaaaccctt gggtttttat tggagggttg ctgcaagcac tcatcaccgc   1320
tctggggacc tcttcaagtt ctgccaccct acccatcacc ttcaagtgcc tggaagagaa   1380
caatggcgtg acaagcgcg tcaccagatt cgtgctcccc gtaggagcca ccattaacat   1440
ggatgggact gccctctatg aggctttggc tgccattttc attgctcaag ttaacaactt   1500
tgaactgaac ttcggacaaa ttattacaat cagcatcaca gccacagctg ccagtattgg   1560
ggcagctgga attcctcagg cgggcctggt cactatggtc attgtgctga catctgtcgg   1620
cctgcccact gacgacatca cgctcatcat cgcggtggac tggttcctgg atcgcctccg   1680
gaccaccacc aacgtactgg agactcccct gggagctggg attgtggagc acttgtcacg   1740
```

```
acatgaactg aagaacagag atgttgaaat gggtaactca gtgattgaag agaatgaaat    1800
gaagaaacca tatcaactga ttgcacagga caatgaaact gagaaaccca tcgacagtga    1860
aaccaagatg tag                                                        1873
```

<210> SEQ ID NO 61
<211> LENGTH: 497
<212> TYPE: PRT
<213> ORGANISM: Homo sapiens

<400> SEQUENCE: 61

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Val Pro Ser Glu Pro
    50                  55                  60

Gly Asp Pro Leu Glu Ala Val Ala Phe Glu Glu Lys Glu Gly Lys Ala
65                  70                  75                  80

Val Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
    130                 135                 140

Leu Ser Gly Val Arg Gln Val Ser Glu Asp Val Arg Ser Pro Ala Gly
145                 150                 155                 160

Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
    210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
        275                 280                 285

Pro Val Ala Gly Leu Leu Ser Ala Arg Asp Phe Leu Ala Ser Leu Ala
    290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
                325                 330                 335

Pro Met Leu Ala Asp Arg Thr Phe Ala Gln Phe Ser Gln Asp Ile Gly
            340                 345                 350
```

```
Leu Ala Ser Leu Gly Ala Ser Asp Glu Glu Ile Glu Lys Leu Ser Thr
            355                 360                 365

Leu Tyr Trp Phe Thr Val Glu Phe Gly Leu Cys Lys Gln Asn Gly Glu
    370                 375                 380

Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
                405                 410                 415

Ala Ala Val Gln Pro Tyr Gln Asp Gln Thr Tyr Gln Ser Val Tyr Phe
                420                 425                 430

Val Ser Glu Ser Phe Ser Asp Ala Lys Asp Lys Leu Arg Ser Tyr Ala
            435                 440                 445

Ser Arg Ile Gln Arg Pro Phe Ser Val Lys Phe Asp Pro Tyr Thr Leu
    450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly

<210> SEQ ID NO 62
<211> LENGTH: 1629
<212> TYPE: DNA
<213> ORGANISM: Homo sapiens

<400> SEQUENCE: 62
acccagaggg ggctttgacg tcagctcagc ttataagagg ctgctgggcc agggctgtgg      60
agacggagcc cggacctcca cactgagcca tgcccacccc cgacgccacc acgccacagg     120
ccaagggctt ccgcagggcc gtgtctgagc tggacgccaa gcaggcagag gccatcatgt     180
ccccgcggtt cattgggcgc aggcagagcc tcatcgagga cgcccgcaag gagcgggagg     240
cggcggtggc agcagcggcc gctgcagtcc cctcggagcc cggggacccc ctggaggctg     300 tggccttttga ggagaaggag gggaaggccg tgctaaacct gctcttctcc ccagggccca     360
ccaagccctc ggcgctgtcc cgagctgtga aggtgtttga cgtttgaa gccaaaatcc     420 accatctaga gacccggccc gcccagaggc gcgagctggg gcccccac ctggagtact     480 tcgtgcgcct cgaggtgcgc cgaggggacc tggccgccct gctcagtggt gtgcgccagg     540
tgtcagagga cgtgcgcagc cccgcggggc ccaaggtccc ctggttccca agaaaagtgt     600
cagagctgga caagtgtcat cacctggtca ccaagttcga ccctgacctg gacttggacc     660
acccgggctt ctcggaccag gtgtaccgcc agcgcaggaa gctgattgct gagatcgcct     720
tccagtacag gcacggcgac ccgattcccc gtgtggagta caccgccgag gagattgcca     780
cctggaagga ggtctacacc acgctgaagg gcctctacgc cacgcacgcc tgcggggagc     840
acctggaggc ctttgctttg ctggagcgct tcagcggcta ccgggaagac aatatccccc     900
agctggagga cgtctcccgc ttcctgaagg agcgcacggg cttccagctg cggcctgtgg     960
ccggcctgct gtccgcccgg gacttcctgg ccagcctggc cttccgcgtg ttccagtgca    1020
cccagtatat ccgccacgcg tcctcgccca tgcactcccc tgagccggac tgctgccacg    1080
agctgctggg gcacgtgccc atgctggccg accgcacctt cgcgcagttc tcgcaggaca    1140
ttggcctggc gtccctgggg gcctcggatg aggaaattga gaagctgtcc acgctgtact    1200
ggttcacggt ggagttcggg ctgtgtaagc agaacgggga ggtgaaggcc tatggtgccg    1260
```

-continued

```
ggctgctgtc ctcctacggg gagctcctgc actgcctgtc tgaggagcct gagattcggg    1320
ccttcgaccc tgaggctgcg gccgtgcagc cctaccaaga ccagacgtac cagtcagtct    1380
acttcgtgtc tgagagcttc agtgacgcca aggacaagct caggagctat gcctcacgca    1440
tccagcgccc cttctccgtg aagttcgacc cgtacacgct ggccatcgac gtgctggaca    1500
gcccccaggc cgtgcggcgc tccctggagg gtgtccagga tgagctggac acccttgccc    1560
atgcgctgag tgccattggc taggtgcacg gcgtccctga gggcccttcc caacctcccc    1620
tggtcctgc                                                             1629
```

<210> SEQ ID NO 63
<211> LENGTH: 1020
<212> TYPE: PRT
<213> ORGANISM: Homo sapiens

<400> SEQUENCE: 63

```
Met Met Ser Phe Gly Gly Ala Asp Ala Leu Leu Gly Ala Pro Phe Ala
1               5                   10                  15

Pro Leu His Gly Gly Ser Leu His Tyr Ala Leu Ala Arg Lys Gly
            20                  25                  30

Gly Ala Gly Gly Thr Arg Ser Ala Gly Ser Ser Gly Phe His
        35                  40                  45

Ser Trp Thr Arg Thr Ser Val Ser Ser Val Ser Ala Ser Pro Ser Arg
50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
        115                 120                 125

Ala Ala Ala Leu Arg Gln Gln Gln Ala Gly Arg Ser Ala Met Gly Glu
    130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
        195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300
```

```
Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
            325                 330                 335

Ser Thr Lys Asp Ser Leu Glu Arg Gln Arg Ser Glu Leu Glu Asp Arg
                340                 345                 350

His Gln Ala Asp Ile Ala Ser Tyr Gln Glu Ala Ile Gln Gln Leu Asp
            355                 360                 365

Ala Glu Leu Arg Asn Thr Lys Trp Glu Met Ala Ala Gln Leu Arg Glu
            370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Cys Arg Ile Gly Phe Gly
                405                 410                 415

Pro Ile Pro Phe Ser Leu Pro Glu Gly Leu Pro Lys Ile Pro Ser Val
                420                 425                 430

Ser Thr His Ile Lys Val Lys Ser Glu Glu Lys Ile Lys Val Val Glu
            435                 440                 445

Lys Ser Glu Lys Glu Thr Val Ile Val Glu Glu Gln Thr Glu Glu Thr
450                 455                 460

Gln Val Thr Glu Glu Val Thr Glu Glu Glu Lys Glu Ala Lys Glu
465                 470                 475                 480

Glu Glu Gly Lys Glu Glu Gly Gly Glu Glu Glu Ala Glu Gly
                485                 490                 495

Gly Glu Glu Glu Thr Lys Ser Pro Pro Ala Glu Ala Ala Ser Pro
                500                 505                 510

Glu Lys Glu Ala Lys Ser Pro Val Lys Glu Glu Ala Lys Ser Pro Ala
            515                 520                 525

Glu Ala Lys Ser Pro Glu Lys Glu Ala Lys Ser Pro Ala Glu Val
            530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Ala Lys Ser Pro Ala
                565                 570                 575

Glu Val Lys Ser Pro Glu Lys Ala Lys Ser Pro Ala Lys Glu Glu Ala
                580                 585                 590

Lys Ser Pro Ala Glu Ala Lys Ser Pro Glu Lys Ala Lys Ser Pro Val
                595                 600                 605

Lys Glu Glu Ala Lys Ser Pro Ala Glu Ala Lys Ser Pro Val Lys Glu
                610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Glu Glu Ala Lys Ser Pro Glu Lys Ala Lys Ser Pro Val Lys Ala
                660                 665                 670

Glu Ala Lys Ser Pro Glu Lys Ala Lys Ser Pro Val Lys Ala Glu Ala
                675                 680                 685

Lys Ser Pro Glu Lys Ala Lys Ser Pro Val Lys Glu Glu Ala Lys Ser
                690                 695                 700

Pro Glu Lys Ala Lys Ser Pro Val Lys Glu Glu Ala Lys Ser Pro Glu
705                 710                 715                 720
```

```
Lys Ala Lys Ser Pro Val Lys Glu Glu Ala Lys Thr Pro Glu Lys Ala
                725                 730                 735
Lys Ser Pro Val Lys Glu Glu Ala Lys Ser Pro Glu Lys Ala Lys Ser
            740                 745                 750
Pro Glu Lys Ala Lys Thr Leu Asp Val Lys Ser Pro Glu Ala Lys Thr
        755                 760                 765
Pro Ala Lys Glu Glu Ala Arg Ser Pro Ala Asp Lys Phe Pro Glu Lys
    770                 775                 780
Ala Lys Ser Pro Val Lys Glu Val Lys Ser Pro Glu Lys Ala Lys
785                 790                 795                 800
Ser Pro Leu Lys Glu Asp Ala Lys Ala Pro Glu Lys Glu Ile Pro Lys
            805                 810                 815
Lys Glu Glu Val Lys Ser Pro Val Lys Glu Glu Lys Pro Gln Glu
        820                 825                 830
Val Lys Val Lys Glu Pro Pro Lys Lys Ala Glu Glu Lys Ala Pro
    835                 840                 845
Ala Thr Pro Lys Thr Glu Glu Lys Lys Asp Ser Lys Lys Glu Glu Ala
    850                 855                 860
Pro Lys Lys Glu Ala Pro Lys Pro Lys Val Glu Glu Lys Lys Glu Pro
865                 870                 875                 880
Ala Val Glu Lys Pro Lys Glu Ser Lys Val Glu Ala Lys Lys Glu Glu
                885                 890                 895
Ala Glu Asp Lys Lys Val Pro Thr Pro Glu Lys Glu Ala Pro Ala
                900                 905                 910
Lys Val Glu Val Lys Glu Asp Ala Lys Pro Lys Glu Lys Thr Glu Val
                915                 920                 925
Ala Lys Lys Glu Pro Asp Asp Ala Lys Ala Lys Glu Pro Ser Lys Pro
930                 935                 940
Ala Glu Lys Lys Glu Ala Ala Pro Glu Lys Lys Asp Thr Lys Glu Glu
945                 950                 955                 960
Lys Ala Lys Lys Pro Glu Glu Lys Pro Lys Thr Glu Ala Lys Ala Lys
                965                 970                 975
Glu Asp Asp Lys Thr Leu Ser Lys Glu Pro Ser Lys Pro Lys Ala Glu
            980                 985                 990
Lys Ala Glu Lys Ser Ser Ser Thr Asp Gln Lys Asp Ser Lys Pro Pro
        995                 1000                1005
Glu Lys Ala Thr Glu Asp Lys Ala Ala Lys Gly Lys
    1010                1015                1020

<210> SEQ ID NO 64
<211> LENGTH: 3721
<212> TYPE: DNA
<213> ORGANISM: Homo sapiens

<400> SEQUENCE: 64
aaaagggccg cgcccctggt gctgccgcag tgcctcccgc cccgtccggg cctcgcgcac      60
ctgctcaggc catgatgagc ttcggcggcg cggacgcgct gctgggcgcc ccgttcgcgc     120
cgctgcatgg cggcggcagc ctccactacg cgctagcccg aaagggtggc gcaggcggga     180
cgcgctccgc cgctggctcc tccagcggct tccactcgtg gacacggacg tccgtgagct     240
ccgtgtccgc ctcgcccagc cgcttccgtg gcgcaggcgc cgcctcaagc accgactcgc     300
tggacacgct gagcaacggg ccggagggct gcatggtggc ggtggccacc tcacgcagtg     360
agaaggagca gctgcaggcg ctgaacgacc gcttcgccgg gtacatcgac aaggtgcggc     420
```

-continued

```
agctggaggc gcacaaccgc agcctggagg gcgaggctgc ggcgctgcgg cagcagcagg    480
cgggccgctc cgctatgggc gagctgtacg agcgcgaggt ccgcgagatg cgcggcgcgg    540
tgctgcgcct gggcgcggcg cgcggtcagc tacgcctgga gcaggagcac ctgctcgagg    600
acatcgcgca cgtgcgccag cgcctagacg acgaggcccg gcagcgagag gaggccgagg    660
cggcggcccg cgcgctggcg cgcttcgcgc aggaggccga ggcggcgcgc gtggacctgc    720
agaagaaggc gcaggcgctg caggaggagt gcggctacct cgggcgccac caccaggaag    780
aggtgggcga gctgctcggc cagatccagg gctccggcgc cgcgcaggcg cagatgcagg    840
ccgagacgcg cgacgccctg aagtgcgacg tgacgtcggc gctgcgcgag attcgcgcgc    900
agcttgaagg ccacgcggtg cagagcacgc tgcagtccga ggagtggttc cgagtgaggc    960
tggaccgact gtcggaggca gccaaggtga acacagacgc tatgcgctca gcgcaggagg   1020
agataactga gtaccggcgt cagctgcagg ccaggaccac agagctggag gcactgaaaa   1080
gcaccaagga ctcactggag aggcagcgct ctgagctgga ggaccgtcat caggccgaca   1140
ttgcctccta ccaggaagcc attcagcagc tggacgctga gctgaggaac accaagtggg   1200
agatggccgc ccagctgcga gaataccagg acctgctcaa tgtcaagatg gctctggata   1260
tagagatagc cgcttacaga aaactcctgg aaggtgaaga gtgtcggatt ggctttggcc   1320
caattccttt ctcgcttcca gaaggactcc ccaaaattcc ctctgtgtcc actcacataa   1380
aggtgaaaag cgaagagaag atcaaagtgg tggagaagtc tgagaaagaa actgtgattg   1440
tggaggaaca gacagaggag acccaagtga ctgaagaagt gactgaagaa gaggagaaag   1500
aggccaaaga ggaggagggc aaggaggaag aaggggtgta agaagaggag gcagaagggg   1560
gagaagaaga aacaaagtct cccccagcag aagaggctgc atccccagag aaggaagcca   1620
agtcaccagt aaaggaagag gcaaagtcac cggctgaggc caagtcccca gagaaggagg   1680
aagcaaaatc cccagccgaa gtcaagtccc ctgagaaggc caagtctcca gcaaaggaag   1740
aggcaaagtc accgcctgag gccaagtccc cagagaagga ggaagcaaaa tctccagctg   1800
aggtcaagtc ccccgagaag gccaagtccc cagcaaagga agaggcaaag tcaccggctg   1860
aggccaagtc tccagagaag gccaagtccc cagtgaagga agaagcaaag tcaccggctg   1920
aggccaagtc cccagtgaag gaagaagcaa aatctccagc tgaggtcaag tccccggaaa   1980
aggccaagtc tccaacgaag gaggaagcaa agtcccctga aaggccaagt ccccagagaa   2040
aggaagaggc caagtcccct gagaaggcca gtcccccagt gaaggcagaa gcaaagtccc   2100
ctgagaaggc caagtcccca gtgaaggcag aagcaaagtc ccctgagaag gccaagtccc   2160
cagtgaagga agaagcaaag tccctgaga aggccaagtc cccagtgaag gaagaagcaa   2220
agtcccctga aaggccaagt ccccagtgaa ggaagaagc aaagaccccc gagaaggcca   2280
agtccccagt gaaggaagaa gctaagtccc cagagaaggc caagtcccca gagaaggcca   2340
agactcttga tgtgaagtct ccagaagcca agactccagc gaaggaggaa gcaaggtccc   2400
ctgcagacaa attccctgaa aaggccaaaa gccctgtcaa ggaggaggtc aagtccccag   2460
agaaggcgaa atctcccctg aaggaggatg ccaaggcccc tgagaaggag atcccaaaaa   2520
aggaagaggt gaagtcccca gtgaaggagg aggagaagcc ccaggaggtg aaagtcaaag   2580
agcccccaaa gaaggcagag gaagagaaag cccctgccac accaaaaaca gaggagaaga   2640
aggacagcaa gaaagaggag gcacccaaga aggaggctcc aaagcccaag gtggaggaga   2700
agaaggaacc tgctgtcgaa aagcccaaag aatccaaagt tgaagccaag aaggaagagg   2760
ctgaagataa gaaaaaagtc cccaccccag agaaggaggc tcctgccaag gtggaggtga   2820
```

-continued

```
aggaagacgc taaacccaaa gaaaagacag aggtagccaa gaaggaacca gatgatgcca    2880
aggccaagga acccagcaaa ccagcagaga agaaggaggc agcaccggag aaaaaagaca    2940
ccaaggagga gaaggccaag aagcctgagg agaaacccaa gacagaggcc aaagccaagg    3000
aagatgacaa gaccctctca aaagagccta gcaagcctaa ggcagaaaag gctgaaaaat    3060
cctccagcac agaccaaaaa gacagcaagc ctccagagaa ggccacagaa gacaaggccg    3120 ccaagggaa gtaaggcagg gagaaaggaa catccggaac agccaaagaa actcagaaga    3180
gtcccggagc tcaaggatca gagtaacaca attttcactt tttctgtctt tatgtaagaa    3240
gaaactgctt agatgacggg gcctccttct caaacagga atttctgtta gcaatatgtt    3300
agcaagagag ggcactccca ggcccctgcc cccaggccct ccccaggcga tggacaatta    3360
tgatagctta tgtagctgaa tgtgatacat gccgaatgcc acacgtaaac acttgactat    3420
aaaaactgcc ccctcctttt ccaaataagt gcatttattg cctctatgtg caactgacag    3480
atgaccgcaa taatgaatga gcagttagaa atacattatg cttgagatgt cttaacctat    3540
tcccaaatgc cttctgtttt ccaaaggagt ggtcaagccc ttgcccagag ctctctattc    3600
tggaagagcg gtccaggtgg ggccggggac tggccactga attatgccag ggcgcacttt    3660
ccactggagt tcactttcaa ttgcttctgt gcaataaaac caagtgctta taaatgaaa    3720 a                                                                    3721
```

<210> SEQ ID NO 65
<211> LENGTH: 559
<212> TYPE: PRT
<213> ORGANISM: Homo sapiens

<400> SEQUENCE: 65

```
Met Ala Asp Glu Arg Lys Asp Glu Ala Lys Ala Pro His Trp Thr Ser
1               5                   10                  15

Ala Pro Leu Thr Glu Ala Ser Ala His Ser His Pro Glu Ile Lys
            20                  25                  30

Asp Gln Gly Gly Ala Gly Glu Gly Leu Val Arg Ser Ala Asn Gly Phe
        35                  40                  45

Pro Tyr Arg Glu Asp Glu Glu Gly Ala Phe Gly Glu His Gly Ser Gln
    50                  55                  60

Gly Thr Tyr Ser Asn Thr Lys Glu Asn Gly Ile Asn Gly Glu Leu Thr
65                  70                  75                  80

Ser Ala Asp Arg Glu Thr Ala Glu Glu Val Ser Ala Arg Ile Val Gln
                85                  90                  95

Val Val Thr Ala Glu Ala Val Ala Val Leu Lys Gly Glu Gln Glu Lys
            100                 105                 110

Glu Ala Gln His Lys Asp Gln Thr Ala Ala Leu Pro Leu Ala Ala Glu
        115                 120                 125

Glu Thr Ala Asn Leu Pro Pro Ser Pro Pro Ser Pro Ala Ser Glu
    130                 135                 140

Gln Thr Val Thr Val Glu Glu Ala Ala Gly Gly Glu Ser Ala Leu Ala
145                 150                 155                 160

Pro Ser Val Phe Lys Gln Ala Lys Asp Lys Val Ser Asn Ser Thr Leu
                165                 170                 175

Ser Lys Ile Pro Ala Leu Gln Gly Ser Thr Lys Ser Pro Arg Tyr Ser
            180                 185                 190

Ser Ala Cys Pro Ser Thr Thr Lys Arg Ala Thr Phe Ser Asp Ser Leu
        195                 200                 205
```

```
Leu Ile Gln Pro Thr Ser Ala Gly Ser Thr Asp Arg Leu Pro Tyr Ser
            210                 215                 220
Lys Ser Gly Asn Lys Asp Gly Val Thr Lys Ser Pro Glu Lys Arg Ser
225                 230                 235                 240
Ser Leu Pro Arg Pro Ser Ser Ile Leu Pro Pro Arg Arg Gly Val Ser
                245                 250                 255
Gly Asp Arg Asp Glu Asn Ser Phe Ser Leu Asn Ser Ser Ile Ser Ser
            260                 265                 270
Ser Ala Arg Arg Thr Thr Arg Ser Glu Pro Ile Arg Arg Ala Gly Lys
        275                 280                 285
Ser Gly Thr Ser Thr Pro Thr Thr Pro Gly Ser Thr Ala Ile Thr Pro
290                 295                 300
Gly Thr Pro Pro Ser Tyr Ser Ser Arg Thr Pro Gly Thr Pro Gly Thr
305                 310                 315                 320
Pro Ser Tyr Pro Arg Thr Pro His Thr Pro Gly Thr Pro Lys Ser Ala
                325                 330                 335
Ile Leu Val Pro Ser Glu Lys Lys Val Ala Ile Ile Arg Thr Pro Pro
            340                 345                 350
Lys Ser Pro Ala Thr Pro Lys Gln Leu Arg Leu Ile Asn Gln Pro Leu
        355                 360                 365
Pro Asp Leu Lys Asn Val Lys Ser Lys Ile Gly Ser Thr Asp Asn Ile
370                 375                 380
Lys Tyr Gln Pro Lys Gly Gly Gln Val Arg Ile Leu Asn Lys Lys Ile
385                 390                 395                 400
Asp Phe Ser Lys Val Gln Ser Arg Cys Gly Ser Lys Asp Asn Ile Lys
                405                 410                 415
His Ser Ala Gly Gly Gly Asn Val Gln Ile Val Thr Lys Lys Ile Asp
            420                 425                 430
Leu Ser His Val Thr Ser Lys Cys Gly Ser Leu Lys Asn Ile Arg His
        435                 440                 445
Arg Pro Gly Gly Gly Arg Val Lys Ile Glu Ser Val Lys Leu Asp Phe
450                 455                 460
Lys Glu Lys Ala Gln Ala Lys Val Gly Ser Leu Asp Asn Ala His His
465                 470                 475                 480
Val Pro Gly Gly Gly Asn Val Lys Ile Asp Ser Gln Lys Leu Asn Phe
                485                 490                 495
Arg Glu His Ala Lys Ala Arg Val Asp His Gly Ala Glu Ile Ile Thr
            500                 505                 510
Gln Ser Pro Gly Arg Ser Ser Val Ala Ser Pro Arg Arg Leu Ser Asn
        515                 520                 525
Val Ser Ser Ser Gly Ser Ile Asn Leu Leu Glu Ser Pro Gln Leu Ala
530                 535                 540
Thr Leu Ala Glu Asp Val Thr Ala Ala Leu Ala Lys Gln Gly Leu
545                 550                 555
```

<210> SEQ ID NO 66
<211> LENGTH: 2286
<212> TYPE: DNA
<213> ORGANISM: Homo sapiens

<400> SEQUENCE: 66

```
ggcgctcggg ctgcgcgggc tctgggcagc agcagcagca gcagcagcat cctctcttcc      60
tttacttccc ttccgcttct ttctcttcct tctccttctt tttccccccc ctcccccttct    120
```

```
tcccctaacc cttctacccc tctccttttt ctccggaggg cgctaagtcc gtgagcggtg      180
gcagtcgcga ccgcgggtgc atccagtttc tgcgcccaga ttttattgat ctaatccaaa      240
gtatcttata acttctggct ggaattaaga ttcttcagct tgtctctaac cgaggaagca      300
ttgattggga gctactcatt cagaaaatta aagaaagaa gccagaaaat attatcaacc       360
ctttgagaac acgacacaac gaactttata ttttaccact tccttgaata gttgcaggag      420
aaataacaag gcattgaaga atggcagatg aacggaaaga cgaagcaaag gcacctcact      480
ggacctcagc accgctaaca gaggcatctg cacactcaca tccacctgag attaaggatc      540
aaggcggagc aggggaagga cttgtccgaa gcgccaatgg attcccatac agggaggatg      600
aagagggtgc ctttggagag catgggtcac agggcaccta ttcaaatacc aaagagaatg      660
ggatcaacgg agagctgacc tcagctgaca gagaaacagc agaggaggtg tctgcaagga      720
tagttcaagt agtcactgct gaggctgtag cagtcctgaa aggtgaacaa gagaaagaag      780
ctcaacataa agaccagact gcagctctgc ctttagcagc tgaagaaaca gctaatctgc      840
ctccttctcc accccatca cctgcctcag aacagactgt cacagtggag gaagcagcag       900
gtggggaatc agctctggct cccagtgtat ttaaacaggc aaaggacaaa gtctctaatt      960
ctaccttgtc aaagattcct gctttacagg gtagcacaaa gtccccaaga tacagctcag     1020
cctgccctag cacgactaaa agggctacat tttctgacag tttattaata cagcccacct     1080
cagcaggctc cacagaccgt ttgccatact caaaatcagg gaacaaggac ggagtaacca     1140
agagcccaga aaagcgctct tctctcccaa gaccttcctc cattctccct cctcggcgag     1200
gtgtgtcagg agacagagat gagaattcct tctctctcaa cagttctatc tcttcttcag     1260
cacggcggac caccaggtca gagccaattc gcagagcagg gaagagtggt acctcaacac     1320
ccactacccc tgggtctact gccatcactc ctggcacccc accaagttat tcttcacgca     1380
caccaggcac tcctggaacc cctagctatc caggaccccc tcacacacca ggaacccca      1440 agtctgccat cttggtgccg agtgagaaga aggtcgccat catacgtact cctccaaaat     1500
ctcctgcgac tcccaagcag cttcggctta ttaaccaacc actgccagac ctgaagaatg     1560
tcaaatccaa aatcggatca acagacaaca tcaaatacca gcctaaaggg gggcaggtta     1620
ggattttaaa caagaagatc gattttagca aagttcagtc cagatgtggt tccaaggata     1680
acatcaaaca ttcggctggg ggcggaaatg tacaaattgt taccaagaaa atagacctaa     1740
gccatgtgac atccaaatgt ggctctctga agaacatccg ccacaggcca ggtggcggac     1800
gtgtgaaaat tgagagtgta aaactagatt tcaaagaaaa ggcccaagct aaagttggtt     1860
ctcttgataa tgctcatcat gtacctggag gtggtaatgt caagattgac agccaaaagt     1920
tgaacttcag agagcatgct aaagcccgtg tggaccatgg ggctgagatc attacacagt     1980
ccccaggcag atccagcgtg gcatcacccc gacgactcag caatgtctcc tcgtctggaa     2040
gcatcaacct gctcgaatct cctcagcttg ccactttggc tgaggatgtc actgctgcac     2100
tcgctaagca gggcttgtga atatttctca tttagcattg aaataataat atttaggcat     2160
gagctcttgg caggagtggg ctctgagcag ttgttatatt cattctttat aaaccataaa     2220
ataaataatc tcatccccaa aaaaaaaaaa aaaaaaaaaa aaaaaaaaaa aaaaaaaaaa     2280
aaaaaa                                                                2286
```

<210> SEQ ID NO 67
<211> LENGTH: 360
<212> TYPE: PRT
<213> ORGANISM: Homo sapiens

<400> SEQUENCE: 67

| | | | | | | | | | | | | | | |
|---|---|---|---|---|---|---|---|---|---|---|---|---|---|---|
| Met | Glu | Leu | Asp | Phe | Gly | His | Phe | Asp | Glu | Arg | Asp | Lys | Thr | Ser | Arg |
| 1 | | | | 5 | | | | | 10 | | | | | 15 | |
| Asn | Met | Arg | Gly | Ser | Arg | Met | Asn | Gly | Leu | Pro | Ser | Pro | Thr | His | Ser |
| | | | 20 | | | | | 25 | | | | | 30 | | |
| Ala | His | Cys | Ser | Phe | Tyr | Arg | Thr | Arg | Thr | Leu | Gln | Ala | Leu | Ser | Asn |
| | | | 35 | | | | | 40 | | | | | 45 | | |
| Glu | Lys | Lys | Ala | Lys | Lys | Val | Arg | Phe | Tyr | Arg | Asn | Gly | Asp | Arg | Tyr |
| | 50 | | | | | 55 | | | | | 60 | | | | |
| Phe | Lys | Gly | Ile | Val | Tyr | Ala | Val | Ser | Ser | Asp | Arg | Phe | Arg | Ser | Phe |
| 65 | | | | | 70 | | | | | 75 | | | | | 80 |
| Asp | Ala | Leu | Leu | Ala | Asp | Leu | Thr | Arg | Ser | Leu | Ser | Asp | Asn | Ile | Asn |
| | | | | 85 | | | | | 90 | | | | | 95 | |
| Leu | Pro | Gln | Gly | Val | Arg | Tyr | Ile | Tyr | Thr | Ile | Asp | Gly | Ser | Arg | Lys |
| | | | 100 | | | | | 105 | | | | | 110 | | |
| Ile | Gly | Ser | Met | Asp | Glu | Leu | Glu | Glu | Gly | Glu | Ser | Tyr | Val | Cys | Ser |
| | | | 115 | | | | | 120 | | | | | 125 | | |
| Ser | Asp | Asn | Phe | Phe | Lys | Lys | Val | Glu | Tyr | Thr | Lys | Asn | Val | Asn | Pro |
| | 130 | | | | | 135 | | | | | 140 | | | | |
| Asn | Trp | Ser | Val | Asn | Val | Lys | Thr | Ser | Ala | Asn | Met | Lys | Ala | Pro | Gln |
| 145 | | | | | 150 | | | | | 155 | | | | | 160 |
| Ser | Leu | Ala | Ser | Ser | Asn | Ser | Ala | Gln | Ala | Arg | Glu | Asn | Lys | Asp | Phe |
| | | | | 165 | | | | | 170 | | | | | 175 | |
| Val | Arg | Pro | Lys | Leu | Val | Thr | Ile | Ile | Arg | Ser | Gly | Val | Lys | Pro | Arg |
| | | | 180 | | | | | 185 | | | | | 190 | | |
| Lys | Ala | Val | Arg | Val | Leu | Leu | Asn | Lys | Lys | Thr | Ala | His | Ser | Phe | Glu |
| | | 195 | | | | | 200 | | | | | 205 | | | |
| Gln | Val | Leu | Thr | Asp | Ile | Thr | Glu | Ala | Ile | Lys | Leu | Glu | Thr | Gly | Val |
| | 210 | | | | | 215 | | | | | 220 | | | | |
| Val | Lys | Lys | Leu | Tyr | Thr | Leu | Asp | Gly | Lys | Gln | Val | Thr | Cys | Leu | His |
| 225 | | | | | 230 | | | | | 235 | | | | | 240 |
| Asp | Phe | Phe | Gly | Asp | Asp | Val | Phe | Ile | Ala | Cys | Gly | Pro | Glu | Lys | |
| | | | | 245 | | | | | 250 | | | | | 255 | |
| Phe | Arg | Tyr | Ala | Gln | Asp | Asp | Phe | Ser | Leu | Asp | Glu | Asn | Glu | Cys | Arg |
| | | | 260 | | | | | 265 | | | | | 270 | | |
| Val | Met | Lys | Gly | Asn | Pro | Ser | Ala | Thr | Ala | Gly | Pro | Lys | Ala | Ser | Pro |
| | | | 275 | | | | | 280 | | | | | 285 | | |
| Thr | Pro | Gln | Lys | Thr | Ser | Ala | Lys | Ser | Pro | Gly | Pro | Met | Arg | Arg | Ser |
| | | 290 | | | | | 295 | | | | | 300 | | | |
| Lys | Ser | Pro | Ala | Asp | Ser | Ala | Asn | Gly | Thr | Ser | Ser | Ser | Gln | Leu | Ser |
| 305 | | | | | 310 | | | | | 315 | | | | | 320 |
| Thr | Pro | Lys | Ser | Lys | Gln | Ser | Pro | Ile | Ser | Thr | Pro | Thr | Ser | Pro | Gly |
| | | | | 325 | | | | | 330 | | | | | 335 | |
| Ser | Leu | Arg | Lys | His | Lys | Asp | Leu | Tyr | Leu | Pro | Leu | Ser | Leu | Asp | Asp |
| | | | 340 | | | | | 345 | | | | | 350 | | |
| Ser | Asp | Ser | Leu | Gly | Asp | Ser | Met | | | | | | | | |
| | | | | 355 | | | | 360 | | | | | | | |

<210> SEQ ID NO 68
<211> LENGTH: 9135
<212> TYPE: DNA
<213> ORGANISM: Homo sapiens

<400> SEQUENCE: 68

-continued

```
ctggcaggaa tttcttgctt ggagctcaga caacaaaggc atagagagat tggttttctt      60
tctctcagca tctccaccca accagcagaa aaccggtctc tgaggttcca ccaaaatatg     120
gaacttgatt ttggacactt tgacgaaaga gataagacat ccaggaacat gcgaggctcc     180
cggatgaatg ggttgcctag ccccactcac agcgcccact gtagcttcta ccgaaccaga     240
accttgcagg cactgagtaa tgagaagaaa gccaagaagg tacgtttcta ccgcaatggg     300
gaccgctact tcaaggggat tgtgtacgct gtgtcctctg accgttttcg cagctttgac     360
gccttgctgg ctgacctgac gcgatctctg tctgacaaca tcaacctgcc tcagggagtg     420
cgttacattt acaccattga tggatccagg aagatcggaa gcatggatga actggaggaa     480
ggggaaagct atgtctgttc ctcagacaac ttctttaaaa aggtggagta caccaagaat     540
gtcaatccca actggtctgt caacgtaaaa acatctgcca atatgaaagc cccccagtcc     600
ttggctagca gcaacagtgc acaggccagg gagaacaagg actttgtgcg ccccaagctg     660
gttaccatca tccgcagtgg ggtgaagcct cggaaggctg tgcgtgtgct tctgaacaag     720
aagacagccc actcttttga gcaagtcctc actgatatca cagaagccat caaactggag     780 accgggggttg tcaaaaaact ctacactctg gatggaaaac aggtaacttg tctccatgat     840
ttctttggtg atgatgatgt gtttattgcc tgtggtcctg aaaaatttcg ctatgctcag     900
gatgattttt ctctggatga aaatgaatgc gagtcatga agggaaaccc atcagccaca     960
gctggcccaa aggcatcccc aacacctcag aagacttcag ccaagagccc tggtcctatg    1020
cgccgaagca gtctccagc tgactcagca acggaacct ccagcagcca gctctctacc     1080
cccaagtcta agcagtctcc catctctacg cccaccagtc ctggcagcct ccggaagcac    1140
aaggacctgt acctgcctct gtccttggat gactcggact cgcttggtga ttccatgtaa    1200
aggaggggag agtgctcaga gtccagagta caaatccaag cctatcattg tagtagggta    1260
cttctgctca agtgtccaac agggctattg gtgctttcaa gtttttattt tgttgttgtt    1320
gttattttga aaacacatt gtaatatgtt gggtttattt tcctgtgatt tctcctctgg     1380
gccactgatc cacagttacc aattatgaga gatagattga taaccatcct ttggggcagc    1440
attccaggga tgcaaaatgt gctagtccat gacctttcaa tggaaagctt aggtgcctgc    1500
gttatatttg ccctgtctaa ttttgcccat acagtcttcc ttctgtagag ggctgtttac    1560
atatacagca cttaaaatgt ttgtgtggga aaaaaaaac tcattggcag atccaagaat    1620
gacaaacaca agtgccccct ttctctggat ctcaagaatg gtggaggacc ctggaaggac    1680
agcaaggcag ctccccagcc tcactcttca ctcctgattg aggcccgggt tgttgtcca     1740 gcaccaattc tggctgtcaa tggggagaaa taaaccaaca acttataatt gtgacaccag    1800
atgcttagga tcctggtgct gggttagcta agagaataga cagaattgga aaatactgca    1860
gacatttccg aagagtttat aaagcacagt gaattcctgg tcaatctctc cactgaggca    1920
atttggaatc aataagcaat tgataatagt ttggagtaag ggacttcata tacctgattc    1980
ctctagaagg ctgtctaaca taccacatga ttacatgaac tgtatggtat ccatctatct    2040
ctgttctatt gaatgccttg ttaacagcca acactgaaaa cactgtgaga atttgttttc    2100
aggtctgaca cctttcagtc tctttttata gcaagaaatc aatatccttt ttataaaaat    2160
tcatgtctgt atttcaggag caaactcttc aggctccttt tttataaact ggtgattttt    2220
cttttgtcta aaaacacat gaagaaaatt taccaaaaaa aaaaaaaaaa gcagaagaat    2280
aatgtagttt agaaattatg ctgtcactgc caaacagtaa cctccaggag aaaacaagat    2340
```

```
gaatagcaga ggccaattca atagaatcag ttttttgata gcttttaac agttatgctt    2400 gcattaataa tttcaatgtg gaccagacat tctaattata ttttaaatga aatgttacag    2460
catattttaa gcaactcttt ttatctataa tcctaatatt tcatactgaa gacacagaaa    2520
tctttcactt gtcttaaca ttagaaagga tttctcttta ctaaggactg atcatttgaa    2580
atagttttca gtcttttgag atacaggttt ataacactgc ttttttttt ctgtaatcat    2640 agcccataat ggcaaagaca actaaattta agtgaaggtc atgcatgcca attctgtgtt    2700
tgcttttagc agatatgaag atttccttat ttctttgtaa ttgtgcagat attttgaaag    2760
gcacagcatt cgaagccaag ctgctgtttg gctactgaat ggcttgcagt tgttcctcca    2820
ctctaaatgg aatgagcttg ctgtgtgtgt gtgtggtggt ggtgggaggg ggtggtgcat    2880
gtgtgtgtgt gtgtgtgcat ctgcagctgc ttcaaaatta ggaaatacta caggacaccc    2940
ctgtaatgga ttggtggcaa ctgggtggca ctgctgatgt gcactgtgta ggggggaacc    3000
cagtggtggt ggggtagctc agatgcccct agacaagctt cagatgtctg tagctaccag    3060
aaacattttc ggttcaggaa aagtgagatg atggtagtac tggtttctgg tgaaattgaa    3120 gaacccaaa tgatgaggat ctcttttgc cccctctcct tttttgtag acccattcaa    3180 aaccattaat aagcccattt tactaagccc ctatttcttt ctagaagctc agggttttct    3240
tagtgcctcc cagaacattt tgtagttaat tgggaaaaag tgatacttgg attaggggt    3300 gtgggcataa agaatggtgg gaggcctgat tttaaacttc aggccagaac ccccaatgac    3360
tccacccata gtctcacttt aggtctcatt tagtccatca cctttatttt aagttgagga    3420
agtggaggct ggtaaagagc aggaccagag gaagaatcca gatttcctta tgcttgggcc    3480
tcacactagc tctctgagta tttccttgat tgcggtatat gtactactag aaaataccaa    3540
atggatatat tttcttaggc ataaccttg aaccaacaat cttcaataac aatagtacat    3600
cttccatctt actttaatc gagtataagg aaatgtttct ttatggccat tttggaggga    3660
gcaggggatg aggcttggca tagtccaaaa tttaagtctc caataattaa ttgcatttta    3720
aattggccca ctttcaaggc aattttttt gtgtgtctgt aactgagctc ctccacccct    3780
gtcattcact tccaattta cccaatccaa ttttagcact caagttccat tgtgttaatt    3840
tctgcacggt caacaaacat caagtcagca agcatttgcc accactccct atacttctcc    3900
ctccttctta cacacacaca cacacacaca cacaatcc atctcttgct tgttcctacc    3960
tcctgatttt tcttccctac agaaatagaa atagggacaa agaagggaa aatgtatata    4020 ttggggctgg gctgaacaac taacttcata agtagtatta actagggta aattgagaga    4080 aaagctcctt ttctcttcac tgttttggaa aggatagcca ttagcatgac tgctttgtgt    4140
ccttatggac tttagtatta gcctagattg aattatagcg ttttctagct ggaaggaacc    4200
ttaagatcac atcatctact cctctactcc aaattctca ttcttcaggc caggaaaccg    4260
agacacagag gtaaagtaat ttccccaagg tcacacagct ggctgggca ggattgggtt    4320 tacaacccac atctcctggc tcttattcca gggccttttc ccactaagta gtattgcctt    4380
ccattaggct cctgagagtt atttctcagg gtcatgttgc atcttggagc cacatgctgc    4440
tgccctgatc tcagtgggaa atccaccag caacctaata cagccccttt tccctgcatt    4500
cacctggttc ccatccacat gggttgcaga tgtccttgaa gagagtgagg cattgagggc    4560
caataggagc aatggggtcc ctggccttgt ccatctgatt caggagatca ctgctccatc    4620
gtgaggagcc ctctgaatag ccccccactg aatgcttgcc ttgcccaaat ggaatggagg    4680
aagattgatt ttctccatca gttcaccttg tgtcatctca taatggttgg tctttccagg    4740
```

```
ctgagggaaa tgtttcttgt tccagagta gaaaaagaaa gagtggaaca atagctttgt   4800
tcatcctaac tttctgagat ggcttttcaa cattttaaaa aaactagtgt ggctaccatt   4860
cactggcaat gatttctttt agaatatggg agtaagatga gctagagaaa ataacctggt   4920
ctcactgtgg ttgccctcat ccacaatgtc cccaaagcca tcctgctctg atgaggacaa   4980
tttccaggta taagcaaggg gctttgtgac aaaaatgtac cctggctgat gttaaacatt   5040
ggctcctgtg tttgcaccaa aatagcaagc tgtgtgctct atacactctt cccatcgtct   5100
tgtgtacact gctcctgtgg ccttccacag cagaaaccag ggcaaaaggg tccaaacaca   5160
tggttttcct tgctgcaagg ctcttcctgg gaactaaggg ggtatttatt agttcagttc   5220
taagagacct ccttctgggc ttaccccact cctcaggtac ttctctctcc ttcctccttc   5280
tcctccacag tcacaagtaa ccaaggaacc tgaaagtgga tgtgtagcta tttgaagaag   5340
gcaaggaacc ctgagattct tctttgaatc ctctagtcca agtcttagac cagtgattgg   5400
tgcttacctt gaacaaaatt ttgtctgtgt tcctaatccc ttcaatactc tgggtacaat   5460
gctcccaatc accctgcaca tttgattcta aatggctttt atttttttaaa aatccatatc   5520 cctaggacaa gagaacagga tgcctatatc cccaaaatga gctccaggac actgatggga   5580
atgatcccaa agatcacccc acctcagaaa cgtctgtgcc aagagacttc cccagataga   5640
aacactggga cagtggtttg aacgacttct tttatggttg tccagtttgc tatggaaata   5700
aaaggcattg attttttaaa aagatgattg gaacctgtct ttggccacat agggccactt   5760
ggatccattt ccaggcctta ctcatatatt gccttcactg aagggctttg gctttaagtc   5820
ccagactggt ctcccaagtg aaccataagt gttttggagc tcatctgggg tgaggcatga   5880
gaatgttgcc ccatctatcc cttcaggaaa aggtgccttc cctcccttc tcctaaagcc    5940 tggtcccag aaattgtttt tgtctccaaa agtctagtat ggtctttata cacccagact     6000
cttagtgttg cgtcctgcct tgtttccttg ttaaggatct atgcagacct cccgctttgg   6060
cttagctagc gtgacattgg ctatcatttg acaagactaa ctttttttt tttttttttt    6120 tgactgagtc tccctctgtc acctaggctg gagtgcagtg gcacaatctt ggctcgctgc   6180
aaccttcacc cttcacctcc caggtcgaag cgattctcct gcctcagtct cccgagtagc   6240
tgggattaca ggcgtgcgcc accaaatctg gctattttt tattattatt attttttagta  6300 gagatggggt ttcaccatgt tggccagact ggtcttgaac tcttggcctc aaattatctg   6360
cccacctcgg cctcccaaag tgctgggatt acaggcatga gccaccatgc ccagctgaca   6420
agactaattt tttatcccct tggtttattgg cttcaacatc ttctggaatc agaggtgatt   6480 tttcttacc ttggatgcct gagactaggg gagtatagaa ttccaattgg taattaaggc    6540
atctttctgc tcctgatcag aagggcaggt tagttgggag aggtcagatg gcacaacaga   6600
agtcaccttg taagtaaggc aaagacttga aggcattagc gtttctcatt actaggtcaa   6660
taacctgagg gaatcaatgg cttttttgccg ctctacctct tgtgtatctc tttgactttt  6720
ctttctctgt ctagtttcct ctgttctcag tttatattct atgttatcag tctctctttc   6780
cacagtacaa acatccatcc tttctcctgt gcaattctgt ctctccctct tattatcttt   6840
atttgtactt tttccttcct ccctgtctag gcattgggca tgtgcctctt cttagcctgt   6900
gattttgcct tgggactgat gataaattat ttccagattc aatcagccct ggtcctaccc   6960
cagtccaatc agaagtatgt tggtgggaat caacctgatc ctggcccttt cttcttctcc   7020
attttcattc gtaatccccc tcagcagatc tttacaagca gtttccttat agctcatgta   7080
```

-continued

```
tctttaggtc tttgccttcc aagcactgta cagaatactt tgtggttcct ttttagtctg    7140
acattttgtg gagcagtgaa gcgtgctcag agacataatc agctgaagag aaaaaatcca    7200
cccatggatt tatatcagct aaatactaat aattgatttt gtttgatgtg cccataattt    7260
ttaaagctgc aatataatat aatgagggac acaggtaat  ttctcctgtc atttgttttg    7320
gctggatggg ggtgggggag taattgctta aagttttacc attacacatt aaactctcta    7380
taataatctt gttttgggct tgctaactgt tgagctgttt taactaaact ggtaggcaat    7440
cggagttgat ttaaatgaaa agataattta acaaatctat actataaaaa gagacatttg    7500
cttaattgac atgtattttt tccttctgag tcacctaaac atttactctt gacaccaact    7560
gttcatgata ctgaatagac agtccatata agagaaatta gtggacctaa agaagccaga    7620
ttgtaggtgt taatttatta aacagagtgc aaagcccttg gaaatgtcac tgcttggcaa    7680
taccatatgg aatgccaaaa tttacaatga ctttcttta  aagttatcc  aaaagggatt    7740 tgaacaagta agaggttatg ccaaaatgtc tccaatgtat ggtcctgtaa tatattgcag    7800
cttgaagcca atgatccctt atgacttgta tacaactaat gcatgtttta ttgaattttg    7860
catttcccac gtgtggtaag ttcttttaaaa tgttttttgat caccttttttg tgccattaaa    7920 cttgtacaga aaatgttttt atggccattt tcaaagggag aaagtttaaa atggaaacag    7980
cccacccttt ctgccctata gctgtagtta gaattgagta cctgtagcaa aacagctgta    8040
attggtggtt gtagtgttag aggtgttagc ttgctagtga ctagctttgg agagtaaatg    8100
catggtattg tacatcacat ttcttaactc gttttaacct ctgaaaagaa tatattcttc    8160
tttgtagtcc ttcttcccac cccttgccc  tctccctctc cctgctccca gttgtcttac    8220
agttgtaaat atctgatttg aggcccaata actcttgcca agtaaagtca gcaaacaaca    8280
aacaaaccaa aatgtgggga aaaggcattt ctcaaccatc tctcagcagt tattgatcat    8340
ttcttaagga acagcattgt gatcaaagac tcaactttac gtaaaaatca gtggtaaatt    8400
ggggttgtat ttggccattt gattacattt caggattgaa tagttttcag aatcacatgt    8460
aatccaaaga cagtaggtag tgatgtccct tatccctgca gctgttttaa gatagagacc    8520
tcagaagact ctgcttgacc gatgaccaat aattatttga aaaaaaaaga aaaaatgaga    8580
gaaataaaac agatatttaa gaactttagc cacctattta gaatagttat agccagaaaa    8640
aaaaacaagg gcatgagttc aaatgcatta ctatcagtgt cctaggcaat acctaaccta    8700
ctctgaaatt gtgattcaaa agcagtattt caagaggcat tctccttttt tggtttgctg    8760
accccacttg gactggtagg tttggtgagg ccccataaaa ccagctggag cagacccttt    8820
tcatctcctg tgcctgtaac acccctcttc ccccaccccc tccgcaattc aatgagggct    8880
ttcttgggtc agaggacttc aaggttgtct agagaagttt gccatgtgtg taaggtgctg    8940
tgaactgtga gtgctgaaga ttcgcagcat tcaataccag gcagccaaag agctgctctt    9000
gcaattattt tggctctcaa gctctgttct tcatcgcatt ctcatttctg tgtacatttg    9060
caagatgtgt gtaatgtcat tttccaaaaa taaaatttga tttcaataaa aaaaaaaaa     9120 aaaaaaaaaa aaaaa                                                    9135
```

<210> SEQ ID NO 69
<211> LENGTH: 456
<212> TYPE: PRT
<213> ORGANISM: Homo sapiens

<400> SEQUENCE: 69

Met Arg Lys Ser Pro Gly Leu Ser Asp Cys Leu Trp Ala Trp Ile Leu

-continued

```
1               5                   10                  15
Leu Leu Ser Thr Leu Thr Gly Arg Ser Tyr Gly Gln Pro Ser Leu Gln
                20                  25                  30

Asp Glu Leu Lys Asp Asn Thr Thr Val Phe Thr Arg Ile Leu Asp Arg
                35                  40                  45

Leu Leu Asp Gly Tyr Asp Asn Arg Leu Arg Pro Gly Leu Gly Glu Arg
50                  55                  60

Val Thr Glu Val Lys Thr Asp Ile Phe Val Thr Ser Phe Gly Pro Val
65                  70                  75                  80

Ser Asp His Asp Met Glu Tyr Thr Ile Asp Val Phe Phe Arg Gln Ser
                85                  90                  95

Trp Lys Asp Glu Arg Leu Lys Phe Lys Gly Pro Met Thr Val Leu Arg
                100                 105                 110

Leu Asn Asn Leu Met Ala Ser Lys Ile Trp Thr Pro Asp Thr Phe Phe
                115                 120                 125

His Asn Gly Lys Lys Ser Val Ala His Asn Met Thr Met Pro Asn Lys
130                 135                 140

Leu Leu Arg Ile Thr Glu Asp Gly Thr Leu Leu Tyr Thr Met Arg Leu
145                 150                 155                 160

Thr Val Arg Ala Glu Cys Pro Met His Leu Glu Asp Phe Pro Met Asp
                165                 170                 175

Ala His Ala Cys Pro Leu Lys Phe Gly Ser Tyr Ala Tyr Thr Arg Ala
                180                 185                 190

Glu Val Val Tyr Glu Trp Thr Arg Glu Pro Ala Arg Ser Val Val Val
                195                 200                 205

Ala Glu Asp Gly Ser Arg Leu Asn Gln Tyr Asp Leu Leu Gly Gln Thr
210                 215                 220

Val Asp Ser Gly Ile Val Gln Ser Ser Thr Gly Glu Tyr Val Val Met
225                 230                 235                 240

Thr Thr His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
                260                 265                 270

Trp Leu Asn Arg Glu Ser Val Pro Ala Arg Thr Val Phe Gly Val Thr
                275                 280                 285

Thr Val Leu Thr Met Thr Thr Leu Ser Ile Ser Ala Arg Asn Ser Leu
                290                 295                 300

Pro Lys Val Ala Tyr Ala Thr Ala Met Asp Trp Phe Ile Ala Val Cys
305                 310                 315                 320

Tyr Ala Phe Val Phe Ser Ala Leu Ile Glu Phe Ala Thr Val Asn Tyr
                325                 330                 335

Phe Thr Lys Arg Gly Tyr Ala Trp Asp Gly Lys Ser Val Val Pro Glu
                340                 345                 350

Lys Pro Lys Lys Val Lys Asp Pro Leu Ile Lys Asn Asn Thr Tyr
                355                 360                 365

Ala Pro Thr Ala Thr Ser Tyr Thr Pro Asn Leu Ala Arg Gly Asp Pro
                370                 375                 380

Gly Leu Ala Thr Ile Ala Lys Ser Ala Thr Ile Glu Pro Lys Glu Val
385                 390                 395                 400

Lys Pro Glu Thr Lys Pro Pro Glu Pro Lys Thr Phe Asn Ser Val
                405                 410                 415

Ser Lys Ile Asp Arg Leu Ser Arg Ile Ala Phe Pro Leu Leu Phe Gly
                420                 425                 430
```

Ile Phe Asn Leu Val Tyr Trp Ala Thr Tyr Leu Asn Arg Glu Pro Gln
    435                 440                 445

Leu Lys Ala Pro Thr Pro His Gln
    450                 455

<210> SEQ ID NO 70
<211> LENGTH: 3440
<212> TYPE: DNA
<213> ORGANISM: Homo sapiens

<400> SEQUENCE: 70

| | | | | | |
|---|---|---|---|---|---|
| agcggagcgg | gcgagcaagg | gagcgagcag | gacaggagcc | tgatcccaca gctgctgctc | 60 |
| cagcccgcga | tgaggaaaag | tccaggtctg | tctgactgtc | tttgggcctg gatcctcctt | 120 |
| ctgagcacac | tgactggaag | aagctatgga | cagccgtcat | acaagatgaa acttaaagac | 180 |
| aataccactg | tcttcaccag | gattttggac | agactcctag | atggttatga caatcgcctg | 240 |
| agaccaggat | tggagagcg | tgtaaccgaa | gtgaagactg | atatcttcgt caccagtttc | 300 |
| ggacccgttt | cagaccatga | tatggaatat | acaatagatg | tatttttccg tcaaagctgg | 360 |
| aaggatgaaa | ggttaaaatt | taaaggacct | atgacagtcc | tccggttaaa taacctaatg | 420 |
| gcaagtaaaa | tctggactcc | ggacacattt | ttccacaatg | gaaagaagtc agtggcccac | 480 |
| aacatgacca | tgcccaacaa | actcctgcgg | atcacagagg | atggcacctt gctgtacacc | 540 |
| atgaggctga | cagtgagagc | tgaatgtccg | atgcatttgg | aggacttccc tatggatgcc | 600 |
| catgcttgcc | cactaaaatt | tggaagttat | gcttatacaa | gagcagaagt tgtttatgaa | 660 |
| tggaccagag | agccagcacg | ctcagtggtt | gtagcagaag | atggatcacg tctaaaccag | 720 |
| tatgaccttc | ttgacaaac | agtagactct | ggaattgtcc | agtcaagtac aggagaatat | 780 |
| gttgttatga | ccactcattt | ccacttgaag | agaaagattg | gctactttgt tattcaaaca | 840 |
| tacctgccat | gcataatgac | agtgattctc | tcacaagtct | ccttctggct caacagagag | 900 |
| tctgtaccag | caagaactgt | cttggagta | acaactgtgc | tcaccatgac aacattgagc | 960 |
| atcagtgcca | gaaactccct | ccctaaggtg | gcttatgcaa | cagctatgga ttggtttatt | 1020 |
| gccgtgtgct | atgcctttgt | gttctcagct | ctgattgagt | ttgccacagt aaactatttc | 1080 |
| actaagagag | ttatgcatg | ggatggcaaa | agtgtggttc | cagaaaagcc aaagaaagta | 1140 |
| aaggatcctc | ttattaagaa | aaacaacact | tacgctccaa | cagcaaccag ctacaccccct | 1200 |
| aatttggcca | ggggcgaccc | gggcttagcc | accattgcta | aaagtgcaac catagaacct | 1260 |
| aaagaggtca | agcccgaaac | aaaaccacca | gaacccaaga | aaacctttaa cagtgtcagc | 1320 |
| aaaattgacc | gactgtcaag | aatagccttc | ccgctgctat | ttggaatctt taacttagtc | 1380 |
| tactgggcta | cgtatttaaa | cagagagcct | cagctaaaag | cccccacacc acatcaatag | 1440 |
| atcttttact | cacattctgt | tgttcagtcc | tctgcactgg | gaatttattt atgttctcaa | 1500 |
| cgcagtaatt | cccatctgct | ttattgcctc | tgtcttaaag | aatttgaaag tttccttatt | 1560 |
| ttcataattc | atttaagaac | aagagacccc | tgtctggcag | tctggagcaa agcagactat | 1620 |
| gcagcttgga | gacaggattc | tgacagagca | agcgaaagag | caaagtcatg tcagaaggag | 1680 |
| acagaatgag | agagaaaaga | gggggaagat | ggttcaaaga | tacaagaaaa agtagaaaaa | 1740 |
| aaaataacac | ttaactaaaa | cccctaggtc | atttgtagat | atatatttcc aaatattcta | 1800 |
| aaaaagatac | tgtatatgtc | aaaaatattt | ttatgtgaag | gtgtttcaaa gggtaaatta | 1860 |
| taaatgtttc | atgaagaaaa | aatttaaaa | atctacgtct | ttattacaca aactatggtg | 1920 |

-continued

```
tgcttatgtt tttgttttgc tttttaaact gatgtatagc tttaacattt tgtttccaaa    1980
gctgaagatc cccattcttt ctctttgaaa aaaaaaaagg cctaatgcat tattttgtca    2040
taaaatgcta ttttaaaatt catggaactt tcatacgtaa aggtgcagtt gctcattgta    2100
gagcacattt agtccaatga agataaatgc tttaaatagt ttacttcact ttcatctgag    2160
cttttaccac tagactcaag gaagaataat tttaacagac atgtatactc catagaaact    2220
aaattaaaat agtttaaaaa tattcccttt ttcaccctat tttcagatag cacatgagcc    2280
caacactcac ttaattctca ttatgaagat gttttagag gggcaaaaat attttgcaag     2340
ctctggaatt gttgaatgta ttcttttata taactacatt aaaagcttta gattgaaatt    2400
tatgactagc aaacaaaaat agaatatata aacgatatat gtaaatatac agcatgagat    2460
tgtacatttt ttactttttt aaaattgtgt tcttaaaata ttgtgtaaga atcactgcac    2520
ttagctgttg gaatgttgtt aaatgctatg gaaatacatt tagaacctgc atttaagaac    2580
agaacagcaa gtatgaacca catggaactt aaaacatatg ggtgtgaagt ccacttatgt    2640
agacaaaact tataatttcc aaactgttgt ctagtataca gtgatcagtt gctctctgtt    2700
caagtcattc cacacatttc cctattttag gctattataa tatagaaaga aaatgggaag    2760
cattagttgg agctagaaaa tgaactgtat attattgcta tatttgctaa taccaactat    2820
ttcaataagt gttgtaccat atgtagcatt aaatataaaa tacataaaag aatgtacaga    2880
aaatagcttt tattgagtaa tattacattt catttatact gtagcaatat atttgtaggt    2940
atactatgta agggctttaa ataaagagg tccattaata cttccttata aaaattctag     3000
tctgtttcat tactgcccag atgttttaga gataaatatt tatgcagaag gtattttga     3060 agtctccttt tgtctgatag agtttaacag atatttaaat ttagtgctca gaatccacaa    3120
gtcacggtct aaacacactt agaatactac agcataaatc tgttagcatt attgccaaat    3180
aagacagttg ggatccaaac ccaagtcttg agcaatgttt ttctcaaaaa gctgctatcc    3240
aatgatatag gaaaatacat tgtgttttcc taaacacact tttctttta aatgtgcttc     3300 attgtttgat ttggtcctgc ctaaatttca caagctaggc caatgaaggc tgaatcaaag    3360
acatttcatc caccaatatc atgtgtagat attatgtata gaaaataaaa taaattatgg    3420
ctccaaaaaa aaaaaaaaa                                                 3440
```